United States Patent
Hastings

(10) Patent No.: US 11,116,785 B2
(45) Date of Patent: Sep. 14, 2021

(54) ANTISENSE COMPOUNDS TARGETING GENES ASSOCIATED WITH CYSTIC FIBROSIS

(71) Applicant: Rosalind Franklin University of Medicine and Science, North Chicago, IL (US)

(72) Inventor: Michelle L. Hastings, North Chicago, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 16/730,517

(22) Filed: Dec. 30, 2019

(65) Prior Publication Data

US 2020/0129539 A1 Apr. 30, 2020

Related U.S. Application Data

(63) Continuation of application No. 15/835,698, filed on Dec. 8, 2017, now Pat. No. 10,525,076, which is a continuation-in-part of application No. 15/045,999, filed on Feb. 17, 2016, now Pat. No. 9,840,709.

(60) Provisional application No. 62/118,794, filed on Feb. 20, 2015.

(51) Int. Cl.
*A61K 31/712* (2006.01)
*C12N 15/113* (2010.01)

(52) U.S. Cl.
CPC ........ *A61K 31/712* (2013.01); *C12N 15/1138* (2013.01); *A01K 2267/0306* (2013.01); *C12N 2310/11* (2013.01); *C12N 2310/321* (2013.01); *C12N 2310/3233* (2013.01); *C12N 2320/33* (2013.01)

(58) Field of Classification Search
CPC .............. C12N 15/113; C12N 2310/11; C12N 2310/321; C12N 2310/3233; A61K 31/712
See application file for complete search history.

(56) References Cited

U.S. PATENT DOCUMENTS

| | | | |
|---|---|---|---|
| 6,573,073 | B2 | 6/2003 | Harris |
| 9,840,709 | B2 * | 12/2017 | Hastings ............ C12N 15/1137 |
| 9,976,143 | B2 | 5/2018 | Krainer et al. |
| 10,525,076 | B2 * | 1/2020 | Hastings ............ C12N 15/1138 |
| 10,544,417 | B2 * | 1/2020 | Hastings ............ C12N 15/1138 |
| 10,822,369 | B2 | 11/2020 | Crooke et al. |
| 2002/0086836 | A1 | 7/2002 | Harris |
| 2003/0008281 | A1 | 1/2003 | Weston et al. |
| 2004/0096844 | A1 | 5/2004 | Accola et al. |
| 2004/0096871 | A1 | 5/2004 | Accola et al. |
| 2004/0229269 | A1 * | 11/2004 | Hashmi ................ C12Q 1/6827 506/9 |
| 2005/0048544 | A1 | 3/2005 | Gardner et al. |
| 2005/0186588 | A1 | 8/2005 | Lyamichev et al. |
| 2006/0147938 | A1 | 7/2006 | Accola et al. |
| 2006/0252722 | A1 | 11/2006 | Lollo et al. |
| 2008/0221317 | A1 | 9/2008 | Khvorova et al. |
| 2012/0094846 | A1 | 4/2012 | Hantash |
| 2013/0203055 | A1 | 8/2013 | Aurich-Costa |
| 2015/0232878 | A1 | 8/2015 | Hyde et al. |
| 2018/0009837 | A1 | 1/2018 | Crooke et al. |

FOREIGN PATENT DOCUMENTS

| | | |
|---|---|---|
| WO | 96/06190 A2 | 2/1996 |
| WO | WO 97/35005 | 9/1997 |
| WO | 01/73002 A2 | 10/2001 |
| WO | WO 2007/110628 | 10/2001 |
| WO | 2005006951 A2 | 1/2005 |
| WO | 2008/102057 A1 | 8/2008 |
| WO | 2014/045283 A1 | 3/2014 |
| WO | WO 2016/077837 | 5/2016 |

OTHER PUBLICATIONS

Crooke et al., "Pharmacokinetic properties of several novel oligonucleotide analogs in mice." J. Pharmacol. Exp. Ther., 277(2):923-37 (May 1996).
Kabanov et al., "A new class of antivirals: antisense oligonucleotides combined with a hydrophobic substituent effectively inhibit influenza virus reproduction and synthesis of virus-specific proteins in MDCK cells" FEBS Lett, 259:327-330 (Jan. 1990).
Letsinger et al., "Cholesteryl-conjugated oligonucleotides: synthesis, properties, and activity as inhibitors of replication of human immunodeficiency virus in cell culture." Proc. Natl. Acad. Sci. USA, 86(17):6553-6556 (Sep. 1989).
Manoharan et al., "Cholic acid-oligonucleotide conjugates for antisense applications" Bioorganic & Medicinal Chemistry Letters, 4(8):1053-1060 (Apr. 1994).
Manoharan et al., "Chemical modifications to improve uptake and bioavailability of antisense oligonucleotides." Ann. N.Y. Acad. Sci., 660:306-309 (Oct. 1992).
Manoharan et al., "Introduction of a lipophilic thioether tether in the minor groove of nucleic acids for antisense applications" Bioorganic & Medicinal Chemistry Letters, 3(12):2765-2770 (Dec. 1993).

(Continued)

*Primary Examiner* — Brian Whiteman
(74) *Attorney, Agent, or Firm* — McDonnell Boehnen Hulbert & Berghoff LLP

(57) ABSTRACT

The present disclosure relates generally to compounds comprising oligonucleotides complementary to a cystic fibrosis transmembrane conductance regulator (CFTR) RNA transcript. Certain such compounds are useful for hybridizing to a CFTR RNA transcript, including but not limited to a CFTR RNA transcript in a cell. In certain embodiments, such hybridization results in modulation of splicing of the CFTR transcript. In certain embodiments, such compounds are used to treat one or more symptoms associated with Cystic Fibrosis.

33 Claims, 41 Drawing Sheets

Specification includes a Sequence Listing.

(56) References Cited

OTHER PUBLICATIONS

Manoharan et al., "Lipidic nucleic acids" Tetrahedron Letters, 36(21):3651-54 (May 1995).
Manoharan et al., "Oligonucleotide Conjugates: Alteration of the Pharmacokinetic Properties of Antisense Agents" Nucleosides & Nucleotides, 14(Issue 3-5): 969-973 (1995).
Mishra et al., "Improved leishmanicidal effect of phosphorotioate antisense oligonucleotides by LDL-mediated delivery." Biochim. Biophys. Acta, 1264(2):229-237 (Nov. 1995).
Oberhauser et al., "Effective incorporation of 2'O-methyl-oligoribonucleotides into liposomes and enhanced cell association through modification with thiocholesterol." Nucl. Acids Res., 20(3):533-538 (Feb. 1992).
Saison-Behmoaras et al., "Short modified antisense oligonucleotides directed against Ha-ras point mutation induce selective cleavage of the mRNA and inhibit T24 cells proliferation." EMBO J., 10(5):1111-18 (May 1991).
Shea et al., "Synthesis, hybridization properties and antiviral activity of lipid-oligodeoxynucleotide conjugates." Nucl. Acids Res., 18(13):3777-83 (Jul. 1990).
Svinarchuk et al., "Inhibition of HIV proliferation in MT-4 cells by antisense oligonucleotide conjugated to lipophilic groups" Biochimie, 75(1-2):49-54 (1993).
The International Search Report and Written Opinion for International Application No. PCT/US2016/018275 from the European Patent Office—International Searching Authority; dated Jun. 20, 2016, pp. 1-14.
Kim & Krainer, "Allele-Specific Inhibition of Nonsense-Mediated mRNA Decay in Cystic Fibrosis" Poster No. 804, Abstract Submitted. The 32nd Annual North American Cystic Fibrosis Conference, Denver, Colorado, Oct. 18-20, 2018, Pediatric Pulmonology vol. 53, Issue S2, Sep. 2018, one page.
Martinovich et al., "Rescue of CFTR Function Impaired by Mutations in Exon 15 in Children with Cystic Fibrosis" Poster No. 205, Abstract Submitted. The 32nd Annual North American Cystic Fibrosis Conference, Denver, Colorado, Oct. 18-20, 2018, Pediatric Pulmonology vol. 53, Issue S2, Sep. 2018, p. 224.
Friedman, K.J., et al., "Correction of Aberrant Splicing of the Cystic Fibrosis Transmembrane Conductance Regulator (CFTR) Gene by Antisense Oligonucleotides", Journal of Biological Chemistry, Dec. 17, 1999, vol. 274 (51), pp. 36193-36199.
Igreja, Susana, et al., "Correction of a Cystic Fibrosis Splicing Mutation by Antisense Oligonucleotides" Human Mutation, Nov. 10, 2015, pp. 1-7.
Qiao, W., et al, "Charge-Neutral Morpholino Microarrays for Nucleic Acid Analysis", Anal. Biochem., Mar. 15, 2013, vol. 434(2), pp. 207-214, doi:10.1016/j.ab.2012.12.001, Epub Dec. 12, 2012.
Sazani, P., et al., "Therapeutic Potential of Antisense Oligonucleotides as Modulators of Alternative Splicing", Journal of Clinical Investigation, Aug. 1, 2003, vol. 112(4), pp. 481-486.
Tsui, L.-C., "The Spectrum of Cystic Fibrosis Mutations", Trends in Genetics, Nov. 1, 1992, vol. 8(11), pp. 392-398.
PCT International Search Report and Written Opinion, European Patent Office—International Searching Authority, dated Jun. 20, 2016, pp. 1-14.

\* cited by examiner

FIG. 4

>human CFTR intron 1, exon 2, intron 2 region (SEQ ID NO: 131)
ATATGCCAGAAAAGTTGAATAGTAGTATCAGATTCCAAATCTGTATGGAGACCAAATCAAGTGAATATCTGTT
CCTCCTCTCTTATTTTAGCTGGACCAGACCAATTTGAGGAAAGGATACAGACAGCCGCCTGGAATTGTC
CCTCCTCTCTGTTGATTCTGCTGCTGACAATCTATCTGAAAATTGGAAGTATGTTCAT
AGACATATACCAAATCCCTTCTGTTGAAGAGAAATTCATATTATTAATTATTTAGAGAAGAGAAAGCAAACATATTAT
GTACATTGTTTAGTTGAAGAGAGAAATTCATATTATTAATTATTTAGAGAAGAGAAAGCAAACATATTAT
AAGTTTAATTCTTATATTTA

FIG. 5

>human CFTR intron 3, exon 4, intron 4 region (SEQ ID NO: 132)
TCTCCTCTAAAGATGAAAAGTCTTGTGTTGTTGAAATTCTCAGGGTATTTTATGAGAAATAAATGAAATTTAA
TTTCTCGTTTTTCCCCTTTTGTAGGAAGTCACCAAGCAGTACAGCCTCTTACTGGGAAGAATCATA
GCTTCCTATGACCCGGATAACAAGGAGAACGCTCTATCGCGATTTATCTAGGCATAGCTTATGCCTTC
TCTTTATTGTGAGGACACTGCTCCTACACCCAGCCATTTTGCCTTCATCACATTGGAATGCAGATGAG
AATAGCTATGTTTAGTTTGATTTATAAGAAGTAATACTTCCTTGCACAGGCCCCATGGCACATATATTC
TGTATCGTACATGTTTTAATGTCATAAATTAGGTAGTGAGCTGGTACAAGTAAGGATAAATGCTGAAAT

FIG. 6

>human CFTR intron 4, exon 5, intron 5 region (SEQ ID NO: 133)
CCTTTACTTAATAATGAATGCATAATAACTGAATTAGTCATATATTATAATTTTACTTATAATATATTTGTA
TTTTGTTTGTTGAAATTATCTAACTTTCCATTTTCTTTTAGACTTTAAGCTGTCAAGCCGTGTTCTAG
ATAAATAAGTATTGGACAACTTGTGTAGTCTCCTTTCCAACAACCTGAACAAATTTGATGAAGTATGTAC
CTATTGATTAATCTTTTAGGCACTATTGTTATAAATTATACAACTGGAAAGGCGGAGTTTTCCTGGGTC
AGATAATAGTAATTAGTGGT

FIG. 7

>human CFTR intron 6, exon 7, intron 7 region (SEQ ID NO: 134)
TTGAATAAAAGAAATATGACTTAAAACCTTGAGCAGTTCTTAATAGATAATTGACTTGTTTTACTATT
AGATTGATTGATTGATTGATTACAGAGATCAGAGCTGGGAAGATCAGTGAAAGACTTGT
GATTACCCTCAGAAATGATTGAAATATCCAATCTGTTAAGGCATCTGCTGGGAAGAAGCAATGAAAAA
ATGATTGAAAACTTAAGACAGTAAGTTGTTCCAATAATTTCAATATTGTTAGTAATTCTGTCCTTAATTT
TTTAAAAATATGTTTATCAT

FIG. 8

>human CFTR intron 8, exon 9, intron 9 region (SEQ ID NO: 135)
ATTATTAAAATTCATATATAAGATATAAGAGTAGCACAATGAGAGTATAAAGTAGATGTAATAATGCATTAATGCT
ATTCTGATTCTATAATATGTTTTTGCTCTCTTTATAAATAGGATTTCTTACAAAGCAAGAATATAAGA
CATTGGAATATAACTTAACGACTACAGAAGTAGTGATGGAGAATGAACAGCCTTCTGGGAGGTCAG
AATTTTAAAAAATTGTTTGCTCTAAACACCTAACTGTTTCTTCTTTGTGAATATGGATTTCATCCTAA
TGGCGAATAAAATTAGAATG

FIG. 9

>human CFTR intron 9, exon 10, intron 10 region (SEQ ID NO: 136)
GCATCTATTGAAAATATCTGACAACTCATCTTTATTTTTGATGTGTGTGTGTGTGTGTTTT
TTAACAGGGATTTGGGAATTATTTGAGAAGCAAACAATAACAATAGAAAACTTCTAATGGT
GATGACAGCCTCTTCTTCAGTAATTTCTCACTTCTTGTACTCCTGTCCTGAAAGATATTCAAGA
TAGAAAGAGGACAGTTGTTGGCGGTTGCTGGATCCACTGGAGCAGGCAAGTAGTTCTTTTGTTCTTCAC
TATTAAGAACTTAATTTGGTGTCCATGTCTCTTTTTTTCTAGTTTGTAGTGCTGGAAGGTATTTTGG
AGAAATTCTT

FIG. 10

>human CFTR intron 10, exon 11, intron 11 region (SEQ ID NO: 137)
CAAATAAGAATATACACTTCTGCTTAGGATGATAATTGGAGGCAAGTGAATCCTGAGCGTGATTTGATAA
TGACCTAATAATGATGGGTTTTATTTCCAG**ACTTCACTTCTAATGGTGATTATGGGAGAACTGGAGCCTT
CAGAGGGTAAAATTAAGCACAGTGGAAGAATTCATTCTGTTCTCAGTTTTCCTGGATTATGCCTGGCAC
CATTAAAGAAATATCATCTTTGGTGTTTCCTATGATGAATATAGATACAGAAGCGTCATCAAAGCATGC
CAACTAGAAGAG**GTAAGAACTATGTGAAAACTTTTGATTATGCATATGAACCCTTCACACTACCCAAA
TTATATATTTGGCTCCATATTCAATCGGTTAGTCTACACATATATTTATGTTTCCTCTATGGGTAAGCTACT

FIG. 11

>human CFTR intron 12, exon 13, intron 13 region (SEQ ID NO: 138)
CATGTAGTGAACTGTTGAAGCAAATCATCTACACTAGATGACCAGGAAATAGAGAGGAAATGTAATTTA
ATTTCCATTTTCTTTTTAGAGCCAGTATACAAAGATGCTGATTTGTATTTATTAGACTCTCCTTTTGGATA
CCTAGATGTTTTAACAGAAAAGAAATATTTGAAAGGTATGTTCTTTGAATACCTTACTTATAATGCTCA
TGCTAAAATAAAAGAAAGACAGACTGTCCC

FIG. 12

>human CFTR intron 14, exon 15, intron 15 region (SEQ ID NO: 139)
GATTCAAGTAAGTAATACTATTCTTTTTATTTCATATATTAAAAATAAAACCACAATGGTGCATGAAACTGTA
CTGTCTTATTGTAATAGCCATAATTCTTTTATTCAGGAGTGCTTTTTGATGATAGGAGCATACCAG
CAGTGACTACATGGAACACATACCTTCGATATATTACTGTCCACAAGAGCTTAATTTTGTGCTAATTG
GTGCTTAGTAATTTTTCTGGCAGAGGTAAGAAGTGTTCTATTGTAAGTATTACTGGATTTAAAGTTAAAT
TAAGATAGTTTGGGGATGTA

FIG. 13

>human CFTR intron 15, exon 16, intron 16 region (SEQ ID NO: 140)
GTGATGTGAATTTAGATGTGGGCATGGAAGGAATAGGTGAAGATGTTAGAAAAATCAACTGTGTCTT
GTTCCATTCCAGGTGGCTGCTTCTTTGTTTGTTGCTGTCGCTCCTTGGAAAGTGAGTATTCCATGTCCTAT
TGTGTAGATTGTGTTTATTTCTGTTGATTAAATATTGTA

FIG. 14

>human CFTR intron 19, exon 20, intron 20 region (SEQ ID NO: 141)
TTTCAGGTACAAGATATTATGAAATTACATTTTGTGTTTATGTTATTTGCAATGTTTTCTATGGAAATAT
TTCACAGGCAGGAGTCCAATTTTCACTCATCTTGTTACAAGCTTAAAAGGACTATGGACACTTCGTGCCT
TCGGACGGCAGCCTTACTTTGAAACTCTGTTCCACAAGCTCTGAATTTACATACTGCCAACTGGTTCTT
GTACCTGTCAACACTGCGCTGGTTCCAAATGAGAATAGAAATGATTTTTGTCATCTTCTTCATTGCTGTT
ACCTTCATTTCCATTTTAACAACAGTACTATGAACTCATTAACTTTAGCTAAGCATTTAAGTAAAAAAT
TTTCAATGAATAAAATGCTGCATTCTATAGGTTATCAATTTTTGATATCTTTAGAGTTTAGTAATTAACA

FIG. 15

```
>human CFTR intron 21, exon 22, intron 22 region (SEQ ID NO: 142)
TAACCAAGTGACAAGTGTTGCAAGTGTTGCATTTTACAAGTTATTTTTAGGAAGCATCAAACTAATTGTGA
AATTGTCTGCCATTCTTAAAAACAAAATGTTGTTATTTTTATTTCAGATGCGATCTGTGAGCCGAGTCT
TTAAGTTCATTGACATGCCAACAGAAGTAAACCTACCAAGTCAACCATACAAGAATGCCAACT
CTCGAAAGTTATGATTATTGAGAATTCACACGTGAAAGATGACATCTGCCCTCAGGGGCCAAATG
ACTGTCAAAGATCTCACAGACAAATACACAGAAGGTGGAAATGCCATATTAGAGAACATTTCCTCTCAA
TAAGTCCTGGCCAGAGGTGAGATTTGAACACTGCTTGTTGTTCAGTAAGTGAATCCC
AGTAGCCTGAAGCAATGTGTTAGCAGAATCTATTGTAACATTATTATTGAAATTTAATTTGCAGAGTCCTGAACCTAT
ACACACATGTTTATTATATGGAGTCATTATTTTAATATGAAATTTAATTTGCAGAGTCCTGAACCTAT
ATAAATGGGTTTATTTTAAATGTGATTGTACTTGCAGAATA
```

FIG. 16

>human CFTR intron 22, exon 23, intron 23 region (SEQ ID NO: 143)
TTCCAATGGTTTTATTGAAGTACAATACTGAATTATGTTTATGGCATGGTACCTATATGTCACAGAAGT
GATCCCATCACTTTTACCTTATAGGTGGGCCTCTTGGGAAGAACTGGAATCAGGAAGAGTACTTTGTTAT
CAGCTTTTTGAGACTACTGAACACTGAAGGAGAAATCCAGATCGAGGTGTGTCTTGGATTCAATAAC
TTTGCAACAGTGGAGGAAAGCCTTTGAGTGATACCACAGGTGAGCAAAAGGACTTAGCAGAAAAAGG
CAACTAAATTATATTTTTTACTGCTATTTGATACTTGTACTCAAGAAATTCATATTACTCTGCAAAATAT
ATTTGTTATG

FIG. 17

>human CFTR intron 23, exon 24, intron 24 region (SEQ ID NO: 144)
GGGTGTTTCTTATTTTAAAATAATTTTTCTACTTGAAATATTTTACAATACAATAAGGGAAAAATAAAAA
GTTATTAAGTTATTCATACTTTCTTCTTTTCTTTTTTGCTATAGAAAAGTATTTATTTTTCTGAA
CATTTAGAAAACTTGGATCCCTATGAACAGTGGAGTGATCAAGAAATCAAGATTGCAGATGAGT
AAGGCTGCTAACTGAAATGATTTTGAAAGGGGTAACTCATACCAACACAAATGCTGATATAGCTGACAT
CATTCTACACACTTTGTGTGCATGTATGTGTGCACAACTTTAAAATGGAGTACCCTAACATACCTGGA
GCAACAGGTA

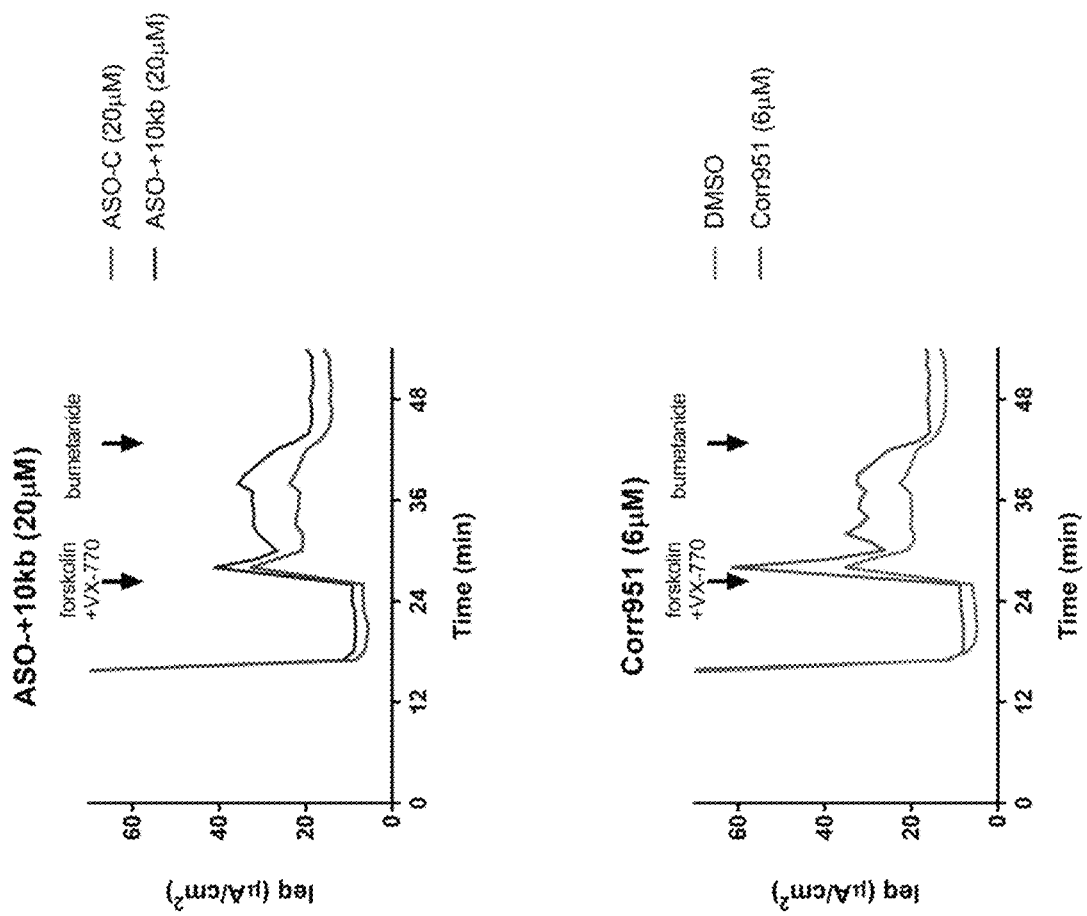

ANTISENSE COMPOUNDS TARGETING GENES ASSOCIATED WITH CYSTIC FIBROSIS

CROSS REFERENCE TO RELATED APPLICATIONS

This application is a continuation of U.S. application Ser. No. 15/835,698, filed Dec. 8, 2017 (now U.S. Pat. No. 10,525,076), which is a continuation-in-part of U.S. application Ser. No. 15/045,999, filed Feb. 17, 2016 (now U.S. Pat. No. 9,840,709), which is a non-provisional application of U.S. Provisional Application No. 62/118,794, filed Feb. 20, 2015, the disclosures of which each of which are incorporated by reference in their entirety.

SEQUENCE LISTING

The sequence listing submitted herewith is incorporated by reference in its entirety.

FIELD OF THE DISCLOSURE

The present disclosure relates generally to compounds comprising oligonucleotides complementary to a cystic fibrosis transmembrane conductance regulator (CFTR) RNA transcript. Certain such compounds are useful for hybridizing to a CFTR transcript, including but not limited to a CFTR RNA transcript in a cell. In certain embodiments, such hybridization results in modulation of splicing of the CFTR transcript. In certain embodiments, such compounds are used to treat one or more symptoms associated with Cystic Fibrosis.

BACKGROUND OF THE DISCLOSURE

Cystic fibrosis (CF), also known as mucoviscidosis, is a genetic disorder that affects mostly the lungs, but also the pancreas, liver, kidneys, and intestine. Long-term issues include difficulty breathing and coughing up mucus as a result of frequent lung infections. Other signs and symptoms include sinus infections, poor growth, fatty stool, clubbing of the fingers and toes, and infertility in males among others. Different people may have different degrees of symptoms.

CF is inherited in an autosomal recessive manner. It is caused by the presence of mutations in both copies of the gene for the cystic fibrosis transmembrane conductance regulator (CFTR) protein. Those with a single working copy are carriers and otherwise mostly normal. CFTR is involved in production of sweat, digestive fluids, and mucus. When CFTR is not functional, secretions, which are usually thin, instead become thick. The condition is diagnosed by a sweat test and genetic testing. Screening of infants at birth takes place in some areas of the world.

There is no cure for cystic fibrosis. Lung infections are treated with antibiotics which may be given intravenously, inhaled, or by mouth. Sometimes the antibiotic azithromycin is used long term. Inhaled hypertonic saline and salbutamol may also be useful. Lung transplantation may be an option if lung function continues to worsen. Pancreatic enzyme replacement and fat-soluble vitamin supplementation are important, especially in the young. The average life expectancy is between 42 and 50 years in the developed world. While CF is a multi-organ disease, lung problems are the dominant cause of morbidity and mortality. Other CF symptoms include pancreatic insufficiency, intestinal obstruction, elevated electrolyte levels in sweat (the basis of the most common diagnostic test), and male infertility. CF is most common among people of Northern European ancestry and affects about one out of every 2,500 to 4,000 newborns. About one in 25 people are carriers. While treatments for Cystic Fibrosis are available, more effective therapies are needed.

SUMMARY OF THE DISCLOSURE

The present disclosure relates to general compounds and methods to treat cystic fibrosis in subjects using antisense oligonucleotides (ASOs) that induce specific pre-mRNA splicing events in CFTR gene transcripts that result in mRNAs that code for proteins that fully or partially restore the function of CFTR (i.e., resulting in increased levels of correctly localized CFTR protein at the plasma membrane and with increased function).

In one aspect, the disclosure provides a compound comprising a modified oligonucleotide having 8 to 30 linked nucleosides having a nucleobase sequence comprising a complementary region, wherein the complementary region comprises at least 8 contiguous nucleobases complementary to an equal-length portion of a target region of a cystic fibrosis transmembrane conductance regulator (CFTR) transcript. In certain embodiments, the target region of the CFTR transcript comprises at least a portion of intron 1, exon 2, intron 2, intron 3, exon 4, intron 4, exon 5, intron 6, exon 7, intron 7, exon 9, intron 9, exon 10, intron 10, exon 11, intron 11, intron 12, exon 13, intron 13, intron 14, exon 15, intron 15, exon 16, intron 16, intron 19, exon 20, intron 20, intron 21, exon 22, intron 22, exon 23, intron 23, exon 24 or intron 24 of the CFTR transcript. In other embodiments, the nucleobase sequence of the antisense oligonucleotide comprises any one of SEQ ID NOs: 1 to 144, or SEQ ID NO:150.

In another aspect, the disclosure provides a pharmaceutical composition comprising at least one compound as described herein and a pharmaceutically acceptable carrier or diluent.

In yet another aspect, the disclosure provides a method of modulating splicing or expression of a CFTR transcript in a cell comprising contacting the cell with at least one compound as described herein.

The yet another aspect, the disclosure provides a method of treating cystic fibrosis, comprising administering at least one compound as described herein to an animal in need thereof.

The present disclosure provides the following non-limiting numbered embodiments:

Embodiment 1

A compound comprising a modified oligonucleotide consisting of 8 to 30 linked nucleosides and having a nucleobase sequence comprising a complementary region, wherein the complementary region comprises at least 8 contiguous nucleobases complementary to an equal-length portion of a target region of a cystic fibrosis transmembrane conductance regulator (CFTR) transcript.

Embodiment 2

The compound of embodiment 1, wherein the target region of the CFTR transcript comprises at least a portion of intron 1, exon 2, intron 2, intron 3, exon 4, intron 4, exon 5, intron 6, exon 7, intron 7, exon 9, intron 9, exon 10, intron 10, exon 11, intron 11, intron 12, exon 13, intron 13, intron 14, exon 15, intron 15, exon 16, intron 16, intron 19, exon 20, intron 20, intron 21, exon 22, intron 22, exon 23, intron 23, exon 24 or intron 24 of the CFTR transcript.

Embodiment 3

The compound of embodiment 1, wherein the target region of the CFTR transcript comprises at least a portion of exon 2 of the CFTR transcript.

Embodiment 4

The compound of embodiment 1, wherein the target region of the CFTR transcript comprises at least a portion of exon 4 of the CFTR transcript.

Embodiment 5

The compound of embodiment 1, wherein the target region of the CFTR transcript comprises at least a portion of exon 5 of the CFTR transcript.

Embodiment 6

The compound of embodiment 1, wherein the target region of the CFTR transcript comprises at least a portion of exon 7 of the CFTR transcript.

Embodiment 7

The compound of embodiment 1, wherein the target region of the CFTR transcript comprises at least a portion of exon 9 of the CFTR transcript.

Embodiment 8

The compound of embodiment 1, wherein the target region of the CFTR transcript comprises at least a portion of exon 10 of the CFTR transcript.

Embodiment 9

The compound of embodiment 1, wherein the target region of the CFTR transcript comprises at least a portion of exon 11 of the CFTR transcript.

Embodiment 10

The compound of embodiment 1, wherein the target region of the CFTR transcript comprises at least a portion of exon 13 of the CFTR transcript.

Embodiment 11

The compound of embodiment 1, wherein the target region of the CFTR transcript comprises at least a portion of exon 15 of the CFTR transcript.

Embodiment 12

The compound of embodiment 1, wherein the target region of the CFTR transcript comprises at least a portion of exon 16 of the CFTR transcript.

Embodiment 13

The compound of embodiment 1, wherein the target region of the CFTR transcript comprises at least a portion of exon 20 of the CFTR transcript.

Embodiment 14

The compound of embodiment 1, wherein the target region of the CFTR transcript comprises at least a portion of exon 22 of the CFTR transcript.

Embodiment 15

The compound of embodiment 1, wherein the target region of the CFTR transcript comprises at least a portion of exon 23 of the CFTR transcript.

Embodiment 16

The compound of embodiment 1, wherein the target region of the CFTR transcript comprises at least a portion of exon 24 of the CFTR transcript.

Embodiment 17

The compound of any of embodiments 1 to 16, wherein the complementary region of the modified oligonucleotide is at least 80%, at least 85%, at least 90%, at least 95% or at least 100% complementary to the target region.

Embodiment 18

The compound of any of embodiments 1 to 17, wherein the complementary region of the modified oligonucleotide comprises at least 10 contiguous nucleobases.

Embodiment 19

The compound of any of embodiments 1 to 17, wherein the complementary region of the modified oligonucleotide comprises at least 12 contiguous nucleobases.

Embodiment 20

The compound of any of embodiments 1 to 17, wherein the complementary region of the modified oligonucleotide comprises at least 14 contiguous nucleobases.

Embodiment 21

The compound of any of embodiments 1 to 17, wherein the complementary region of the modified oligonucleotide comprises at least 15 contiguous nucleobases.

Embodiment 22

The compound of any of embodiments 1 to 17, wherein the complementary region of the modified oligonucleotide comprises at least 16 contiguous nucleobases.

Embodiment 23

The compound of any of embodiments 1 to 17, wherein the complementary region of the modified oligonucleotide comprises at least 17 contiguous nucleobases.

Embodiment 24

The compound of any of embodiments 1 to 17, wherein the complementary region of the modified oligonucleotide comprises at least 18 contiguous nucleobases.

Embodiment 25

The compound of any of embodiments 1 to 17, wherein the complementary region of the modified oligonucleotide comprises at least 19 contiguous nucleobases.

Embodiment 26

The compound of any of embodiments 1 to 17, wherein the complementary region of the modified oligonucleotide comprises at least 20 contiguous nucleobases.

Embodiment 27

The compound of any of embodiments 1 to 26, wherein the nucleobase sequence of the oligonucleotide is at least 80% complementary to an equal-length region of the CFTR transcript, as measured over the entire length of the oligonucleotide.

Embodiment 28

The compound of any of embodiments 1 to 26, wherein the nucleobase sequence of the oligonucleotide is at least 90% complementary to an equal-length region of the CFTR transcript, as measured over the entire length of the oligonucleotide.

Embodiment 29

The compound of any of embodiments 1 to 26, wherein the nucleobase sequence of the oligonucleotide is 100% complementary to an equal-length region of the CFTR transcript, as measured over the entire length of the oligonucleotide.

Embodiment 30

The compound of any of embodiments 1-29, wherein the nucleobase sequence of the antisense oligonucleotide comprises any one of SEQ ID NOs: 1 to 144, and SEQ ID NO:150.

Embodiment 31

The compound of any of embodiments 1-30, wherein the modified oligonucleotide comprises at least one modified nucleoside.

Embodiment 32

The compound of embodiment 31, wherein at least one modified nucleoside comprises a modified sugar moiety.

Embodiment 33

The compound of embodiment 32, wherein at least one modified sugar moiety is a 2'-substituted sugar moiety.

Embodiment 34

The compound of embodiment 33, wherein the 2'-substitutent of at least one 2'-substituted sugar moiety is selected from among: 2'-OMe, 2'-F, and 2'-MOE.

Embodiment 35

The compound of any of embodiments 31-34, wherein the 2'-substituent of at least one 2'-substituted sugar moiety is a 2'-MOE.

Embodiment 36

The compound of any of embodiments 1-47, wherein at least one modified sugar moiety is a bicyclic sugar moiety.

Embodiment 37

The compound of embodiment 36, wherein at least one bicyclic sugar moiety is LNA or cEt.

Embodiment 38

The compound of any of embodiments 1-37, wherein at least one sugar moiety is a sugar surrogate.

Embodiment 39

The compound of embodiment 38, wherein at least one sugar surrogate is a morpholino.

Embodiment 40

The compound of embodiment 38, wherein at least one sugar surrogate is a modified morpholino.

Embodiment 41

The compound of any of embodiments 1-40, wherein the modified oligonucleotide comprises at least 5 modified nucleosides, each independently comprising a modified sugar moiety.

Embodiment 42

The compound of embodiment 41, wherein the modified oligonucleotide comprises at least 10 modified nucleosides, each independently comprising a modified sugar moiety.

Embodiment 43

The compound of embodiment 41, wherein the modified oligonucleotide comprises at least 15 modified nucleosides, each independently comprising a modified sugar moiety.

Embodiment 44

The compound of embodiment 41, wherein each nucleoside of the modified oligonucleotide is a modified nucleoside, each independently comprising a modified sugar moiety

Embodiment 45

The compound of any of embodiments 1-44, wherein the modified oligonucleotide comprises at least two modified nucleosides comprising modified sugar moieties that are the same as one another.

Embodiment 46

The compound of any of embodiments 1-44, wherein the modified oligonucleotide comprises at least two modified nucleosides comprising modified sugar moieties that are different from one another.

Embodiment 47

The compound of any of embodiments 1-46, wherein the modified oligonucleotide comprises a modified region of at least 5 contiguous modified nucleosides.

Embodiment 48

The compound of any of embodiments 1 to 47, wherein the modified oligonucleotide comprises a modified region of at least 10 contiguous modified nucleosides.

Embodiment 49

The compound of any of embodiments 1 to 48, wherein the modified oligonucleotide comprises a modified region of at least 15 contiguous modified nucleosides.

Embodiment 50

The compound of any of embodiments 1 to 48, wherein the modified oligonucleotide comprises a modified region of at least 20 contiguous modified nucleosides.

Embodiment 51

The compound of any of embodiments 45 to 50, wherein each modified nucleoside of the modified region has a modified sugar moiety independently selected from among: 2'-F, 2'-OMe, 2'-MOE, cEt, LNA, morpholino, and modified morpholino.

Embodiment 52

The compound of any of embodiments 45 to 51 wherein the modified nucleosides of the modified region each comprise the same modification as one another.

Embodiment 53

The compound of embodiment 52, wherein the modified nucleosides of the modified region each comprise the same 2'-substituted sugar moiety.

Embodiment 54

The compound of embodiment 52, wherein the 2'-substituted sugar moiety of the modified nucleosides of the region of modified nucleosides is selected from 2'-F, 2'-OMe, and 2'-MOE.

Embodiment 55

The compound of embodiment 54, wherein the 2'-substituted sugar moiety of the modified nucleosides of the region of modified nucleosides is 2'-MOE.

Embodiment 56

The compound of embodiment 52, wherein the modified nucleosides of the region of modified nucleosides each comprise the same bicyclic sugar moiety.

Embodiment 57

The compound of embodiment 56, wherein the bicyclic sugar moiety of the modified nucleosides of the region of modified nucleosides is selected from LNA and cEt.

Embodiment 58

The compound of embodiment 50, wherein the modified nucleosides of the region of modified nucleosides each comprises a sugar surrogate.

Embodiment 59

The compound of embodiment 58, wherein the sugar surrogate of the modified nucleosides of the region of modified nucleosides is a morpholino.

Embodiment 60

The compound of embodiment 59, wherein the sugar surrogate of the modified nucleosides of the region of modified nucleosides is a modified morpholino.

Embodiment 61

The compound of any of embodiments 1 to 60, wherein the modified nucleotide comprises no more than 4 contiguous naturally occurring nucleosides.

Embodiment 62

The compound of any of embodiments 1 to 61, wherein each nucleoside of the modified oligonucleotide is a modified nucleoside.

Embodiment 63

The compound of embodiment 62, wherein each modified nucleoside comprises a modified sugar moiety.

Embodiment 64

The compound of embodiment 63, wherein the modified nucleosides of the modified oligonucleotide comprise the same modification as one another.

Embodiment 65

The compound of embodiment 64, wherein the modified nucleosides of the modified oligonucleotide each comprise the same 2'-substituted sugar moiety.

Embodiment 66

The compound of embodiment 65, wherein the 2'-substituted sugar moiety of the modified oligonucleotide is selected from 2'-F, 2'-OMe, and 2'-MOE.

Embodiment 67

The compound of embodiment 65, wherein the 2'-substituted sugar moiety of the modified oligonucleotide is 2'-MOE.

Embodiment 68

The compound of embodiment 64, wherein the modified nucleosides of the modified oligonucleotide each comprise the same bicyclic sugar moiety.

Embodiment 69

The compound of embodiment 68, wherein the bicyclic sugar moiety of the modified oligonucleotide is selected from LNA and cEt.

Embodiment 70

The compound of embodiment 64, wherein the modified nucleosides of the modified oligonucleotide each comprises a sugar surrogate.

Embodiment 71

The compound of embodiment 70, wherein the sugar surrogate of the modified oligonucleotide is a morpholino.

Embodiment 72

The compound of embodiment 70, wherein the sugar surrogate of the modified oligonucleotide is a modified morpholino.

Embodiment 73

The compound of any of embodiments 1 to 72, wherein the modified oligonucleotide comprises at least one modified internucleoside linkage.

Embodiment 74

The compound of embodiment 73, wherein each internucleoside linkage is a modified internucleoside linkage.

Embodiment 75

The compound of embodiment 73 or 74, comprising at least one phosphorothioate internucleoside linkage.

Embodiment 76

The compound of embodiment 73, wherein each internucleoside linkage is a modified internucleoside linkage and wherein each internucleoside linkage comprises the same modification.

Embodiment 77

The compound of embodiment 76, wherein each internucleoside linkage is a phosphorothioate internucleoside linkage.

Embodiment 78

The compound of any of embodiments 1 to 77, comprising at least one conjugate.

Embodiment 79

The compound of any of embodiments 1 to 78, consisting of the modified oligonucleotide.

Embodiment 80

The compound of any of embodiments 1 to 79, wherein the compound modulates splicing of the CFTR transcript.

Embodiment 81

The compound of any of embodiments 1 to 80, having a nucleobase sequence comprising any of the sequences as set forth in SEQ ID Nos: 1 to 144, and SEQ ID NO:150.

Embodiment 82

The compound of any of embodiments 1 to 81, having a nucleobase sequence comprising any of the sequences as set forth in SEQ ID Nos: 64, 65, 66, 71, 76, 78, 79, 81, 82, 84, 91, 92, 93, 94, 102, 111, 116, 117, 120, 122, 127, 128 or 129.

Embodiment 83

The compound of any of embodiments 1 to 81, having a nucleobase sequence comprising any of the sequences as set forth in SEQ ID Nos: 1, 4, 8, 9, 10, 12, 13, 17, 18, 19, 20, 22, 23, 24, 26, 27, 36, 37, 38, 42, 43, 44, 47, 48, 49, 50, 53, 55, 57, 59 or 60.

Embodiment 84

The compound of any of embodiment 82, having a nucleobase sequence comprising SEQ ID NO. 91, 97, 99, 100, 103, 104, 110, 114, 126, 127, 128, 129, or 150.

Embodiment 85

A pharmaceutical composition comprising a compound according to any of embodiments 1-84 and a pharmaceutically acceptable carrier or diluent.

Embodiment 86

The pharmaceutical composition of embodiment 85, wherein the pharmaceutically acceptable carrier or diluent is sterile saline.

Embodiment 87

A method of modulating splicing of a CFTR transcript in a cell comprising contacting the cell with a compound according to any of embodiments 1-86.

Embodiment 88

The method of embodiment 87, wherein the cell is in vitro.

Embodiment 89

The method of embodiment 87, wherein the cell is in an animal.

Embodiment 90

The method of any of embodiments 87 to 89, wherein the amount of CFTR mRNA without exon 11 is increased.

Embodiment 91

The method of any of embodiments 87 to 89, wherein the amount of CFTR mRNA without exon 16 is increased.

Embodiment 92

The method of any of embodiments 87 to 89, wherein the amount of CFTR mRNA with exon 23 or exon 24 is increased.

Embodiment 93

The method of any of embodiments 87 to 92, wherein the CFTR transcript is transcribed from a CFTR gene.

Embodiment 94

A method of modulating the expression of CFTR in a cell, comprising contacting the cell with a compound according to any of embodiments 1-86.

Embodiment 95

The method of embodiment 94, wherein the cell is in vitro.

Embodiment 96

The method of embodiment 94, wherein the cell is in an animal.

Embodiment 97

A method comprising administering the compound according to any of embodiments 1-84 or the pharmaceutical composition of embodiments 85 or 86 to an animal.

Embodiment 98

The method of embodiment 97, wherein the administering step comprises delivering to the animal by inhalation, parenteral injection or infusion, oral, subcutaneous or intramuscular injection, buccal, transdermal, transmucosal and topical.

Embodiment 99

The method of embodiment 98, wherein the administration is by inhalation.

Embodiment 100

The method of any of embodiments 97-99, wherein the animal has one or more symptoms associated with cystic fibrosis.

Embodiment 101

The method of any of embodiments 97-99, wherein the administration results in amelioration of at least one symptom of cystic fibrosis.

Embodiment 102

The method of any of embodiments 97-101, wherein the animal is a mouse.

Embodiment 103

The method of any of embodiments 97-101, wherein the animal is a human.

Embodiment 104

A method of treating cystic fibrosis, comprising administering the compound according to any of embodiments 1-84 or the pharmaceutical composition of embodiments 85 or 86 to an animal in need thereof.

Embodiment 105

Use of the compound according to any of embodiments 1-84 or the pharmaceutical composition of embodiments 85 or 86 for the preparation of a medicament for use in the treatment of cystic fibrosis.

Embodiment 106

Use of the compound according to any of embodiments 1-84 or the pharmaceutical composition of embodiments 85 or 86 for the preparation of a medicament for use in the amelioration of one or more symptoms associated with cystic fibrosis.

Embodiment 107

A compound comprising a modified oligonucleotide consisting of 8 to 30 linked nucleosides and having a nucleobase sequence comprising a complementary region, wherein the complementary region comprises at least 8 contiguous nucleobases complementary to an equal-length portion of a target region of a CFTR transcript.

Embodiment 108

The compound of embodiment 107, wherein the CFTR transcript comprises the nucleobase sequence of SEQ ID No. 130.

Embodiment 109

The compound of embodiment 107 or 108, wherein the complementary region of the modified oligonucleotide is 100% complementary to the target region.

Embodiment 110

The compound of any of embodiments 107-109, wherein the complementary region of the modified oligonucleotide comprises at least 10 contiguous nucleobases.

Embodiment 111

The compound of any of embodiments 107-109, wherein the complementary region of the modified oligonucleotide comprises at least 12 contiguous nucleobases.

Embodiment 112

The compound of any of embodiments 107-109, wherein the complementary region of the modified oligonucleotide comprises at least 14 contiguous nucleobases.

Embodiment 113

The compound of any of embodiments 107-109, wherein the complementary region of the modified oligonucleotide comprises at least 15 contiguous nucleobases.

Embodiment 114

The compound of any of embodiments 107-109, wherein the complementary region of the modified oligonucleotide comprises at least 16 contiguous nucleobases.

Embodiment 115

The compound of any of embodiments 107-109, wherein the complementary region of the modified oligonucleotide comprises at least 17 contiguous nucleobases.

Embodiment 116

The compound of any of embodiments 107-109, wherein the complementary region of the modified oligonucleotide comprises at least 18 contiguous nucleobases.

Embodiment 117

The compound of any of embodiments 107-116, wherein the nucleobase sequence of the modified oligonucleotide is at least 80% complementary to an equal-length region of the CFTR transcript, as measured over the entire length of the oligonucleotide.

Embodiment 118

The compound of any of embodiments 107-116, wherein the nucleobase sequence of the modified oligonucleotide is at least 90% complementary to an equal-length region of the CFTR transcript, as measured over the entire length of the oligonucleotide.

Embodiment 119

The compound of any of embodiments 107-116, wherein the nucleobase sequence of the modified oligonucleotide is 100% complementary to an equal-length region of the CFTR transcript, as measured over the entire length of the oligonucleotide.

Embodiment 120

The compound of any of embodiments 107-119, wherein the target region is within intron 1, exon 2, intron 2, intron 3, exon 4, intron 4, exon 5, intron 6, exon 7, intron 7, exon 9, intron 9, exon 10, intron 10, exon 11, intron 11, intron 12, exon 13, intron 13, intron 14, exon 15, intron 15, exon 16, intron 16, intron 19, exon 20, intron 20, intron 21, exon 22, intron 22, exon 23, intron 23, exon 24 or intron 24 of human CFTR.

Embodiment 121

The compound of embodiment 120, wherein the target region is within exon 11 of human CFTR.

Embodiment 122

The compound of embodiment 120, wherein the target region is within exon 23 or exon 24 of human CFTR.

Embodiment 123

The compound of any of embodiments 107-119, wherein the target region is within intron 1, exon 2, intron 2, intron 3, exon 4, intron 4, exon 5, intron 6, exon 7, intron 7, exon 9, intron 9, exon 10, intron 10, exon 11, intron 11, intron 12, exon 13, intron 13, intron 14, exon 15, intron 15, exon 16, intron 16, intron 19, exon 20, intron 20, intron 21, exon 22, intron 22, exon 23, intron 23, exon 24 or intron 24 of mouse CFTR.

Embodiment 124

The compound of any of embodiments 107-119, wherein the modified oligonucleotide has a nucleobase sequence comprising any of the sequences as set forth in SEQ ID NOs: 1-144, and SEQ ID NO:150.

Embodiment 125

The compound of any of embodiments 107-119, wherein the modified oligonucleotide has a nucleobase sequence consisting of the nucleobase sequence of any one of SEQ ID NOs: 1-144, and SEQ ID NO:150.

Embodiment 126

The compound of any of embodiments 107-119, wherein the modified oligonucleotide has a nucleobase sequence comprising the nucleobase sequence of SEQ ID NO. 64, 65, 66, 71, 76, 78, 79, 81, 82, 84, 91, 92, 93, 94, 97, 99, 100, 102, 103, 104, 111, 114, 116, 117, 120, 122, 127, 128, 129, or 150.

Embodiment 127

The compound of embodiment 125, wherein the modified oligonucleotide has a nucleobase sequence consisting of the nucleobase sequence of SEQ ID NO. 64, 65, 66, 71, 76, 78, 79, 81, 82, 84, 91, 92, 93, 94, 97, 99, 100, 102, 103, 104, 111, 114, 116, 117, 120, 122, 127, 128, 129, or 150.

Embodiment 128

The compound of any of embodiments 107-119, wherein the modified oligonucleotide has a nucleobase sequence comprising the nucleobase sequence of SEQ ID NO. 91, 97, 99, 100, 103, 104, 110, 114, 126, 127, 128, 129, or 150.

Embodiment 129

The compound of embodiment 125, wherein the modified oligonucleotide has a nucleobase sequence consisting of the nucleobase sequence of SEQ ID NO. 91, 97, 99, 100, 103, 104, 110, 114, 126, 127, 128, 129, or 150.

Embodiment 130

The compound of any of embodiments 107-129, wherein the modified oligonucleotide comprises at least one modified nucleoside.

Embodiment 131

The compound of any of embodiments 107-130, wherein each nucleoside of the modified oligonucleotide is a modified nucleoside selected from among: 2'-OMe, 2'-F, and 2'-MOE or a sugar surrogate.

Embodiment 132

The compound of embodiment 132, wherein the modified nucleoside is 2'-MOE.

Embodiment 133

The compound of embodiment 132, wherein the modified nucleoside is a morpholino.

Embodiment 134

The compound of embodiment 131, wherein at least one modified nucleoside comprises a modified sugar moiety.

Embodiment 135

The compound of embodiment 134, wherein at least one modified sugar moiety is a 2'-substituted sugar moiety.

Embodiment 136

The compound of embodiment 135, wherein the 2'-substitutent of at least one 2'-substituted sugar moiety is selected from among: 2'-OMe, 2'-F, and 2'-MOE.

Embodiment 137

The compound of any of embodiments 135-136, wherein the 2'-substituent of at least one 2'-substituted sugar moiety is a 2'-MOE.

Embodiment 138

The compound of any of embodiments 107-137, wherein at least one modified sugar moiety is a bicyclic sugar moiety.

Embodiment 139

The compound of embodiment 138, wherein at least one bicyclic sugar moiety is LNA or cEt.

Embodiment 140

The compound of any of embodiments 107-139, wherein at least one sugar moiety is a sugar surrogate.

Embodiment 141

The compound of embodiment 140, wherein at least one sugar surrogate is a morpholino.

Embodiment 142

The compound of embodiment 141, wherein at least one sugar surrogate is a modified morpholino.

Embodiment 143

The compound of any of embodiments 107-142, wherein the modified oligonucleotide comprises at least 5 modified nucleosides, each independently comprising a modified sugar moiety.

Embodiment 144

The compound of any of embodiments 107-143, wherein the modified oligonucleotide comprises at least 10 modified nucleosides, each independently comprising a modified sugar moiety.

Embodiment 145

The compound of any of embodiments 107-143, wherein the modified oligonucleotide comprises at least 15 modified nucleosides, each independently comprising a modified sugar moiety.

Embodiment 146

The compound of any of embodiments 107-143, wherein each nucleoside of the modified oligonucleotide is a modified nucleoside, each independently comprising a modified sugar moiety.

Embodiment 147

The compound of any of embodiments 107-146, wherein the modified oligonucleotide comprises at least two modified nucleosides comprising modified sugar moieties that are the same as one another.

Embodiment 148

The compound of any of embodiments 107-146, wherein the modified oligonucleotide comprises at least two modified nucleosides comprising modified sugar moieties that are different from one another.

Embodiment 149

The compound of any of embodiments 107-148, wherein the modified oligonucleotide comprises a modified region of at least 5 contiguous modified nucleosides.

Embodiment 150

The compound of any of embodiments 107-148, wherein the modified oligonucleotide comprises a modified region of at least 10 contiguous modified nucleosides.

Embodiment 151

The compound of any of embodiments 107-148, wherein the modified oligonucleotide comprises a modified region of at least 15 contiguous modified nucleosides.

Embodiment 152

The compound of any of embodiments 107-148, wherein the modified oligonucleotide comprises a modified region of at least 16 contiguous modified nucleosides.

Embodiment 153

The compound of any of embodiments 107-148, wherein the modified oligonucleotide comprises a modified region of at least 17 contiguous modified nucleosides.

Embodiment 154

The compound of any of embodiments 107-148, wherein the modified oligonucleotide comprises a modified region of at least 18 contiguous modified nucleosides.

Embodiment 155

The compound of any of embodiments 107-148, wherein the modified oligonucleotide comprises a modified region of at least 20 contiguous modified nucleosides.

Embodiment 156

The compound of any of embodiments 149-155, wherein each modified nucleoside of the modified region has a modified sugar moiety independently selected from among: 2'-F, 2'-OMe, 2'-MOE, cEt, LNA, morpholino, and modified morpholino.

Embodiment 157

The compound of any of embodiments 149-156, wherein the modified nucleosides of the modified region each comprise the same modification as one another.

Embodiment 158

The compound of embodiment 157, wherein the modified nucleosides of the modified region each comprise the same 2'-substituted sugar moiety.

Embodiment 159

The compound of embodiment 157, wherein the 2'-substituted sugar moiety of the modified nucleosides of the region of modified nucleosides is selected from 2'-F, 2'-OMe, and 2'-MOE.

Embodiment 160

The compound of embodiment 157, wherein the 2'-substituted sugar moiety of the modified nucleosides of the region of modified nucleosides is 2'-MOE.

Embodiment 161

The compound of embodiment 157, wherein the modified nucleosides of the region of modified nucleosides each comprise the same bicyclic sugar moiety.

Embodiment 162

The compound of embodiment 161, wherein the bicyclic sugar moiety of the modified nucleosides of the region of modified nucleosides is selected from LNA and cEt.

Embodiment 163

The compound of embodiment 157, wherein the modified nucleosides of the region of modified nucleosides each comprises a sugar surrogate.

Embodiment 164

The compound of embodiment 163, wherein the sugar surrogate of the modified nucleosides of the region of modified nucleosides is a morpholino.

Embodiment 165

The compound of embodiment 163, wherein the sugar surrogate of the modified nucleosides of the region of modified nucleosides is a modified morpholino.

Embodiment 166

The compound of any of embodiments 107-165, wherein the modified nucleotide comprises no more than 4 contiguous naturally occurring nucleosides.

Embodiment 167

The compound of any of embodiments 107-165, wherein each nucleoside of the modified oligonucleotide is a modified nucleoside.

Embodiment 168

The compound of embodiment 167, wherein each modified nucleoside comprises a modified sugar moiety.

Embodiment 169

The compound of embodiment 168, wherein the modified nucleosides of the modified oligonucleotide comprise the same modification as one another.

Embodiment 170

The compound of embodiment 169, wherein the modified nucleosides of the modified oligonucleotide each comprise the same 2'-substituted sugar moiety.

Embodiment 171

The compound of embodiment 170, wherein the 2'-substituted sugar moiety of the modified oligonucleotide is selected from 2'-F, 2'-OMe, and 2'-MOE.

Embodiment 172

The compound of embodiment 170, wherein the 2'-substituted sugar moiety of the modified oligonucleotide is 2'-MOE.

Embodiment 173

The compound of embodiment 171, wherein the modified nucleosides of the modified oligonucleotide each comprise the same bicyclic sugar moiety.

Embodiment 174

The compound of embodiment 173, wherein the bicyclic sugar moiety of the modified oligonucleotide is selected from LNA and cEt.

Embodiment 175

The compound of embodiment 169, wherein the modified nucleosides of the modified oligonucleotide each comprises a sugar surrogate.

Embodiment 176

The compound of embodiment 175, wherein the sugar surrogate of the modified oligonucleotide is a morpholino.

Embodiment 177

The compound of embodiment 175, wherein the sugar surrogate of the modified oligonucleotide is a modified morpholino.

Embodiment 178

The compound of any of embodiments 107-177, wherein the modified oligonucleotide comprises at least one modified internucleoside linkage.

Embodiment 179

The compound of embodiment 178, wherein each internucleoside linkage is a modified internucleoside linkage.

Embodiment 180

The compound of embodiment 178 or 179, comprising at least one phosphorothioate internucleoside linkage.

Embodiment 181

The compound of embodiment 179, wherein each internucleoside linkage is a modified internucleoside linkage and wherein each internucleoside linkage comprises the same modification.

Embodiment 182

The compound of embodiment 181, wherein each internucleoside linkage is a phosphorothioate internucleoside linkage.

Embodiment 183

The compound of any of embodiments 107-182, comprising at least one conjugate.

Embodiment 184

The compound of any of embodiments 107-183, consisting of the modified oligonucleotide.

Embodiment 185

The compound of any of embodiments 107-184, wherein the compound modulates splicing of the CFTR transcript.

Embodiment 186

A pharmaceutical composition comprising a compound according to any of embodiments 107-186 and a pharmaceutically acceptable carrier or diluent.

Embodiment 187

The pharmaceutical composition of embodiment 186, wherein the pharmaceutically acceptable carrier or diluent is sterile saline.

Embodiment 188

A method of modulating splicing of a CFTR transcript in a cell comprising contacting the cell with a compound according to any of embodiments 107-187.

Embodiment 189

The method of embodiment 188, wherein the cell is in vitro.

Embodiment 190

The method of embodiment 188, wherein the cell is in an animal.

Embodiment 191

The method of any of embodiments 188-190, wherein the amount of CFTR mRNA without exon 4 is increased.

Embodiment 192

The method of any of embodiments 188-190, wherein the amount of CFTR mRNA without exon 16 is increased.

Embodiment 193

The method of any of embodiments 188-190, wherein the amount of CFTR mRNA with exon 23 or exon 24 is increased.

Embodiment 194

The method of any of embodiments 188-193, wherein the CFTR transcript is transcribed from a CFTR gene.

Embodiment 195

A method of modulating the expression of CFTR in a cell, comprising contacting the cell with a compound according to any of embodiments 107-185.

Embodiment 196

The method of embodiment 195, wherein the cell is in vitro.

Embodiment 197

The method of embodiment 195, wherein the cell is in an animal.

Embodiment 198

A method comprising administering the compound of any of embodiments 107-185 to an animal.

Embodiment 199

The method of embodiment 198, wherein the administering step comprises delivering to the animal by inhalation,

Embodiment 200

The method of embodiment 198, wherein the administration is inhalation.

Embodiment 201

The method of any of embodiments 198-200, wherein the animal has one or more symptoms associated with cystic fibrosis.

Embodiment 202

The method of any of embodiments 198-200, wherein the administration results in amelioration of at least one symptom of cystic fibrosis.

Embodiment 203

The method of any of embodiments 198-202, wherein the animal is a mouse.

Embodiment 204

The method of any of embodiments 198-202, wherein the animal is a human.

Embodiment 205

A method of preventing or slowing one or more symptoms associated with cystic fibrosis, comprising administering the compound according to any of embodiments 107-185 to an animal in need thereof.

Embodiment 206

The method of embodiment 205, wherein the animal is a human.

Embodiment 207

Use of the compound according to any of embodiments 107-185 for the preparation of a medicament for use in the treatment of cystic fibrosis.

Embodiment 208

Use of the compound according to any of embodiments 107-185 for the preparation of a medicament for use in the amelioration of one or more symptoms associated with cystic fibrosis.

These and other features and advantages of the present disclosure will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

A better understanding of the disclosure may be obtained in light of the following drawings which are set forth for illustrative purposes, and should not be construed as limiting the scope of the disclosure in any way.

FIG. 4 shows the genomic DNA of exon 2 in human CFTR and surrounding introns (the sequence of FIG. 4 is given the sequence identifier SEQ ID NO: 131).

FIG. 5 shows the genomic DNA of exon 4 in human CFTR and surrounding introns (the sequence of FIG. 5 is given the sequence identifier SEQ ID NO: 132).

FIG. 6 shows the genomic DNA of exon 5 in human CFTR and surrounding introns (the sequence of FIG. 6 is given the sequence identifier SEQ ID NO: 133).

FIG. 7 shows the genomic DNA of exon 7 in human CFTR and surrounding introns (the sequence of FIG. 7 is given the sequence identifier SEQ ID NO: 134).

FIG. 8 shows the genomic DNA of exon 9 in human CFTR and surrounding introns (the sequence of FIG. 8 is given the sequence identifier SEQ ID NO: 135).

FIG. 9 shows the genomic DNA of exon 10 in human CFTR and surrounding introns (the sequence of FIG. 9 is given the sequence identifier SEQ ID NO: 136).

FIG. 10 shows the genomic DNA of exon 11 in human CFTR and surrounding introns (the sequence of FIG. 10 is given the sequence identifier SEQ ID NO: 137).

FIG. 11 shows the genomic DNA of exon 13 in human CFTR and surrounding introns (the sequence of FIG. 11 is given the sequence identifier SEQ ID NO: 138).

FIG. 12 shows the genomic DNA of exon 15 in human CFTR and surrounding introns (the sequence of FIG. 12 is given the sequence identifier SEQ ID NO: 139).

FIG. 13 shows the genomic DNA of exon 16 in human CFTR and surrounding introns (the sequence of FIG. 13 is given the sequence identifier SEQ ID NO: 140).

FIG. 14 shows the genomic DNA of exon 20 in human CFTR and surrounding introns (the sequence of FIG. 14 is given the sequence identifier SEQ ID NO: 141).

FIG. 15 shows the genomic DNA of exon 22 in human CFTR and surrounding introns (the sequence of FIG. 15 is given the sequence identifier SEQ ID NO: 142).

FIG. 16 shows the genomic DNA of exon 23 in human CFTR and surrounding introns (the sequence of FIG. 16 is given the sequence identifier SEQ ID NO: 143).

FIG. 17 shows the genomic DNA of exon 24 in human CFTR and surrounding introns (the sequence of FIG. 17 is given the sequence identifier SEQ ID NO: 144).

FIG. 23B shows ASO-+10kb rescues CFTR function similar to Corr951 in patient HBE cells. Representative Ieq traces of treatment (Corr951 or ASO-+10kb) compared to control (ASO-C, top, or DMSO, bottom).

Figure 1A:
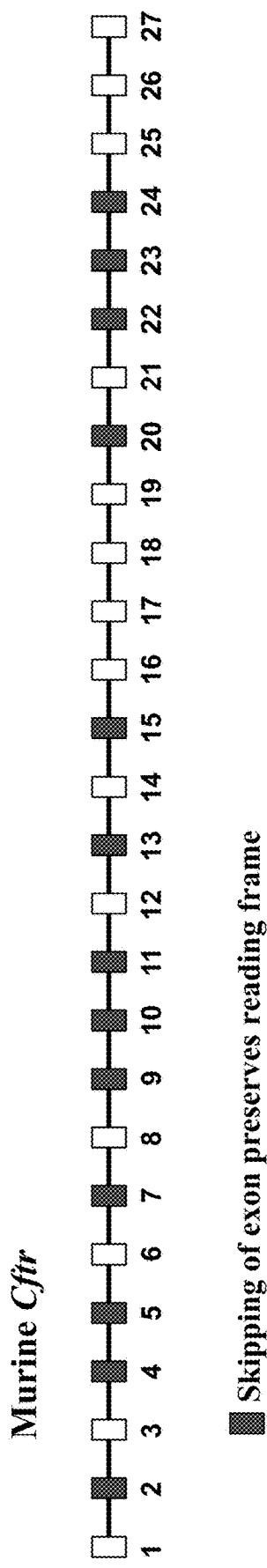
FIG. 1A shows a map of the murine/mouse CFTR gene. Boxes represent exons and lines represent introns. The exons that can be skipped or spliced out of the mature mRNA and still maintain the open reading frame of the mRNA are shaded. The CFTR mRNAs lacking any one of these exons will code for a full-length CFTR protein with an internal deletion of the specific targeted exon sequence.

Skilled artisans will appreciate that elements in the figures are illustrated for simplicity and clarity and have not necessarily been drawn to scale. For example, the dimensions of some of the elements in the figures can be exaggerated relative to other elements to help improve understanding of the embodiment(s) of the present disclosure.

DETAILED DESCRIPTION OF THE DISCLOSURE

The present disclosure relates to general compounds and methods to treat cystic fibrosis in subjects using antisense oligonucleotides (ASOs) that induce specific pre-mRNA splicing events in CFTR gene transcripts that result in mRNAs that code for proteins that fully or partially restore the function of CFTR (i.e., resulting in increased levels of correctly localized CFTR protein at the plasma membrane and with increased function). For example, some ASOs can base-pair with the target RNA and correct aberrant splicing caused by mutations, and other ASOs can induce skipping of exons with mutations that cause open reading frame-shifts. In such instances, skipping of the mutated exon using ASOs can restore the reading frame and generate an mRNA that codes for a CFTR isoform with partial function.

The CFTR gene encodes a member of the ATP-binding cassette (ABC) transporter superfamily. ABC proteins transport various molecules across extra- and intra-cellular membranes. ABC genes are divided into seven distinct subfamilies (ABC1, MDR/TAP, MRP, ALD, OABP, GCN20, White). The CFTR protein is a member of the MRP subfamily that is involved in multi-drug resistance. The encoded protein functions as a chloride channel and controls the regulation of other transport pathways. Mutations in the CFTR gene are associated with the autosomal recessive disorders cystic fibrosis and congenital bilateral aplasia of the vas deferens. Alternatively spliced transcript variants have been described, many of which result from mutations in this gene.

Human (*Homo sapiens*) cystic fibrosis transmembrane conductance regulator is located on chromosome 7: 117, 465,784-117,715,971 (forward strand; SEQ ID NO: 130). The gene is 6132 bp mRNA (Gene ID: 1080; Official Symbol: CFTR; Official Full Name: cystic fibrosis transmembrane conductance regulator) and is assigned NCBI Reference Sequence: NM_000492.3 (SEQ ID NO: 145); ACCESSION: NM_000492; Ensembl: ENSG00000001626; HPRD: 03883; MIM: 602421; and Vega: OTTHUMG00000023076. CFTR is also known as: CF; MRP7; ABC35; ABCC7; CFTR/MRP; TNR-CFTR; dJ76005.1. Human CFTR protein is assigned NCBI Reference Sequence: NP 000483.3 (1480 aa; SEQ ID NO: 146).

The mouse (*Mus musculus*) cystic fibrosis transmembrane conductance regulator is located on chromosome 6: 18170687-18322768 (SEQ ID NO: 147). The mouse CFTR gene is 6305 bp (Gene ID: 12638; Official Symbol: Cftr; Official Full Name: cystic fibrosis transmembrane conductance regulator), and is also known as: Abcc7; AW495489; ATP-binding cassette sub-family C member 7; ATP-binding cassette transporter sub-family C member 7; ATP-binding cassette, subfamily c, member 7; cAMP-dependent chloride channel; channel conductance-controlling ATPase; cystic fibrosis transmembrane conductance regulator homolog cystic fibrosis transmembrane conductance regulator homolog; ATP-binding cassette, subfamily c, member 7. The mouse CFTR gene has been assigned NCBI Reference Sequence: NM_021050.2 (SEQ ID NO: 148), and Ensembl: ENSMUSG00000041301. The mouse CFTR protein is assigned NCBI Reference Sequence: NP_066388.1 (1476 aa; SEQ ID NO: 149).

Antisense compounds, (e.g. antisense oligonucleotides (ASOs)) have been used to modulate target nucleic acids. Antisense compounds comprising a variety of chemical modifications and motifs have been reported. In certain instances, such compounds are useful as research tools, diagnostic reagents, and as therapeutic agents. In certain instances, antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

Pre-mRNA splicing involves the precise and accurate removal of introns from the pre-messenger RNA and the ligation of exons together after intron removal to generate the mature mRNA which serves as the template for protein translation. Pre-mRNA splicing is a two-step reaction carried out by a spliceosome complex comprising protein and small RNA components which recognize conserved sequence elements within the introns and exons of the RNA. Recognition of these sequence elements, including the 5' splice site, 3' splice site and branch point sequence, is the primary mechanism directing the correct removal of introns.

Splicing requires direct base-pairing between small nuclear RNA (snRNA) components of the spliceosome and the splice site nucleotides of the mRNA. This interaction can be easily disrupted by gene mutations or by artificial blocking using short oligonucleotides complementary to the RNA. Such so called antisense oligonucleotides (ASOs), when designed to be complementary to a splice sites, will compete for base-pairing with the snRNAs, thereby blocking an essential step in splicing at the site. In this way, antisense oligonucleotides can potently block unwanted splicing or redirect splicing to alternative splice sites, and can result in mRNAs that code for proteins that fully or partially restore the function to target transcripts.

For example, ASOs can target the 2789+5G>A mutation in intron 16 of the CFTR gene that causes cystic fibrosis. This mutation has been observed in 521 patients with cystic fibrosis. Because aberrant splicing of exon 16 due to the mutation is the cause of cystic fibrosis in patients with this mutation, improving splicing using antisense oligonucleotides to interfere with the deleterious effects of the mutation, can have a therapeutic benefit to the patients. In a non-limiting example, an antisense oligonucleotide that targets the 2789+5G>A mutation of the CFTR gene that causes cystic fibrosis can be SEQ ID NO: 97.

In another non-limiting example, antisense oligonucleotides can target the 3849+10kbC->T mutation in intron 19 of the CFTR gene. This mutation has been observed in 496 patients, and in 1,100 patients in CFTR2 database. The 3849+10kbC>T mutation creates a cryptic splice site that results in an aberrant mRNA that does not produce CFTR protein and antisense oligonucleotides targeted to the region of intron 19 surrounding and encompassing this mutation can potentially block splicing to this cryptic splice site. In a non-limiting example, an antisense oligonucleotide that targets the 3849+10kbC>T mutation of the CFTR gene that causes cystic fibrosis can be SEQ ID NO:150.

In yet another non-limiting example, antisense oligonucleotides can target the 3272-26A->G mutation of the CFTR gene that causes cystic fibrosis. This mutation is found in 186 patients. The 3272-26A>G mutation creates a cryptic splice site that results in an aberrant mRNA that does not produce CFTR protein. Antisense oligonucleotides targeted to the region of surrounding and encompassing this mutation can potentially block splicing to this cryptic splice site. In a non-limiting example, an antisense oligonucleotide that targets the 3272-26A->G mutation of the CFTR gene that causes cystic fibrosis can be SEQ ID NO: 114.

In another non-limiting example, antisense oligonucleotides can target exon skipping in exons that have nonsense mutations. For example, skipping of exon 4, exon 23 or exon 24 all can result in an mRNA transcript that is in-frame so that translation will continue to the natural stop-codon (i.e., mutations such as CFTR 621+1G>T and CFTR 406G>T). Exons 4, 23, and 24 have a number of different patient nonsense mutations that cause cystic fibrosis and any of these can be treated by ASOs that induce exon skipping of the exons that house nonsense mutations to correct the reading frame and allow translation through to the natural termination codon.

In yet other non-limiting examples, 70-90% of all Cystic fibrosis (CF) patients have a mutation in exon 11 (deltaF508) which can be targeted by ASO 11-6 (SEQ ID NO.: 91). Five percent of CF patients have a splice site mutation in intron 16 which can be targeted and corrected by ASO 16-8 (SEQ ID NO.: 102); 2.5% of CF patients have a nonsense mutation in exon 23 which can be targeted for skipping and frame-shift correction using ASO 23-4 (SEQ ID NO.: 126); 2.5% of CF patients have a nonsense mutation in exon 24 which can be targeted for skipping and frame-shift correction using ASO 24-1, 24-2, 24-3 (SEQ ID NO.: 127, 128, 129; respectively); CF mutation databases indicate that nonsense and splicing mutations in and around exon 4 are common and can be targeted for gene expression correction either by splicing redirection or frame-shift correction using ASO 4-1 (SEQ ID NO.: 65); and CF causing nonsense mutations in exons 2, 5, 7, 9, 10, 13, 20 and 22 are also commonly annotated in the Human Gene Mutation Database and can be targeted by ASOs 2-4, 5-1, 7-4, 9-1, 11-6, 13-1, 15-1, 20-2, 22-1 (SEQ ID NO.: 64, 71, 76, 78, 91, 92, 94, 111, 116; respectively).

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "antisense compound" or "antisense oligonucleotide (ASO)" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to, furanosyls comprising substituents at the 2'-position, the 3'-position, the 5'-position and/or the 4'-position.

As used herein, "2'-substituted sugar moiety" means a furanosyl comprising a substituent at the 2'-position other than —H or —OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring).

As used herein, "MOE" means —OCH$_2$CH$_2$OCH$_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments, the 4 to 7 membered ring is a furanosyl. In certain such embodiments, the bridge connects the 2'-carbon and the 4'-carbon of the furanosyl.

As used herein, the term "sugar surrogate" means a structure that does not comprise a furanosyl and that is capable of replacing the naturally occurring sugar moiety of a nucleoside, such that the resulting nucleoside is capable of: (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group.

As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein, the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)-0-2'bridge.

As used herein, "locked nucleic acid nucleoside" or "LNA" means a nucleoside comprising a bicyclic sugar moiety comprising a 4'-CH$_2$-0-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more substructures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to, pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "transcript" means an RNA molecule transcribed from DNA. Transcripts include, but are not limited to mRNA, pre-mRNA, and partially processed RNA.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, 20 or 25 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment. Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36:3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36:3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *Pharmacol. Exp. Ther.*, 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_2$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid. In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments antisense compounds and antisense oligonucleotides comprise single-strand compounds. In certain embodiments antisense compounds and antisense oligonucleotides comprise double-strand compounds.

Pharmaceutical Compositions

In certain embodiments, the present invention provides pharmaceutical compositions comprising one or more antisense compound. The pharmaceutical composition may comprise a cocktail of antisense compounds, wherein the cocktail comprises 2, 3, 4, 5, 6, 7, 8, 9, 10 or more antisense compounds. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations.

Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide (DMSO) are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or pharmaceutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human. In certain embodiments, the animal is a mouse.

In certain embodiments, the present invention provides methods of administering a pharmaceutical composition comprising an oligomeric compound of the present invention to an animal. Suitable administration routes include, but are not limited to, oral, rectal, transmucosal, transdermal, intestinal, enteral, topical, suppository, through inhalation, intrathecal, intracerebroventricular, intraperitoneal, intranasal, intratumoral, and parenteral (e.g., intravenous, intramuscular, intramedullary, and subcutaneous). In certain embodiments, a pharmaceutical composition is prepared for transmucosal administration. In certain of such embodiments penetrants appropriate to the barrier to be permeated are used in the formulation. Such penetrants are generally known in the art. In certain embodiments, pharmaceutical compositions are administered to achieve local rather than systemic exposures. For example, pharmaceutical compositions may be aerosolized and inhaled directly in the area of desired effect (e.g., into the lungs).

In certain embodiments, a pharmaceutical composition is administered to an animal having at least one symptom associated with Cystic Fibrosis. In certain embodiments, such administration results in amelioration of at least one symptom. In certain embodiments, administration of a pharmaceutical composition to an animal results in an increase in functional CFTR protein in a cell. In certain embodiments, the administration of certain antisense oligonucleotides (ASOs) delays the onset of Cystic Fibrosis. In certain embodiments, the administration of certain antisense oligonucleotides prevents the onset of Cystic Fibrosis. In certain embodiments, the administration of certain antisense oligonucleotides rescues cellular phenotype.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety. Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence

EXAMPLES

The Examples that follow are illustrative of specific embodiments of the invention, and various uses thereof. They are set forth for explanatory purposes only, and are not to be taken as limiting the invention.

Methods

Antisense Oligonucleotides (ASOs).

ASOs with phosphorodiamidate morpholino (PMO) chemistries were generated by GeneTools LLC and were dissolved in 0.9% saline.

Cell Culture and Transfection.

T84 cells are a human colonic adenocarcinoma cell line and the mouse primary cell line, 208EE, was established from an adult C57BL/6 mouse kidney. ASOs (15 µM final concentration) were transfected into cells using Endo-Porter (GeneTools). RNA was collected 48 hours post-transfection.

RNA Isolation and Analysis.

RNA was isolated from tissue and cells in culture using TRIZOL™ reagent (Life Technologies, Carlsbad, Calif.) according to the manufacturer's protocol. For human tissue, RNA was isolated and treated with 4 µg of DNase-I (RNase-free) (Life Technologies) followed by reverse transcription with GoScript™ reverse transcription system (Promega, Madison, Wis.). Radiolabeled and cold PCR was carried out using primers specific for human or mouse CFTR region encompassing the ASO target exon. PCR products were separated by polyacrylamide or agarose gel electrophoresis and bands on gels were quantitated by densitometry analysis using Image J software.

Figure 1B:
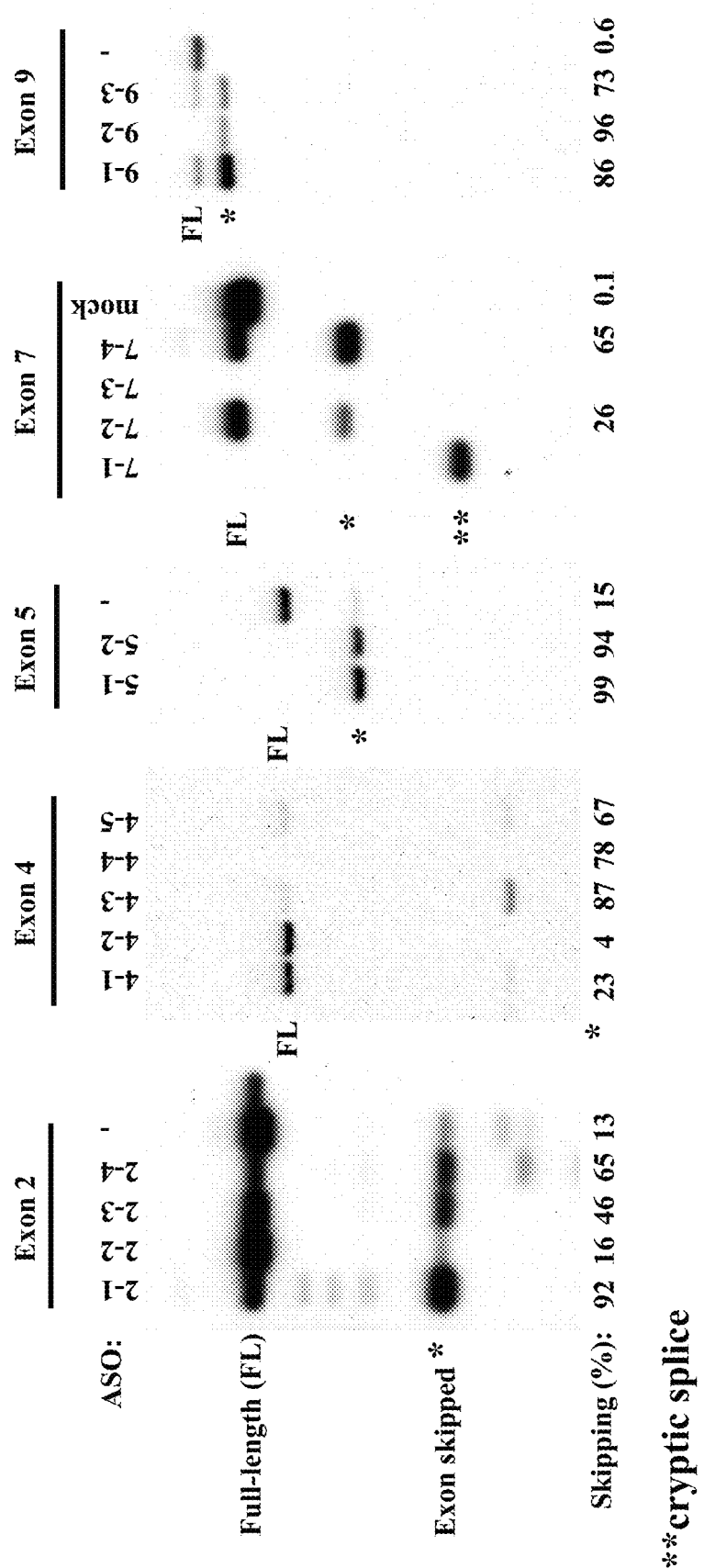
FIG. 1B shows antisense oligonucleotides induce skipping of targeted exons 2, 4, 5, 7 and 9 of the murine CFTR gene-derived pre-mRNA. Polyacrylamide gel images of radio-labeled reverse-transcription/polymerase chain reaction (RT-PCR) products separated by electrophoresis are shown. RT-PCR was performed on RNA isolated from a mouse primary cell line treated with the indicated ASO or treated with vehicle (saline) only (−). The products were amplified with primers specific to exons flanking the specific ASO-targeted exon in order to resolve the full-length (FL) and exon-skipped (*) products. The targeted exon is indicated at the top of the gel image. PCR products were quantitated and the percent of the products that are skipped [Exon skipped/(Full-length+skipped)]×100 is shown below the gel image.
Figure 1C:
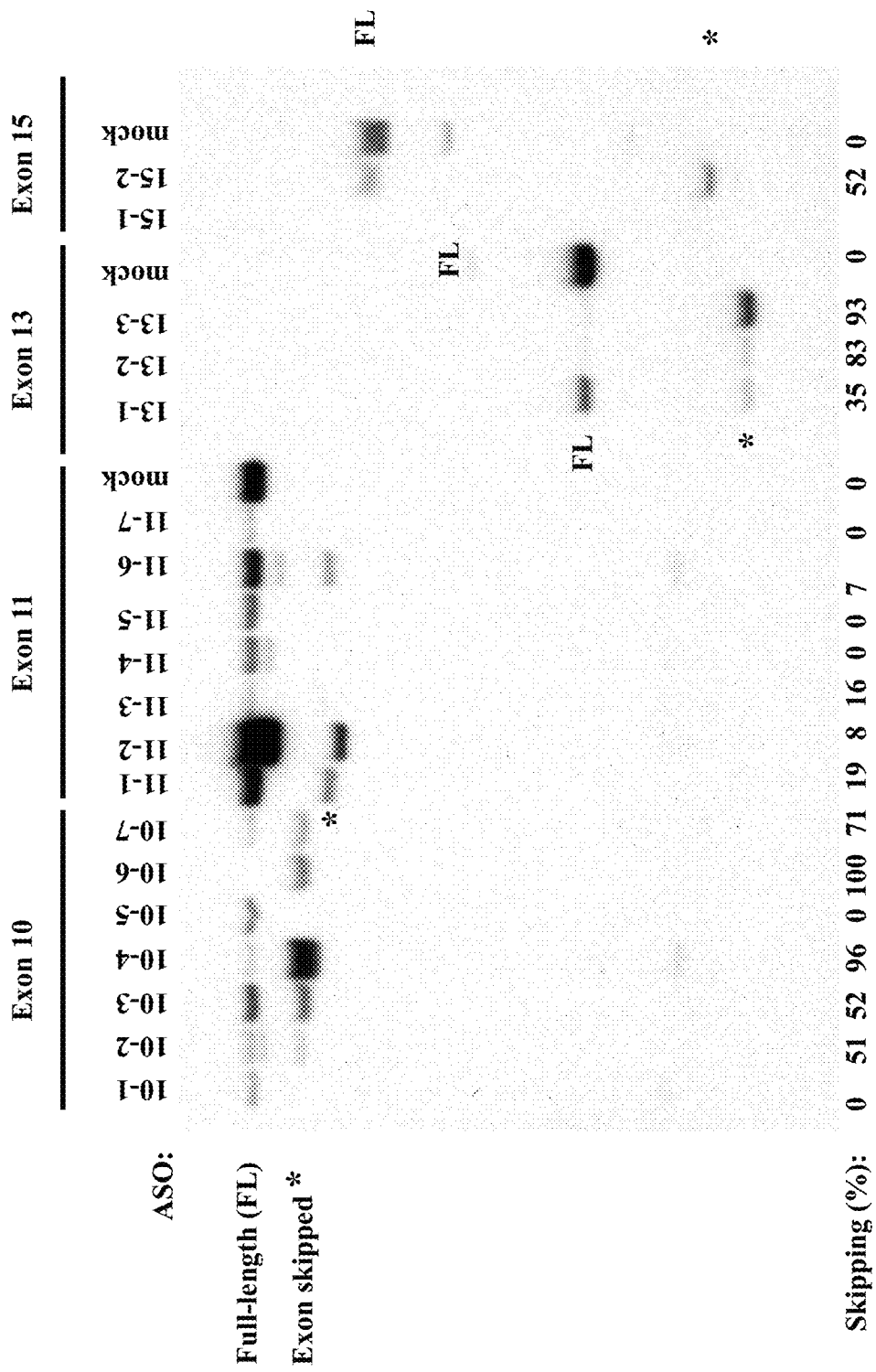
FIG. 1C shows antisense oligonucleotides induce skipping of targeted exons 10, 11, 13 and 15 of the murine CFTR gene-derived pre-mRNA. Polyacrylamide gel images of radio-labeled reverse-transcription/polymerase chain reaction (RT-PCR) products separated by electrophoresis are shown. RT-PCR was performed on RNA isolated from a mouse primary cell line treated with the indicated ASO or treated with vehicle (saline) only (−). The products were amplified with primers specific to exons flanking the specific ASO-targeted exon in order to resolve the full-length (FL) and exon-skipped (*) products. The targeted exon is indicated at the top of the gel image. PCR products were quantitated and the percent of the products that are skipped [Exon skipped/(Full-length+skipped)]×100 is shown below the gel image.
Figure 1D:
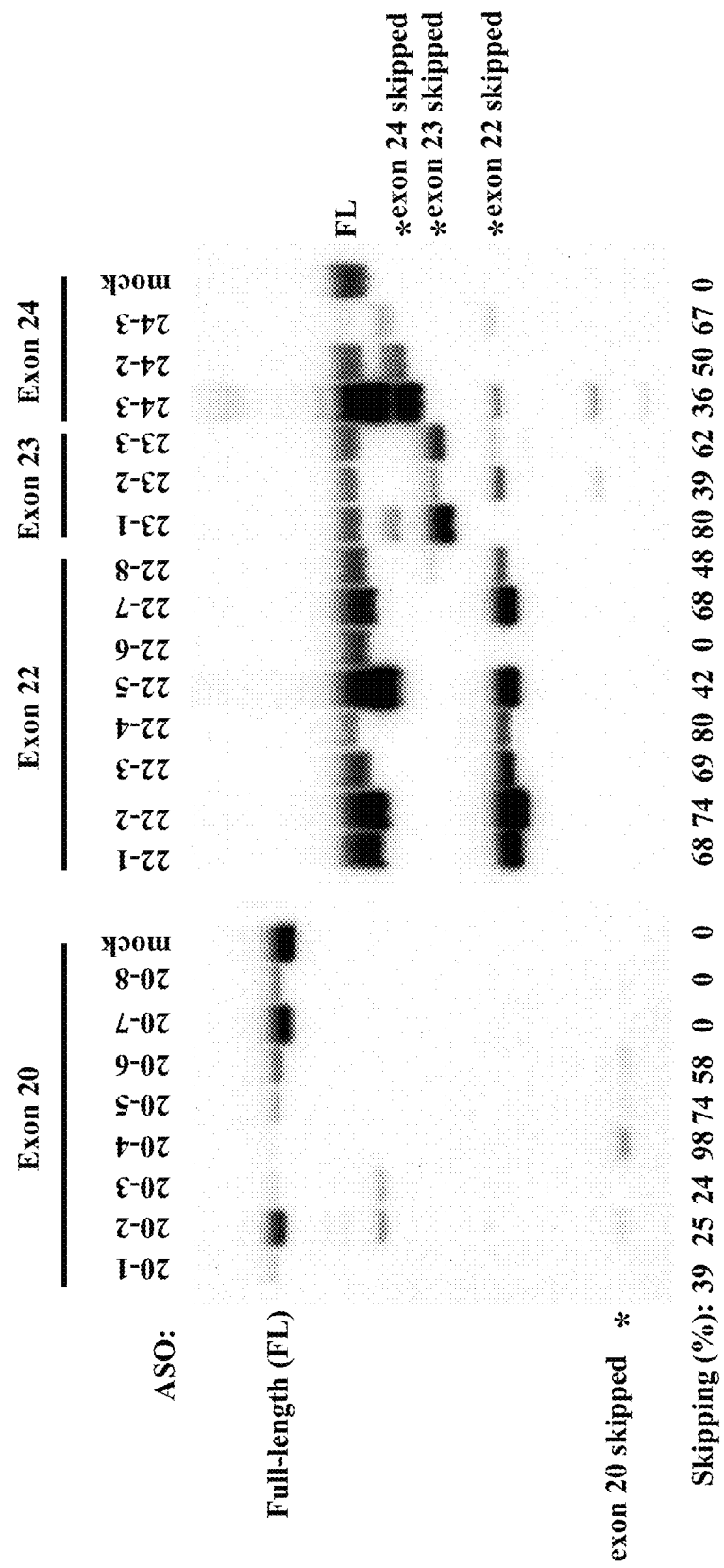
FIG. 1D shows antisense oligonucleotides induce skipping of targeted exons 20, 22, 23 and 24 of the murine CFTR gene-derived pre-mRNA. Polyacrylamide gel images of radio-labeled reverse-transcription/polymerase chain reaction (RT-PCR) products separated by electrophoresis are shown. RT-PCR was performed on RNA isolated from a mouse primary cell line treated with the indicated ASO or treated with vehicle (saline) only (−). The products were amplified with primers specific to exons flanking the specific ASO-targeted exon in order to resolve the full-length (FL) and exon-skipped (*) products. The targeted exon is indicated at the top of the gel image. PCR products were quantitated and the percent of the products that are skipped [Exon skipped/(Full-length+skipped)]×100 is shown below the gel image.
Figure 2A:
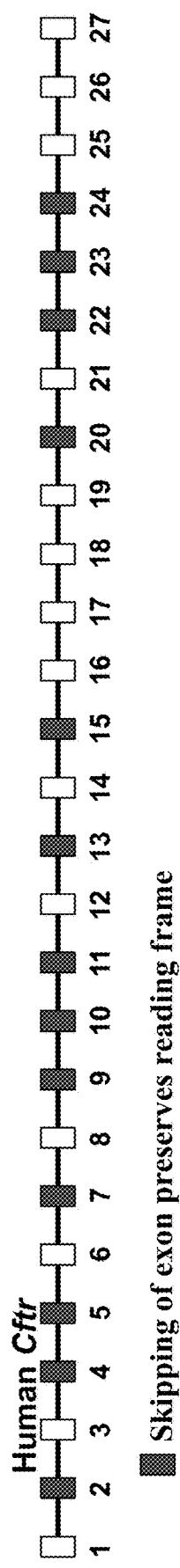
FIG. 2A shows a map of the human CFTR gene. Boxes represent exons and lines represent introns. The exons that can be skipped or spliced out of the mature mRNA and still maintain the open reading frame of the mRNA are shaded. The CFTR mRNAs lacking any one of these exons will code for a full-length CFTR protein with an internal deletion of the specific targeted exon sequence.
Figure 2B:
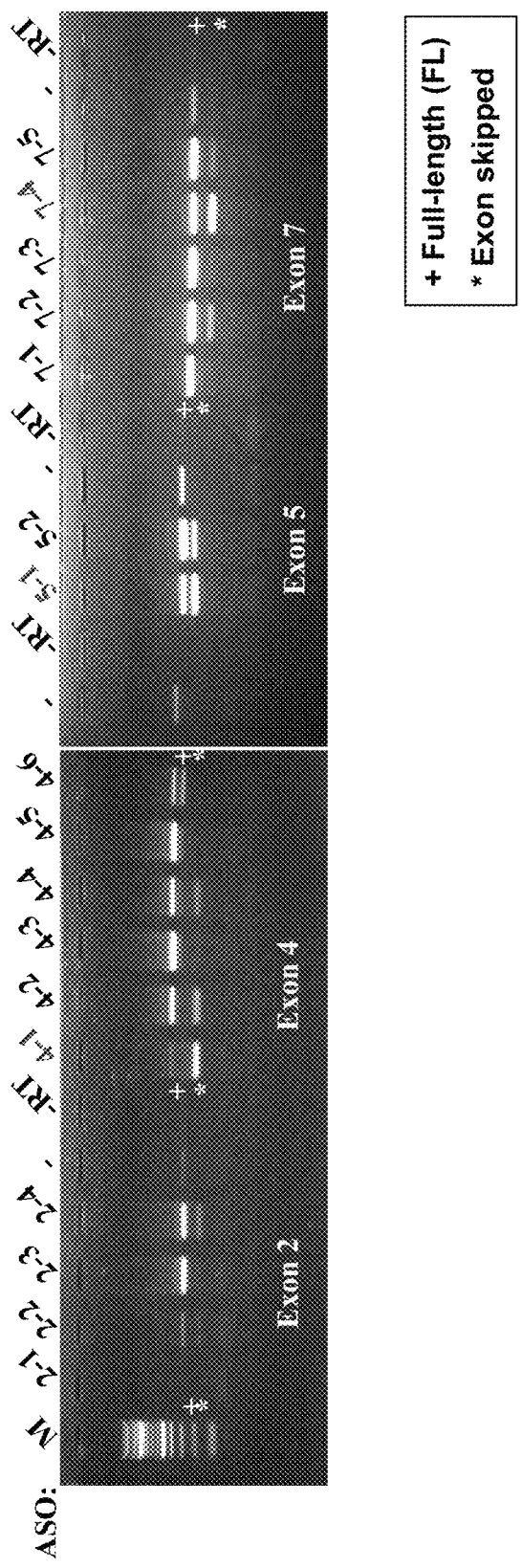
FIG. 2B show antisense oligonucleotides induce skipping of targeted exons 2, 4, 5 and 7 of the human CFTR gene-derived pre-mRNA. Agarose gel images of reverse-transcription/polymerase chain reaction (RT-PCR) products separated by electrophoresis are shown. RT-PCR was performed on RNA isolated from human T84 epithelial cells treated with the indicated ASO or treated with vehicle (saline) only (−) or a reaction lacking cDNA (-RT). The products were amplified with primers specific to exons flanking the specific ASO-targeted exon in order to resolve the full-length (FL; +) and exon-skipped (*) products. The targeted exon is indicated at the bottom of the gel and by the first numbers in the name of the ASOs.
Figure 2C:
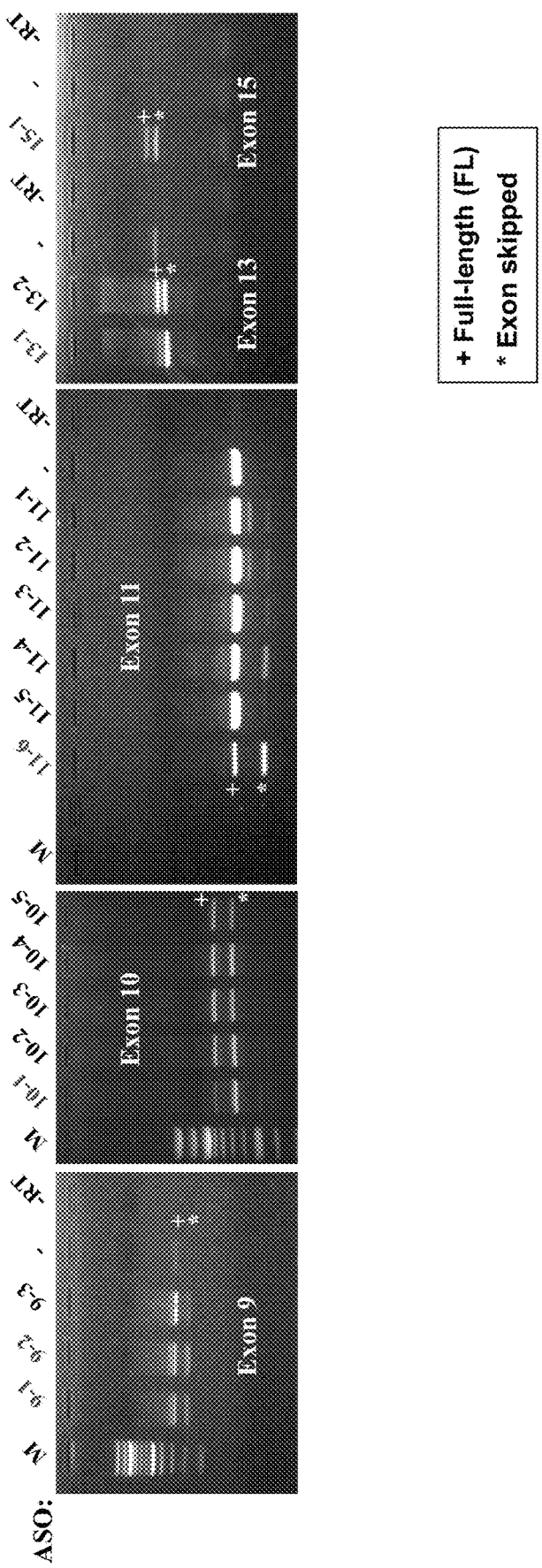
FIG. 2C show antisense oligonucleotides induce skipping of targeted exons 9, 10, 11, 13 and 15 of the human CFTR gene-derived pre-mRNA. Agarose gel images of reverse-transcription/polymerase chain reaction (RT-PCR) products separated by electrophoresis are shown. RT-PCR was performed on RNA isolated from human T84 epithelial cells treated with the indicated ASO or treated with vehicle (saline) only (−) or a reaction lacking cDNA (-RT). The products were amplified with primers specific to exons flanking the specific ASO-targeted exon in order to resolve the full-length (FL; +) and exon-skipped (*) products. The targeted exon is indicated at the bottom of the gel and by the first numbers in the name of the ASOs.
Figure 2D:
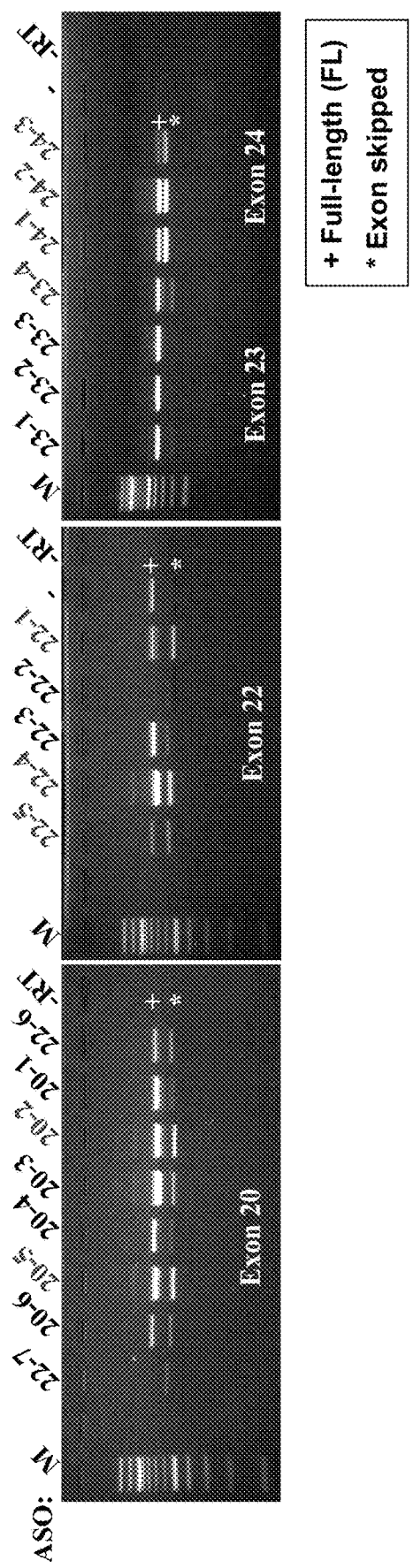
FIG. 2D show antisense oligonucleotides induce skipping of targeted exons 20, 22, 23 and 24 of the human CFTR gene-derived pre-mRNA. Agarose gel images of reverse-transcription/polymerase chain reaction (RT-PCR) products separated by electrophoresis are shown. RT-PCR was performed on RNA isolated from human T84 epithelial cells treated with the indicated ASO or treated with vehicle (saline) only (−) or a reaction lacking cDNA (-RT). The products were amplified with primers specific to exons flanking the specific ASO-targeted exon in order to resolve the full-length (FL; +) and exon-skipped (*) products. The targeted exon is indicated at the bottom of the gel and by the first numbers in the name of the ASOs.
Figure 3A:
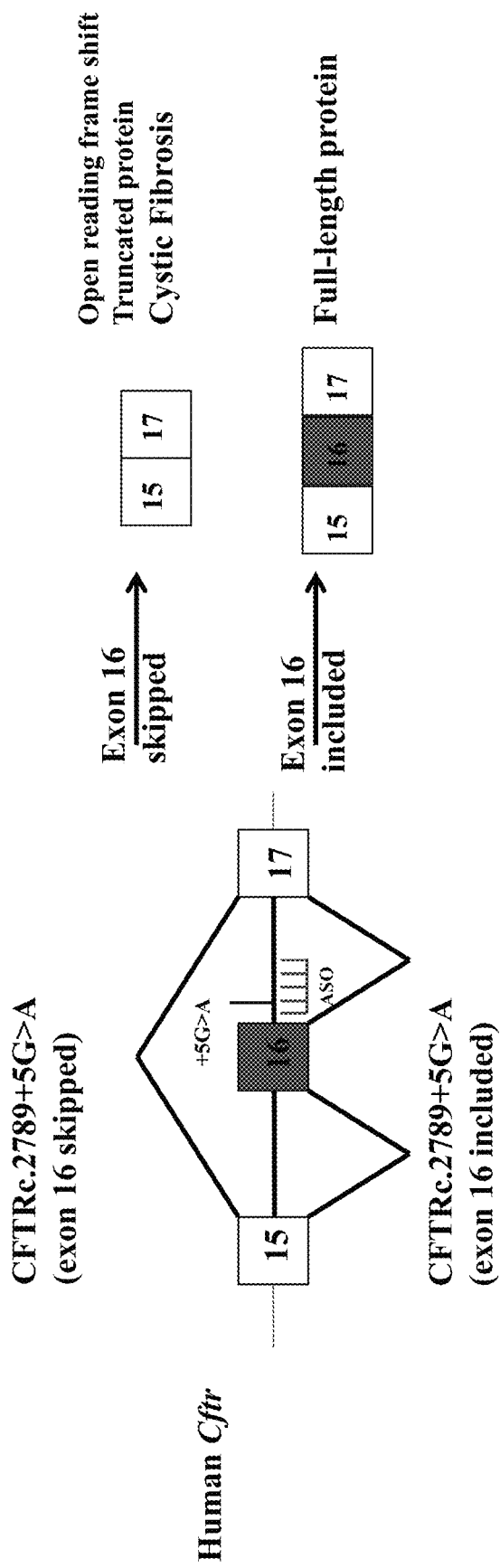
FIG. 3A shows a schematic of the splicing pattern of human CFTR c.2789+5G>A without and with ASO targeting. Boxes are exons and lines are introns. Diagonal lines indicate splicing pathway FIG. 3B demonstrates that antisense oligonucleotides correct splicing of human CFTR exon 16 with c.2789+5G>A mutation. Polyacrylamide gel images of reverse-transcription/polymerase chain reaction (RT-PCR) products were separated by electrophoresis. RT-PCR was performed on RNA isolated from human lymphoblast cell line GM11859, whose donor is homozygous for G-to-A substitution at nucleotide 2789+5 in intron 16 which results in an mRNA splicing defect (2789+5G>A). Cells were treated with the indicated ASO. The products were amplified with primers specific to exons flanking the specific ASO-targeted exon in order to resolve the full-length (FL) and exon-skipped products. ASO 16-8 was effective at correcting exon 16 splicing of CFTRc.2789+5G>A.
Figure 3B:
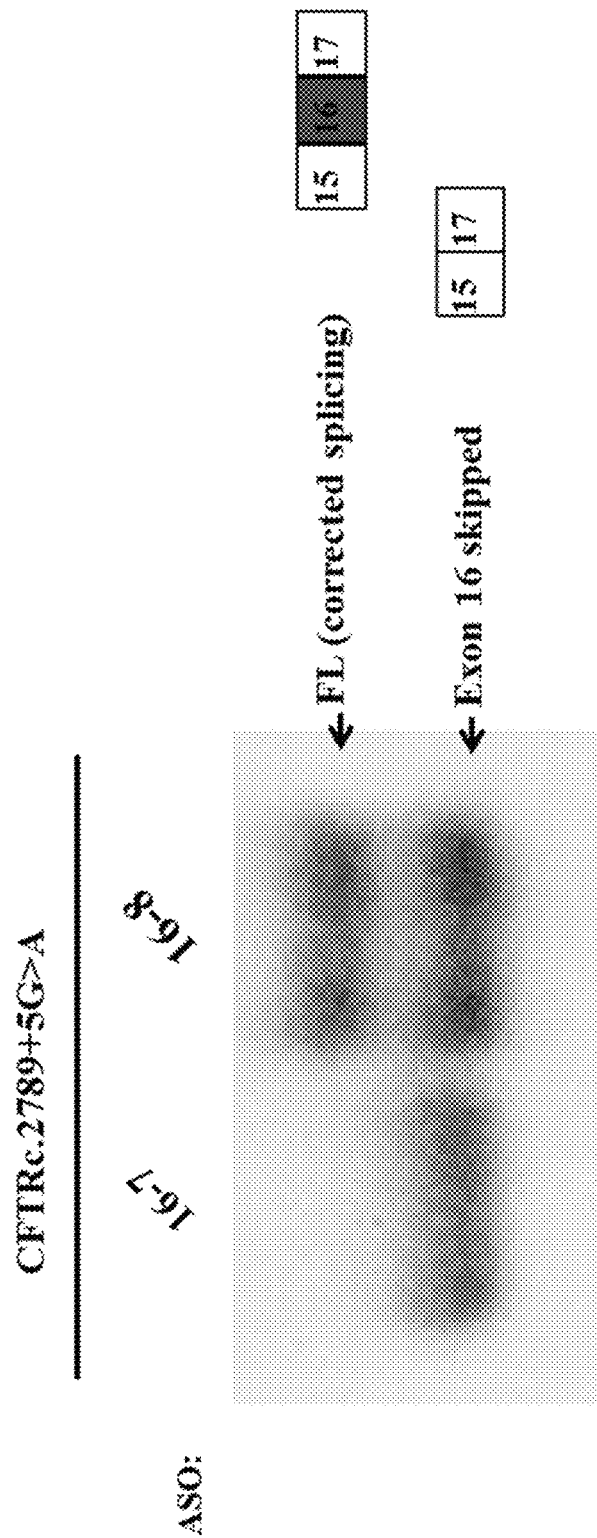

Example 1: Antisense Oligonucleotides Induce Skipping of Targeted Exons in Murine CFTR Gene-Derived Pre-mRNA Various ASOs (see Table 1; SEQ ID NOs: 1-60) were tested in the mouse primary cell line, 208EE (which was established from an adult C57BL/6 mouse kidney). ASOs (15 µM final concentration) were transfected into cells using Endo-Porter (GeneTools). FIGS. 1B, 1C and 1D demonstrate that ASOs induce skipping of targeted exons in murine CFTR.

TABLE 1

Antisense oligonucleotides targeting mouse CFTR induce exon skipping.

| Name | Target Exon | Sequence | % skipped * | SEQ ID NO. |
|---|---|---|---|---|
| 2-1 | 2 | GGTCCAGCTAAAAGAGAAGAGGGCA | 92 | SEQ ID NO. 1 |
| 2-2 | 2 | CTTTCCTCAAAATTGGTGTGGTCCA | 16 | SEQ ID NO. 2 |
| 2-3 | 2 | TATGTCTGACAACTCCAAGTGGTGT | 46 | SEQ ID NO. 3 |
| 2-4 | 2 | CTAGTTTTTCAGACAAGTGGTCAGC | 65 | SEQ ID NO. 4 |
| 4-1 | 4 | TTCCTAGCAAGACAGGCTGGACAGC | nd | SEQ ID NO. 5 |
| 4-2 | 4 | ATAGGATGCTATGATTCTTCCTAGC | 23 | SEQ ID NO. 6 |
| 4-3 | 4 | ATAAGCCTATGCCAAGGTAAATGGC | 4 | SEQ ID NO. 7 |
| 4-4 | 4 | TGTCCTGACAATGAAGAGAAGGCAT | 87 | SEQ ID NO. 8 |
| 4-5 | 4 | AATGCGATGAAGGCCAAAAATAGCT | 78 | SEQ ID NO. 9 |
| 4-6 | 4 | TAGCTGTTCTCATCTGCATTCCAAT | 67 | SEQ ID NO. 10 |
| 4-7 | 4 | CATCTTCCAAAAAGTATTACCTTCT | nd | SEQ ID NO. 11 |
| 5-1 | 5 | TTGTTCAGGTTGTTGGAAAGAAGAC | 99 | SEQ ID NO. 12 |
| 5-2 | 5 | ATCAAGAACGCGGCTTGACAACTTT | 94 | SEQ ID NO. 13 |
| 7-1 | 7 | CACGAGTCTTTCATTGATCTTTGCA | 20 | SEQ ID NO. 14 |
| 7-2 | 7 | CTGATTCCCAACAATATGCCTTAAC | 26 | SEQ ID NO. 15 |
| 7-3 | 7 | CAATCATTTTCTCCATCGCTGATTC | 42 | SEQ ID NO. 16 |
| 7-4 | 7 | ATTATGTCAACTTACTCTCTCAAGT | 65 | SEQ ID NO. 17 |
| 9-1 | 9 | GCCTGTGGTCATTAAGTTATACTCC | 86 | SEQ ID NO. 18 |

TABLE 1-continued

Antisense oligonucleotides targeting mouse CFTR induce exon skipping.

| Name | Target Exon | Sequence | % skipped * | SEQ ID NO. |
|---|---|---|---|---|
| 9-2 | 9 | CTCCTCCCAAAATGCTGTTACATTT | 96 | SEQ ID NO. 19 |
| 9-3 | 9 | TATTTAGAAATCTCACCTCCTCCCA | 73 | SEQ ID NO. 20 |
| 10-1 | 10 | CTTTCTCCAGTAATTCCCCAAATCC | 0 | SEQ ID NO. 21 |
| 10-2 | 10 | GTCACCATTGCTTTGTTGTACTTTC | 51 | SEQ ID NO. 22 |
| 10-3 | 10 | CTGAAACTGACATTGTTCTCATCAC | 52 | SEQ ID NO. 23 |
| 10-4 | 10 | AGGATTTCCCACAAGGCAGAGATGA | 96 | SEQ ID NO. 24 |
| 10-5 | 10 | ATAGCCAACATCTCTCCTTTCTCTA | 0 | SEQ ID NO. 25 |
| 10-6 | 10 | CTTTCCTGATCCAGTAGATCCAGTA | 100 | SEQ ID NO. 26 |
| 10-7 | 10 | TTAAAGAGACAGTACCTTTCCTGAT | 71 | SEQ ID NO. 27 |
| 11-1 | 11 | TCCAGTTCTCCCAAAATCAACATCA | 19 | SEQ ID NO. 28 |
| 11-2 | 11 | TGTGCTTAATAATTCCCTCTGAAGC | 8 | SEQ ID NO. 29 |
| 11-3 | 11 | ATTGAGAGCAGAATGAAACTCTTCC | 16 | SEQ ID NO. 30 |
| 11-4 | 11 | GATATTTTCTTTGATAGTACCCGGC | 0 | SEQ ID NO. 31 |
| 11-5 | 11 | ACACTCTTATATCTGTACTCATCAT | 0 | SEQ ID NO. 32 |
| 11-6 | 11 | CTGCTGTAGTTGGCAAGCTTTGACA | 7 | SEQ ID NO. 33 |
| 11-7 | 11 | CATAAATATGCTTACCTGCTGTAGT | 0 | SEQ ID NO. 34 |
| 13-1 | 13 | GGGAATCTAATAGGTACAAATCAGC | 35 | SEQ ID NO. 35 |
| 13-2 | 13 | CAAATCAGCATCTTTATATACTGCT | 83 | SEQ ID NO. 36 |
| 13-3 | 13 | ACTCAGTCATAGAACATACCTTTCA | 93 | SEQ ID NO. 37 |
| 15-1 | 15 | AACAAACATACTTACCTCAACCAGA | 52 | SEQ ID NO. 38 |
| 20-1 | 20 | CCTGCCTGTAAATCATCCCATAGGA | 39 | SEQ ID NO. 39 |
| 20-2 | 20 | CAAGGTGGGTGAAAATTGGACTCCT | 25 | SEQ ID NO. 40 |
| 20-3 | 20 | CGAAGTGTCCAGAGTCCTTTTAAGC | 24 | SEQ ID NO. 41 |
| 20-4 | 20 | CAGAGTTTCAAAGTAAGTCTGGCGT | 98 | SEQ ID NO. 42 |
| 20-5 | 20 | TTGGCAGTGTGCAAATTCAGAGCTT | 74 | SEQ ID NO. 43 |
| 20-6 | 20 | CTATTCTCATTTGGAACCAGCGCAA | 58 | SEQ ID NO. 44 |
| 20-7 | 20 | AGAGGACAAATATCATGTCTATTCT | 0 | SEQ ID NO. 45 |
| 20-8 | 20 | ATGGAGATGAAGGTAACAACAATGA | 0 | SEQ ID NO. 46 |
| 22-1 | 22 | AACTTAAACACTCTGCTCACAGATC | 68 | SEQ ID NO. 47 |
| 22-2 | 22 | CTAAAACGTCAGATGATCCTTCTCT | 74 | SEQ ID NO. 48 |
| 22-3 | 22 | TATCACTTTTCTTCACATGCTCATT | 69 | SEQ ID NO. 49 |
| 22-4 | 22 | ACCATTTCGCCTCCAGAGGGCCAGA | 80 | SEQ ID NO. 50 |
| 22-5 | 22 | CATCCATGTATTTCACAGTAAGGTC | 42 | SEQ ID NO. 51 |
| 22-6 | 22 | ATGTTCTCTAATACGGCATTTCCAT | 0 | SEQ ID NO. 52 |
| 22-7 | 22 | CCTCTGTCCAGGACTTATTGAAAAA | 68 | SEQ ID NO. 53 |
| 22-8 | 22 | GTAATGCTGAAATCTCACCCTCTGT | 48 | SEQ ID NO. 54 |
| 23-1 | 23 | AATTCCATGAGACACCATCAATCTC | 80 | SEQ ID NO. 55 |

TABLE 1-continued

Antisense oligonucleotides targeting mouse CFTR induce exon skipping.

| Name | Target Exon | Sequence | % skipped * | SEQ ID NO. |
|---|---|---|---|---|
| 23-2 | 23 | GTACTTTTCCTGATCCAGTTCTTC | 39 | SEQ ID NO. 56 |
| 23-3 | 23 | CATTTTTGTGCTCACCTGTGTTATC | 62 | SEQ ID NO. 57 |
| 24-1 | 24 | CATCTTTCCATTTTCCATTGGGATC | 36 | SEQ ID NO. 58 |
| 24-2 | 24 | CTCATCTGCAACTTTCCATATTTCT | 50 | SEQ ID NO. 59 |
| 24-3 | 24 | TATTTGTCATCCTTACCTCATCTGC | 67 | SEQ ID NO. 60 |

* percent of the mRNA transcripts that skip out the targeted exon

Example 2: Antisense Oligonucleotides Induce Skipping of Targeted Exons in Human CFTR Gene-Derived Pre-mRNA Various ASOs (see Table 2; SEQ ID NOs: 61-129) were tested in the human colonic adenocarcinoma cell line primary cell line, T84. ASOs (15 µM final concentration) were transfected into cells using Endo-Porter (GeneTools). FIGS. 2B, 2C, 2D and FIG. 3 demonstrate that ASOs induce skipping of targeted exons in human CFTR.

TABLE 2

Antisense oligonucleotides targeting human CFTR induce exon skipping

| Name | Target Exon | Sequence | % skipped * | SEQ ID NO. |
|---|---|---|---|---|
| 2-1 | 2 | ATCCTTTCCTCAAAATTGGTCTGGT | 0 | SEQ ID NO. 61 |
| 2-2 | 2 | GTATATGTCTGACAATTCCAGGCGC | 35 | SEQ ID NO. 62 |
| 2-3 | 2 | CAGATAGATTGTCAGCAGAATCAAC | 18 | SEQ ID NO. 63 |
| 2-4 | 2 | GTACATGAACATACCTTTCCAATTT | 37 | SEQ ID NO. 64 |
| 4-1 | 4 | GAGGCTGTACTGCTTTGGTGACTTC | 77 | SEQ ID NO. 65 |
| 4-2 | 4 | GAAGCTATGATTCTTCCCAGTAAGA | 54 | SEQ ID NO. 66 |
| 4-3 | 4 | GTGTAGGAGCAGTGTCCTCACAATA | 0 | SEQ ID NO. 67 |
| 4-4 | 4 | AATGTGATGAAGGCCAAAAATGGCT | 39 | SEQ ID NO. 68 |
| 4-5 | 4 | GCTATTCTCATCTGCATTCCAATGT | 0 | SEQ ID NO. 69 |
| 4-6 | 4 | CCTGTGCAAGGAAGTATTACCTTCT | 0 | SEQ ID NO. 70 |
| 5-1 | 5 | CTAGAACACGGCTTGACAGCTTTAA | 58 | SEQ ID NO. 71 |
| 5-2 | 5 | TGGAAAGGAGACTAACAAGTTGTCC | 42 | SEQ ID NO. 72 |
| 7-1 | 7 | ACTGATCTTCCCAGCTCTCTGATCT | 15 | SEQ ID NO. 73 |
| 7-2 | 7 | ATTTCTGAGGTAATCACAAGTCTTT | 37 | SEQ ID NO. 74 |
| 7-3 | 7 | AGTATGCCTTAACAGATTGGATATT | 28 | SEQ ID NO. 75 |
| 7-4 | 7 | ATTTTTTCCATTGCTTCTTCCCAGC | 44 | SEQ ID NO. 76 |
| 7-5 | 7 | ATTGGAACAACTTACTGTCTTAAGT | 38 | SEQ ID NO. 77 |
| 9-1 | 9 | TCCATCACTACTTCTGTAGTCGTTA | 56 | SEQ ID NO. 78 |
| 9-2 | 9 | CTCCTCCCAGAAGGCTGTTACATTC | 53 | SEQ ID NO. 79 |
| 9-3 | 9 | TTAAAAATTCTGACCTCCTCCCAGA | 33 | SEQ ID NO. 80 |
| 10-1 | 10 | GGCTGTCATCACCATTAGAAGTTTT | 64 | SEQ ID NO. 81 |
| 10-2 | 10 | AATTACTGAAGAAGAGGCTGTCATC | 56 | SEQ ID NO. 82 |

TABLE 2-continued

Antisense oligonucleotides targeting human CFTR induce exon skipping

| Name | Target Exon | Sequence | % skipped * | SEQ ID NO. |
|---|---|---|---|---|
| 10-3 | 10 | TAATATCTTTCAGGACAGGAGTACC | 49 | SEQ ID NO. 83 |
| 10-4 | 10 | GATCCAGCAACCGCCAACAACTGTC | 52 | SEQ ID NO. 84 |
| 10-5 | 10 | AGAACAAAAGAACTACCTTGCCTGC | 47 | SEQ ID NO. 85 |
| 11-1 | 11 | CTCCCATAATCACCATTAGAAGTGA | 2 | SEQ ID NO. 86 |
| 11-2 | 11 | ATTTTACCCTCTGAAGGCTCCAGTT | 2 | SEQ ID NO. 87 |
| 11-3 | 11 | ACAGAATGAAATTCTTCCACTGTGC | 2 | SEQ ID NO. 88 |
| 11-4 | 11 | GTGCCAGGCATAATCCAGGAAAACT | 14 | SEQ ID NO. 89 |
| 11-5 | 11 | ATGCTTTGATGACGCTTCTGTATCT | 2 | SEQ ID NO. 90 |
| 11-6 | 11 | TTTTCACATAGTTTCTTACCTCTTC | 72 | SEQ ID NO. 91 |
| 13-1 | 13 | TCTAGGTATCCAAAAGGAGAGTCTA | 90 | SEQ ID NO. 92 |
| 13-2 | 13 | GGTATTCAAAGAACATACCTTTCAA | 66 | SEQ ID NO. 93 |
| 15-1 | 15 | ACAATAGAACATTCTTACCTCTGCC | 93 | SEQ ID NO. 94 |
| 16-1 | 16 | TCGTTATTTGGCAGCCAAAGTTACT | n/a | SEQ ID NO. 95 |
| 16-2 | 16 | GAGCCACAGCACAACCAAAGAAGCA | n/a | SEQ ID NO. 96 |
| 16-3 | 16 | TCCAAGGAGCCACAGCAC | n/a | SEQ ID NO. 97 |
| 16-4 | 16 | TTCCAAGGAGCCACAGCA | n/a | SEQ ID NO. 98 |
| 16-5 | 16 | TTCCAAGGAGCCACAGCACAACCAA | n/a | SEQ ID NO. 99 |
| 16-6 | 16 | AACAGAAATAAAACACAATCTACAC | n/a | SEQ ID NO. 100 |
| 16-7 | 16 | TTTCCAAGGAGCCACAGCACAACCA | 0 | SEQ ID NO. 101 |
| 16-8 | 16 | ACAATCTACACAATAGGACATGGAA | 56 | SEQ ID NO. 102 |
| 16-9 | 16 | CACAATCTACACAATAGGACATGGA | n/a | SEQ ID NO. 103 |
| 16-10 | 16 | ACACAATCTACACAATAGGACATGG | n/a | SEQ ID NO. 104 |
| 16-11 | 16 | GACTTTTTTTCTAACATCTTCACCT | n/a | SEQ ID NO. 105 |
| 16-12 | 16 | ATGGAACAACACACAGTTGATTTTT | n/a | SEQ ID NO. 106 |
| 16-13 | 16 | ATCGAACAAGACACAGTTGATTTTT | n/a | SEQ ID NO. 107 |
| 16-14 | 16 | GAGTGGAACAAGACACAGTTGATTT | n/a | SEQ ID NO. 108 |
| 16-15 | 16 | CACAATCTACACAATAAGACATGGA | n/a | SEQ ID NO. 109 |
| 20-1 | 20 | CAAGATGAGTGAAAATTGGACTCCT | 2 | SEQ ID NO. 110 |
| 20-2 | 20 | CGAAGGCACGAAGTGTCCATAGTCC | 29 | SEQ ID NO. 111 |
| 20-3 | 20 | AACAGAGTTTCAAAGTAAGGCTGCC | 8 | SEQ ID NO. 112 |
| 20-4 | 20 | AGTTGGCAGTATGTAAATTCAGAGC | 6 | SEQ ID NO. 113 |
| 20-5 | 20 | TTCTATTCTCATTTGGAACCAGCGC | 45 | SEQ ID NO. 114 |
| 20-6 | 20 | GGTAACAGCAATGAAGAAGATGACA | 35 | SEQ ID NO. 115 |
| 22-1 | 22 | ATGTCAATGAACTTAAAGACTCGGC | 59 | SEQ ID NO. 116 |
| 22-2 | 22 | GGCCAGATGTCATCTTTCTTCACGT | 65 | SEQ ID NO. 117 |
| 22-3 | 22 | ATCTTTGACAGTCATTTGGCCCCCT | 7 | SEQ ID NO. 118 |
| 22-4 | 22 | CCACCTTCTGTGTATTTTGCTGTGA | 45 | SEQ ID NO. 119 |
| 22-5 | 22 | TCTCTAATATGGCATTTCCACCTTC | 67 | SEQ ID NO. 120 |

TABLE 2-continued

Antisense oligonucleotides targeting human CFTR induce exon skipping

| Name | Target Exon | Sequence | % skipped * | SEQ ID NO. |
|---|---|---|---|---|
| 22-6 | 22 | CCAGGACTTATTGAGAAGGAAATGT | 37 | SEQ ID NO. 121 |
| 22-7 | 22 | AAGCAGTGTTCAAATCTCACCCTCT | 63 | SEQ ID NO. 122 |
| 23-1 | 23 | ATCCAGTTCTTCCCAAGAGGCCCAC | 0 | SEQ ID NO. 123 |
| 23-2 | 23 | AGCTGATAACAAAGTACTCTTCCCT | 0 | SEQ ID NO. 124 |
| 23-3 | 23 | AAGTTATTGAATCCCAAGACACACC | 0 | SEQ ID NO. 125 |
| 23-4 | 23 | CTAAGTCCTTTTGCTCACCTGTGGT | 24 | SEQ ID NO. 126 |
| 24-1 | 24 | GATCACTCCACTGTTCATAGGGATC | 59 | SEQ ID NO. 127 |
| 24-2 | 24 | CTCATCTGCAACTTTCCATATTTCT | 53 | SEQ ID NO. 128 |
| 24-3 | 24 | ATTTCAGTTAGCAGCCTTACCTCAT | 66 | SEQ ID NO. 129 |

* percent of the mRNA transcripts that skip out the targeted exon

Example 3: HCAI-CFTR Deletions in Fischer Rat Thyroid Cells

Figure 18A:
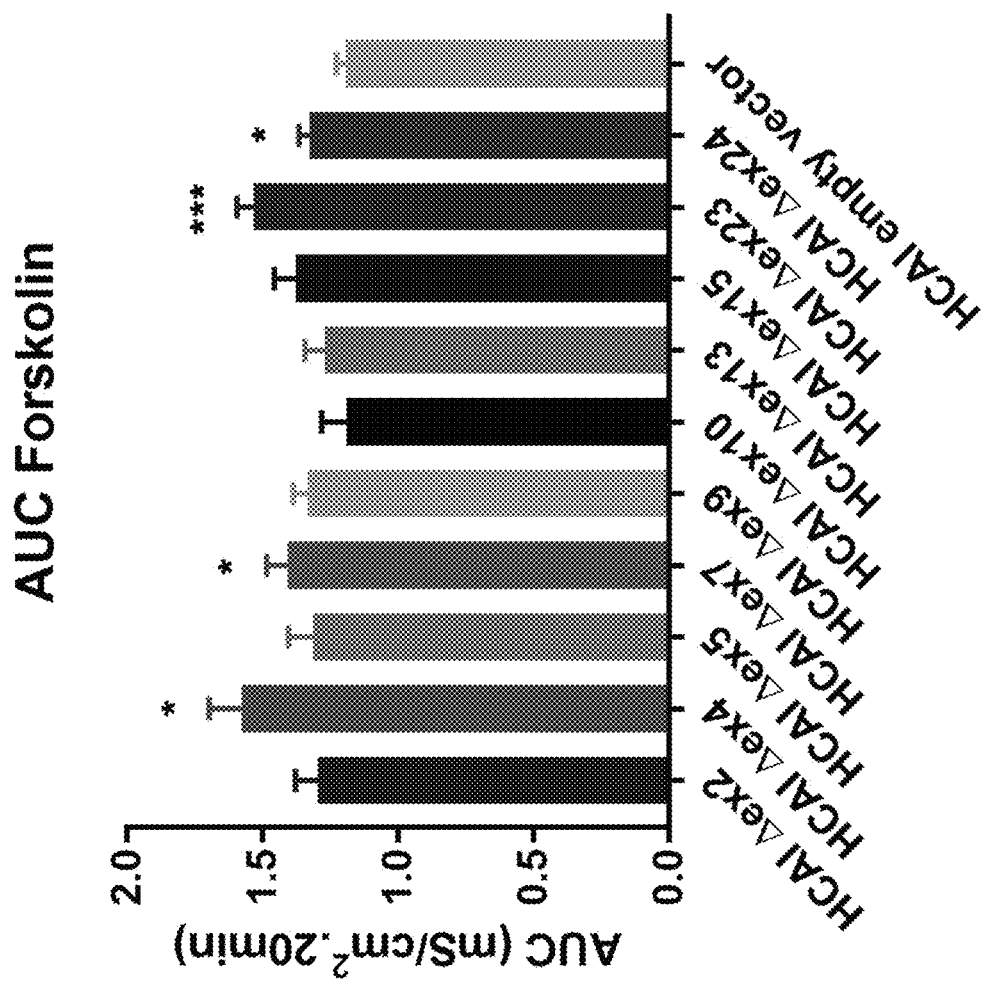
FIG. 18A shows a comparison of the AUC forskolin-stimulated HCAI-CFTR exon deletion channel activity in Fischer Rat Thyroid (FRT) cells to HCAI empty vector. Error bars represent SEM (*r.05, ***r.001, n=4, two-tailed t-test compared to HCAI empty vector).
Figure 18B:
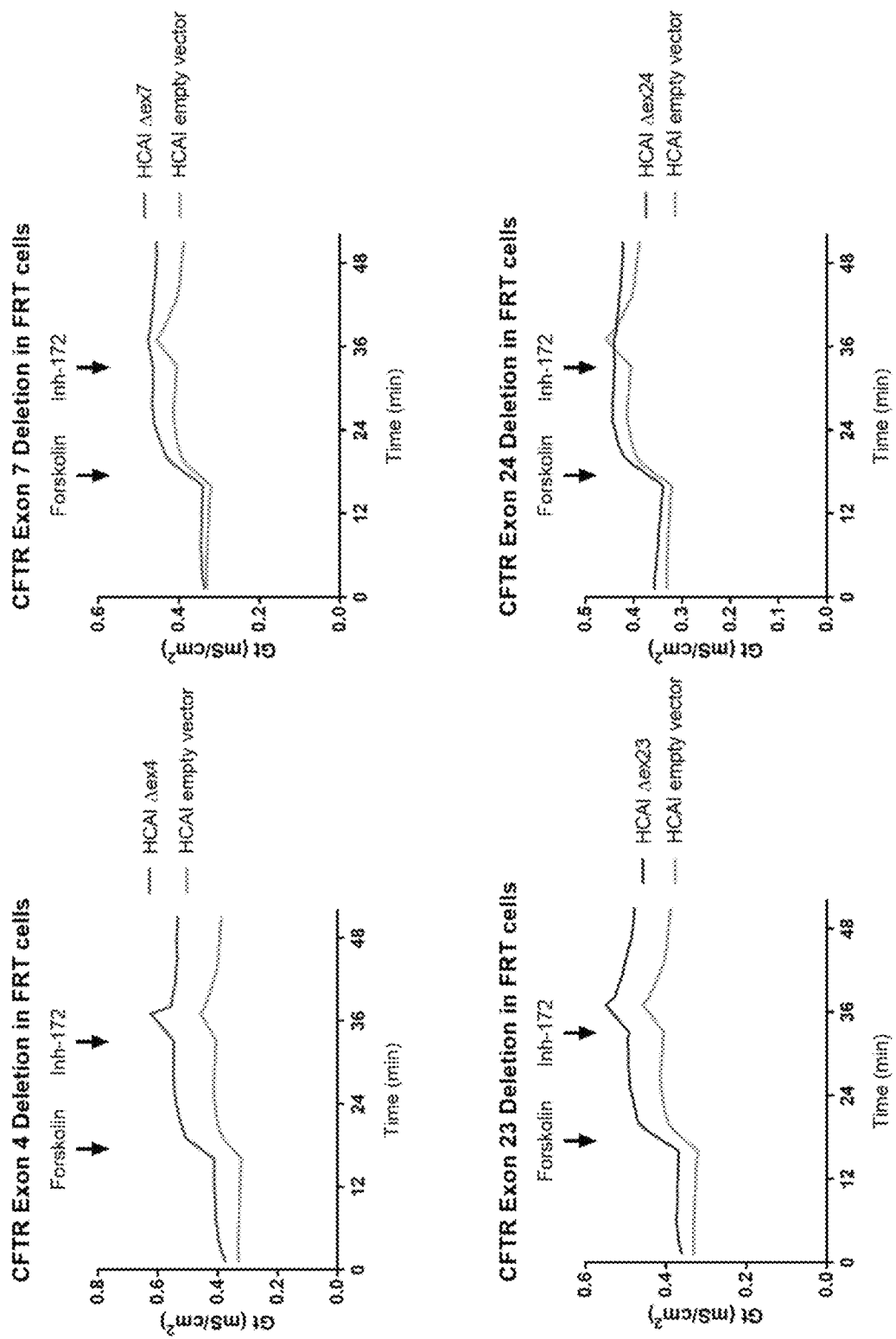
FIG. 18B shows representative Gt traces of CFTR exon 4, exon 7, exon 23, and exon 24 deletion constructs in Fischer Rat Thyroid (FRT) cells in comparison to HCAI empty vector.

Fischer Rat Thyroid (FRT) cells, which lack functional CFTR, were stably transfected with nucleic acids encoding human CFTR with deletions of exon 2, 4, 5, 7, 9, 10, 13, 15, 23, or 24 (HCAIΔex2, HCAIΔex4, HCAIΔex5, HCAIΔex7, HCAIΔex9, HCAIΔex10, HCAIΔex13, HCAIΔex15 HCAIΔex23, or HCAIΔex24). FRT cells stably the HCAI-CFTR exon deletions were seeded onto HTS Transwell®-24 well permeable filter plates (0.4 µM pore size, Polyester, Corning) and differentiated for 2 weeks. Transepithelial conductance was assessed in Gt assays that were performed 14 days after cell seeding. The data were recorded with 24-channel transepithelial current clamp (TECC) Robot system (Design, Belgium). HCAI-CFTR activity was measured by the change in Gt upon stimulation with forskolin (10 µM). CFTRInh-172 (10 µM) was used to confirm CFTR dependence. A comparison of the AUC forskolin-stimulated HCAI-CFTR exon deletion channel activity to HCAI empty vector is shown in FIG. 18A (error bars represent SEM; *p<0.05, ***r.001, n=4, two-tailed t-test compared to HCAI empty vector). Representative Gt traces of CFTR exon 4, exon 7, exon 23, and exon 24 deletion constructs in comparison to HCAI empty vector are shown in FIG. 18B.

Figure 19A:
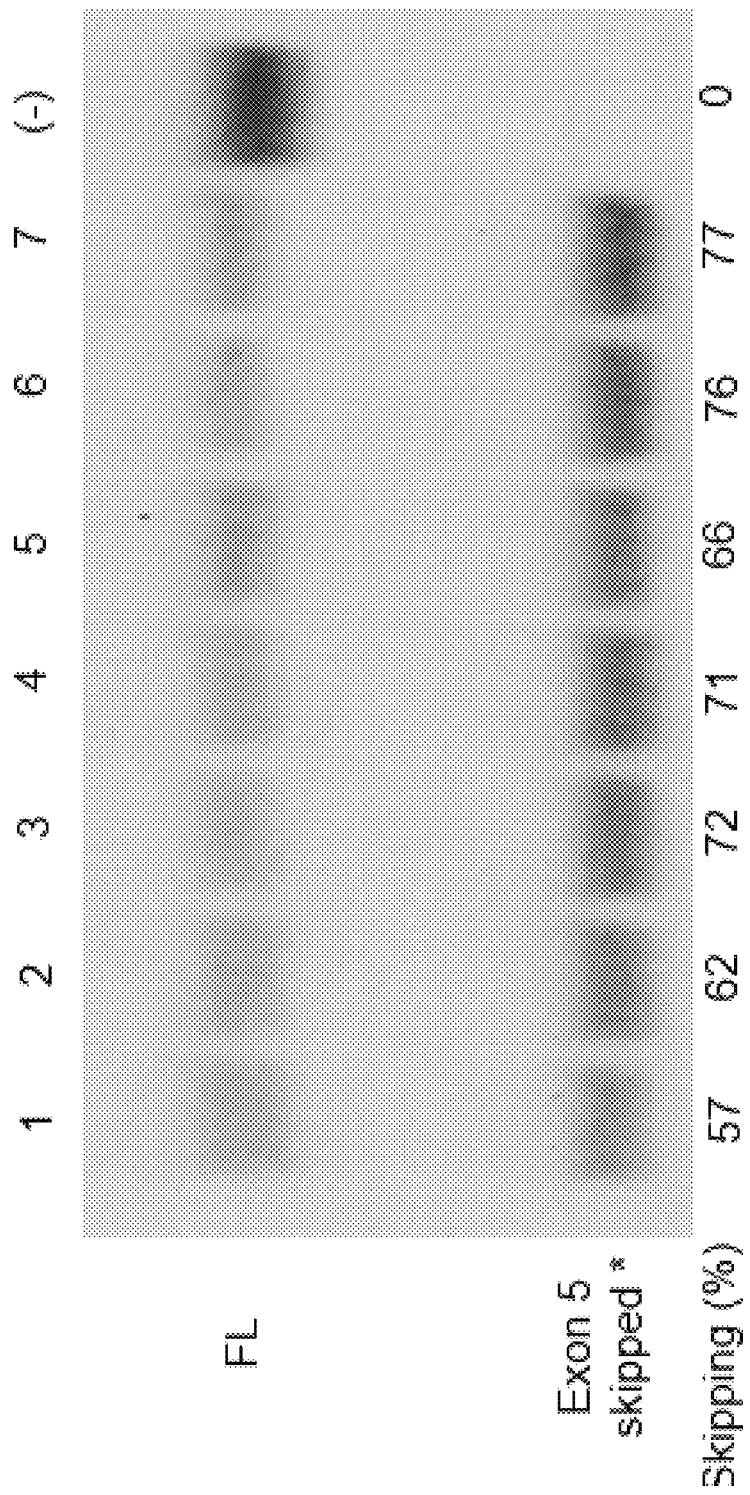
FIG. 19A shows a radioactive RT-PCR of CFTR RNA isolated from hippocampus that demonstrates that ASO 5-1 induces CFTR exon 5 skipping in vivo. Splice isoforms are labeled and exon 5 skipping quantification is shown at the bottom.
Figure 19B:
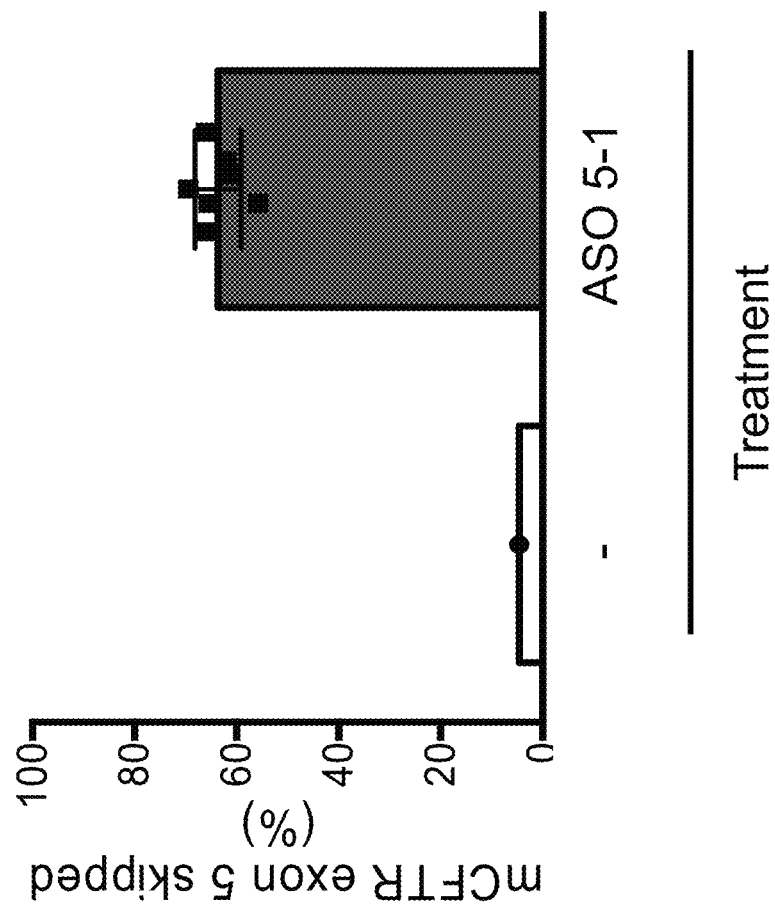
FIG. 19B shows a quantitation of the RT-PCR analysis of the RNA exon 5 skipping induced by ASO treatment. Approximately 60% of mouse CFTR gene exon 5 is skipped when mice are treated with ASO 5-1 by ICV injection.

Example 4: Antisense Oligonucleotides Induce Exon Skipping of Exons with Nonsense Mutations in CFTR In Vivo and Restore the CFTR Reading Frame ASO 5-1 (SEQ ID NO:12) was tested in mice and shown to induces CFTR exon 5 skipping. Intracerebroventricular (ICV) injection of mCFex5-1 was performed in wild-type mice (C57BI/6) on post-natal day 2, and mice were euthanized on post-natal day 12. RNA was collected from the hippocampus. Radioactive RT-PCR of CFTR RNA isolated from hippocampus is shown in FIG. 19A (splice isoforms are labeled and exon 5 skipping quantification is shown at the bottom). A quantitation of the RT-PCR analysis of the RNA exon 5 skipping induced by ASO 5-1 treatment is shown in FIG. 19B.

Figure 20A:
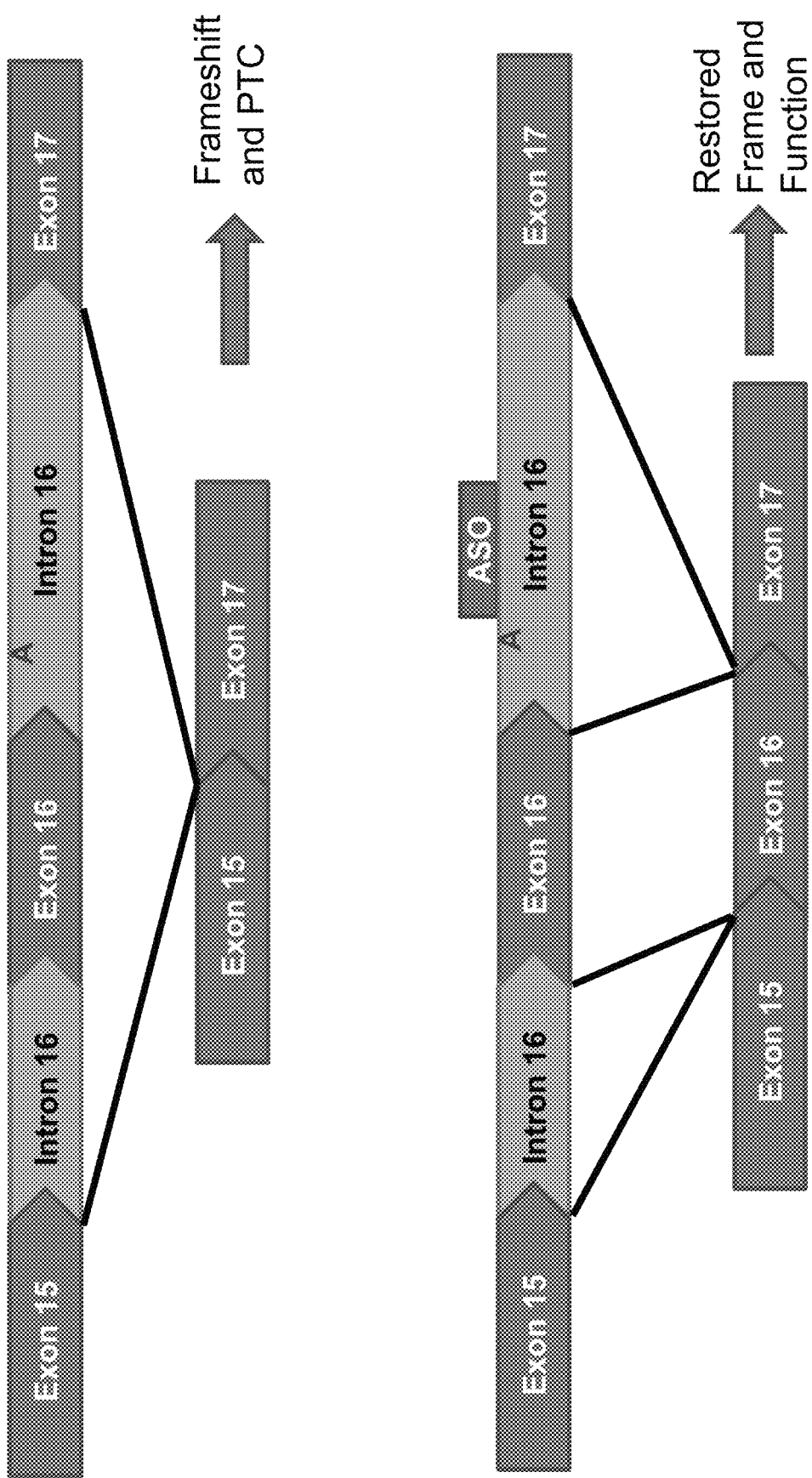
FIG. 20A shows a schematic for antisense oligonucleotides to correct CFTR 2789+5 G>A splicing mutation.
Figure 20B:
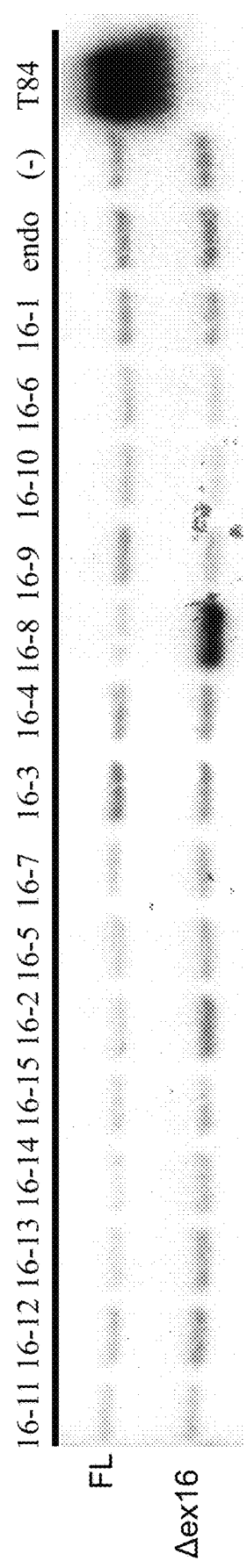
FIG. 20B shows a radioactive RT-PCR of CFTR RNA isolated from 2789+5 patient lymphoblast cells transfected with ASOs (15 μM) for 48 hours. The results demonstrate correction of CFTR splicing in 2789+5 patient lymphoblast cells using ASOs. The CFTR spliced isoforms are labelled. T84 cells were analyzed as a positive control for wild-type CFTR splicing.
Figure 20C:
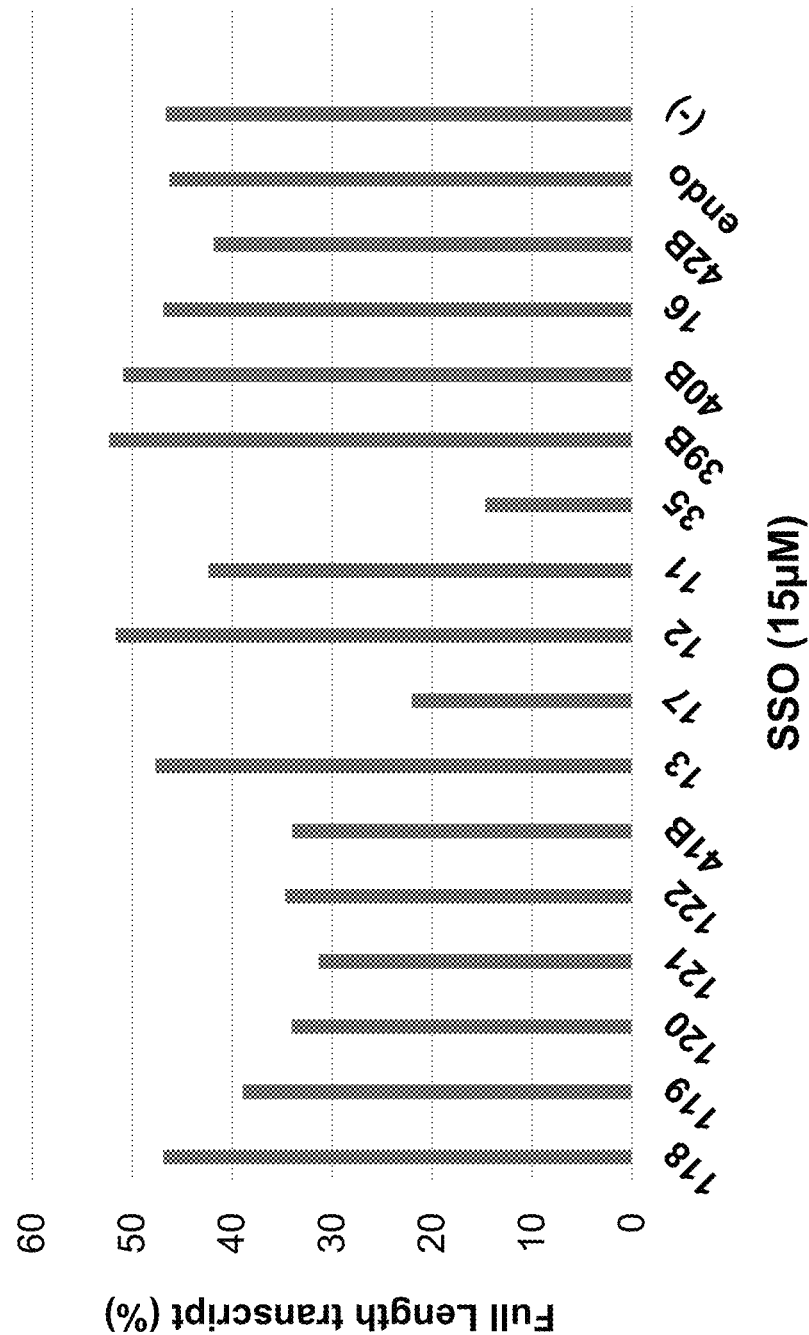
FIG. 20C shows a quantitation of the RT-PCR analysis of the RNA splice correction induced by ASO treatment in patient lymphoblast cells.

Example 5: Antisense Oligonucleotides to Correct CFTR 2789+5 G>A Splicing Mutation Antisense oligonucleotides were designed that increase correct splicing in 2789+5 G>A in patient lymphoblast cells lines. The lymphoblast cell line 11859, which is homozygous for the 2789+5 G>A mutation, was transfected with ASOs that were designed to correct the splicing in CFTR 2789+5 G>A (ASO concentration of 15 µM; and cells were treated for 48 hours). Correction of CFTR splicing in 2789+5 the lymphoblasts using ASOs is shown in FIG. 20B (CFTR spliced isoforms are labeled; T84 cells were analyzed as a positive control for wild-type CFTR splicing). A quantitation of the RT-PCR analysis of the RNA splice correction induced by ASO treatment in patient lymphoblast cells is shown in FIG. 20C. A summary of the 2789+5 ASOs targets, sequences, and correction activity in patient lymphoblast cells is shown in Table 3.

TABLE 3

ASO sequences tested in the 2789 +5 lymphoblast cell line.

| Name | Target Region | Sequence (SEQ ID NO.) | % Full Length |
|---|---|---|---|
| 16-11 | Intron 15 | GACTTTTTTTCTAACATCTTCACCT (SEQ ID NO.: 105) | 47 |
| 16-12 | Intron 15 | ATGGAACAACACACAGTTGATTTTT (SEQ ID NO.: 106) | 39 |
| 16-13 | Intron 15 | ATCGAACAAGACACAGTTGATTTTT (SEQ ID NO.: 107) | 34 |
| 16-14 | Intron 15 | GAGTGGAACAAGACACAGTTGATTT (SEQ ID NO.: 108) | 31 |
| 16-9 | Exon 16 | CACAATCTACACAATAAGACATGGA (SEQ ID NO.: 109) | 35 |
| 16-2 | Exon 16 | GAGCCACAGCACAACCAAAGAAGCA (SEQ ID NO.: 96) | 34 |
| 16-5 | Exon 16 | TTCCAAGGAGCCACAGCACAACCAA (SEQ ID NO.: 99) | 48 |

TABLE 3-continued

ASO sequences tested in the 2789 +5 lymphoblast cell line.

| Name | Target Region | Sequence (SEQ ID NO.) | % Full Length |
|---|---|---|---|
| 16-7 | Exon 16 | TTTCCAAGGAGCCACAGCACAACCA (SEQ ID NO.: 101) | 22 |
| 16-3 | Exon 16 | TCCAAGGAGCCACAGCAC (SEQ ID NO.: 97) | 52 |
| 16-4 | Exon 16 | TTCCAAGGAGCCACAGCA (SEQ ID NO.: 98) | 42 |
| 16-8 | Intron 16 | ACAATCTACACAATAGGACATGGAA (SEQ ID NO.: 102) | 15 |
| 16-9 | Intron 16 | CACAATCTACACAATAGGACATGGA (SEQ ID NO.: 103) | 52 |
| 16-10 | Intron 16 | ACACAATCTACACAATAGGACATGG (SEQ ID NO.: 104) | 51 |
| 16-6 | Intron 16 | AACAGAAATAAAACACAATCTACAC (SEQ ID NO.: 100) | 47 |
| 16-1 | Intron16 | TCGTTATTTGGCAGCCAAAGTTACT (SEQ ID NO.: 95) | 42 |

Figure 21A:
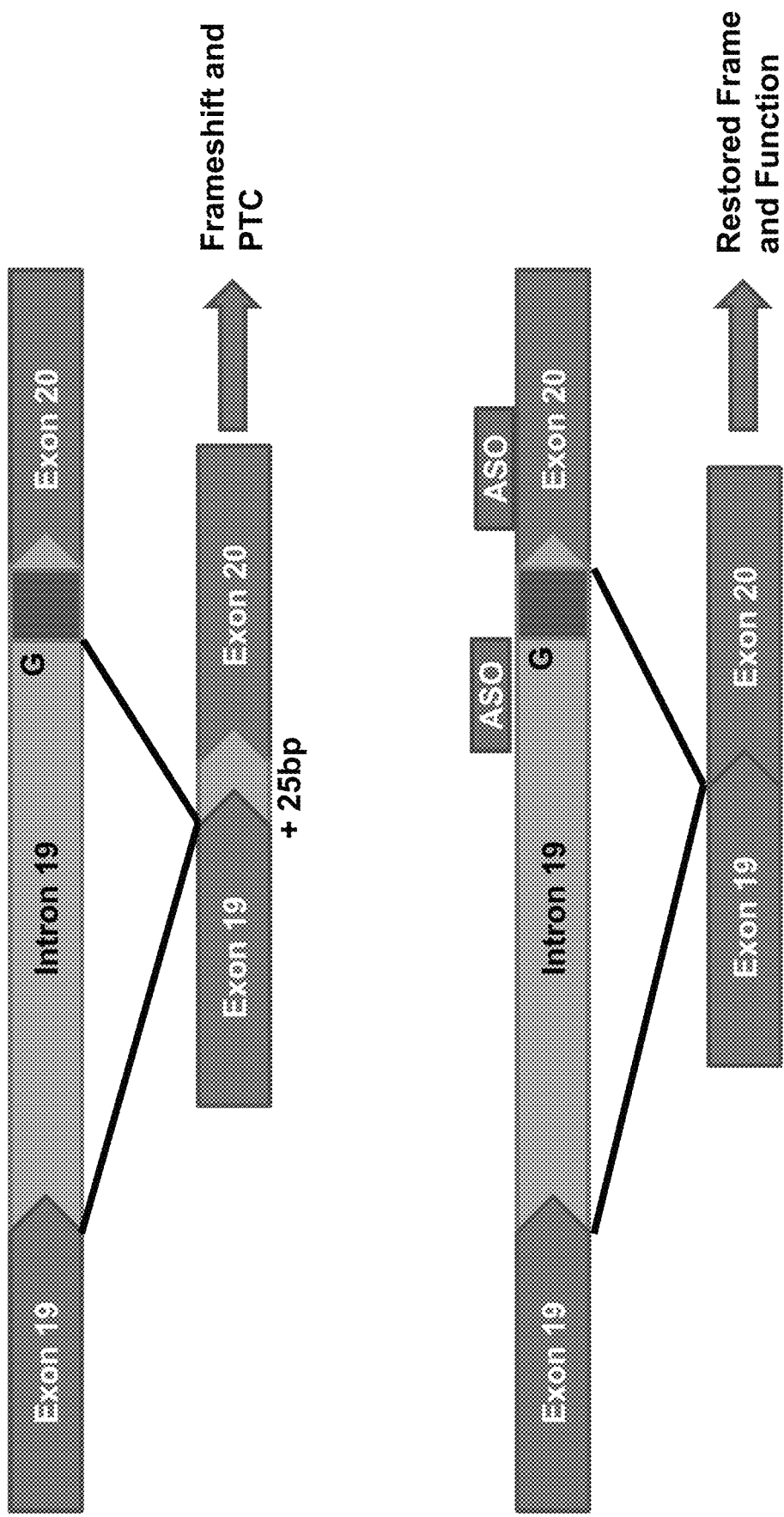
FIG. 21A shows a schematic for antisense oligonucleotides to correct CFTR 3272-26A>G splicing mutation.
Figure 21B:
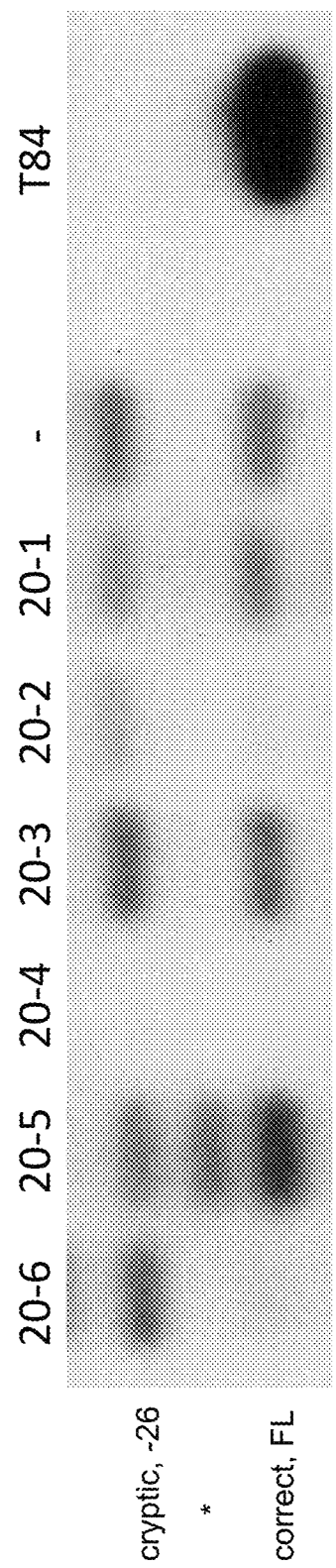
FIG. 21B shows a radioactive RT-PCR of CFTR RNA isolated from 3272-26A>G patient lymphoblast cells transfected with ASOs (15 μM) for 48 hours. The results demonstrate correction of CFTR splicing in 3272-26A>G patient lymphoblast cells using ASOs. The CFTR spliced isoforms are labelled. T84 cells were analyzed as a positive control for wild-type CFTR splicing.

Example 6: Antisense Oligonucleotides to Correct CFTR 3272-26 A>G Splicing Mutation Antisense oligonucleotides were designed that increase correct splicing in 3272-26 A>G mutation in patient lymphoblast cell lines. The lymphoblast cell line 18801 (18801 is from a male donor with one allele carrying the 3272-26 A>G mutation, and no mutation was identified in the second allele) was transfected with ASOs that were designed to correct splicing in CFTR 3272-26 A>G (ASOs were transfected with Endo-Porter, the ASO concentration was 15 µM, and cells were treated for 48 hours). Correction of CFTR splicing in CFTR 3272-26 A>G in the lymphoblast cells using ASOs is shown in FIG. 21B (CFTR spliced isoforms are labeled; T84 cells were analyzed as a positive control for wild-type CFTR splicing). A summary of the CFTR 3272-26 A>G ASOs targets, sequences, and correction activity in patient lymphoblast cells is shown in Table 4.

| Name | Target Exon | Sequence (SEQ ID NO.) | % Full-Length |
|---|---|---|---|
| 20-1 | 20 | CAAGATGAGTGAAAATTGGACTCCT (SEQ ID NO.: 110) | 60 |
| 20-2 | 20 | CGAAGGCACGAAGTGTCCATAGTCC (SEQ ID NO.: 111) | 3 |
| 20-3 | 20 | AACAGAGTTTCAAAGTAAGGCTGCC (SEQ ID NO.: 112) | 50 |
| 20-4 | 20 | AGTTGGCAGTATGTAAATTCAGAGC (SEQ ID NO.: 113) | nd |
| 20-5 | 20 | TTCTATTCTCATTTGGAACCAGCGC (SEQ ID NO.: 114) | 56 |
| 20-6 | 20 | GGTAACAGCAATGAAGAAGATGACA (SEQ ID NO.: 115) | 12 |

Figure 22A:
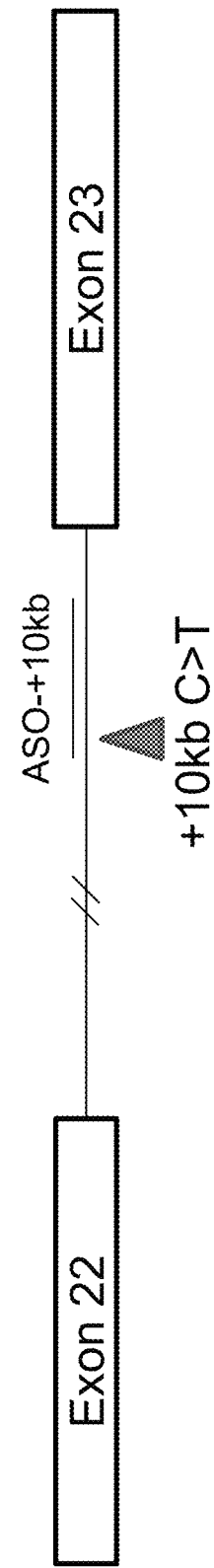
FIG. 22A shows a diagram of ASOs used for the correction of CFTR splicing in 3849+10kb patient lymphoblast cells using ASOs. The +10C>T mutation is labeled.
Figure 22B:
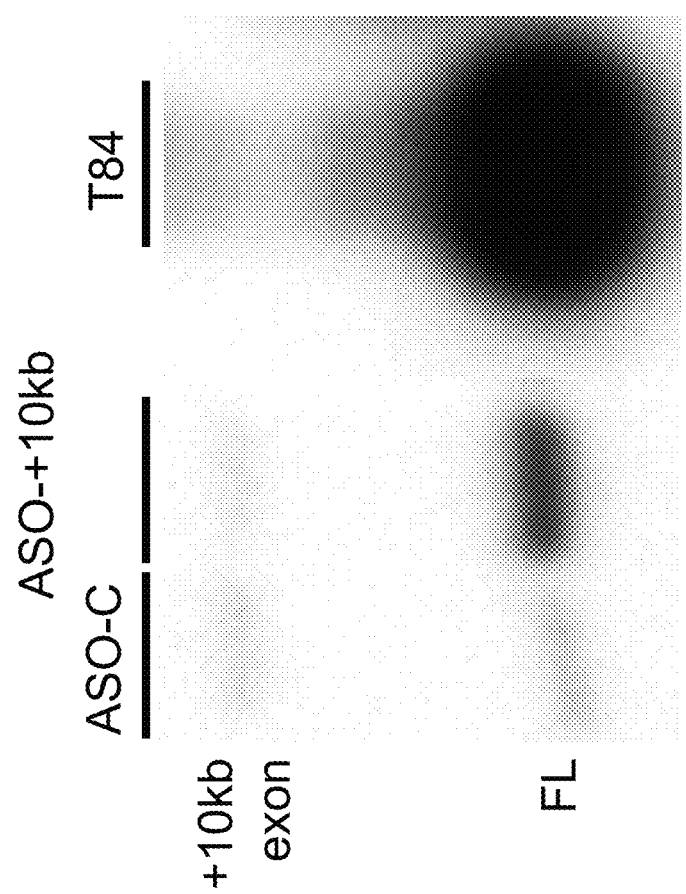
FIG. 22B shows the results of a RT-PCR assay of CFTR RNA isolated from 3849+10kb patient lymphoblast cells transfected with ASOs (15 µM) for 48 hours. Results indicate a correction of CFTR splicing in 3849+10kb patient lymphoblast cells using the ASOs. CFTR spliced isoforms are labeled. T84 cells were analyzed as a positive control for wild-type CFTR splicing (FL=Full-Length).
Figure 22C:
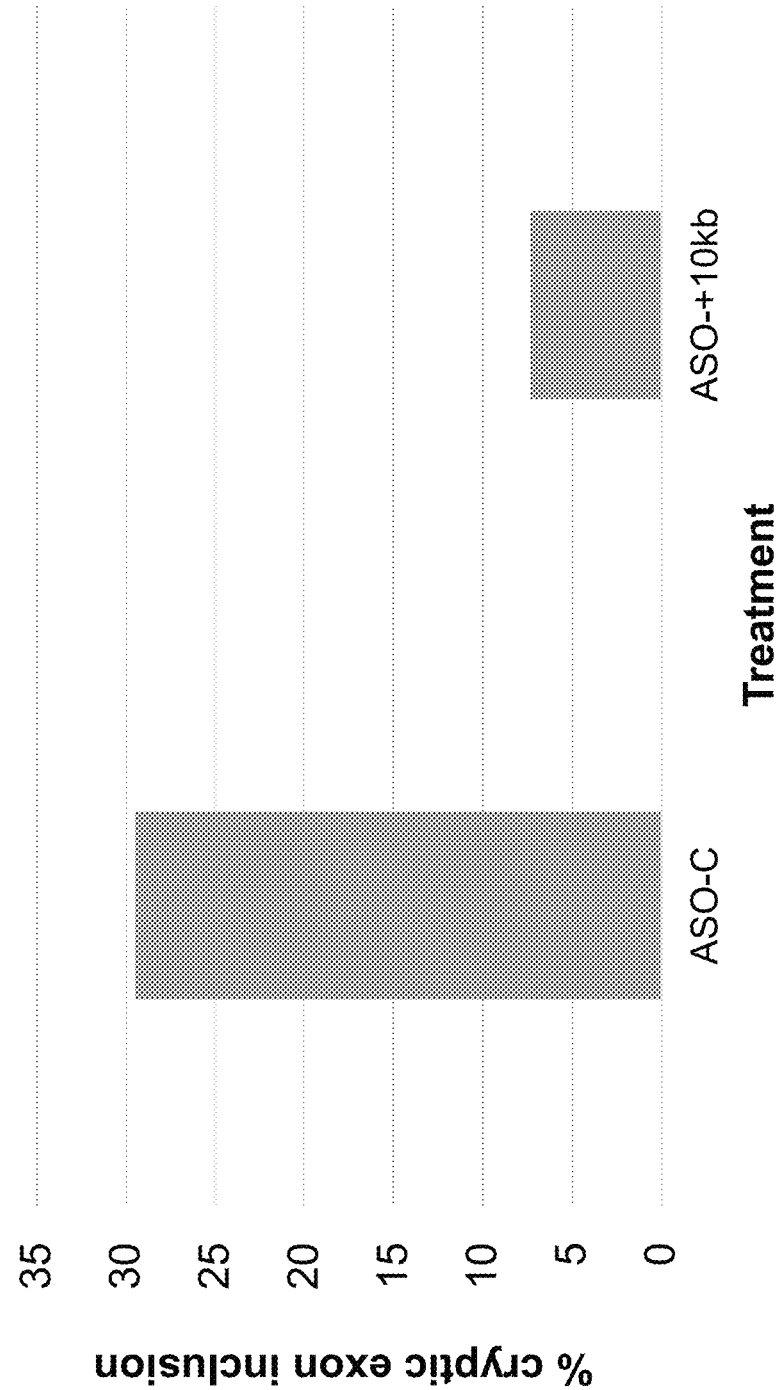
FIG. 22C shows a quantitation of the RT-PCR analysis of the RNA splice correction induced by ASO treatment in patient lymphoblast cells. The results indicate about a four-fold reduction of inclusion of the cryptic exon, resulting in approximately 93% of the CFTR transcripts being full-length.

Example 7: Antisense Oligonucleotides to Correct CFTR 3849+10kb C>T Splicing Mutation Antisense oligonucleotides were designed to repair the 3849+10kb C>T splice mutation and restore CFTR function. The C>T mutation creates a cryptic 5' splice site that results in the inclusion of an 84 bp insert from intron 22, and the mutated allele produces both wild-type and aberrantly spliced transcripts. The lymphoblast cell line 18860 (18860 is homozygous for 3849+10kb CFTR mutation) was transfected with ASOs that were designed to correct splicing in 3849+10kb C>T (ASOs were transfected with Endo-Porter, the ASO concentration was 15 µM, and cells were treated for 48 hours). Correction of CFTR splicing in 3849+10kb C>T in the lymphoblast cells using ASOs is shown in FIGS. 22B and 22C (CFTR spliced isoforms are labeled; T84 cells were analyzed as a positive control for wild-type CFTR splicing). A summary of the CFTR 3849+10kb C>T ASO target, sequence, and correction activity in patient lymphoblast cells is shown in Table 5.

| Name | Target Exon | Sequence (SEQ ID NO.) | % Full-Length |
|---|---|---|---|
| ASO-+10 kb | Intron 22 | CCTTTCAGGGTGTCTTACTCACCAT (SEQ ID NO.: 150) | 93 |

Example 8. Analyzing CFTR Function in Patient Epithelial Cells Treated with ASOs Primary patient human bronchial epithelial (HBE) cells (cells are compound heterozygotes with the 3849+10kbC>T and ΔF508 mutation) were seeded on HTS Transwell®-24 well permeable filter plates (0.4 uM pore size, Polyester, Corning) and switched to air/liquid interphase after 3 days. Ieq measurements were carried out 99 days after seeding. Cells were treated basolaterally with C18 (Corr951/VX-661, 6 µM) or DMSO (0.1%), and apically transfected with ASO-+10kb (SEQ ID NO:150 at 20 µM or 80 µM) or ASO-C (20 µM or 80 µM; 5' CCTCTTACCTCAGTTA-CAATTTATA 3'-SEQ ID NO:151) 4 days before Ieq measurements were taken. C18 is a corrector compound that improves F508del-CFTR folding and function. Cells were transfected using EGTA (4 mM) and Endo-Porter (Gene-Tools) for 10 hours, then EGTA was taken off and the cells were transfected again using Endo-Porter in the absence of EGTA. The data were recorded with 24-channel transepithelial current clamp (TECC) Robot system (Design, Belgium). Sodium current was inhibited by benzamil (6 µM) and CFTR activity was measured by the change in Ieq upon stimulation with forskolin (10 µM) and VX-770/KALY-DECO™/Ivacaftor (1 µM), which is a CFTR potentiator that improves the transport of chloride through the CFTR channel. Inhibition with bumetanide/BUMEX™/BURINEX™ (20 µM) was used to confirm CFTR dependence.

Figure 23A:
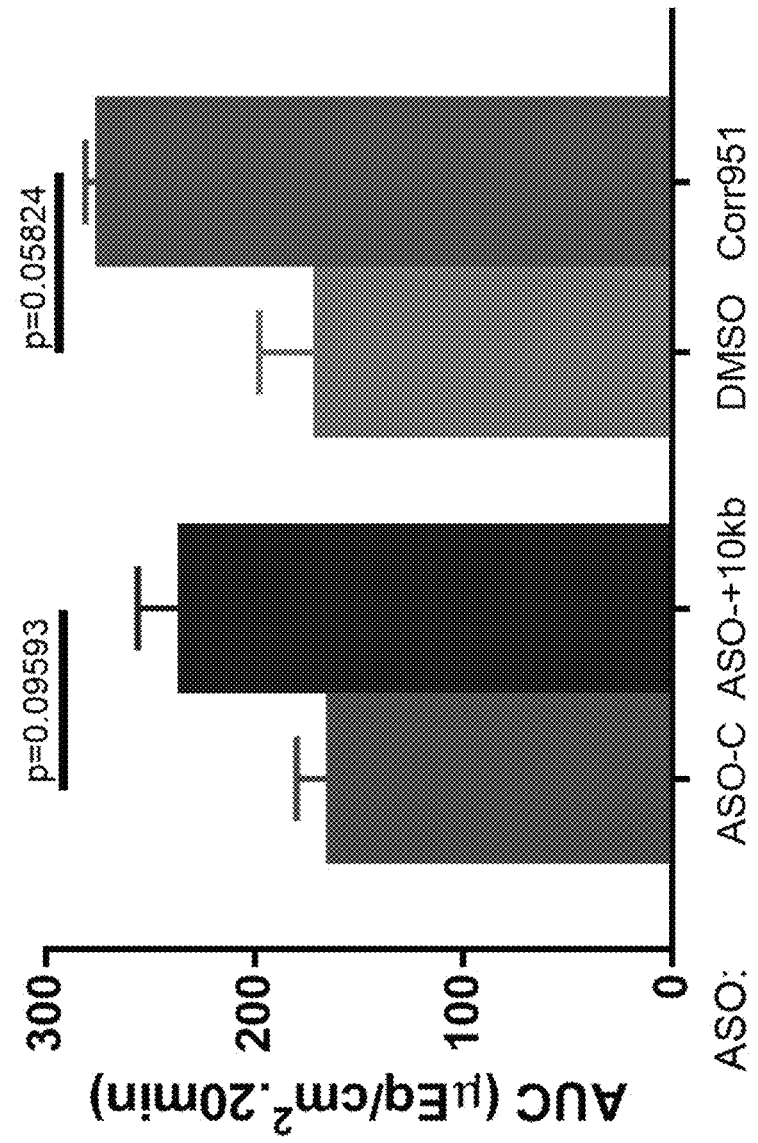
FIG. 23A shows that ASO-+10kb rescues CFTR function similar to Corr951(VX-770) in patient HBE cells. The graph depicts the area under the curve (AUC) of time from forskolin+VX-770-stimulation of CFTR channels following indicated treatment. Error bars represent SEM (two-tailed t-test, n=2).

The results demonstrate that ASO-+10kb (SEQ ID NO:150) rescues CFTR function similar to Corr951/VX-661 (CFTR corrector 106951 (1-(benzo[d][1,3]dioxol-5-yl)-N-(5-((S)-(2-chlorophenyl)((R)-3-hydroxypyrrolidin-1-yl) methyl)thiazol-2-yl)cyclopropanecarboxamide)) in patient HBE cells. As shown in FIG. 23, ASO-+10kb rescues CFTR function similar to Corr951 in patient HBE cells. FIG. 23A is a graph showing the area under the curve (AUC) of time from forskolin+VX-770-stimulation of CFTR channels following indicated treatment (error bars represent SEM; two-tailed t-test, n=2). FIG. 23B depicts representative Ieq traces of treatment (Corr951 or ASO-+10kb) compared to control (ASO-C, top, or DMSO, bottom).

Figure 24A:
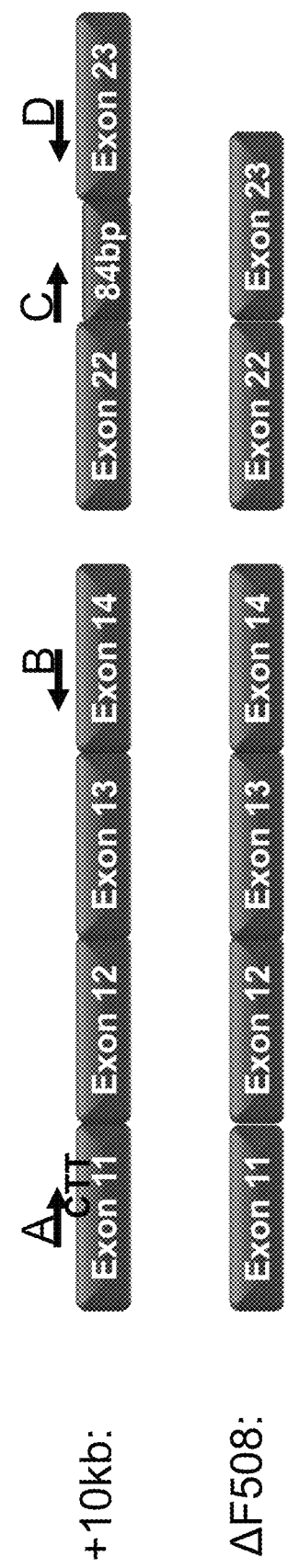
FIG. 24A shows a diagram of primer sets used to analyze splice correction by ASO-10+kb. Primer set A-B is designed to amplify ASO corrected WT isoform splicing specific to the splice mutant allele. Primer set C-D is designed to analyze the amount of uncorrected mutant splicing FIG. 24B show a quantification of total mRNA transcribed from the CFTR 3849+10 kB allele indicates an increase with ASO-+10kb treatment (A-B primer set shown in FIG. 24A).
Figure 24B:
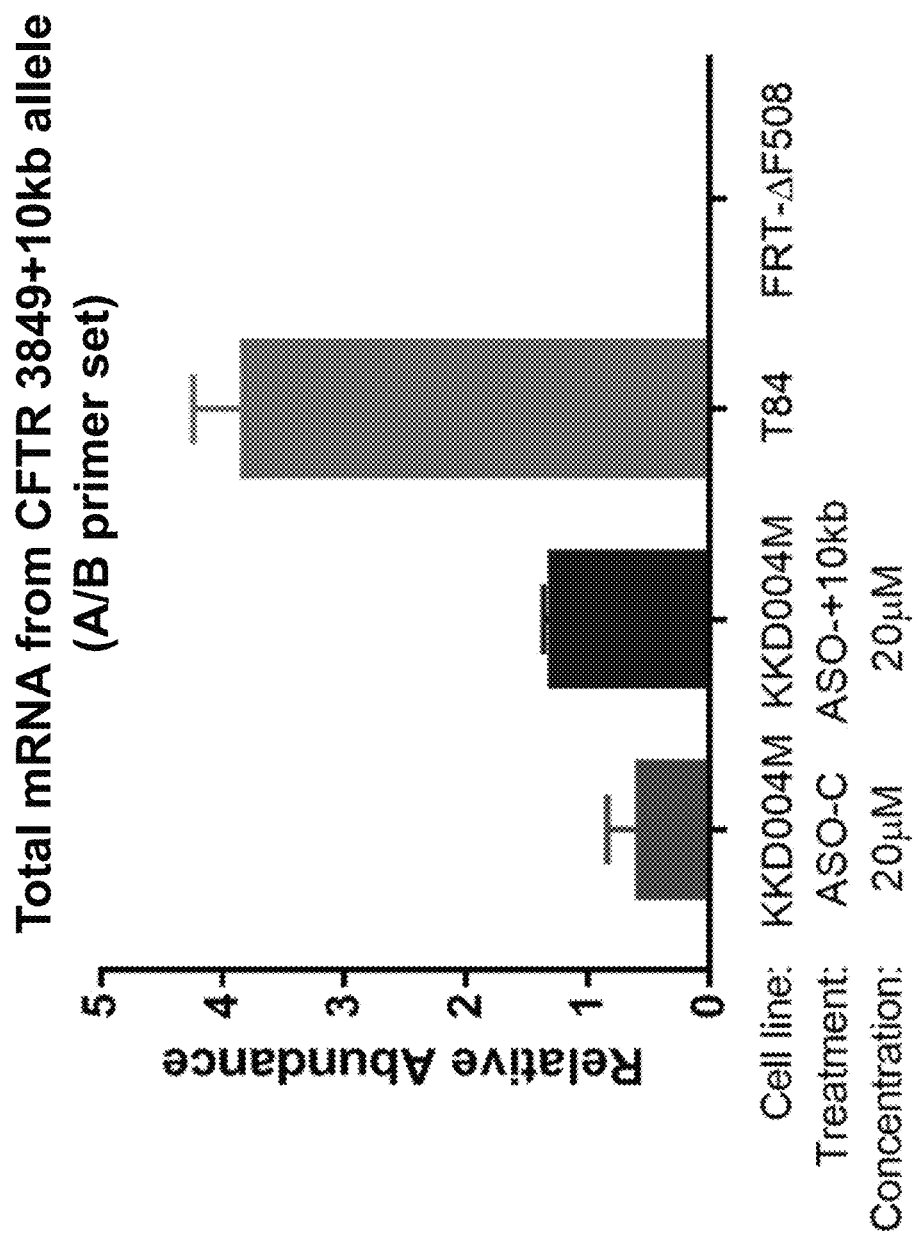
FIG. 24C shows a quantification of mutant, cryptically spliced mRNA isoform shows decrease of aberrant mRNA with ASO-+10kb treatment (C-D primer set shown in FIG. 24A).
Figure 24C:
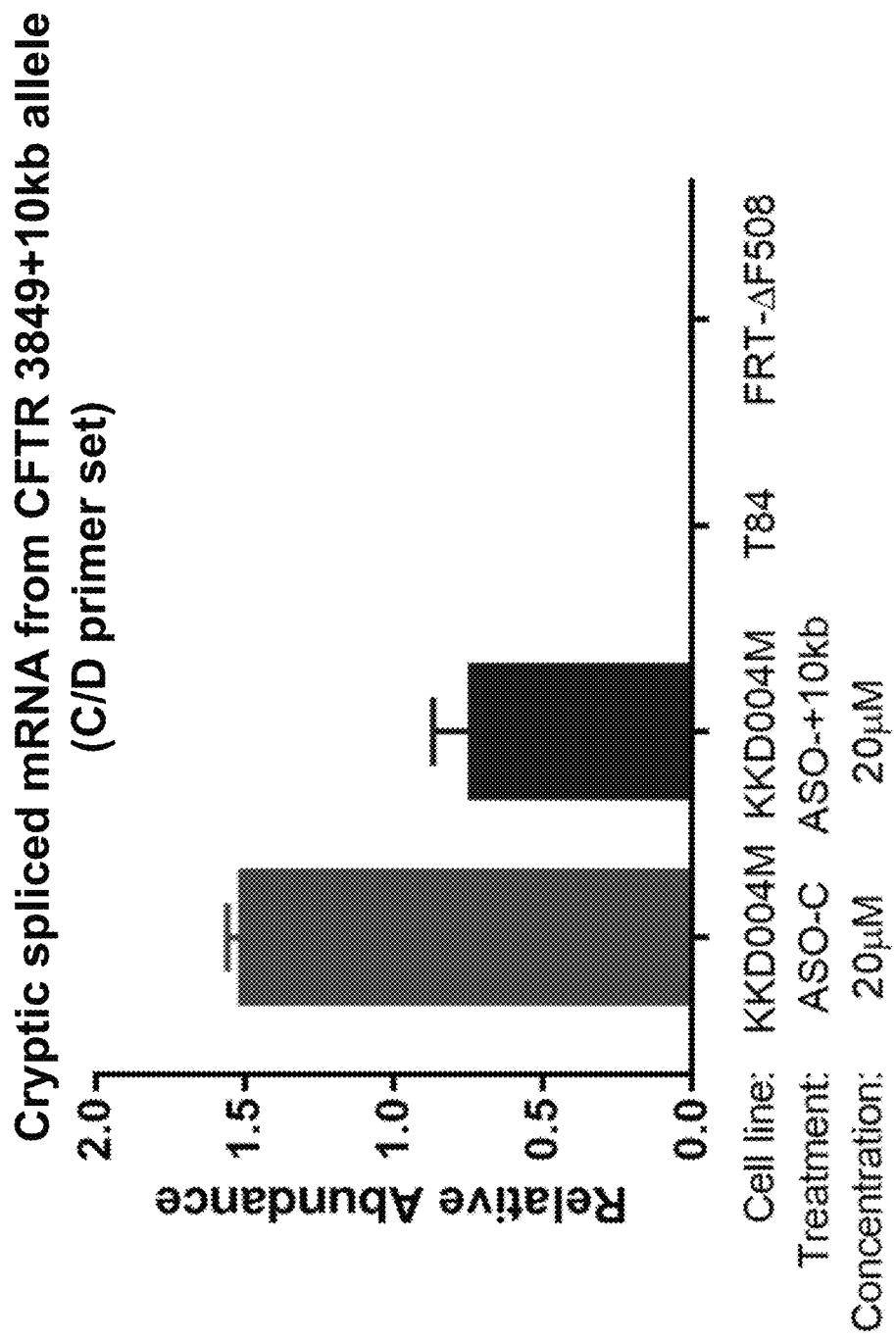

Additionally, the results show that ASO-+10kb (SEQ ID NO:150) increases WT splicing in 3849+10kb patient HBE cells. Primary patient HBE cells are heterozygous for the 3849+10kbC>T mutation were transfected with ASO-+10kb (20 uM). Total mRNA was isolated, reverse transcribed, and analyzed for splice correction using SYBER™ Green quantitative PCR. FIG. 24A depicts the primer sets used to analyze splice correction by ASO-10+kb (primer set A-B is designed to amplify ASO corrected WT isoform splicing specific to the splice mutant allele, and primer set C-D is designed to analyze the amount of uncorrected mutant splicing). FIG. 24B shows a quantification of total mRNA transcribed from the CFTR 3849+10 kB allele, and indicates an increase with ASO-+10kb treatment (A-B primer set). FIG. 24C shows a quantification of mutant, cryptically spliced mRNA isoform, and shows decrease of aberrant mRNA with ASO-+10kb treatment (C-D primer set).

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A compound comprising a modified oligonucleotide of 21 to 30 linked nucleosides and having a nucleobase sequence comprising at least 21 nucleosides of the sequence of SEQ ID NO:126, wherein the modified oligonucleotide comprises at least 21 contiguous nucleobases and is at least 80% complementary to an equal-length portion of a target region of a cystic fibrosis transmembrane conductance regulator (CFTR) transcript.

2. The compound of claim 1, wherein the modified oligonucleotide is at least 90% complementary to an equal-length portion of the target region.

3. The compound of claim 1, wherein the modified oligonucleotide is at least 95% complementary to an equal-length portion of the target region.

4. The compound of claim 1, wherein the modified oligonucleotide is 100% complementary to an equal-length portion of the target region.

5. The compound of claim 1, wherein the nucleobase sequence of the modified oligonucleotide comprises SEQ ID NO:126.

6. The compound of claim 1, wherein the modified oligonucleotide comprises at least one modified nucleoside selected from a modified sugar moiety, a 2'-substituted sugar moiety, a 2'OME, a 2'F, a 2'-MOE, a bicyclic sugar moiety, a LNA, a cEt, a sugar surrogate, a morpholino, or a modified morpholino.

7. The compound of claim 1, wherein the modified oligonucleotide comprises at least 5 to at least 25 modified nucleosides, each independently comprising a modified sugar moiety.

8. The compound of claim 7, wherein each nucleoside of the modified oligonucleotide is a modified nucleoside, each independently comprising a modified sugar moiety.

9. The compound of claim 1, wherein the modified oligonucleotide comprises at least two modified nucleosides comprising modified sugar moieties that are the same as one another or that are different from one another.

10. The compound of claim 1, wherein the modified oligonucleotide comprises a modified region of at least 5 to at least 20 contiguous modified nucleosides.

11. The compound of claim 10, wherein each modified nucleoside of the modified region has a modified sugar moiety independently selected from: 2'-F, 2'-OMe, 2'-MOE, cEt, LNA, morpholino, and modified morpholino.

12. The compound of claim 10, wherein the modified nucleosides of the modified region each comprise the same modification as one another.

13. The compound of claim 12, wherein the modified nucleosides of the modified region each comprise the same 2'-substituted sugar moiety selected from: 2'-F, 2'-OMe, and 2'MOE.

14. The compound of claim 12, wherein the modified nucleosides of the region of modified nucleosides each comprise the same bicyclic sugar moiety selected from: LNA and cEt.

15. The compound of claim 12, wherein the modified nucleosides of the region of modified nucleosides each comprises a sugar surrogate, and wherein the sugar surrogate of the modified nucleosides of the region of modified nucleosides is a morpholine.

16. The compound of claim 1, wherein the modified nucleotide comprises no more than 4 contiguous naturally occurring nucleosides.

17. The compound of claim 1, wherein the modified oligonucleotide comprises at least one modified internucleoside linkage.

18. The compound of claim 17, comprising at least one phosphorothioate internucleoside linkage.

19. The compound of claim 17, wherein each internucleoside linkage is a modified internucleoside linkage and wherein each internucleoside linkage comprises the same modification.

20. The compound of claim 19, wherein each internucleoside linkage is a phosphorothioate internucleoside linkage.

21. The compound of claim 1, comprising at least one conjugate.

22. The compound of claim 1, wherein the compound modulates splicing or expression of the MR transcript.

23. A pharmaceutical composition comprising at least one compound according to claim 1 and a pharmaceutically acceptable carrier or diluent.

24. The pharmaceutical composition of claim 23, further comprising one or more antisense compounds.

25. A method of modulating splicing or expression of a CFTR transcript in a cell comprising contacting the cell with at least one compound according to claim 1.

26. The method of claim 25, wherein the cell is in vitro or in vivo.

27. A method of treating cystic fibrosis, comprising administering at least one compound according to claim 1 to an animal in need thereof.

28. A method comprising administering at least one compound according to claim 1 or the pharmaceutical composition of claim 23 to an animal.

29. The method of claim 28, wherein the administering step comprises delivering to the animal by inhalation, parenteral injection or infusion, oral, subcutaneous or intramuscular injection, buccal, transdermal, transmucosal and topical.

30. The method of claim 28, wherein the animal is a human or a mouse.

31. A method of treating cystic fibrosis, comprising administering the pharmaceutical composition of claim 23 to an animal in need thereof.

32. A compound comprising a modified oligonucleotide having 25 to 30 linked nucleosides having a nucleobase sequence comprising SEQ ID NO: 126.

33. A method of treating cystic fibrosis, comprising administering the pharmaceutical composition of claim 24 to an animal in need thereof.

* * * * *

SEQUENCE LISTING

```
<160> NUMBER OF SEQ ID NOS: 151

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1
ggtccagcta aaagagaaga gggca                                       25

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2
ctttcctcaa aattggtgtg gtcca                                       25

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 3
tatgtctgac aactccaagt ggtgt                                       25

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 4 ctagttttc agacaagtgg tcagc                                        25

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
```

```
ttcctagcaa gacaggctgg acagc                                               25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
ataggatgct atgattcttc ctagc                                               25

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7
ataagcctat gccaaggtaa atggc                                               25

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
tgtcctgaca atgaagagaa ggcat                                               25

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 9
aatgcgatga aggccaaaaa tagct                                               25

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10
tagctgttct catctgcatt ccaat                                               25

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11
catcttccaa aaagtattac cttct                                               25

<210> SEQ ID NO 12
<211> LENGTH: 25
<212> TYPE: DNA
<213> ORGANISM: Artificial Sequence
```

```
<220> FEATURE:
<223> OTHER INFORMATION: Synthetic oligonucleotide

<400> SEQUENCE: 12
ttgttcaggt tgttggaaag aagac                                25

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 13
atcaagaacg cggcttgaca acttt                                25

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 14
cacgagtctt tcattgatct ttgca                                25

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 15
ctgattccca acaatatgcc ttaac                                25

<210> SEQ ID NO 16
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 16
caatcatttt ctccatcgct gattc                                25

<210> SEQ ID NO 17
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 17
attatgtcaa cttactctct caagt                                25

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
gcctgtggtc attaagttat actcc                                25
```

```
<210> SEQ ID NO 19
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 19
ctcctcccaa aatgctgtta cattt                                                25

<210> SEQ ID NO 20
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 20
tatttagaaa tctcacctcc tccca                                                25

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 21
ctttctccag taattcccca aatcc                                                25

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 22
gtcaccattg ctttgttgta ctttc                                                25

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 23
ctgaaactga cattgttctc atcac                                                25

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 24
aggatttccc acaaggcaga gatga                                                25

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide
```

<400> SEQUENCE: 25
atagccaaca tctctccttt ctcta					25

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 26
ctttcctgat ccagtagatc cagta					25

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 27
ctttcctgat ccagtagatc cagta					25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 28
tccagttctc ccaaaatcaa catca					25

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 29
tgtgcttaat aattccctct gaagc					25

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 30
attgagagca gaatgaaact cttcc					25

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 31
gatattttct ttgatagtac ccggc					25

<210> SEQ ID NO 32

<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 32
acactcttat atctgtactc atcat                                          25

<210> SEQ ID NO 33
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 33
ctgctgtagt tggcaagctt tgaca                                          25

<210> SEQ ID NO 34
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 34
cataaatatg cttacctgct gtagt                                          25

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 35
gggaatctaa taggtacaaa tcagc                                          25

<210> SEQ ID NO 36
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 36
caaatcagca tctttatata ctgct                                          25

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 37
actcagtcat agaacatacc tttca                                          25

<210> SEQ ID NO 38
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 38
aacaaacata cttacctcaa ccaga                                          25

<210> SEQ ID NO 39
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 39
cctgcctgta aatcatccca tagga                                          25

<210> SEQ ID NO 40
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 40
caaggtgggt gaaaattgga ctcct                                          25

<210> SEQ ID NO 41
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 41
cgaagtgtcc agagtccttt taagc                                          25

<210> SEQ ID NO 42
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 42
cagagtttca aagtaagtct ggcgt                                          25

<210> SEQ ID NO 43
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 43
ttggcagtgt gcaaattcag agctt                                          25

<210> SEQ ID NO 44
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 44
ctattctcat ttggaaccag cgcaa                                          25

<210> SEQ ID NO 45
<211> LENGTH: 25
<212> TYPE: DNA

<213> ORGANISM: Artificial Sequence
<220> FEATURE:
<223> OTHER INFORMATION: Synthetic oligonucleotide

<400> SEQUENCE: 45
agaggacaaa tatcatgtct attct                                    25

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 46
atggagatga aggtaacaac aatga                                    25

<210> SEQ ID NO 47
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 47
aacttaaaca ctctgctcac agatc                                    25

<210> SEQ ID NO 48
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 48
ctaaaacgtc agatgatcct tctct                                    25

<210> SEQ ID NO 49
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 49
tatcactttt cttcacatgc tcatt                                    25

<210> SEQ ID NO 50
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 50
accatttcgc ctccagaggg ccaga                                    25

<210> SEQ ID NO 51
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 51
catccatgta tttcacagta aggtc                                    25

<210> SEQ ID NO 52
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 52
atgttctcta atacggcatt tccat                                         25

<210> SEQ ID NO 53
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 53
cctctgtcca ggacttattg aaaaa                                         25

<210> SEQ ID NO 54
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 54
gtaatgctga aatctcaccc tctgt                                         25

<210> SEQ ID NO 55
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 55
aattccatga gacaccatca atctc                                         25

<210> SEQ ID NO 56
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 56 gtacttttc ctgatccagt tcttc                                          25

<210> SEQ ID NO 57
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 57
catttttgtg ctcacctgtg ttatc                                         25

<210> SEQ ID NO 58
<211> LENGTH: 25
<212> TYPE: DNA
<213> ORGANISM: Artificial Sequence
<220> FEATURE:

<223> OTHER INFORMATION: Synthetic oligonucleotide

<400> SEQUENCE: 58
catctttcca ttttccattg ggatc                                              25

<210> SEQ ID NO 59
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 59
ctcatctgca actttccata tttct                                              25

<210> SEQ ID NO 60
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 60
tatttgtcat ccttacctca tctgc                                              25

<210> SEQ ID NO 61
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 61
atcctttcct caaaattggt ctggt                                              25

<210> SEQ ID NO 62
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 62
gtatatgtct gacaattcca ggcgc                                              25

<210> SEQ ID NO 63
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 63
cagatagatt gtcagcagaa tcaac                                              25

<210> SEQ ID NO 64
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 64
gtacatgaac ataccttttcc aattt                                             25

```
<210> SEQ ID NO 65
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 65
gaggctgtac tgctttggtg acttc                                          25

<210> SEQ ID NO 66
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 66
gaagctatga ttcttcccag taaga                                          25

<210> SEQ ID NO 67
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 67
gtgtaggagc agtgtcctca caata                                          25

<210> SEQ ID NO 68
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 68
aatgtgatga aggccaaaaa tggct                                          25

<210> SEQ ID NO 69
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 69
gctattctca tctgcattcc aatgt                                          25

<210> SEQ ID NO 70
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 70
cctgtgcaag gaagtattac cttct                                          25

<210> SEQ ID NO 71
<211> LENGTH: 25
<212> TYPE: DNA
<213> ORGANISM: Artificial Sequence
<220> FEATURE:
<223> OTHER INFORMATION: Synthetic oligonucleotide
```

<400> SEQUENCE: 71
ctagaacacg gcttgacagc tttaa          25

<210> SEQ ID NO 72
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 72
tggaaaggag actaacaagt tgtcc          25

<210> SEQ ID NO 73
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 73
actgatcttc ccagctctct gatct          25

<210> SEQ ID NO 74
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 74
atttctgagg taatcacaag tcttt          25

<210> SEQ ID NO 75
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 75
agtatgcctt aacagattgg atatt          25

<210> SEQ ID NO 76
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 76
attttttcca ttgcttcttc ccagc          25

<210> SEQ ID NO 77
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 77
attggaacaa cttactgtct taagt          25

<210> SEQ ID NO 78
<211> LENGTH: 25

```
<212> TYPE: DNA
<213> ORGANISM: Artificial Sequence
<220> FEATURE:
<223> OTHER INFORMATION: Synthetic oligonucleotide

<400> SEQUENCE: 78
tccatcacta cttctgtagt cgtta                                        25

<210> SEQ ID NO 79
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 79
ctcctcccag aaggctgtta cattc                                        25

<210> SEQ ID NO 80
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 80
ttaaaaattc tgacctcctc ccaga                                        25

<210> SEQ ID NO 81
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 81
ggctgtcatc accattagaa gtttt                                        25

<210> SEQ ID NO 82
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 82
aattactgaa gaagaggctg tcatc                                        25

<210> SEQ ID NO 83
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 83
taatatcttt caggacagga gtacc                                        25

<210> SEQ ID NO 84
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 84
```
gatccagcaa ccgccaacaa ctgtc					25

<210> SEQ ID NO 85
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 85
agaacaaaag aactaccttg cctgc					25

<210> SEQ ID NO 86
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 86
ctcccataat caccattaga agtga					25

<210> SEQ ID NO 87
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 87 attttacccct ctgaaggctc cagtt					25

<210> SEQ ID NO 88
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 88
acagaatgaa attcttccac tgtgc					25

<210> SEQ ID NO 89
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 89
gtgccaggca taatccagga aaact					25

<210> SEQ ID NO 90
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 90
atgctttgat gacgcttctg tatct					25

<210> SEQ ID NO 91
<211> LENGTH: 25
<212> TYPE: DNA
<213> ORGANISM: Artificial Sequence

```
<220> FEATURE:
<223> OTHER INFORMATION: Synthetic oligonucleotide

<400> SEQUENCE: 91
ttttcacata gtttcttacc tcttc                                              25

<210> SEQ ID NO 92
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 92
tctaggtatc caaaaggaga gtcta                                              25

<210> SEQ ID NO 93
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 93
ggtattcaaa gaacatacct ttcaa                                              25

<210> SEQ ID NO 94
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 94
acaatagaac attcttacct ctgcc                                              25

<210> SEQ ID NO 95
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 95
tcgttatttg gcagccaaag ttact                                              25

<210> SEQ ID NO 96
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 96
gagccacagc acaaccaaag aagca                                              25

<210> SEQ ID NO 97
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 97
tccaaggagc cacagcac                                                      18
```

```
<210> SEQ ID NO 98
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 98
ttccaaggag ccacagca                                                  18

<210> SEQ ID NO 99
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 99
ttccaaggag ccacagcaca accaa                                          25

<210> SEQ ID NO 100
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 100
aacagaaata aaacacaatc tacac                                          25

<210> SEQ ID NO 101
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 101
tttccaagga gccacagcac aacca                                          25

<210> SEQ ID NO 102
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 102
acaatctaca caataggaca tggaa                                          25

<210> SEQ ID NO 103
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 103
cacaatctac acaataggac atgga                                          25

<210> SEQ ID NO 104
<211> LENGTH: 25
<212> TYPE: DNA
<213> ORGANISM: Artificial Sequence
<220> FEATURE:
<223> OTHER INFORMATION: Synthetic oligonucleotide
```

```
<400> SEQUENCE: 104
acacaatcta cacaatagga catgg                                              25

<210> SEQ ID NO 105
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 105
gacttttttt ctaacatctt cacct                                              25

<210> SEQ ID NO 106
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 106
atggaacaac acacagttga ttttt                                              25

<210> SEQ ID NO 107
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 107
atcgaacaag acacagttga ttttt                                              25

<210> SEQ ID NO 108
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 108
gagtggaaca agacacagtt gattt                                              25

<210> SEQ ID NO 109
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 109
cacaatctac acaataagac atgga                                              25

<210> SEQ ID NO 110
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 110
caagatgagt gaaaattgga ctcct                                              25

<210> SEQ ID NO 111
```

```
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 111
cgaaggcacg aagtgtccat agtcc                                         25

<210> SEQ ID NO 112
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 112
aacagagttt caaagtaagg ctgcc                                         25

<210> SEQ ID NO 113
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 113
agttggcagt atgtaaattc agagc                                         25

<210> SEQ ID NO 114
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 114
ttctattctc atttggaacc agcgc                                         25

<210> SEQ ID NO 115
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 115
ggtaacagca atgaagaaga tgaca                                         25

<210> SEQ ID NO 116
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 116
atgtcaatga acttaaagac tcggc                                         25

<210> SEQ ID NO 117
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 117
```

```
ggccagatgt catctttctt cacgt                                               25
```

<210> SEQ ID NO 118
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 118

```
atctttgaca gtcatttggc cccct                                               25
```

<210> SEQ ID NO 119
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 119

```
ccaccttctg tgtattttgc tgtga                                               25
```

<210> SEQ ID NO 120
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 120

```
tctctaatat ggcatttcca ccttc                                               25
```

<210> SEQ ID NO 121
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 121

```
ccaggactta ttgagaagga aatgt                                               25
```

<210> SEQ ID NO 122
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 122

```
aagcagtgtt caaatctcac cctct                                               25
```

<210> SEQ ID NO 123
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 123

```
atccagttct tcccaagagg cccac                                               25
```

<210> SEQ ID NO 124
<211> LENGTH: 25
<212> TYPE: DNA

<213> ORGANISM: Artificial Sequence
<220> FEATURE:
<223> OTHER INFORMATION: Synthetic oligonucleotide

<400> SEQUENCE: 124
agctgataac aaagtactct tccct                                         25

<210> SEQ ID NO 125
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 125
aagttattga atcccaagac acacc                                         25

<210> SEQ ID NO 126
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 126
ctaagtcctt ttgctcacct gtggt                                         25

<210> SEQ ID NO 127
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 127
gatcactcca ctgttcatag ggatc                                         25

<210> SEQ ID NO 128
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 128
ctcatctgca actttccata tttct                                         25

<210> SEQ ID NO 129
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 129
atttcagtta gcagccttac ctcat                                         25

<210> SEQ ID NO 130
<211> LENGTH: 250188
<212> TYPE: DNA
<213> ORGANISM: Homo sapiens

<400> SEQUENCE: 130
tgaatgagag gtgccccatc aactggactt ctcctgagtg ttgaaaaggt aagagggttt     60
tgcttcttta ttcactcctt tcttactatt tgcattgtaa tataactctc ttgggactca    120

```
agggaacaaa ccatacagtg tcttttgcta aatgccaaaa atcaagaagc cagttgaagt       180
tttcagttca aattatttca caagtgttac acagtagaaa acctttatgg tggctcacgc       240
ctgtaatccc aacactttgg gaggccgagg tgggtggatc atgaggtcag gagtttaaga       300
ccagcctggc caagatggtg aaaccccgtc tctacaaaaa atacaaaaat tagccaggcg       360
tggtggcggg cacctgtaat ctcaactact ggggaggctg aagtagggaa ttgcttgaac       420
ctaggaggca gagattgcag cgacctgaga tcgcgccact gcactctagc ctgggcgaca       480
gaccgagact ccatctccaa aaaaaaaaaa aagaaaaga aagaaaaga aaagaaaaa          540 aaaagaaaa acaacaacaa aaaaaaacca aaacaaaaaa ccttttttt ttttttgtctc        600 agtttgaggt ctcttgttac aaatttaaag aaaattaatt ttacaatttc ctattctcaa       660
tgattttgat ttactgatat tttaccctac aacaatatag tgaaaaagtg tggtcatggg       720
attggttaga cctaattcag gactaccaat actagatgtg aggctatagg caggtgtgtt       780
aaagattctt tggaatctta ttttactcaa gagtaaaaag tatgtgtagt aataattatt       840
tcataagtat attgagagca ttaaatgggg aataacaacc atataaaagg cttagcatat       900
tagagactta atacaaatca atttcttgca ttttgcttat cctggatata tcgtgggttt       960
gcttcatatt ggaaaacaag acagcaacaa agatccatgt ttcattcttc agtgacttaa      1020
aatattagtt gttctggcca ggtgtagtgg ctcacacctg taatcccagc acttcaggat      1080
gctgaggtag gatgattgct ggagcccagg agtttgggac cagactgggc aacaaagtga      1140
ggccctgtat ctacaaaaaa taaaaatcgt agccaggcat ggtggtgtgc acctgtgatc      1200
ccagatacac gagaggctga agcaggaaga ttgcttgacc ttagaaggtt gaagctatag      1260
tgagccttgt ttatgccact gcattccatg tattagttgt tctacaaata aaaatatttt      1320
actttcaaaa catgttttac taaaagttttt tcagtaagga tgtaaaaact attaatggtc      1380
aactttgact acttccaaaa tgcttttttt gagtgaaatg ttacacctct ttgttagttc      1440
attgcaataa tacttaaata tttaaaattg aaagtcagta atggtaaata tagaagaatt      1500
agaggataaa atgagtggag atatggaaag gtacagattg aatataatta tttaagtaaa      1560
atcctttcct agagaaaata gaaaatagaa ctttgaggtt gaatctcttt taatgtaatg      1620 ttttctcga atccaagtgt ttttacacta tacaatagga gtagaaattt gtcaccactc      1680
tgtggccaaa ctcactttttt ctttctttt ttatttttac attaaaaaaa aattttactt      1740
taagttccag gatacatgtg caggatgtgc aggtttgtta cataggtaaa tgttttattt      1800
taaatttaat ttaacacttt ttattttaa gtcatacaac tctcatagcc agtagttaat      1860
attaccttgc aagtttggta tggttgatga attgcatcct gttaataatt gctacagatt      1920
tttgaataat tgcagaccag tttgatggtc ctgggttggc ataagtacat gaagatttac      1980
tttttcctgt gagctttctt gggatgaaga aatttagtgt tttttttaa tttttaagaa      2040 atatttatta ttttttacat gatttatttc ccactgaaaa ataaatccca ccgggcataa      2100
agtgtatttt tttaagtcac agagtaaccc aacttgaagc tagttttttca gacttaggca      2160 gttcatgctg taagcccgag atctcatggt caccccttgca agagaaatat ctaattgaaa      2220
aaaaatatga agagtattaa ttttgatagt gctaaaatga cataaaggga tctcactggg      2280
cttgagatat taagtattaa aattgttaaa ggtttaaatt gttagtaact tgttattgca      2340
tagaaaatgt gccaaatgtc agtaaataaa aaactttttt ttaaaataaa aatttacaga      2400
aaaattatga cgatactaca aagaggttct gtacaacccc ctcccagttt ctcttactat      2460
```

```
taacatctta aattagtatg ttacatttgt cacaattagt gaaccaatat tgatacatta    2520
gtactaacta aagtcagtgt tccttttact ggagaatggt gttagaaact aaggtctggg    2580
cactgtggta tggtggttgc tattgagatg ttgttatttt taggttcttt ctcagctgac    2640
agagcaaaga aatatatgtg tgtatattaa cctatgtgta cacatacatc tatgattatt    2700
tcgatatgta acatctgtat ctttattaag ctaaatatga gttcatatgg tgtcttcaat    2760
tctaatcaat tactgtatag attattctag cctcttcctc ttgcttatct gtaacttcct    2820
atttcaaacc gtgaaaaatc tgtcttccac cacctactat ctgcttacct aatttctcat    2880
ttccagttta tgtatacagt ggcttcagaa ttattacata tagccctgtg ggatacaact    2940
tgtcaactga gagtggtgct tatgtaagtt cttctatctt tagttttact gactctactc    3000
attttcaaag ttgcttagtc cagaacattt cactcatact cctcctagtg aagttgtttc    3060
atatgttagt aacacagatt cttttttttgc agtctgcatt ccattttagg gttccctcct    3120
ctccaatctc ctaaattatt attttttaaa ttcatataca tcaaggttta ttctttgtgc    3180
tgtaaagttc tataggtttt gacaaataca aagtgtcatg tacccatcat tacaatgtca    3240
tacagaatcg tttcactgcc ctaaaaatat cccttgtcct ttgcctattc aacccttccc    3300
ctcctttccc aaactcctgg caaccactga tctgtttatc gtggagctgt gtctcttcca    3360
gaatgcatat aattgaaatc atacaatatg tagacttttc accctggctt attttgttag    3420
caatatgcat ttaacattca tccatgtcct tatgtggctt gtagttcatt acttttttact   3480
gctgggtagt attctatcat agaaatgtac cacagtttgt ttatccattc gctgattgaa    3540
gtatatcaat ataccttgga acatgactgc tagatagtat agtaagacta tatttagctt    3600
tgcaagaaac tgccaaactg tattttaaag tggctgtacc attgtgccac cagcaactcc    3660
tgccagtgat ccagtattgt cagttttttg gattttagcc attctaaaag gtgagtgatg    3720
gtatctcatt gtcgttttaa tttgtaatac tctaatgaca aatgatggtg gatttctttt    3780
catatgtttg tttcccatttt gtatatcttc tttagtatgt gtctgttcgg atgttttgct    3840
tacttttttt aaactggggtt gattgttttc ttttctttt ctttttttc ttttgagacg     3900
gagtctcgct cttagccag gctggagtgc agtggcgcca tctcggctca ctgcaagctc    3960
tgccttccgg gttcaagtga ttttcgtacc tcagcctccc gagtagctgg gactacaggc    4020
gcccgccacc acacctggct aattttttttg tattttttggt ggagacgagg tttcaccatg    4080
tcggtcaggc tggtcttaaa ctcctgacca tagatgatct gcctgtcttg gcctcccaaa    4140
gctaggatta caggctagga ttgcaagtag gataggcgtg agccactatg cccggctgat    4200
tgttttctta ttgttgagtt ttatattcct ttattttgga atggagtaaa taagcacaat    4260
aaaactggtt gagaagataa tcattttaaa aaatcataat gaattatatg atacacattc    4320
tattatttca tgagaaaaat catggaagag tcagttcaat attcagtgaa tcattaatgt    4380
gaggatgtaa aatttgatac acacacaatt tattgagcac ttatcctatg tcaatcagtg    4440
cgctaaattt ttttctttta tattaactca tttaattccc actacagccc tgtgtaatgg    4500
aagctgttct tcccaccatt ttataaatga tgaaacctta gatcacactc agtggaagag    4560
ttctaaagcc ctatgtggtg ctgtctgata gaaaatatat tttaaaatga gatgatctaa    4620
ggtatgttta cctacagagc taaggaaag tatgtcttaa atttaataat gagtgattat     4680
agaaacagat tacaggaaat agtccatctt tcttgaatta ccaaagtgt tacaagcctc     4740
aaattcattg ttgtttgtat gagaacacat ttaggtgatc ggatacaagt atatagtttt    4800
tcccagatgt ttatttcaca tcaacttttt tttcatctttt actttcttca aggcaagtag    4860
```

```
gatagaatgt aataatcaaa taggttttc ccccacccca ttttagagca gtaaataatt      4920
ccaagaggca tttgctttgt tattggataa gtaattaaca aaaagaattc ctaaagacaa      4980
ttagaatcat gaccatactg ggtcttgaaa acatagcagt gcaatacag ccaatggctg       5040 gcttggtggc tggcgatgag cctgcagcat gggactgggt gttccaccac ggcttggctg      5100
ttgtccaggg agctttcagt cgctggggtt cccacagtgc caagcacgag gcaggtgcag      5160
aaaggataaa ggtttctgtt ccccattagt gttgagggca tgcaggtcgt ctgacatgag      5220
gggcatgaga agtgaagttc ctgctttgct ttgggtaagg aatctgcatt gacaggggct      5280
taagaacctg ctcttatacc tcacatgtct tagcctggcc tttgagatga gtagggagtt      5340
tgagtgggag tttgagtttc tcttagaga aacagaactg agtgaggcac tttcattttt       5400 tagttttccta gtaccttttg ttaaggaaaa aaaagccaaa atgagtgtta aaaatttaaa     5460 attttagat tttaaatttg catttaaaaa attaatgctt ttttttttag atggagtttt       5520
gctcctgttg cccaggctgg agtgcaatgg cgtgatcttg gctcactgca acctctgcct      5580
cccaggttca gcgattctc ctgcctcagc ctcctgagta gctgggatta caggcgcccg       5640
ccaccacacc cagctaattt ttgtattttt agtagagacg aggtttcacc atgttggcca      5700
ggctggtttc gaactcctga cctcaggtga tccacctgcc tcggcctccc aaagtgctgg      5760
gattacaggc gtgagccact gcgcccagcc aaaattaatg ctcttaacat gtaaaaagta     5820
aagtgcagtg gaactttggc acttatgcaa gataatacaa cttaaaagat ttataagaat      5880
attaactgct aatgaacagt agagggatct aattaacatt gaaagttaca tgaagaaagt     5940
gtttgtcttc tattcccaac agggcatctt tgtaactata atgactcttg agaagatttt     6000
gttttcagtc ttaaaacagg aatgggggaa aaatgtaggc ctgggtaagt acaaaaaagg     6060
gaaatcgaag gagactaggg agttactgta gattttgcag gactgaggaa agtcagaata    6120
aatacaagag acaatgatgc tggtaatttt cttttgggctc agagaagtaa tgctttgctt    6180
tgtcagagtt gtagtaaaat ttagatctaa gaagctcgtt ggaagttgta gcagaatcct    6240
gtcttgttta ctatgtccac tgcctggcac agagatggaa cactataagc tttccaaaaa    6300
catttgtgga atgaatcag aaagtcactt tactttccaa gatgcaattc tttatttga     6360 aacataaata tttaaaaagt ttataaattt ttgacataat tatgacatac atccttccag    6420
gcttttttca atgcttatgc aaacatgtat atgtgacctg taggtctcct tttacccagt    6480
ttttggagta caaataaggt cacatctctt cttaacttta aatgtttaaa acattgaagt   6540
tagcaagaag cccagaaact ttttctaaag aacttttct accctaatt gtccaagaac     6600 tccaagtttt cttggttcaa agaggtaatt tctgtttcta aacactagaa aaaggagaat   6660
atgaaggatc tgactagtcc attgtcacat gccccacccc attttctgct gcaagagcct   6720
ctgtcaccac agcattgtgt cactgatgaa ataggtcct cccacagagt cagatgcatc    6780
ccagtctatt gctactatta tcaccctgtt ggaacagatc cctgcacagg tcacagcagt   6840
tcctggaaga tgaaactcat tctcccagcc ttaatatcag ccaggaatac tttattcttg   6900
gacttccaaa gttgctatag tagttttcaa agcccaccta gcacctaagg atgggtgagt   6960
aaagacaagc ttccagtttc agctgcagaa acaagaaccc atctcccacc acatagtagg   7020
tgttggcatt aaacttctct cttatgatgt aatgtgttct ccttgggatc tttggtattt   7080
ctgtttgcat acttcatttg gggtcatctc aacacaccaa acagattcta actacactga   7140
atctcaaaag aaatagaagt agtctttgtc aagccacaga aaagagcttg ttcttctttc   7200
```

```
ttctcctcct agacacctgc atacttttca ttcctctaat gaagagggtc cattcaataa    7260
attcagaaga aatgaagaaa aaaatacaag tctagtttgt gataagtcct tgtttcacc    7320 taaacagaga agcaagaaca taaattatat aaggcacctt ctcttaatta aataaacaaa    7380
agagttctat gtggtctagt tacacagaga tcacagtgat taactactca gctctggagc    7440
cagacaactg ggtttgttca gattctggca ctctttcttg aatttgggca tggcatttga    7500
ccttctgtac ctcagtttct tcatttgtaa attgggatgt taataataaa atgtactaac    7560
tttatagggt cttcctgag gcacataatg taatttaaac aacaaacaag tatacataac    7620
agacattttt ttcttacaaa gacggtacca tactaaactt aatttgcttt ttttgaaaaa    7680 ttatatttt aggtaaaact tgtaagtta attttttgg gtgaaaaaca tgatacaaat    7740
ttatcaattt gattttgctt cattagcatg atatactttg ttctagaaag tacttaggca    7800
attttcatac atgtctttaa atataatttt tgcacatgta aataagagtt ccaaagtatt    7860
ttgccatcac ttcatcagtg ttgcctctca acagcctttg aagcgaggag atgccagtca    7920
ctgtctcaga cacaaggatg caggctgtgg aggccagtga gccatagtca ctgaactggg    7980
aattggctgt cctttgacc atacagatta tcactgtag tttcaccaat cacattgaac    8040
ttgaagatca ataaatgacc ctaaaacaat gagattcat agactcttc tatatagtgg    8100 aagtaaaagc aaatcagaaa ggagtccta aactgtgaa ttcttgaatt ttagttttcc    8160
aggtcaacaa gccttcttta agtgacttca tgtcccgtcc ttggttttg atcatagact    8220 ggtataagaa atgaccataa aataaatgtt tttgagaaaa ttatagctga aaatactgtc    8280
catgatacca ctcagtgata taagtctcta acagcaaac tcttccatga atggggtgga    8340
gggaagatgg ttttctttc caggtgaact tacatattgc cttttctcag atatcagatt    8400
atgagaataa tacaatggac tgggcttga cagccaagac tttcagaatt gctgttagtg    8460
cccatgtgca ataaaatttt tctatcatgt ctctcttatt atttcaaatg ccctgtttta    8520 ctgtttgat tactaattat ctatttagag gaaacagtt ataaataaat aattcactgt    8580
tctacttact gtgcaccct gccttctaa atataactct tctatgtagc atgtaaatta    8640
ccacagaact catctcagaa aaagatcac tactttctt tttagaattc aaattataa    8700 tatctaattc tataggtggc atctggcctt tagcatgata tcaccaatga aatttaatc    8760 tgtgttatga attcccttgt ttctagaaaa gcttcagcag gaaatgaga agagaaccca    8820 taaaaccat aaacatttc atgaatggta gctttagaaa atcttacagg atttggtagc    8880
ttttacattt atgacaaagt gatatttttg atgttgttca taattattc agttcattag    8940 cagcattaat aagctcccgt tttgtacagc ttgaagatct ttaagacttc cttaatgaga    9000
aactaccttt aagctacgga agacccatca gggtgccaaa ttccatctgg acacagttac    9060
aaatacacca ctgttgatga gctgaaaatt agagcaacca aacaacagag ctttaaaatg    9120
ttatttcaat gcaaagggac attttcacca tagaaaaata gaagtttgcc tctaaataaa    9180
aatgatttta caattgcaag agtacttgat ttacccccttt acatttagtt caaataccaa    9240
aaatttctta aggaatgaga aattccaatg ttcctgagaa ttctgatagc ttttagagag    9300
ttcagttttc tgtagcattc cattttgcaa tcctatacaa atttctaatt tataaccagt    9360
ggtatgtaat gataatttct aatatttatt aagtgtttat tgggttctaa gtgctttacg    9420
tctgatatat gtatcacatt taatttattt catccagtgg ttcttaactg gggacaactt    9480
tgtacctctc tccccaacat atttggcaat ctctggagat agtcctggat ctccagatcc    9540
atctgtcaca acctaggatg tatgtggtcc tacgagcatc cagtgaatag aagctagaga    9600
```

```
tactgctgaa cattccacag tacaagggca accccacat caaagaatta tccacaccca    9660
aatgtcagta gtactgaggt agagagaccc taacttaatc tgttcaacaa tcctatgagg   9720
tgatttttt tttttttttg agataaggtc ttactctgtc acctaaactg gagtgcagtg    9780
gcatgatcac agctcactgc agcctcgatc tcccaggctc aagccatcca cctgcctcag   9840
cctcccaagt agctgagatc agaagcatgc accaccacac ctggctattt tttttatttt   9900
tttgtagaga caaggtctta ctgtgttgcc caggctgatc tcaaactcct gagctcaagc   9960
aatcctcctg cctcagcttc tcaaagttct gggattacag gcatgagcca tggcacctga  10020
ccaaggtgag tgtatttaac ctcattttca ggcaaggaaa caaagacag aaaagttaag   10080
tagcttactt aaggtcacag agctaagtgt ggtgccagga ttgaaaacct agttctttat  10140
tgctttagca caagctattt ccactatact ctgtcatgtt cagagaatgt tgatgtccat  10200
cagtggattc taaattttga aggatggaga tactgcctta ttctgtacat ctgctttagc  10260
acccaagctc ttgcttggtg aaaaattaat agtaaacatt catcttttga gcatcttcaa  10320
atatccccttt tagaatgaca ttcaattatt aggtcagtaa ccccaagaga aaacggttgt  10380
ttgagtgtat atactgtatt acaaaataag gggtgaattc aaaggaaaac ataagatgca  10440
attcgtgcct ccaaggaggt tgtagggaag aggggttatg aatgtatgta aatagaagtt  10500
ggtgtgcgtg tgtgtttata aacagaattg tcagaccaaa cattattttg gaagcagtaa  10560
aagtaaacta gaatctggcc tagtcatgtc ccaggacacc tctttcaagt cctgaaacat  10620
ctttgtaaga ctgtaatgtg tgtttacatc ctaggtaatc actgtggccc actgttgaag  10680
agctgtggct gttcttaccc ttctagctta gataaactta taagcacaac cagactacat  10740
atatgaagct gaagagacct tgtcttttt taacgagctt ttcttcccga taggagtgac  10800
tattttcttt cttcttccac atttttcaggt tttagtgtac ttgtgattgc tacccactta  10860
tcactattaa agtctactca ggagagaatc tgagaaacac tctcaaatta agttgaacat  10920
gatggataag taaagtattg tgaaagttca ctctcatgat ttctaatggt gaaacctggc  10980
agggtgacta atctttgacg agaaggttat cacttataat ctttcatata ttgagatcat  11040
ttgtaagaag cacccagcac attgctgaac acaaagtagg tattaaataa atgttggctt  11100
ccttttctcc tactcatcct cgctcttctt tttaatatac cttaaaatg atgccacaga   11160
aatggccacc caatcttcta tatttaaggt cagttcttgc attaggaaat tctatagggg  11220
aagtatgtga agtatgtgta gtcagtcatt aaatgcttgg gctctggcca cagattgttt  11280
aggtttaaat cccagtttcc tctttttatta ttaattgtgc aacttgcttg ggaaaacatg  11340
aaacttgttt ttcctcaggt tcattatctg taatatatag tgaatgaaga gtttcctgt   11400
cccatgaagg tgttgtaaag attaaaaaag gcaaattagg ctgtgtattt gtcataataa  11460
ttggcatata tggtaagtga ccaacaacca taaggtatta taaaattgtt ataaaatgat  11520
atgagctatc attgagcagc atgaaagaag agcttcactg tttcacctac tatcaccctg  11580
gcccattaat ctctttcctg ttcctgacat ttcagagata cgtttaggat ttcaatcatg  11640
accttaagcc acatttgaac aatttttctgg tggataagtc ctcattccca cattatgtat  11700
gtacctagat gcaaatcctg aatatcatgt cgcaattagt gcatctggac atgcttgcta  11760
actgtgttaa agctctgaat aatggtaaag ttttatttct accaaaacaa atttgggctg  11820
taatgttta tgataaaaat ctgtggtctt cctatgtaca tgtgtgtgta catgcttaaa   11880
atgcaatgtt atagttaaat gtaattcatt aaaagtatgt aactccagtg gctacttagt  11940
```

```
ttggctactt ggtttgtaga tttctgcttt cctgtttcat tgttaaacag gtctagaagt    12000
tattatttca tgaaactaat gtgaggaaaa agactatgtt gatatataag tgacattata    12060
taaatacatg agggatgatt tgattagaag cagtattaca cagtgatagg agtaatggtt    12120
tagaactaga ctcaggtttg aatcttagct ctatcattat aggcatttac ttaactttc     12180 ttgtttgctt aactgaaaac tgaagataat aacacctatt tacatggttg ttataagggt    12240
tatatgaata atgtctggca aatagtaaga actcaagtaa ctgtttcact ctttccagaa    12300
ggagattggc tgaaaaatat ttggagtctc ctccagccat attccttggt cagcttctat    12360
gatcctcttt ggagcttaat tcttaatccc tttattttca cttgcttgtt gataacaaag    12420
aagaactaat tattaattta tttcaaaatg catgtattat atttgatggg ccacactaac    12480
agttataaac caacaacag attgggaatg gggaagtgga tgtggtgagt tcaatcacat     12540
gtctgggaaa agtcaatagt gaagacagag tctcacaatt ttttgtcata atggagagat    12600
gaaaacacag gtagaggatt tcaaacaaca gagtggatgg tgagttaaaa atgctgaaat    12660
tctttcctgg tgtctaactt aatgcaatgt ggtttatctc tttgctcttt tctctactat    12720
tcaaatttag gataataaag attaaatgtt tctaaatctt actttacaat atcaagaaaa    12780
aaaggtatgc ttttgcccac ggaagggcaa agcagagcta tgaaacctg ctgaacacat     12840 tctttatttt caacacaggt tcttgtcttt ccatcatgaa atgcacattt tatttgtact    12900
gtatttgggt gaccacaagt caacaacaag ataattcaca agacccttgc cttagatgtg    12960
tcggcaataa agtaatcagg ccaaaatttt tactttcctt tgaattttc aattcaaaca     13020 caatgtatgc ttgcttttac acagtagggt tcagggatta gagggttggc tctttaaaaa    13080
ccgtcagaga cacaggcaat cctacacaaa attctcagaa ggaaggcgcc tacgcctggg    13140
aatgcccaga tgcccctcag agagttgaag atggcgtttc tctgagtcag gtcaaagtta    13200
acacattacc ttcgcttcaa agactgcttg gcttcctttc ggtggattag tcaagatgtt    13260
ttgctgactg agactaggaa atctatagga gggcgggtta gtttacattg ttccttgtca    13320
ttatcgctaa aacactccaa agccttcctt aaaaatgcgc actgggctaa aaaggataga    13380
caaggaacac atcctgggcc ggtaattacg caaagcatta tctcctctta cctccttgca    13440 gattttttt tctctttcag tacgtgtcct aagatttctg tgccacccctt ggagttcact    13500 cacctaaacc tgaaactaat aaagcttggt tcttttctcc gacacgcaaa ggaagcgcta    13560
aggtaaatgc atcagaccca cactgccgcg gaacttttcg gctctctaag gctgtatttt    13620
gatatacgaa aggcacattt tccttcccctt ttcaaaatgc accttgcaaa cgtaacagga    13680
acccgactag gatcatcggg aaaaggagga ggaggaggaa ggcaggctcc ggggaagctg    13740
gtggcagcgg gtcctgggtc tggcggaccc tgacgcgaag gagggtctag gaagctctcc    13800
ggggagccgg ttctcccgcc ggtggcttct tctgtcctcc agcgttgcca actggaccta    13860
aagagaggcc gcgactgtcg cccacctgcg ggatgggcct ggtgctgggc ggtaaggaca    13920
cggacctgga aggagcgcgc gcgagggagg gaggctggga gtcagaatcg ggaaagggag    13980
gtgcggggcg gcgagggagc gaaggaggag aggaggaagg agcgggaggg gtgctggcgg    14040
gggtgcgtag tgggtggaga aagccgctag agcaaatttg gggccggacc aggcagcact    14100
cggcttttaa cctgggcagt gaaggcgggg gaaagagcaa aaggaagggg tggtgtgcgg    14160
agtaggggtg ggtgggggga attggaagca aatgacatca cagcaggtca gagaaaaagg    14220
gttgagcggc aggcacccag agtagtaggt ctttggcatt aggagcttga gcccagacgg    14280
ccctagcagg gaccccagcg cccgagagac catgcagagg tcgcctctgg aaaaggccag    14340
```

```
cgttgtctcc aaactttttt tcaggtgaga aggtggccaa ccgagcttcg gaaagacacg    14400
tgcccacgaa agaggagggc gtgtgtatgg gttgggtttg gggtaaagga ataagcagtt    14460
tttaaaaaga tgcgctatca ttcattgttt tgaaagaaaa tgtgggtatt gtagaataaa    14520
acagaaagca ttaagaagag atggaagaat gaactgaagc tgattgaata gagagccaca    14580
tctacttgca actgaaaagt tagaatctca agactcaagt acgctactat gcacttgttt    14640
tatttcattt ttctaagaaa ctaaaaatac ttgttaataa gtacctaagt atggtttatt    14700
ggttttcccc cttcatgcct tggacacttg attgtcttct tggcacatac aggtgccatg    14760
cctgcatata gtaagtgctc agaaaacatt tcttgactga attcagccaa caaaattttt    14820
ggggtaggta gaaatatat gcttaaagta tttattgtta tgagactgga tatatctagt    14880
atttgtcaca ggtaaatgat tcttcaaaaa ttgaaagcaa atttgttgaa atatttattt    14940 tgaaaaagt tacttcacaa gctataaatt ttaaaagcca taggaataga taccgaagtt    15000
atatccaact gacatttaat aaattgtatt catagcctaa tgtgatgagc cacagaagct    15060
tgcaaacttt aatgagattt tttaaaatag catctaagtt cggaatctta ggcaaagtgt    15120
tgttagatgt agcacttcat atttgaagtg ttctttggat attgcatcta ctttgttcct    15180
gttattatac tggtgtgaat gaatgaatag gtactgctct ctcttgggac attacttgac    15240
acataattac ccaatgaata agcatactga ggtatcaaaa aagtcaaata tgttataaat    15300
agctcatata tgtgtgtagg ggggaaggaa tttagctttc acatctctct tatgtttagt    15360
tctctgcatg tgcagttaat cctggaactc cggtgctaag gagagactgt tggcccttga    15420
aggagagctc ctccctgtgg atgagagaga aggactttac tctttggaat tatcttttg    15480 tgttgatgtt atccaccttt tgttactcca cctataaaat cggcttatct attgatctgt    15540
tttcctagtc cttataaagt caaaatgtta attggcataa attatagact tttttttagca    15600 gagaactttg aggaacctaa atgccaacca gtctaaaaat gcagttttca gaagaatgaa    15660
tatttcatgg atagttctaa atactaatga actttaaaat agcttactat tgatctgtca    15720
aagtgggttt ttatataatt ttcttttac aaatcacctg acacatttaa tataggttaa    15780
aaaatgctat caggctggtt tgcaaagaaa atgtattaca aaggctgcta agtgtgttaa    15840
gagcatactc attctgttc tccaaaatat ttcataaggt gctttaagaa taggtatgtt    15900
tttaaaagtt aagttcctac tatttatagg aactgacaat cacctaaaat accaatgatt    15960
acaaacttcc ttctggcctt ctggactgca attctaaaag tgtaaaaaac atattttctg    16020
cattaagtta ggcagtattg cttagtttc aaagtggtag gctttggagt cagattattt    16080
tgattcagat cctacatcta ctgtttagta gctctgttgc ctgaggcagg tcccttaaca    16140
tctctgtgtg tgacttgacc tttaaaattt ggagactgtc atagggtta atcccttgag    16200 aaaatgaatg tgaaaagtta gcctaatgtt aactgctatt attatggatt accatatttt    16260
cacattcatc acagtacatg caccttgtta atataagatg ctcaattcat ctttgagtat    16320 aatttgtga ctctcaatct ggatatgcaa tgagtgggcc tgtatgagaa tttaatttat    16380
gaaaaattgt gtttcacatg gccttaccag atatacagga aacacgtcac atgtttctat    16440
tgtatgttgt taaatgcctt agaatttaac tttctgaata ggatcccttc agtttgagag    16500
tcataaaaga gtaaaattat tatggtatga gttatagatt gtattgaata tctctttata    16560
tgtctaggtt ttgtcattgg aaaaccaaaa agtttggaaa aaaatctaa gttatttctt    16620 actttcttaa ttttgtgtgg atttcacatc aagtataaaa tttgaagaac atctgaacta    16680
```

```
tcataatcca tatatatata taaaataaac ataatctaag agagaatttc accatgaaaa    16740
attcaggtag ttcatgacta tcagagcaaa caagtacatt aaattgaaac ttttatgaaa    16800
ataacattta tgaaatagga agctattttt aaactagaag tgatatatta gcatataatt    16860
tataattcat atacaagtgg gattgattta taaatggtca ccaacagaga ttgtgctatt    16920
taatttggga aaattttta aatttacatt ttctcacaac ttttaaggta gttattcagt     16980
ttgttcctct ctgtctcttc tctcatgccc tgaattttc atatttcgtt tagttgtaag    17040
agtgtatatc aaaccgtgtg tcacatgaca taacttgaat tttcgtcgtg atatctgtgc    17100
tatgtctagg tctatactga ggaactgtgg gaaccccaca gaatccaagt atacagtgcc   17160
actgatttct tacaagggat gtgggtctc ctgtaaactc tgcagttagt ctcaagtaag    17220
accaaagagt aaaatattgt taggatctaa ggtggaaatt cagcaaagaa tcacatagtc   17280
taagtctcga gtttaacagt aagataattt gagatacttt tgtaattatt aaacacaaag   17340
taatgagaga ttttaaaaca aacaaataca cctgaattta tatatcagaa taggtatggt   17400
ggttcaaaat agctatctaa taaaaccac actcctattc taaacatttg cctttgatca    17460
aaataatttt gggtctctta ttatgaaatt gcctttctaa ataatacata aatttcttct   17520
cataagtata tattagccac attattttat tgttattgtt ttatattcat agcttgcttt   17580
agattaaaaa ttatattacc cagactggtc tcttggactt gcttccaagt gacttttgac  17640
tgtatcacaa aatcaaattc actctgaaaa tataaagatt tttcatcata atttcctttg   17700
ttaacagcca agtgctacct aatttttaggt gttttcatta aaaaaaaatg cattgcaaac  17760
tttaaagaca attcttttgt ttgtttgttt taaaagaca gagtctcact ctgttgccca   17820
ggctagagtg cagtgacaca atcataactc actgcaacct ccacctcctg ggctcaagtg   17880
agccttccat cttgcctcac gagtagctgg gtcttcaggt gtacaggtgt gtaccaccat   17940
gcctggctaa cttttttttt ttttaagtta tatagagaca gtatctcact atgttgccca   18000
ggctgctctt ggagctcctg gcctcaagtt atcctcccac tcagtctccc aaagtgctgg   18060
gattacaggc gtaagccacc tcaccctgtc agcctaaaga cagtgcttaa tgaagagaaa   18120
tataagtgct ttgagcaatg gaagtataat taaaattata ctatgaaaga tttataaaga   18180
tgaccatttt gaatgggacc acacttattt ggttatataa attatgatac actattaaaa   18240
attcatcatg atgattttgt atttacattt tatttacatg tttgcaattt gtgaggaaag   18300
ctaaaattat ggctaagcca taaatatttt tgcagtttgt tgagggtgtt tgtaaaagtg   18360
ttgccaagga agaccagttg gctacccaaa caagggttta gtctaggtct gatcaataca   18420
tacacattat ctcaggtttg tctatcagaa aaaccttagg ttatccaaat caaaataaaa   18480
tagatgcata aaacaaaggc caatatgtgt tgaacaatta tattgtgata tacaactgcc   18540
aagcattccc gattaccatg actccattta gtcagtccat gggcaaatgc catcaatgag   18600
gacagcccag ggtttccata ttctctcttg gctttacatc ctataggaat tggaggggcc   18660
cacctctggg ataggagccc ttctgtcttg aacaatgttg tctgaacact aacaaatgtt   18720
gactttctac accagtccct caatagtctt ttctatttat ccttttgctg accatgtttt   18780
gttattacac agttgagatt tttcagctgg gaatctgtgt taattttgta ttaattttga   18840
ttagcttaac tctcagagtt ctaaaagtac ctcctgtacc tgatatatga caaaaattat   18900
aattacattt atttatatat aaaatatctt tgtatatgta aaatatcttt gtatatataa   18960
ttatataatt gtttctttta atttttgcaaa ttttaaaaag ttctcctttg ttttgaagtt  19020
tattcctata gttttttata tgctagttaa attattaatc acttgattca agtaatattc   19080
```

```
ttatatactt ataaggaata gtgtagtttt aatatttaat tccttgctaa agagagaagt   19140
ggaatctatt tttcttagct acttcatcaa tattttatgt ttgatgtgac agtcaaaata   19200
tccctcagag ctaactgtta cactaggaa atcacggttt tccagttttc catttatgtg    19260
ttatgggagg gagtggaact tagtgtaata atattcaata cataaatgtt aacacttgtt   19320
taaaggtcct tgagtgagta ctgctataaa atgcattatt attgctagtg tcatttcaca   19380
agagcctata atttcagtgt gatagagcta caatataagt atagtattgc aaaaccatca   19440
ggaagggtgt taactatta gcatgcagtt atgtgttggt tgtcaaaacg ttaaaaacat    19500
ctctgactca gcagcaattt tggcaattt gatcctgagg catctgtgta gggcatcttc    19560
ctggagaaaa acctctgaga tgcaatgagg tcaaagggg aaaacagact atgataaaga    19620
tcaagttgtt tggagatctt gtagaaagat taatttacaa atatgtcaag tgcattatca   19680
tggaggaaaa cattgctatt tctgttggtt ctcttcagag ctctagaatc aatttaccac   19740
atagttgttt cagtgtgaaa ttagcattac agagtggctt tacggcttta ctgtagggca   19800
ttgtgtcagc aaagagctta ggcttctttt agcaagaagc ttgtaaaaat ttaatttact   19860
cttagattgc ttgatgtaga gaattacatt cctacagagc tctgaaaaat cttttttcag   19920 agttttcac agctgtattc aagttgcaag gcttgtcaac tttgctattt ttctgtgcag     19980
ctctgttaac ttattattat cttttgacat aaattatgat tccaaattgt aaagctctgg   20040
atgtcagggc cttttctaat ttgtttagta tgatattcag accatttcaa gactcttccg   20100
tggaacaatt taataaagat ttttttgtga tgttaatgag ttcatggtga tcaaccctag   20160
agacctgtgt ctattgtaga tcgatgacat tcaacagtcc tgcagtgctg gcatcatttt   20220 gataaaagg ggtcaaagca agtgggactg tgggcagatt tttaatgctt agaacaatta    20280
ttccatcgaa gttttcttgt gtcccttctg ccttagcctt tgtaggatag catgcttgct   20340
aatttcttgc tcatgggta aggaaatgaa gattttttgct aggtccgtag gattattagg    20400
actactcagg cctgaagcta tgcctggata tagccagaaa actctcccat agcttgctcc   20460
aaggagctga gatacagcag tacttccttt gtaggtcatg attctgggta acctggaaga   20520
tgacctcatt catattctgt attctatgtg agacgttaag aaggtagagg tggccaagaa   20580
ggaaattgtt gctgccttta tggaacaaat tatctgaaac ccagctttct cgagggcttc   20640
attgaagtac tcaactgggg cacttaaccc agtctaaggc tggtcaagga aggcttgctg   20700
ggggaagtgt cttttgtatt cacacctaaa ggaggttatt caattagaat tatccaaaga   20760
gggtagggat gggctaggaa aaatttaaac aggtagtgtg gaggactgac aggataagta   20820
agcatggcac cttcaaaata tcctgagaag ttccctatga cgggaacata aaatatgtga   20880
cagagatttg tgggagatgg gtctggaaac tctagcaggg gccagatcgt aaggggcttt   20940
tgtaggcttt gtaggctttg tttgggcttt atcatactgg aagtgaaaag ccatggcttt   21000
taaacaggag agggacataa tcagttcata tactgttgca gttttgtaaa agaaaagatg   21060
agctgaaaga gtggccatgg tggaggtggg tggggtgggg gggaggggggc ggggagagag  21120 agagagagag agagatttga aagcattta ggaggtaaaa tcaactggtt tggtaatcaa    21180
ttagtagttg aaggtgaagg aaagagaaga gttaaggata acatctatat ttgttgattt   21240
ggataataga ggggacagtg gtgctgctta ttgaatgaga aaatttaatc ggagaagaag   21300
gcatggagca ggagtgcaga cctatgtgac tctacttctc tcaaaaccag aaacggaaat   21360
gatgtatatg gctcagggtt aggtaatatg gttatttgaa aatgtattaa agtgatttag   21420
```

```
agcttagtct taggtaagag atataagatg tctgaggtga cagttttata aatatgtaga  21480
gtgcccactt gtttggcctt attgtggcat agtgtgacct gagagtgtta ggaagaagca  21540
gctgagttct agggacagta ctggttaaat tctacttaga aattatactt agaactctcc  21600
tatataacct gctaactgat gtctgaacct cctgataact tcactccttt aggcagtgct  21660
tttcacatca cgggacacaa catatgagag atcatagaaa ttcaatgtgg tatgaaaatc  21720
tgcttgggac ttcagatatt gtctccagtg attgaataaa aataggagct cacctactat  21780
gatgaggttt ctgtgtgtgt taaaagaagg ttttcattac ttttgaaaag gttatgtatc  21840
cttgttttat gttaaaactt tgagctttgt taaatatgca gagttctctt tcttagcatg  21900
gactacagag gtgcaactac ctcctacctg acttcacatc tactcccaaa tgcctagtga  21960
aggcttaata atttcaaaaa gggactctag aatttcattt gataccagtc agacaaatgt  22020
gtgaaaatta agcataatag gcagaatccc aggggtactg acagctgtat taagaggtga  22080
ttcaagggct aaaccttaga gtccagcatt ggttatgggt gtgacaagaa aatgaagcct  22140
atgttggctg ggattagcaa ccacagttct agaggaagca aggtggagaa actatatagg  22200
gggctcccctt tgtacgtttt atttatttta aacatctcta taaactctag aaattaaaac  22260
aacaatacca acacaaaagc atcacttttt cgaccaaaga ccattgctat acttttttgt  22320
gtaaagggct agatagtaaa tattttcagc tttgtgggcc acataagtct ctgcaataga  22380
caatatgcaa acaaataagc atggctgtgt ttcaattaaa ctttattatg aacattaaaa  22440
tttgaatttc ataaactttt tacatgttgc aaaatattct ttatttaaat tctattgcaa  22500
tatgctttaa aagatacagt ttttagtctt tcttagttta aaataaaatc tagaaaaaat  22560
tttaagtctt ctataacttt ttttcggtaa ctgaataatt ttaaaagtaa gtgaaacatt  22620
tagacatgca aaatggactt ttcagaagaa gaaaatggta gcttaacagt tattagatta  22680
ttgtccagaa taattttgga cttataagtc tctgttgacc atttcattgc ctctttttt   22740
ggaatatgca tcttttaatg tgtccttcaa ggcaaaggct ctatcttatc tatcttgtgt  22800
cttgcatttt cccagggcaa tgttttcac aatttttta aaaacaata ctgtaatcaa    22860
ttttcaaata aaattttcca tgggaccgca gtgtatacaa atagcagtga caataaaaga  22920
taataactct cccataaata caaagaaaca gttaacctag tgctctaaag taaaggctac  22980
agtgattttg tataacattt atatgtaatt ttcttgatcc tacatggttg tgttttcac   23040
agtgttatgt ttctgaaatc gagatgcctt ttataattga tgtcaaaaga aacttgtcag  23100
ccacaaggcc caggaataag ttgtaatatg ggaacttagc aatacataaa ggtatatata  23160
ctcctgtgac ctcagctgaa ttatttgcat tggttgcatc ccacaaggtt gactcttaaa  23220
taaatttagt ttgttgcttg aaatttcttg ggataaatta ctttgtgatg tagttttgaa  23280
aaaaaaacag gtaatattta gtctgaagtt tgtctgacat actaagcaat gtaattaaag  23340
tagaagtcgc ctaagctcag cactttatta tgccttgaaa ttatactgcc tgtcctacag  23400
gtgaaggtgt tatgaatgca gtttgtcact gtaactctat tcatagctct gaaaggctga  23460
gagtgactca gaagaatatt tttgctctga atatgaagaa cgcttagact aaaactttaa  23520
ttacgatgct gaagaagaaa gtggtaggtg attgcatgaa taagtatgta atattgttaa  23580
tttctaaaaa ctgtgtatag ttaatgtagt gcttcttttt ggaaaggcta ttgttaaatt  23640
gatggtaaat tctataacca atatcacctt aaagcaagta cgcatgataa agtattataa  23700
aaccatgata atatcatatg tggcttatta ttgttccctg agtgttgtac aactctgtta  23760
tgctgtgatg aaacctcatg caaacaggta tgtcaaagat atgatgggct gttaactgag  23820
```

```
cttggcccac atatggtgta gtgacatgct cactaatgca gtgcagagat aaccaataac   23880
agatcataac aggtttaaat atgtgcaagg agatgtcagc agaagctttc ctacatagtg   23940
aatactaaac aagcctgaca gcccaggatc atgttcggat caatctagtg tgctaaaatt   24000
aacatatagt cctacatttg agaatgtgtg attttcttgg ttcctgtcta taaaataata   24060
ttttaaaata catacatttc aaatcagaag ttggtgaatt cactgaaata tttctagaga   24120
acactaggta ttggggctca tagtgtgaaa accactgact taattcttcc cccatcttgg   24180
ttgttcctga tcttcccttg tgtccccatt ccagccattt gtatccttag aaaatgatct   24240
catattctac ttcatctttta tcttcattgt caactgtcag gtagcaatat atgatggaag   24300
aagcatgtac tttggaatca gacagacctg gctggaatcc taactctgtc acttattaac   24360
aatgtgatct taggcaattt acttaatctc tctgaacctc agctactctc gtcagtacaa   24420
tgagttatcc ttatctttac atggcacagt attattatga tatcaaaaat tcattgagta   24480
tttactctgc atattagtca aggttctcca gagaagtaga accaatgata cacacacaca   24540
cacacacaca cacacacaca cacacacaca caatttatta taaggaattg acttacatga   24600
ttatgatggc taacaagtcc aaaatctgca gtatgggtca gctggcagga aacccaggag   24660
agtcaatgtt ccagtttgag tctgaaggca gtctgttggg gaatttcgtc cttctctggg   24720
aggccagcct ttttgttcta tacaggcctt caaccgattg gatgaagttc acctttatta   24780
gtgagggcaa tctgctttaa ccaaagttta ctgatttaaa tgttaatctc atccaaaaac   24840
acccacccag ttgacacata aaattaacca tcactctctg taagcacttt ctatgcatta   24900
agtgatagca ataatgcca gacatagggc gtctttaata aatggtaagc actgttatca    24960
gcaacaacag gattattata attagcacct tttcatcttt ctgtctgggc tctgagaaag   25020
tacctctctt ctctaaattt atccctcctt tcctatgaat tagacccagt gctttctctg   25080
aattatgaag gtcacactcc tacaaatgcc ccttcccaat tgcacatctg tcggcttttct  25140
ttgccattga ctttttatctc tagctttttaa atttacaggc atatgtcagt taacaatggg  25200
aatgcgttct gggtaatatg tccttaggca attttatcgt tgtgagaata ctatagagta   25260
tacctacaca agcctagatg tcgtatagcc tactacacac ctaggcaata tgacatagtc   25320
ttttgcttct aggctacaaa cctgtacggc ttgttactat actgaatact gcaggcagtt   25380
gtgacacagt ggtatttgca tatcggaaca tgtctaaaca cagaaaaggt gcactaaaaa   25440
tactatgtag tgatctcatg ggaccaccat tgtatatgca gtctgctgta gactgaaatg   25500
tcatgcagtg cataactgta tcttaaatac tcaaagtatc acctttgttt gtttgtcccc   25560
ttgtgtgcat catcctaacg tggaatttct ctgttgatta gggccagcgt attagtttgc   25620
tagggctacc ataacaaaat accacaaatt tggtggctta aataacagga atttattatc   25680
ttatggtttt gaagactaga agtacaagat caaggtgttg gcaggttttt cttctaaggg   25740
ccatgaggaa gagtctattc catgcctttc ccctaccttc tggtggtttg ctagaaatcc   25800
ttggcattcc ttgacttaca gaggcatcac cctgatctct gttttcatct tcacatggca   25860
ttctccctgt gagcctgtct ctgtgtccaa acttctttac tattaatata aggacaccag   25920
tcatattgga ttagggtcta ctttagtgac ctcattggaa tgttattacc tctgtaaaga   25980
tcctatctct aaataaggtc acatccttag gtaccggggg ttaggactca aacataccttt  26040
tttttgggga aacacaattc aacctataac aattgataac actctttagg agcagaatgc   26100
gatatggaag taatttgaga ccataaagta tatacatgta gggagttaat ctatgaaacc   26160
```

```
tattgaaagc catatatacc tcatgtatag tggtccataa atagcatgga gacattgcag   26220
aggatgttaa gtgatatgat acaggaacaa tccaagaagg tcataagaaa aaggaccttt   26280
tgctcttgag aggactgaag aatgactttc catttatgaa attttggtac atgtccacta   26340
aaaataggat gaaggccaaa cttaggaaga atattttgat aatggagaag gttgcatata   26400
aaaacatttt attgaggaca attaaataat gttggctgga agttttagga tgatcatctt   26460
taggactcag aaaaagagaa gaaacattat taaagaattg tccctgaaca agtataggca   26520
ccctcacatt tgcattgcat ttactataga attgaaaaat gttttgacct tttttttttg   26580
gcttttaata tatttgacca agagtaacag ctaagcaata cctatttgca atcagtgtca   26640
tcatgtgggc tccaaacata tcatgtttgt gtaattaatt gattgaccca ttaatttgtt   26700
caatttctgc tctgttccag gcactgaaca acatgatgga gataaaagat aaatattaca   26760
cctgccttgt cctcaagaag ttagtcttct gagggaaaga aattagcaaa caaattgtaa   26820
tctcagttat gtgccatgtt ccatgctggg cacaggggat acagtagttt aaaaaaaaca   26880
caagatctat aaggtgtttc ttcttgtgga ccttacagtc tagggtgctt ggaaacatgg   26940
ggcgttggca gacaagtaaa tacacatttt gtggtaaagg ctcaggtaga agaagtacag   27000 gatagaaatag agcacaccat ggggaattaa tctagacttc agagaggctc acacatacat   27060
aatttatgtg tgactatttc aatgcatttg aggtttcttg gaaatagagg ttaggttta   27120 ttttaaggaa gttaccattt ttttttcag tgtgatgtgg ttgaaccaaa gaatgccatg   27180
cccagtgatg gtaataggat aatcttttta aaaattaaga gccacctaat aaatcaatag   27240
tttcattcag cgggagctcc tgcagagttc aaaaagaaga gaatctggca cagcgtttcc   27300
tttaaagttc attttcctag agtgtgaatg gaagcaagag attataacat tttgaggtca   27360
aaaaaattct gaaatgccta taaaaattat tttctccaaa ttatcatcat ttgtgctttt   27420
aatgacctga ttgcaaagat gaacattttg aattcttaaa ttgcttatta ggattggtta   27480
atgaatcaat tatctattac tgtatgtttt gctattggaa aaaatagcaa cttaagtgtt   27540
ttgcagacct ttacttaggt atatgttgct tttatgaaaa aaagatgta aatattaagt   27600 aaaagggatt taaagcaagg cttttgaggt agagtcttat taattccttg gtaaaccttg   27660
agccaattgt tgtctatgtt ctctgcctct gtcttgctcc ttccttctgg gattcactgt   27720
gggaatgcgg gattgttaat ctggggatgc tgtccaatcc tgcctctctc aagctttgct   27780
attgatctcc ctcccagtga taataaagct tgaagaaaat gaaagtagcg ttagtattgg   27840
tcctcaaact caagaacagg atgaaactta aatcttgagt catacaattg tgtctacata   27900
ctgctcccca aaagagaag taagaagat gctaactttc cctttaatt tgcagtactt   27960 agcaatttgt tttcttgagg gttaagtaat aacagtggaa gaaaaaggg ttaaaatgcc   28020 accaagaacc caattccatg tttagtttga agtgggaaa tcagctgcca ctgggaagtc   28080
tgaatccaat gccatgatgt tctttgaatc cttctgagaa ataatcatgt gtagccataa   28140
catacctgta taacagagca gagaacataa acaaatgaag gtgaagggaa gattaagaca   28200
gaagagaaaa attccagaat cgactgatca ttttatctg tttagatgat tcaggcaga   28260 atcctagaga ccaactttat cacaactgaa ttttaaaaat caccagcttt gtcattgtga   28320
tgcagcatca gtttcagtat tatccttgga gtattaattc ttaatcatct tcatcttaga   28380
acatttttga ggtcacttct agtctctatt tcaccagtga agaaacaaaa atccccaaac   28440
tatatcaggt ggaattacac agtatttttt ttttaatttt ggggaaagtc gattcaaggc   28500
agtaacttgc aagctagtgt tagaaaggat ttaataaata gtggtttttc tgtacacata   28560
```

```
gtgagaggtc attacatcat ttggttgttg aaagtcataa ggatgtctag catgcgcttt    28620
gcctgtagtg gttcatgcca ggcagattcc tgactcctat aacccagagc ttatcagagc    28680
atttatgtcc ccaaagagaa atgtcacctc catctttcaa taaacacttt agcaaagaaa    28740
aatcaagtac tttaattcca aatcttgagt taattccaga ataacaatga tggctcggaa    28800
aaatatgggt atttctgtca aaggacagag aaacctagta gagagtattt actttgggtc    28860
ctagtgatgg tatctgaaca agctaggtga acaaagagcc tcaataaggg attttgaggt    28920
ctagaaaaag agaggaaata ccaaataaat ggaataatta taaaataaat accagcaaag    28980
ttaaatcaat atatcatgtg ggagatatcc ttatatcact catgtgattt ctattttgtt    29040
cctatattag gccaaggaga ggtggaactt gttttccttt ttccctctca gctacgaatg    29100
gacatactta aaactgtttc tctgcttctg ttctctaaaa tgtgattgtc taacagtaac    29160
cgtgatgacg ttttgacagt tgcacaagtt tctttcttta agctttaaaa atgccagcca    29220
gtaacccagt ggcatttcta ctataaaatc ttaaggccaa tccatttccc cttttcctta    29280
ttttcttggt ttcaaatata tttttattgc caatggaaat aaaaatccta aattagagag    29340
caatggcatc ccttgtcttg tgaataaaga gctcctaaat gtgaacttat acaggatgca    29400
gcaatttata gggtagttaa tcattcttct ttctagccag ttgttccagc tacagttttg    29460
tggctcttgt tagtggcttc attcccagat agaataaaaa tcaaaccaaa atcctggaaa    29520
ggcactctga ggatgcttct ctaaagtaga tgggcatcaa ctataaatca caatgctttg    29580
tttcctctgt tatgtttcaa gatgggtggg attttttttg tagcattact tattattgcc    29640
tctcaagtgc ttgagtcttt gaaatccaag tcatgtgagt gaattagata cagctgttag    29700
aagtggcctt tcaatgccaa tggtacacat tccttggttt ctttacgata ctattgctct    29760
tacaactttt atctgaagtc ataaattcat agttgtccca gaagttaagt tccttgcttc    29820
tagaggacag aaaacaaaca atttacacaa ctcatggtgc atgtcaccag tccttagatc    29880
tcatgaaata tgcatgaaat cttaaatcac ttgctgtagc cacccagcca ttgacatatt    29940
tgaaagactt tagtgtatca aagtcactat aatgaaaatt ttgatttcac cagttctagg    30000
agtgaaaaat caaatgttta gtaaaacttt ctaaaattaa cactgacagt tgatttctgt    30060
atactgttgt tcttaataat agctttattg agatataatt catattcaaa acaacttacc    30120
catttaaagc atacaatcca atgatttttt agtatcttca aagagttgcc tatcaccata    30180 accaattta gaacactttc atcactgtaa aaagaaactc cattcctatt agcagtcatt    30240
ccttattcca aatcccctg ctcgccctag acaactacaa atgtactttc catctctata    30300
gatttgcctg ttctggaaat tttatgtaaa tagaacaaag tgttcttttg tgactggctt    30360
atttcactta gcatttttt tcaaagattc atccctgttg tagcgtgtat cagtgcatca    30420 ttcttttta ttttttaga cagggcct tgctctgttg cccaggttgg aatgtgcagt    30480
ggcatgatca tgggtcacta tagctttgaa gtcataggcg aaagcggtcc tcccacctca    30540
gtctcccgag tagctgagac tacaggcttg caccacatga ctgtctaatt tataattttc    30600
tttagagaca gggtcttgtt atgttgtcta ggctgctctc aaactccagg gctcaagtgg    30660
tcctcctccc acagcatcct aaagtgctgg gattataggt gtgagccaca gcacctggct    30720
tgcatcattc tttttattgt tgaataatat cccacttgta agaatatgta ttttatttat    30780
cctttcccca gttaatagat atttcgattg ttcctaattc ttgtctatta taataatgg    30840 tgctatgaac atttgtgtac aagttttgt gcagacatcc attttccttt cttttgggca    30900
```

```
tatacctacg agtgtaatgg atgggccata tagtaacttt atgtttaata tttgaggat    30960
ttttcaaact gttttccaaa gtggctgcat cattttaaat tccttccacc attgtgtgag   31020
tgtttcaatt tctccacata tttgcaacac ttactattat ctactcttaa aaattacagc   31080
catcctactg ggcatgaagt ggtatttcat tgtgagtttt tttttctttt tctttttttt   31140
cttttttgc taatgtttgt ggattttctt ttcattttct tgatggtgtc ctttgaagca    31200
caaaagtatt taattttgat aatttccaat ttattttttg ttattgctgt ttgtgcttct   31260
ggtgttgtat ctaagtgtat gctactttaa aaattagtt gtaatatggc aaattggata    31320
catgtgtagg ctttggtgtc acaatcctaa ttttaaaatt ctgactctgc ccttgacaaa   31380
ttaactaatt aagcttcctt agcctcagtt tctcaactgt aagttggaga tattaccaag   31440
acctacctct tgaattgttg tggggatcag atgaaataat gtatgtgaaa tatttagaat   31500
tatgcaagtc tgtggtaatg aatactaatg ttagctatca ttattgttat aatcccaata   31560
ataaattctg gtgctttgaa aattaaacca aagccaagca gttgatatga agaagcatgt   31620
aataatgtac agacataatg ctttatagac aacattgaat ttggctctca tgaacatcag   31680
gaatagtggt catggtagtt attatctcca gcaggaactg tagctgagag atcttcagag   31740
cttttccaa ggcgatatca ctgggaaata atagagacaa ggttacaagc tagggctgtg    31800
ttttcttctt aaaatcttta gttcagtttt tttcaataac agatttgtag taggcatcag   31860
gtgactgggg attcgtattc ttcaagttga aatattacct tgttgagaaa gaaaccatgt   31920
gtgagacaac catgttgaga agaaaaagt gattttatag aaaattaata ttgatagtga    31980
gcattatatg aaaatcatga agttagaaca tatttggcca gaaaatttac attaatagtt   32040
acccatagca attaatgcat tataattaca catacctttt ctttaatgaa aaagaattct   32100
ttccttccaa agttatgcat gctattgtta aacattagag aatatagaga agcaaaaaag   32160
aaaatatctt ttttgatatt ttcttaacat acgtctgttc ctaataatgt ttatagttta   32220
gaagcattgc atgaaatggg tagatcaatt ttctatttaa tgtttggatt cattaggtac   32280
gaagttagca aattaatttc cattagggtg cctgtatggt tgtaaatcct ggacctgcag   32340
aagattttc agtattggtt tgtagtcttt tgtttagcag caaataatta gttctccaga    32400
gcttctgaaa ttaattgacc actttaatgg tgtttaccta cctagagaaa gaaaagaac    32460
ttctccaagt cccttggtaa aattaagcct catgaacaat taactcaaat atacacaagg   32520
cttgtcttta gcgagcatat actccctaaa gttgattaag ctgaccaagt gattactgct   32580
tataaattca ccattttatg gagaagaagc aaacactgct aaataccttg tggaatcaga   32640
ggagggaaa ttagtaactt gaccccaata ctgcgatttt aaattgaatt cttgaagcct    32700
acaagtttta cacaggactt tagagagctg gatagtatca ctttgtcaag tcctacttt    32760
actatgattc tttgagaaaa atacatctga ctaaataact ctgaatctaa attggataaa   32820
ataaatgtga cattcaaaat gttatttatg attttagaaa aatatcctta tagacactag   32880
atgagtttta gtctcaaatc aatcctccct atcatagtca cttatcaaaa taactaaagc   32940
aaagtggtag agctgtgctc tagaagtttg ggatttatga tcacaatctt ttccaatgag   33000
tccctcttt cctctgcctg tcttcaacat ttgtttttt tttttttgg ttaggactat     33060
ccagattgtg tggcctattt caaactcatg gcaaatacat tggatgatca gaaattttct   33120
aatgtatttg aatttgtcta cacaaactag agtaattgct attaattcct caagtgttaa   33180
ttatttcatg caaaaaggaa aaaggctatt agtctttaag tgtattagta tgtcaatatt   33240
tgggagaagt gtcatgcaat tagtggtttg aatttcctat tttatttat tgcattttat    33300
```

```
tttatttgcc tagtcaaata aaaagtaatg ttaaatacat ggaagcatga ttgttttcta    33360
cactaaaaat cattttgact tgaaaagatc tgatatccat gaccttcatc tgaagttttg    33420
gcagatgaaa atgtcagatg cgtcttttgg attaataaaa ggcaaaagtc agatcgaaaa    33480
atgagtataa gctttaatta tatgacttta ggaggatatg ttatgaaaat caaagcttta    33540
atagtgatta taattggcaa gttctttttt tataaggaat tacaagtcac tctatacaaa    33600
aattggaatt tttgtcctaa gaaatgaaat ttactatagt ttcatctgtg tgtgtgtgtg    33660
tgtgtgtgtg tgtgtgtgtt taaaaaatca agtgataggg cttttcctca ataaaatctg    33720
aaatctctta tagttaagtg aacagaacag tgtatctagg atgctagact ttttttttcaa    33780 agttagttta aaacttatac atagtaaaat ctgtatgcct tagggatctc tgtttgctat    33840
cccatagtga atgattaatt agtttctgtt agaaatagtc agaactaggc tgggtgtggt    33900
ggtggctcat gcctgtaatt ccaggacttt gggaggccaa ggcaggagga tctcttaagc    33960
ccaggaattt gcaaccagct tgggcaggct ggtgagatcc tatctctaca aaaacaaaca    34020
aacaaacaaa ggacaataag aaagaaagaa atagccagag ctttgaacaa aatttctaag    34080
tagaccaatg taaagtctg tcgtcaatat gtagtggcta tgaatggagg ttatgaatga    34140
aagagaagga taagatgaac tagaggtgag aggggaagac agcaggccca agtgaaaggc    34200
agagccgagt ttattgcttt ttggttattc caggtgtgtc tgctttgtct catgaaacac    34260
ctggatgatc actgatttct agtggaagaa atgctgaaaa gtccttactg tgcatttaaa    34320
cattctaggt ttaatatact cagggttttt caaaagaaag ggtggctgga gttttgcact    34380
aactaatatt tcataaagtg tctaagtata gatgtctggt ttttttttgt atttctaaga    34440
ctggcttgag gtaggcatgg agaattcttt gatgggacat aatttcttc ctttcttttt    34500 tttttttttt ttttttttt gagacggagt tttgctcttg ttgcccaggc tggagtgcaa    34560
tggcacaatc tcggctcact gcaacctccg cctcccaggt tcaagcaatt ctcccacctc    34620
agcctcccgc gtagctggga ttacaggcat gtgccccat gcctggctaa ttttttttgt    34680 attttagta gagatggggt ttctccatgt tggtcaggct ggtctcgaac tccttacctc    34740
aggtgatcca cccacctcgg cctcccaaag tgctgggatt acaggcgtga gccacgcgc    34800 ctggcctgat gggacatatt tttcattcaa ttttattgat ttaacctcac aaaataaaat    34860
atttccttaa gatgactctg tggtcattgt tgggcagcat aagcttaatg gattttagtt    34920
atcataattt accttaaacc caatttgtat ttcaggatat aaatagaggt ttattgtagt    34980
gaatcttcca ggaaatacta agtgatacta ataattatag atggtgaact taagtctttta    35040 tattactgaa tttgtttggt ttgatgatgc taggctatgg cattcttgct aatcaaaacg    35100
atgtgtcatg gtgtaacata acttattaaa atgggcacag ataacacagg aagcttttta    35160
taaaagcagc tcacaaattg tgttactttg aactgaactg gccatttatg ggaaaggtca    35220
ctgggttgta aataaggacc aaagagtta cgtttatatt ttttaaaaga gattgaggag    35280 atttatttt acatttcttg aaaatgcctt attttggtat ggtattgaca gatagtgaaa    35340
ttctgctcat ttgtaaatat agtgtcatat tttaataatt tcaaacatat tgaaaatgca    35400
gaatttatta atagtgggag cacatttttcc ttttactaa atgttctaca ggttcttttc    35460
tttccatcca cacacagtgc cattaccctc attctaagcc tttcaaacat ctggcagtaa    35520
gtgatctgct gcacttagct cttttccagct gagctgattt ttaaattttc agaaaatttg    35580
tgagctaatt gttaaacatg gccattatta aaaattaaat tatttcaact tataattaaa    35640
```

```
taaattatat taaaacaaaa gtattaaaaa ctcaaaagtt ggctgggcgc actggctcac   35700
gtctgtaatc ccagcacttt gggagaccga ggcaggtgga ttgcctgaag tcaggggttc   35760
gagaccaacc tgaccaacat ggagaaaccc tgtctctact aaaaatataa aaaaatagcc   35820
gggcatggtg gtgcatgcct gtaatcccag ctactcagga ggctgaggca ggagaattgc   35880
ttgaacccag gaggtggagg ttgtggtgag ctgagattgc gccattgcgc tccagcctgg   35940
gcaacaagag tgaaactctg tctcaaaaaa aaaaaaaaa aaaaaaaga aacaaaaaaa    36000
aaaaaaaac aaaagcaaa caaacaaaaa aacaaaaatt atcacttcct aattattttg    36060
cattttacta ttatctatgc tattaacgtt atttgccttc attgtatttg aaaggtggac   36120
tatattctat tgcactttca ttgtactata ttctaatatg caactgtgta tcccttccca   36180
actctgtgtt caatgacttt atatttggtt gctttaaaat gatgacgatg agagtattta   36240
tatcatagaa attggcaaat gccgtaagtc agtttttgtt tttgtttttg ttttccggag   36300
aggggattgt taaatatttg cctgcatgca acaccactac atgcagtctg ctatctttg   36360
ttcttcctgc tttcaggctc ctctcccagc tgtctgtcta gcacaaccca gcataccaaa   36420
ttttcttaaa tagggaaagt tgaacatggt aaaagaatga atgaagtcaa agaatgtgg   36480
aaagacctag gctttgccat ttagtaaagt ttagcatctc taagcctcca tctctttatc   36540
aataaaattg agcaatgatc ccttttagtt ctacccattt aagaagattt tcaaatgaaa   36600
accacaacct gctcatgttt atgaaggcac tttggaaagc gctaaataca cgggttttta   36660
ttagtagtaa acacttactt caccttttc acttcttgac tttagtttac aagggctcat   36720
aatctaaatt atatcataaa ttgctgtccc agatttttt acagcctaat tgccacctgt   36780
atgttcgact ttccttctgt tctttatgtt agatactggg atagtatgca ccaggtgggt   36840
gtgccatcac tttctcagat gatgtccact gaagaccttg catgatcatg gcattcattt   36900
tcctgctgta ttcagactgg cctcaactat tttctttatt gctctccagg aaaaattaca   36960
aatgaatcag actgggcaat gaagggtaaa cctaattatc gctctttgtt aaagacagct   37020
cttgttaaaa tgcggatatt gcaaattaat ggaaaaaata tgacatagta aaccatactc   37080
acttattaat atcttagtaa ggaataattg atgaagttac ttaaccttag agccctaatt   37140
cagttaagtt ttaatgaagg acaagttgta gagatatcga gaacccaggg caggtgccta   37200
ctgaagaagt tccagaccaa ggaagtataa agaaggacct gggtgggagc agtgagattg   37260
gatatgaggg ccactggcaa agttttgccc cagaacagtg tcaaaatgtt tgcatttggc   37320
atagcccttt ctcttttgt tctgaatggc tttgctagaa tatctttct ataatgaatt    37380
tatcctgctt ctcagatatt gctaaagcac tcccttttga attttggtgc tttaacatgc   37440
attttgatac attaccaaat aaggtctgaa tgacacaaat tttagaactc tccagagaaa   37500
agaaagatgc tgagggaaaa agcataggtt tgggactcac taaatcccag ttcaattcct   37560
ttctttaata aatatattca attttacctg agaaagctct cgtgctctcg aattttattt   37620
agaaatttct ctttgtacat gattgatttc acaatccttc ttctgcctcc tcttctactt   37680
tcttcttct agattttcct atctttatga agattattct gccttatcct caacagttag   37740
aaacaatatt tttgaaaatc actacggtat cctgcatagt gatttcccat gccaacttta   37800
ctaatttcca ttataaatta ttatttattg atgcctagag ggcagatgag tgtagctgct   37860
atggagtgag gagacaaaac ataagaaagt tatgatccta ccctcaggta atgattcaga   37920
catgataatt aagtcaacaa attgataaa actaatcact aactctctgg ctatagtcat   37980
tctttcaatg aatagctcat tactgagtat gcatgctaca gtaacaaaat tatataaggc   38040
```

```
tgttgattaa atgttgatta agtgcatgtc ttattcagag tttttttata tttgaaatgg    38100
aagaggctgg acttcagtaa tttgctataa actgctagta tatgattatt tgggggcagt    38160
tattttttaa agaataattt aaatatgaaa tgtttagcag tttgtttttt ccctgggaaa    38220
aaccatacta ttattccctc ccaatccctt tgacaaagtg acagtcacat tagttcagag    38280
atattgatgt tttatacagg tgtagcctgt aagagatgaa gcctggtatt tatagaaatt    38340
gacttatttt attctcatat ttacatgtgc ataattttcc atatgccaga aaagttgaat    38400
agtatcagat tccaaatctg tatggagacc aaatcaagtg aatatctgtt cctcctctct    38460
ttattttagc tggaccagac caattttgag gaaaggatac agacagcgcc tggaattgtc    38520
agacatatac caaatcccct ctgttgattc tgctgacaat ctatctgaaa aattggaaag    38580
gtatgttcat gtacattgtt tagttgaaga gagaaattca tattattaat tatttagaga    38640
agagaaagca acatattat aagtttaatt cttatattta aaaataggag ccaagtatgg     38700
tggctaatgc ctgtaatccc aactatttgg gaggccaaga tgagaggatt gcttgagacc    38760
aggagtttga taccagcctg ggcaacatag caagatgtta tctctacaca aataaaaaa     38820 gttagctggg aatggtagtg catgcttgta ttcccagcta ctcaggaggc tgaagcagga    38880
gggttacttg agcccaggag tttgaggttg cagtgagcta tgattgtgcc actgcactcc    38940
agcttgggtg acacagcaaa accctctctc tctaaaaaaa aaaaaaaaaa ggaacatctc    39000
attttcacac tgaaatgttg actgaaatca ttaaacaata aaatcataaa agaaaaataa    39060
tcagtttcct aagaaatgat ttttttttcct gaaaaataca catttggttt cagagaattt    39120
gtcttattag agaccatgag atggattttg tgaaaactaa agtaacacca ttatgaagta    39180
aatcgtgtat atttgctttc aaaacccttta tatttgaata caaatgtact ccctgggaag    39240
tcttaaggta atggctactg gttatcaaac aaatgtaaaa attgtatatt tttgagtacc    39300
tgttacatgc caggtagaat atctcctctc agccactctg agtggaaagc atcattatct    39360
ctattttaca gaaaagcaaa ctgaggctca gagagataat atactttgcc agttaatgaa    39420
tgatggagcc atgattccag ctgaggtctg tattgccttg ctctctagga atggtagtcc    39480
cccccataaa gaatctctca gtttcctttc caatcaaaag gttaggatcc ttttgattgc    39540
cagtgacaga acccaatttt actagcttaa gtaaataaaa ggaacgaatt tattggctca    39600
tgaagcctga actatgtgaa gacctaggtg gagaactggc cttaggaact caatgggacc    39660
aaggactcaa atgccacctg gtggcatttg ccttatgctg gttttatttt ctcagaccgg    39720
accagctttc tacataaagt gggtccctgg ttagaactct ttgctcctat ctttaaggac    39780
cacgaaagaa ggagcccttt gtccttggct aaatgtgaaa aatcccagag actcttgagt    39840
catagtgctt accccttggg ccactcatag tctagaatga actaggctga gtctcgtgcc    39900
aacagcacag gcctgatgcc agataaaagg gtgagtgaag ggggataaaa aataagacat    39960
agctactaaa ttattgcacc aaagtaaaaa cattgagttg acttgcaatt tgtttctttt    40020
aattaaattc atttcctttt tttggcattt tgaaggcaaa gtaagatatt aaactttatt    40080
tttattgatt ttattcaaag aattaagcta gtgggagtag cagattcaca cttctaagat    40140
caagggccag cttctattat tgaacacttg gtgtgtgcaa atgccatgag gtagggatac    40200
tttgttttgt tttttatttt ttattgggtt cgatctcttt tgtttatgat gtatccccaa    40260
gtgcctagaa tagggcctgg catatggtat atactcaata aatatttgtt gaatgaatcc    40320
atgatggaat gtgaaatggc tagcattaca tagaaacctg tagcattgct ggagagataa    40380
```

```
aatatataaa cataatccat tgcaggtata ttgacaagtt caaaataata taatgggtat    40440
tgaatatcta aatgtttgtt gttgttgttg ctgttgtttt tgagacagag tcttgctctg    40500
ttgcccaggc tggagtgtaa tggtgcaatt ttggctcact gcaaacttcg tctcctgggt    40560
tcaagtgatt ctcctgcctc agcctctcga gtagctgggt ttacaggcac tcgccacaat    40620
gcctggctaa tttttgtatt ttagtagatg tggagtttcg ccatgttggc caggctggtc    40680
ttgaactcct gacctcaagt gatctgccca ccttggcctc ccaaaatgct gggattatag    40740
gtgtgagcca ctatgcccag cttgaatat ctaagtttta attggatgct gagggaatga    40800
ttaatcagag tagggctggg ttaattgaaa aatgtgatac atttgtattt atggccagat    40860
agagaacatg aatctgaatt tgcagaatta tctggcttaa catttttttc tttccagttt    40920
tcactgtatc ccccatgttg attcaattta aaaaatatac ctattttact tcaattcaac    40980
aatgctatgc cagtacaaac ccatacgttc tattatttt gttttgtttt gttttgtat    41040 ctccaccctg ttacttcttt tcttataaaa ttggtatttg aaatttattg aaatattttg    41100
gaagagtgac ataccatttt tggtactttg tacctctgca cccttgggaa gtgaccctgg    41160
cttcacattt cataactgcc ttgtgaccat ggccctcaag tggttgccag atggttgaag    41220
aacattaacc tatctggctc aattttgtga ccatggattg aatcctctac ataactgcag    41280
tgtgcaaacc acacatccgt tccaagattg tagtcaggat atgaactttt taagaataaa    41340
acttcttccc ttctgatctg ggcctggtat gtggtcctac tagaaccaca tcacctactc    41400
ttggtgctaa caatttgtgg caccaagttg ttcaagtttc acccattaaa gaaattcccc    41460
gaccttgcct tctcctcagg taactacccc attctatttt ttctttcata gctaacattc    41520
tctgctctcc tggtctctct acttcacttt catttacatc tcagctcctg aagtatggtt    41580
tccaccatgt tcctaaaact acattgccca gggtcactag agacctctta tgaaatataa    41640
caacaccttt ctacattact tccgtgtgga ccactttttc acattgaacc cattttgttg    41700
gtttatgtac acaccccttc cttggctttc ccatctgatc catttctcct ttgatggaga    41760
aggtgagtct gctccatatt tagcttctta ctctgagtaa ccaaatgtta tggatgggag    41820
gttagctctg tgtgtgagag aaaggtggag aagcatgtgg ggagggaaat agatgggaaa    41880
aggtaattag gctttataga agggctctca ttagcaagct tctaggggat gccaagatcc    41940
atgcttagag attgccaggc ttgtcttcaa atctcagctg tgtattactc ctttatgttt    42000
tttgtttgtt tgtgttgttt gttttgaga cagagtctcg ctgtgtcacc caggctggag    42060
tgtagtggtg tgatctcagc tcactgcaaa ctctgcctcc tgggttcaag cgaatctcag    42120
tctcctgagt agctgggact acaggcatgc accaccaggc ctggctaatt tttgtagaga    42180
cggggttttg ctatgctggc caggctggtc ttgaactcct gacctcaagt gatctgcccg    42240
ccttggcctc ccaaagtgtt gggattagtg gcgtgagcca ctgccccggc ctattactcc    42300
tttagagtga tttagagcca tgtttactta tggtaacttg acagtaatgg gaataaccac    42360
tgatgaaacg taaagccttt gtctaattgt ttacctagtt cttccttgtg gttcatgaaa    42420 ttttcatct ctgtacagtt tgaaaattaa gatgataata tttagagata ttttattcct    42480
ttgtgaagag aaaaaaggct ttcattaaca gaaatcagtg gcaataactt aataaataca    42540
atcagctggt gttcctatag tatttaaaag aaaacagaaa gtttactaga tttcagccag    42600
ttttcagact atttaatgtc tattcttact ataatagaaa atatataatt tgatcttgtt    42660 ctcattttc aaagaccttt aatacatgat tttagtagtt gaaaatgaag tttaatgata    42720
gtttatgcct ctacttttaa aaacaaagtc taacagattt ttctcatgtt aaatcacaga    42780
```

```
aaaagccacc tgacatttta acttgttttt gatttgacag tgaaatctta taaatctgcc    42840
acagttctaa accaataaag atcaaggtat aagggaaaaa tgtagaatgt ttgtgtgttt    42900
attttttcca ccttgttcta agcacagcaa tgagcattcg taaaagcctt actttatttg    42960
tccacccttt tcattgtttt ttagaagccc aacacttttc tttaacacat acaatgtggc    43020
cttttcatga aatcaattcc ctgcacagtg atatatggca gagcattgaa ttctgccaaa    43080
tatctggctg agtgtttggt gttgtatggt ctccatgaga ttttgtctct ataatacttg    43140
ggttaatctc cttggatata cttgtgtgaa tcaaactatg ttaagggaaa taggacaact    43200
aaaatatttg cacatgcaac ttattggtcc cactttttat tcttttgcag agaatgggat    43260
agagagctgg cttcaaagaa aaatcctaaa ctcattaatg cccttcggcg atgttttttc    43320
tggagattta tgttctatgg aatctttta tatttagggg taaggatctc atttgtacat    43380
tcattatgta tcacataact atattcattt ttgtgattat gaaaagacta cgaaatctgg    43440
tgaataggtg taaaaatata aaggatgaat ccaactccaa acactaagaa accacctaaa    43500
actctagtaa ggataagtaa aaatcctttg gaactaaaat gtcctggaac acgggtggca    43560
atttacaatc tcaatgggct cagcaaaata aattgcttgc ttaaaaaatt attttctgtt    43620
atgattccaa atcacattat cttactagta catgagatta ctggtgcctt tattttgctg    43680
tattcaacag gagagtgtca ggagacaatg tcagcagaat taggtcaaat gcagctaatt    43740
acatatatga atgtttgtaa tattttgaaa tcatatctgc atggtgaatt gtttcaaaga    43800
aaaacactaa aaatttaaag tatagcagct ttaaatacta aataataat actaaaaatt     43860 taaagttctc ttgcaatata ttttcttaat atcttacatc tcatcagtgt gaaaagttgc    43920
acacctgaaa atccaggctt tgtggtgttt aagtgccttg tatgttcccc agttgctgtc    43980
caatgtgact ctgatttatt attttctaca tcatgaaagc attatttgaa tccttggttg    44040
taacctataa aaggagacag attcaagact tgtttaatct tcttgttaaa gctgtgcaca    44100
atatttgctt tggggcgttt acttatcata tggattgact tgtgtttata ttggtcttta    44160
tgcctcaggg agtaaacag tgtctcccag agaaatgcca tttgtgttac attgcttgaa     44220
aaatttcagt tcatacaccc ccatgaaaaa tacatttaaa acttatctta acaaagatga    44280
gtacacttag gcccagaatg ttctctaatg ctcttgataa tttcctagaa gaaattttc     44340 tgactttga aataatagat ccataatata tattcttatg gaaatctgaa accatttggg     44400
catttggggg taaaaagtat tttattagta aatttaaatg aggtagctgg ataattaaat    44460
tacttttaag ttacctttga gatgattttt ctcaatcaga gcaccaccca gagctttgag    44520
aaacaatttt attcacagct tctgattcta tttgatgtaa tttttagaaa ataagttttg    44580
ctggttgctt tgaatcaggg tatggagtac agttcactct gatcctatca tataaatcat    44640
gtaagtatat aacattttca ataagtgatt gttggattga agtgaatgat atttcaagta    44700
attgttatgt catggccaag atttcagtga aactcaaaat ttctcctggt tgtgttctcc    44760
attgcatgct gcttctattg attaacctaa gcactactga gtagaagctg gaagagggt     44820 ctaattagaa ggccccttc tatgctctgc ttggcttgta aaataattta tttctctaga    44880
tcccaccaac atagtagttt catgtatgca aaaacaccca cctaaatgtc aaagtttgta    44940
tgatacatgg acatatctat agaatttttt ttggtctggt gcatgccaaa aaataaacat    45000
gatatagaag aatttaatat ttattgagta cctaatctgt tccagttcaa tatgaaggtc    45060
tttatgcaga ttatttttact taattttcct agtaactcca tggagcaaaa attatctcta    45120
```

```
atttatataa caggaagttg agcgtgaggc aaattaagta actttcccaa agttacacat    45180
atggtaagtt tgagagatat cccagtctct ttagctccaa agcctttgac cctttcacca    45240
taccagatta tgattgctat taatatataa ttataattat aatgattgta tttaggtact    45300
caacagaatg gtgactctag taaccagcct tggttctgct gagcttctct gcgtcttctc    45360
aggagacaca ggctacagag cttgaaggct gaggattctt ccagggtcac ttcaggggca    45420
aatctgaaac tttcttcagg acaggaatca acgagatctt ctcacttact tatacctggg    45480
ggaggaactg tatgaaatcc acccaagaac cagtcatgct aagggccaaa cctatagaca    45540
aaaaaaggga taggagaatg gagtatgtat ggagaaagac taaattgttc ttaaacttct    45600
caagcttaaa aatatcccag caaaagagat cgtaaaagcc cttcatggcg tattaattat    45660
ccatgcatgg gggtgagtgg aaaggtactc ctgagcccga ggctacagct ttggaactag    45720
cagcaccttt gaaggggaaa gcgtgtttcc atcatctcaa ctcctactga taaccaatgg    45780
aatattggtg agtaaaggat cctgggggaa gaagcagctg aaatgtgtag gtgagaaggc    45840
agagagaaga atatttatat tgggaatggc acaagtgtga tgaggctgca ggttttttcac   45900 ccttgtcata gagaaaaaac cacgctgaca ccatgcagtt ttaaatagtg agaaatttgc    45960 aaaattgttag atcttaaata atttagataa acatagtggc catttagatt attgcagttt    46020
tttcaggata tctgatctct tgatttcatt ctttttgtct cttataagaa taaaaggggg    46080
ggagaaaatt tagccattat agtatttctc tacattttct ctgtcctttt acataactta    46140
caccagtgcc ttcctattta tggtattatt tatgggtatt tcttctttttc tttcactgag    46200 caaggataaa tgagccaggg attcttgaaa ctactgtaac acttctctta gaaatagatg    46260
gtcatacttt cagaatctct acacattctt agtccctcta aacaatgata gttgtggcat    46320
aaaaatattt gcttggtttc aggactgata gagaaaagta ctataaaatt tgctgttaac    46380
tgtgaaaggt taaaaaaaag gaggtgccat catgaaggag ctaatctttc tgaagtactg    46440 ctgtagttttt aaatattatt agctatgact tctcaccatt aactatgcac ttgctttttc    46500
ttcatctgac tcagcagcca gatagatgca acattgtctt taacatttaa gactcctagc    46560
aagtccgggc acgggggctc acacctgtaa tcccagcact ttgggaggcc gaggtgggca    46620
aatcacaagg tcaggagttt gagaccagcc tggccaatat ggtgaaaccc tgtctctact    46680
aaaagtacaa aaatcagcca ggtgtggtgg cgtggtggcg ggcacctgtg gtcccagcta    46740
cttgggaggc tgaggcagga gaatagcttg aacctgggag gcagaggttg cagtgagctg    46800
agatcgcacc actgcactcc agcctgggtg acagagcgag actccatctc aaaaaaaaaa    46860
aaaaaaaaaa agactcctag catggaagag aaactggctg ttgaaaacct gaatgtgaga    46920
gtcagtcaag gatagtttga gggaagccaa gtagaggaag ctctcacaag cagattggtg    46980
agagaatatg attatacaat gcatttatta tgataagaaa ttcacaagca ttcattcaaa    47040
atactcttga ttcctaggca gctctgggca tatttccacc aacaaattga ggcatatgtc    47100
agtgcagcct aggtcagact acctttttttc attaaacctc acaaaattaa aggacataca    47160
ggagaagtcc tggtactcat gttgcagact acagtctata tggcaaagga ggatctctgt    47220
cccttatgtt tggatgaaaa cattgggtag gcatttgaat acaagcctac tgctaatatg    47280
gggctaaggt cttttggcccc ctaaaggttt gctgaaatat tactgacagg aggcagattg    47340
ataagaggaa aagcacataa atgtatttga catgtataca tgggagcctt caggatgaag    47400
acctaccctc tcagtgcagt atggaagctt gtataccatc ttgaggttac agaaagaatg    47460
ggggtttgga tctttgtaaa acaggtttca gtggcaagac aggttatgag aaggagaaag    47520
```

```
gaagagactt gggtagcaaa gggggtcttg ttttgtaggt aaatcgttgg cagcccacag    47580
agaaaataga tggagaatgt ttcttttcag accttggcag gtgtcagatt ctcagttaat    47640
ctctcctaga tttgaaaaaa aaaaaaaagg tctagaaagg gagagcctgg ctgcactaac    47700
acattttcta cagatgcaaa tttctcccac aaaatacagc tttgcaggtc cacttctatc    47760
tgctgggcct gtggcaacca tttcaaaata tgtgaatgaa atatatgtgg gggtaaacta    47820 ttttattta cttccctaaa gaagggatgg tgttctctcg ggaattctgt gcatagagag    47880
cctgtggctt aggcactttg atttatgtat atctcttcct gtgattggct atctagggac    47940
tgctatctcc agcaaatctt ctaaatgtct gccatgtaga attcctttct catctttctg    48000
tctcaccccc ttatctagct gcttctctaa ccctagagtg acactgcact ccccacaatc    48060
tcctatgtcc tgaatatttt accccatcct aaactccatc tctaacacag atgcactttc    48120
ttgtgctgcc tactgcattg tacatcttcc ccttagttcc catgatgcaa ctctgcccta    48180
ccccagaaaa tgtaatttaa ttggtctggg ataaaacctg ggacactatc attcttgaaa    48240
tattccccaa gcgattctaa ttatatagcc aaagttgaga actatttgta gacaggcatc    48300
agcatgatca cttaatgatt tgacttttgc tagatctaag gtgaggaaat tggagagtgg    48360
tatccatagg aagaactgtt tagtttaatt ttttttttat ttttctttct aaaaaaaaat    48420
ccaacaacga gatacatgtg cggaacatgc aggtttgtta cataggtata atgtgccatg    48480
gtagtttgtt gcacctattg acccatcctc taagttccct ccccactctcc ttacttccca    48540 acaggccctg gtgtatgttg ttcccctctc tgggtccacc tgttctcaat gttcaactcc    48600
cttttacgag tgagaacaca tggtgtttga ttttctgttc ctgtgttaat ttgctgagga    48660
tgatagtttc cagcttcatc cacgtccctg caaaggacat gatctcattc cttttatgg    48720 ctgcatagta ttccatgatg tatatgtacc acattttctt tatccagtct gtcattgatg    48780
ggcatttggg ttggttccat gtcttttgcta ttgtaaatag ttctgcagta acatatatg    48840 tccatgtgtc tttatagtag aatgatttat attactttgg gtatataccc agtaatgaga    48900
ttgctgggtc aaatggcatt tctggttcta gatacttgag gaatcgccac actgtcttcc    48960
acaatggttg aactaattta cactcccact aacagtgtaa aagcgttcct atttctccac    49020
agcctcacca gcatctattg tttcctaaca ttttaataac tgctattctg actggcatga    49080
gatggtatct cattgtggtt ttgatttgca tttatctgat gatcagtgat gctgagattt    49140
ttaaaatatg tttgttggcc atgtaaatgt cttttgtgaa gtgtctgttc atatcctttg    49200
cccaccttaa tagggttttt tttttcttgt gaatttgttt aagtgccttg taaattctgg    49260
aaattagatc tttgtcagat ggatagattg caaaaatttt ctcccatttt gtaggttgcc    49320
tgttcactct gatgataggt tcttttgctg tgcagaagct ctttagttta attagatcca    49380
atttgtcaat tttggctttt tttgcaattg cttttggcat tttcctcgtg aagtctttgc    49440
ccgtgcctat gtcctgaatg gtattgcgta ggttttcttc tagggttttt atagttttgg    49500
gttttacatt taagtcttta atacatcttg agttaatttt tgtataaggt ataaggaagg    49560
ggtccagttt cagttttatg cataatggct aggcagtttt cccaccacca tttactgaat    49620
aggagatctt ttcctcattg cttgtttttg tcagatttgt cgaagatcag atggttgtag    49680
atgtgtggtg ttatttctga ggtctctgtt ctgcaccatt ggtctatatg tctgttatcg    49740
taccagtccc atgctgtttt ggttaccgta gccttgtagt atattttgaa gtctggtagc    49800
gtgatgcctc cagctttgtt cttttgctt aggattgtct tggctatatg gagtcttctt    49860
```

```
tgattccata tgaaatttaa aataattttt ttttattctg tgaagaatgt caatggtagt    49920
ttgatgggaa tagcattgaa attataaatt actttgggca gtatagccat gttcacaata    49980
ttgattcttt ctatccgtaa ggacgacact ttttccattt gtttgtgttc tctcttattt    50040
ccttgagcag tggtttgtag ttctccttaa agaggtcttt cacatccttt gttagctgtg    50100
ttcctaggta ttttgttctc tttgtagtga ttgtgaatgg gaattcattc ttgatttgcc    50160
tctctgctgc ctgttgttgg tgtaaacaaa attcatttct tgttcttatt tgtgaaattt    50220
tggaaccaaa tctattttca aattagaaat tgcttgtgat aatggttttg caacttagac    50280
tggatatgag acgatgagat attagttctt tcattccttt gtaggaatat ggtgcatctt    50340
gcattatttt agctaactag tgtcctttaa tgactaatga atatgacatg gtgaaacaaa    50400
gtaaaatata tatgatgcac taagtatgca ttgtttccaa aggttcagca ttttttttt     50460
gttaactctg ctgggatctg ctttatgcac tgataacata acttatttta tgatcttaag    50520
caaataaaaa cacttatctg gacctcagtt tccttaactg tacaactgag ggaaactgta    50580
tagtatagct atagtacagt ataccatctt taccgtcact tccatctttt aaattatgtg    50640
tatataagat agggcctaga taaatggtat ttatcttaaa ttacagtgat actagcttat    50700
aacttaattt gctaggtcat gttgaactga taacaatgtg tgaactgatg agcaactgag    50760
aagtaaccag gttgtgttat aacagtttgt ttttgattta gggttatcag tgagggtggc    50820
ggtggggagg ggactttgga gtctaactgt ctagttcaaa tattagtttt tgtttatttt    50880
tattttaat ttttgtgggt acatagtaga tgtatatatt tatggggtac atgtgatgtt     50940
ttcatatagg catgcaatgt gaaataagca catcatagag aatggggtat ccatcccctc    51000
aaacacttat cttttgagtt accaacaatc caatgacact ctttaagtta tcaaatcaca    51060
gttttgccag ctactagcca tgtgattttg ggtaggttac ttaaattctc ttcatctcaa    51120
tttcattatt gtaaagtgga gataatgata gcacattttt tctttttctt ttttctttta    51180
ttttttatta ttatacttta agttgtgtga tacatgtgca gaatgtgcag gtttgttaca    51240
taggtatcaa caactctata aaacatgttc tatccaggaa aagaaactat catcagagtg    51300
aacaggcaac ttacggaatg ggagaaaatg tttgcaatct agatggcgat tgcaatggcg    51360
gttcgctgca tccatcagcc catcatctac attaggtatt tctcctaatg ctatccctcc    51420
ccttgctccc caccccctca caggcccctg tgtgtgatgt tcccctccct gtgtccatgt    51480
gttctcattg ttcaactccc acttatgagt gagaacatgt ggtgtttggt tttctgttct    51540
tgtgttagtt tgctgagaat gatggttttc agcttcatcc atgttcctgc aaggacatga    51600
actcatcctt ttttatggct gtatagtatt ccatggtata tatgtgccac attttcttta    51660
tccagtctat cattggtgga catttgggtt ggttccaagt ctttgctatt gtgaacgctg    51720
cagcaatgaa catacataag catatgtctt tctagtcaaa taagttataa tcctttgggt    51780
atgtacccag taatgggatt gctgggtcaa atggtatttc tggttctaga ttcttgagga    51840
atcgccacac tgtcttccac aatggttgaa ttaatttaca ctcccaccaa cagtgtagaa    51900
gcattcctat ttctccacat ccgctccagc atctgttgtt tcctgacttt ttaatgatca    51960
ccattctaac tggtgtgaga tggtatctca ttgtggtttt gatttgcatt tctctaatga    52020
ctagtgatga tgagcttctt ttcatgtttg ttggctgcat aaatgtcttc ttttgagaag    52080
tgtctgttca tatcctttcc ccacttttg atggggttgt ttttttcctg taaatttgtt     52140
taagttcctt gtagattttg gatattagcc ctttgtcagg tggatagatt gcaaacattt    52200
tctcccattc tgtaagttgc ctgttcactc tgatgatagt ttcttttgct ggatagaaca    52260
```

```
tgtttttatag agttgttgtg agaattaaat gcattaagca catagaatag attctggtac    52320
atagcaagtg ctctctctat atatggaact ctatatgtag ttggtgcaaa agtaattgtg    52380
gttttcacca ttgaaagtaa tggcaaagac catcattacc ttttcaccaa tttaaatata    52440
tggaaggaat atatatataa aacctatata tatatgtcac atatatgtct ctaacccatt    52500
attataatat ataatacaat atatattata attataattg tatataacat atgttatata    52560
ataatatagt aatatttatt ctaaataaat atataatact ataaataata taataattta    52620
tatatatgat tataatatat aataggctat attatatatt attaacatat acatatgtgt    52680
atatatatgt ctttcataga cttaaatata tagagcaata ataggttaga aaatagcaaa    52740
catgtatata taaacatata tacatataga aaacatatat aaaaacatat atatatatat    52800
atatatgtgt gttttctgcc tttcatttttt agagacaggg tctcatcatg ttgcccaggc    52860
tggtctcaaa ctcctgggct caagtgatcc tactgctttg gactcccgaa gtgctgggat    52920
ttcagacatg agacactgca cccagtccag tccctgtctt tttaaataga ctctctacct    52980
aagtgcacaa atactcatta tttacattta gttatttctg tatatatgct ataagcaaat    53040
cttgtagcac cagtttgatt tttataaggc acaagaatat attttactaa tgctttaaaa    53100
tggcagctag attctagtat tactttagaa attaaaatta atattttaac acatctttca    53160
ttattgtgtt atctgaacca aacctattat tgctgctatt tcagcaaatc caggggcttt    53220
ttcttataaa atatgaagaa tatagcttag atttctagtg aagatgttac cagtaataat    53280
taataaaatc agtaagcact aaaaggaaaa taccaaaact aaagcatttt gaattagtca    53340
ttgaatctaa aagaaaggta gattttttttc tgagattctg ttctaggtgt ggtatatgtg    53400
tattttttgca aaaactataa acaattgtgg caaaatgaag gaaatatttta aaaacaaacc    53460
tcttaattct tcagtggatt aagcgtgaat atgtttttat tttctatgat gaatatggaa    53520
aaattcattt ccttagcaat ttgtatgagc ccaaaaacta ttgtcagact ctgctgtatc    53580
aaaatagaca aaaaattgac actcactttt accctgccaa aagcaaaatc ttaaactttt    53640
gctttagtat ataagccagc attcattgta tcctatgatg ggttctgagt gtaggtgtat    53700
ttgctttctt ccattttttg tatgcatgtt ttcttttttat ttattattgt aagttgtatg    53760
aaattttttat ccaatttttt atttttcttct gattaataat cagaataatc agataattac    53820
tggtaaattt gatgttaatc cttccagctt ttttccatgg gaatttatac ttaataaagg    53880
ggagaagtca tcattacata atgtgcatat taatctgctt ctccctttaa tgtgttgtga    53940
atgcctttcc atgtcattag atgttttttct acctagttac tttcatgaat catatggctg    54000
taccatgatt tatttaatca gttcctcatc attgagtatg taaattgcct ccatttttttt    54060
attactataa aagtgtccttc agtacacacc cctttaaaag ctgactctta gaaggtgttc    54120
ttgactctct acctaagtgt aaaaatacaa ataaattgct ttccagaaaa ggtgcactac    54180
tatttttactt tcctgatact aaactatgaa aattcagtcc taacaataga tatttaaata    54240
aagttttaaa aatgccaagt gaaaaagagc atattattat tttcatttgc attacttttg    54300
gttcctggtg agtttaatct gttttttgtat attaattatg catttatatt tcttttttgtg    54360
tgtgtgaatt gcctttcatg ttctttgtgt gtttttattt tgttgtattt gtctctttct    54420
tgatatatga gagaatatttt tccctagcct gtcaattgcc ttgtaattttt gtttctagtg    54480
agttttttttt tttttttta caattaaaag ctttaatttt tgaaaatttt gctggcaaat    54540
ctatatatct ttttctttgt tttctgcttt gacattattc ttttataaag gcccatgcca    54600
```

```
cccaaatatt atgtaagcat gcatctatgt ttttattact tcatctttta catttaaata    54660
tctactctat ttagaattca ttgtgatgca tgtatgaggt agaaatctaa tttcaaaaag    54720
atgagtatcc agtttgtcca tcatttattg catgatctct ttctccactg aattaaaatg    54780
ccgtatttta taatatatta aagtattaca tgtgcttgga catgttcctg gacttttgag    54840
ataaatcagt ctatttcttt gtcatgtcac atattattat ggctttatga tttaatatcc    54900
agtaatgtaa accctctgac acattattct tattcctcaa atgttttga tgagttttct    54960 tccaaatgaa atttataatc attttattca ttgattcaac aaatatttgt tgaatggata    55020
ttctgtgctt ggtattgtgc atggtattag gattgttgca aaaattgaga ctgacagtcc    55080
ctactcttac ggtgctaaaa attcacttcc aaaaaaatct ttaaatgttg atgaagattg    55140
cactaatctt ataaaataac ttggagggga atgtaatctt tgcaacatta agttcttcat    55200
tttagaaagt tttaagactc tccatttatt tgagactttt aaaatatgtc ccaataatgt    55260
tttgtgagat gtatatttta agatatatat cttattgcta ttacattgta tcttttgtta    55320
tattgttact atgaatggga tactcattta attagatgtc attttggta tatagaaatc    55380 tattttctta gcatagtcat ttttaaacc tcgatctatt aaattcttga ttcatttaca    55440
tttgttacac aatcatattc tatgctgata atacttcttg cttctttcca atatttgtac    55500
ctcgatcatt tttcttgttg agttgtatta gctagaagtt ctagaaaaat gttaaatggt    55560
agtaatagct agtattctgt ttttttcctga ctctaaatgt aatgcatcta gacttttata    55620
attatggcat tgattgtaac attttgagga agaaatcctt tttcaggtta ataatgtatc    55680
tttatattca agtttattaa gaacattat tggaaacata ttgaaatttt atcagattcc    55740
ttttcagttg ttactgagat aatcataggt tcttctgtat tcttttaatt aatttctcaa    55800
aattaaactg tcctattatt cttggaataa cgacatataa agtactgtat atttaaaaga    55860
agttaaaatg ataatggtga ttttattaag tgacctcaca caatagaaaa cagtgtagcc    55920
ttagaagttt tccaagtgac cattctactt agaaacaacc ctgctttggg atcagaactg    55980
taatttttaa agtaaagttt tctgggttta attcatttag tgtaattaca agcatgagtt    56040
caggtttcta tttttttcac ctgaactttc cttcatggtt tgaatatcta gaaaagcag    56100 actttcctat ctctagacta aacatttgat cctatcttag gtatgcatta caattttta    56160 accataaatg gttaaagaat ttagactcat ctacaataac tttgaagctc tggtcttgaa    56220
gaacatgtga gaaatgagat ataactccta gaagatatag gagacatttt tagtcttcca    56280 aatttccct gggaggctga tctaaattga gtcacaaaat tgttcccacc aggaatgcaa    56340
tcacttgagc tgttttctaa tctgagcccc tctacccaga tgatcttctg aactcatact    56400
gttcagactt tcatccttct gagtagaaaa cagccatagt catggcagga tgagggctag    56460
gacaattacc caaggaattc ttggcctctg ccatgggact ctgcagactc agatcatata    56520
atcagagatg ttagcactgg aggggacatc acaattagct ttctccacct cttagtttat    56580
cagtgaggaa aactgtccag agcgcggaag agactaaaat aacacagcca atgtaggtaa    56640
tgtgctggat aagaatttgg aattcacgat tttgaattca gtgtttatttt caccatcacg    56700 ctggcttaca cgttggtatc aggcttcttc tattattgaa gtgagccatt aagtgaattc    56760
catcttgatt tgtgtctgat acagagtaat aaactatttt attaaatatc caaataatta    56820
tacattcctc cttcttacat gcaagcctaa gtttgcttgt actatttcat gtggtagcaa    56880
atcaggacgc ttcttgtgtc tctgaaaata ctctgagtaa tggagtacag tcagctttct    56940
tgtaccaaga atatagggac tatgtttctc ccagtcattc tggggataat ttttgtgaag    57000
```

```
gattgcactt cataggttaa gctaggtatc agttaccagt gttttttcca aataaaaaaa    57060
aaatcaggtg atatctgtaa atggttccat tgtaaatatt aaagaacatg atgcttaaaa    57120
cagattaggg aaaactatag aaggggtggg gtttcggagt gctaattttg tccttgaatg    57180
gtaacagctc catgtggtgg tgaggtttat gttggtttgc tgtttgcaga tgatcttatt    57240
attagaattt ttcataccga aaataaactg cattttagtt tgtaaacatg cccttccaga    57300
gtaatgctac cagttctttg tgaaatagct actgttgttc aaaggatgac tatgtcctct    57360
tcggttgagg aaagatgaca acaaactcag taatgacatg taaaataggt attacaaacc    57420
aggtatggtg gcatgagcct gtaatcccag ctacttgaga ggctaaagca ggaggatctg    57480
ttgatctatg gatttgaggc tgtagtgtgt tgtgatggca cctatgaata gcccttgcac    57540
tccagcccaa gcaacaaagc aagactgtct ctgaatttt gttttgtttt gtttttgtt    57600 tttttttttt tgagacagag tcttgctctg tcacccaggc tgaagtgcag tggcgcgatc    57660
tccactcact gcaagctccg cctcctgggt tcacgccatt ctcctgcctc agcctcccga    57720
gtagctagga ctacaggcgc ccgcctccac gcccagctaa atttttgta tttttagtag    57780 agacgaggtt tcactgtgtt agccaggacg gtcttgatct cctgaccttg tgatcctcct    57840
gcctcggcct cccaaagtgc tgggattaca ggcgtgagcc accgcgcccg gcccctgtct    57900 ctgaatttt taaaaaggca ttccactcaa attaatacac attttaattg tgttttgttg    57960
taaattacaa ctgaataaaa attcagcaaa taagtctgtt gtggtaggga aagtctatt    58020 gtgatctgga aaatataatg gagaaatcca gtggaagaga ttttatttca cattactcaa    58080
aataaaaaaa tcttatacaa gtctttacac ttgtaacttg aaaaattctg tgctaaaatt    58140
tagcttggtt gctaaaatat ttctcttttt ttctcagaag cttcttttta gcatcctata    58200
gacacaagtt acttttaaa atatttgcat acttgctttg caatgtattg tttatcagta    58260
gttctatatt ctttgagata gtctatccag tctttctgta tttatcgtat gtctgtatag    58320
atatatatta gcagataaat gagttctgaa agggagaaa tgtgattatg ctaatcatga    58380
tataaagaat tgactttata agcagtgttc acaggtcata cctttcccgt tactgtctta    58440
cagtgaacaa gaaatgatgc tttgtctggt atgcatggta aataatgccc cttgctctct    58500
gcttcatgat cacatgtgat acttctaaca tagatagcac atgtaaatcc agtggccttg    58560
actgcaactc aagagagcat tttggccaag tacaaaccca ctagtcatga aaaaaaaaa    58620 aaaaccaaat caaagtaaat tgatggtatt gacatttgtc tatgaaaaac aacataatat    58680
agaacaattc tggggtaaaa tattgatcta aaataatttt aaggattaaa tattgccatt    58740
gtaagcatac tatgagcaat tatgtttgta atgcagatat atttataatt ttaaatccaa    58800
gatttacctt aattgtacat tttcctaatt taaaaaagtt attttgaaaa aaaatcctc    58860 gaatctagag aaaggttggc aaatacatat ggaactttgt aaaaaacatc cagggcagca    58920
ctttcactga ttgcagtagc ttaggagtga aaaacaacac aactgctcca atgtatggca    58980
atgggcaaat atcccgattt attcacaggg tggcatgtta ggcagtgctt agaataaatg    59040
agttggttat acaagtatca atagggataa atgtgaaaaa cacagtgtta agttttaaa    59100 aagttgtaaa aagcacagta ggatgttatt tatataaaat ttaaaaacct caaaaaccat    59160
tcttctttga tatatattct aaagatgaac atatatgtaa tagaagtaca aaacatacat    59220
aaaataatat acactatgca gtcatttgtg tacttacttt tcaaaaatat ttcagtagat    59280
atagcaaaca gttaacatgt aatatttgga taggaggttg gcaattttct ttttagcacc    59340
```

```
tgcctgtctg ctatcattca aactcacatt taaaatgtgg ctatgtgaga tgagagaact    59400
ataatattcc aggtttgtga ttagtttgga aacttttaa aagtttgaat gtggtctgag    59460
agatagtttg ttataatttc tgttctttta catttgctga ggagagcttt acttccaact    59520
atgtggtcaa ttttggaata ggtgtggtgt ggtgctgaaa aaaatgtata ttctgttgat    59580
ttggggtgga gagttctgta gatgtctatt aggtctgctt ggtgcagagc tgagttcaat    59640
tcctgggtat ccttgttgac tttctgtctc gttgatctgt ctaatgttga cagtggggtg    59700
ttaaagtctc ccattattaa tgtgtgggag tctaagtctc tttgtaggtc actcaggact    59760
tgctttatga atctgggtgc tcctgtattg ggtgcataaa tatttaggat agttagctcc    59820
tcttgttgaa ttgatcccct taccattatg taatggcctt ctttgtctct tttgatcttt    59880
gttggtttaa agtctgtttt atcagagact aggattgcaa cccctgcctt ttttttgtttt   59940 ccattggctt ggtagatctt cctccatcct tttattttga gcctatgtgt gtctctgcac    60000
gtgagatggg tttcctgaat acagcacact gatgggtctt gactctttat ccaatttgcc    60060
agtctgtgtc ttttaattgg agcatttagt ccatttatat ttaaagttaa tattgttatg    60120
tgtgaatttg atcctgtcat tatgatgtta gctggtgatt ttgctcatta gttgatgcag    60180
tttcttccta gtctcgatgg tctttacatt ttggcatgat tttgcagtgg ctggtactgg    60240
ttgttccttt ccaggtttag cgcttccttc aggagctctt ttagggcagg cctggtggtg    60300
acaaaatctc tcagcatttg cttgtctata agtatttta tttctccttc acttatgaag    60360
cttagtttgg ctggatatct ctcagaccac agtgcaatca aactagaact caggattaag    60420
aatctcactc aaagccgctc aactacatgg aaactgaaca acctgctcct gaatgactac    60480
tgggtacata acgaaatgaa gacagaaata aagatgttct ttgaaaccaa cgagaacaaa    60540
gacaccacat accagaatct ctgggatgca ttcaaagcag tgtgtagagg gaaatttata    60600
gcactaaatg cctacaagag aaagcaggaa agatccaaaa ttgacaccct aacatcacaa    60660
ttaaaagaac tagaaaagca agagcaaaca cattcaaaag ctagcagaag gcaagaaata    60720
actaaaatca gagcagaact gaaggaaata gagacacaaa aaacccttca aaaatcaat    60780 gaatccagga gctggttttt tgaaaggatc aacaaaattg atagaccgct agcaagacta    60840
ataaagaaaa aaagagagaa gaatcaaata gacacaataa aaaatgataa aggggatatc    60900
accaccaatc ccacagaaat acaaactacc atcagagaat actacaaaca cctctacgca    60960
aataaactag aaaatctaga agaaatggat acattcctcg acacatacac tctcccaaga    61020
ctaaaccagg aagaagttga atctctgaat agaccaataa caggctctga aattgtggca    61080
ataatcaata gtttaccaac caaaaagagt ccaggaccag atggattcac agccgaattc    61140
taccagaggt acaaggagga actggtacca ttccttctga aactattcca atcaatagaa    61200
aaagagggaa tcctccctaa ctcatttat gaggccagca tcattctgat accaaagccg    61260
ggcagagaca caaccaaaaa agagaatttt agaccaatat ccttgatgaa cattgatgca    61320
aaaatcctca ataaaatact ggcaaaccga atccagcagc acatcaaaaa gcttatccac    61380
catgatcaag tgggcttcat ccctgggatg caaggctggt tcaatatacg caaatcaata    61440
aatgtaatcc agcatataaa cagagccaaa gacaaaaacc acatgattat ctcaatagat    61500
gcagaaaaag cctttgacaa aattcaacaa cccttcatgc taaaaactct caataaatta    61560
ggtattgatg ggacgtattt caaaataata gagctatct atgacaaacc cacagccaat    61620
atcatactga atgggcaaaa actggaagca ttccctttga aaactggcac aagacaggga    61680
tgccctctct caccgctcct attcaacata gtgttggaag ttctggccag ggcaatcagg    61740
```

```
caggagaagg aaataaaggg tattcaatta ggaaaagagg aagtcaaatt gtccctgttt    61800
gcagacgaca tgattgttta tctagaaaac cccatcgtct cagcccaaaa tctccttaag    61860
ctgataagca acttcagcaa agtctcagga tacaaaatca atgtacaaaa atcacaagca    61920
ttcttataca ccaacaacag acaaacagag agccaaatca tgagtgaact cccattcaca    61980
attgcttcaa agagaataaa atacctagga atccaactta caagggatgt gaaggacctc    62040
ttcaaggaga actacaaacc actgctcaag gaaataaaag aggacacaaa caaatggaag    62100
aacattccat gctcatgggt aggaagaatc aatatcgtga aaatggccat actgcccaag    62160
gtaatttaca gattcaatgc catccccatc aagctaccaa tgactttctt catagaattg    62220
gaaaaaacta ctttaaagtt catatggaac caaaaagag cccgcatcgc caagtcaatc    62280
gtaagccaaa agaacaaagc tggaggcatc acgctacctg acttcaaact atactacaag    62340
gctacagtaa ccaaaacagc atggtactgg taccaaaaca gagatataga tcaatggaac    62400
agaacagagc cctcagaaat aacgccgcat atctacaact atctgatctt tgacaaacct    62460
gagaaaaaca agcaatgggg aaaggattcc ctatttaata aatggtgctg ggaaaactgg    62520
ctagccatat gtagaaagct gaaactggat cccttcctta caccttatac aaaaatcaat    62580
tcaagatgga ttaaagattt aaacgttaga cctaaaacca taaaaccct agaagaaaac    62640 ctaggtatta ccattcagga cataggcgtg ggcaaggact tcatgtccaa acaccaaaa    62700 gcaatggcaa caaaagccaa aattgacaaa tgggatctaa ttaaactaaa gagcttctgc    62760
aaagcaaaag aaactaccat cagagtgaac aggcaaccta caacatggga gaaaattttc    62820
gcaacctact catctgacaa agggctaata tccagaatct acaatgaact caaacaaatt    62880
tacaagaaaa aaacaaacaa ccccatcaaa agtgggcga aggacatgaa cagacactac    62940
tcaaaagaag acatttatgc agccaaaaaa cacatgaaga aatgctcatc atcactggcc    63000
atcagagaaa tgcaaatcaa aaccactatg agatatcatc tcacaccagt tagaatggca    63060
atcattaaaa agtcaggaaa caacaggtgc tggagaggat gtggagaaat aggaacactt    63120
ttacactgtt ggtgggactg taaactagtt caaccattgt ggaagtcagt gtggcgattc    63180
ctcagggatc tagaactaga ataccatttt gacccagcca tcccattact gggtatatac    63240
ccaaaggact ataaatcatg ctgctataaa gacacatgca cacgtatgtt tattgcggca    63300
ctattcacaa taggaaagac ttggaaccaa cccaaatgtc aacaatgat agactggatt    63360 aagaaaatgt ggcacatata caccatggaa tactatacag ccataaaaaa tgatgagttc    63420
atgtcctttg tagagacatg gatgaaattg gaaaccatca ttctcagtaa actatcgcaa    63480
gaacaaaaaa ccaaacaccg catattctca ctcataggtg ggaattgaac aatgagatca    63540
catggacaca ggaaggggaa tatcacactc tggggactgt ggtggggtcg ggggaggggg    63600
gagggatagc attgggagat atacctaatg ctagatgaca cgttagtggg tgcagcgcac    63660
cagcatggca catgtataca tatgtaacta acctgcacaa tgtgcacatg taccctaaaa    63720
cttagagtat aaaaaaaaa aaaaaaaag tttgaatgtt ttcttgcatt cagagccttg    63780
gttgacatag ttaattaaaa ataaaacatt gtatataaag cacagaatga gcagctacac    63840
aaagctgctc aatcaatgac agctctatat gggttagggt ttcttgtggg gatgacattg    63900
atgtagaaag catggtcatc tattgagaat gatggggctg gaggtattgg atacttgagg    63960
tttagaaaat acattgtaga aaatggacaa aaaccctca aattaaggga tgaggcagaa    64020
taatgcttgg caataccagg ggtaggctgc agtctttctt ggaaatatat attttaaatg    64080
```

| | |
|---|---|
| gaaccaatta tcatagcatc atttcctctc agggttaccc tctgatccct attttactaa | 64140 |
| atcgttataa aacaaaatga ggaattatgt gtccttccct tttgaagcca atgtaacaag | 64200 |
| atgggtaaga attagacctc ctgagttcaa aatccctgga ttcagatcta ttcctgtata | 64260 |
| ttcaggagaa gtggtaataa attcgatgga caatttggtt tagtagtcga ttgaggaccc | 64320 |
| tgatgaggta tatttgggaa aacataactt ccgctctctc tcattgactc acgggccttt | 64380 |
| gaggagtcca ggagtcattg gaatctggcc tgaggttgag gctgctggca aaactccttc | 64440 |
| cccaaagtcc attcctattg ctgactgaga agggactagc attggaagtg gctgatttta | 64500 |
| aataccgcta gtgctggtgt gctcctccct cccattccca gctctgcttt gtgtagttgc | 64560 |
| cttgagaagc taagttcatt ctgaaaataa tgccattgca caaaacactt ttgaaagttc | 64620 |
| tagtttgaaa ttcatcagg tcacttggtc tgtgtggcct cagtttcttc atctgccatg | 64680 |
| tgaaaataat aatgcctact ctgtagcaaa gaaagtctct atagtaaaca aaaaaaaagc | 64740 |
| ctactctgat actgaaagtt gttatgaaaa ataaaaaagg gaaatgcttt agaaactgtt | 64800 |
| aagtgctatg tagatgttac taattaacaa accatttcag aaactatact ttttatttta | 64860 |
| tggccactat tcactgttta acttaaaata cctcatatgt aaacttgtct cccactgttg | 64920 |
| ctataacaaa tcccaagtct tatttcaaag taccaagata ttgaaaatag tgctaagagt | 64980 |
| ttcacatatg gtatgaccct ctatataaac tcattttaag tctcctctaa agatgaaaag | 65040 |
| tcttgtgttg aaattctcag ggtatttat gagaaataaa tgaaatttaa ttctctgtt | 65100 |
| tttccccttt tgtaggaagt caccaaagca gtacagcctc tcttactggg aagaatcata | 65160 |
| gcttcctatg acccggataa caaggaggaa cgctctatcg cgatttatct aggcataggc | 65220 |
| ttatgccttc tctttattgt gaggacactg ctcctacacc cagccatttt tggccttcat | 65280 |
| cacattggaa tgcagatgag aatagctatg tttagtttga tttataagaa ggtaatactt | 65340 |
| ccttgcacag gccccatggc acatatattc tgtatcgtac atgtttttaat gtcataaatt | 65400 |
| aggtagtgag ctggtacaag taagggataa atgctgaaat taatttaata tgcctattaa | 65460 |
| ataaatggca ggaataatta atgctcttaa ttatccttga taatttaatt gacttaaact | 65520 |
| gataattatt gagtatcttc tgtaaactgc ctctgttgta gttttttttt tctcctaatc | 65580 |
| atgttatcat tttttggaa tccatggttt cctgttaaga tgactcacac agcctacata | 65640 |
| aaagtaattg acaaaatatc atcttatagt aaaatgccac atatctttat gttcagcaag | 65700 |
| aagagtataa tatatgattg ttaatgataa cccaaacaac aaaagatttc accttaactg | 65760 |
| gttgtcataa gtagtagtat ccaccgcctt attttgagtt ggattttat catcctatga | 65820 |
| gccctacaaa tttaaagttt ttggaacagc acgtgcattg aacccataag aacctactct | 65880 |
| gcttttctgc atgtattgtc cagacaagag accaaattgc cgaggcatca tttaggtgaa | 65940 |
| ttctaattaa catttagcta ccttacaacc acaattcaag gttgtttcaa aggcatgtgc | 66000 |
| ttgcatcatc ctgattcact accatgtgtt actaacttgg atctgcaaag tcattataaa | 66060 |
| aagctgtttt gatggactta tttggatatt gctttacctt tcttctctct tttctttat | 66120 |
| caatgtaaaa acattatatg ttaaatactt ggcttttaag agcatagatc tgaaatctgc | 66180 |
| ctctagcaaa taaccataa cacttctaag atatacctgc aaggtcaatt gtgttgtaaa | 66240 |
| accttgataa ccatacttta ttgttcaaaa aagccttta tgaaggcaga agttaaaaaa | 66300 |
| aaaaaacaaa aaaaacagag tccacagtta tcacctcagc tacaatctca tcagttcaca | 66360 |
| agtaccagca aaacatgtga taagtcaaca aatgttttat ttcaatctga acattttacg | 66420 |
| taagtgaaga cttttgttaga tatcatttgg aatgtggaat ctacacagtt ggcatatcag | 66480 |

```
agaaggttga attcagttta ataaatgttt atagaaagtg cttgttatca taatgataat    66540
agctcaggat gtgcatgaca agcttttaag cgattgggta cactatctca tttgatcttc    66600
tgcacaacta ttaatggtag gtactattat ccctatctta tggataagta aactaagatt    66660
taaaaagtac agaacatggt gtgaacactg cttcaaaatt tctaaaatag gtaaatcacg    66720
atctctaaac tggagggttg tccaaccact agggacaata gagtactgat atttagtggt    66780
cagactgtaa tgcgggaaga gacaggcatg ggctaaacgg gtgtagagat caaataaggg    66840
gcaggttagt ttgtaaacat gtccatatgt aacatttagc acaaatacag gatataggtg    66900 cttttcagacc cagctgcatt gataaaaagt taggtggtat tgtatctgtc ttcctttctc    66960
aatgttgcat atctgtgttc ttgcccagtt tgcttcatct ctctagccac acttattggc    67020
ctacaatggc atcatcacca aagaaggcaa tcccatctcc gtgtggcttt ggtttgctcc    67080
ctaaagtaaa ccttgtgttt acttttccca ggtctcatgc tttcccatat ctgacctgtt    67140
ttgtcctcat ggccaggata tgtgggacct ttcctacaat gttccaaagt ttgtaataga    67200
gctcttctct gctttgttcc aaattctgca acatttact ttaaataatg aatttaaata    67260
caaacaaact tgagctttgc ctatactttt caagaatgca gagataacta aattaataaa    67320
aatattcatt gagtccttac tgtgcacaca gctctatgtt aagccttgtg cagaactcaa    67380
agtcactcga gattaagcct gttactaagt tatgtgcaat ttagctcagt ggatttcccc    67440
cacttcatat tgctctgata atgttttgga attaactgcc ttgattcctt cttttctctg    67500
cttgtctata cactatttat tattctacac catctcaaat tctaactcct caagaaaatc    67560
cttccagatg attttctaa ccaggagttt taacttcctt ttaactaccc tattactttc    67620
tacttcctta actcatctat catattatat ttagttattt atatactagg tcgccttgaa    67680
gaagggattg tgttttcata atcttaata atccctgagg catcaagtac agtgatttgc    67740
atttactaaa tgctcaacaa atatgtgagg gattcacttg aaactaatat tagataattc    67800
ccagtcaaag tgatctaata gcaaatcaat tcttcagttt tataggcaaa gtatgactct    67860
ggttttccat aatcataatt aatttgtcaa ctttataatt ttaattaagt aaatttaatt    67920
ggtagataaa taagtagata aaaataatt tacctgctta actacgtttc atatagcatt    67980
gcatttttct ttgtaaaatt taagaatttt gtattaataa acttttttac aaaagtatta    68040
attattcagt tattcatcat atactttttat tgacttaaaa gtaattttat tcaaaagagt    68100 tagtataga ctacatgaaa aattcaaggc caaggcttaa tttcaaattt cactgccttt    68160
ggctctatct tttaaaacaa aacaaaaaac tcccgcacaa tatcaatggg tatttaagta    68220
taatatcatt ctcattgtga ggagaaaaaa taattatttc tgcctagatg ctgggaaata    68280
aaacaactag aagcatgcca gtataatatt gactgttgaa agaaacattt atgaacctga    68340
gaagatagta agctagatga atagaatata attttcatta cctttactta ataatgaatg    68400
cataataact gaattagtca tattataatt ttacttataa tatatttgta ttttgtttgt    68460
tgaaattatc taacttttcca ttttctttt agactttaaa gctgtcaagc cgtgttctag    68520
ataaaataag tattggacaa cttgttagtc tcctttccaa caacctgaac aaatttgatg    68580
aagtatgtac ctattgattt aatcttttag gcactattgt tataaattat acaactggaa    68640
aggcggagtt ttcctgggtc agataatagt aattagtggt taagtcttgc tcagctctag    68700
cttccctatt ctggaaacta agaaaggtca attgtatagc agagcaccat tctgggtct     68760 ggtagaacca cccaactcaa aggcacctta gcctgttgtt aataagattt ttcaaaactt    68820
```

-continued

```
aattcttatc agaccttgct tcttttaaa actttaaatc tgttatgtac tttggccaga    68880
tatgatacct gagcaattct tgttctgggt tgtcttatgt gaaaaataaa ttcaaggtcc    68940
ttgggacaga taatgtgttt tatttatctt tgcatatcca ttacttaaaa cagcattgga    69000
cccacagctg gtacaaaatt aattactgtt gaattgagca atatttatt ctaaatgtct    69060 ctgtcaaatg acagagtgtg gttgtgtgga ttaagtccct ggagagagtt ctttgttctc    69120
tcatgttcta tgctgtggtt cttgctttat gcaaaaagaa gtaagttact taaaacctgg    69180
acatgatact taagatgtcc aatcttgatt ccactgaata aaaatatgct taaaaatgca    69240
ctgacttgaa atttgttttt tgggaaaacc gattctatgt gtagaatgtt taagcacatt    69300
gctatgtgct ccatgtaatg attacctaga ttttagtgtg ctcagaacca cgaagtgttt    69360
gatcatataa gctccttta cttgctttct ttcatatatg attgttagtt tctaggggtg    69420
gaagatacaa tgacacctgt ttttgctgtg ctttttatttt ccagggactt gcattggcac    69480
atttcgtgtg gatcgctcct ttgcaagtgg cactcctcat ggggctaatc tgggagttgt    69540
tacaggcgtc tgccttctgt ggacttggtt tcctgatagt ccttgccctt tttcaggctg    69600
ggctagggag aatgatgatg aagtacaggt agcaacctat tttcataact tgaaagtttt    69660
aaaaattatg ttttcaaaaa gcccacttta gtaaaaccag gactgctcta tgcatagaac    69720
agtgatcttc agtgtcatta aatttttttt tttttttttt ttttgagaca gagtctagat    69780
ctgtcaccca ggctggagtg cagtggcacg atcttggctc actgcactgc aacttctgcc    69840
tcccaggctc aagcaattct cctgcctcag cctccggagt agctgggatt agaggcgcat    69900
gccaccacac ccagctaatt tttgtatttt agtagagaca gggtttcacc aggttgccca    69960
ggctggtctc gaatgcctga cctcaggtga tccgcccacc tcggcctccc aaagtactga    70020
tattacaggc atgagctacc gcgcccggcc taaaaaatac ttttaagat ggtgtaaata    70080 ttactttctg tatcaatggt acatttttta cttgtcagtc tctagaattt ctttataaat    70140
atgttgattc agttcatttt tgtagattat aaaacaggta aaaaggata aaacatttat    70200 gtgaattaaa gggaatacct aattttttgtg tagagtttat tagcttttac tactctggtt    70260
tatggatcat cacaccagag ccttagttac tttgtgttac agaataacta atatgagtga    70320
atgaatgact tacacaagtc actgcttagg ataaagggct tgagtttgtc agctagagta    70380
tgacagaaag tatctaagtt ttggagtcaa atagcacttt gtttgaatcc cagattgcat    70440
gcttactagt tatgtgacct tagtcaagcc acttcacctc actgagtctt tgcttttttc    70500
atctctaaaa tagagatacc caccgctcat aggctgtcat aagggataga gatagcatat    70560
ggaatgagtc tgtacagcgt ctggcacata ggaggcattt accaaacagt agttattatt    70620
tttgttacca tctatttgat aataaaataa tgcccatctg ttgaataaaa gaaatatgac    70680
ttaaaacctt gagcagttct taatagataa tttgacttgt ttttactatt agattgattg    70740
attgattgat tgattgattt acagagatca gagagctggg aagatcagtg aaagacttgt    70800
gattacctca gaaatgattg aaaatatcca atctgttaag gcatactgct gggaagaagc    70860
aatggaaaaa atgattgaaa acttaagaca gtaagttgtt ccataatttt caatattgtt    70920
agtaattctg tccttaattt tttaaaaata tgtttatcat ggtagacttc cacctcatat    70980
ttgatgtttg tgacaatcaa atgattgcat ttaagttctg tcaatattca tgcattagtt    71040
gcacaaattc actttcatgg gctgtagttt tatgtagttg gtccagggtg ttatttttatg    71100 ctgcaagtat attatactga tacgttatta aagaatttcc tacatatgtt cactgctgct    71160
caatacattt atttcgttaa aacaattatc aagatactga aggctgattg gtaactcaca    71220
```

```
tggaactggg agagtataca attctgaacc aaatagatga ttctctatta ttatatctta    71280
atttatgtgt tatggtatat taaacatgaa aaaaattgta tttggttaga atatgtttgc    71340
tcttccttaa ctcgggaatg acatagggta atattcacag attgggttcc tataaatcct    71400
ccacttgaag tgaagtcagt tcaagtaatg aaagctacct cctgagatag aatcagtact    71460
tggcacctat ctctagtgtt ctttcacctc ataaaccttt tcactgatta gtaaagatta    71520
tatccaacaa agaaagtaca gcacagactg agatatgatt actgagataa atttgggcaa    71580
aatataaact acagcatttc tgtagcaatg agaccatttt tcttcagttg agctccatgt    71640
tctacaaact tcaatcaaaa aaggttctag gagactcagt gaaagttgat acactgttca    71700
aggaacaaat aatttcagca catgggaatt tcacagggaa aaatatacta aaaagagagg    71760
taccattttg gatggtgtca atatgggtta tgaggaattc aggctgctga gtccagtgta    71820
caatggaaac tgagctgcag gtgtgtgatt gtaacaacaa agaaatgct gaaatattaa     71880 gtcctttgcc atgtaaatag aaaaagagta tttatttccc aaacattatt gctcacctgt    71940
ttttgttatg cctttcaaga taaatccagg aaaggaattg cattttcttt ccagaaaaca    72000
agttcttggg ggaattgttc aattggtaga tgttgttttt ctcattaaca agtgagtgct    72060
ccatcacact tgctgagtgc tccatcacac ttgctctctg cattactcct ctgcctgcaa    72120
acacatatat agcaagggtg atgacaagga tatcagaggg tctggttttc tcaaactcat    72180
gataaactca tggctgggtc attcttggtg ctgattttac tttgttttt gttgttattg      72240 ttccctcttc ctcaaaagat gaaatctatc cctcttactt ggaatttctc tttgatatat    72300
agcgaatgtt tggttgtaac ctgtataatc tggcatgaaa ttgtcactcg aaaaggctag    72360
aagtgttgac ataaatatgg gacagcaaga gttgctccta ctcaagagag caaatataat    72420
gttctggaag agattggcag aattcacatc aaaggagtga ttacttcagc ctgggccact    72480
gttgtactgg tcaaaaggct gtgcaaagct ctctgaaaat ccactctttt attgctcttt    72540
agtaataaag tcactttcaa ttttaaaaat aacaaactga tatattttta tgactcataa    72600
aatgttagca attatattat ggagaatcta ctttctgggt gattcttaca aatgttcttg    72660
gatctatttt tttttcttat agtacctatt cttcccattt ttctcagctc tagttaatat    72720
atttcaacaa cagttcaaca aatttaacat ttttataaaa agtgtttcct atcatttat     72780 aaataccagc ctagtccatg ttattccttt tcttgttgag gagaaaggac acacattgta    72840
aattcaaata tagacctcta ctgtgctatt taatcttggt aacaactcca caaggagat     72900 gacatgtttt ccttctatag aggtagattc tgtaaagtta gagggaagag tgacttgctt    72960
aagatggcat aagctgtaac tggcagaacc aggattcaaa gccaggtggg atgccaaaat    73020
cataatctgt cttcagtgtc aagttactga aattggtaaa cattagacct aaatagacgg    73080
aattgcaatc cgggttgggc acattaaact ccatttctt catcaatgtg ctcagattac       73140 atttacttt tcaggctaaa aatggaaaaa aagagtccct cttagttctg cacttgaaa        73200 tgagaatagc ttttctgaat tatacaagga agaagaacta atgcccaaat gccaggtacc    73260
cacatgcact atgccatggc acagctgttg ccccctttca ccagagccct ctctctgtat    73320
cctggttgac ctttccttgg gcaagagctg ggtggggagg atcacaagtg actccaattt    73380
ggatggcttc gggaagactg ggaccgagct gaaggcagtg ttgtcctctg cactccctgt    73440
tttctgtctg ctggagcact gaagcctcac atatgtatta aaaaaataat ttccatttgc    73500
atttcagact agaagattga acgtatagtg taatgtgatt gcaaataatt atattgaaat    73560
```

```
gagacagaga ggatgtagta tctactgtca taattttca aaacccacct gcaacttgaa    73620
ttaaaagaac cacttgggtt ttttttttg tttcaaacgc aaatcctgga aacctactga    73680
gactcattca gtcagtatct ctaagaggca agcttgagac tgtatattta aaaagcatct    73740
caggtgattt ttacacatgc taaggcttaa gaaccacttc tctgtagctt atatgttatt    73800
ttcaatgttc ctcaaagcca agttagaatt tccaaagtgt taagaatcca ttagacaatc    73860
acagaattgt cttttccctt tataaatctt gcaatgttgt tctcatttcc atacttaatt    73920
acttaaaaca ccaaccaacc aacaagcaaa aaatgattag tctaactaat attacaagtt    73980
aataatgaag taaaggttta aaataatgt cataataatg ttaataacaa attattaatt    74040
ataatttaaa aataatattt ataatttaaa aataatattt acaagtacta caagcaaaac    74100
actggtactt tcattgttat cttttcatat aaggtaactg aggcccagag agattaaata    74160
acatgcccaa ggtcacacag gtcatatgat gtggagccag gttaaaaata taggcagaaa    74220
gactctagag accatgctca gatcttccat tccaagatcc ctgatatttg aaaaataaaa    74280
taacatcctg aattttattg ttattgtttt ttatagaaca gaactgaaac tgactcggaa    74340
ggcagcctat gtgagatact tcaatagctc agccttcttc ttctcagggt tctttgtggt    74400 gttttatct gtgcttccct atgcactaat caaaggaatc atcctccgga aaatattcac    74460
caccatctca ttctgcattg ttctgcgcat ggcggtcact cggcaatttc cctgggctgt    74520
acaaacatgg tatgactctc ttggagcaat aaacaaaata caggtaatgt accataatgc    74580
tgcattatat actatgattt aaataatcag tcaatagatc agttctaatg aactttgcaa    74640
aaatgtgcga aaagatagaa aaagaaattt ccttcactag gaagttataa aagttgccag    74700
ctaatactag gaatgttcac cttaaacttt tcctagcatt tctctggaca gtatgatgga    74760
tgagagtggc attttatgcc aaattacctt aaaatcccaa taatactgat gtagctagca    74820
gctttgagaa attctaaagt tttcaagtga taagactcaa tttatacaaa gctaattgga    74880
taaacttgta tatgattaag aagcaaataa atacttatta tgcttttttg ctgtttattt    74940
aaatatttaa cccagaaaat aagtcactgt gacagaaata aaaatgagag agaagggtga    75000
gccactctta ggtagttctg gcattatta atctaggcca gaggttgcaa atggtgtccc    75060
atagaactaa ttttggctcc tagacctgtc ttatttaacc ttttcatttaa aaaatttgta    75120 ttggttgcca gcaattaaaa attgggagat gtctcacaca cacacacaca taaacacaca    75180
cactcatgtg tgcagcctct tttgaagaat tggaataact agtcaactgc gtcctccttt    75240
tccacaagct gtgacagctc cctgctcaca gagcacctgc cctctcctgt tcatcatgct    75300
ctcttctcag tcccattcct tcattatatc acctatttgg tcctgagact aagtgagttt    75360
gagatctgtg atttagacaa agtggtgaat ctagctctga atcatagtaa gtagctctgg    75420
gaatcatctt gtcttctgtt agcccattga gagagaaata gagagagaga gagagagaaa    75480
gaaagaagaa gaaacagatc tggggagagt cactgaatgg gagcatagag acagagaaac    75540
agatctagaa aaccaaactg ggagaaaatg agagaaacca aaagagaggt agagaggagc    75600
agagaagaaa atgaagaagc aaggcaagga ccaggctttt tcattatttc ttatggccaa    75660
gacttcagta tgcgtggact taattcttcc ttatgctcct accttcccta gggaaactga    75720
tttggagtct ctaatagagc ccttctttta gaatcacagt ttgatgcctt aaaactagtt    75780
atataccttc acatgcttcc ttaacccaca gaagtgatgc taatgaggcc cttaataagg    75840
agcgtgctat taagatgaag acattcattt ttttctccg tccaatgttg gattaaggca    75900
cattagtggg taattcaggg ttgctttgta aattcatcac taaggttagc atgtaatagt    75960
```

```
acaaggaaga atcagttgta tgttaaatct aatgtataaa aagtttata  aaatatcata  76020 tgtttagaga gtatatttca aatatgatga atcctagtgc ttggcaaatt aactttagaa  76080
cactaataaa attattttat taagaaataa ttactatttc attattaaaa ttcatatata  76140
agatgtagca caatgagagt ataaagtaga tgtaataatg cattaatgct attctgattc  76200
tataatatgt ttttgctctc ttttataaat aggatttctt acaaaagcaa gaatataaga  76260
cattggaata taacttaacg actacagaag tagtgatgga gaatgtaaca gccttctggg  76320
aggaggtcag aattttaaa  aaattgtttg ctctaaacac ctaactgttt tcttctttgt  76380
gaatatggat ttcatcctaa tggcgaataa aattagaatg atgatataac tggtagaact  76440
ggaaggagga tcactcactt attttctaga ttaagaagta gaggaatggc caggtgctca  76500
tggttgtaat cccagcactt tgggagacca aggcgggtgg atcacctgag gtcaggagtt  76560
caagaccagc ctggccaaca tggtaaaacc cggtctctac taaaaataca aaaaattaac  76620
tgggcatggt ggcagatgct gtagtcccag ctgctcggga ggctgaggca ggagaatcac  76680
ttgaacctgg gaggcggagg ttgcagtgag ctaagatcac gccactgcac tccagcctgg  76740
gcaacaaggc gagactctgt ctgaaaaaga aaaaaaata  aaaataaaaa taaaagaag   76800 tggaggaata ttaaatgcaa tataaaagct tttttatt   ttaagtcata caatttgttt  76860
cacataacag atcaggaaat aatacagaga tcataagttt tggagctggg tttgaatcct  76920
ggctctgcca tttactttct gtgtaatcta agtcaagtta ctgaactttg tgggccctct  76980
ggctctccat gtgtaaaatg gagaatatta atatttacct tgcaagtttg ttgtgaagac  77040
tgaaggagag aatttaggta aaacattcat cagagtacca tgcacacagt tgttcctcaa  77100
taaacattag cttctctgat tgcaagttcc agtctaaagt gctttatata taccagccaa  77160
taaaaggatg cgagagagat ataccagtgt attgttttct accatttaa  acctatttc   77220 atccactgtt acaaattcta tcatactgct ccacataaaa aatattatca atgatttta   77280 gtctctgaag tgcaatattt gattattgag cacacctgtt gaagttttag tttcttctca  77340
cttacatggg ttgtgtaaag gtaggaggta taaaaccagt gtcctaggtc taaatctttc  77400
ttaatgtcat actttggatt cattgatata agtaacttga gcaccagcgc ttcatttac   77460 ttcatttttt aaagatatag taagagtaat tcccatctgc ctagcaaaat tgttttgtag  77520
aaaagtttgt ggatcagatt tatttactt  tgatttagg  aatttcaagt gtcttcgtcg  77580
gcatgaagga aaaatatgca gtttgacatt ttctactact ttcaggtcat tattttccta  77640
ctctggtgca aaaaccctca attcctgtct cactccatct aatcaaatag gtagcatgct  77700
tgagccctta ctatgtgcca ggcactagga taagcacttt atatgttttg tcccaattaa  77760
ttctcacagc atttctatga cctaaataaa attaatattt tcatttcacc aataataaaa  77820
tggaggcttc aaaaagttta gggacttggc tcagctcaca caactggcaa ggactgaaaa  77880
tggattttag tcccaaatgt cataggctag agccctttca ctaaactgtt gtcttccatc  77940
tggtggcatc ctcttcctcc agtctttgtc acctaaactc tgggcacccc ttgatggcat  78000
ttacttatga tggtgatgct tgttaaactt cctgtttgcg acttcaacgt ccatataaat  78060
gagtcttcca atactgtact tagaacttat atttgtagt  gacttcttta aaagctttct  78120
ctcttagtca tatcctgagt tttgttagca cctggactta ccttactttg gaaatgttgc  78180
actctgaaat ctctttctca gcttggaatt tcctaatctt ccaactgttt gagtctttta  78240
attctacatt tactgccttt ccatttcatc aggatttcta gtctctttaa ttcttccttt  78300
```

```
tgaactcctc ctgatttaac ctctgcttat tcgaagaaca ataatttat tctctcagct    78360 gcactctcaa ttcccttttc cttttggtga ttttctttt tcctacagaa cacttacttt    78420
atcagttttg gagaaggaag tgctatctgg gtaacagtag tgctatctgt tgactctagt    78480
caactgtaag ttttatacat ttattgttta aaccttatat gggtctataa tccttcttgg    78540
gaaatccttt catttgtctt taatttcctt taccatttcc ctaaaggcta ttccagattt    78600
ttatcacatt cacaaaattc ccgtcttttc tcaggatctg ttcaccccca gtagatagcc    78660
ttgtctccca caatacatgg agaaaataga ggccaccgtc atatttgaat gtttccaact    78720
tctctcttca cctttggaat tatctttttc ttcttttgtg tctaagagaa agatgtatac    78780
ttcttcttac ccttgtctga actactctat tttgcttcat cttctcagaa caggggacca    78840
gcaattattc ttcctccaga agcttcaaca tcttttgtca actgactcct tctcatgttt    78900 aaatatttc aagttaaaca atttcttcc tgactttcgc tcacgcaacc tcatgcccaa    78960
aaccttatca ctcttcttcc ctttgctgtc aaggctgttc tcacttcttc acttttgtg    79020 gacttctccc cactacaaca tagattctgc tatcaccaat ctattaaaac tgttatactc    79080
ttgtggaatt tatcatttaa tttagcttca gtgaaccgtt cttttccagat tattttggcc    79140 tcagaccatg acttctaagt ctgccgtgct tgccacttaa gtgatgatgg gccagtgggt    79200
ccccacctag gcctctgtgt tagtctgttt tcatgttgct gataaagaca tacccaagaa    79260
tgggcaattt acagaagaaa gggggtttgag ggactcacag ttccatgtga ctggggaggc    79320
ctcacaatca tggtggatga tgaaaggcat gtctcacatg gaggcagata agagcataga    79380
acttgtgcag ggaaacttcc ctttattaaa ccaccaggtc ttgtgagact tcttcactat    79440
cacgagaata ggatgggcaa gaccctcccc catgattcaa ttatctccca ctgggtccct    79500
cccacaacac atgggaatta tgggagctat aattcaagat gagatttggg tgaggacata    79560
gccaaaccat atcagcctcc ttctggcttt ttatgttctc cgtgggtgac ctctctcagg    79620
ctcaagtgat aaccaatgtg ctgatgactc tcaaatgcgc atctctggct tcagtttctt    79680
ccttgaactt catacatatg tttccaaatt tcctgcgtgt acctcaaggt tcttgttcat    79740
cacttcccaa gcttcataaa cgcactcatt ttagtgtatt ctctgtctcc tttgatagca    79800
tccctgagag gcaagtccct ggtgagttat atacaactcc tcccttgctc caaacctgag    79860
agtaagtaac attcctatta acatattagg aagctgaggc ttagacagtt taagtaactc    79920
aagcatggtt acacaactag ctagggcaga gctaaaatgt caggctaggc ttctgtgact    79980 ccaaagcct ttctcactta gcatatcatc acttattttt ttttttaatc acatatatga    80040 ttttttttc tttaagagat agaatcttgc tctatcacgt gggctggagt gcagtggcac    80100
aatcatagct cactgtaacc ttgaacttgg gctcaagtga tcctcctgcc ttagcctact    80160
gagtagctag ggctacagac acacaccacc atgcctagct aatttatttt tatttattt    80220 tatttttga cacagagtct cactctgtca cccaggctgg agtgcagtgg tcgatcttg    80280 gctcactgga acctctgctg cccgggttca agcgattctc ctgcctcagc ctcctgagta    80340
gctgggatta caggtgcctg ccactgtgcc cagctaattt ttgtattttt agtagagacg    80400
gggtttcacc atcttggcca ggcttgtctt gaactcctga cctcgtgatc cactcgcctc    80460
ggcctcccaa agtgctggga ttacaggtgt gagccaccac gcctggccac ctacctaatt    80520
tttaattttt ttgtagagac agggtctcac tacgttgccc aggctggtct tgaactcctg    80580
ttctcaaaca atcctcctgc ctcggacacc ccaagtgcag ggattacagg catgagtcat    80640
tgcagctgac ctgtatatat gattttagt atatgtaaat atacatattt attaaatgta    80700
```

```
aatataaata taaatgtgtg gagtgatatc cattgaaatg ttaaacatag ttctcagtgg   80760
tacaactaca ggtgatttct cttttcttat ttctggtttt ctgtgttttc caaatttctt   80820
gaaatgtgtc ttctgtaatc agaaataaaa gttattagta acaacagtct tccactggta   80880
caagtgctta ttggataaaa gtcccacttc taagcatgat actcacaact tttaggttaa   80940
tagcctttgt caccttgcca tatacatctg atccagccac tcacaccatt cctgagatat   81000
attttgttcc tttgtgccta aatcattgtg catgcagatc catcttcctg gaacacctat   81060
aaccatttct tagtcctgtg aaatcctact tacatccttc atagcctagc atgtatgtca   81120
tttatttggt caagggtgag ttggttgttc tcttgaatgt actgccatat gacgtggtgt   81180
gatttcaatt gtagcaccaa gctcattgca atattaattc gtttgtcatt ctcccatgta   81240
ggatgtttga agtagtttct aacacagaga ttatactcaa taaatattta ttagataaat   81300
aaatgaataa gggaataaca aatgcctttg tctcatttta aaatactttc attgttagct   81360
acccatataa taaaaaacta aaagcagtag ttttcaagca tgattgttta tgtatgcctt   81420
aaaagaattt tgaaaaccta tgtaccccctg acacactttt aagttaactt ataaatttttt   81480 caacatagtt ttaagtggtg gcaaatgatg tagtttcttg tgtattttaa actgcttaag   81540
tatgctatac atggatttct tcaaaaccct gaagctgcag tttcagtgca ttcaatttat   81600
ggaaaagaaa ttaatttata aaattggttc ttattgtcaa gtcaatcagc taaatataac   81660
ttgctttctg tcaggaaaag tctgacttta aaatacagat aagtaataac tattattaat   81720
taattaaatt attaaaatta aaataattaa ataatttgtt aattaaaatg ccttattccc   81780
ctacttattt ctgcaatttg actctaagaa tagataggac atgtagattg ccttaggttt   81840
gaaatctggg tgaaataaga tactgcctcc ttcagtattt ctgcctttgc ttttatggga   81900
gcctctttca agaaaaagtc attctctcat ggtccctttg tttgagtccc agaggttttc   81960
ctactccaga aagtgcaacg tagtgagact agtactatac tcccttgcat ggtaagtgag   82020
aaggctgtct gtataaaatg agggaaggac tcatgagagg gaagtaggtc aggagaaatg   82080
ataggttctc aggcaggtta attttaggaa agagtgaata gagtccctta aaacaaggtg   82140
catctgcttc ctcctgatca atctttagga ctgtttactt tgatttgaag accactatgc   82200
taaagcttcc cacggggggca atagtgaggc aaggaatttt taaaagggaa ttacttcttc   82260
gtagctactt ttgtgaaatg aattcatttg aattatctgg caatctcttc atatttatat   82320
tcaacaataa ttacttaaag aaatgctttg agcttctcag aggagggtgc taccagtgtg   82380
atggagtaga attcagattt gggtagtgac tttaaagctg tgtgacttta gtcatttaac   82440
tgctgagtca cagtctacag ctttgaaaga ggaggattat aaaatctatc tcatgttaat   82500
gctgaagatt aaataatagt gtttatgtac cccgcttata ggagaagagg gtgtgtgtgt   82560
gtgtgtgtgt gtgtgtgtgt gtatgtgtat gtatacatgt atgtattcag tctttactga   82620
aattaaaaaa tctttaactt gataatgggc aaatatctta gttttagatc atgtcctcta   82680
gaaaccgtat gctatataat tatgtactat aaagtaataa tgtatacagt gtaatggatc   82740
atgggccatg tgcttttcaa actaattgta cataaaacaa gcatctattg aaaatatctg   82800
acaaactcat cttttatttt tgatgtgtgt gtgtgtgtgt gtgtgttttt ttaacaggga   82860
tttggggaat tatttgagaa agcaaaacaa aacaataaca atagaaaaac ttctaatggt   82920
gatgacagcc tcttcttcag taatttctca cttcttggta ctcctgtcct gaaagatatt   82980
aatttcaaga tagaaagagg acagttgttg gcggttgctg gatccactgg agcaggcaag   83040
```

```
gtagttcttt tgttcttcac tattaagaac ttaatttggt gtccatgtct cttttttttt    83100
ctagtttgta gtgctggaag gtattttgg agaaattctt acatgagcat taggagaatg    83160
tatgggtgta gtgtcttgta taatagaaat tgttccactg ataatttact ctagtttttt    83220
atttcctcat attattttca gtggctttt cttccacatc tttatatttt gcaccacatt    83280
caacactgta tcttgcacat ggcgagcatt caataacttt attgaataaa caatcatcc    83340 attttatcca ttcttaacca gaacagacat tttttcagag ctggtccagg aaaatcatga    83400
cttacatttt gccttagtaa ccacataaac aaaaggtctc cattttttgtt aacattacaa    83460 ttttcagaat agatttagat ttgcttatga tatattataa ggaaaaatta tttagtggga    83520
tagttttttg aggaaataca taggaatgtt aatttattca gtggtcatcc tcttctccat    83580
atcccaccct aagaacaact taacctggca tatttggaga tacatctgaa aaaatagtag    83640
attagaaaga aaaacagca aaaggaccaa aactttattg tcaggagaag actttgtagt    83700
gatcttcaag aatataaccc attgtgtaga taatggtaaa aacttgctct cttttaacta    83760
ttgaggaaat aaatttaaag acatgaaaga atcaaattag agatgagaaa gagctttcta    83820
gtattagaat gggctaaagg gcaataggta tttgcttcag aagtctataa aatggttcct    83880
tgttcccatt tgattgtcat tttagctgtg gtactttgta gaaatgtgag aaaaagttta    83940
gtggtctctt gaagcttttc aaaatacttt ctagaattat accgaataat ctaagacaaa    84000
cagaaaaaga aagagaggaa ggaagaaaga aggaaatgag gaagaaagga agtaggagga    84060
aggaaggaag gaaagaagga aggaagtaag agggaagcag tgctgctgct gtaggtaaaa    84120
atgttaatga aaatagaaat taagaaagac tcctgaaagg caattatta tcaatatcta    84180 agatgaggag aaccatattt tgaagaattg aatatgagac ttgggaaaca aaatgccaca    84240
aaaaatttcc actcaataaa tttggtgtca ggctgggtgc agtggctcac acttgtaatc    84300
ctagcacttt tggaggcaga ggcaggtgaa ttgcttgagt ccaggagttt gagaccagcg    84360
tgggcaacat ggcaaacccc acctctacaa aaaacacaaa caaagaaaa tagctgggtg    84420 tggtggtgtg tgcctgtagt cccagctact tgggaggctg aggtgggagg atcacctgag    84480
cctgagaagt ggaggctgca gtgagccatg attgcaccac tgtaccctag cctaggtgat    84540
aggctcaaaa aaaaaaaaaa ttggtgtttg caatgctaat aatacaattt ggttgtttct    84600
ctctccagtt gttttcctac atacgaaaca gcttttaaaa caaaatagct ggaattgtgc    84660 atttttctt acaaaaacat tttctttctt aaaatgttat tattttcttt ttatatcttg    84720
tatattatta ctagcagtgt tcactattaa aaaattatac tataggagg gctgatacta    84780 aataagttag caatggtcta aacaaggatg tttatttatg aaaaggtagt aattgtgttt    84840
catagaattt ttaaaattaa ttctgcgtat gtcttcaaga tcaattctat gatagatgtg    84900
caaaaatagc tttggaatta caaattccaa gacttactgg caattaaatt tcaggcagtt    84960
ttattaaaat tgatgagcag ataattactg gctgacagtg cagttatagc ttatgaaaag    85020
cagctatgaa ggcagagtta gaggaaggca gtggtcccctt gggaatatttt aaacacttct    85080 gagaaacgga gtttactaac tcaatctagg aggctgcctt ttagtagtat taggaatgga    85140
acactttata gttttttttg gacaaaagat ctagctaaaa tataagattg aataattgaa    85200
aatattaaca ttttaagtta aatcttaccc actcaataca atttggtaat ttgtatcaga    85260
agcttaaaag ataacctaat agttcttcta cttctataac ttacccaaat atgtttgcag    85320
agatcttatg taaagctctt cattataaca ctgctttcag gagccaaaaa ttgggtgggg    85380
gagccccata aatgttgaat aataggggtt tgattagata aattttggtg tagttctata    85440
```

```
atggcgtgtt attcagccaa taaaaggttt gttaaagaat gactgtgacg gatgtatatg    85500
atatactctt aagtgaataa agagttacaa aatgttatgt acaagttaca aaatgtatgt    85560
acattatgat ccatttttca taaaatcata tgtatgtata tatgtgtgtc tggaaggata    85620
aatttatcaa gttgttatct ctgaaatttt gggtatattt tatatttcta gattttctgt    85680
tactttgtta ctttactgat aaagtaataa cgttgttgac ttttgtcact ctcccctatt    85740
aataatcatc taggctgcaa aaggatcatg tcttctttat ttttatattc caaggactgt    85800
caacaagtgc ctagcacttg acaggtatat tatagaaatt taactgaata tctttaggaa    85860
atagattttt gtttgtagtt gttctagtct acattaaatg tcttgcgctt atgaaacttc    85920
cttgaattat tttagtgaag caatattagt atagaatttt gcatcactgg atgcccttga    85980
ctgaaagctg gctatggca tctcaccagt gtgtggggag tttcagtcct tctgttgtct     86040
gcatcacagc tgaagcagtg ctgttgctga caattcctga caccaccttg tctctattat    86100
tgatcattgc ctcactatgg tactgagttt tagcttattc ttgtaataac tgggactcat    86160
atgtatagaa taagctatta gctcacgttt ttgcttgctt tttatacaga atacatgtct    86220
gcaaatagtt ttatcaatat tttggaattt tgggagatat gaagttaaaa acatcattga    86280
atatatatat atacacacac acatatatat atgcacactat acatgattta ttttatttaa   86340 ttttaaaat tttattcttt ttagagatta ggtcttactc tgtcacccag gctgaacttc     86400
agtggtgtga tcatagctca ctgtaacctt gaactcctgg gctcaattga cctttccgct    86460
tcagcctccc aaagtgctgg gtttataggc atgagccact gtgtctggtc caatatgcat    86520
atatatattt ttaacctgga ttatcagagc tatattgtgt ttaggtttat aaagctgtac    86580
tatgtgaaaa tatcacttct aggtttaatt ttgtacaaag gaattttata tagaaatgag    86640
gtaattcaga ttttttccca tgtaataaga attgtaaaat ttactgaaac aaacatcaaa    86700
aagatatctg ttacatgacc ttcctttctt ttgaatatat ttcaggtgat attatttatt    86760
aaaatttaaa aatgaaaatt aaaatatata aaaagttgaa aattattcct ttctttactg    86820
tctctcatct gtccattttc cattctcctg cattccctca tccaaccaag gtagccaatc    86880
caggtaactt ttttagtat cttcccagag atgtttctct ctatatatat aatcaatata    86940 catttttat tattccccac ctctctttt atgtaacaat atgcagagtt ttgcttcttg      87000
cttttcccac tatcttggac aactttccat attcaaagca cagaggactt gcacatatgt    87060
tcagactgct gaatatttct gtctctcccc tgccattcat atgttgaaat cctaattccc    87120
aaggtgatgg tattgcaggg tggggccttt gggaggtgat tagtccatga gggtgaagtc    87180
tttagtaaat gagattagtg tctttataaa agaaaccttta gagagaccct cacaccttag   87240
agagaccctc accctttct gccatgtgag aacacagcag gaagacagct ggctatccag     87300
gattcaggag tctcttagca gacccaaatc tgctggcacc ttgatcttgg acttccagc     87360 ctccagaact gtgagaaata aattcctgtt gtttataagc cacacagttc atggtatttt    87420
gttatagcag cctgaacaag gacacacaca cacacacaca cacatgcaca cacatttaaa    87480
tagatgcata gtattctatc atatggatgg atattctatg atataatgaa tcactattga    87540
ttgacatttg ggttgtttcc aatattttgt taacacaaag aacaacacta caaataactt    87600
tatatacata tcatttagca catctgcaat tgtatcagta ggcttcctat aagtggtcaa    87660
gcatttgtgt acttgtgatt ttggtagatg ttgtcaaatg tccttccctg aaattttgtac   87720 caattcgtac tcatgccata cactctaaat agagtgctga tttccccaca gcattactaa    87780
```

```
cagatgatat tatctaattt aaaaagtttc tcatcttata gggaaaatag tatgtcaatg   87840
tattcttaac ttgcatttct tttattataa gtagtgtaaa atatcatttc aacttataca   87900
caggaggaat ttctctctat ataaagtgat cctagaatca taatgaaaaa tatcaccaac   87960
tcattaggaa aatgtacaaa ggattgaata gatatctcat caaaaataaa aatataagtg   88020
gcctttaaac attgaaaggt aacatttgaa caaagacttg caggaggtga gggattaggg   88080
aatgcagact ctgggaagag tcttccaagt agcaggtgaa gcaagtgcaa agctttcaga   88140
tgggactgac tatacctgtc tggtttgaag aacagtaagg aggtcactga ggctggcata   88200
gagtaagaca gggagggtag aatactgtca gagaagtaat cggcggtgga ggtaggggt   88260 aaaccataaa gtgctcgtaa agactaaggc ttatttctct gggtgagatt agaggccact   88320
ggagagtttt aaacagaagt aacagggcca ctttggctaa tgttttagg ctattctgta   88380 gggagacaag ggaggaagca aggagatgag ttaggagtct attgtgccag ttcaggcaag   88440
tgatgatggt ggcttgatcc aggtagtagt ggaagtagta tagtaggaag tgatcagatt   88500
caggacatgc tttgaaggaa gatccaatag gattaatgga taagttgaac aatggcatat   88560
gagaaaagtc acagaggagt caaagatgat tccaagcttt ctggactgag taactggaag   88620
gataaatgtg ccgtttacta gaaagataat gggagaaaca ggttttggat ggagcttggt   88680
ttgggaatat taagtttgaa atgcctatt gacatccaaa tagagatgtt agttggatgt   88740
acaagtctag tttcaaggaa gaggggctg gtagtgtgaa gatggggctg ataagattc   88800 taaaggaaag agggttgata agaagagaaa ggggtgtagg ggttagccta agggcattct   88860
aagtattaga ggttaaggag gtgggtgaag aaaacccaat aaaataaaag tctgagaaga   88920
caaagctagt gaatgaatgt ggtatcccgg aacccaactg atgtcaagca gaagggtgtt   88980
atcaactagg tcaaatgctc attcatcaag taagatgaaa ctgttataat taaccggtgt   89040
cttctgaaat acggagataa ctcgtgactt aatgaaagca atagtagaga aggtcaaact   89100
tgaccagaat gaaattagaa agaataagag gaaagaaaag accaaataca gacaaccatt   89160
gatgccttat tcttttgata tactcctgga gtccacttgc taatacaatt gacccttaaa   89220
caatacaggc ttgaactgca tgggtccact tatttgtgaa ttttttttca gttaatacat   89280
tggaaaattt ttggggtttt ttgacaattt gaaaaaactc acaaactgtc tagcctagaa   89340
ataccgagaa aattaagaaa aagtaagata tgccatgaat gcataaaata tatgtagaca   89400
ctagcctatt ttatcatttg ctactataaa atatacacaa tctattataa aaagttaaaa   89460
tttatcaaaa cttaacacac actaacacct accctacctg gcaccattca cagtaaagag   89520
aaatgtaaat aaacataaaa atgtagtatt aaaccataat ggcataaaac taattgtagt   89580
acatatggta ctactgtaat aatttggaag ccacttcctg ttgctattac ggtaagctca   89640
agcattgtgg atagccattt aaaacaccac gtgatgctaa tcatctccgt gtgagcagtt   89700
ctctctccag taaattgcat attgcagtaa aaagtgatct ctagtggttc tcgcatattt   89760
ttcatcatgt ttagtgcaat gccataaacc ttgaataaca tcaagcaatc catacaaagt   89820
gccactagtg atgcacggaa aagttgtaac agtacaagaa aaagttgag ttgcttggta   89880 tttaccatat attgaggtct gcagctacag ttgcctgcaa tttcgagata aatgaaccca   89940
gtataaagac tgttgtaaca aaagaaaaga aaatgtgaaa ccatcagtgc agctatgcca   90000
gcaggtgtga agtcttgcac ttttttgcaaa atacaaaata tgaaatatgt gttaattgac   90060
tgtttatgtt atctgtaagg tttccactca acaataggct attagtagtt aagttttttgt   90120 ggagtcaaaa attatacgtg gattttttgac tatacagtgg gttggcaccc ctaaccttca   90180
```

```
tgttgataaa gggtcaatgg tatattattt aattttttg tatttatatt cataaataag    90240
attaaatcta tatttccaag taatctctat aagattttgt tattaatatt actattattt    90300
ttgagacaga gtcttactgt caccaggctg gagcacagtg gtgcgatctc ggctcactgc    90360
aacctctgcc tcccgggctc aagcaattct cctgcctcac cctcccaagt agctgggact    90420
acaggcacgc acaaccacac tcagctaatt tttgtatttt tagtagagac ggggtttcac    90480
catgttggcc aggatggtat tgatctcttg acctcatgat ctgcctgcct cggcctccca    90540
aagtgttggg attacaggca tgagccactg tgcacagcca ttaatattat tgttacccaa    90600
taaaaaaaat ttggaaactt gtcttctttt cccctgattc tgtttaaata gcactggagt    90660
tacctgtttt gaattttttt tccaagcggt cccttatgag ttttctctat gttttatttg    90720
tttcatttct tttttttttt ttttttttt ttttgagacg gagtctcgct ctgtcgccca    90780
ggctggagtg cagtggcggg atctcggctc actgcaagct ccgcctcccg ggttcacgcc    90840
attctcctgc ctcagcctcc caagtagctg gactacagg cgcccgccac tacgcccggc    90900
taattttttg tattttagt agagacgggg tttcaccgtt ttagccggga tggtctcgat    90960
ctcctgacct cgtgatccgc ccgcctcggc ctcccaaagt gctgggatta caggcgtgag    91020
ccaccgcgcc cggcctgttt catttcttat atcgtatttt tgcaactcct ttattgatac    91080 tttctcct gattaggttt ctactaaaac caaacaagct ttccatgaat tagcttttag    91140
atttacttat tagtttaact gttctgttgt attgtaactc attaatttat aattttatct    91200
ttattaatta ttctattttt cttcgctttt ttgttgtttt tctagtttt gagttagatg    91260 tttgacgctt ttttaaaaag ctgtgcattt tcctctgggt aatactttag ctgtatatta    91320
tgtattctga tatatagtgt ttccattaca ttgttttcta gaaaatctgt agctttgatt    91380
tatatttgtt tcctctttga cctaagatat cctaagggaa aatttaacat ttccagaaa    91440 gaaaacaaat tttctttgtt ttccaagaat gttgttcaaa ttatttctac tgcttggaat    91500
ttttatcatt tttgtgtatc cagtaaatag tcaatatttg tacttgctct ctgaccacat    91560
aaaagaatat attcgtgtag tttctattaa tagattagag ttcaattcag atattaaatg    91620
tacatcatta ttcatgatat ttaggtcttc tacatcttca cttatctttt ttctacttgc    91680
tttgccatta acagataaag ttgaattaaa ggcttctact acatacattt ctccctgtta    91740
ttccttatag gttctgtaat ttttgcttca agaatattgc ttttaaatt taatatatag    91800 atacttataa ttacactcta gcattataaa gagccttttc tttttcattg aatgtatttg    91860
ggcctgcata tgtctaacat gaaaattata gtccttttt tgtttctttg tttgtattta    91920
cagttttaag ttccattttc aacctttatg cactctttgc tttaggtgtg tctcttttag    91980
ttagcataaa gttaggtttg tctttaattt cacctgaagt cttttcctct aatagatgg    92040 gttaagccaa ctgaaaaata aaactgactt atatactttt atttcaagta tgtcctccac    92100 aaatatttt tgaatagatt agcttatata ctttggaatt tgttaaaaaa agattttat    92160 aaaaaataat tgtggtgaaa tgtacataac ataaaattta tcattttgac cattttaag    92220 ggcatagctc tgtggcataa agtatactca catagttgtg caactatcac ctccttttga    92280
ttttttttta ctaattttgt aaatttgttt catctgagct gtcttattat gttttgtttt    92340
atgtttttct ttcctttatt atgaagtcac tgtattgtct gtaggctata tgtatctgtg    92400
agtgtgtgtg tatatgtgtg tattatggtt tttaaaaaag tctatatttg ttttccagtg    92460
gctatactta atactaataa ctttatgtta aatttttcat tctatgtgac tctagttcac    92520
```

```
taatatgagc tctgataaaa tcagtgcttt ttcgaggtta ggagatcaag accatcctgg    92580
ctaacacagt gaaactccgt ctctactaaa aatacaaaaa attagccaga cgtgatggcg    92640
ggtgcccgta gtcccagcta ctcgggaggc tgaggcagga gaatggcgtg aacccaggag    92700
gcagaacttg cagtgagccg agatcgcgcc actgcactct agcctgggtg acagagtgag    92760
actctgtctc taaataaata aataaataaa taaataaata aataaaatca gtgcttttc     92820 ttcctctgct acctcctttc cttctactca gttttagtca gtagtattat cttttttcag    92880
atttatcttt gtattgttaa atctgcttat gcttctatta ctttatttat tagctttaaa    92940
tgataccttt tgactttcag cttttcttaa taaagcaatc agcaaatttc ctttacactc    93000
cacacttata ccccatttcc tttgtttgtt tatttggttt ttacttctaa cttttcttat    93060
tgtcaggaca tataacatat ttaaactttg tttttcaact cgaattctgc cattagtttt    93120 aattttttgtt cacagttata taaatctttg ttcactgata gtccttttgt actatcatct   93180
cttaaatgac tttatactcc aagaaaggct catgggaaca atattacctg aatatgtctc    93240
tattacttaa tctgtaccta ataatatgaa ggtaatctac tttgtaggat ttctgtgaag    93300
attaaataaa ttaatatagt taaagcacat agaacagcac tcgacacaga gtgagcactt    93360
ggcaactgtt agctgttact aacctttccc attcttcctc caaacctatt ccaactatct    93420
gaatcatgtg cccttctct gtgaacctct atcataatac ttgtcacact gtattgtaat    93480
tgtctctttt actttcccctt gtatcttttg tgcatagcag agtacctgaa acaggaagta   93540
ttttaaatat tttgaatcaa atgagttaat agaatcttta caaataagaa tatacacttc    93600
tgcttaggat gataattgga ggcaagtgaa tcctgagcgt gatttgataa tgacctaata    93660
atgatgggtt ttatttccag acttcacttc taatggtgat tatgggagaa ctggagcctt    93720
cagagggtaa aattaagcac agtggaagaa tttcattctg ttctcagttt tcctggatta    93780
tgcctggcac cattaaagaa aatatcatct ttggtgtttc ctatgatgaa tatagataca    93840
gaagcgtcat caaagcatgc caactagaag aggtaagaaa ctatgtgaaa acttttttgat   93900 tatgcatatg aacccttcac actacccaaa ttatatattt ggctccatat tcaatcggtt    93960
agtctacata tatttatgtt tcctctatgg gtaagctact gtgaatggat caattaataa    94020
aacacatgac ctatgcttta agaagcttgc aaacacatga aataaatgca atttattttt    94080
taaataatgg gttcatttga tcacaataaa tgcattttat gaaatggtga aattttgtt    94140 cactcattag tgagacaaac gtcctcaatg gttatttata tggcatgcat ataagtgata    94200
tgtggtatct ttttaaaaga taccacaaaa tatgcatctt taaaaatata ctccaaaaat    94260
tattaagatt atttaataa ttttaataat actatagcct aatggaatga gcattgatct     94320
gccagcagag aattagaggg gtaaaattgt gaagatattg tatccctggc tttgaacaaa    94380
taccatataa cttctagtga ctgcaattct ttgatgcaga ggcaaaatga agatgatgtc    94440
attactcatt tcacaacaat attggagaat gagctaatta tctgaaaatt acatgaagta    94500
ttccaagaga aaccagtata tggatcttgt gctgttcact atgtaaattg tgtgatggtg    94560
ggttcagtag ttattgctgt aaatgttagg gcagggaata tgttactatg aagtttattg    94620
acagtatact ccaaatagtg tttgtgattc aaaagcaata tctttgatag ttggcatttg    94680
caattccttt atataatctt ttatgaaaaa aattgcagag aaagtaaaat gtagcttaaa    94740
atacagtatc caaaaaaatg gaaagggca aaccgtggat tagatagaaa tggcaattct     94800
tataaaaagg gttgcatgct tacatgaatg gctttccatg tatatactca gtcattcaac    94860 agttttttttt ttagagcccc attcttattt tttatacact ttgagagcat aatgaaaaga   94920
```

```
aaagctacct gcaaaagttt tggacttacc tcaaagagga tatacttcat tcctcaaaag   94980
gccttcttcc aggaatagta tttcataacc tggaggttgg aaaaatctgg atttgttaca   95040
aaaaaatctg agtgtttcta gcggacacag atatttgtct aggaggggac taggttgtag   95100
cagtggtagt gccttacaag ataaatcatg gctttatttt acttacgagt ggaaaagttg   95160
cggaaggtgc cttacagact ttttttttgc gttaagtatg tgttttccca taggaattaa   95220
tttataaatg gtggtttgat ttcctcaagt caacctttaa aagtatattt agccaaaata   95280
tagcttaaat atattactag taataaattt agtactgtgg gtctctcatt ctcaaaatga   95340
gcatttacta atttctgaac actgtgctag gtcctgggaa taccaaattg aataagacat   95400
agtctatttt tctgaagggt ttatagcaga gtcccctgtg ttaataatga aggagtgtgt   95460
ggtatgtgaa tcatatatca atagggttgt taaaaataat gaaaaaagga gaagaggaag   95520
aacatctttt tttttctga ttgcacgggc agccttaaaa ttattttga agtgtacaat    95580 tcagtgtttt tttagcatat tcacagggtt gtattatcat caccatattt ttggcctctt   95640
gaaaagaaat cctgtgccta ttagcatcca attaccgttc ctttgtagct aagtctcccc   95700
cattccagct ttaaacaatc acccatctac tttctgtctc tataaatttg tctcttttgg   95760
acatttcaca taaatgaaat aatataatag ggttttttgt gcctaaataa gcttctaaag   95820
aagaataagg taaggaatca tcattcagca aatatttatt aagacttgct ttattttata   95880
cagtgtacta ggagctggag atgaaaatat gtgtagaaca tgaatcatat acttcgggaa   95940
tttgtggact agtgggaaag attgacatat caataacaaa tcgaattagt gatgtaaatag  96000 aggcattttt acaggagtaa aatgaggtag catggactct atctgggtct gaataatgtg   96060
aggagtaacc tccttacaca aagaggcaca aggctaatgt cctctgatgg aatgattcac   96120
catgcaattc taagggtgac aagaatgaaa gttagggcct tgaagaaata ttttgattaa   96180
gagctgccaa taaagtagag taaagattag attgatgtga agaagtggga gattaatgag   96240
taaatggtca ctggcttgtt gagaagatta aatgagatgt acatgtaatg tacctaacac   96300
aacgtcttgt acaaagtagc cattcagtag agactagctt gtattatctc cctttgaggt   96360
aaagaaaact gttagaaata gtatttctac tactgatagt atttcttcta cttatgcctc   96420
cctttgaggt gaagaatact gttagaaaac atgacatagg agaaataccc ctgagagaca   96480
gttcttatta gtgactactg tgcagaaaag atggaggttg gtgtaattaa ggagaaggaa   96540
agccatgaag ccaaagtatt atgaaaaagc atcaatatga atttcatgt tgacaaagtg    96600 gtataaaaga taattataaa gatggtcact tataaatacg gtagttctgt gtgacacaat   96660
ttacagaagt tggtatatcg tgtggaagaa acagcataa gatcctgaag gtttgaactg    96720
tgggcacatt ggctccatgc tcaggaaatg gcaatggggt tgggaagtga ttccacttta   96780
tgtccctttc agacacataa aaattacttg tgtgagtatc ttatgccaga cactattcac   96840
tgtgtagtga gcatggtggg tatgaaatga caactttatt gtctttcctg tcaaagaact   96900
tgtaggctgg ttgggggaaa gagaccattt caatatgaag tgctgagcta gaggtaccct   96960
tagggcacta cagaagccta gctgatggct tttagcctgg ctagacagtt caggatctct   97020
aaaagcaggt gccttgaagg ctgagtcaaa tacaaaaatg tattttggac agaggaaatt   97080
gtatgaacag aaacacagaa catgaaacta cttggttggt gcagggtatc atcagcatag   97140
aaccagacag aaccagagtg taaataagcc agaaggccat gtcatggagg ccttgtatac   97200
cagtctcagg aatttggttg tggagagctt tcatcagggg aatgatgtaa tcagcttgga   97260
```

```
aatgtagata tatcactgac tgtgatagtg aggagcagaa ttaaggtgga cgtgattaga    97320
agctttgtga atagcagaaa gaacatagat tttgaaagct ggcagacgta ggttactgaa    97380
gaaagttact taaccttgct atgtctttag ttttatcctc tgcaatatgg ggataatact    97440
gcctattttg tagagtcttg tggattcttc tggcatatat aatagaaaat aaaacagcta    97500
ttattattat tgttgatggt actatttgct atatctgact acaaggagaa agactaatag    97560
gaaaccattt caggaatcca gatatggtca tgatggacag gaagagacaa gagttacata    97620
gaggaattct gggaagataa gaaatgtcat ttttatgtac tgtttgcatc catcagacaa    97680
ggcatcagga aaaatgatcc ttcaggaaag agtgattttt tttcttcaag aaattagaag    97740
aggggagaaa ttggtttaag attaaggact ccatgcataa gagaaactgg gagggaagac    97800
aggtagaaat gctatggggt taggaaggaa gaatgcagag gtggattact tagaattgag    97860
acatctgatc aagacagagg gatcacagct tttgctaaca aagtactagt ggaggatgcc    97920
actaggtgag gtttaataaa taattgttga caataagttc catttaaaaa ataaacaatt    97980
tatgcttctt ctttgcctaa gtgtcaaata aaacattcag atttttattt caaagtatcc    98040
ctgagtccct gttcccttttt ttgtcctgct gacttttgga actgatttag gcttccttag    98100
tcatctcata atagaaaaaa tcagccaggt atttcctaca tttcttgtat tttaaaaaaa    98160
tgtaatggat gtaatgaatt ttaagcaaat gtaatgaata caataagtaa cttagtatat    98220
gctgttttct tctctatgct gaatgtttca tacatgttat tttctataca actacatggt    98280
caattccttg aaaatatcaa ctccaaaatc tttattttgg tatactccac gtagcacatt    98340
gagagagttt taaactcttg ttggatgact gttttcaaaag tgttttgaag taggcatgtc    98400
agttgcaaaa agtttgctca gcaaatgttg ttctgtctca cagtctcaga cattgagcag    98460
atgattacat gacagcacgt gattgctggg agtaacagac aaaagtaact gaaagtgctc    98520
ggttatcttg acagtcaaaa tcaaagtgt cccctatttt cagtgaccta agagtttctt    98580
tttgtgtttt tggtattgtt gttaaataag tgttctcacc tttgaaaagg tcaataagaa    98640
ttcaatacag tataatgtct gtgtgccaaa tgaaggtgcc ccttattttt aagtgtggag    98700
gagttttgat cataagaact tgaaatacct acagaatcct tgatggttaa gcagctggtg    98760
ccagcacaag aatccctcaa tatgttctct atgaagcccc gatcaccaaa tgcaaacatt    98820
catgattcag tatattttca tcttgactgc caaagttgat ctgtttctta atatattaca    98880
tctagacttg gaactggaga tgagaacaga atattatctt cctcattttt gtgttttgt    98940 tcaactctaa tgtctgcaaa gcacttgcgt atgtaatgat gctcagtgtc ataggagcag    99000
gcaggtaagt gtaaatttgt ctggatagga gaaagcatgc acaacatatt tcacatagtt    99060
ttctgatttc agtttgtttt tgcaaattat tcactcagtg agatagctta aagacgttat    99120
cacagggaaa ggcatggaga tagttctgtg ttgatagaaa acttgtaatg tacagccatg    99180
agtgagaagt caggttcaga ttcttcacct tcagtcctcc tctttcataa acagctccat    99240
gtcctatttt acatatccta ctttaaaacg agattataga agaatgaatt tctaggcaaa    99300
gtgacactta tttaaaata ctattacgta tccctgtgcc cattaactta tcctaccatt    99360
tttcttcccc tgtgtccaaa ccacctttag aatctcctaa atatttgtag ctattgtaaa    99420
cagcactgga gactttgcta gtttaaaagg agaaatcaac gcaattaagc cctagttaat    99480
ttacttatcc cttatgagat tataattgta ttttgttatt aaaaggggga cagagtacac    99540
tgttctcttg ccttttttaat ttccagacta ccacttctcc tgcacttgac aataccgcag    99600
tctaccacgt agtcccatgg ctgacaggag gagaattcta ggcaggccag tgtttgagta    99660
```

```
gtgagtaatt ggactgtctt tacccagcaa ctcactgttt tgtaaatgta cctgagtttg   99720
gagaagtaat tggcttttat aagggtgcg gggtggaggg ttggggtggg gagagtgaga   99780
aggaggtcag agcttaggga tatataattg gtctccacaa agttgttgtg atacttttgg   99840
aaccacgtaa tggtcttcat taactaagtg tctgtcatga cagccattac atatgcatta   99900
taataaaaat ttatttacag tgtaagttga agaaggtaaa atctggatgt agtttctaaa   99960
ctctgcttgg cagttttcat atttaagcca ctagaagaaa aaaattggga gggaagctga  100020
gaagaattta ctgaaagaaa aaaatacttg ggagggaaat tggcaagaag tatgaaaaag  100080
cttgggaggg aagtaagcaa ataaatgagt taatgactgt tctggaaaat aaactctatc  100140
atgcagatat cacatgactg attaaatttg aatttgacct cctgctttcc aggtctggta  100200
aaaactaacc tgtaagaact tgaaacttag ccttttgaatg gtcaatccac cactgtagga  100260
gaatttatga atgttcagtt gagagaactg aaaataaaga agtaccatag gaattaacat  100320
ttgcattcag tagccaagat ataatggaca tctgaaacag gtatttgagg ccaggcgtgg  100380
tgtctcatgc ctgtaataat agcactttgg gaggccgagg tgggtggatc acaggaggcc  100440
aggagttcaa gaccagccta ctaaaacaca cacacacaca cacacacaca cacacacaca  100500
cactagccag gcgtggtggt gcacgtttgt agtccaagct acttgggagg ctgaggcatg  100560
agaatagctt gaacccagaa ggcggaggtt gctgtgagct gagattgcgc cactgcactc  100620
tagcctgggt gacagagtga gactctgtct caaaaataaa ataaaacata tatttgaaac  100680
acattgaatt atgtcccctta aacaagaata aacatcacta aatgactgta ccttgaacta  100740 cctgtaatt tctcctgata ggtaattaag cttcaaagta ctgacactta tttactgtaa  100800
tatgaagcaa taacttaaaa aaaaaaaaaa actattgaac cagaaccaaa caggaatgcc  100860
atagcatttt gtaaactaaa ctgctatttc atttcatttg agccctggaa cttgaaaata  100920
aatgctagct aacatctgtg aacagaacat acccatcagt actgtgctaa gcacctttca  100980
tgaactggtc attaaatcct cacttttccat ttatttagtg acaacttcac ccagagtttg  101040
cagtcaaagt gaaaatgtgc tgaattccaa aagtgtgagc taggttttag aagttaatca  101100
caattctgga acaaattact agcttaacaa atgagagttc ttatgtctct aaaaccaaaa  101160
tagccctaag tctgtccctc ccagtaagat ttgggccagt caatggaaca gtaatataca  101220
aatataatta cagctgtcta ggagcaaact atcctatgaa tagataataa aattaagaca  101280
cttaagccat gttttcatat taaaacacaa agtaaaaaat cattgttttc caaagataaa  101340
agccatactg tatcatgaca tatatatgcc cgatgtttcg accctcttga agaattgaga  101400
ttctcgactc tacactctta gcgttttcta tattgaacag atgtttaatt taaggaggtc  101460
aagagaaatc ttacacttat ttttttaatgg taccttagac atagaaggaa cctcagaaat  101520
ctctggctga atatttccat ctgcagatga tcatgtcatt aggcttctga ctctatagcc  101580
atagaaaaat attcatgaag accttttcagg aagggaatgt tggtatttct aaaaattgag  101640
tacaagtatt ctctagacaa aacagctctt gaaatggcag attgtattcc cattattata  101700
tttcagaatc aagacattaa tacctacttt ttatttacca ggtttagtta tccttgaatt  101760 agatttttata aattaaagaa atagatttca ataaatattt gttgagttcc tagtatggaa  101820
acatcgtgtt tggcaccagg gatgttgcct gcaagtataa caggagttcg tatttgtaat  101880
gagtttatga tttacagata tttgggggggc aaagatatca ttcggtaaat acttatgagt  101940
gcaaactttg aactagggac tgggccaaac tctaggaaca tatttgatga cagagacaca  102000
```

```
atccctgtcc tcaaggagct ttcattctag tagagaagat gaaaaccagt acagtttggt   102060
aagttagatg atattggtta atgtagggtt cttatgtaag tctagagaag tagcatttaa   102120
tctgttctta gaaggtcagg aaagatttcc ctggaggaag tgacatttaa gctgagagag   102180
gatggataaa caggagtcat ctgagtgaac aacaggaga acattccaga aagagaacaa    102240
aatgtacgag gcctgatgcc aagagagaac attcattgca ttggggaact atagtcactt   102300
ctgtgtggct gggatgtaga atgaaatgag cctggaccca agagagcact ttgccctttg   102360
gggaagctgt aggtattaca gtaaggttgg agtctggaaa gaaagggta tattgtgaga    102420 tctgaattgg gagaggacag ttatatccag acctttatat gctccagtaa aagagactgaa  102480 ctttacactg ggggccatgg gactcactga atggcattaa atttgagagt ggtcatatga   102540
ccagatttgc atttacaaa gattgtcatt gactgcaaca tgaagtatgg agtattggag     102600
gagcggtaag gctggtggca gggagataat ttaggaggct ttaggtgagg gatgataatg    102660
acttgccagg taggaaggag taaatttctt ctcagtggat aattagaaga ttgaatggat   102720
ggacttggtc actatttggt atagaagggg aaaaagatg tcaaagatga tgccaatttt    102780
taaaaataat ttaacattta ttttttaaata ttttttcagc cttattaagg tataatggac   102840
aacaattgta ggtatatgtc atttacaaca tgatgttttg atttatgtat acattgtgaa   102900
atgactgcca tagtcaagct cattaacata tccatcactc acataattaa cattttgtgt   102960
gtatgcagtg agaacatcag gctctactct cttagcaatt ttcaagtata gattacattt   103020
gttaccaact atagtggcca cactatacaa tagagctcca ggacttattc atcctgccta   103080
actaaaactt tgtactcttt gaccaacatc ttcccattcg tctctcctcc ccatgccaag   103140
tttccatctt ggtcagttgg gtggatagta gtactatctg ccgaggcagg ttggtagggt   103200
gaaaacaatg tgttcccttt tggaaatgct gaggtgacca gggaacttcc aagggaatct   103260
gtctggatct agagcttaga agagatgttt gggctggaaa cagacatcag gtattcttca   103320
gtatatgggt tgtaaatgaa gtcacaggag tgggtgatat caccaatggt gagtgtagta   103380
taagaagact ggactgagga cagatttcca aggaatttca atacttaaga ggtacgcaga   103440
gaaaagaggg gctgtgaagg acaccaagga ggagactaag agccaggagg gaaaactttc   103500
aagagagtat tgcattatgg aagggaagaa gagagaacat tttaaatgat acgcaatgct   103560
caataatggt atccgctttg gagaggccaa gtaagattcc taagtaccca ttggatcaag   103620
gtccttaatc ttacaaaaac ttatgcaaat caataataaa gagatgataa cccgataatc   103680
aaaaatagac aaggcatata agaagaaaat gaattaaaaa tattcaaagc attcaacata   103740
tacaaatgcg ctcaatctga tatataatga agaaaagta aattaaaaca acaatgggca   103800
tgactaaata acagtatgag ggagcctgag gagaaggagc atttgaaatt tcagtacaga   103860
agagaaaagg ggtgacttat agaaaaagga gacagaaacc atagaacatg tttggaggat   103920
aagactcaaa caggtagtgg ggacccttt ctagagtagg atgaaaacag gtaatgtgtg    103980
tggatgcaaa tatgaggtag gatgtaatgg gaagttgagc gaattcatat ttagtcattc   104040
attcaaaaat acttaattga gttactgctg tgtggcaagc atcattctac aaacagaggg   104100
cacagtgata agcaagccag tttgtactct cgtgtaactt acattctact ttgagaagac   104160
agattataaa taggttaaaa agtcaataat atgatgtttc agcatcaaca ataaaaatt    104220 agggtgatat atagagtgcc agggaaagtg cttttcatgga cctcttcatt ctctcctctc   104280
ctggtgtcat aagctactcc ttcatccatg ctgccatttc tcttggttta cggttccagt   104340
atagtactca tcacattatt actatagagc catccacctt atgaaggtga aggtgtccat   104400
```

```
ctccttactt aaaaaaaaaa aaaacaaaca aaaaaacaaa aaacccgaaa aacaaaaaaa  104460
gaggcagaaa gacagaaggt cctccactaa ctttcacgtg ccatgtaacc agcgaaatcc  104520
aattatttta cagcattcta gctatagaag agtttgggaa gcgtagtgct tagtgttcta  104580
gcctttgtag cacaggaaag ggcctggaag gaaaggaatt gtgtcttccg cagttgcttt  104640
tctttatggg gaagtgctat agcccaaaca atattttagg aattttcatc tattgtcaat  104700
atgcaaactg gaagggggata atgaaaatgt tgtggttaga agtttatgaa atattgttat  104760 tcacattttta aagtaaaaag agggaatgtt taagagactt gtttaagatc acatgtctca  104820
taattggtgg gaccagcaat acaatccaaa tctaactact tatcttttttg ctatgcccta  104880 ttagtgttca tattagaaaa gaaattctat ctcagacact aatgatttgt tctttggaca  104940
ccaatgactt taagttaaaa cttcatacta gttaatttaa ttatggtgta gcagtattat  105000
taaactatca agactataaa ttttctattt gtaaaggaga ttatgatacc aaagattagt  105060
gaactaatga tattgagaat tctatgacat aattttgaaa aatatttgca ggatatttat  105120
ttttgtgtaa atgatgcttt caagctacca taatcctaag taagtgtata tttgggaaaa  105180
ccacctattc taacacactt gaaatttaaa taagtcagga aattttttttc cagatcttct  105240 cccaaattat cttcatcttt ttcctctccc cttgggaaag aatctcttca tgcctcataa  105300
tatcaaattt aaactatgga agtccaggtg gtggacagtc agcaaggggg aagatgagaa  105360
gcttgtgtta taaagccagc tcttgtcaga ataaggatct ggtaggaact tcagaagtga  105420
tgggtaggta agtatgaagg ccaggtccta agatctaaat tacaaagcag aagacttact  105480
taccagggag ctggaaaaca tgttaggaaa tccagagcag gaacagattt caagatagca  105540
caataatata gcagtgaagt actgagaaaa gagttttttt cacgggttgg atttattcta  105600 gcatttttagg cagcatttgg gcatttctaa gtggtcagac ttagaggaga tagttaagga  105660
attagcagct gctaaatgcc aattcttaga ccagttgaat caaaatcatc taaaaagctt  105720
tcagaaacca gactttttaa gggccatttg agagactctc aaatctggaa tccagaaatc  105780
tatagctaga tgagtttaag gtagagccag aataagaaaa ataaaatagt ttgtttgttt  105840
caggtatctt ttccaatatt atttccgaac ctaccccaaa caccttaaat cactgcattc  105900
tatagccatt ctttttaaaaa tgcttgagtt attagttttc aaaaacaaat acaaatctgc  105960
acacatacag aaataaacat taaagagaca taaagatatt aaacagagtt acatatactt  106020
acaacttcat acatatatat tatatataaa actgaatatt aagtgtttga tattagtgac  106080
aaaatctgta acatccatta tattagtgct tttttgtactt tttgttgggt gtagtaaaaa  106140
ttgcattcga atttgagttt tctgctatat atttggtcag ttcctatcag tgaaggaaaa  106200 acctttttttt attatttttat tgttttttta tttttttgaga cggagtcctg ctctgttgtc  106260
caggctggag tgcagtggca tgatcttggc tcactccaac ctctgcctcc cgggttcaag  106320
cgattctcct gcctcagcct cctgagtagc tgggactaca ggcacctgcc accaggtcca  106380
gctaattttt gtattttttag tagaaatggg gtttttgccat gttggccaag ttggtctgga  106440
actcctgacc tcaggtgatc tgcctggctt ggcctcccaa agtgctggaa ttacaggtgt  106500
aagtcaccac gcctggcccc ttttttatttt taagctgat tgaagattct tagttctcat  106560
gctttctagt ggtgattaat ctttagccaa tatttctata tacagttatt agtaatcatg  106620
tttgacttag gtcaacaaac aatctttcct aaaaaaacag aaccccaatt ttaatttctg  106680
aattatttag tatctatttt ctgctgtgga agttgaatta tgttgataga tatcatacag  106740
```

```
ggccatgtaa cactctcaga tacacgttca catgtatagt agctgtatac aaaaatgtta  106800
cttcattctc tctctcttta taatactctt ggctctctta cgttctctca cacactctac  106860
tcttcccttc ctctgttctt tctacttgtt ccctctgctc ctaccacact tattccccccc 106920 ttgtccattt tccttgtgca taaagcacaa gtgcttagta attatcaaat attaataaca  106980
atgacactaa ccacccaatg atttagtgtt aatgacatgc tttattgaat ggcattacct  107040
ctaaagttca tgtttccttt acccaaccaa gcttcttacc ctcctccctt accacaagca  107100
tctatattgt caaggttgtt ataaagagta ataagccagc cattaaaaaa gggtttatgg  107160
tattttccta tctacaaagt cacaggaagc tcaaatgtac tcagtaaata ttgcaaaatt  107220
acacaggacc attaaatgta acactccacc ctttctctct ctctctctct ctcttgctct  107280
ctctctctct ttctgtcaat atagcaacac cctatatcat tgccctttgt atgtgcaaat  107340
cagagttaat aagctttata ttagcaatta ctccttaaca acttctggtt tgtttggtcc  107400
agttgaataa tgtaagcact taaaaaaatg aaattataaa catttatgtg aaaagtgcat  107460
atatcacatt ggatatgttg ttatgcactc cttaataata aagtaagtta atctttattg  107520
cacacttatt ataatattac tttgaccctc tctagtactc tttatctaag tattctcaag  107580
tgctttacaa tctcaaacag acccaatgtg ttgtatacac agaatccttt gaagctgaca  107640
tttgcctttc tgaccagctt gttgtaaagg aaatcagcca aaaacaagt atctagatga   107700 gtagctcaaa cattagtaca catagtaatc acaggtcaaa atgcagatag attaccctgt  107760
ccaaattctc ctgagtaaga gtaggtgaaa cattttttaaa taagctcccc aggtgattct 107820
gaaattggtc caaggaccac atattaagaa ctaatgatcc aaacaatttg acttttttatt 107880 gtagattaaa ccatgctgag aaaattatta aaaattgaaa tggcagtgga ggatggtttg  107940
aaagaaaggt ttttcagggc cctttcaaca ataaaattaa ttgaacacaa tattaaaact  108000
ctatatttga tttaagacta aggttttcat tgttttttaaa tctcagtaat ttttatgtaa  108060
caggtcaatt catacccagc atcttaattc caatgaatga tttcccacaa caattttgt   108120 ggataactcc aagggaactc gaaggaagtt gtagtatgaa caaagagaag tagaatttgt  108180
ccctgtgtgt aaggcttctc tgataagcag cacaggctct catactgctt tttaaaaaaa  108240
ttatgatagc atcaagtgga attaatttt tttagattat actttcatgg aagggaagat   108300
ctactgtgaa ggctggaaaa ccaacaccct taagataaat atattaccag atttgagcgc  108360
tcttagtaat cagcaaagat aaatgtttaa cagtgcatac aaaatgaagt gttttatgtt  108420
aaatcaaata gagaaagcca aacactaata atgtggttac aaatgaacaa taaattaggt  108480
aatcagaaca ggtacagaca ttaatagcag gatattggta ttattaatgt attttgtttt  108540
aaaataatga acttaattac aattctcctc atcctacccc actatttat tttattccag   108600 attcagcagc ttcatattat gtctctgaaa cacttattat taaagttatc caaatgtaca  108660
catttctctt tatataaatg tttcagtcca gaaaaggagg ccaaatacat tagctcagaa  108720
catcaaatct tctcagatgt gggaatcttt tattttcaca ctttaaagg taatctgtat   108780 ttctagcgtc tattatagac agaaaacttt catatgacaa cattcctatt ttcttaactg  108840
ccttgatagg ggcgaagaca aattctaagt aggactttt accccattct tcttaccatc   108900
attctttcac aaaaccccca gctttagaca atcgctatta tgaatttgac atgtactatt  108960
ccaatccatt cccataaaatt tacacccata tatacatata gttatctatg aacaatattt  109020
agtagctttt ttgtgtgtgg ctttaaaatt tacataaatt gtataatttg tgcacattct  109080
tctttaattt gccttcttgg ctacggttat cttttttgaga tctagctatg ctgctggtat  109140
```

```
gtagaattct atttcattct tttttcattg ttgttttgta cccataacgt gtcacatttt    109200
atttatacct tctgttcctg atggacattt agattcttcc aggattttac tcaatactgc    109260
aatgaaaatc tttgaatttt tctcttttgc acatattcaa gagactttc tgacatatat     109320 atctataggt gaattgtgta gtcatatgat acatacacac atttaaatt tcactagata     109380 ctgccaattt gcccttgaa atagccatac aatttatagt accaccagcc acttatgaaa     109440
gttcccattt cctcaaatct ttgaaagttc ttattataaa cagacatatt aattcttgcc    109500
attctgattt gtaaatcaga atctctattg ttctacctct agttctaatt tggaattccc    109560
caattacttg taagatgcta tatttca tgtttgttag tcattctgat ttcatatcct       109620
ttaccaatta tcttttggt aagttattgt ggtggccatg agatgtgcct tacagaggcc     109680
ttgctagagg gaatgtgatt gaatgagagc cccagatgct gtgtattaaa atcctgcact    109740
gagtttgtct caagatttct tgcacgtgaa tgaatgagta cagctgggat actaaagcag    109800
atgtgtattt gggagatatg agacttcttt agtggctgat ttttggctca taaatgactt    109860
tgccaaacct tccttagact gctcagtgtt ctaacatctt ccatccagcc ttctacccttt   109920 cttcctta ctaggggat gaatttacat tgaggtctca tagccttctc tgcctctctc      109980
cttatttcct tttatacaaa tatttcccct aataaatcca tgcacattta ataccatttt    110040
gctatttgca acctgcaggt cctggactaa cacagttcta tacattgcat taccattctc    110100
tagagtggga tcttttgttg tagagagttt taaaattttt atgtagtcac ttttatccat    110160
attttctttt atggtttata tttttgtgtc ttctctttaa cacatctttt ctagcagaat    110220
tcataaatat attattctat attgccaaaa gtttgaaagt tgcaatcatt agaattaatt    110280
tttgtatatt gtgtaagtta agaatctaat tttattgttt ttcattggaa agccatttgt    110340
cccaagataa ttttttagta gtccctcctt cccctattgt cattctgaca tatttttct     110400 aggttccgat ctatgcatgt gtttctttat ggaagagttg gccctttgta tctttgagtt    110460
tcaaatccat ggattcaatc aaccacagat agaaaatatt tagaaaagcg tcagaattga    110520
acatgtacat acattttgct tgtcattatt ccctaaacaa tatagtataa caactattta    110580
tgtaggattt acattgtatt aggtattgta agtaatctag atgatttta aagtatacag     110640 gaagatgtgc atatgttaca tgcaaatact accccattta tataagggtc ttgagcattc    110700
atggattttg gtatccacag agagtcctgg aaccaattcc ccacagatgc caaggcacaa    110760
ctgtatttat tctatcatct acttgtttaa tctcacatca gtatctactt ttgaaataac    110820
aataacttta ttatttaact tttttattta cttaggatta gagaatttcc tctggtgagg    110880
catcatagtg tctcaagctg gccataaaga caagtgaggg ctaggatcgg taagactggg    110940
cagaggaaga tacaacagat ctcctatgca tgaagcaaaa gtgcagctca gaagccagct    111000
ctttcattaa gttgtcctct ataccctcac tagattgtaa gctcttgaaa tgagaggcta    111060
taccttaatt gtctctgtta tctaaaatac ttccactcac tgcttggaac atattgcctg    111120
caataattaa gcttgccctg gctcccaaag catagagcaa atcacactcc tccccttgcc    111180
tttgagaagc tcacagtctt cgaaggtaga gatatgtgaa cagataagaa aatggatgac    111240
aggagaacag aaacgcatga ctgtcagaga agtcattgga gactttacag aggaaattaa    111300
atttttattg atcttgaaag agtttgccag atgaagtaga ggacaggcat tttagacaaa    111360
gggaacagga aatgtgaaaa cacaaagtga tggaagtcat ggtgagtttg gagaactata    111420
aaacttcaat gtggctgaag ggtaaggtgg atatagagga gtgctgggag gtgaggctga    111480
```

```
agaaataagc taggaaatgt cttttatgc cattttttaa agtttggact ttattctgaa    111540
gttcacatgg atccaatatt ttttgttttg tgttgtttta agcagaagcg tgacatgatc    111600
agcttgaatg atgaacaact tgaattgttt aaagtggatc acacagtcta ctgttttaca    111660
gttattcttt gaccaagata ttctttatta actgaggaaa aaaagggctt tcctgaattt    111720
tgcagtcatg ggatatatga taagcattct tgatttatca tcttcaatcc tgttacataa    111780
cataataacc attgttatta cctttagcaa tgctttcctc agtattatct aatggcctat    111840
aaaatgtgac tttcatttgc aaatacagta catctaacaa gaacttacca cagctgctat    111900
gcaaaatacc aatacaattg acccttggac aatgtggggg ttaggggtgc tgattcccca    111960
tgcagttgaa catgttacat aacataatac ataaccattg ttattatgta acaggattga    112020
aaatgataaa tctttggaaa gtggggcaaa tgaattctta tgaattccat atcttccaca    112080
tgtgttttac ttttttgata agaagtagta acctagttca gaaagaaaat aatcatcccc    112140
ttttacttat gcaggatacc aagtctatct tagcaccata atagtgaatg ataggaatca    112200
agctctatga atacattcac atgtacatat atatggctat ataggacaca tgcatgcaca    112260
tatacatata tacacttgca tatatgtgta tatacatgta catatatgca tgtatattca    112320
attgtatatg tgtatatagc caagttattg tacagttgac ctttgaacaa cacgggtttg    112380
aactatgcag gtccacttac acgtattttt ttttccgtt tctgacaccc ctaaggcaac    112440
aaggccaact cctcccttg ctcttcctcc tcagctgact caacatgaaa actatgagga    112500
cgaagacctt tatgaagatt cacctccact taatgaatag tacatacatt tcttttttccc    112560
catggttttc ttaataacat tttcttttct ctagcttgct ttattgtaat aatatagtat    112620
ataatacata taacatacca agtatgtgtt aattgactgc ttatgttatc agtaaggctt    112680
ctggtcaaca gtagactatt gctagttaag tttctggtag ttacaagtta tatgtgggtg    112740
ttcgactgca tggggagtca gcaccccaac cctcatgttg tccaagggcg ttgtccaagg    112800
gtcagttgta attggtattt tggatagcag ctgtggtaaa ttctggttag atgtactata    112860
tttataaatg aaactcacat tttataggcc attaaatatt attgaggaga gcatttctaa    112920
gggtaaaatc ttgtctaatg cttgaaacat cttcattttc ctgtcagttt agatcttttt    112980
gaagtaattc tgaaaatctc tcttttaagc taaatttaac acaaccaaat agccaaatat    113040
ttaagttcca ctaatgaaga tatctaaatt tctgttaaaa atttaagata tatgttaaac    113100
ccttctaata taactcttct ctcagtcaaa ctttttttt taacagttgc tttgcttctt    113160
ctttcaaagt catacttcaa caaagttgct attgaatatg tctgactaaa catgttagct    113220
atatgataag atggctggat aagagataaa tatagaaaat gtagcttttt ttctacttgc    113280
aataacccttt aggaattaa aatggaaaac taataactat ttgattcata atagtagcaa    113340
accgtaaaat atttagacat aaatctacta agaaatttat aagacatata tggagaaaat    113400
tcaattgaat aaaccgttat tgaagtatat aaaataagat ctggatgaat agaaagatca    113460
taattttaa taaattttg catcttaaaa agtgaaccct ctccaaatat atgcacattt    113520
aataaaatta taaatacatc ccaatgaggt tggttttgaa attttgttaa ttggaactta    113580
aatttcacct aagaagaaaa aataaagaat agttaagagt gcatgctttg tagacaaatt    113640
gccttagtta gaatcctggc tctatcatct attagctatg ttatctttgg gataacattc    113700
atctttttctt atagatatgc ttaaaacagt gcctgacata tagtaagcac aaatatccat    113760
tagctattct tcttattatt tatgttatta gtattgttaa tatttgttat tatatggaag    113820
actaaatgac caaagagagt caagaaattt atgaataaga tttatgcgtt gttagatatt    113880
```

```
agagccatta aaaaaaaaaa aaccaaagtg ccaaaaaacc tagcacagtg ttaatacagg    113940
aataaaaaaa tggatcagag gaaccaaaca gaaaagccag aaatggatct taggaaacat    114000
gagaatatga tatatgatag atgctaaatg aattcagtat aaaaatatta atgtaataaa    114060
tcatgcttgc tattcaagta aaagaaaatg aggttagatt catgtctcat accaaatata    114120
accataaatt ataccttgat taaatttttt aattaaaaag caataatatt tgaaagaaa     114180 tataggatac tcaatgtata acctgaaggt tgggtagtac ttttcaacaa atataggaat    114240
ttttcacttg aaatactaga agaaaaaaag atagcaaaca aatacaggaa ttccaatttc    114300
aagcagatat aatgatttca tgaaatgtta actgtgcaca tgatagatgg tctatggata    114360
gtgcaaaaga aaagagaaa  agaaaaaatg ttttttaaca tatgcagcaa aaaaggtttt    114420
taacatctat tacatacaaa taaaaatgaa tgtataacac agacttcaat aaaaatag gc   114480 atttcacagg agaacaattc agatggccag tatttacaat ttcataggta ttaaggaaaa    114540
tacaaattaa aatggcaaat tagcaaaaat tgaggtgtga ttatattaat atctgttggt    114600
ggtggtgatt atggggaaaa gggtactttc aaaacttgct aatataaata taattctttt    114660
ggttgttttg taaggaacc  tgacaatatc ttttaaaaat aaagaaaacg catacttttg    114720
acctagccat cccattcatg agggtatgtc ttagaaaaat aagatcacaa aatcatagag    114780
atttatgtgc aatgatatta ttggtaggtc attttttatga ggaggggtgt ggatagtaaa   114840
tgccagggta aatcacatag catctaataa acgtatttat gaactacaaa agcttacact    114900
ttcagtctag tctagtccag actgcaaata aatgtgagca agtgaattca agcacagaag    114960
tgcttgaagg caggtttcat aaatctactt tcttacagta tcctgatatt gacttatcga    115020
gacagttact gtggggttga ttattaaaat atttatgtat ctaggtattt ttcattcagt    115080
agtatgttat tcaattagca acaagtgtgg ggatttaaag atattcttgt ttgttttta    115140 tgctgaaaca tattctagtg gaaatttcga ataaacgatt agtcatccta aaagcaagat    115200
acattttctc agaaaagaca aggtaaagaa cttgtatatc ctccctcaat tcgtttataa    115260
ggtaataaga tgaataaaaa tatcatagta caatttagca ttgtaaaata aaattaattg    115320
gtcatctcta gtgtggtcgt gcttggaagg tgaaagaagc caagatcttg tctgggaata    115380
tcatgtctac cttgacctca cccttaagaa tcctagcctt tagtttaaaa tcacatggct    115440
acatacatac caacttcaac aatagtacat ctggcaaggt catgcaaacc tgggacttga    115500
gcttctgatt ctaagtccag tgcttttgt  gtacatcatc tcttgtacat accttatgat    115560
gatatgctaa taaaagctac gtgatcaggc cttaaaaatc tgcttttttt ttgtaatggt    115620
agaatggggc atattatcac atcaggtaaa cactctattc aaggataaat ggaaatgaat    115680
gtcatatata gatcattgat aaatatctca ttacaaaatt atgagagtta ccaatgtttg    115740
agtgtatatt atgggccagc cctttatatt aaattacttc aaattttttac aactgttaaa    115800 ggaagatatt attatacccca tttttatagat ggacaagtta gggccagaaa agacttcctc   115860
aaagctgtta gtccagtaat ggagacaggg ctagaaaaca ggtcattttg ctctttgact    115920
aatgttacta ctcatgtttt gtattttgtt taaagttta ttttattttg ctttatttat     115980 ttttgagac  aagatcttac tctgtcaccc aggctggagt gcaatggagt gatcacggtt    116040
cattgcagcc ttgacctcct gggctcaagc gatcctccca cctctcaatc tccagagtag    116100
ctaggactac tacaggtgtg tgccaccata cctggctaaa ttttgcattt tttgtgggga    116160
cagggtttca ctatgttgcc caggctggtc ttgaactcct gggctccagc gattcacctg    116220
```

```
ccttgacctc ccaaagtgcc agtatcacag gcttgagcca ccatgtccag ccaagtttta    116280
ttttagaatt aaaaaaaatt ccacttggat tgttacattt tatctcattg ctttatattt    116340
atagaattac tttataaatg ccactttctt aattttcata gttagcactc tttatgaaac    116400
ataaactatt atttgaccca ggttttttgtt agaggaattg agtcagagag ctgttaagta    116460
actgagattt cacaataagc cagacagacc agggttcaaa ttctgggtct cacattatcc    116520
aattcaatat tccagctttg ttacttattg agcaaccact acaagcacag tttacatgac    116580
atctgatagc tctcaaaatg aatttttacaa acataattca gatttcaact cagcagtgac    116640
tcaggagaaa ggacacttgg atgcatttct ttatggcatt tttcccaggg tacacgcaac    116700
ctggaagatc tcccaagtat gggggaaggt ttcaccctga ggaatcccat tccctctaat    116760
ctgggacaag ggggaggaga gtactgtctc ttatcagcca tctccccagg gaggcctggg    116820
ccctcctgga atgcatacca tggcttactg actcaaagtg ttgaaaagac caggcattgg    116880
gacacacaac actactctta aaataaaaaa agaatcagag tagcttgtgg ttataattga    116940
aatggacaga gtaacatggt accaagaaac tattagcaat tccttcccta aatccctcat    117000
tttcttaaag cattttctcc ttttcctcaa caagctttaa gttggatttg aagaatgata    117060
agactaaaag gagggctgtt tctggtcttt ggaggaattt gatattccat tcgatctgag    117120
tgtgcaaagc ctgagttcac atgaactctt ctgatctctt tctctaatat tttttcacct    117180
tattcatatg ggaagaagg aggggaatac tttagttcca ttctccctcc tcctatttcc    117240
ttgacttgtt taaaatataa atgttataga cacctaagat agaaatttga ctgaaacagc    117300
ctcttaatta ttgtcttaaa aaattggtat aatgaaattg catttgtagt ctttggacat    117360
ttaaatccag aagggatatt ttcttttttct tttttaaaaa tttaattcaa tagttttttgg    117420 gctacaggtg gtttttggtt acatggataa gtgctttagt ggtgatttct gagattttga    117480 tatcccatc acctgagcag tgtgcactgt acccaatatg tagtcttttta tcccccccccc    117540 gctccaccct tcctttatcg tccccaaagc acattatata attattatgc ctttgcagcc    117600
tcattggtta gctcccactt gtaagtgaga acatgcgata tttggttttc cattcctgag    117660
ttacttcatt tagaataaat tgtctctagc tccattcaag ttgctgcaaa ggccattatt    117720
tcattccgtt ttttggctga atagtattcc atagtgtata tatgccacat tttctttatc    117780
cacttgttga ttgataggca tttaggttgg acccatattt tcgcaattat gaattgtact    117840
gctgtaaaca tgagtgtgct ttttttttttt ccatataatg acttcttttc ctttgggtag    117900
atacccagca gtgggactgc tggatcgaat ggtagttctc cttttagttc tttaaggaat    117960
ctccatactg ttttccacag tggttgtact agtttacaac cccaccagca gtgtaaaact    118020
gttccatttt cagcacatcc atgccaacat ctattatttt ttgactttttt aattgtggct    118080 attcttgcag gagtaagatg gtatctcatt gtggttttaa tttgcatttc cctgataatc    118140
agtgatgttg agcattttttt cctgtgtttg ttatttgttt gtatatcttg agaattatct    118200
attctgtcct ttgcccactt tttgatggaa ttatttgttt tttttcttg ctgatttgtt    118260 tgagttcctt gtagatcctg gatactagtc ctttatcgga tgcatagttt atgaatattc    118320
tttcccactc tgtaggttgt ctgttaccca tgctaattat ttatttgct gtgcaaaagc    118380 ttttcagttt aattatttcc catctatttta ttttttgtttc tgttttattt gcttttggga    118440
tcttagtcat gaactttta cctaaaccaa tgactataag agtttttcca atgttatctt    118500
ctagaatgct tatgttttct ggtcttagat ttaagtctttt gattcatctt gagttaattt    118560
ttgtataagg tgagcattga ggatccagtt tcattcttct acgtgtggct tgccagtttt    118620
```

```
cccagcacca tttattagat agggtatcct gtccccactt tatgttttg tatgctttgt     118680 caaagatcag ttgactttaa gtatttggct ttatttctgg gttctctatt ctgttccatt    118740
gtctacttgc ctatttgtgt accagtacca ggctgtttta gtaactatag ccttgtagta    118800
taatttgaag tcgggtaata tgatgcctcc agatttgttc tttttgctta gtattccttt    118860
agctatgtgg gctcttttt agttccctat gaattttagg atttttttct agttctgtga     118920
agaattatga tgatattttg atgggaattg tattgaattt gtagattgct tttggcagta    118980
tggtcatttt catagtattg attctaccca tccatgagca tgggatgtgt ttccatttgt    119040
ttgtgtcacc tgtgatttct ttgagcagca ttttgtagtt ttccttgtag agatctttaa    119100
cctccttggt taagtatatt ttcatgtatt ttagttttt tttttgttt gttttgtttt     119160 gttttgtttt gttttgcag ctgttgtaaa agggattgag ttcttgattt gattctcagc     119220
ttggttgttg tcagcaggga cattttctaa agtatagact gtagttcctt atcttctatc    119280
tgtttcttac tgtccccttc agtattcttg tccttttttc ccgctattat cttttgacc     119340 ttttaatata tagatatcta cttctacttc tgacaatttt tgcttctcca attttcttc     119400 tttttctcct ctgcacacat ttatttattt tcttctatgt acttcttat ttttaactta     119460 atatttgatt aacttccctt ccctgtctct tttccttctt tccataaatc ttcattaatt    119520
gcctgcactg agctaggatt ctatactctc taaatcaata atctattttc tatagtcaac    119580
tgtgttataa tcgtactgtc aagataacta cttatttta atacttaaaa atattttgaa     119640
attttaacca atttaattaa tacaatgttg agttcaaatt tgaaaaaaac aatggaaaac    119700
tgtaataatt ctagcaacct cctgctttt aataatgtat tagaaaattt gcctctttt      119760 caaaagccta cagtgaatct attcatacaa ggcaaaagca aaccattctc ttcattctct    119820
ttttttctcc aaaagattta agtgtttttt gtttgtttgt tttgttttgt tttttagata    119880
ttgagtcttg ctctgtcatc caggctgcag tgcagtggtg tgatcatagc tcgctatagc    119940
ctcgaattcc tgggttcaag caatcctcct ccctcaccct cctgagtagc tgggctaca     120000 ggtgcatgct accatgccca gctaatttaa aaggaaaaaa attgtgtaga gatgggtctt    120060
gctatgttgc ccaggctggt ctcaaacttc caatctcaag catttctccc acccagcatc    120120
ctgaagtgct gagattataa gtgagccact atgcccaacc agatttagtt tttaaaaga     120180 gaatacgatt tgaaaaagga aaatgtgag gcaggagaga agaaatacac acgagctg       120240 ttttgtaatt gctgtaaaac tgaaatcttc agcctcacta aaggagcact tgcatgaaca    120300
cctctaaatt accttattac cttctaaatt aggtgtgaag tctaacttct aaattatgag    120360
tgaaatccac tgcaattctt gttatttgga tggaatccta ggtatgtggt ccagttcatg    120420
agttgaacaa aagcatgctc atttaggcca ggtagaaaga aataaagacc tatgttttac    120480
atgtctcata accactgaag gtccttctca taagcagtgc ttatgggtat taacgacctc    120540
tctatatttt acttctccag tgcctaagta gccgagtcca ctgagtcctg ctacatctcc    120600
tccaacatgt cagcattttt ttcacaggcc ttttgttact ctagatcaga aatgttgata    120660
gcaacagttc cttgagggca gcagctagca tgatgccagc caacaggaac caccaaatgg    120720
ttcttaatat aaaattactac ttattaatct atttactttg tgcatttgga gttttgcatg   120780
taaagtccta tttatgtcca tatggtagat aaatggaaca aatgaataac agaagtaacc    120840
attttgatac tttagatata gataatattg gattatttct ggattgtgaa agaagaagga    120900
agaagcatat ggaagagaag ttttagtaga ggggaggaag gaggaggtgg aaacgaatgt    120960
```

```
acaaggatgg gaggagaaaa gggagagaga cttttttttt tttaaggcga gagtttacta    121020
cctatctaac tcttcgcatt cttgaagtct cagaccaaat cccatcggtt tgaaagcctc    121080
tagggtattc tatctattgt atacttctgt tatgtacaaa attaatttgc caattaattg    121140
tgaactgttt tataaactat cttaaaatgg ttagttaaat ctttgggata gtatttagct    121200
ttctccagga ttatgactta ccttctaaat tagacataca atgcctagga gtcaaggact    121260
attttgcata aattccagtc ttcttttaca atgcctagaa tgattgttac cacagaaata    121320
ttcattacct gggagaaagg atgacaggag gggcagaatg aatggagaga ggtcgtgaga    121380
atgaggtgct gaggatggac gaggaagaaa gctgttttag ttgggaggat aggtgacaga    121440
agcatggaaa ggaattgcct tggacccatg gaagcccagt gaagatactt agatcctgca    121500
ggggtgtgaa taatgttctt ttagtttctc ttcttaggag gtttgttcat tttgggagat    121560
ttcttttgaa aagagtgaac ttaaattgga gaaaagtaca ttttagtatg ttgataacat    121620
ttgaatttgt aaaatggacc tatggatgat ctacacatat ttatataccc ataaatatac    121680 acatattta attttggta ttttataatt attatttaat gatcattcat gacattttaa    121740
aaattacaga aaaatttaca tctaaaattt cagcaatgtt gttttttgacc aactaaataa    121800 attgcatttg aaataatgga gatgcaatgt tcaaaatttc aactgtggtt aaagcaatag    121860
tgtgatatat gattacatta aaggaagat gtgcctttca aattcagatt gagcatacta    121920
aaagtgactc tctaattttc tattttggt aataggacat ctccaagttt gcagagaaag    121980
acaatatagt tcttggagaa ggtggaatca cactgagtgg aggtcaacga gcaagaattt    122040
ctttagcaag gtgaataact aattattggt ctagcaagca tttgctgtaa atgtcattca    122100
tgtaaaaaaa ttacagacat ttctctattg ctttatattc tgtttctgga attgaaaaaa    122160
tcctggggtt ttatggctag tgggttaaga atcacattta agaactataa ataatggtat    122220
agtatccaga tttggtagag attatggtta ctcagaatct gtgcccgtat cttggtgtca    122280
gtgtatttgt ttgcctcata gtatagttta ctacaaatgg aaaactctag gattctgcat    122340
aatactggac agagaagatg taaatatctg ttagttccat catagaccct gccactccaa    122400
tgtacacacc agctttaggc ttcttggtat agataaacat acattttcaa aattttcat    122460 cataattttc ataacaaaat aggaaggcaa atgatgtcac ttggcttaaa atctataata    122520
tttaaaataa acaggacaaa tgcattaaca ttgttggggg aggaggtccc ttagtagaaa    122580
cactcttggt ccaagcattt taaagctgtc aaagagatgt aaatatagat aatgtatgtc    122640
aaggagagag ctttgtggtt aaactgtaac tttcagtta acaattatt ggtgactctg    122700 atgtcaaatg tttctcaagc tttatctgaa caaaattctt ctcactttgt tgccaaagtc    122760
gttaacaaga aatcacattg actcattgat gttttggctc cttccctta ctttctgttg    122820 ctttccaaaa gctgagacag gaaactaacc ctaactgagc acctgcaatt gcctggtagt    122880
attctagtca tgtgtgtact tttgtgtgta tgtaatcccc ttacagctct gcaaagtaag    122940
aattgttctc cctgctttac agaagagatc ataagataat tgaggctgtt agatgttaac    123000
ttgccaaaag ccatacagga aaatggtaga gtcacagttt gaaccaggtc cttttgattc    123060
tttacattaa accatgcttt gatcttggaa atacactgta aggcaataaa tcaatagata    123120
cggataattc acaggcttct aaataaatgg aagttgattg ttttatctg tgagccaaag    123180 taagacttat tctaagaatt ccacaaattt agataagata gagtatatgg cttctagaca    123240
tccaacatag aactgagttt gtgttatcag tttaagattt ggtttgctg taaggtgcac    123300 acactttgag gaactaaaaa taattgtctg ttcttattct gatcagaatg tgtaatgtgt    123360
```

```
tgtccagttt tggatgatga atttcttatt tctaatctca taagaaactt gtcatagatg  123420
tgagggagag aattaagaac agagtgtggg gaagaaactg tgtacatttt gatgggatcc  123480
attatgtagc tcttgcatac tgtcttcaaa aataagttac actataaagg ttgttttaga  123540
cttttaaagt tttgccattg ttttttaaaa aaattttaa attggcttta aaaatttctt  123600
aattgtgtgc tgaatacaat tttctttatt acagaagtac caacaattac atgtataaac  123660
agagaatcct atgtacttga gatataagta aggttactat caatcacacc tgaaaaattt  123720
aaatgttatg aagaaattat ctcatttcta ttaatatggg aactgtgtct tcatctttat  123780
tactgttcta aggtcaactc aatgtagatt ttacttgctt atggtttcat attttagcta  123840
aatagtaaaa taatatggat atacattttg ttgtgactta ctcatacttt ccttatttgg  123900
aacttttatg aatatgatat agagactgaa actacaagga acaaaatgca atatcaatta  123960
tacagttgtg gcagcactgc tatcaatttg ttgatagtgg ttaacactta gaaaaacatt  124020
ttaaaaataa tttcacataa gtaatgtaat ttattagctg tctctgacat tttacagttt  124080
ggaatagttt attttctttt tggtgtcctc accaaaaccc aacatcttca agggcaggaa  124140
ctgtataatt tttgccattg tatttttgagc acatagcatg gtacttgcct ctaaatagat  124200
actattgtta aaatatttt taaggtaata ttttaaagtg tatgctatgg tacagttcag  124260
tttgtgactt ttgctagttt atgccactta cagttagcaa aatcacttca gcagttcttg  124320
gaatgttgtg aaaagtgata aaaatcttct gcaacttatt cctttattcc tcatttaaaa  124380
taatctacca tagtaaaaac atgtataaaa gtgctacttc tgcaccactt ttgagaatag  124440
tgttatttca gtgaatcgat gtggtgacca tattgtaatg catgtagtga actgtttaag  124500
gcaaatcatc tacactagat gaccaggaaa tagagaggaa atgtaattta atttccatt  124560 tcttttaga gcagtataca aagatgctga tttgtattta ttagactctc cttttggata  124620
cctagatgtt ttaacagaaa aagaaatatt tgaaaggtat gttctttgaa taccttactt  124680
ataatgctca tgctaaaata aaagaaagac agactgtccc atcatagatt gcattttacc  124740
tcttgagaaa tatgttcacc attgttggta tggcagaatg tagcatggta ttaactcaaa  124800
tctgatctgc cctactgggc caggattcaa gattacttcc attaaaacct tttctcaccg  124860
cctcatgcta aaccagtttc tctcattgct atactgttat agcaattgct atctatgtag  124920
tttttgcagt atcattgcct tgtgatatat attactttaa ttattattat acttaacatt  124980
tttatttact ttttgtgtta gtattttatt ctgtcttctc cttagatagt aaccttctta  125040
agaaaatata tatgctaagt gttttactgg tttaatatgc ttagactact catctacctc  125100
aatacttcct tggagatctc ctcctcagtc acacagagct caggacttat atttccttgg  125160
aactcctgtt agggtccaat gtacatgaaa ttccctagac agacagacag tcagttatat  125220
ggcttgattt caaagtttca aaatgattta atggactatc aagtagttta ttaggagaac  125280
agttattata ctcttctaaa aataaagact ttaagcaata aagatgtata tgtatataaa  125340
atggctgggt tattcctaga agtacctttc ttagaattta gttaaattta atatccaaga  125400
tactatcttt tcaaccctga gattgtgaaa agtaacttct atcaatataa actttactac  125460
atttgtattg tgttagtgtg ttacagtata atctagaaca atgtgtcttt ctatatgata  125520
tatgacattt taatgcctaa aaaaactgat atgtcttaga tgattctagt caggatttac  125580
ttctagaata gattaaaatt ctatttgagg agagtcaaat taattatcga attctcagtt  125640
gttattattg ctgtttttatt tttagtgaaa cagattagtc ttaatgtaaa cacttgagaa  125700
```

```
ataaattgat ggtcaaccta aaatgtaaaa aagaaattaa tagaaaattt aaagagcaac  125760
aaagctctga catttaaaag aaatgaagta caaatctcta gggaccttaa agatcatcta  125820
ataatttcct cattttctag ataaataaac tgagagaccc cgaggataaa tgatttgctc  125880
aaagtcaaat atctacttaa tataggaaat ttaatttcat tctcagtctg ttaacatgca  125940
acttttcaat atagcatgtt atttcatgct atcagaattc acaaggtacc aatttaatta  126000
ctacagagta cttatagaat catttaaaat ataataaaat tgtatgatag agattatatg  126060
caataaaaca ttaacaaaat gctaaaatac gagacatatt gcaataaagt atttataaaa  126120
ttgatattta tatgttttta tatcttaaag ctgtgtctgt aaactgatgg ctaacaaaac  126180
taggattttg gtcacttcta aaatggaaca tttaaagaaa gctgacaaaa tattaatttt  126240
gcatgaaggt agcagctatt tttatgggac atttttcagaa ctccaaaatc tacagccaga  126300
ctttagctca aaactcatgg gatgtgattc tttcgaccaa tttagtgcag aaagaagaaa  126360
ttcaatccta actgagacct tacaccgttt ctcattagaa ggagatgctc ctgtctcctg  126420
gacagaaaca aaaaaacaat cttttaaaca gactggagag tttggggaaa aaggaagaa  126480 ttctattctc aatccaatca actctatacg aaaattttcc attgtgcaaa agactccctt  126540
acaaatgaat ggcatcgaag aggattctga tgagccttta gagagaaggc tgtccttagt  126600
accagattct gagcagggag aggcgatact gcctcgcatc agcgtgatca gcactggccc  126660
cacgcttcag gcacgaagga ggcagtctgt cctgaacctg atgacacact cagttaacca  126720
aggtcagaac attcaccgaa agacaacagc atccacacga aaagtgtcac tggcccctca  126780
ggcaaacttg actgaactgg atatatattc aagaaggtta tctcaagaaa ctggcttgga  126840
aataagtgaa gaaattaacg aagaagactt aaaggtaggt atacatcgct tgggggtatt  126900
tcaccccaca gaatgcaatt gagtagaatg caatatgtag catgtaacaa aatttactaa  126960
aatcatagga ttaggataag gtgtatctta aaactcagaa agtatgaagt tcattaatta  127020
tacaagcaac gttaaaatgt aaaataacaa atgatttctt tttgcaatgg acatatctct  127080
tcccataaaa tgggaaagga tttagttttt ggtcctctac taagccagtg ataactgtga  127140
ctataagtta gaaagcattt gctttattac catcttgaac cctctgtggg aagaggtgca  127200
gtataaataa ctgtataaat aaatagtagc tttcattatt tatagctcgc aaaataatct  127260
gtatggaagt agcatatata aggtatataa acatttagcc tcttgatagg actaactcac  127320
attctggttt gtatatcagt cttgcctgaa tttagctagt gtgggctttt ttttatcttg  127380
tgagtttgct ttatacattg ggtttctgaa aagatttctt ttagagaatg tatataagct  127440
taacatgtac tagtgccaat cttcagacag aaattttgtt ctattaggtt ttaagaataa  127500
aagcatttta ttttaaaac aggaaataat ataaaagga gagttttgt tgttttagta  127560 gaaaacttaa tgccttggat gaaatgagcc atgggcaggg ttgtaatgaa ttgatatgtt  127620
taatagtata gatcatttgt gaataatatg acctttgaca agacacaagc cattaacatc  127680
tgtaggcaga agtttccttc tttgtaaaat gagggaataa aatagatccc taaagtgtgt  127740
aattttagta tttctaaact ttatgaaggt ttcctaaatg ataattcatc tatatagtgt  127800
ttttttgtgt gtttgtttgt ttgtttgttt gagatggagt ctcgctctgt cacctaggct  127860
ggagtgcaat ggtgcaacct cggctcactg caacctctgc ctcctgggtt caagctaatc  127920
tcctgcctca gcctcctgag tagctgagat tacaggcatg caccaccatg ccgagctaat  127980
ttttgtattt ttagtagaga agggggtttca tcatgttgac caggctggtc ttgaactcct  128040
gaccttgtga tccacccacc tcagcctccc aaagtgctgg tattacaggc gtgtgccacc  128100
```

```
acgtccagcc tgagccactg cgcccagccc atctatatag tttaatatca atctaaatga   128160
atttctcagt cctgagccta aaaatttagt tgtaaagaat gatatccttg actaataata   128220
gtttctatta atggattgca tctagtgcta ggtggcatat atttagtccc cacaactacc   128280
ctggaaggta tttaaaattt ttcacatttg cagataagga aactaaagtt cagagttcgg   128340
caacatgctt gaattcaagc agctcctagg atgttaatgg tggaggttgg gttcaaatcc   128400
agatctgtct gactcaaaaa atgcatactc ctaaccagtg cactatatcc caattccata   128460
ggagcccttc tttgtgattc atagcacttt cccatgagtt ttgttgattt tgtgagaaac   128520
aaaactcttt ttcctttgga ctgtctggaa tctctctttt tcaaattttt gaatgtatt   128580 tctatgccaa aagacaaaga tttctagagg aatatgccta ggatgagaat tatgtaattt   128640
aaatcacagc tggaaagaga gaaagtccta agttactaag aaatgttcaa acacaaatga   128700
gctttcagtc tattggaaga cctttatagc tagaagtata ctgaactgta cttgtccatg   128760
gacccctgaa gaaacaggtt aaatcaaaga gagttctggg aaacttcatt tagatggtat   128820
cattcatttg ataaaaggta tgccactgtt aagcctttaa tggtaaaatt gtccaataat   128880
aatacagtta tataatcagt gatacatttt tagaattttg aaaaattacg atgtttctca   128940 ttttttaataa agctgtgttg ctccagtaga cattattctg gctatagaat gacatcatac   129000
atggcattta taatgattta tatttgttaa aatacactta gattcaagta atactattct   129060 tttatttca tatattaaaa ataaaaccac aatggtggca tgaaactgta ctgtcttatt   129120
gtaatagcca taattctttt attcaggagt gcttttttga tgatatggag agcataccag   129180
cagtgactac atggaacaca taccttcgat atattactgt ccacaagagc ttaattttg   129240 tgctaatttg gtgcttagta attttctgg cagaggtaag aatgttctat tgtaaagtat   129300
tactggattt aaagttaaat taagatagtt tggggatgta tacatatata tgcacacaca   129360
taaatatgta tatatacaca tgtatacatg tataagtatg catatataca cacatatatc   129420
actatatgta tatgtgtata tattacatat atttgtgatt ttacagtata taatggtata   129480
gattcatata gttcttagct tctgaaaaat caacaagtag aaccactact gatattttat   129540
tatttcatat tacatataaa atatatttaa atacaaatat aagaagagtt tttaatagat   129600
ttttaataat aaaggttaag agattcgaaa gctcaaagta gaaggctttt atttggattg   129660
aaattaaaca attagaatca ctgttgatat tttattattt catattacat ataaaatata   129720
tttaaatata aagataagag ttttttaatag attttataat aaatgttaag agattaaaaa   129780
actgaaaata gaaggctttt atttggattg aaattaaagg ccaggcatgg tggttcatgc   129840
ctgtaatccc agaattttag gagactgagt ggggaggatt gcttgagccc aggggtcaag   129900
accagcctgg gcaacacagt gagacaccgt atctacaaaa taattaaaaa attagctggg   129960
catggtggtg tgtgcctgta tgctaccatt aactaaggag gctgaggtgg gagaatcgct   130020
tgagcctggg aggtcaaggc tgccctgaac tgtgattgtg ccattgcatt ccagcctggg   130080
tgccagagag agaccctatc tctaaataaa taaataagta aataaataaa cagcaacaac   130140
aaaaacactc aaagcaaatc tgtactaaat tttgaattca ttctgagagg tgacagcatg   130200
ctggcagtcc tggcagccct cgctcactct cagggcctcc ttgaccttga cgcccactct   130260
ggctgtgcgt gaggagccct tcagccctcc cctgcactgt gggagcccct ttctgggctg   130320
gccaaggcca gagccggctc cctcagcttg cggggaggtg tggagggaga ggcgctgggg   130380
gaactggggc tgcgggtgcc ttgtgggcca gcgcgagttc tgggtgggtg tgggctgggc   130440
```

```
aggccccgca ctcggagcag ccggccggcc ccgcgagccc caggcagtga ggggcttagc    130500
acctgggcca gcagctgctg tactcgattt ctcactgggc cttagctgcc tccctgcggg    130560
gcagggctcg ggacctgcag cctgccatgc ctgagcctcc ccccaacctg ccgctgcagt    130620
gggctcctgc gtggcccaag cctcctgacg agcaccgccc cctgctccac ggcacccagt    130680
cccatagacc gcccaagggc tgaggagtgt gggtgcaggg cgcagggctg gcaggcagct    130740
ccacctgcag ccccagtgcg ggatccactg ggtgaagcca gctgggcttc tgagtctggt    130800
ggggacttgg aggatcttta tgtctagcta agggattgta aatacaccaa tcagcactct    130860
gtatctagct caaggtttgt aaacacacca atcagcaccc tgtgtctagc tcagggtttg    130920
tgaatgcacc aatcagcact ctgtatctag ttaatctggt ggagacttgg agaacccttta   130980 tgtctagcta agggattgta aatataccaa tgtgcactct gtatctagct caaggtttgt    131040
aaatacacca atcagcactc tctgtctagc tcagggtttg taaatacacc aatggacact    131100
ttgtatctag ctaatctagt gaggaggtgg agaacttttg tgtctagctc agggattgta    131160
aacgcaccaa tcagcaccct gtcaaaacgg accaatcagc tctctgtaaa accaatctgc    131220
tgtctgtaaa atggaccaat cagcaggatg tgggtggggc cagataagag aataaaagca    131280
ggctgcctga gccagaagtg gcaacctgct ggggtctgta gaagctttgt tcttttgttc    131340
tttgcaataa atttttgctac tgctcacttt ttgggtccgc attgcgttta tgagctgtga    131400
cactcactgg gaaggtctgc agcttcactc ctgaagccag cgagatcacg aacccaccag    131460
aagaaagaaa ctcctaacac atccgaacat cagaaggaac aaactcagga cacgcggcct    131520
ttaagaacta taacactcac tgcaagggtc cttggcttca ttctcgaagt cagtgagacc    131580
aagaacccac caattccgga cacaatttga ctgcagaaaa tggatgtcca accctgtggt    131640
ttccctgggc cacattggaa gaagaaagga gttgtcttgg gccacacata aaatacactt    131700
actatagcag atgagctaaa gaaaagaaaa aagtccatgc gtaatctttg tgatatgtgc    131760
caccaccaat aagcaaaatt gttctcttat tcaaaaggtt ggacacagct gctctagata    131820
ttttattatt aaatatgcag gcaattactg tttaaatgaa gatttcctca cagaatgaga    131880
ttaaaagtat atattagtgg cttagcattc atttttagaca accattttag agattcaaat    131940
cacacacttg cttacagaaa ttttgttgtc ttcaatgtcc ccattgtggt ttctttacca    132000
agcctctact gttcttcaca tcaccaagtt aaaaaaaaaa aagggcggg ggggcagaat     132060 gaaaattgca tggtaggcca caagttcaga tcctcatcga cacaagaggt gcctgaagca    132120
gtggatgagg cttttctatg gatcatgagc agccacataa atgcttaaaa gggcctggca    132180
gggagcatca gtgggtgatg tggctgggag gctgaatgga gagcatttgt tcttcagtta    132240
tctatagaag gcagctgtca ctcagcacca gctaagggct tcccatgagg gaactgggga    132300
tcaggtttcc cagatctttt tatgtaacag gataagacag agatccagct ttttttgggt    132360
aattatttcc tattttaaaa tacgggtagt tgattaaata aaaacaaacg aatgaacacc    132420
atatgggcac aacaaaacac atctgtggct tggattcagc ttgtgaatga ttactgcaga    132480
tatttattct agaggacacc cctgggtatg tcctaatata aaacctaaat ctaaactcaa    132540
gtcccatgct accttcagag aataaatgac ccagaaaaag aaccacctct cctaaggaag    132600
tataaatttg taaataactg agacccaaac ttacaactat acattttttct tattgttggg   132660 ctgttgctaa cctcaattaa gaaggcttga tgatatttgt aaagtgtcat cactccacca    132720
tggtccagta acatctgatc actccaccat ggtccagtaa catctgaatg gtcaagaaat    132780
atctaaacgt atgtaccaaa aatttgtgta tactactgta ccaataaacc atttgtttcc    132840
```

```
atttgatctc tgagtgtggt aatacatgtt atttgccctg ctgttgtaaa taaacaaacc   132900
aaatggaggc ttgatgcaag atgcagtgta gcatagtgcc aactctggac tccgactact   132960
cagggtgtaa attctaactc tgttctatta acaccatgaa actgagcaag ttagttaaaa   133020
ctcgctgggc ccattttctc atttatacaa tggagatttt aatagtacag ctacataggc   133080
cattttgtgg tttaaaatac atcatgatta tgaaacactt aatgtagggc ttgctacata   133140
atgagcaagg tttgttgctg ttatcattaa tatccttaat tctcattatt ataaaacttg   133200
agatagtatg aggtgaacaa gttcataaca gcaatataat gaaaatttta ataattcctt   133260
ttatacttta acaaaaatac gagattgggt aatttattat ttttacatga gtaataaata   133320
ttgcattaaa atatatttaa aatttaccac attaatgtct gccagtcatg ccaaatgacc   133380
aacatgaatg tgaataaaac tcagtctgtg cccatttaat cttaaccaac cctttataat   133440
tgttaatgat ttgaacctct gccttgaaag atcacattac ttgattgtct tcaacttatc   133500
tgaatgtggt agtgatttct gtaaatttat aggacctttg tctcatgcag ctccatggag   133560
ttgaacttat gcacctttaa aatggtatat acttaattaa ttaagtgttg atctgcttca   133620
catgtgtata atattattag ctcactaaac caagaaaaca gtggtccttt agggaaagaa   133680
actaaattac aacagagaat ataaatacca tataaatatc tattatttat tgaactgtca   133740
caattattgc aaaaaattac cttttagtgg acaaaacaat tgatattgcc cttttctgga   133800
aaagaaataa tgtaatatat gatgaatagt tttggccagt atcctctaga ccttgccagt   133860
taactggctc tcaaaatttt gaataataaa aacttggtga tagtagaaaa atagtaattt   133920
tttaaaagta tgtgcacaat tatacaacta aacaattcat tcaccagtgt tcacaattct   133980
attgccttct ttgaatcaaa atttacatag tttttctttt agactaagct cctttatgat   134040
accagtgtgc ccatttctca ttaccattga aatgtctcat gagcatgtca cattctggta   134100
caactgctaa tccaggatga cagtttagtt cttttaaatc caattgagag ccttctactc   134160
atgaccagag aacctaaaga aaggttaaga tacatttatt ccttggtgta agtgattgt    134220
ctattttttag ttttcctaag ggtcatattt caatttagat ttttttttat aggttaggta   134280
aaataggctt cccttttgca atatgaaata tgtagtcttt taaaaaattt cttcaaagct   134340
attaaactga aaaaaaatta atttggtcta ttcagtttgt tagcacttac catttttggaa  134400
agagagtgac tctactttttg tatttggtaa catttttccct actacagggc agtatctttt   134460
gtaagttctt agatattagc accaaataaa taggcaaaaa aaatctatta tgttaattct   134520
tagaaccct gcttggcagt gcatcattga ctagatggag aagaaatgaa aataatacat    134580
taggaagcag tttcctggtt cttttgaaaa caactagaga gtcttgttgt tgactggaat   134640
atctgaagat cctgtttaat gctttcattc tatgattgtt aagaatatgt catagaactg   134700
ctgtatcctg tttctttatg tcttcccttc tgtttgttga ttagaaatcc ctgagtggct   134760
ttacattatt agtacagtag atatgtagta tattcccata ataccactgc tgctattgac   134820
taatagtaat aattttaggg cagctttatg acagttggtt tatgttttag ggtgtcattt   134880
gacttgtgaa gcattgaaat ctgggtatta agcacactgt tttctatgtg gtatggaatg   134940
attcttaaag ccctgagaaa atggaaaata aaaatatttt tcctttttac cataatcacc   135000
tatgactgtc actctatcat aaactgcata aactttataa cctcaaaaca ttttggaaat   135060
gaaatgacag aacttgctta ctcaattgct tctatataca ccaaatattt ttttaaagta   135120
ttatgttaag tccttgaaaa tattttgttc tactcaatag aagcagttta ggttggtagt   135180
```

```
tctatgtgga aaccgtgagg aaataatttt atattatgat gactagacca gtctttgaac    135240
atcactttgg ttattgttcc attagtaaat attataatta tttctgagat ttactcacct    135300
tcaaagaatg ttggcaatgc cagcattatt aacactcctc tagttagaac aaagaggaaa    135360
tgtaataaca aaacataata atagccaaat aaagagtgac ttagaatgta caccottatc    135420 taggatcctg agtaattcga ttattcttag gaaatacact tttgtgctag aacaaagact    135480
tttgaaatag ctaatttctg ggtttctttt cattttgaat taacttgaat ttcaaggaaa    135540
caagggtagt ttttacagat acagtgcata gaagctctgt gtacaatgaa gaaaagtagg    135600
aaagtgagaa aaatgccatt agatttttca tcgttatact atctgatatg tgaatttaac    135660
taaaacttat atacctcatt atagtacttc ctaatgtaat ttcttaattt aagtgttccc    135720
cataaggttt tttttatat aaacttaagt actgttaaat atttaaggca aattcaggta     135780
taaaataaga cttgttgata tcttattcca agcatatttg tttctctcct atttattttt    135840
attctgtgtt catttccaaa attgttttac tcacaactgt tgttttttc tgtttcattc     135900 tgtggtaaag gtatcatttg gctaattgta taatttcagt gtcatttcta atattccaat    135960
tgtgatagta tcaacacaag attaaatttc tctacatggt ttatgagaat ggaatgccaa    136020
attgaaatag aacagagcac agatgatcta aatataaaaa gaactacaaa aatcacagtt    136080
gtttaaaaag gttttttgtt tgtttatata tggtgcagaa catttgttcc ttagccaaat    136140
gtttccacct tgagaaagct atagagattc tatgtagtcc tagtaccaat aatatgtttt    136200
aacctgaatg taccttatct ttattcataa actgtgactt tttacactgc tgaaactttt    136260 tttttttaaga caatctcact ctgtcgtcca gtctggagtg cagcagtggt gtgatcttgg   136320
ctcactgcaa cctctacctt ctgtgttcaa gcaattctgg tgcctcggcc acctgagtag    136380
ttgggatcac aggtgtacac caccaggcct ggctaatagt ttttgatatt tctagtagag    136440
atgagttttg ccacattggc caggctggcc tgaaactcct ggcctcaagt gatctgcctg    136500
ccttggcctc ccaaagtgtt ggtattacaa gtgtgagcca ctgtgcctgg cctgaaactc    136560
ataattcatt tccattaata ttaatctcac cttttccaat aattaattga tttcacaagt    136620
attagtcccc tataatcatt gaatggctaa taaaattatt tatagcaaac agattaatta    136680
tctgccagca gtctgagatt agtttctttta aaaaatgttt attatttaaa acattcagct    136740
gtgatcttgg ctttcttgtg aggttcaata gtttctattg agtaaaggag agaaatggca    136800
gagaatttac ttcagtgaaa tttgaattcc attaacttaa tgtggtctca tcacaaataa    136860
tagtacttag aacacctagt acagctgctg gacccaggaa cacaaagcaa aggaagatga    136920
aattgtgtgt accttgatat tggtacacac atcaaatggt gtgatgtgaa tttagatgtg    136980
ggcatgggag gaataggtga agatgttaga aaaaaaatca actgtgtctt gttccattcc    137040
aggtggctgc ttctttggtt gtgctgtggc tccttggaaa gtgagtattc catgtcctat    137100
tgtgtagatt gtgttttatt tctgttgatt aaatattgta atccactatg tttgtatgta    137160
ttgtaatcca cttgttttca tttctcccaa gcattatggt agtggaaaga taaggttttt    137220
tgtttaaatg atgaccatta gttgggtgag gtgacacatt cctgtagtcc tagctcctcc    137280
acaggctgac gcaggaggat cacttgagcc caggagttca gggctgtagt gttgtatcat    137340
tgtgagtagc caccgcactc cagcctggac aatatagtga gatcctatat ctaaaataaa    137400
ataaaataaa atgaataaat tgtgagcatg tgcagctcct gcagtttcta aagaatatag    137460
ttctgttcag tttctgtgaa acacaataaa aatatttgaa ataacattac atattagg     137520 ttttcttcaa atttttttaat ttaataaaga acaactcaat ctctatcaat agtgagaaaa    137580
```

```
catatctatt ttcttgcaat aatagtatga ttttgaggtt aagggtgcat gctcttctaa  137640
tgcaaaatat tgtatttatt tagactcaag tttagttcca tttacatgta ttggaaattc  137700
agtaagtaac tttggctgcc aaataacgat ttcctatttg ctttacagca ctcctcttca  137760
agacaaaggg aatagtactc atagtagaaa taacagctat gcagtgatta tcaccagcac  137820
cagttcgtat tatgtgtttt acatttacgt gggagtagcc gacactttgc ttgctatggg  137880
attcttcaga ggtctaccac tggtgcatac tctaatcaca gtgtcgaaaa ttttacacca  137940
caaaatgtta cattctgttc ttcaagcacc tatgtcaacc ctcaacacgt gaaagcagg   138000 tactttacta ggtctaagaa atgaaactgc tgatccacca tcaatagggc ctgtggtttt  138060
gttggttttc taatggcagt gctggctttt gcacagaggc atgtgccctt tgttgaacct  138120
ccatttgact ggcatgcaca tgtctcagat attataggtt atcatatatt gttgctccta  138180
atatttctgt gttagataat tagagtagct tggtttgtaa gaatgtgatg ttggtgggac  138240
tgtagcagaa caagaaggcc cttatgggtc agtcatacct ctcttttcaa atatttggtc  138300
tagctctctt ctgggcatct tgttgccaat atatagtatt gctcaaaagg gcaggagatt  138360
tgaagtgatc aaggaaaata tattttttct attgattaag tcttttgatg gggtagaata  138420
atctaatttc atgtaactgc tcaaagttat atggtagggg gatcccaaat gtattttaaa  138480 actatttta tatcatcata tttgaagtaa tagaaagtca gagtagcaga ataaaggtac  138540
taaaaatttt aaaaactaat aaggtacttt gaaagaaatc aattatgttg attcctcatt  138600
aaacaaattt gcacttaaag actgaggtta ataaggattt ccccaagttt tttcatagca  138660
acctgtgagc actttctctg ttgaggcatt tatggtatga aagatgagt aaggcacagt   138720 tcttgccctg gagaaggtca caggtgagag gaggagttga cacagaaaca tttgataaa   138780 agcaaggaat aaattccaag actaaaattt tcagaaatct aaaaaactca agataagaaa  138840
aacccattat attttctggg taacaaaatt tcagtgttat taacatgtag gaagatcttg  138900
atatttattc tgaagcccat gtgtgttgct gaaatattgc cgcatttgca tatactcatc  138960
accatcctct gttttggagc taagaatttt agactcaaga tgtctaatta agttgatcca  139020
ttgattttat tttttatgga aatctgagac ccacagaagg caggggattt gcccacattt  139080
ctagaagagt cagacatgag cgatgaggca cagtggaaag aacatgagca ttgcctgagc  139140
tctgagttgg cgctataaga gcagtgatca tgggcaagtg actcttctga gccttggcct  139200
cctcacctgt taagtgaaga aaagaatatt tcagaagatc tttgtgagaa tgaaacaagg  139260
caatttactt gcctgctaca tagccaatgg gaaatcaata taagttcccc gtggttccct  139320
tctgtggggt tttgttccca cagagggtgc actggccatt ccacttcttc ttttccaagc  139380
tcctcattcc ctttaacgct gttcatagtt ggttccaaac catttgaaat ataataagca  139440
ccaggatggt ttttctttc caccaaagca aatttcattt tctaaacact gtttataaat  139500
atcaatggct attttttcaa tttttgatta tcatgaaaat atacaaatat gtttaattaa  139560
atatgctaaa gaatgtatta ataaatatgt attaaataat tcctacatat aaggccttt   139620 tgcttggggt atgggtgata caaaataaat gtggcatgaa cccactgacc tctagcaatt  139680
tataacctag aaaagagtt atgatatgtt tataagttcc tgtgatataa gacatgcata   139740
tagtcattat aacagaggtg caaacaagat gtatcaagta tgtccagagg aggaagagat  139800
taatcccagc tggaggaaac actgatgctt cttgcagca ggggcatttg agttgagaaa   139860
gggaggaaac atagattttg acaatgagag ctgagggaa agggtttca ggtggaggga    139920
```

-continued

```
accgcatgtg gaaagcaggg aggtaggaaa gtgtagagtg tgtttaaaga atagaccagt    139980
ttggctgaaa caggatattt gagcagagga agcttgtact aggtaggtgg gttgaggcca    140040
aattatgcaa ggcattaaat attaaactag gaattttgga ctttatcctg cagtttatgg    140100
ggggtaaatg ataagattca atatcacttt atttgtacag tattatgtta cattttatct    140160
aattgtttgt ttaattcctg tctagacaat gaattcctca agggcaagga gcatggctta    140220
ttcacctcag taatttcagt gcctagcatt gtgcctggta caaagtggac acttgtatat    140280
aacctttttt aattgaagca acaagttgtc aaccttacaa atgtgaatcc gtgattcaga    140340
tgacaggttg aaatgtagat tgtctgcgaa gagggcagaa agagagtatg acaaaggagg    140400
acaagacagt ggggcaggca gggagagaga gcagccaggg tttcggtaga ggtatgtcaa    140460
aaaggtatgg aagtcagagg agaaggagac ccctatgtta tagaatacaa atggaaggga    140520
aatgatgaca acagtaagtt gtcattaaat gcaaggttgc aaaagtaaga ttgtaaagca    140580
ggatgagtac ccacctattc ctgacataat ttatagtaaa agctatttca gagaaattgg    140640
tcgttacttg aatcttacaa gaatctgaaa cttttaaaaa ggtttaaaag taaagacaa     140700 taacttgaac acataattat ttagaatgtt tggaagaaa caaaaatttc taagtctatc     140760
tgattctatt tgctaattct tatttgggtt ctgaatgcgt ctactgtgat ccaaacttag    140820
tattgaatat attgatatat ctttaaaaaa ttagtgtttt ttgaggaatt tgtcatcttg    140880 tatattatg gtgggattct taatagattc tccaaagata tagcaatttt ggatgacctt    140940
ctgcctctta ccatatttga cttcatccag gtatgtaaaa ataagtaccg ttaagtatgt    141000
ctgtattatt aaaaaaacaa taacaaaagc aaatgtgatt ttgttttcat tttttatttg    141060
attgagggtt gaagtcctgt ctattgcatt aattttgtaa ttatccaaag ccttcaaaat    141120
agacataagt ttagtaaatt caataataag tcagaactgc ttacctggcc caaacctgag    141180
gcaatcccac atttagatgt aatagctgtc tacttgggag tgatttgaga ggcacaaagg    141240
accatctttc ccaaaatcac tggccacaaa gtgtgacatt ttggcattgg catcactatt    141300
tgatggaagc caacctcccc ccaaaaggcc tgtattagaa tgaagatgga ttccctgggt    141360
gggttacact tgaaactagc ctcacccatg aacactttgg cacagattag ctagcccatt    141420
cccccacagt aaggaccata aggaagggac agaagcaaag ataagtttta gaacaaaaga    141480
gaggggaaag aaaaaatcta gggttttatg agggctgtcc ctgagtgata gatgtgaata    141540
ggcctccagg gcaggctggc tcagaggctg actctttggg ttggggtgac tgattggtgg    141600
tgaggatgga gaagaaaagg ggagtggagg aggtgaaagt gaccttggga cattaggtct    141660
ccataagtga caggatttaa ggagtgttgt aagctgtggt tgttggacca ggtttaagca    141720
cagcttcctg agcttcctga ctggtttagg tcaagctcca gagagcaaat gcccacagtct    141780 cagtgatctc cttggagaaa cagttggaat aggatgttgc ccatgttggg atgagtcatt    141840
gtccgctctt gctctttccc taccctgca aaataataat actgtatttg attgaacata    141900
taaaacaaaa gaaggattat cacataagta tgtatatata accaacattg gcaggtgcag    141960
aaaaaccaga ctgtcagttt gcctcatctg aaatgattga cacaaacaaa tatatttact    142020
gtcccaagtg aactttggca ttttggatat ccttcagttg ttctgtttaa agatataact    142080
tagaagcagc tgatggaata tttaaatcca tgcgttgaat tcatgcattc aaagaaacat    142140
gtcctgagtc actaaatgct gacatttgtt tttcatgtta agagtgtaaa taactggtcc    142200
caaatataat attattacat cagataaaaa ctggaatgtg aacctcttaa cttgattgtg    142260
aaagtatttg ccaatggtgc ctcttgataa ttatttgagg ctcacttcag aactcctctg    142320
```

```
gaagggttaa ttttaaata gtcattttat aaattaacat ttttgacata tgtgatggct 142380
ctcaaatttt ttctttatg ccagtttgaa tcatttctgc tcaattttt ttttaaattg 142440 ggatggagtc tcactctgtt gcccaggctg gagtgcagtg atgcaatctt ggctgactgc 142500
aacctccacc tcctcggttc aagcgattct ctcgcatcag cctccagagt agctgggatt 142560
acaggcgcgc accaccatgc ctggataatt tttgtattat tactagagat ggggtttcac 142620
cacgttggcc aggctggtct tgaactcctg aactcctgac ctcaagtgat ccacctgcct 142680
cagcctctta aagagctgga attataggtg tgagccactg caccaggccc tgttcaactt 142740
ttaatgctaa gattcatttg ttgttgtttc acaagtgatt aggcagaggt cttttatatt 142800
aatttaccca ttttatttgt aagagagtct catattaagg aagcataata tatgacaatc 142860
caaatacagt acaaatttgg ttaatttga ttttgttaaa taattaatca cagggtcct 142920 tcaaattgtg agctcctctg gttatactta tgttttacct ctggttatac ttaatttcaa 142980
acaaatgaaa tttcattcta ttcatgatat ttcagaagca gatctgttgc acaaaataaa 143040
gcatacctat aaattttctt tttttaaaaa aaagtctctg ttcactctat tttctattat 143100
ttttctcttt ttaaaatttg aatttattg tggcaagtcc acttaacatg agatttaccc 143160
tcttaacaga ttttatgtg taaaatacaa tattgttcac catgggtaaa tgttgcacag 143220
cagatctctg gaacttattc attttgcact actgaaattt tatacctgtt gattagtatc 143280
tccccatttc cctctctccc ctgtcctgtt acccatggtt ctgttctttg cttctttgag 143340
tttgagtatt ttgatacctc atgtaatctt cattctattt tctaactttg acaatgttct 143400
gacaaatttg ctttccggat tggagcactg tatagtgaaa attgaaaatc ttggttattt 143460
tctacagatt cccactattt taccttgagc agacacttat cttgaagggt ctcagatttg 143520
tcacttgtag aatggggaat ataaacctga taatggtccc tttcagttct aaagttatat 143580
cagttgaaaa tacatgtgtc acttatggta acgggtagag aactggctca ctgaacagca 143640
tatggatatt ataaagtggt tttttttaat cctttctgca gacagttact ttatacttta 143700
ttcaaatgga ttattgtgaa gtacatgtta gcggactttg tacctttaa aaatgtatgt 143760 atttggtgta atgtagaaat atagaaattt attaagtatg atttatttca atgttaagca 143820
tgagaaaata tgctccgaaa ggttagatag cttgcctaaa tgacaagctt gtatttcaag 143880
cagaactttc tgaatcaaaa gactccaaga cgaatgccca gctttcaaaa actgtctaac 143940
caaaataaat cctaagattc accttcatac taaaattatt taaaaatagt ttattttaaa 144000
ttaatattca cttaaaatgt atttatcatg caatactta aagtgtctgg gaaatgaaaa 144060
tatccaaaga tcaaagaaca ccatgttttc aaacttcaaa aatgttatca gtgacctaaa 144120 caattttaa aattttcata gagcctatga aaaatgtact tgcaaatggc tactttctga 144180
ctaggaatag aatggggaga gtatttagtc caacaatgat agactggatt aagaaaatgt 144240
ggcacatata caccatggaa cactatgcag ccataaaaaa tgatgagttc atgtcctttg 144300
tagggacatg gatgaaattg gaaaacatca ttctcagtaa actatcgcaa gaacaaaaaa 144360
ccaaacaccg catattctca ctcataggtg ggaattgaac aatgagatca catggacaca 144420
ggaaggggaa tatcacactc tggggactgt tgtggggtgg gggagggggg gagggatagc 144480
actgggagat atacctaatg ctagatgacg agttagtggg tgcagtgcac cagcatggca 144540
catgtataca tatgtaacta acctgcacaa tgtgcacatg tacccctaaaa cttaaagtat 144600 aataaaaaa ataaaaaaaa gtttgaggtg tttaaagtat gcaaaaaaaa aaaagaaat 144660
```

```
aaatcactga cacactttgt ccactttgca atgtgaaaat gtttactcac caacatgttt    144720
tctttgatct tacagttgtt attaattgtg attggagcta tagcagttgt cgcagtttta    144780
caaccctaca tctttgttgc aacagtgcca gtgatagtgg cttttattat gttgagagca    144840
tatttcctcc aaacctcaca gcaactcaaa caactggaat ctgaaggtat gacagtgaat    144900
gtgcgatact catcttgtaa aaaagctata agagctattt gagattcttt attgttaatc    144960
tacttaaaaa aaattctgct tttaaacttt tacatcatat aacaataatt tttttctaca    145020
tgcatgtgta tataaaagga aactatatta caaagtacac atggattttt tttcttaatt    145080
aatgaccatg tgacttcatt ttggttttaa aataggtata tagaatctta ccacagttgg    145140
tgtacaggac attcatttat aataaactta tatcagtcaa attaaacaag gatagtgctg    145200
ctattactaa aggtttctct gggttcccaa atgatacttg accaaatttg tcccttt ggc    145260
ttgttgtctt cagacaccct ttcttcatgt gttggagctg ccatttcgtg tgcccccaaa    145320
ctctacttga gctgttaggg aatcacattt tgcagtgaca gccttagtgt gggtgcattt    145380
tcaggcaata cttttcagt atatttctgc tttgtagatt attagctaaa tcaagtcaca     145440
taaacttcct taatttagat acttgaaaaa attgtcttaa agaaaattt ttttagtaag     145500
aattaattta gaattagcca gaaaactccc agtggtagcc aagaaagagg aataaatatt    145560
ggtggtaatt ttttaagttc ccatctctgg tagccaagta aaaaagagg gtaactcatt     145620
aataaaataa caaatcatat ctattcaaag aatggcacca gtgtgaaaaa aagctttta     145680
accaatgaca tttgtgatat gattattcta atttagtctt tttcaggtac aagatattat    145740
gaaattacat tttgtgttta tgttatttgc aatgttttct atggaaatat ttcacaggca    145800
ggagtccaat tttcactcat cttgttacaa gcttaaaagg actatggaca cttcgtgcct    145860
tcggacggca gccttacttt gaaactctgt tccacaaagc tctgaattta catactgcca    145920
actggttctt gtacctgtca acactgcgct ggttccaaat gagaatagaa atgattttg     145980
tcatcttctt cattgctgtt accttcattt ccattttaac aacaggtact atgaactcat    146040
taactttagc taagcattta agtaaaaaat tttcaatgaa taaaatgctg cattctatag    146100
gttatcaatt tttgatatct ttagagttta gtaattaaca aatttgttgg tttattattg    146160
aacaagtgat ttctttgaat ttccattgtt ttattgttaa acaataatt tccttgaaat     146220
cggatatata tatatatatg tatatatata tatatatata tatatatata catatatata    146280
tatagtatta tccctgtttt cacagtttta aaaaccgatg cacacagatt gtcagatagc    146340
aattctgtga ttgaaggggga aatatgtcac ctcttcatac tcatattggt gaagggtcct   146400
agcttcaaaa ttaatagatt cctaaagagg ggaaatgaaa catccgcatt tacacacaca    146460
cacacacaca cacacacaga gttcctcttg tcggtaagtt ttgtttttt taaatctcta     146520
ctagataaaa tttgttatct aattgtgagt tttacacaaa gaaaaactgt cacagaaaag    146580
aaagacagtg tcacatttt caaaagaaaa agaagaaaag aaagtgccat gttttcaaa     146640
tacaaatgtt ctggattgat tttaggatct ttagtgaaaa acaaagtatt tcataataag    146700
taaaataaaa atctatgtag gtaaatttgt ttctctaatt taagaatttg aatttctgag    146760
tatttatgat aagtgttgaa ataacttctt atatgtgaca gtgaatactg gcagagcaaa    146820
tgccaaatca atgccaaatc tgtaggatca tttgattgta ggaacagaat tctactcaaa    146880
ccgaaagcag gcatttgctg gagttacaga aaggcctcat ggaacaccga gaaggtggtg    146940
ccattcgact cttaaagaag ctgcaacagg cacaagagag tcagctgcag ctcttcttct    147000
tgagtctata tctgtcctgg gtccattcct ttttgtggtt gcttcattcc tttctctctc    147060
```

```
tgaagactgg tttttctggt ctaccagggc tatgccacat tgactttatg tagtgtctcc  147120
attctggcct cctgaattta caggagagtt cctctgtaca aactcaaagt cctggagaga  147180
acagaaaaca gcttccttt ggctcagggg tccaactgca gtctactctg ctgctatgag  147240
gatagtgggt tcaccacctt tgttgttctc tcagctaggg cagtgggaaa tgactctatg  147300
aaaggaatat acatgggcag gcaaatgtac taatcctcat cagtactgta atttttaagca  147360 actttaaaaa attcttttaa gttatttgaa aataagatca aagaaggctg aattacataa  147420
atgaagattt gttaacaatt aattcaaacc aatataacac atgctataac atggttgagt  147480
gtgattgagt cttgatttat taggggcaat aatcaaaaca tttaacaatc attatagtac  147540
agaacttacc aatcaaatca gatgctcagc cggagtggat gttggccacc cagctattat  147600
tatccctggc tcaattggtc ttcagctgtg ttaacttgca aacattaatt aactatctaa  147660 gccctcatt ttcctcaagt gtaaatagac acaataatat tacctattcc ataggtgtgg  147720
ggtgaatagt aaatgtaata atttgtccaa aacacttagt atagtgcctg gtccatggta  147780
aatactaaat aaatgttatc tgacttatta ttaaaatttt atcttctcag cttaaccttc  147840
agaacagtaa tatattgggg tctagataaa tcttgcctat atgaaaataa tttaatacta  147900
catgcagata tatgctgtgt atattatgcc ttctgttaga ggaattgcag aaacaaaaat  147960
ttcaattaat aataagatga attatttctc ccaattgtag aatcttttga caattttatc  148020
atgcattaca gatgtaagaa ctcttgattg ggacttgata gtctaacttt ataataattt  148080
aagaacattc ctcttagaga atttctatgg ccataatact gaacacatga attttaatta  148140
gctgtcctct ttagccctaa aaaaaaatt actgtaattt aacacttaag tgttgttctt  148200
cccaggtaca gtaatctttt ttttttttt tttttttttt tgcatagagg gtaatctttt  148260 ctcttttccaa atggcagaac tgttagtttt ctgactgtcc ggtgaaattc taagtccact  148320
tacttcccaa tagcatgcaa ttagcaaagg tcctccttgc aaaggcacag aacacaccta  148380
aacatcttgc agatgctgtt tggacactct tcccctgctt ttggtctctt tgtaaagcag  148440
ctcatctgga tacaggatct cttttcccca ttgcccattc taatatatgt taccgttatt  148500
acttatagaa taatagtaga agagacaaat atggtaccta cccattacca acaacacctc  148560
caataccagt aacatttttt aaaagggca acactttcct aatattcaat cgctctttga  148620
tttaaaatcc tggttgaata cttactatat gcagagcatt attctattag tagatgctgt  148680
gatgaactga gatttaaaaa ttgttaaaat tagcataaaa ttgaaatgta aatttaatgt  148740
gatatgtgcc ctaggagaag tgtgaataaa gtcgttcaca gaagagagaa ataacatgag  148800
gttcatttac gtcttttgtg catctatagg agaaggagaa ggaagagttg gtattatcct  148860
gactttagcc atgaatatca tgagtacatt gcagtgggct gtaaactcca gcatagatgt  148920
ggatagcttg gtaagtctta tcatctttt aactttatg aaaaaaattc agacaagtaa  148980
caaagtatga gtaatagcat gaggaagaac tatataccgt atattgagct taagaaataa  149040
aacattacag ataaattgag ggtcactgtg tatctgtcat taaatcctta tctcttcttt  149100
ccttctcata gatagccact atgaagatct aatactgcag tgagcattct ttcacctgtt  149160
tccttattca ggatttctta ggagaaatac ctaggggttg tattgctggg tcataggatt  149220
cacccatgct taactgagtg gtgccaaatt gtcctcaagt ctgttgtact gatatatatc  149280
cccatcaaga gagtacaaga attctctatag ctatgtatct tcaacaacac ttggtgtctg  149340
gtagatgtga agtgattact aaaaatatag ggaagctgca tacataatta ttggcttttg  149400
```

```
ctgttctctt acattaattt cttattcatg ttgattactc atttgtcacc tagtttttc  149460
ttccttaatt aaattgtagg aatttatgaa ttatggattg atcatcagct ctatacattt  149520
caaacataat ccctcagtca gtggcttggc ttatagagtc ttttgatgaa agaagcttt   149580
taagtttaat aaagttcaat ttattgtctt ttcctttatg ttttgtgctt ttggtatctt  149640
gattaagaac tccttcctta tattgggttc tcaaatttag cagcataaca ttttcatact  149700
attatttaaa ttttttttcac attatttagt gatagcacct ttcttattcc taaagtgttt  149760
atcattgcct tctgtctttc tgcttgataa atattgccac acatttgtat actttattag  149820
tgtgtacaaa gaccacattt tagttgtgtt atttctcttg ttttggtttt ctagaatgca  149880
gagccattaa tattatagta atgcttatgt gctaatacca tatcaggggc acaaatccca  149940
ttgcagcggg actgagaaat taaggaaat gatgcacatt tactcatttt tgtttaaaaa   150000
atcaaatgca tattttcaa tcagactata tggttggtct ggatagcttc atcattgaat  150060
ttttaaagta ttttttgtact actgtattta aaattattca ttcaccactg cttttgtaga  150120
tggtttagaa acccaagtta ggaatgactg tgcaacacta ttattatact cttttaaaa   150180
ttatactttt tgcttaagtt tcttttcctg ttctctgaga cagtgttcat gttcccaaac  150240
cacacacatt tattcagcta taaaatttgt atgatcaact cctgtcagaa caaacatcat  150300
tataaaaaat atctccagga aaagaaaac ccttttaatg ctctcttctg gttcatgtgt   150360
cttcttattt tctttaagca ttttcataac ccattgagct gtaatttaat tggaacatga  150420
tttatactaa agttggtttc tttacccttta acttttttt ttagtttgat cagctctctt  150480
tagcttctgt agttcggtct ttaattccat tccagtatgc ttttggagtt gggtctcata  150540
aatgtataga aatgtttctg ttgggaaaca gcaggagaat attaaataaa tattgtgctt  150600
acatctattt aattctttgc ccaacttct acaactttga cttt a cattt aagctcctca   150660
tgcacttaca tgtttctta cctaaaaata tcttttcacc atgggtgtgt acaattcctt  150720
tgtccttgct gtattaattt tcttggttta catagtagcc tctacacatt gatgtcaaaa  150780
cctctgtttg gtgcatttct actctgcgtg ttcaatctcc atgaaagttt ctgtaaggta  150840
ttttcattcc tctagttttt cacatgtgca tcctggcttt gtgacctgtg ctttgatatc  150900
gtgcctttca tcttgtggca ttgaaggatc tttgcaagga cctattgtgt tataatacag  150960
tctatgaaaa atatcaatat ttgcatttga tcacatttaa aaaaatcaca ttcttttgtt  151020
tgaatatcaa agctaatatg tgagtgattt ccctgccaaa tagcacaagt agcctttcct  151080
gggtgtttat gggcatttat ctggttaatg attcccatca tagtgctgtc acccatgcca  151140
ttgctaaact tatacagtaa cttttttgtt ttcacctcag catatgttga gagtaggaaa  151200
tagataggac tatgccctca aattttacgt ttatatgatg ttaatcctaa aggtccttgt  151260
gacttctgaa gtaaaaactc agtgttgtca ttttacttac tgaattgtta gctgagttta  151320
gagttgagtt tacaatggag taaacaaggt gtttagtttg atgtatgctt ttagtctttc  151380
agaaaaaaat gtttatactt ggaaagaata gtttatttac ccatctggcc tagtttagac  151440
aaaaacacag agtcaaatgt caacagaatt ctgaagttat aaaaatgaca gtgtggcttt  151500
ttttttttttt aaccttccac ctggtgctta tgcccaagtg cctagctttc tttagctctc  151560
aactaataaa ggtaatgttt agataacatt taacgttaag ttgcattgtg tttatgatca  151620
catatctcaa atattggtac acgaaactgt acaacaacct tttttattag attttcctac  151680
gaaattcctt attatattcc ctaagatagc ttttcccac cttcttcttc cttctccctt  151740
ctcaggtgct ccaataattc caacccctgc agccagtgac tttattatat ctttttttaa  151800
```

```
aaatctaaaa aaaaaaattg atgcaaccag gaagaattt  ctcatttctc tccaccagtt  151860
gtaccagcct actgcacctc tcctcatgca ccaccttctg cctgtgttct tgctcctata  151920
ttcaggagca agtaatatgc aatacctccc tctttgtggg atctttctca ttagcataaa  151980
aatactttcc cttgatctcc agctactacc ccatttcttt gacctacata tagcaaaata  152040
tttgagaaag gaccactttc catcttttcc tcaatctact tccatttttt tctcaatcca  152100
cttttcatttc attgttctcc tcaacccatt ctttccacaa cctacttcat tttatttcca  152160
tcagccccat aactcaggat caacatcttg ccagagccaa tttccttgtc tcccttaaca  152220
gctccagcag tatttatgcc atggacaaat tattcttctt gtgatacttt ctctcttgct  152280
tccatgacac tactcccact tcattttctt tctacctctc tggctcttcc ttggtccctt  152340
ttcctggccc cttctctctt tcagatctct aaacatcagc tatatctcag ccctgttcta  152400
ctgacactct ctagctgtta ttttctaaac ccatgtttca gaaaccatat cttgatgaat  152460
cttggaaggc cgaggcaggc gaattacttg aggtcgggag tttgagacca gcctggccaa  152520
cgtggtgaaa ccccatctct cctaaaaata caaaaattac ctggccgtgg tggcatgcac  152580
ccagctactt gagaggctga ggcacaagaa tcgcttgaac ctgggaggtg gaggtttcag  152640
tgagccgaga tcctgccact gcactccagc ctgagcaata gaggagactc cgtctcacac  152700
acacacacac acacacacac acaaagaaaa taaaccatct cttgatgaat cataaatttg  152760
tgtctctagt ttagacctct atcctgctct ctaaatgatg tatccaacta tcatcttgac  152820
accatcatat gttcataaaa cataattata gaatatcttt cagtaggctt gacattttaa  152880
ggcatgagtt tccgttcagt atctccttaa aatatacca  gggtctcagg agactattca  152940
aacaggacaa agcttctatt ctacttacta atgtgtctgg ccctatttgg caggttggat  153000
aaaaagtcat ctgaacattg tcactttatg aataatatag tttaatagtt tgtgaatcac  153060
ccctgcaatt taaaaaatag taaaattatc agaatctaat ttaataattc ctattggaac  153120
accccatgtt agggatttc cagttatttc aattgatatc tcaatgtttt aaagattgtt  153180
tatttctatt actaattcac tcttatttt  aacataaatt gtggctatct atctctattc  153240
atttcaatta tatttctcat accattctat agatggggtg aaaagaaaag tgttaatttt  153300
ttaaaactcc atacctcaaa tactatatga atttatagtt gttattgcta aagcaattat  153360
cttacatctt ttcctccaaa acaaagttat gtgctggttt attttctttg tactcataag  153420
atgccttcca ttttagtaa cataagtctt gtctttctcc tattcttagc tacttaagca  153480
ttatgtagct taaataagca ctaaagattc ctatctgtat gaaaaaataa agattaaata  153540
aataagatct agaaagggtg acaaggtgat gcttcaaaat gaaccatacc aagccatcta  153600
gcgattgata aattactcac actcataatc acattgttgg aaagaagcca ttgacaattc  153660
agtttgtttc acaactgtct atcacatagt gagcacaact aaaagactac tttttgtctt  153720
ttactgcttg ttttgttgat caagtgactg attgtacaat gaccaacaag aagtctgatg  153780
tgtagagaaa aggggaacct ggcttttctg ccttactcct gatgcctaat tctgagcatg  153840
tgaatattat tctgtttctt taattctcca agtgaagcag cagataaacc atccttgttt  153900
ccattagctg tctaccctgt tcaactgtgt gtttctaata acataagaat aagaaagcca  153960
ccagggtgag cagggaaggc aatgagtctg caaggcttgt ggatagattt ctgttagtga  154020
ggctctagaa agttcttcca agattgatgc aatctgagaa gagttttctg tcaatacaaa  154080
ctccctgggt ttctcctttg tccttttact gcctgtgttt gttttgggtt ccagtaaaga  154140
```

```
tcaagtgact gattgtacca tgaccaacaa gaagcctgat gtgtggagaa aagggaacc    154200
tggcttttct gcattactcc taatgcctaa ttttcttgta ctgaaagtag ttttgctgt    154260
aagaatctga ggggaggagt catttcttca attttttttt ttggtctcct tttaatggtt   154320
tcttgatcat gtctatcctt attttctgt  tttcacaaat ttttgtggta tattttcctc   154380
tcatgacctc tgtctcaaga cttctttcca tccatctctt ctcatttcat cctgtagagt   154440
gtctgtggta agagccctgc attctactct ggccttgcca tgtgtggcct tgggcaagtc   154500
ctagcctcct tgagggtctt attttctca  tttgtaaaat gaaacagttt gatgagaagt   154560
tttctaaggt tccttcaagc tttgacaatc tctctcttct ggatctttt  cccatgaaaa   154620
atttcaactc ttgattagca tgtaggcagg gattattcca catccttata ggaatcacat   154680
ttctgctact gtccctgaat gctagagtcc attgattaag ttattcactg ctgcaattgt   154740
cagagctgat caaagaactc tgaaccagtg tgttactaga actaacaaag aaaatgccat   154800
tatgatgttc tagagtcttg aattagtaga agaggtttaa taagaaccct aagggattgc   154860
tagaatgtta aaaacaaaca aacaaaaaaa aaggttgaaa agtttagaaa attcactggt   154920
ctttgtgccc atcattttac ttccagggtt tagataatct cattttgca  atgaaggaat   154980
ggattagatc acaagttctc atcctagtag cacatgcaga atctttataa aaacacagag   155040
tagccaggtg cggtggctca tgcctgtaat cccagcactt tgagagcctg ggcaggtgg    155100
atcacttgag aataggagtt gaagaccaag ctggtcaaca tggcaaaacc ctgtatctac    155160
taaaaattca aaaattagcc aggcatgatg gcacatgcct cccagctact ggggaggctg    155220
aggcaggaga atcgattgaa cccgggagat ggaggttgca gggagctgag atagctccac   155280
tgcactccag cctggtgaca gggtgagact ccatcacaaa caaaacaaaa caaagaaag    155340
caaaaacaca gattactcag ggtccactaa gaccagtgaa gtcagttctc ttggtagggg    155400
gcagggtgac tgagcatgat gttttgtaatt ttaaaagtgc tccaggtgat tctagcgtgt   155460
atcaagcaag acttgtgaac cactgaacta catgctaaga ctcattttag ctctgatttt    155520
ctgtgagtca tagcagaggg ctcagcaaac ttttctata  aatgctaaga tagtaaatat    155580
tttcagcttt gtgggctgta tcgtctttat gacaactcaa ctcagtcttt gtagagaaaa   155640
gcagctgtac ataatatgta aactaatggg agtagctaga tgtgtcctgt gggccatagt    155700
tttgctgact cctggtctat gtcatagaat ttcctttga  attgatggac caccagcaaa    155760
tgatttttgt cctgtatcaa tcaatgatac atacataaat ctctacaaga catgtaaagg   155820
atgaggctta atgacagagt actttgggga agacataata ttgcaaaatt aagatgctta    155880
gagaaaaatc atattaaaat agtgaaaact gtgagaaggt attttgattt gttgttttgg   155940
attcctcttt ttgcaaattc ttttgaaata ttttcagtgg aagctacata gatccaattg    156000
tattcaccaa gctagattgt aattaagctc cagagtaagt aatagatttg atgagtgatg   156060
tccaaccttt tacatggaag agtaagtttg agtcttcctt tgcccattga cacacttagt   156120
accatgttta ccaaagttct tagttattga aatgggcacc agcatatttt gaaacgttgg   156180
tgttaacttg ggatatgcct tttgtcatgt tgcaaataga ttttgtttct gttttgtgaa   156240
gatcaccatc tctgtcactt ctgatagaaa aagtgacact gacttctcaa gtgatttgac   156300
acaggttaaa atatgtaaac catttctgta gagagcaagc tgtaataata tactaaaggg   156360
ctaggtttat agtataatat aaataactca tttatgctgt taataattta tagcaacatg   156420
gcatttgact gactttttat gtgctctagt catgtaagta atagatgtgg aaacatagac   156480
cagagtttca agaacatgtt ttgggcagag tctgtttct  tgctattatc tcttaagttt   156540
```

```
atgttcatgg cctaaagatt atgctaatgg atctgccttg gtcttgggtg tcaggtctgt  156600
gttagcgagt attgaaaagc atagtttttg cctactggga aggatttatg atttaaaagc  156660
cctaaatctc cccttttatg tacttcatac ttagaaaatt tttcctgtaa actgtgtgac  156720
ttttttacat tgtgccagtt ttctagatga ctctcgtcat atttatttct tgcaatcctt  156780
ctataactat cagttatgaa gtctctttat agtgttgcca gccaggtctc aggtgtgtga  156840
aatgtatttt ctattatgga ttttggggta tgatggcaca tagtttgggt gttaatgcct  156900
aatcttgatg tactggcttc tgaacaacca aaaggatgaa aggaaataga acaaatattt  156960
ttgtgaggga gaggagtctg gcttcttgac ttactctaga aaaagcctgt aagcctcctc  157020
ttccctcctt gtcacacaaa gtgacaaaga aaatcaagaa ttgttttctt cttggcttaa  157080
atgcatccct tataaagtaa ggctgagatc aggctgtgaa gctatctttt tgtcaagact  157140
gtcataattc caaaacactt tgttcttcta atgcttaggt tagtaacttt aaacattttt  157200
ataaagatag tgaggtccag ttttaaggat tgacccccttc tcaaggggct cagaagaggt  157260
tttggagaat aataaaatta aataatgaaa ccaataattt aaaccagatc atgatcctta  157320
agaaaaaatc ccatcaaatt tgggctaaac tctaatatac agaggtctgc acaacttatg  157380
tcaagtattc ttccccacaa atgaagaatg gggttcattg tgtcattggt tgggtctcat  157440
tttggcttca tcttctattt ctcaaagtct aagaaaagtg ctcctacgga agtgggtgtt  157500
ggctatcatg agactttgct gctggcaggc cagcttgctg ctctagacag agatatccct  157560
cgatcctcct tggacaactg ttttctgtgc acaggaagca gcaggctggg gttaaggagt  157620
ttgccaatcc agtcattctg ataattgctg aatatgaatt tctatccagc acaatctagg  157680
tagctacaat ggcacagtag ttttttatgta tcaggtgaaa atgttttaata ggcactctaa  157740 atgagagaaa aggttaagtg aggttaaaag ctcaatgaaa acaaatagat gagactaaaa  157800
atagttcaat aggttgtaac ttccatctca tccaaacagc aatgaatatt ttgaggctga  157860
ggcgctgagg ggtaaaattg cagcctggac tacttgctaa tgtagaccta cagcactgtc  157920
attcttactg cacagacact gctttctgca taggaggtag aataatgaat tcatttatta  157980
ttaacaaaga tttattaagt gactgcatgg tgctaaccac tagatgggga gggatgtttt  158040
gaactgtcca ttgtttgact ataacaagga acgctttgaa cgaggttact atcataggca  158100
gaatttgttt aacatgaagc ctatgagaca taagccacag gtcctctcac gtgcaggaac  158160
tcctttgaag gccctatact taatttttata tgcatagttt ggatttggat tcttttttttt  158220 ttaagagttc cccaaattac ttaagcttca ggctccacaa aacctggatc tacccctggt  158280
agcagctatg aatctttgac tatgaaatta agtgtacaag aaatatgact ttactttttc  158340
tgtgattgag tttattttct atttgagcac gcattccact gagtgaaaga aataatatca  158400
ttgaattcag agattttgct gggttctaag tggagtttac agaatgccat gatattagga  158460
attaaggagt gtgttgccct acatcatctt ttgtccgtgc tcactgtctc tgaggcactg  158520
atgttcctat gtgacctaga ggggcatggt ccaggtagat ggagtctgtc cttgttctca  158580
ctgtgagctc tcgcttgctg acccttcttc agtttcttcc atgcccctga ggggtaaaaa  158640
gattcaaatc tgaagctata tcaagccatc tgtgcataga cattccaagc aaccatgttc  158700
actctactgc tcccatgtca tgcaaggcac aggaagcttc actatggcat gagtatttcc  158760 tgggcttttgc cttggaattg aggcacgggc ctcctttgtt ctaaaattcc ccaaatctac  158820
ttgaggatag aaccaggatt tggttgcaag gcagaacttc tcttagagga cctggtatct  158880
```

```
aaaccctctt gttaccccca tttatggacc ccatttatgg ggtgaggaga gtgactgctt    158940
ctaatccatc ataattttg tctatggcta ctgttttgc atagacacta tgttttgagt     159000
ccttaggctt tggcttttgg cgcttaatgg ccaatattca catggctcaa aattttcaaa   159060
tgatccatat ctgacttgag tttcaaaagt cagtttttga aacttaaatg atcagaattg   159120
atttgttctg ctctggttct gatgtggcct ctccttccag aggtactgga ggtagaatat   159180
ccaaggtgga aagcccacga ctacaaggaa ttggttagta attcataatg ttagctgtcc   159240
acatctattc agtaatggca tttcagtggc tgcacaactg accatggtga aagtgtctgc   159300
acaagccact ttttcttcct gtcagaaaat gttctcaccc actgaattga atgactgtct   159360
gctcatatgc tgtgaatgag tgcccagtct taagattaaa tcacacgttc ttggctatgc   159420
atatttgggc atgctgtggg gagttataat aggctgtctt agagtcacat taagcagcta   159480
gacagacaat gagttggaaa gttacatttt ctaaatttga ttggtacatt ccatttgtca   159540
catttgacat tagaagttct ggattcaccc tctatggtga gcttcactaa tggagaatgt   159600
aatttgcaat gctcaaacac aagtcctaaa cagaaaacat tgtatgttac attccagtgc   159660
taccaaaata gtggttttga aagtcctat tttctaatac tactatgtgt aattttgagt    159720
catttagata gcaacagtta aatgttttat agattgtttg gaagtattaa aatgtgaagg   159780
attttttgtta tatagtgtct ttcctatctt gcttaataaa atataagttt agaattgtgt  159840
atagaattaa catgcaaaaa tatcaagtct caactttata cagttaatct acatttgtgt   159900
ataccccttca attatttcaa gagagggata ctattcttat gcaggataaa tacaataaga  159960
tattttaaat gaattttaac tacatctctg gcagtttcat ctcaatagta gttgtaattt   160020
tatctcccag accttattat agactagcag ctctctatga aaattagtga cagtgtgagt   160080
gtattaaat tcaaagttaa tcaagaatga ctgagtcaag agttagctac ccctgaaagt    160140
aactcataat tcagaattta aaatattaca tgtggaacaa tcatgactat atgccttta    160200
ctttctctat cattatttag gttgtgggct ttgggtcctt ttcacatccg ttaacgtgg    160260
gcttgacttc aaaggattat tttcttgaat cttgaataat tgctgaagac aattttgaaga  160320
tattttcaag atgaaggaaa ctgaagcaca gaatcactag agtgaaaaaa gaacttcaca   160380
aacagtgcag gcttgatcaa tggcatggga aaacaggcaa tacagttaga attgctaaga   160440
tggaattta acgttcaatt aaggatctat ctctaaactc ctctgcttta tccaccaatc    160500
attccatatt aaagatgaag aattgttccc atttcacctt ttgataagga aaaatagaaa   160560
taacagaagc aaatacactt tgcccacat ttttttccaa aaagaataat ttttgaagtc    160620
taaacgtttg gtgtaaataa gatgatgtgt taatattgta aaggaaagct agttaagttt   160680
ttgactgaat aaagccagca tcaataatta ctagtaagac taaaataag agcagtaaaa    160740
ttgtgtctaa tcagctacta atatctggga aggattgagc cacaggatca aagatggtat   160800
cttttaaaaa tagaagttga gtgaattcgg tcttcaaatt cttctttttt attcatttat   160860
atttatttac tcattagtat attcattcct ttattcatgt attgttcaaa tatatattgg   160920
gtacttatta tatgccaagt tgttttaaa atcacattcc aaattcccgt aagtcataat    160980
tattcagaga tgtatgtttt ttttaaaaaa aattgaacac ctttaaaaat tatcaagtcc   161040
ttttatttct gtatgcatta aagataaact ttactaaatg ttacatgaat agatttataa   161100
agcagataaa tatttaattt caaatataac ccttatatgc aattatattt tccttagcac   161160
taaaaatgaa tatttaagta atttatatta aaagtgtaat tatttaactg cagatgtatg   161220
ccaatgactt aaattgttta aagattatag caaagttgtt taaaattgtc taatcatgaa   161280
```

```
gagttcactt aaccacctgg ttgacacata aaattatagt tagttactaa ggtagttcga  161340
gagaaagaga agaatcttca gtagtggttt tgaggtgtgg tacattttat tataatatac  161400
cggttataca gcattgtgca gtgctgctca tagtagaaat aaattttctc tttgatgtca  161460
tctattccct tgtgtggctt acataactga gaattaggtg atcacaaaaa taaacaggcc  161520
tatacagagc ccatttatat aagtcctggt tatttctctt cagttaaact tttaattata  161580
tccaattatt tcctgttagt tcattgaaaa gcccgacaaa taaccaagtg acaaatagca  161640
agtgttgcat tttacaagtt attttttagg aagcatcaaa ctaattgtga aattgtctgc  161700
cattcttaaa aacaaaaatg ttgttatttt tatttcagat gcgatctgtg agccgagtct  161760
ttaagttcat tgacatgcca acagaaggta aacctaccaa gtcaaccaaa ccatacaaga  161820
atggccaact ctcgaaagtt atgattattg agaattcaca cgtgaagaaa gatgacatct  161880
ggccctcagg gggccaaatg actgtcaaag atctcacagc aaaatacaca gaaggtggaa  161940
atgccatatt agagaacatt tccttctcaa taagtcctgg ccagagggtg agatttgaac  162000
actgcttgct ttgttagact gtgttcagta agtgaatccc agtagcctga agcaatgtgt  162060
tagcagaatc tatttgtaac attattattg tacagtagaa tcaatattaa acacacatgt  162120
tttattatat ggagtcatta ttttaatat gaaatttaat ttgcagagtc ctgaacctat  162180
ataatgggtt tattttaaat gtgattgtac ttgcagaata tctaattaat tgctaggtta  162240
ataactaaag aagccattaa ataaatcaaa attgtaacat gttttagatt tcccatcttg  162300
aaaatgtctt ccaaaaatat cttattgctg actccatcta ttgtcttaaa ttttatctaa  162360
gttccattct gccaaacaag tgatactttt tttctagctt ttttcagttt gtttgttttg  162420
tttttctttg aagttttaat tcagacatag attatttttt cccagttatt tactatattt  162480
attaagcatg agtaattgac attatttga aatccttctt atggatccca gcactgggct  162540
gaacacatag aaggaactta atatatactg atttctggaa ttgattcttg gagacaggga  162600
tggtcattat ccatatactt caggctccat aaacatattt cttaattgcc ttcaaatccc  162660
tattctggac tgctctataa atctagacaa gagtattata tattttgatt gatatttttt  162720
agataaaata aaagggagct gaaaactgaa ttgcaaactg aatttttaaaa ctttatctct  162780 ctgtggttaa ttgcaaacac agatacaaaa atatagagag agatacagtt agtaaagatg  162840
ttaggtcacc gttactaaca ctgacatagaa acagttttg ctcatgagtt tcagaatata  162900
tgagtttgat tttgcccatg gatttagaa tatttgataa acatttaatg cattgtacaa  162960
attctgtgaa acatatata taggatgtgc gaaaagtccc tgtgtatcat gtgaaatggc  163020
ttaaaacaga acaccatagg tattcatatc agtgaatacc ataggtagct gaaagtgttt  163080
tttcctgggg tcgccaagat gaatgccaaa agtgatatca ttattataaa caatagccag  163140
aataggttgg tataaacctg gtagaaagcc ttgataaatt gactttctct cctcctgaca  163200
tcctgccacc cctttgcttt gctgatgctc atttgtccac taaattaaac tcaagcaagc  163260
cctagtaaag taatagaatt tgtggagtcc tcattagtat aggaagtttc cctgatgtga  163320
gattagtaat tagagatgta gcaaaatgag aaagaagtaa tatgcttaga tatttcattt  163380
tctctgaacc tgtatataca aaataggcca tgcgtgttca gtaactattc actgcaaggc  163440
actctctagg tactttgggg gaattggaaa ttactcacat aaggctatgg attgtgccat  163500
ttgtcaaaag acaaaatgac aacaaattta gtttaaagac ctcagtcagc tttatttct  163560 attctagatt tggacagtcc ttcatttcac aaattggagt aagtgttcca ataagttgag  163620
```

```
caaaggagct tggctttata gacccaaaaa aagggccaaa ggaagcagaa acaaagaaca   163680
ataagagaat tggtcatttc aaagttactt ttcttgaaag gtggggacaa ggagacagaa   163740
taatagaaaa gtcactgatt ggttaacatt ggattaagaa ttaaaacaga ggaaacttta   163800
agattgaagt ttgaaactga cttgtttggg aaatcaggct gtcttctttc ttgatttctt   163860
agaaggccgg ataacaactg agttttgctt tggtgaacat gggtgactcc atttttactt   163920
ttagtctggt ctgttgaggc ctcgtgagag agcttaatct aaaacaatga cttcctataa   163980
tttttgtttg acacatccaa agagggactc taatatttat tgagagctta tcatatctta   164040
agtactgttt aaacactttt atttgctatt acatttgatc ttattataac tctaaaggca   164100
gaaatgattg cttttatttt ccacaatgga ggaaactgag gttcaattaa gtgagtaagg   164160
aagcagggat cttaaaccca gataccattg ctcctcttta aggtggaag aacagaaaac    164220 atggggcagg ggaagagaga aagtttctgt cccaggacat gataatctaa aagggaaaac   164280
gtaagatcca ctgaaacctg aggcagattt attgtggcaa taacaaagct taagtttcac   164340
agaccttcat ttgcctgagc caactttgaa ggccatgtat ctaattttgt ttttataatt   164400
ctataatctt tattcttgaa aagagccctc cctccaaatt tacaagcttt gggcccccaa   164460
aatccttgaa atgcccttga ataagagata tccaggtaaa tgctatggga attcagagga   164520
ggaagcagtt agtatcagtt ggcggagagt taggctatta agagaaggtt ttatatagga   164580
agtggcattt agaatgaagc tttgagaact gagctgtgta tttgaacaag taaaggtggt   164640
gttgcagaat tttgctcctt agttctatta aaacccgggg ttcttgtcac atgatccgga   164700
aaatttaggc acacagatac attgaagcat gagtagagca ggattttatt gggcaaaaag   164760
gaaaaaaaga aaactcagca aatcgagatg gagtcttgct cacagattga atcccaggcc   164820
accacaaagg aactgaagag atcgggcttc tcccctgcat aaggtgcaaa ttccccatgg   164880
ctccacccac ttccccttag tgtgcatgtg gggctccagt ccacggtggg catgcccaga   164940
caagccttgg gcaggttccc tcatctgtgc aaaagcatct gatgtaaaca cttgaggggt   165000
ggttcggaga ttctctggga cccttttatt ttcttatctg cctaggcatt tggctgtctc   165060
agtgggtggg aaagggtgct ccaggcaaag ggcataacat gaggcaaagg gcatgcacag   165120
aaaacagtga ctggttcagt caggttgggg gatgccaaag gaagtaatgg gagacaagat   165180
tggagcaaga tagataagag attgtggatt tttttctttt tttatctata taaatacaga   165240
gacagggtct cactatgttg cccaggctgg tctcaaactc ctggcctcaa gtgatcctcc   165300
cacctcatcc tcccaaagtg ctaggattac aggcatgagg cactgtgccc aacctccaat   165360
tttggatttt gagagctaaa gcaatatagt cgaaaactca gataatccag gtagattttg   165420
ctattaggtg ctatttggtt cctggtacag agctaaaacc cttggaattt cctaagtgat   165480
aagagctaca ggagcatctt tgttatatg tttccccccc tagttcctga aatagctcta   165540
gagaaataca ggtgaataac atcctttgtt attcatatca agcccctatc aaccataccc   165600
cagtttctat ttatgaagtg ctttggga agtccctaaa gacaggagtg gggaaaggct    165660
ggttgtcagg gggatgggtt gaaactttca tcttcccccc ttgacctcca gggagggatg   165720
agtggctgaa aattgtgtaa aatcaacaat ggccagtgat ttaatcaacc atgcctatgt   165780
aatgaagcca cccgataagc cttaactgga acttttgga gagcctccag gctggtgaag    165840
acattgaggt gctcagaagg tggtattcca gagagagcac agaatctctg ttcccctccc   165900
cacattcatt ttgctatgca tctctcccat ctggctgttc ttgagaggta tccgtttata   165960
ataaactggt aacctagtaa gtaaactgtt accctgagtt ctgtgagcca ttctagcaaa   166020
```

```
ttatcaaacc taaagagttc atggatacgt gcaatttaca gatgcacagt cagaagcaca    166080
gatgacaatc tgggcttgcc attggcattt gaagtgtgtt gggaggcagt cttacaggaa    166140
tgagcccctta tcctgtgggg tctatgctaa taacagacag ttgtcagcat tgcttggtgt    166200
cgaaaaccca cattgttggt gtcagaagta ttgtcagtag gatagggaaa acagtttgtt    166260
ttcttttttt agtggtcttt ggtcatcttt aagagcaggg cttctcaaag tgtggtcctt    166320
gaaccagcat cacctgtacc acgtaagaac ttatgagaaa tgttcattct tgggccccaa    166380
caaagaatta aaaattctga gggtgtgaac ggggtctgag tttcagcaca acttcccgac    166440
catgctgatg cattcttgcc caagcatgaa agccctccct tgtttaagaa ggccattagg    166500
gccgggtgtg gtggctcatg cttgtaatcg agcactttga gaggacatag tgggaggatc    166560
acttgagccc tggagttcta gacaagcctg gcaacatgg caaaatgctg tctccacaaa    166620
aatcacaaaa attaggtggg cgtgtgttgt gtgcctatag gcccagctac ttaggagact    166680
gaggcaggag gatcgcttga gcccaggaga ttaaggctgc agcgagctgt gatggcacca    166740
ctacagcctg gatgacagag tgagacactg tctcaaaaaa aaaaagaaa aagaaaaaga    166800
aaaaagaaag gaaaatgaaa aagaacgcca ttaggtataa aggagcaatg gtaaaagacc    166860
agttgcaaaa ggttagggaa tgggtggtta ctgaaataag aagctatgta gaacactagt    166920
gttggtggca ggaagtagaa agcaagagca ctgctctgtg ggggatggtc atagcaaatg    166980
caatatggag gcatttgcct ctgcactgag gagaaaacta tcttttccaa gataggagga    167040
aaggagataa gtggaattaa agagaacctt tgagcacaga gttgggaaac tgaaggtatt    167100
tgtgttgtgc tccctcaatc tttaattca actataagct aaacccatga aacttgagta    167160
gtttcagtta tctgacttt ttcttctctt ttgatacagt gttggctatt ctgggtcttt    167220
tgcctctctt tatgtactta agaatcagtt tgccaatgta tgcaaaataa ctggctggga    167280
ttttgattgt gattggcttg aatctataga tggagttggg aaggactgac atcttgacaa    167340
tgttgaagct tcctattcat cattatgaaa tatttctcca tttgtttgat tctttgattt    167400
cttttatcag aatttagttt tcctcatata gtctttttaaa atattttgtt atattttgtt    167460
caagtatttt gttttttgagg aatgccaatg taaatggtat tgtgatttta atttcaaatt    167520
ccaattttc attgctgtta tataggaaaa tgattttttt tgcatgttag ccttatatct    167580
ttcaactttg ctataatcaa ttattgatag tttcaaggat ttttttggtca attatttga    167640
atcttctaca tagattatca tcatctgaac ttagttttat ttcttccttc ccaatctgta    167700
tacctttatc tcctttttctt atttcattag ctaggacttc cagtatgatg ttgaaagtag    167760
tggtgagagg ggatatcttg gtcttgttct tgatcttagt gggaaaactt caagtttctt    167820
atcattaagt atgattttag ctggagggtt tttgtagaag ttttttttttt ttaagttgaa    167880
gaagtctcct tctattttta gtttgctgat ttttaaaaag aatcaggaat gggtgttaaa    167940
ttttgtgaaa tgcttttctg caactattga tttgagcact ttatttttct tctttggctt    168000
gttgatgtga agtacattaa ttgattttttg aatgctgaat caaccttttg tacctgagat    168060
taatcccgtt tggttgtggt atataattat ttgtatacat gttgagttcg atttgctaat    168120
acttttgag aattttttgca ttggtgttca tgaaaaaata ttggtgtgta gtttttttgtg    168180
acatctttat ctgcttatgg ttttaaggta atgctggcct catagcatga gttagggagt    168240
atttcctcta cttttacatt tgagaagaga ttgcagagaa ttagtaaaat tcctacttta    168300
aatatttgt ggaattcacc agtgaaccca tctggacctg gtgctttctg ttttggaagg    168360
```

```
tcattaatta ttttaaaata gatataggcc tattcagatt acctattttt tctcatgcga    168420
gttttagcag attgtctttc aaggaattgg tctatttcat ttaggttatc aaatatgtca    168480
acgtagagtt attcatagta ttcttttatt atccttttaa tgtgcaaggg atctgtagtg    168540
atgtcccctt ttttgtttta ttgatattag caatttgtgt cacatctttt attttgcttt    168600
gttagccagg ctagagatat ctctatttttt gatgttttttg atgaaccaac ttttttgtttt   168660
attgattttc tctgttgatt tcgtgatttc aatttcatga ttttttaaatt atgcttacat    168720
ttgatttaat ttgatcttct tttgctagtt atccaaggtg gaagcttata ttgttaagat    168780
ccttttgcat tcttatgcat tcaatgatgt aaatttccct ctaagcactg cttttttctgc   168840
atctcacaaa tattcatgag ttgtattttc atgttcattt agtttgaaat attttttaaat   168900
ttctcttgat atttctcttt tgacccatgt gttacttaga agtgtgttgt ttaatcacca    168960
tttttaaaaa ttttctagct atctttctgt tattgatttc tagtttaatt ccattgtggt    169020
ctgagagcat atattgtata attttaattt ttataaaatt tgttaaggtg tgattttatgg   169080
cccagaatgt ggtctatctt ggtgaatgtt ccatgtaagc tttggaagac tgtgtattct    169140
gctatatttg aatgaggtag tctatagaca tcaattatgt ccagttgatt gatggtgctg    169200
ttgaattcaa ctatgtcctt actgattttc cacctgctag atctgtccat tctttgcaga    169260
gggacactga agtctccaac tctagtagtg aatattctat ttcttgttac agttttatca    169320
acttctgctt catgtctttt gatgctttgt tgctagaaac atacacatga agaattggta    169380
tgtcttttgg agcatgaccc atttatcctc ataatgcc cctcattatt tcctcgccct    169440
gatgtctgtt ctctctgaaa gaaatatagc ctctccaggt ctcttttggt tggtgttaaa    169500
atgacttaac tttctttatc cccttactt ttagtttata tgtggtttta aatttaaagt    169560
gggtttcttg tagacagcaa atagttcaga gttgtttttc gatccacttt gacaatcttt    169620
gtcttttaat tggtatattt ggactattga tattttaagt gattattgat atagttagat    169680
aaacatctac tatatttatt actgttttct gtctgttaca ctacttgttc tttgtttata    169740
tttttattgt ctactctttt tctttccatt gtggttttaa tcgagcattt tatatgtttc    169800
cattttcttt tcttagcata gtaattcttc ttttaaaaaaa catttttttag tggttgcccc   169860
tagagtttgc aatatacatt tacaactaat ctaagtccat tttcaaataa tactaaataa    169920
tttcatgtgt agtgcaagta ccttttaata ataaaacact cccagttcca ccttccagtc    169980
tcttgtatta tagctataat ttagttcact tacatatatg ggtataccta agtatataca    170040
ttatcatatt tatgattgaa tatattgatg aaattattt gaaaaaactg ttatcgtaa    170100
atcaattaag agtaagaaaa atagttctaa ttttattata aaatgaaata ccttcattta    170160
ttcattctct aatacactttt ctttctttat gtagatccaa gtttctgacc tgtataattt    170220
tcctttttctc tcttcagctt ctttgaacat ttcttaccag ccagacctac tgacaacaat    170280
tttccccaat ttttgtttgt ctgatagaga ctttatttct tcttgacttt tgaagaataa    170340
ttccacaggg cacagaactc tagattggtg atttcttccc ctcaaaccct taaatatttc    170400
attccactgc cttcttgctt gcattgtttc tgagaagtta gatataattc ttatctttgc    170460
cttttctatag gtaagatgtt ttttcctctg gcttctatca agattttttc tttatgaaca    170520
tgatatgcct ttcttttga acatgatatg cctttctttt tgaacatgat atgcctttgt    170580
gtcggatttt ttttggcatt attctgcttg gttttctctg agtttcttgg atatgtggta    170640
tggtatctga cactaatttg gaaaaattct cagtcattat tgcttcaaat atttcttctg    170700
ttctttttttt tcctttattc tccttctggt attcccatta catgtatgtt acagttttttg   170760
```

```
tagtcatccc gctgttttgg atattctgtt tttttcagtt ttttttttcct tcgcatttca  170820
gtgttggaag tttctattga catattctca acctcagaga ttctttcttc agctgtgttc  170880
agtctaccaa tgagtccatc aaaggcattt tacatttta ttacagaatt tttgacctat   170940
agaatttctt ttgattccat ctttgaatct ccatttctct tctgcttttc atctgttctt  171000
gcatgttgcc tacttttcc atgaaaacct ttagcttttt ttttttttct ttttgaggtg   171060
gagtctcact gttgcccagg ctggagtgca gtggtgtgat cttggctcac tgcaacctct  171120
gcctcctggg ttcaagtgat tctcctcctc agcctcccaa gtagctggga ttacaggtgc  171180
ctgccaccat gcctgagtaa ttttttgtatt tttagtagag atggggtttt atcatgttgg 171240
ccaggcgggt cttgaactcc taacctcaag tgatctgccc accttagcct cccaaattgc  171300
tgggattata ggtgtgagcc accatgccct gcctttagca tgttaatcat agttgtttta  171360
aattcctgat ctgttaattc caacatccct gtcatatctg actgtggttc tgatgcttgc  171420
tctgtgtttt caaatggtgt ttttttttt ttgccttta gtaagccttg taattttta   171480
ttgaaaggtg gacatgatgt gctgggtaaa aggaactgta gtaaataggc ctttagtaat  171540
gtactggtag gtgtagcaga gggtgaggga agtattctgt agtcctatga ttaggtttta  171600
gtcttttagt gagcctgtgc gcctgcagct tggaagcact tgtgaagtgt ttttcaccc   171660
cttttggtgg gacatagtga ctagtgtgag cgggagttga gtatttccct tcccctaggt  171720
cagttaggct ctgaaaaaac cctgataggt taggcatggt aaaatagtct cttttgaggg  171780
caggcattgt tataagaata gaatgctctg gggccaggtg cggtggctca cgcctgtaat  171840
ccccgcactt tgggaggcta aggcaggtgg atcacctgag gtcaggagtt cgagaccagc  171900
ctggccaaca tggtgaaacc ccgtctctac taaaaataca aaaatcagcc aggtgtggtg  171960
gcacacacct ataatcccag ctactcagga ggctgaggca ggagaactgc ttgaacccag  172020
taagtggagg ttacagtgac ccaagattgt gccactgcag tctagtctgg gtgacagagc  172080
aagactccgt ctcaaaaaaa aaagaatgct ctggcatatt tgaaaatggt tacttttccc  172140
ttttttctc tgatcttcac tgtgagaacc tggtaagcat cctataggca aaattcataa   172200
aagtatagaa gtcggccagt gacttggacc cacttggaat tttcttgctc tcacatcatg  172260
cacactgaat ctccagcaat ttttcactta cagtttaggt tttcctaccc tactactggt  172320
tctctcagag gtttctgctt attggttct gttttgtaag ttgtgattct ctgtacctaa   172380
ctgcctgtct cccatttgg ggggcagtgg tttgccctgt gacctcactt ctctgacaga   172440
tctaagaaaa gttgtttatt tttcagtgtg ctctgctttt tacttgttac gatgaagcca  172500
accactttca gaatttctac aaaccagatc agaatctgga agtcctgttt ttttattttt  172560
tttatccctt tgtttagcat gttacctatc ttaacacatt ttaaataagt gaatgcatag  172620
cttatatcta cttctaggtt atatgcttcc ttagaatagg aattgattct taaaatgtcg  172680
ttctgctcac gcctgtaatt ccagcacttt gggaggccaa ggcaggcgga tcacttggg   172740
tcaggagttc aagaccagcc tggtcaacat ggtaaaaccc tgtgcctgca aaaatacaa   172800
aaattagctg gcatggtgg tggccatctg taatcccagc tactagggaa gctaaggcat   172860
gagaatcact tgaacctggg aggtggaggt tgcagtgagc tgagatcgcg ccactgcact  172920
ccagcctggg tgacaagagc aaaactccat ctcataaata aataaataaa taaataaata  172980
aataataaaa ataaaaaat aaaataaaac aaaaattta ttctgagcag tctctgaaga   173040
atataaattc tactgccttg cctttagaac ttataacagc atctcgcaaa ctatcacaag  173100
```

-continued

```
atgctccaaa catacttctt atgtgctgaa ttaagaagtc aactcaaatt tagtatacta  173160
gtaatatttt tggatatccc aaaacactgc cagctcagct ttaggctgcc cttcttgggg  173220
gggaaaaaag cagttgaaat ttaggactta agtgggcatc tcgtttaatt tttaatggat  173280
ttctatgttg ttggttatgg tgaagaggtg aaaagaataa atattctgtg cagaaaaatt  173340
attcagtctt catgtgaaaa cactttgtcc atagcaatta ctttatgaaa aagatgtggt  173400
attactttct ttgctcttaa ctgagaccct taatttaaag aacctatact ttacaagttt  173460
ttattttcaa tgcatgaaaa atgtagcagc tatttcacaa cctttacttt taaaatccat  173520
ttttcttttt aatctcaaat agttttttct taaaacctt tgactttta tctaaattgt  173580
aatagccaga gcaccttccc acaactagaa tatctcatcc ttttgtctt ttcttttcc   173640
tctcaaaatg cctactggga acttaatttg gagtcagatt cttcatgata aatctggact  173700
taatcaaaat tcctcatatg gtatattgta tatatcacag tactggatag tcctctgatt  173760
aaatagatat ttgatagtac tttaaggtct atacttttgg atgaacttaa ctgctttctc  173820
catttgtagt ctcttgaaaa tacagaaatt tcagaaataa tttataagaa tatcaaggat  173880
tcaaatcata tcagcacaaa cacctaaata cttgtttgct ttgttaaaca catatcccat  173940
tttctatctt gataaacatt ggtgtaaagt agttgaatca ttcagtgggt ataagcagca  174000
tattctcaat actatgtttc attaataatt aatagagata tatgaacaca taaaagattc  174060
aattataatc accttgtgga tctaaatttc agttgacttg tcatcttgat ttctggagac  174120
cacaaggtaa tgaaaaataa ttacaagagt cttccatctg ttgcagtatt aaaatggcga  174180
gtaagacacc ctgaaaggaa atgttctatt catggtacaa tgcaattaca gctagcacca  174240
aattcaacac tgtttaactt tcaacatatt attttgattt atcttgatcc aacattctca  174300
gggaggaggt gcattgaagt tattagaaaa cactgactta gatttagggt atgtcttaaa  174360
agcttatttg cgggaagtac tctagcctta ttcaacagat cactgagaag cctggaaaaa  174420
caaatcccgg aaactaatta ttatgtgcca gttatataaa caagaagact tgttgggta  174480
caaccagtg attccttgcc tttgaaaaat gtgtcagata tcatgcatta ccagcagttc  174540
aatgatataa ggaaaccaga gtaatagcta aaacctttaa agctaaaacca aagatttaca  174600
aattgcctct tcatccagtc tttcccaacc taaaaactga gttctctaaa aattttagta  174660
ttttttctg aagaaaaggg aacatggaca tttatctaat cctcattaga aatctgacta  174720
atgataacaa ggatttagac ctcaagcact tcttaccaaa attcttgata tgaccttata  174780
gcaaattact ttcacctgtt gaactttcct ttcttttatt cccctgtacc tcacctgcac  174840
tgggcatatt caagttgctt atacaacact ttactattgt gttagaaaaa tcatgacaca  174900
tgatgaatgt gtttgtgcaa catgagctga ttcataaatg aaaatgtgca ttgaaattcc  174960
acaatatttt aaaattagga gtttatctag caattgaaca aaattgatta aatccattat  175020
tgttagatc agctaaatta cataagttca ttcatctgct cataaatcca tccattcttc  175080
catctggcta tcccttagtc aattcaaata aatatttatg gggcactttg ggtaagccag  175140
gtgctaagaa ttcaatgcaa aacaagatag actccctgt ccttgttgaa cttatatttt  175200
tggtacaaac aaaagcaata atcaagaaaa ataaaaaaa gtactgattg tgattaataa  175260
tatgaagaaa ttcaacagag tattgtactt aacatttgat tgatctgatt ttctcagttg  175320
tctgagaaca acatttgtg aaaatctcat tgtagagttc ttacgatgga taggggtca   175380
actgtgtcat tattgcttat cagcttatcc caaagaccta gtttattacc agattgcaaa  175440
tagtgttcaa taaattattc ttattaaggg ttgttatgta ctctaaaaca tttattgtgg  175500
```

-continued

```
tcccttcact ggttctggtt tacaaactta cttttctatg atgacatagt atagaaattg    175560
agagtgaata tttagaagtt cattttatt atatatttt gaagtattga tatgtagtga     175620
attagaaatt taaaagaaa acaaaactgt ccttcactac agattgaaaa gcattatact    175680
aaaagaccat ttgctcagtt atagtatata aaggccaaat gacttaaaaa caaattatgt   175740
aaggagaagg aaacaaccat ttattcagtg ccactaactg tcagccagtt ttttcagtgg   175800
tcagttaatg actgcagtag tgttctacct tgctcaaagc accctcctca agttctggca   175860
tctaagctga catcagaaca cagagttggg gctctctgtg ggtcacctct agcacttgat   175920
ctcctcatgc agtgcatggt gctctcacgt ctatgctatg ttcttatggt ctttaggtaa   175980
caagaataat tttcttct ttccttacta tacattttgc tttctgaaat tcccttctcg     176040
ccaatccagg tgaatgtcag aatgtgattt gacaactgtc caaagtactc attcactgag   176100
gagtggtaag gccttcgccc aacctgcctt ctctgggaat atactgctgc ctgaacatat   176160
cattgtttat tgccaggctt gaacttcacc aaattaattt attagggtca acatctaaat   176220
attagaacta tttcagatta atttttaagt cgtatccact ttgggtacta gatcaaattg   176280
caggtctctg cttctggctt gagcctatgt ttagagatga tgtgcatgaa gacactcttt   176340
gcttttcctt tatgcaaaat gggcattttc aatctttttg tcattagtaa aggtcagtga   176400
taaaggaagt ctgcatcagg ggtccaattc cttatggcca gtttctctat tctgttccaa   176460
ggttgtttgt ctccatatat caacattggt caggattgaa agtgtgcaac aaggtttgaa   176520
tgaataagtg aaaatcttcc actggtgaca ggataaaata ttccaatggt ttttattgaa   176580
gtacaatact gaattatgtt tatggcatgg tacctatatg tcacagaagt gatcccatca   176640
cttttacctt ataggtgggc ctcttgggaa gaactggatc agggaagagt actttgttat   176700
cagcttttt gagactactg aacactgaag gagaaatcca gatcgatggt gtgtcttggg    176760
attcaataac tttgcaacag tggaggaaag cctttggagt gataccacag gtgagcaaaa   176820
ggacttagcc agaaaaaagg caactaaatt atatttttta ctgctatttg atacttgtac   176880
tcaagaaatt catattactc tgcaaaatat atttgttatg cattgctgtc ttttttctcc   176940
agtgcagttt tctcataggc agaaaagatg tctctaaaag tttggaattc tcaaattctg   177000
gttattgaaa tgttcatagc tttgatagtg ttttcagaa gaccaaattt acagtgggag    177060
ccttgggctt ttgttttta acagctcttt tttgttcctg cttcagtggc ctgacctcca   177120
agttagcaat cgccaggttg agaaatgctt tgcgagacat aacagatgct cctgaaataa   177180
caaacacttg gaatcatgag gtagtggaat tgaaaataga aagtgtagtg attgtttttt   177240
gttatttgga tgggatgaac aatgtcagat tagtctgtaa ctattttttt ttaatgtcac   177300
tctgatttgg tcacaaagga tctctagtct cattgcctta gtatcattct acgaattaga   177360
atgtgttact gtgtaagagc acttcttgta tatgagagaa atagcaacag ttccagttta   177420
aagtgatata aatggaaacc aagaaatgtc tttactggga ccaaatctgg acagcattta   177480
ctgtattttt gctggtattt tctctagtct ttccgggtat attcacattt aatgatcact   177540
tttctccctt tgtgctaatg gacactgaat ccattccact accatagttc ttgctaatac   177600
tactctactt tttacacaaa attaaaatgc caggagcacc tccaggtaga ctgactataa   177660
atctagactg aaaaaaaagc ttgtatttct taacagatta ccttgtggaa catttgctcc   177720
tttcaactaa tgaggcacta aatattgtaa ctgctcaact ggtgctttta atttatttgt   177780
ctagactttg tcatgttgcc agaagcttta tcctggttgg agttttgaaa acagtattgt   177840
```

```
ttcttcagaa agaaaaaagg gattgtcaga tgatctaaaa ataaagaaac actggaaata 177900
caagtatccc aaggtgatag cattaggcaa gataaaaatg ttgaaaagcg aaaaagaact 177960
ggttgataga gaagtgttgt tattcagtag aacctaagtc ttgtggtccc attttttaatg 178020
aaaaatggtg aatttttttgg tttttattgt tcttgttcac acaaatctgc ccattagaat 178080
aagccaagcc ctaaaaatta atttcagttt cactgggaat cctttagttt atctactatg 178140
tagtagagag gttttgtttt attgcatgtt tgacgtagga acgtatatat gcaagacatg 178200
gaggaaaacc aagtgggcca gagttttgaa aattctttat ctttttctttc tgccaaagtg 178260
agtctcccaa gtttgtcttt tttttttcat ttccactctt ctatggtttc tagcattata 178320
taaaccaaac aaaaaaaata cgttcagaga ttccttcaga aatgctggat gatcttgata 178380
tcgatgcttt tcatatatgt gtttatgatg ctggtttctg gggctggctc tcagtatcac 178440
aaagatgtct gtaaacagaa tatgctattt cttctttgtg acaaattttg aacattatgt 178500
gaatgtccaa gaaagagcaa aagagggcaa acttctcata cattttttgat gtcgaaacca 178560
agagacgctt ttatttttcct aacttttctt tgaaagttca aattaagtaa ttttatcctg 178620
tcctaaagtt taaaagaaa aaaaaaagga agaaggaatt aaaaatccaa agaaaattat 178680
gtttgtttgc ttttctgttt ttttcttcct tccaactccg agactttgca agggcatagt 178740
tctgaagatc tctgacactg agacattaga gatctctgta tcaatggatc atttgttttc 178800
agacatatga aacaggaact ttgaacaaga aatttcccct cttttttctca tagtgatcct 178860
gagacatcag ctgtggaatc acaacacgtc attagttttg gcaggtcctt gcaggtgttt 178920
tgttttgttt tattaatgtt cttccctcct gtagctagac agcaatcttg gagaatctgc 178980
cagcttggaa gactattgtg taaatttcaa ggtggagcct cctttaattt gttctgtgtt 179040
acctgtgagc tgtgaggtca tgaagaggag acaatgaggc taatcatgag agccccattg 179100
gtttaggcaa ttagaacaac aagatctaaa atggtttatt agccttgaat tgtgttaagc 179160
acataattca taaaaaacag aaaaaaatatt tttaaatgta tgtctaaatc ttcagttaca 179220
agtttgaaag gtgacaaact attctgagga aatgattagg cctattcttg caacgagtct 179280
ttatgatctg aaaagaatct atgtccacac ataactccca cctcaaagat ggggcatctt 179340
ttgctctggg agatatcaaa tgcgaccaaa acaagtgttt gtagatttga atgatgattc 179400
agcagtgtag cagttctcac tcattttata ataattaaca acttaataat taattattaa 179460
actcctacat gcttaacatt ataagtatga aacttctgt ggttacataa aagatataca 179520
tagcacttgt ccttgatctg tcacagtgag gtcccaatcc aacctatgag cttcaaatga 179580
aaagttcaaa attacactca ttgtcataag tcagagatca aaggaagaaa ggatttaacc 179640
aaaatgataa attaaatata ggtgattaaa tatagtcatg gttcaaggca tgggccagtt 179700
agggagtgtg atgtgggtaa ttatgaaagg ccagctccca agccctgttg ttgctactcc 179760
cccacatcag tcatccttcc ttttttttcta cttctactgc agtgccttcc tcatcttttc 179820
ccttgcatcc ctccattata tgagtcatac aaattagact tttcaaagca acattaacat 179880
tgtgtgaatt tggggttttt gactaatccc aacattccac ccccacattc cagtcccaca 179940
tgggatttgg agccttgttt ataaacctgg cacttctaat atatcttatc ttagagtaat 180000
ccttgtatttt gtttaatttc cacttagcat tgtaaatact tgcaggtatc ctagttaaga 180060
aagcaaggtt taaacacaaa atcatcacca attaaagcag gctagataaa gaatgtaata 180120
gaaatgctag ataaaacaga ttttttctta ctaagttttc tgtcccttat agagtgcata 180180
acacaataac ttgcttgata agaattcaat gtacattgtt ttgtgctgaa tcactaaatg 180240
```

```
cttgatttct gtaacaagag attgtggttc catcagtatc tggattttag tctgtgtaat  180300
cttaggcaag ttatttgatt tctctgtgcc tctgttttct tgtctgtaaa atgagtataa  180360
tggtagtaac taattcattg tgttttgtg aggattaaat gagttaataa ctagtactcc  180420
tccctggcac atagtaagta caatatgctg tgctgtggtg gttgttatta tttttatag  180480
ttccttgagc aaaagaaata atgtccccat cttagtataa tattggaggt atataccata  180540
gaagtgaaca aaagaatata gtttcacaaa gaaagtgata attaaggcgg ttcataaagg  180600
gtcataaagc ttgtagattt tagaaatgtg ggggcatgag gatgtggaga gggtattcca  180660
ggatgccaga cagggagatt atggatgagt actaagatga gaactagaaa aagctgaggg  180720
gcaaaaggtc agaggaggcc acaagttagg gagtattagg aaaaagaagt taatacttga  180780
caagtgccaa catggcttca cgaggaatgg gttgggcctt tttgagtgag gaagaggctg  180840
gtgaaagggt ggtggaggac actgctgctg ctgatggcat ggggtgtagg tggcaggaga  180900
ggcagggaca tgagctagga aactctccag ctatgaagtg atgagtctgg agtaatataa  180960
ggacagtagg ggtggagtgc tgaacttaag ggaggagaga aaaataattg gtatggaagt  181020
aggtacaatg caattttatt atttctgagc ctaaaaatgt gaaattttg attatttggt  181080
cagaccaggg aagtattttc ttttatgcta tctctgaaaa tgtatacact aaaaagttgt  181140
agtataaaaa ggttgtaaag cattaagtaa ttttagagga aacaataatt tggatatttt  181200
acatgcaatc atttatatgc aaatatatgt aaatattaca aaattattct ctatttgtta  181260
caaaccttaa atatttttga ctgaggaata ttttattcat ctaattatag ctactttgtt  181320
ctaactaata gatattcttg aaaacaaagc aacacttttt tggagacaga gtcttgcact  181380
gtcacctaga cttgagtgtg ttaccttgaa ctccagggct ccagtgatcc tcccacctca  181440
gtctcttggg taggtggatt acaggcccac actaccatgc ccagctgtat tagtccatcc  181500
tttcattgct ataaagaaat accggaaact gggtaattta taaagaaaat aaatgtaact  181560
ggctcacggt tcttcaggct gtacgggaag catagcagca tctgcttctg aggaggcctc  181620
aggaagtttt caatcatggt ggaaggcaaa taagaagcag gcatgttaca cgacgaatca  181680
ggagcaagac aaagtgaggg aggaggtgcc acacactttg aaatgagcag atctcatgag  181740
aacagcgcca agaggatggt gctataccgt tcatgagaaa tccaccccca tgatccagtt  181800
acctcccacc aggccccgcc tccaacactg ggaattacaa ttcaacatga gatttgggca  181860
gagacacaga tccaaaccat accaccagct aataccaaaa aaaaaaaaaa attttttttt  181920
taagacatgg tcttactatg ttctacaggc tggtcttaaa ctcctggcct caagtgatcc  181980
tcccaccttg gcctcccaaa gcactgggaa ttcagacatg agtaacagtg cctggccaat  182040
acttattttt aaacattctc taccataaac ttaggatctt gatttgttca cattgaacag  182100
atttttatta tacagattga atttataaga aaatgttgca gacattgtca aaaagggacg  182160
tccaaaccac tgtgatattt ataagcattt gggccacatt ttgatagaac tatacacgga  182220
gtgtgtgtgt gtgtgtgtgt gtatatatat atacacacac acattattta tatatatgta  182280
tatatgtata tatatatatg tatttatata tatgtgtgta tatgtatgta cacattattt  182340
acctacctac tgtgtgagtg tgtgcatata tacacgcaca cacacacaca caaatatata  182400
tatttcccctt ctgagacaaa gccaaacagc actgtatgct taaagaaaaa cagtcacact  182460
tcccacttat gtaatttata ttcacatccag tcaccacacc agccaaactg ctttattgtt  182520
ttttgtttga catccaatgc taaagcataa tgcctgttgc agtgaaatat acatgagcaa  182580
```

```
ccctgagaac tcaatatagc ctcacgtgtt gccactgagt tgagttgagg agtcaagctg  182640
tagcaaaaag gtttgtcacc gggtgagtaa tggtgctctt attttctct gggtctcaag   182700 aagtgctctt tatgacatat atggcattaa ataaatatca gatatttgca catcctaact  182760
ttcctattgg tgaagtttct taaaagagag ataaagggcc attgtgtgat tgatagtttc  182820
aggtatattt ttgctgcaca gtcagtccga gtgtaccacg tagggcaaac cacgtaactt  182880
ctcagggcct tgactgtttc atttgtaaac cagagaaaag gacttgggtg acctccaaag  182940
acctttcaaa tttggagatg agtttgtgga aagttcaaac agtttagaaa acagaactaa  183000
gacacccact ggcaccccctg gaagcaagag agtgccaggt actatttgta atacaggaat  183060
gaaataccta attgtatgaa attgaattct aactgaacca gtttgttcag ttaaattttt  183120
tttttcaatt agagtgctta cttcagtatc taacactaga cagtaaactg tagcaaaaag  183180
acctacagaa tttctgaatg gtatcaaatt caccacactt aaaactttgg gatgtctaat  183240
ttcaaccaac agcttctttt cttcataatg ttgaatatat gtgtatctat tttagctaaa  183300
tttaatatat atcaatatac tttgatagat atttttatata aactattaga ctatagtatt  183360
atgagtaaaa gacccaccat ttcccaagca attataaaga acgatcaaaa ttttaatggg  183420
ttgttagtat tatttcttta aagattgtga tactgataaa tatttggcca cattttaata  183480
gaattataca tgggatgtgt gtgtgtgtgt gtgtgtgtgt atatgtgtgt gtgtatatat  183540
atatggcagt agagatatat atatctacac acatctagat atatatatac atgtatatct  183600
atatatacac acatatatct gtgtgtatat atacatatgt atatataccct acatacatat  183660 gtacatatac atacatgcat atatctgtac atatatatat agtgtgtgtg tgtgtatata  183720
tatatatata tatatatttt tttttttcctg agccaaaaca aaatactagg ttgtaatagc  183780
tgttctttca gaaggaagaa aaacaacatg tgctgaactc tgagtttgat gtttttgtat  183840
tttacttcct attttcatat cagtccattt atttattcag gaagaattta ttgagcatat  183900
attatgaaca cagcttttgc taaggacagg gtatgcagca gttatggcct agtaggagat  183960
atggatgtta aaaacaaaat gctcacaaat gcacatataa tcttaatact cattgtaagc  184020
tatgaaagca gagtgtgagt attatgagac catatgttgg gagattttat ttggtattga  184080
ggatcaggaa agataccct gaggaagtga tatttaatt gaaacctaaa gaaagcagtt   184140
ggccatggga agaaggtagg gaatgagatt cccaagcaat aggaatccaa tgtgtgaaga  184200
agctgaggga gtgaaagaaa gctagtgtgg tggcaggaag aaagagaaga gaatggagaa  184260
gggcactaaa tgagtcagag aagtaggagg ggctaaacca tgtagggtcg tgtaggccat  184320
cttaaaggcc tgagtgtagt ggaaaacctt tgaaggtttg ttaaaaggtc aatgaaatgt  184380
tctaatttct gttgtagtga attgcttga ttgctgaatg cgaatggatg ggtagagatg   184440
caagagtgaa agggaagaaa tcaattagga ggctcttgcc ctgctccaga taggactgat  184500
aattaatttt atttgggaag atcagggaga aagataagtc atgaatgact cccaagtttc  184560
tggattgaag aaatgaaggt accatacact gagatggaa agcctagggg tagagtagct   184620
ttgagaagaa aggtagcatt tccccattc ataaacatg gaagaacaaa gaggctggat    184680
tcctgtttgt agacataccct tccaggccag aactgcatta ctacaacatc tttgcaagcc  184740
acattgcctt tcataactct gtgtcagtgt tgatgccgta acatctttgg ccttccccct  184800
accatcctcc cgcagtcctc catgataatg ccattattcc gtttcaaatt gtgtgcttcc  184860
attggatgtg tgagtctcct tgaaagttat aatgaggctg tagcccatat gaaatgcttc  184920
aactcaggtc ctgcatagga agaggaagct aatctctcca ggaactgagc ctgtggctag  184980
```

```
agggatggat aattgtttaa ataaagaata tgctgctgag tactgatggg ctctttatgt   185040
acccatttgg ctgctgctgc ccaacccttta atctttcctg agctttaaat aggaaggaaa   185100
aaatggtcca caaaggattt gagccatttt gctgtggtga tgaggagcac gggtttagag   185160
acaaacactc ctgtgtttga attccagctc ctactatctc ctagctaagt gaccttggac   185220
aagtcactta ccttctccaa cctgctgttt cttcatgtac gtaataggat ttacctcatg   185280
aggttgacat gaagattgaa agaggtaaca tatagaatga gcctgtccca ggacatggtt   185340
catgataagt ctgccataaa tgggagctat gtgtcccacc cttttggagg agataactgt   185400
tctgtagcag gtaatatatt gtttgatact tggttaaccc ttacaattat catttcctgt   185460
tcttctcaat aatgctagaa acctttttatt taaagaacca caatataaaa tgaaaaatat   185520
ataaaaaaag caaatggaaa aattctattg gcaaggcttt ttaactttat atactaaata   185580
aatccaattg cttaaataat gaactgactc aagttctcag cactgcttct tgtttaattc   185640
tctttagttt ttcagaattc tccaataatg acctttgtct actctcttca gtttattcag   185700
aaattacttt tatttacata gaagtttgga agtggataca caaacatatc cctcacatat   185760
cttatgatcc tatgagtcat atactcatct cttatattcc ctctgtaaag caatgtaggt   185820
acctttcagg aaggtgattt ttatgtaggt tgagaaatat cagcatggag gtcctagctg   185880
acctctctag agagtttctg agacatttga caacaacttt ttctttaagt catcagttat   185940
gccccggggt atgaaatttc taacatgatc ctcagtaaac ttggctgcct tgctgaggat   186000
actctccatc tgcctgagag acacagacac cattaattgg gaattgactt gacttgtgtg   186060
gttccttgtg gaccagatgg ccactaaata ttctcatttc aaggcaattg gtaaaaacta   186120
cacttcaaga aatttcattc ttaattcccc ttagtggatg ttattaacca aaggcaaaag   186180
aaaaaaaggg taaaaaaaat attctaaatg ttaatatcaa aaatattatt ttcaattcac   186240
cccaggcaca gagaactaag tattattatt gctattgcac cggcattccc caatgagaca   186300
gtgatttttct tttaagacat ttttaaataa tataggcaga attaagtaga cggtgatctg   186360
gtaagtagat gttttcagggt aacagctgtg caatgctcca tgcagggaat tagattgtca   186420
ttttattcct taccaggaac atacattcag ttaaacaatt atttgacttc tgctcttcca   186480
ctgatttcta agttgaggct ctctcttgtg cctgtctgat cagataagta gagttgtgcc   186540
ttggtttata gatgagataa atgtgtattt gaataagcat aagttaaaga aattttaaaa   186600
tcccttagga agctaggctt atcagagaaa tccaaggaaa tacattaaca aactaggaat   186660
ttgttctaac aggttaatta taactcataa acttattggg tttttttacc ttttaatttt   186720
atattacatt tgcttataat aaggaatatt gctaggaata aaatttttta atattctaca   186780
attaacaatt atctcaattt ctttattcta aagacattgg gattagaaaa atgttcacaa   186840
gggactccaa atattgctgt agtatttgtt tcttaaaaga atgatacaaa gcagacatga   186900
taaaatatta aaatttgaga gaacttgatg gtaagtacat gggtgtttct tattttaaaa   186960
taattttttct acttgaaata ttttacaata caataaggga aaaataaaaa gttatttaag   187020
ttattcatac tttcttcttc ttttcttttt tgctatagaa agtatttatt ttttctggaa   187080
catttagaaa aaacttggat ccctatgaac agtggagtga tcaagaaaata tggaaagttg   187140
cagatgaggt aaggctgcta actgaaatga ttttgaaagg ggtaactcat accaacacaa   187200
atggctgata tagctgacat cattctacac actttgtgtg catgtatgtg tgtgcacaac   187260
tttaaaatgg agtaccctaa catacctgga gcaacaggta cttttgactg gacctacccc   187320
```

```
taactgaaat gattttgaaa gaggtaactc ataccaacac aaatggttga tatggctaag  187380
atcattctac acactttgtg tgcatgtatt tctgtgcaca acttcaaaat ggagtaccct  187440
aaaatacctg gcgcgacaag tacttttgac tgagcctact tctctcctca ctggtatggc  187500
tccaaccatc aggccctatc ttggtccatt taggctgcta aaataaaata ccaaagactg  187560
agctgcttat aagcaatctt tggaggctga gaagtcaaag atcaaggtgc cagcaggttt  187620
gctgtctcgt gagagcatac ttcctggttc attgatggtg ctttcttgct gtgtcctcac  187680
ataatggaaa gggcaagacc tctctggtgt ctcttttaca atggcactaa tcccatcatg  187740
agggctttgt tctcatgacc taatcacctc ccacatgtcc tacattctaa tactatcacc  187800
ttgggggtta ggattttaac atatgaattt gaggaggtgg cggggggac acaaatattt  187860
agaccatagc atttcactcc tgacctccaa agttcatgtc ttcttcacat gcaaaataca  187920
ttcattccat cccaatagcc cccaaagtct taacttgttc cagcatcaac ttacaaggct  187980
aaagtccaag gtttcatcta aatatcagct aaatcagcac aaacagctaa atcaggtaga  188040
gtgggactta aggtgtgatt cctctttagg cagattgctc tccaactatg aaattgtgaa  188100
atcaaaccta ttatgtactt tcaaaataaa atggtgaaac aggcacaggc tagacagtcc  188160
catttcaaaa aagagaaata gaaagaaaa aaggagtgac aggtctctat aagtctaaaa  188220
ctttaaggct tgagaataat ttgctttgct ttgcctccag gctcactggg gtggtgtctt  188280
acctctggac acactggggt ggaggctcta tcctcatgga tttgagtgtc tcattctttg  188340
tggcaggtct gtgctccaat cccacaccta tggctccctg agtgtgcaat gcatgcctg  188400
gtggttctac tggtctggga ttgcataggt ggcccagcct tcatagctcc actgggcatt  188460
gccctaatgt gggctctatg tggtgacctc accctgggc ctctacctgg gcctgtgac  188520
tccctggggtt cttgaaatct aggtggaggc agccatcccc ctacagttgt gctgagtgta  188580
gtgcatgagt gctgggtct gctagagcta tacctagggt ggtggagatg tatggcaatg  188640
gagtatgggg agctgatatg gtttgggtgt gtccccaccc aaatcttgtc ttgaattata  188700
atttccataa tctccatgtg ttgagggagg gacctggtga gaggtgactg gatcatgggc  188760
atggttttcc catgctgttc atgtgatagt gagtgagttc tcacgagatc caatggtttc  188820
ataaggcagt tttccctgct cttgcaccct cttttcttgcc tgtcaccatg taagacataa  188880
ctctttccct tccgccatga ttgtaagttt cctgaggcct tcccagccat gtggaactgt  188940
gagtcaatta aacctctttt ctttataaat tacccagtct ctttacagca atgtgaaaat  189000
gtgctaatac aggagcaaag actgcagtgt gaggtggcaa tgtgaagtct gcaatgtgag  189060
gtggcacggg gcagttgtag cccctccttt gaaatctttc ttccctaccc caggcctctg  189120
cactctgaac tatgatggga aaggcagctt ggaagatctc caaatggctt tggagtcatt  189180
cttccattgt cttggactat aaattctggc ttctgtttag gtggctgact aatatcccca  189240
ctgtctgaat gcatagcacc tagtttctgt tgagatggct agtccatagt aatttactta  189300
tcaaatttgg ccacacccctt tgtattctct cctgagcagg ctttctcatc tttcacaata  189360
tggataggct gagaattttc caaattttga agttctgctt cccttttgat caataattcc  189420
attttaaagt catttctcat cttgaatttt actatgagca gtcaagagta actaagctgc  189480
tccttcaact ttgcttggat atttcctcag tcaaacattc aatttcattg ctttcaagtt  189540
ctgccttcca caaaacacta ggacacaaac agctcagcca agttctttga cattttataa  189600
gaaggatagc ttttcctcca ttgtccaata acatgttcct catttccatc tgaaaaccca  189660
tcagattggc ctttaccgtc catatttctg ggaacattct gctcatgacc acttaggtat  189720
```

```
tcggtaagaa gatagtagct ttctctatag ctctcctcct ctctggagcc ctcaccagaa  189780
tggcctttaa ttgtccattc acagcaatgt aggcttttc tagcatgtac ctgaaaactc  189840
ttccagcctc tactcattac cttgttccaa agctgcttcc acattgagta tttgttacag  189900
cagtacccag atcccagtac caatattctg tcttagtcca ttggggctac tacacgatgt  189960
cttataaaca acagtaaaat ttatttttca cagttgtgga ggctgggaag ttcaaaatct  190020
ggtgccagca gattttgtgt ctggtgaagg ccttcttcct cacagatggc tgtgttctca  190080
ctgtgttgtt acatggcaga agagtgggca ggctagctct ctgggatgtc ttttataagg  190140
gcagtaatcc aaatcatggg tttagggtag agccctcatg acctaaatca cctcccaaag  190200
gccccacctc ctaataccag catctttgaa gttaggattt caacatatga ctttggcagg  190260
gggacagaag ctttcagttt atagcaaacc ctataggtag cactactttg tcctttccta  190320
atcaatttgc gtcaatgaaa catgaattag aagagaccta ggcgactcca ctatactggg  190380
attattccca gtataaatta tcatctctcc acaccttctc atctactccc tatctgagtt  190440
ctgaagctct ccactacaag aaggaggctt tggtttgact tgatatactt ctctgggaaa  190500
caggtttagc ataaaacagt gatgctcatt ctagaacacc tgcaaatgac aatagttttc  190560
tttcgaagtc gccaggaatc gtctgccttt gggtatgtgg ctgtgagcac tgccgggcaa  190620
aatgccatat gacctagatg aggcatatgc catcctttga agccattagg acattatata  190680
ggaaatatat taactaaaat ggaataaaat tttctaaata acaccttatg tttatccaac  190740
aggtggttca ttatacttga gagcattata cagaggaatt tgatggggag gagagctgga  190800
gaaattctcg aaattctggg tttctttaac agaatactct agctataaac ttataatttt  190860
aaaaaataag cattatatta aagaaaaggg aacataaatt attttgtttt attaaactta  190920
agtccaaagg tctggattgt ggcagaatag gatcagggga cctaaaatgt tgagcctcaa  190980
aggtcttctt agagaacaac tgtattccac tattagcgct tttggtcctt ttagcccaat  191040
ttctgtttat cccaaatgtt cttccctttt ctgccttcct tcacagtgga ccctgccagg  191100
agctttgaaa tgcctgtgag tgttaaacac ttacccattg agtgcccaac cttaacatgc  191160
ccctaataaa atgtacttag attaaccgtt ttcattatca aagtttcctt attacccaac  191220
aaacacaggc gctttaaaga aaacattaac taaattgcaa gtgacacatt ttaagatctt  191280
tgatatgact tcagagaatg cactatagga acacaatgca atgggaggga aacttgggag  191340
ggaagacatt agcctttata aaatctgcaa gtattgccaa atcaaaataa aatttacagg  191400
aaagcaggat cataaatata atctaaaatc ttagaacctg tggttatgat tttaaatact  191460
aatacaatgc aaaattttta cctgtttagg tttttatttc atcagttcat atttaggtat  191520
atacttttac tgttctcctt tttataatt taccattcac aaagatgatg atgttagtct  191580
aactttaatg tcatgagtgc tttgagtagt agtgctaagt ttttgttgag tagtagtgtg  191640 ctttttttgat tagtagtgat aggttttga tgagtaagcc tgctagcagc atacaaacaa  191700
acaagcaagt atcagcctag agaagcagaa aaggcatttg ggtttcaaag tcacaaggcc  191760
taggctttag tctaatacag ctgataatac aatttgtcca acaggacat ttttgggtgt  191820 gtcaaacact aaactggaca ggacattatg acaaaagtgc aaagcaggac tttccggggc  191880
aaaccaggat gtatgtcatc tcactgagtc ctctctttgt ccttgccatg actagtatct  191940
ctagaggtaa atgaacagag taatgacaaa tagccagaca cctgaatctt atcccaacag  192000
cacctcctac ataattcccc attatcccaa atggaaatta aaaatatata cagtgataat  192060
```

-continued

```
tccaggccaa gaaatgcttt atttctagct tggacttggc ttccatgtcc agtgtagaat   192120
cttatccttg ctgatctgga ctgtatctca tgaagccatg acttgtacct agttactagc   192180
tggaaggctt agaacaaaag ctggtccaga gagcctcctt tttccttatt tcctgggtcc   192240
acacctttac catggcagtc tgcctatcat ttgatggagg aatttaaagc aagtccaagg   192300
gaagggaaga gagtttctaa aatctagaac ttggatagtt taatttacct atcccaaaac   192360
agcttaggcc cagacagctt ctctccaaga ttggtgccaa actgaaatta ccagctgtgt   192420
agaccaaaga gaatttcaaa agaaactgaa tcccaagaga aaaaaaaaag acttctggca   192480
ttgtggccca ataaattggt aggattgttg tgacttttca agtttacatg taaaatgggc   192540
ccagcgcagt gcctggcaaa tatgggtact aagtaaaagt aactataatc atgttttttt   192600
aatctggact tcacttggtc atcctttaaa tggtgtctga cagaatccta gttcttgtct   192660
cactttactt agtttccctg ggaaatttca tgtgtccttt tggctttaat taatatctct   192720
attttgatga cctccattat ctgcctattc ccagagcttt ccacctgata tctcagcaca   192780
tgaaaagcac cttatgtcaa taagtgagtt ccttccctgc cccaccacat acctgtcctg   192840
tgttcctaat tccactgaat ggcatcccat cctccagttt cccaaggcca agacctggga   192900
ctcatctttc actctcaagt tcctccacgg gtacccacat gtcacatcct gtcaatgctg   192960
tccctgggga gtatctgaaa tatattcact tttcttcatt tccacctgac accactatta   193020
acacttgcac aaatttctga ggttcctggc tcatttccct cattgacccc caatagttca   193080
ttctgctctt tgcagctctg gtgatctttc caaaccccac atctgatcac ttgtttcttc   193140
ccttcatatg gctcccttaat gccttctgga ctaagtccac actgcttaag gtggcttacc   193200
aggtccttca tgattttgtc tttgtttggc tttctacact cactgcccaa cttcccctta   193260
cttcccatga ttcagttata ctgaatttct tggttctct aaagcacatg tgctttctgt   193320
tctgcagagg ctttttttgtt cacttgctat tctctacctg ggaaactccc ccagcccttc   193380
actgcctcct tctaccatct ttcaggcctc tccttacaca tcacttcttt ccaaaaatct   193440
gccttgacac tccaggtctc ggtttcctag gtgtacccta taactccacc cctttcatag   193500
catttctcac tctggctgga gatttacctt ttaacttgtc catgtccccc actggagtgg   193560
aagttcctgg aggtcaggga ttatatccta ttaattgttg tatttccagt gcctagagta   193620
gtcttgcata catggatggt attcaataaa tattggttga atgaataagg agttctttca   193680
tttcatatgt aatagatcat ggaaatagcc ttgtgattga tacacagcag gtattaccat   193740
cctcacttta gaatgaggac tcagagcctt gagatgtctg agggccttga ctgggacagc   193800
tggcagatgc aggagcagag ctgcatcacc cctgtgggct atctcagggt tgtctgtaat   193860
ctaagtacaa tgtctgttga ttttggactg aaggcttttt gggtaattgt ttgctttttc   193920
aatacttata aaatagtttc catccttact cattgatagt aaggttagtt attttagaaa   193980
acaagctaaa tagcagaaat agtggccttt taagttgaaa atttaccctg aaaaatctac   194040
agagtagcaa acagagtatc aaaaggagtt gactgtatct attttataa ctgccactta   194100 tggattattc agtaaaacca caattcactt ttatgatttt ttttcatgtt tctctgtcac   194160
aagagcaaac tcttgctcca taataacatt ccagaataca gcaatagcaa aagtcaacat   194220
tttgaatcct ttacaaactc ttagacattt ttttttttt agtttaacat gttacaaaac   194280
aaaatttctt cttttttcac agcagttttgg gaagtacata ctatttatta gctcatcagc   194340
atgaagctgg aaaattcttt ttcctaaagt tctttatatc tacaaactgt tgatgttttc   194400
atttatttat ttttaatgct acgttgtaat gaaaatcatt ggaaaacttt agattctagt   194460
```

```
aattttgaag tcttcttagt ttggacagga ctgagctaaa gtttgtactt tttttaattt  194520
attgaaaaat ggtttctaat gatagtatta acaagattat attgggggca ggacgcagtg  194580
gctcacactt gtaatcctag cactttggga ggccgaggcg gttggatcac ctgaggtcag  194640
gagttcaaga ccagcctggc caacatgtag aaatccsctc tccactaaaa tacaaaaatt  194700
agctgggcat ggtggcaggc actgtaatcc cagctacttg ggaggctgag gcaggagaat  194760
tgtttgaacc tgggagtcgg aggttgcagt gagcccagat cgcaccactg cactccagcc  194820
tgggcaatag agcaagattc tgtctcaaaa aggaagaaag aaagattata ttggggatat  194880
atatgtgtgt gtgtgtgtgt gtgtgtatat acacacacat atatatatac atatatacat  194940
atatatacat atttaaagga taaggattc tgctgccaca gatcactaaa tcagatgatc   195000
tctagcaatt tcctgtttgt ttgttttttg cccatagtgc ttatctcttt gaacagtaat  195060
tttccactta ctattttct cccttttgg accataattt cctttaaggc agagcctcct    195120
gttactcatc tttgaatctg ggtctgtca gagtacctag aatttaataa actctcatta  195180
agagccagtt gaaagaatat atgactaagc agtcatttac atccaaaaga tccgtaggag  195240
aattcttatc agcacatgtg attggtaaca ataactttgt acttttcaaa aacaattact  195300
aatctatctt gctttccatt atctcaccaa aacctattag catgtctggc agaaaataga  195360
tacttaataa atttcttaaa tgtttactga cttcaatttt aagttttatt aactatgttg  195420
acttttctct aatgaagatg attctaaaaa gctttttact atacttcaca gtgaataaaa  195480
cagtgagata ggaatattgc aaaatgtccc ctgtgttggt cagtcttagt gtcattcatt  195540
ttaaaaattc tgttctctaa atattgacag ttatatataa atttatgtaa ttgtttactt  195600
ctaataaaga atttcatctg gggaaaaaca tactttgctc agctctttgc cacaagtgca  195660
aagtctaaga cagtcaaata gctttcctag tacggccttta ggaacttagt atatgactgg  195720
tgtgaatcta gagggagcat actgcattct gaccaaaatc tccaccctgt tactatggcc  195780
atcactaact tcgcagtatt gcagtacttc ctgctagctt agttcccaag gcaacttgtg  195840
aaggaaaatt tttacaaagc tgttgtcaca caaaggtagt gtttcagttc ctgagcccat  195900
gtccttggag ttgcccaggc tccaataata ctaataatta ctgtacatta ggtacttacc  195960
atgtgccata ttctgtggga gccgcttttcc acaaattatc tctggtaatc cttgtaacaa 196020
cccctttgaca tcaatattat tattttctcc attttttttac atatgagata aatgagactt 196080
aaaataatgt gcctgatatc atcagcaaat gagctgagga gggcagattc aaagctgatt  196140
gtgtttgact ctagagctgc agtcttaagc cagaccttt cttgctggtt aattttactg    196200
aaaaaaaaa aaaaaaaaaa aaaccctcaa atactgctga ttgatctaaa gtactaacat   196260
ttctatcagt gttagggaaa ttttaatttt ataatttgat tttgtgagaa atttatagca   196320
tcttgaatac tcacatgcaa agtgatatgt cttagataac attttacaat ggcagagctt  196380
aagccagtgc tcagtcattc attcatcctc aagttttgat tcatttatca ttcatcaaaa   196440
ctctgttttg tttggccacc cacattctag gagctcagta catatttgat aaatgaatga  196500
attgttgagg ttgacagtta cccaggactg gcattaggaa cacagagctg aagagcacgt  196560
ttttaccctc aagaagctta cagtctaacg agggaacttg cacaaatact actatcacta   196620
ggtgcctggt tgaatggctt aagagatgat cagggatatt cagaaggata tgtcaggctc  196680
agcaatggca tcacttgaga gcatcaaggt gtttagggaa ctacaagatg tttggttctg  196740
ctgggaataa gagtgaaggg ggctccattt ggatgcctca tacaccaggt gagagatctt  196800
```

```
agattttatt ccaccaggag gagaactacc ataggattta aaacagaaat gatatggtca  196860
aacctacatc ttaggaagat ccctggggtg tttgtatggt ggacttgcaa tttgactaat  196920
tgagatttgt aggatgattc ttaagagatg atgatgaccc agactgggat cactataata  196980
gagttggtaa ggaggagaat gatttaaaaa gtagttggaa gaattctagg gatggagata  197040
aacatttgaa aattattaac ttataggtgg tcatcaatac cctgaaaatg actgggatct  197100
cagaggagag tctggagagt tggaaatgac aaagactaat attcaagggg gcaggaagag  197160
ggagagttgt tcacacatga caataggaag aaatggccat agagtgtgtg gtttctctca  197220
agccaaggaa tagatgtttt aagaaaggaa aattcttgtg gtgggaagca gtagagatga  197280
cagatacaca ttaatttctt gagatttcta gatgactaaa tgggcagatg ttgaatgata  197340
gctaaaggag aacccagaaa caagggaggg attttgtttt tgtttttta aaaagataga   197400
ccatagcagc ttcatagact gaaacaataa aaagttgaa ggcacaaaga aagacacagg   197460
tcctctaact ccctgcccag tgcccttat tcatattctc agcacttgta tttctaagtt    197520
ttatgtttga gtcttcgggg atacatcaga gtagtccccc ttgtctaata aatgtgttta  197580
catttcctgc cataccagaa acccttctca aactttaatg aatttctaca aggtgagatt  197640
actttaatga gaaaccaacc aaggaaagga gtatcatctg caatatactt tcaaatgttt  197700
tttgcttgtt tgtttcttgt ccagctaaaa aaaaaaaaaa aaaacaagcc attggtccta  197760
acacaacttt catattctac cccaatatca agaggctta aaatctcctg gtcgtgtgat  197820
gggcacacag ttaatttttt gtgaacaaac acagtgttat gggccatttc tgaatttatc  197880
tctgaaatca taagattctt tctgagccat tatctcattc tatattacag tcaggtggag  197940
cccatcttac ctcctcatac taaattctag acttctcaag ggcaggagac aatcatctgt  198000
atatctcttt ggccttcata cactcaggag tacttgccaa aaataaacat ttaatgcaca  198060
tttatttgaa taattgataa gatccaatac ttcaataact ttgtcatatt tttatagaat  198120
gggtttctat atctcatttg cattttcaaa ctttactttt actgtctagc tttaaaaaaa  198180
aagcctttga ctctaataca gccctcatat tctaccccaa tatctaagag gctttatatc  198240
tcctagtgtt gtaccactat tttaactcca gtatttttta cttcatagtt ttacctattt   198300
gttacagtta gtttttatga attcaagaga tgaatagcaa ttttccatat gtaatttaaa  198360
aaaccccaca gttgactatt ttatgctatc ttttgtcctc agtcatgaca gagtagaaga  198420
tgggaggtag caccaaggat gatgtcatac ctccatcctt tatgctacat tctatcttct  198480
gtctacataa gatgtcatac tagagggcat atctgcaatg tatacatatt atctttttcca  198540
gcatgcattc agttgtgttg gaataattta tgtacaccctt tataaacgct gagcctcaca  198600
agagccatgt gccacgtatt gttttcttac tacttttttgg gatacctggc acgtaataga  198660
cactcattga aagtttccta atgaatgaag tacaaagata aaacaagtta tagactgatt  198720
cttttgagct gtcaaggttg taaatagact tttgctcaat caattcaaat ggtggcaggt  198780
agtgggggta gagggattgg tatgaaaaac ataagctttc agaactcctg tgtttatttt   198840
tagaatgtca actgcttgag tgttttttaac tctgtggtat ctgaactatc ttctctaact  198900
gcaggttggg ctcagatctg tgatagaaca gtttcctggg aagcttgact ttgtccttgt  198960
ggatgggggc tgtgtcctaa gccatggcca caagcagttg atgtgcttgg ctagatctgt  199020
tctcagtaag gcgaagatct tgctgcttga tgaacccagt gctcatttgg atccagtgtg  199080
agtttcagat gttctgttac ttaatagcac agtgggaaca gaatcattat gcctgcttca  199140
tggtgacaca tatttctatt aggctgtcat gtctgcgtgt gggggtctcc cccaagatat  199200
```

```
gaaataattg cccagtggaa atgagcataa atgcatattt ccttgctaag agtcttgtgt   199260
tttcttccga agatagtttt tagtttcata caaactcttc ccccttgtca acacatgatg   199320
aagcttttaa atacatgggc ctaatctgat ccttatgatt tgcctttgta tcccatttat   199380
accataagca tgtttatagc cccaaataaa gaagtactgg tgattctaca taatgaaaaa   199440
tgtactcatt tattaaagtt tctttgaaat atttgtcctg tttatttatg gatacttaga   199500
gtctacccca tggttgaaaa gctgattgtg gctaacgcta tatcaacatt atgtgaaaag   199560
aacttaaaga aataagtaat ttaaagagat aatagaacaa tagacatatt atcaaggtaa   199620
atacagatca ttactgttct gtgatattat gtgtggtatt ttctttcttt tctagaacat   199680
accaaataat tagaagaact ctaaaacaag catttgctga ttgcacagta attctctgtg   199740
aacacaggat agaagcaatg ctggaatgcc aacaattttt ggtgagtctt tataacttta   199800
cttaagatct cattgcccct gtaattcttg ataacaatct cacatgtgat agttcctgca   199860
aattgcaaca atgtacaagt tcttttcaaa aatatgtatc atacagccat ccagctttac   199920
tcaaaatagc tgcacaagtt tttcactttg atctgagcca tgtggtgagg ttgaaatata   199980
gtaaatctaa aatggcagca tattactaag ttatgtttat aaataggata tatatacttt   200040 ttgagcccctt tatttgggga ccaagtcata caaaatactc tactgtttaa gattttaaaa   200100
aaggtccctg tgattctttc aataactaaa tgtcccatgg atgtggtctg ggacaggcct   200160
agttgtctta cagtctgatt tatggtatta atgacaaagt tgagaggcac atttcatttt   200220
tctagccatg atttgggttc aggtagtacc tttctcaacc accttctcac tgttcttaaa   200280
aaaactgtca catggccagg cacagtggct tacatctgta atcccaatac tttgggaggc   200340
tgaggtgggg ggattacttg aggccaggaa ttcaagacca gcccaggcaa catagtgagg   200400
ccccatctgt ctttattaaa acaaaacaaa actgtcacag cttcttttcaa gtgatgttta   200460 caaattccct atggtttagt cacaaggaag ttctgaggat gatgtatcac gtcatttctg   200520
ttcaggcttt tgagcctcct ggaggtaaat ggtttcctta ctgaaggctt gttattacca   200580
tgattatcac taagcttgaa gtaacaaatt agggggggcag actcacaacc tcttgccctg   200640
ccatggacaa gttcaagaat ctaagtaaag tcctctattg tctgatcttg gatttgctca   200700
acctgaacaa gccaaggagg tgtattaaac tcaggcacat cctgaccaat ttggaattct   200760
taagcttcag atcactgtgg aagaggctca actcttatg tgtgctgtaga cttacgctca   200820 ttttctaggt aatttataag ggacctaata ttttgttttc aaagcaactt cagttctact   200880
aaacctccct gaagaatctt ccagctgctg agtagaaaat cacaactaat ttcacagatg   200940
gtagaacctc cttagagcaa aaggacacag cagttaaatg tgacatacct gattgttcaa   201000
aatgcaaggc tctggacatt gcattctttg acttttattt tcctttgagc ctgtgccagt   201060
ttctgtccct gctctggtct gacctgcctt ctgtcccaga tctcactaac agccatttcc   201120
ctaggtcata gaagagaaca aagtgcggca gtacgattcc atccagaaac tgctgaacga   201180
gaggagcctc ttccggcaag ccatcagccc ctccgacagg gtgaagctct tccccaccg   201240 gaactcaagc aagtgcaagt ctaagcccca gattgctgct ctgaaagagg agacagaaga   201300
agaggtgcaa gatacaaggc tttagagagc agcataaatg ttgacatggg acatttgctc   201360
atggaattgg agctcgtggg acagtcacct catggaattg gagctcgtgg aacagttacc   201420
tctgcctcag aaaacaagga tgaattaagt tttttttaa aaaagaaaca tttggtaagg   201480
ggaattgagg acactgatat gggtcttgat aaatggcttc ctggcaatag tcaaattgtg   201540
```

```
tgaaaggtac ttcaaatcct tgaagattta ccacttgtgt tttgcaagcc agattttcct 201600
gaaaacccct tgccatgtgct agtaattgga aaggcagctc taaatgtcaa tcagcctagt 201660
tgatcagctt attgtctagt gaaactcgtt aatttgtagt gttggagaag aactgaaatc 201720
atacttctta gggttatgat taagtaatga taactggaaa cttcagcggt ttatataagc 201780
ttgtattcct tttcctctcc tctccccatg atgtttagaa acacaactat attgtttgct 201840
aagcattcca actatctcat ttccaagcaa gtattagaat accacaggaa ccacaagact 201900
gcacatcaaa atatgcccca ttcaacatct agtgagcagt caggaaagag aacttccaga 201960
tcctggaaat cagggttagt attgtccagg tctaccaaaa atctcaatat ttcagataat 202020
cacaatacat cccttacctg ggaaagggct gttataatct ttcacagggg acaggatggt 202080
tcccttgatg aagaagttga tatgcctttt cccaactcca gaaagtgaca agctcacaga 202140
cctttgaact agagtttagc tggaaaagta tgttagtgca aattgtcaca ggacagccct 202200
tctttccaca gaagctccag gtagagggtg tgtaagtaga taggccatgg gcactgtggg 202260
tagacacaca tgaagtccaa gcatttagat gtataggttg atggtggtat gttttcaggc 202320
tagatgtatg tacttcatgc tgtctacact aagagagaat gagagacaca ctgaagaagc 202380
accaatcatg aattagtttt atatgcttct gttttataat tttgtgaagc aaaatttttt 202440
ctctaggaaa tatttatttt aataatgttt caaacatata taacaatgct gtattttaaa 202500
agaatgatta tgaattacat ttgtataaaa taattttat atttgaaata ttgacttttt 202560
atggcactag tatttctatg aaatattatg ttaaaactgg gacaggggag aacctagggt 202620
gatattaacc aggggccatg aatcacccttt tggtctggag ggaagccttg gggctgatgc 202680
agttgttgcc cacagctgta tgattcccag ccagcacagc ctcttagatg cagttctgaa 202740
gaagatggta ccaccagtct gactgtttcc atcaagggta cactgccttc tcaactccaa 202800
actgactctt aagaagactg cattatattt attactgtaa gaaaatatca cttgtcaata 202860
aaatccatac atttgtgtga aactttgttg ttttcagatg cgttcacttg tcatgtttca 202920
tcagtctctc actccaattt ctaagcttca tggaacatga aacacgaatc tgtcttttag 202980
atatagcctt ttttgagaat tcacatgaat tagaacacac atttttagtt atctgtttaa 203040
actatggtaa aatatacata acataaaatt ttccatttta accattttaa agttcagttc 203100
agtgtcatta ggtacattca catggttgtg caaatatcac catcatcctt ccacagaatt 203160
tttttcttgc aaaactgaaa ctctttttac ccgttagtca ataatcccgc atttatcttt 203220
cctctaatgc ctggcaacca ccattttact ttctgtctct gattttgact actcgaagga 203280
cctaggagtg ggatcataca gtatttgtat ttttgtgctt atttcatcta gcataatgtc 203340
ttcaagcctc atccatgttg caacatgggt caattttctt ccttcttaag gttgaataat 203400
attcattata gagtagtccc cccttatcct tggggaatat gttccaagac ccccaatgga 203460
tgcctgaaat cactgatagc actgaacctg attactgtgt ttattcctat acatacacac 203520
atacatatga taacatttaa tttataaatt aagcacagta atagattaac aacaataatc 203580
ataaaataga acaattataa caatatatta tgacacgagc gatacaaatg tggtctctct 203640
ctttctcaaa atatctcatt atactgtgcc acaggtaact gaaaccacag agagcaaaac 203700
cttggatagg gggaccactc tataaatatg taccacattt ttcctcaccc attcatccat 203760
cactggctac ttggtttgct tccactttt ggatatagtg aataatgctt ctataaatat 203820
gggtgtacaa atgtttcttc atgtccctgc tttcattact taggatatgt ttgaagttat 203880
tttatttttt aaatggaggc ttatagaaca caaaagattt atattctgca agtgtccatc 203940
```

```
tatttcttt  aaagcttatt  caaaaagtgg  tagctatctc  atagctcttg  gtaagttaaa  204000
aatcttcatc  aacgaaaata  ctatttctgc  gttggcacct  gcatggattt  tctttgtcca  204060
aatccctctt  tttaattgat  gaggcttctt  tagttccttt  ttttcttcct  tgttgagctt  204120
cttcatgaaa  tgtgcagttg  ctagcatgtg  gtggacggac  tgcagatccc  tactgaatgc  204180
caggccctcc  ggccctgtgt  tctctttctt  ggagaggttt  gttttcacac  gtaaccccaa  204240
gagggcagtc  tcagagcgtg  ttctagtcta  gttcttttt   taaaattact  aaactttatt  204300
ttttttaggg  cagttttagg  ttcccatcaa  aattgaacaa  aaagtatgga  gagttcacat  204360
ataacttctc  catacatgat  agcctccccc  attcaacatc  ccacactaaa  gtagtacatt  204420
tgttacaact  gtgaaagcaa  atagaatttc  aagaccccaa  gctcactatg  ccaaagggca  204480
agttaagctt  cagagctgaa  ttactcaata  ttgccttcct  tttgttccct  aacagccgta  204540
acttcacaat  cttgtgtgat  agcctcatcc  ataaaccagg  ttcccacaat  gatagaaggc  204600
cacatatctc  cccaaatgac  ctccctcaca  attgtgccca  aggaaaatcc  ttgtgagacc  204660
ctatcttta   ggatacatat  ccctcctata  aaatagccct  aaaactgagt  tatgttgaat  204720
ttcaccctga  tgatgtcaat  taccagcttg  tcttcatagg  cacaggacgc  gggcaagacc  204780
agaaatcatc  gtgctgtcta  ccctgcaatg  aacacataat  tgacttttcc  tttactccct  204840
cttttacct   ataaaatttg  gatttactga  acactaacca  aagcctcccc  tgaatagaac  204900
catttgcctc  actgcctacc  ctctatcctc  ttttccttct  ccgtgtttgc  actttactct  204960
ttaaatatta  aagttcccaa  accctctttg  gaaaagcaca  ggtcacagat  gctcctctgg  205020
cttgtgttct  tcctgggtgc  atctgcaaac  tttggctaaa  caaacctcta  tcgattaaga  205080
cacctgcctc  agtcactttt  tccttaacac  aaccaatgaa  cctacattga  cacattatta  205140
ttgcccaaac  acaatagttt  atattagggt  tcattattgg  tattttacat  ttcatgggtt  205200
tggacaaatg  tgtaatgaca  agttaactac  cattacagta  tcttacaggg  tagtttcact  205260
gcccaaaaaa  tactttgtgc  tctgcatatt  cattccccctt tctcccctaa  cttttggcaa  205320
ccactgacct  ttttattgtc  tccatagttt  tgcctttacc  agaatgtcat  ctacttagaa  205380
ttacgcagta  tgtggccttt  tcagattggc  ttctttcact  tagtaatatg  catttaagtt  205440
tcctccgtat  cttttcatgg  cttgatagct  catttctttt  tagtgctgaa  ttatattcta  205500
ttgtcagatg  taccacagtt  tattcattga  cctactaaag  gacatcttgg  ttgcttcaac  205560
gttttggcaa  ttttcaataa  agctgctgaa  acatctgtgt  gtgggttttt  gtgtaaatat  205620
aagttttaat  ttctttgggt  aagtaccaag  gagttcaatt  gttggatcat  atagtaaaag  205680
atgtttcgtt  ttgtaagaaa  ctgccaaact  gtcttcaaag  tggctgtacc  attttgcagt  205740
cccaccagta  acgaatggga  gttgtggttg  ctccttatca  ttgccagcat  ttggtgtcct  205800
cggcgtttta  gaatttggcc  attctaatag  ttttgtggtg  gtatctcatt  gttatttcaa  205860
tttgcatttc  cctgatgaca  tgatgtggag  tatgttttca  tatgcttatt  tgccagctgt  205920
gtatctttt   tggcaaggca  tctgttaagg  tctttggccc  gtgttttgat  caggttgtgt  205980
cttgttgttg  agttccttta  ctggattct   tttgttagca  tggtataact  ttatccatcc  206040
ctttattaat  ctacctgggg  ctttaaattt  aactaggttt  cttatagaca  tcatgtaagt  206100
cttgcttttt  gattcactct  cacaatcttt  gttttttagc  tcttgacatt  taaaatgatt  206160
attgatataa  ttggattaat  atctaccata  tttattcctg  ttttctgttt  gtttcctttg  206220
ttctttattc  ctatttttac  tttcccccatt ttttgcctt   tttaaatttt  attgagcatt  206280
```

```
ttacaggatt ctattttctc accttcttaa catagcaatt cttctttttt taaacttttt 206340
tagtggttgc cctacagttt gcaataaaca tttacaagtg acctatgtgc ctttaaataa 206400
caatattcca tttcatatca gtgcaagtac cttaaattac aaatttctag cttctgtccc 206460
ttttaccatt tcaggtattc atttcattta tatattagct tatatatatc cctacacttg 206520 attttcctc atatgagatt ttctttcctc tttcccattt aaaaaaataa aataaactat 206580
tatagccaca gactttctat ttttatttgt tttctgtatt gaagtcttga ttttggggct 206640
ttacttgtcc ctgtctatgc ccactcctat ctgacacaca ctttcttaat ttatttccta 206700
gttgtttcac tttgtttatc ttcattatga ggaaaaaaag ccaaaacctg aaatgaatat 206760
gcttccttcc agtaaccagg gaccttccat ggttgggaaa ttgttaccta ttcgagtgaa 206820
aggctaataa aaccccccaag gtaaatattt tagtacttca ctaaagaaag aacctcaaat 206880
actatgtgga agacaattta aaatgaggtt taaagagctc aatataaaaa cctgtttgac 206940
ctgttaaaac aggtgtggac aatcacaatt ccctatttaa aaatacagtg aaaaaaccta 207000
caaatgcaag acaaatacat tggagcatga gaactccaaa ttgttaggtt aggaattaga 207060
agctgttccc agtgtgtaga gctaagagac ccaagtcatt gtcagttgac agggagccgg 207120
gactcaatac ctgtgtactt tctcagagaa aggagaggtc ttggcaaaat tttgggttta 207180
tccttaattc catacaatgg gaatattcaa ttgctctttta atcactcagt attgataggg 207240 acaggggca gagaaattct aggcagaaaa gggcgggacc ctggtgaaac cccacccctca 207300 atccgaaaaa cctgaaactg ccaccgaaag tgagaacttc tatccctgtt ttcccactcg 207360
aatgttgcct ttttctaaac tacccgtggc ctgctccacc cccatccttt gcctataaaa 207420
accccagact cagttggtag atgggactat aactggacat tggagagaag tggcttgact 207480
tcagagcgac agcttgacag catactttgg agaagaatct gagaggagaa ggcaagactt 207540
caggggaaga ttacctatct gccctgtccc ctgttcagct ctatttccca ctgaaagcca 207600 cttttcatcag caataaaatc cctcatttac catccttcaa ttcgttcatg tgacctcatt 207660
ttttctggac gccagacaag agcttggagg ccacgagtat ggatacaaaa ggctgtcaca 207720
ctggctgttt gcccttgctg gtggagggca gctgcctcac atgaaaaggc aaagagctca 207780
ctgagctgtt aacacttaag ccttccgcag acggcagagc tgaaagagca ctgcaacaca 207840
ccctctgggc ctcaggctct caggcactcc tacctggttg cgccgctggg cccgcacaga 207900
gtttgctact gccggcacct gaaagcggtt ggctggttcc tgcactcgct cgttctggtt 207960
cctgcactta ttcattcgca cgctccctcc cacaaggggt agacggggcg ggatgggtaa 208020
atgaggcacc cctgtctcaa gtcccgtgaa ggcgtcaggg aaataatctg cttcagtttc 208080
tctagttgta aaatggttaa gaacattatg aaaggtggtc aacaactta taagtgaata 208140 tgctaatgct ggccttaatt ctaaaatgct acttggatca aaagttatga ttcagttcca 208200
atacatcttc tattcattga agtacagaat ctgtacacaa agtacaattg tatcttcaaa 208260
aactgccacc ttgtggagat tggtttttat tgttaagaca gccagtgcca acaacagaaa 208320
tgagtacaga gcctcacata ctaatgtaag tgaatctcaa agacatttta tctttaagcc 208380
attttgaaaa gtagaaatta agcctgaata gttttgggc acaaattgct ctttaactct 208440
cttctttccc attcaccttt gtcactgatg gaataataga aggagcaatc tttatcagca 208500
atggcagatg tgctgataaa tgaaaccaaa actgaattga caaatattga cacaaatact 208560
tatagaagca atttaaaaat ctaccttgca attaatcctt atgaaattta agtcataatt 208620
tactaaaaat tataatataa agaaataaac tttctctgtt ttattaaaag aaaggatcaa 208680
```

```
tacatttggc cacaattgat tggccataat ttttgtcaat gttctataag ctaattgaaa  208740
ataagactat tttaaatata attatctccc ttctcctttg cctttcatt ggcagcaggt   208800
gccatgggct tattcatatt ctaaaagaga agttgtgtga gcaaatttgt catcataggc  208860
aatcctcttg taaggaaaaa attatgattt gatttttatt ttctcttatc tcctaattgg  208920
gtcagatact ccagtgtcct cggggagcca aaccaggagc cagtgtgtcc ttacacaaac  208980
acagcttcct tcctgcttgg agctcacacc aagcatttgc atttgaacca agcaatgttg  209040
acaggctatt gagccacaga agttaaacat tccaagtgag cctgagacga ccattacatt  209100
cttttacatt ttctggtcga ttaaaattt aattgtttaa aatttcaaat agatacaaaa   209160
atagacatag agtataataa acttcacacc cctgtcactg aacttcaata gttatcagct  209220
cacagtcaat cttattcat ctatgctccc tcatgcttcc ctcctatatt attttgtgca   209280
aatccaaaca gcatataact ttagctctat gtgtctctaa aagacacggc tttctctatc  209340
attcttttc ttttgaaact gatccatatt acctttacca gaactagaaa aacagtcatc   209400
tttaatatcc tcaaatattc actccatgta taaacgtcat tgtcagtttt ttcccaaata  209460
taggtagtcc tcatgttgca cattaatatg gcactatgaa atcaccatg caagataatt   209520
taaataatta atgggggaaa aattgttcca tgacctttaa aaatattaaa aatttaaaac  209580
tttcttactg ttggttataa acaataggga cacaaaaata gtgaaacatt tagtaagtaa  209640
tttaaaacat tagaaacact gagaattaaa atgtttctt taaactactt atcaagagta   209700
gtttgagcaa tacttggttt cttttggtta tgtaacttgc aatatgaaga aagcatcttt  209760
tctatgcctg ggcaagttgt catactcctt tctaatttag gaccagcttc caacattgta  209820
tccttcgtga cttcaatgtt gtaaaatatc tccaagagtt tgtttaaggt aatgattttt  209880
gctgatgtca cctcctctgg ggcatctgac aggcattcct gctaggtcaa cctatagcag  209940
agggtggaag ggcccagaga tgcaagaga gaaaaggggg gaaccttta gaggtgatta    210000
ggctatgagg gctctgcttt catgaatgga ttaatgccat tacggcagtg agttcattat  210060
aaaaggacaa gtttgccccc cttctctctc tttcttgctc tcttttgcc cttttgcctt   210120
ctgccatggg atgacacagc acaaaaaccc tcaccagatg ctgaccccctt gatactggac  210180
ttcccagcct ccagaactgt aagccaacaa atgtgtgttc tttataaatt accccagctg  210240
tggcattctg ttatagcagt acaaaataga tcaagacaaa gggggattgc aggcaggaag  210300
ggagcccctg acctcttagt ttcactcatc tggaatttag ccactacaac acagagctgg  210360
ggcttgaggg gataagaaat gctattgacc tgcacttccc agggtgatag tacagttaca  210420
ggctgtaaac tcaagggaga gggaatgcca tcatcttggc cacatcagcc tggagtagag  210480
cttctatcac accaagttgg gggagggaag agggagcagc ttgtgactga agtgccataa  210540
acttttgttc ttactgagat tagtatattt tctggaataa acgctgctgc ttttgctgta  210600
tgtgcttagg gccattttca gagactttaa atgattgata attgttacca gtaatggtta  210660
ttttgatggg tagttggtcc acagagctcc tcaccttgct gttctagaaa ttgtcttta   210720
gcttagtatt aattcctgaa ttttcagtt tttctgatct tttacctcca ggatgactct   210780
ttgaaacaac tctaaattat tgactgaaac ttttatgtat aattctcatt tgttcttca   210840
cacaatctct gtgaaggagg ttctaagaac taagaggctt agagagggta aggatcttcc  210900
cagaaattac acagcactcc cagatttgga acctttagaa agtttatata cttattgaa   210960
aacttagctc attttaatc agagggaagt cattttacag tgccccatac agggagtcag   211020
```

```
ataactactt cctagttagg ttttcctctc tatagagagt caaccagccc tgctgtactt   211080
tcccgtggga tctgaaactg cagaaatcta ctgagaaaaa cagaatgctc acagcaggat   211140
aaagctcatg ttttctagag ctactaagat tcaggcttat gcctctgtgt ttgattttt    211200 aatagtcttg ctaatgtcaa agtgattcta tcttacacac cccaaagtct gtaaaggtat   211260
aataacaagg ggtgagattg tcttaaatct gcagtttctt gatctgttta gtgggctact   211320
ataggttact gcaggacctc tcaaggtttc tagtatgcaa aggtgcattt tgactctgta   211380
agagtggaat atcatatgta atgtttctca attgatttgt ctacataacc gtattttctt   211440
gtgccattta tatcctgtgt tttggggaag gttggcctag aacatttatt ctaaaaggaa   211500
agggcatggg aaattcttac cattggcagt gtcggggagg aaaaaatgca tacttcttac   211560
ccatttagtt tattttgcta gtttacaaat taaattgaga taagacagat taataggaga   211620
aaatcaactt taattatgtg tgtatacatg ggagtcccac aaaaatgtaa gactcaagga   211680
agcagccaga tgattgagac ctatatatta tcctgagcta cagaaaggga taagggtttg   211740
gggcttttgc ggggttgtgg aggcaaattt tgggaaggcg aggagaggaa atgtatgatc   211800
aataaatgtt gccttgttgt gcagataaaa gtgtcttagg tgataaagat gtttccaaag   211860
agtagttctc ttcatggtac agatatttta ctcatgatca tttcctttat agatataaat   211920
ttcctttacg aaaggggaaa ttttatttta tgtagttagt ggagaagtcg gtaaagagct   211980
tttcctgtat tggctgattc tcagttttt  ttagctcaaa atgatcaata tgccgaagtg   212040
gcatgttctg aaatgacata ttctgaatcc tttcagctgg aatatatttg tatatcaaca   212100
gtgtttccat ctgtcagccc ttagggtctg cttatgaaag atataagcac ctggatgacc   212160
atgacgaaaa tctggagatt ttgagaaaac actggtgcaa ggctccatcc aaaatcaatt   212220
aaagaagaat cttggaagat ggggttaggt cactgatagc ttgaaaggca tcccaggtga   212280
ttctaatacg cagccagttg agaagcacgg atttttttat tgggttttttc aggctggctg   212340 aaagaactgc gatgctcagg aaaccagggg tgcctggcag gagtttgacc ggggagactg   212400
aagcctgtca acagggacaa gaacggtagg ctggtgcctg gcacctgagg gtacttcaga   212460
ggtgctcatt aaaaaagagg aggggacatc aagcgagaat tcttaatcag acattcaaca   212520
aattgagggt cgtctatgtg ttctaggtgc taagaactcg gcagcaaaca aggcaaagtt   212580
ctcagtgtca tggagtttac attctagtgg atgaggacaa aagtaagtaa atgttaaaaa   212640
tatatagcag atggtaacta aagagacaaa gcagagaatt aggttatttg ctgtaacatc   212700
atcaaaaagt cattagtatg gtggcaattg agcagaaaca tgaaggaagt gaggaagtca   212760
gctgtgtggg tgtcttgaac agtgtttgaa gcaagggaa gagcaaatgt aaaggcagaa    212820
tcatggctgg gatgttggag gagcagcaag gaagtgctgt gaatcttggg gaaaagagg    212880 tttagatgat atgggcctct gtaagagccc tggcttttac tttaagtcat aagggaaaac   212940
ttcggagttt tgagtgaaga gtgatgtgat tggaggcaca ttatagcagg gtgactctga   213000
tgctgtactg acaccagact gaaaagtgta gagcatggaa gcaggagac cagttaggag    213060 tctattgtaa tagtcctggt gagagaccac agcggcttgg actaagatgg caactaaggt   213120
atatctgaga ggtggtcaga ctctgcattt atcttgggaa cagaagcatc cagatttgct   213180
gatgaattgt atatactgta ggagaaggag aggactcaag gatgatgtga aagatttcag   213240
tctgaggagt tttaaggatg agactgggaa gaatgaagga gaagttggtg ggatgggaag   213300
gatttagggc attttagaca ttaagtttga gacatcttgg tggaatgaca agcaagcagt   213360
tgaatctgag tctgaagttc aggaaaaaga ttcagagtgg agacagaatt ataaaagtta   213420
```

```
tcaaaatgga gattgtattt aacacgagtg tgaactagat tcttgttact tgcaccatca 213480
acatcacctg ggagcttgtt agaactgaag actctcagac cctacctcgg aactgctgag 213540
tcagtatcag gatattgtca cgatcccagg tgatctgtag gtactttaga gtttgaggat 213600
tcctagatta gatcatctag ggtatgaatg aatgtagaag agaaagactg agaacctgag 213660
acaatctatc tctggaggcc ttggaaaaga gctggagact gagatgatat aggaaagggg 213720
aatttagaga gaatagtgtt caaatccaag ttaagaatgt gtttcaagaa agagggagtt 213780
aaatgcgtag gtcaattaaa atgaggaatg ctagtttacc actggatata gaaatatgaa 213840
tgtcatttgt tacttctata agagcatttt aataggattc aagatattgg gaagagaaat 213900
gttagagact gaggatagac cttcatgagt tttttctaaa ggaaaggaga gaaaggggag 213960
gtaagtggat gggaaactca aggcaggtaa aagttctggg cacggtggct catgtctata 214020
atcctagcac tttgggaggc ttgggagaat tgctagcacc caggaatttg agaccccatt 214080
tctacaaact gaaaaaaaaa ttagccaggc atgatggcat gtgcctgtgg tcccagctac 214140
tcaggaggct gtggtgggag gattgcttaa gccccggtgg ttgaggttgc agcaagctct 214200
gatcacgaca ctgcactcca gcctgggaaa tggagtgaga ccccatctca aaacacaaaa 214260
aaggtgagag aagtaacatc ctactggcat agtggatata tagataacaa attaaggggt 214320
ggggcatttg gtggagctgg gggtatgtgg aggccaaagc aactctgtct tggaggctaa 214380
ttcacaattt tgacttctga ttaaccccctt ttctgggaat gcctctaaga tttctatttt 214440
atctactgtt ccttgtgtaa gagcatgtac ttaccataaa tcctgccctt aatcaattgt 214500
tctatacatc ccttctgaag cacatatata tcctttccct atggtgtata agcccggggt 214560
atggaaagta agagtgtgga gatccagcat cttgtctcac tgccactgag atacagacat 214620
ggcttctgtt tttaagtctc tattaaatgt ttctttccaa gaaactggat acatcagcct 214680
cttccttcag cttcagcttc taagtttggg tatatccgcc cacagcagaa caggggagaa 214740
ttgagagtca ttccaggata ccctgaatag ttgagaggga aggaacgctt ggaacaagag 214800
aagggatcac ctttagtaag gaggatggaa agtcactcct agaagtagga gaaaaggtag 214860
cttggtagat gtggggatag aaaattgtaa gttttctttc aattgactca gttgttatca 214920
atgtaaaggg aagaatgtca ttaattaaga atgaggatgg gaaagaagct actggagatt 214980 taagggggaat aacatatgaa ctgtcactta agacagttcc cccaacgttt taaagccatg 215040
gcacacataa aaaatgagaa tatttgagtg acaactagga ggggatttgg atccctggcc 215100
aagtttactg gggcaggagg caaatggctc agggggtctg gttgccattt gcccagatgg 215160
ctaaagaaag taatatcttc tggcatcctg gttctgtttg acacatgaat tggggagctc 215220
tgaaagaaga gatgggaatg aataaagcag acaggcagaa aggtagtcag atagcaggaa 215280
ataccttatg tgagtgaaat tcatgaattt gaagaggagc tggtgaggat ggtcatattt 215340
ttaaccactt cagctacaca ggtatagtaa tgcaataggg ggagaactgg atttaactaa 215400
gtttggggtt atgcctagca agtatgacag agaggggatg agggagttga ggagagatgc 215460
caagtgtaga ctaattatga tcatgtaata taaactaggt gagaagagat attaggacat 215520
ggaataggag gggaatattg gaaaggtagt ttggattctg aattttgtgg ggtttcactg 215580
tttttggaga taagagagag aaggagatga ctggagaata gaatgcttgc aattgatcac 215640
tgatgagatg caggtgatgg taatgacaaa gtcagggtgt tatatgggag tgggaagtgg 215700
aggcaccgtg gaggagaaga ggctgttgga ctgagaggtc atggtattgg aggagttatt 215760
```

```
tacattgata ttaaaatctc taagagtgat ggcaggaggg tgacagtgaa cctggaggta 215820
aaattcaaca attcatttgc ttcattgaac aaatgaagca aatttagtag caaatttgt  215880 tgtataaccc caacaaattg acatgactat gaaaagaagg gccagtgtag tctggtggta  215940
gagtctgagg tcagaacttc agaaaggggc atttgtcggg gagggagata caatgtgtgg  216000
aagtgacaat aaggagcaag gaggccatca tcctctacct ccatgtctgg ttatcaaaga  216060
tattggggga ggaaagcagc ctgcttgaga aggcctctgg aaaaactgtg ttccccaaag  216120
ggagccaggt tttcattagg accatgtggt gaaagaactg tttaaagatg caggaagttt  216180
tgctgagaag gttgtgactc tggagggcac aaggagatag tttggggaaa ttgagaaggt  216240
ttgagagatg agagcccatt gtgggatgtg tgaggtacta aggagatgag agctcaagtg  216300
ccaaggtctg gcttgaagag gcaggcttct tgttatgaaa actgctgctt tatggatact  216360
ggagagcaaa caactccaga tagcttcagt gttttctacc caagcaacta caggttatct  216420
aacatcactt ttcagagatc atgtttcttc tggagacaga aaataatttc cccataatcc  216480
agctgagaaa attgcttggc cttcccttaa cccttccttg aaactttccg taaaattatc  216540
gattccagaa atgagaaatg aaagagaatc ttgttttgt ttgtttattc tgttttgttt   216600
tgttttgaga tggattctag ctctgttgcc caggctggag tgcagtggta tgatctcggc  216660
tcactgtaac ctccgcctcc tgggttcaag caattctcct gcctcagcct cccgagtagc  216720
tggtattaca ggtgtacacc actacgccca ggtaattttg tgttttagt agagacaggg   216780 tttcgccatg ttggccaggc tggtcttgaa gtcctgacct catgatccac ctgcctcagc  216840
ctcccaaagt tctgggttta caagcgtgag ccacagtgcc tggccaagaa tcttatctta  216900
atcctctgtc ttaagacaat ttatcctgga aaatgatta tccatttct tcaagtctct   216960 ctccataaaa cctctttatg gaatctcctt ttgatttgaa ctttgatcca aatcataaac  217020
aatcctcatt ccctcttaat gttatgtatc acggatgtga gactgggtgt ataccggtgt  217080
atatgtgggg gaacagtggt gtcctgaatg ccctttagac ctgatcttta tgaatccacca 217140 tgatatttct atttcctatg acctgtgtga ttttggttg ttacttatct tgacaaatat   217200
tcttttcaaa aacattgcgc actgaaggac atctggaaaa ttccaggagt ctgtctaggt  217260
tctaattgag atgcaatttc ctaccttcat agcctttat tgggcaatgt tgttgacac    217320 ttgttttcca agttactgga ttactcattt cagagttcag ttacccagaa accacctact  217380
tctatgccta caataagaag caaacaagag gttttgcaa taaagacaat cagtatctag   217440
gataagggct ggcatgtggg ctggtcccat cttttgctgtg aagctacggg gaggaggtag  217500
ggaggggaga gtctggcttt tcagtttgt tgagtaaccc cagcgggaca tcctgcctca   217560
catcctggca gttgaattag ctgggctttt caaggtcaca agaaggaatc ctataccat   217620 cacctgcaat gataggagtt tattgttcaa atagtaggta ggaggggaag gatgggaaac   217680
ttcctcatca ctgttcaatt ccccctggtc ccagggcttc agagctggaa taacacacaa   217740
cagacttctt acctccaatc aaagggcagg caggtaattt gtcttctttt tgtttccctc   217800
acacaatgga gagtgcacaa ttgggtcggc ttttgatctc tcactataat gctctacaac   217860
tggacatggt taccaagtcg cttctgtgat ggtcagcttt tccagcatta ggagttttaa   217920
ctgaggcttc aggattcat accctgcccc tcgccctggg attttgtgcc agaatgaggg    217980
tctgagcatg tgtgcatttt tttgcgaaag gatatgatcc tgtttataaa ggggcctcaa   218040
tctttgcttc aattcactgt ggctagcgta acagatttat gttttactca tagctcgtga   218100
caatgcaggc agggatgagc ccatttgaat caccatcctc aaaaagaatc catatgctgg   218160
```

```
cagcgagtga ctcctcctgc agctggtcat gtatcagagt gttgtgtgag gtaatcccct 218220
cacttcctca cactgatttc tgatacctct ggtccttcca caagtcacag aaatgccccc 218280
atcttctggc tgtgtacacg tgctcataca ccacccctgc ctccatgaca gaatgtagaa 218340
aagttttctt gtgtggttct atagccaaat aagtcccttt catgctattc aaataggggt 218400
tcatagtgct gcactcagtt ctattttct tttaaaatga tcaaggttga ctaaatgaaa 218460
ggcatttcag gattttagt tcctagaaag cagatggttt atatatcaat ctcctactct 218520
ttagtagcaa agattctaca actgcacata caaacttcaa gaattccagg caatcctaaa 218580
ggttttcctg ggccaagcct ctgtgcagag gtatgttttt aaccatctcc aatgggattt 218640
tcagtatttt cagcattgac tcaactccag tcaacagcga tatcaaaaca agtgaacatc 218700
aagtctgaaa agaaagtctg aatactgtta tccaatcaca aaaagacgg gtgatgtgaa 218760 tgtgtgttgc tctttaaagt tggttatttt aagtcaaatc cactcacctt tcaatataat 218820
cagtaacctt catagcttgg ggctgcctgg gcttcagaca gcagagttag agaaaacaga 218880
acagtgattt gtgtgtttgg cttttggagca atgcaatatg cagttcaaat tcaacctcat 218940
ttcattaact ctgtaactga agtacctgat agcaactacc aaaactaaca tgtagaaaat 219000
aaactttatt tcacccaaga gttcagttca ctgacatcga aaggcttcag agatttggat 219060
cacatgaata taacatgaga gctttacaat ttttaaaaac aagtatgttt agaatagga 219120 tgaacactat tctgtcagca tcaagaatca tttctaattc ttgtagactc ttttccatga 219180
taagatcaat gtaatttgta acaaattacc cttgggttga gtccttggag aaagctggac 219240 tcattttaa aaagagaatg aaaattaatt tcaatcaaag gcacttaagg cttttattta 219300
tactttgcat ttgttttagg gaattttgt acgtttatca atagtccttt attacaatat 219360
tttatccttt gaggttaaaa aaacaaaaca aaaacaaaa caaaacaaaa aaacctggct 219420
gggcatggtg gctcacgtct gtaatcccag cactttggga ggccaaggca ggcagatctc 219480
ttgaggccag gagttcaaga cctgcctggc caacgtggtg aaacccatc tctactaaaa 219540 atacaaaaca ttagctaggt gtggtggtgt tcgcctataa tcccagctac tcggaggctg 219600
aggcaggaga actgcttgaa cctaggaaac ggaggttgca gtgagctgag atcatgccac 219660
tgcactccag cctgggcaac agagccagac tctgtcttaa aaaaggcaaa aaagctaata 219720
ttcagtaata cgtgcttaat acaaaccta agttcccat ataaacctgg aatcaattct 219780
aggaaagaca cataaaatat ggtgattata ttttatttca ctctgctgtg ggaagaggct 219840
gggataatgt ttaaattaaa acaaaagtga caatacccct atgaaggaga ccaggtcaac 219900
ataaccggct ggcatcatgt ttatcttctc agcatttaaa acacacacac acacacacac 219960
acacacacac acacacacac acacacacac aaacttttg gctctacttc tgaccttggc 220020
ttttatattg gtgttcattt gtttttcaga ggggcttggt tcttttattt gaagatacat 220080
cctatttgtt ggaagaactt ccattaaatt atccttgtcag ttctcactaa attttctttt 220140
cacagctctt gctgtctggg ttataaaaac ccatggcaaa catgggaggc cccaaggaa 220200 tgtgtgctgg gatcctcttg aaatattatt gccctggatc ctttgagctc tttgagtcca 220260
gaaagcagca tggagaagga gggcaaacct gcatagtttc tcagaatgga tgagttttc 220320 ttcagagtag ccatgtagag cagctcagga aatgactgct cttaagctga caggctggca 220380
gaatattaat aaaatgcaaaa taagcaactg tcctgcaagt atttcttgga tgctgtttat 220440
acttgatttc tatccaatgc tctttagcac atcttctcag agtctagaaa gttgtctcct 220500
```

```
tttcccctca agccaaatgg gttactgctt tcaagctatt tttgctatga agacaacaat  220560
aacaaaacag ctatgccaaa ctacttctta ttttcaaaac cagtttgatt tcctctgaca  220620
aaccatcagg ccagtgtgac tttgcatcac tggattaggt tagtgtaggt gctgtggttt  220680
gaatgtgttc cctaaagctt attggaaact taatccccac tgcaacagca ctgagaagtg  220740
ggagctttaa cagctgagct gattaggtct tgagggctcc attccttgtt actgggttaa  220800
tgtcattata atgggagtaa gttaatcagc cagggagtga gttcctgata aaagatgag  220860 ttccccaatt cccctcttct cttctgcaac agacatgctc tcttgacctt ctgccttctc  220920
ccatgggatg actcagcaag aagacccttg ttaaatgtgt gccctcagc cttggactta  220980 gcctgcagaa ctgtaagaaa taaatttctg ttctttacaa attcccact ctcaggtatt  221040 ttgcttattt atagcagcac aaaatggact aagacagagt gtaactagat gtatgaggaa  221100
atgacctctc tctacatagg ctgtctatct ttggagtaca gctccaggtg gacagtggca  221160
ttgtttaggc ttgctaggag gacagctagg agtgaattaa aaaaatccat tttgcttcta  221220
aaactaaaag ggtcatttta attaaaataa taccataaac ataatttata ttaaaaacaa  221280
agtcatatac aaattagaga aaaatacaaa gaaatgccat ttcctaggtt tgattcgggc  221340
atcttcattt ctaaaattaa ctattcctga gttctgctaa tgtgtcctgc cacaagtgta  221400
ggcataaaaa ggtgaaggaa ttaaactacc aggctctgaa tcaagggact tgtttaatag  221460
aattatgtat aatgaagaat cctactcgct ttgaattcaa cgtggaagtt attcctccca  221520
ccaaaagaag cagagaggga aggaacctcc cagaaaagtc caggcagaac ttacaagttt  221580
gagccatatg aaacaggtaa tatttgacca tttttgctga agaaacatat caattccata  221640
ttgattgaca caatagaatc atcaacttct ataatgggag ctgtggcctt tccactttt  221700 tccttctcc tatatttgag cagaaaattcc cagaagggag taaaacttgc tctacctata  221760
gaataggcaa gaaattgttt tctcttcctc catccttctg caatatcaaa aaatatcttt  221820
aagtattcaa gagacgtgaa cattattcct attctctcct gggattcagc catccagcct  221880
tcttaccccc agtgggcctc aaagttctct ctctctcttt tttttttttt tttttttttt  221940
gagacagggt ctccatcatc caggctggaa tgcagtggtg caatcactgc aggctcaact  222000
tcccgggctt aggttattct cccacctcag cctcctgagt agctaggacc acaggtatgt  222060
gctgccacac taggcttttt tttttttttt ttttttttgc attttagta gagatggggt  222120 tttgccatgt tgtccaggct ggtctcaaac tcctggactc aagggatcta cctgccttgg  222180
cctcgaaaag tgctgggatt acaggtgtga gccaccacgc tcagccctta aagttctctc  222240
ttaattaatc ctcctaagtt tgctggggca gaggagggt ggggcggata tgggagtact  222300
ttatatgtat aaaattttgc catagggtag gttttaattc tcagttctta tgttttcata  222360
atttcttgga gtaaagaact ccttcaggta ttgttcatga tatatatcta taacctcaac  222420
tgactatctc aattaagatt ttggtacaca atgagtgtag gccacataat cctcatccct  222480
tacggaatgc tgtttagtga gtgttatacc tgtctaggca tgtttcttgt tacacttatg  222540
taagttttaa ctttcttgaa ggctgtctca gaatatattc ctatggctca atgccttta  222600 tgttcttggc ttcccgtcaa tagaggccat agcaatgtgt gcttgctcac ctcatctgct  222660
gttcaactga gcacacatta cctggcatgg ggaaataact tcaaatttct tcagacaaag  222720
gtccaacagg ccagacaagc tcatggctag ttccttgacc tgaacaatct tgttatttac  222780
agaatctcca acattcaaaa tggaggaact tccagctcat gattaaactc tttagcattc  222840
tttcaacatt ggcaccatta tatatttcga ttaacagcat tttaaaaaga gatagtgtat  222900
```

```
tagcttcctg ggctgttgtg acaagggacc acaatctaga tagattaaaa agcagttatt    222960
ctctcacagt tttgaaagtt ctggaagtct gaaatcaaga tattagcaag gccatgctct    223020
ctctgaaggc tctagtgggg gattatttcc tgcttcttag cttctggtgg ttgctggtaa    223080
tctttggtgt tccttggctt gtaaatgtat cctttgaatc tctgcctcca tcacatggca    223140
ctctccttct gtgtggctga atttctctct tattatcctt aaggatacct tcatccattg    223200
tggcctcatg ttgatacgat taaatttgca aagaccctat ttccaagtaa ggccatattc    223260
acaagtttgg atagacatga atttggggca tactattcac ctccgtgcaa gtagtcttga    223320
agatttgctt ctaaatataa taaatccatt taaataaaac taaatgtgat tcaaataaat    223380
acttatacat aaataatcac cactatgtcc caagctccat cagctccatg tttatattta    223440
ttcatttgtt aatttaacaa atacagatta aaagtctatc atgtgttctg agcagtactg    223500
gggccaaaat aatgaaccag agggacaagg tccctgttta cgggatgttt atgttctagc    223560
tgggagagtg ataaacaagt ataatttcat ttgtgctctc aaagcaatat tgagaactga    223620
ccaagtgaca gtcactgaga atgaaaaagt gaaaagagta aagtccatgt cttcatagaa    223680
cttacattct attggtaggg agataatgca taaatgagta gataagtaca caaacaaata    223740
acattagcta gtgataagtg ctatcaggaa ttaagaggca gggcaaatgg ttgcagggtc    223800
agagagcttt gtgtcttttc atctgagccc tgaaggaagc cagggaatga gtcttgtgaa    223860
tgtttgggtt tagtgttctg gtgggaggaa ctgcagatac aaagaccttg aagagagcaa    223920
gttcctggtg tatttgggaa gaacaggagg ccagtgaggc ctcttgatgt gaatcaggac    223980
agagaaaggg attgagtggt agcctggggc tcaaacatcc tggtaaacca tgacaagagc    224040
tgttactcca agtactatgg gaaagcaagc agagggtttt gagcaggaga gcaacatgaa    224100
tgtacttgaa ttttaagggg agaccctctg gcgacggtgt gagtactgga ctgtagggaa    224160
caatgggtgg agaaggggtc acgcttgggt gggattttga ctacagagcc tgtggtattc    224220
agagagtgga aagtgctatg aagtagacat ggcatgatgg agagggggt aggaaggaag    224280
gtcattcatt gggtagctag catgtagaga ggcttcaccg agaagacgat gttttcgctc    224340
atatgtgaat gactagaaat cgccagcctt gtgaagatct tggaagatat tttcaagtag    224400
aagcaaaaat tggaaaaaga aaattggaaa gctctagctg tggtgtgttg gagaaaagaa    224460
aggaggacag ttgaaaccta gtaagccaga agatgccctg taggagacaa aggaaaacag    224520
ggaggcaggg cagtgtcagg aaggcccctg tggtccttcc tggtactgtg aacttcctga    224580
gagtactaga agaaagagtc tctgtccata gcttgctggc gcctgctatt ttgtatggta    224640
taacattacc caatgtgaga ggaggaagtg atgaacgttc taaggtgcat agagttagag    224700
gatgtctctc tacaaatttt acaggtcaca atttaaaaat gtcgatggcc ttacacatag    224760
caaaataatt tctaggaatt tatcctacag aaacaaaatt acagatactt aaatttagag    224820
cataaatatt ttactgtggc cttgactaca atagcaaaag taaccaaaaa taaccagaaa    224880
cacctggaaa cagtccattg ttaagaaaac agatgaataa tttatggtgt atgtataagt    224940
ggacatgtat ttagctatta aaataatgtg tgggagctat atttgttgtt gacttagaaa    225000
aatgtccaca atttatattt caaatggtaa attgacctac ataaataata tgtaaataaa    225060
gtataataca caaaatataa aattattttt aaaaactcac catggtggct gggtgcagtg    225120
gctctcgcct ataatcccag cacattggga ggcaggcaga tcatttgagg tcaggagttc    225180
gagagcagtc tggccaacat ggtgaaaccc tgtctctact aaaaatgcaa aaattatccg    225240
```

```
ggcgtggtgg cgcaggcctg tagtcccacc tacttgggaa gctgaggcag gagaatcctt  225300
tgaacccggg agggcggagc ttgcagtaaa ctgagatctt gctactgcac tccagcctgg  225360
gagacagagc gagactccgt ctccaacaaa acaaaacaaa gcaaaacaaa aaaacaacaa  225420
aaacacccac cgtgaggtga tggaagtgtt ttaaatctta tttttgctgg tagtttcaca  225480
ggtgtacaca actgtcaaaa cacgtggaat tatactttaa ggaaaggcag ttccttgaac  225540
atagtttctc aaagttgaac aaatgttctg tatcttaaaa agtgtctgtc ttctatcatt  225600
ttggtgtgta cctacatttg agtaggtttc tatgagcaaa ggaagaaaat ataggaagat  225660
acagtggtta catagagatg ggtttggaga gaatggtacc taattttgta accctagagt  225720
gtccttagcc ccaaattcct gtccaaccaa aatatctcaa tgtgaagata cacctttgtt  225780
gtctactgag cagaggtagc taaacatttg gactggctaa gtaaggaaaa acttcccat   225840
gtcacttctg aacttttgt acatgtgcga gttggggaga ggtggcaagg acattctcca  225900
gcatggtggt agtcagctaa aattaaactt aagccagtga ttggaggatc aacaaaagga  225960
taattatcgt tttgcagtct atcatggaac atagtggaag aacaagatct ttgaggtcag  226020
aaatacctga attttaactc cagccttgtc ccttcctggt agaacaagtt ttgtgtggct  226080
ttggaaaatt aatctacatg gtcttattt tcctcaaatg caaacaataa ctcccatagt   226140
gttgtagtaa agattaaatc agatgaaacg gtcacagggc cttctatatt gtagaatgtc  226200
agtacttgat atcattatcc actgtggaag aaaagattgt aaatttctta ttctgaggat  226260
tagtgagttt aaagtgctta tttgcatggt tggcctaggt gttgttcttc aaaaaggact  226320
aattctagac tctgctacaa gcccactata caatattgtt gtgatctgat aagcttttaa  226380
aaattgaatc tgtaggccag gtgcagtggc tcacgcttgt aatcccagca ctttgggagg  226440
ccgaggtggg cggatcacga ggtcaggaaa ttgagaccat cctggctaac acggtgaaac  226500
cccatctcta ctaaaaaaga atacaaaaaa tttagctggg catagtggcg gcgcctgta   226560
atcccagcta cttgggaggc tgaggcagag aattgcttga acccgggagg cggagcttgc  226620
agtgagcgga gatcgcaccg ctgcactcca gcctgggcga cagagagaga ctctggaaaa  226680
aaaaaaaaaa aattgaatct gtaatgactt cagcatgctc tccaatatcc caatggaatc  226740
attatgttta gtcagattgc tcaaaatttt ctgagctctg ttgtgccaag tttaaggcag  226800
ccggaactct cttcccttgc agacagtgaa atttctctgg tgtgaaatga tgctcataga  226860
tgtttatatg atgctcatat tgggaggatg acttgcccca aatggcctgt caccccaaat  226920
ggttggtggt cttgtggtct attatccagg gagacaccat tgctccctgt cacattggtg  226980
acaagcagaa gagattaggt tgtcctttga tttgttgata cacatgccac gctgtcagat  227040
gatatttgag attatgccct gagctcagag atgcatagcg tgaggatgac atgtgacggg  227100
tatctctgtg ccccattact gtggagcagc ctctgctgca agacctgacc tctctggcat  227160
ttacagaaga tcctccttat ccatggtttc gctttccata atttcagtaa tgtgagatca  227220
actgggtct gaaaataggt gagtataata caatgagaga gagagagaga gagagaacat  227280
taacatactt gttactaaag tatattgcta tacattttct attttattat tagtgttgtt  227340
aactcttact gtgcctgact tacaaactaa attttatcat aggtatgtat gtatagaaaa  227400
aacgtatata gggttcagta ctatattcca tttgaggcat ccattggggg tcttggaaca  227460
tatcctccac agctaaacag tgacttctgt accctctgtc agtgcagaat gaggtgcact  227520
gcattagcat cgtaggcctc ggtttctctt tacaacagac ttggtaggta gctttacgtt  227580
aatcactttg ggtccaagct atgcatctgg aaactgggga taagaatact atttccatat  227640
```

```
ctgtcaaaag gcagaggagt gaccacatgg tccttccaac tttaagtgtt attacaccca   227700
attttaatt tttctgcttt tctcttgcca aattctttct ggttgtcctg tcctttatag   227760
ataggcatc atcacctgaa attgagatat ggagaaccaa gctcagaatt ttatgttaga   227820
aactactatc cacgcacttc ctaatttta gagggacaga ataagggtga tttgcatgtt   227880
tgtctttact ctcctgacaa ctgagacagg aaaccaagga taggagctca tgcaggtaaa   227940
gaagaaacag gttcagatgt ggacatgaca actttgaagt cactgtctga catctacttc   228000
acagccaatt agatcaaatt tacaagccac cacacacata tatagtgcta gtaaatatca   228060
gcatataagt ggttaaacca tgggagtgga tgagatccct caggaaaatt gcattgagtt   228120
gaagaggagg tgtcaagcgt aaattgtgct tggatgtttg gggtgaacag aagaagacat   228180
tgcagtgaag aaggctgaga agcaccatca gagcagaaag accaacagca cttggtgtca   228240
tgggggccat ggaaggagaa agcctttatg ggggcaggag gagcctgatc agtaatgtcg   228300
aatagaacag acactatata atcgaaggct ttaacaacaa acatgaaaaa aggctcaaca   228360
tcactgatca ttagagaaat gggaatcaaa accacaatga tataccatct catgccagtc   228420
agaatggcga ttattaaaaa gtcaagagac agcagatgct ggtgaggctg tggagaaata   228480
gaaatgcttt tacactgttg gtgggaatgt aaattggttc aaccattgtg gaagacaatg   228540
tgacaatttc tcagagatct agaaccagaa ataccatttg acccagcaat cacattactg   228600
gatgtgtacc caaggaata gaaatcattc tattatagag atacatgcac gtgtatgttc   228660
attgcagcgc tattcacaat agcaaagaca tagaatcaac ccaaatgccc atcaacgata   228720
gactggataa aatgtggtac acatacacca tggaatacta tgcagccata aaaaggaatg   228780
cgataatgtc ctttgcaggg acatggatgg agctggaagc cattatcctc agcaaactaa   228840
tgcaggaaca gaaaaccaaa cgctgcatgt tctcacttat aagtgggagc tgaacaatgt   228900
gaactcatag actcagagag gggtaaaaca cacactgggg cctgttgtgg ggggtgggga   228960
taaagagagg gagagtatca ggaaaaacag ctaatgtgtg ctgggcttaa tacccaggtg   229020
gtgggttgat aggtgcagca aaccaccatg gcacacttt acctatgtaa caaacctgca   229080
catcctgcac atgtattcca gaaattaaat ttaaaaaaaa attgaaggca ttaaaaatta   229140
cctttgctt ctgaagacca gacggtcatt ggtgatttta ggaagagcat tttcactaat   229200
agagtgggca tagagcacat tttagttgat taaagaataa aggagaggaa gacaagcctg   229260
gattagacaa tctggaaaga gatgtcagtt gttagaaggt gatccttttt gtctcttcac   229320
tggggctttt tgagtgacat gctggctcaa gggaaagatc cacagcaagg gaagatgaag   229380
gcaaccaagt agatcattga gggagcaaag tcctggagta attgtatagg tgaaagggaa   229440
aagtctcatc ttattatctt ttgtaataag aagtagttta gttcattttc tctaagaaga   229500
agctatgaag atgtgattag atgtgcaaga gattcgttga gataacactt gtaaaggata   229560
aagaagaaag tggggagact cttcagatct caggagaggc ctgacacctg tgaaggagag   229620
gggaagaaaa gaccaggtag gaaatgtgtc tagctgtaag acagttccaa gaaaggccta   229680
tggagtgaaa aaaaccttca tttaagaag acacatgtcc cacagaaatg ggcgtggaaa   229740
tgtcccctcc attctcagtc aacaatggg agcagcatgc tggaagcctg gtcccaaagc   229800
agatgcagag ggggacccag agtgtagcag ctgaagtcag cagcaattac gcacgctctg   229860
gacatctgag cagtgcgctt tcatggtaaa acctctgatat aactggctga tctggatgtg   229920
cagaaatgag aacaggaaga taagtgagtt cccaggtggt ggcctcattt attttgaag   229980
```

```
tatgaagtat taggattatt ctagctagaa tgggaataga gaatggaatt ggagaaactt   230040
gagtgatggt ttagaagagc agaaactgaa agaaggtagg actttgatct gcacaaggtc   230100
tcattgagaa tgggtcctgt aagggactgt gatgtgttgt ggcattaaca tggcatgact   230160
atgattttcc tctagaagga tgtagtaaga atagagaagg tagattttgt gacttatctc   230220
tttactgtta atgctactcc tggttccaag gctgccccag ttttataatt cttaagttat   230280
tagtaacttg tcctttattt gattaaacac acaaaaaaat acattgattg agccttatgt   230340
atgaagcaca ggaggagata taagaatgga tttctgccat ccaggagtgt gtacttaaca   230400
gcaataccta tgatgcaagg cagactacga caggtaatat aagagaggta gaaataaagc   230460
ctatggaact tcagaagagg aatagagtat ctgagtaggt aaaagagagg acagactcaa   230520
agactttatg gaggtggctt ggtttgggat tcataaagtg ggtataattg tgacagattt   230580
gttatctatg tctactattg tatggtagaa acctttcttc tttttaatct gcctttcaag   230640
gccttcatct aggctggatg gtgaccacct catgcccaga ttactaatga attgctcagt   230700
ccctctttaa atctactgtc tcatatattt gattacaaat acaactgggt aaattatgtt   230760
gttcatataa cctagaagtt ttggggcect ctcccctgtt tctcaagcat aactgatgct   230820
acagtacttt gtccttttg cacatttcca tgatgtctta ttgtactaat aagtgctctc   230880
tagactgtga tgaactagtt gagttataac cttgggtagg aaattacata agcttggtac   230940
atggtagtgt tagagcaagg tcttagttat ttgcttagtt ttctcacctg ccagtgagtt   231000
tgtaaatcac agtcaaggtc ttggtttgga gaggaaggga ggtagctctg ctgtattatt   231060
taatctgatt taccagtaaa gaagctaatg ttgaatgttg attcttcact tggataagac   231120
tccagttgtt tataatatgg aattgtaata tggaataata ttttcacacc tcagtaatcc   231180
ataatgagtt cctcttccac ctttccagtt acttgggata aaaactacct gaaattacaa   231240
gatatgcaaa atgttgtata atcagggcct ctatcttaaa aactgattta ctactatttc   231300
tgggaaatgt gcctatttta cactttggac cttattcact gttgttaaat ttttcagata   231360
aagctcaaca cagtccagca actagctatg cttagcctcc ttatcttcat ttttaatgcg   231420
acaccgtgaa ctccagtcaa gaaaacacat ttaagaccct ttacacttga ctgatgcacc   231480
tgaggctttg cagtgttatg cagaggtatc agtaaatatt taatagttgt gaatgaaatt   231540
aaagtcctgg aacccttgtc caactaaata ggcccctcca agagactgct ctgatgtcat   231600
ttactcacat agccagtgct tagatgcttc atgattagta attttgtat cctttctgga   231660 ggttttttgc tctccatttg gtggtaaact ctggtaatga attttcact ccaatttttg   231720 cctaggttgc tactattggt ctattagggt gccttttttc agacgaaaag acatcatctt   231780
ttaggaaacc ttgtcaaggt caacaaaaca tgaacttatt ttaataatcc ttttgtatta   231840
acagtattta cttttagaat tatgaagatg tgtttatcct tccaagcagc agtctgggtt   231900
gttgccactt gaaaaaaaaa tacggtctat tggagttgga gaataggcag gaaccttgat   231960
gtcataaagg aaaggaggta aatggacagt accttagtgt ggttaaggaa agggctgagg   232020
gaggtttagt ctctctcaga tgtggtagaa acttccatgt gagaacattt gccacctcag   232080
atgagaacac tttttccatt ctccataagt ctaactctaa gctttttttt tcttttttt   232140 tttttgtac tttatttat tctttgagag gtggggaggt gagctgccct ttctttgact   232200
taaggttctt acttttttgg cttacaattc tcagagactc tggctgtctg catacagagg   232260
ccattcagag ctccatttca acaagcaatt gcatatttga tccaataatc ctccagcacg   232320
aggatttggc aatcctttca aaaacatttt ccaagtagtt cttaaaacca tccctttca   232380
```

```
ttaggcaagt gccaggtgaa taaacatggc cctaaacact gtccaccctg ccttggcaag    232440
ggaacatcta aggcttgggt aattgatttc cccgtggttg caagaagttc acataacatt    232500
attcaatcat ctctcaagtt tgcttgtgat tgctaaatca tttgtgacat tggcctgacc    232560
tcttacattt agacttcctt attcttacct ataaaacaag ataaaaggat tacttgattg    232620
atgtctccaa atggccagtc tgtggaccac tgaagcacac tggctgcctc atgtccaagt    232680
tcaactgtga acttcctata acacaagcct taataactcc atcctcttcc tctccaactc    232740
ctctcttaga gacccttgta attaatttag gtaaatggcc agcgctcagg cctaaaatta    232800
ggatctgcca aaggaattta ccatgaagtt acacttgtaa tgaccctccc taaacctcca    232860
aatattctcc tcagaggtcg caagataatg aagtagtcac agccatgtgc tacagtcctg    232920
caccagctag acctgtaccc tcatacttcc actacttgac cctggtagat ctcatccaga    232980
atcaaagtct atcttttgct ccgagtagaa aaatatgaat gagtaagatt gtgctttctg    233040
gtccagatga tcatgactca aactacatgg ccatctggcc cctccatcta cagttagaag    233100
caccaccttg gcaataattg aaatgaactt tcaacaaatc tgctagagtc aagactgaat    233160
tatgcattgt tttataatat cattgccata tgaagaggga acaattgtg tgtggcctat     233220 gaaaaggtg ttaccatccc tggattgcaa ttttttttgtt agttttttttt gagacagagt    233280 ctcactctgt aaccaggctg gagcgcagtg gcgtgatctc ggttcattgc aacctccgcc    233340
tcccaagatt aagcgattct cctacctcag cctcccaagc agctgggact acaggcgtgc    233400
accatcacac ctagctaatt tttgtatttt cagtagagac gggctttcgc catgttggcc    233460
aggatggttt cgatctcttg acctcgtgat ctgcccacct tggcctccca aagtgctggg    233520
attccaggca taagccactg tgcctggcct gttagggttt tgtttgtttt ttttttttgg    233580
catgacaact ttattgagat ataattcaca tacacatagg atatcataca atttgcccat    233640
ttaaagtata cagttcagtg cttttagta tattcagttg tgcaactatc accactatca     233700
attttagaat cacctcaaga agaaaaccca ttccctttaa ctatcagccc ctgtcctttc    233760
tatctccccc agtcctaagc aacacttaat ctactttcta tctctgtata tttgtaaaat    233820
tttaaaaaag attgttcaat tggaagaatt tttaaaatat atccacaata atatagttta    233880
tatgtgttat atatcatttt cttaacatgt gttctctagc ttggatttct cccttttcta    233940
gatcattgat gtggagaaat agacactggg tcctgttctc tgccctccat ttgatctagt    234000
gcccacaact aaacacaatt ttctacaaaa ataaaggcag gacaaatggg atagcataac    234060
tgacccttct gatatacttt ttttataaaa aaggggaaaa aaattatctt ctcaagttag    234120
gaactacaga attgacctgg aaaaagagtg ggcccaaaag aaagattcct aaagtatctc    234180
attagtgcca tgactagcag gcaacataag cagctcgatt agctcaccat atgattgaca    234240
ggagatggag aagatgttgg gggtggtggt ggtggtggta gaattggggg aagagttatt    234300
tatatttggg tgtggcatat gagtttcctc agagattctt gctttgggta ttaaaagtgt    234360
ttaattttta taaaaatttt caataaaaag gcaaataccc aagtgccctg aagaagtttg    234420
agacttagat accaattcaa aattcaagaa ttatgactgt tctagaagtc ttatgaaact    234480
tgtatacttc atctgtgtga tatttggcaa tgtgcatctt gacttggca tagataagtc     234540 actcacctga ggttttaaag caataacttt ttaatttagg gtagactctt ttttcagctt    234600
gttcatgagt gatagatact ctgggaaggt ggacacttttt ctcagtcgaa gggaggtatt    234660
attcatatgg aattctatat aaatgtatat aaatggtgtc ccctaaagca taagtctgtt    234720
```

```
gatgagtctt taaagagact ataccggtta gattctacaa tatacaggtt gacaatatcc   234780
gatgggaaat gtggcttgat ttgaaattag aaggcagaca ttcaaatgac taatctcaag   234840
tctgccccca aggtactgta taattctatg attctgggct tcattttga aaagtctaaa    234900 gagatgatga agtacatctg tcaagaaagg catgagaaga aacaaaatga tccatcttgg   234960
ctgtgcaaat gctgtaatga atggggaagt tggtagatgt ggtcttaaca gggtgtaggc   235020
ttgtgctgaa ataaataaat aaataaataa atacaaacca caagactgac gtgactgccc   235080
agttgtgaac attgtatgaa ggtttagttg gcagagtaat gcttttcaag tatgttggat   235140
aaatattagg tttaaaggcc aagatactta taagtattta caggattaag tgaggtataa   235200
aataatattt agtgtctcaa aggatgggaa ggaagatagt gttgtggtca ttccacagag   235260
gaagttagaa ctgcacatcc aaaatttggt tcagatatca atgctaatga tgacacaaat   235320
acacacatac atatacacat acacctcaag atggtattaa caattttatt attcatataa   235380
tgaggtcttc tgagaaaaac aggccaggct cccaagcaag tctaaaaatg gattgagaga   235440
acagggaggg agaattgact tggggtttta tgtggtggag tagtgtggct ggagagagag   235500
ttgtcttgtg taagctgggg cttatttggt ttgaatttct caataatgca aaagttgagg   235560
catccaagca tctcatcagc ttctctagat gtggcttgag ttgccaggag gcaaattcaa   235620
ctgttagtgt tttgtgtcct aagacatctt gtctaatctg aggtaaaagc tttttcctat   235680
tttttagaag gtgtataatt ttggctcttc tgcttagctc taccatccat tttgagttga   235740
tttttatata tgttataaat taaggattgg agttttcttt tattggtatt tattgataat   235800
acaactgttt cagcatcatt tgttgtaaag attgttttc tccatggaac aactttggca    235860
ctttataaaa aaaaataagc atgtgtgagt gggtctattt ttgaactcta ttctgttcca   235920
ggatctgtac atttgtcctt atgccagtac caccttatct taattaccgt agttttatag   235980
taagtatttt ctgttaatgc caattctaca actttatttt tttcaaaatt gttttggcta   236040
ttttatatcc ttcatatttc catataaatt ttaggttcag cttattattt tttataaaaa   236100
atcggaagtt tttttgcaac ttctgcaaag gttatcaaaa accatcaaag gagattgctt   236160
tgaatctatg aattatttgg gggagaattg acatcttaaa aatattgatc cttctcatcc   236220
attgacatgg tacatctcca tgttttttag gttacagtgt acacatctta tatattttat   236280
taaagtaccc atagatattt cttaattttg atgctattat aaatatctta aattacagtt   236340
tgctagtatg tggaattaca atttattttt atatattgat cttgtatctt aggaccttac   236400
taacttattt attagtttta gttgcttact tttaggttcc ttaattttta taacatcaat   236460
cacatctgca aaaaagtttt tactactttt tcaccatgca aactttaatt ttctttatct   236520
tgtctattta tactagctag aatctcacgt acaatgatga ctagaggagg caaaagtggt   236580
catctttgtc atatttctga tctcagggc aaacataatg ttagctgtgt tcattttgtt     236640 tgtttttac agatgtactt ttcaagttaa gtgccttctc ttcctggtca gctgagagtt     236700 atttttaat cacaaatgaa tgttaaattt tgtcttatgt ttttctgcct gtattgaaat     236760
gatcatgtgt tttcctctcc tgtgtttcac ctttgtttta gaaagatatt ttcactagat   236820
aaagttttta ggttgacagt gttttcttc cagcacttaa gaaatacttg attttcttcc     236880
agcacttcag aaatatttga ttttcttctg cagaatacag tttatgataa atcagaagtc   236940
attctttcct gtaacatgcc ttttctctg gctacgttta agattttctc tttatcactt    237000
agtacttcct aattaaaaat ccatgcccca gcagtggtca gctagcattc taaagaggaa   237060
tgctgaggca gctaccacaa acacttctct aactttatta ttgattgaca ttacagcctt   237120
```

```
tgctaattag tgtaataaat gtcagaaatt agtaacttga cagtcagctt actggaagtt    237180
agaattacga tcttgttggt taaataagta ttcaaattct gtagcctggc taaagtattt    237240
tgaagacact cttgagagag actagaacat aagcatcaaa ggaacccaag caccttctgc    237300
aaggcagaag gggttcggtg ggtatgaaat gatggaggtg ggaaaggaag atcaaaaaag    237360
gggttgggta atgccaaaac ccaaatactg gggattatta aagacatgg ttcaagagag     237420 aagctaatcc atgggtgcag gccagtgtcc agagagagag accactgcaa gaggccctgt    237480
ctggatgttc aggacctctg agaatatatt gtttgctggc tgattgccca ctttccacag    237540
ggccagttct atttctttgt tttttgccct cctattatcc acttactcca tgcaatgtga    237600
ccgcaagagt tctaaaagcc tacataatag acatgtaaat accggtggtg gtgacagagg    237660
tggtgagagt gagaaactca caaatttaat tgagaggaac ttgaactgaa atgggttctt    237720
ggttaggcta ggacaccacc attatatcat gatgatcata tttttatagt tcttgtcaaa    237780
catatatctc ctatagtact tgtatatgat agtactaggt attggaagcc aaaataaatg    237840
agtaaagtat gaatagactt cgccttcaag cagctgacag ggtttggttg gtagtaaata    237900
tttggaacat ttttttttccc cttaaagttc ctggactcag ctaggactag ccaaatgaaa    237960
tgtctcttta ccaaaatgct catcttcagc ctgtgttgct tttttgcact cgtgtccact    238020
tttccggctt ttggcccatt tccttggctt tgttgctccc cacttcggtt ccagcaggtc    238080
cttggtcact accccccaca taacaacatg cacctggggg catcgcctga gcttaaaggc    238140
ccccattcct caattgtatc tgatcccttc cctctaacta aatgcaggat tctgattcca    238200
ttccctcagc atttgggcag gaaaagaaat ctcaactatt tgagatgtgc ctgatgaatt    238260
acagaagcaa agaattctgg agttagaagt tatcttagtt ccaagttaaa aatccaggcc    238320
caggaaagtg tcacatggtc aatgacacaa atcactcacc ggcagaacag ggaggagttt    238380
cactacttca attctctatt taccatatca caaaatatgt aagatatcac attctaataa    238440
tgtaattcag aaataagaga aggatagcgt agcaggaaca ccacaccttg cctctcaaat    238500
tacaccacac agaggctgca tattacacta gttccaattt cattactcac aaagccaatc    238560
ttgaaaatgc ccaggtaaag taaattgtca ggaagttctg aataataaac tcgtttgata    238620
aaaccaactc acaatgcttc ttccttaaaa atattttggt ggaaatatta ttatatttgg    238680
acataaatac cccctgaagg acttgttagg aagaaaatag atcattgttt aggtccctta    238740
gcacagaggt ctgaaagtca aataaacttg gtcaggctgt tttctcttcc taaagagaat    238800
aaaaggcccc caatcaatgg gtggtcacca tagaaaaaat tcggctctaa gtcagagtga    238860
cttgaatatc tgtgtgctat tttatttca gaaaaccaag aagacacacc aaaaaatccc      238920
gattaaaagg gaagaaatgt gtttaaagag cttgttgact tcttaaaaac aaaaattcct    238980
gcatagattt tggttaggat tgctttaaat ctgtagattt ggagattttc aaaaatatag    239040
tacattatta ttattattgt ttgagacaga gtctcgctct gttgcccagg ctggagtgca    239100
gtagcacgat ctcagttcac tgcagtctct gccttctggg ttcaagcaat tctcctgcct    239160
cagcctccca agtagctggg attacaggtg cccgccacca cacccagcta attttttgtat  239220 ttttcgtaaa gacagggttt caccatatca accaggctgg tctagaactc ctgacctcag    239280
ataatccacc cccctcagcc ttccaaagtg ctgggattac aggcatgagc cactgtgcat    239340
ggccaatata ttattattaa ccatagtcat catgatgtgc aatagatctc ttgaacttat    239400
ttctcccttc tgatttttttt ttttttttg agacagggtc tggctttgtt gcctaggcta    239460
```

```
gagtgcagtg gcatgatctt ggctcacagc aacctccacc tcctgggctc aagccatcct    239520
cccaactcag cctcccaagt aactagtact acaggtgtac accaccacac ctggctactt    239580
ttttttgtat tttttgtaga gatggggttt tgccatgttg cccaggctgg cctcaaactc    239640
ctgagctcag gagattcacc tgcctcagcc tcccaaagtg ctaagattac aggtgtgagc    239700
caccatgcct agcctttaac tgaaattgtg tacccttgga gcataccttt cccaatctcc    239760
tctccattct actctctact tctatgagtt catattttt aaagattcta ccacgtaagt    239820
gagattatgt ggtatttgtc tttctgtgcc tgacttattt tgcttatcat aatgtcctcc    239880
aggttcatcc acgttgtcac aaatgacagg atttccttaa gactgaatag cattccattt    239940
tgtatgtatg ccatatttc tttatccact catctgttga tggacactga ggatgattcc    240000
atatcttgga agttgtaaat agtgctacag taaacatggg agtacagata atctctttga    240060
cacgctgacg tcatttcctt tggaaatagc cctaccagta gtatgattgc tggatcctat    240120
gttctatttt tcttttctt tttccttttt ttttaatttt ttattttttg agacagagtc    240180
tcgctctgtt gccaggctgg agtgcagtga tgcaatcttg gctcactgca acctctgcct    240240
cccaggttca acaatttc ctgcctcagc ctcctgagta gctgggatta caggtgcatg    240300
ccatcacacc cagctaatta ttgtattttt agtagatatg ggattttcacc atgttggcca    240360 ggatggtctt gatctcttga ccttgtggtc tgcctgcctc agcctcccaa agtgctgaga    240420
ttacaggcat gagccaccat gcccaaccta tttttaattt ttaaaggaac ctctatactg    240480
ttttttataa tggctgtact aatttacata cctaccaacg tgtacaagg ggccactcta    240540 catcctctcc aacacttgtt acctttcatc ttttcgata atgattattc taacaggtgt    240600
gaggtgacat atccttgtgg ttttaattg cattgccctg atgattcata tgttgagcat    240660
tttttcatat ccctgttgcc ttctcttgag aaatatctat tcaggtcttt tgcccactta    240720
attgggttgt tttcttgcca ttgagttgac ttttatata ttttggatat taatccttat    240780
cagctatgtg gtttgcaaaa atgttcttcc attctgtagg ttccttcttc actctgttga    240840
ttgtttcctt tgctgtgtga tgcttttaa tttaatgtaa tttaatctca cttgtctatt    240900
tttccataag aagagttgcc agtgctgttt accctggctg ctacataccc tgatccctga    240960
agaccgtttc ttgaaccatt ctgctctaaa gtaatcctcc ttccatgatc tttaccaagt    241020
gctttgtatt attaatacat cactatactg atttcctta tagaacatac acaatgaaaa    241080
attatcttgc tttgtttatt tactcactgt ctcagcccta ttaagatgga aaatgcctgg    241140
catgtcttaa tgctttattc ctagtcccta gcacgatatt actttaatga ataagtaagg    241200
tttgaagcca ctctgagtag atgtgaatat ttgaattagc ttaggagaaa tatattctcg    241260
atttccttaa attacaactg aaatgacttt tgtgatatgt atagctgatg cccttactat    241320
aaggtatcag gatatactgg aaaaacttgc aggattttt attttccat tgtgttttc    241380 tttctaggag gcagaaaaac cttctgaatt tttaccatga tgacattaaa gccagagatg    241440
ttaagtgtca ttgtagttag ctctgtgcc agaacctgag ctggcaactc ctgatatgag    241500
tgcttcacta tgaaagacag actagatatg gcaagtaact gcacattcct tctcagtgtg    241560
tttcccagtc ttctctttca aattaacact caatgggcat cctgatacac aactaaacat    241620
acatattcat ggtcaaatcc aggctaatag aggatatcta ttcactcatt tcctcctttg    241680
acacctgtag aatgttatct gaataaaatg atttttgcaaa gggatgggat agaatttaga    241740
aagcatcgca ttacttcaga gagtgacttt tctttaatgg gtcttagttg ttaagaacag    241800
atgcctaaat aaggtgatgc ctaaagtgat gcctggggct agtcaactga atttaatgtt    241860
```

```
cactaaggat taactgctca caaaaactgt atttgtgaaa aattgacctt gtctatccaa 241920
attggctact tctaataact agcttttata gtctacttgt tttctttttt acataaacaa 241980
ctacaaaatg tattagtcta ttttggagaa actcttaaaa tagaatgaaa ttgaaaattg 242040
ctaaagtgtt atagttattt tcagttagat atttctatga attattttat acactcatgg 242100
tttaaaatcc aattttcata atatagttgc cagcatctgt gaattattac aatttgaaaa 242160
gatttggaat gccataactt tttaaaaatg ttctgctctg atctttattt cctttcttct 242220
aactctgggc ttagtttgtc cttgttttct tttttttat tattattata ctttaagttc 242280
tgagatacat gtgcagaatg tgcaggtttg ttacatagtt atacacgtga catggtggtt 242340
tgctgcaccc atcaacccgt catctacatt aggtatttct cctaatgctc tctctaccct 242400 agcccccccac ccaccgacag accctggtgt gtgatgttcc cttccctgtg tccatgtgtt 242460
ctcgtggttc aactcccact tatgagaaca tgcggtgttt ggttcctgtg ttagtttgct 242520
gagaatgatg gttccaact ttatccatgt ccctgcaaag gacatgaact catccttttt 242580
tatggctgca tagtattcca cagtgtatat gtgccacatt tctttatcca gtttgtcact 242640
ggtgggcatt tggggtggtt ccaagccttt gctattgtga acagtactgc aataaacata 242700
cttgtgcatg cgtctttata gtagaatgat ttataatcct gtgggtatat acccagtaat 242760
gggattgctt ttctaatgtc ttgaggtatg acatttaggt tattggat ctttgtcctt 242820 ttttaatgta tattactata aacttccctc ataaaactgg tttgccgcac cccgtaaggt 242880
ttggtatggt gtttccattt ttgtctcaag acatttaaa tttgccttt aatttattca 242940 ttgatccatt ggtagttaag catgttaatt ttcatatatt attgaatttt ctgaaatttc 243000
ttattgattt ctaatttcat accataggtc agaaaagata tttgatatga tttcaatctt 243060
cttaaagcta agtcttgttt tgtggcttaa taatgaccta tcctggagaa tgttctgtgt 243120
gtgcttgaga agaatatatt ctgctgttgg aagaaatgtt ctgtatatac ctatgtccat 243180
ttggtctaaa gtgtagttta agttcaatat ttccatatcg attggatgat ctgtccattg 243240
ttgaaagcgg gatattgaag tctcctactg ttattgtatt gctccaactt ctgatcctta 243300
aaatttgctt catatagaat accataaaaa gttctgagat attgattact tattttatga 243360
atgtgtgagg caactaggaa ggctttactg cgttatctaa cactcatgga caacctgtag 243420
gtttttttaa ctacagagaa aacgtaatag aaaagatgtg ccaggcacag tggctcatgc 243480
ttgtaattaa tcccagcact ttgggaggcc gaagcaggtg gatcacttga ggtcaggagt 243540
ccaagaccag cctggccaac atggtgaaac cccgtctcta ctaaaaataa aaattagct 243600 gagcgtggtg gtgcatgcct gcaatctcag ctacttggag gttgaggctg gagaatcgct 243660
tgaatctggg aggtggaggt tgcagtgagc tgatattgca ccactgcact ccagctgggt 243720
gacagagact ccatcttaaa aaaaaaaa aaaaaaaaa aaagattaac ttgtctcatg 243780
ccacacagct aataaatggc agtgcttaat tcatccccaa ggctgtttac caccaaagac 243840
tatatgaccc ctcaatgcag cctccactta agtaatgcag ttaagaactg ccaacactag 243900
gtgccatgat agggtattga ctctcaaaga tatttgacca tgacccagtt atatttgtg 243960 tcacatatac atacattcct acatccacga tagaaacaaa agtctcacca acagttcttg 244020
tattgactgt gagacaataa aagatgactc tgacattttc taattttaa tgctagttgt 244080 aactcactaa attgctataa tgacccactg gtattatacc tgtatttgaa agccgtgttc 244140
taaatgtcct tttagacat cttgcagtct gccctcaatt acaaaaagtg catttgttga 244200
```

```
atgttactga cagtcacatg gatcaattac tacaagtcat cttaataatg tattccaaaa    244260
atggttttgt tttctcacct ctagtccttg agtacactaa tgggatcttt atcttcagaa    244320
aagctgctaa tataaaacac aatgccttat cactaacaaa tcaaattaga tataatctaa    244380
gcaggtgtat gtgagcagga aaaaaaccac attagagcca cctgaatcta gatatgatct    244440
atgattttga cagcattcag ttttgttctc aagatcagtg acataatctt tactacatat    244500
tgttattttt aaggtatgtg cagttttgta acagcaatac aatgcaggta tgtacacttc    244560
attgtaaata accattctgg cgaaaaaaag ctttcaatg actttggaca agtaaatgat    244620
tcttggtaca aaatcatact tctttggtat ttatgaaaaa aaggaaggt gttttaactc    244680
tgagcaccca attcctggtg ctccatttaa gtatttaaga tgtttctaat tagggttgag    244740
tcttgttgtg aacagctagt gaaatactaa catgggaggg caagttttat gagcattgat    244800
aaattgaaca caaattatct gttacagaga ctacaaagag ctatagataa aaagtacagc    244860
aaaatgattt catgaaatca atatttatt cagtgtcaaa gcatcttaac tgaattgtgt     244920
aagtaatttt gtctgtaatt ttagaagtaa catttgtaga aaatatcaat attatcagtt    244980
gtgctactag aaatattgaa ggagttaatt ctgaatttat tcatttatgc agttatctat    245040
atccacttag gtacaaaact tttgtaagaa agataacact tttattgcat tataatttca    245100
tattttacag gagtcataat gcaaacttat aagcataaat atatacatga tgctaccaaa    245160
tggcaatgta accactaaga gatttaaaac ataaaactag aatttaacaa gcaaatact     245220
taatatggct tttaatggaa ataactgtt tagaaatgat tgttattgc cccattctag       245280
tcattcccca tcaagtgaac ataaaattat gatctccatt taaaacggta caagttatct    245340
aagccaactt tgtactttt tgctactttt ttgtagcatg tatgcagtat gatttctgga     245400
cttccttaaa tatacataca tatatacata tacagata tacagtacac agttctgttt      245460
taataccct gaacatcttg attaaaacta ttacaattt tctattataa aactacttga      245520
aaagttggca taacttcctg gtattgaagt tcaatcctac agaattaaaa aaaaaagcaa    245580
caaaatgttg gttataaata cattctttac aaaaaaaat tgaatagtgg tcccgcactc    245640
ataatttata ttacagtgaa aacattttat caatttaaag gtatttgtat cttgttgtcc    245700
ttggtttctg tgtgaaatag aggaagttaa taatgagaat attgtaggca ggcctatttg    245760
ttaggttttt ctaggtgttc attttttgtgt aagttccaat tcacttcttt tgagttgttg   245820
ttgatttcta tttgccttgt attactgctg ctgctgcttc ttttggtgtt ctgggaacac    245880
tgggtgactt tacttctagg aacaggaaga aaagatttaa ctcttgaaac acccaactca    245940
gtctttgatt tactgttgct gcattcagta gtttgatggc tgctgagagg actgacctcc    246000
tgtaagagac aagaaaccac acaagtttat cacaaacttc tcctgttatg agccctaccc    246060
ctgcctcctc tttgagcaaa tgtacaggag tttctctcta aaactatagg ttctcgtgaa    246120
aaatcaaaag aaaatggaga ggagaagctg agtaattaat ttcctataga cttactgcat    246180
gattttcatt aatccatctg ctgttacaaa attcctaaat acaggagtca gtgaatcaag    246240
tgctaaggcg tcgatctcct taccaacaga aacttcacaa aattacaggc atgaggaaat    246300
caccaaattg gagtagtccc atttgtaggt agctctacaa actatgtcac cttgggtaaa    246360
tcacctaact tttctgcttt ctactttcaa gtcttaaaag tgaactatta ctcaataatc    246420
aaataatctg ggggcatata ggagaaaaca taagagaaac attccttccc tagcagaacc    246480
tacattcatc tatggttagg ccactcaaga tcttccatac ttggaagctg catgttctca    246540
tttctctaat gtttcagaaa tcctgtgatt acctggtcaa tgtctctcat tttgcccatg    246600
```

```
aagaatctga gagctggata ggtaagatga tttgcccaca gtgaacggag tggtgaagct  246660
gggacaagac ctcaggtctc ccaactttca ctcaaggtat tttccctata ttgcattaaa  246720
ttctgcaaac taacaaacat gacatgactc ctactaagtg acctactctg aatgcctctg  246780
aaggagttga ccttgataac ttctcctctt caaaagtaat aatgcaccca acagcaatat  246840
aaccattaca agaatttaaa acaaaactaa aatttaacag gaaaaatctg gcttcatctg  246900
gcagttgcgg cagttgcatt ctcctgggta tcgtctttata tgacattgga atcacctggg  246960
ggagctttaa tagtcattgg ctgggccta ttaccagaga ttcatattta atagttctgg  247020
ggtgtggcat ggacatacga ttttaaaaaa tcttgcggcc aaagaacgcc tagcttaact  247080
cctcactatc cttttctcc attgagcaat taaatcaagg gtccccaagc cacaggctgt  247140
ggaccagtcc atggcctatt aataactggg cagcacagca ggacgtgagc gggggcgagc  247200
cagtattacc acctgagctc cgcctcctgt cagatcagca gcattagatt ctcatagtag  247260
tacaaaccct cttgtgaatt gtgcaagtga ggggtctagg ttgcccagtc cttgcgagaa  247320
tctaatgcct aaagatctga gatggaacag tttcatccgg aaactaccca ggtccgtgga  247380
aaaattgtct tccacgaaac cagtctccag tgccaaaatg gctggggact gctgtcctaa  247440
atggtagcat ttttcttagc cctctataag tcacacattg ataatctttc ccttcagagt  247500
atttcaagct ctaagtattt cccaaagttc tttctttagc cctcatttat ctcctgcatt  247560
tccaccccac taattcacct atatgtctag ccacacttca aattctttct aaaactgtat  247620
ttattgcatt tcttcaatac taatttctaa agccttccg cttggctcat tactggctaa  247680
tgctgctctc ccagtgaatt tagcaggaaa tcctcagtta tctttagcag ctgcctttct  247740
ctctctcctc accaacctaa tccaatgtta cccacaaaat gggcagagaa ttatggctgt  247800
gtttgtgtga ataggaaggt aaaggataag tcctcactaa ctggcatgtc actaaagttc  247860
ttttaaagtt tggctccaat cccctttaaa tcctatttt cctttacttc cctgttaaag  247920
tcctaattct ttaaagccca acacaacatg ttcattaaac taccctaaa tcaccaaagt  247980 gaaatctctt ggggtcagat tttcagactc agctaatctt aagtggaaca gcaatgtaac  248040
tctaatatat acttggctag tggtttggga aaatataaaa acactgaaac aacaaatatg  248100
taatggagaa taagaggggg acaaatctgg ggtccaggcc acctgcattt acagggaaag  248160
gaaagagaag tctagactgc aagaagctag cttagaaagg caagagcttc ctgataaaac  248220
aaaaaacaga tgggctcggt tttaactacg tccgaggaag cctggaaaaa ggctgagcta  248280
catctggtga gggaacacat cctagtccat cctcgtcacc tccatgtgta cttgatggta  248340
tgttaagggc gaatctgctt agtatgttct gcttttgttt tgtaaagatg cttatgctgt  248400
caagttacca gaaagaaaat gagaagttac attgcttgtc atgagttgga tggtgatagt  248460
cacaactgta aaaacagtgc aggtaccagg atccaatctc attttccta acaagaaatt  248520 actgttaagt ccgcaaaatg ggacttggtc atgggcctac taaggccaat tagaacttgt  248580
aatttggttt aaaacaccag caaatgcaac acatacgtag tattcagaaa acatgaaata  248640
tggcattata ataaggataa cagttagttg ctatacagaa tctggtggtg aggggagttg  248700
tttaattttg ccattattgt caaatctaca gagttaatta atgccatggc ccagaggaag  248760
gaaaggagac atacactgtt ctagtctgtt tctgtacctg caacatgatg gtgaggggag  248820
tgtaccttca tggtctgagg caggaaatat ccacatgaaa taaagtactg agaagtaccc  248880
agaacaacta aaaacatgta gtttggtcag tccctggaag tgtgaggcta gaatggaagg  248940
```

```
agttaggatg agaacatgga gaatcacttg ggcttagcgt gagccacagc aattcaaggc    249000
caggagtgca agaatagagc aggtgaccaa tgcacagcat cctgcctgaa aagtgctcct    249060
gacaccctgg aagtcaagcc tagggggcag cggagtttag gagcaggaga gttacaggtg    249120
tttaatgctt cctgggctaa aaccccgaa ttatctgtat taaatgtata acgtttacta    249180
tccatattgc tgtgcatgtt aaactcaaaa actaatttgt gtagaaaggc actgacctaa    249240
agtaagtttt atttagcctt aaagaattgg taaatcagag caattcattc aatacacagc    249300
atctactaga agctaagaag atattgtaat tcctctagat gggaaagtta ggggcaggag    249360
gaaaagaaca acatgtaggg aaggtggcat tgggggtgag tctttaaaga ggcacaggac    249420
tgtgacgaga gaaggttcta tggggaggag tacagaggga agtagtaaat tacatgtaaa    249480
aaaggaacat gtgaaaagct acatgaaggc atctcaatcc ctctaaagat atatttggaa    249540
agaaagaaat gggtggaaaa tgaagatgac agatcagggc tatgttttag aacagtgggt    249600
ctcaaccctg gatgcatgta agaatcacca gggacctta aaaaacccat tgtccaggct    249660 tccctcaga ctagagtcca ggccctgaag ttaaaaaaaa aaaaaaaaaa gaagcctcaa    249720
gtggatttca tcatgcaacc aaagatgtga acttgtcctt tcagaggatt agtttggatt    249780
tacataaaag gaaaacattt attaacattt gttcttcctg ttgatttaaa tatgtatatt    249840 tgttttaat tcagaaggcc tgctaaatgc cacttgatta gtaaacccaa ttactctccc    249900
ttactgttag agcagtgagg agttatattg ttgcaaataa taaagataac ttactcattt    249960 ttgtttttcca acagataatg atggttgcag ggcccctctt caatggaggc attgccagcc    250020
ttctggccat gaaggagaaa gtgatttcaa ctaacccagg aaaactcttac ctctaaatgg    250080 agatacttcc tgataacaga agaaactggg catctaaccc agaaatacca gctgagtagg    250140
agaagagaaa aggcatcagc cagtcaaggt ttcagaaggc tgccaaca                  250188

<210> SEQ ID NO 131
<211> LENGTH: 300
<212> TYPE: DNA
<213> ORGANISM: Homo sapiens

<400> SEQUENCE: 131
atatgccaga aaagttgaat agtatcagat tccaaatctg tatggagacc aaatcaagtg     60
aatatctgtt cctcctctct ttattttagc tggaccagac caattttgag gaaaggatac    120
agacagcgcc tggaattgtc agacatatac caaatccctt ctgttgattc tgctgacaat    180
ctatctgaaa aattggaaag gtatgttcat gtacattgtt tagttgaaga gagaaattca    240
tattattaat tatttagaga agagaaagca aacatattat aagtttaatt cttatattta    300

<210> SEQ ID NO 132
<211> LENGTH: 420
<212> TYPE: DNA
<213> ORGANISM: Homo sapiens

<400> SEQUENCE: 132
tctcctctaa agatgaaaag tcttgtgttg aaattctcag ggtatttat gagaaataaa      60 tgaaatttaa tttctctgtt tttccccttt tgtaggaagt caccaaagca gtacagcctc    120
tcttactggg aagaatcata gcttcctatg acccggataa caaggaggaa cgctctatcg    180
cgatttatct aggcatagg ttatgccttc tctttattgt gaggacactg ctcctacacc    240
cagccatttt tggccttcat cacattggaa tgcagatgag aatagctatg tttagtttga    300
tttataagaa ggtaatactt ccttgcacag gccccatggc acatatattc tgtatcgtac    360
```

```
atgtttttaat gtcataaatt aggtagtgag ctggtacaag taagggataa atgctgaaat    420
```

<210> SEQ ID NO 133
<211> LENGTH: 300
<212> TYPE: DNA
<213> ORGANISM: Homo sapiens

<400> SEQUENCE: 133

```
cctttactta ataatgaatg cataataact gaattagtca tattataatt ttacttataa     60
tatatttgta ttttgtttgt tgaaattatc taactttcca ttttcttttt agactttaaa    120
gctgtcaagc cgtgttctag ataaaataag tattggacaa cttgttagtc tcctttccaa    180
caacctgaac aaatttgatg aagtatgtac ctattgattt aatctttag gcactattgt     240
tataaattat acaactggaa aggcggagtt ttcctgggtc agataatagt aattagtggt    300
```

<210> SEQ ID NO 134
<211> LENGTH: 300
<212> TYPE: DNA
<213> ORGANISM: Homo sapiens

<400> SEQUENCE: 134

```
ttgaataaaa gaaatatgac ttaaaacctt gagcagttct taatagataa tttgacttgt     60
ttttactatt agattgattg attgattgat tgattgattt acagagatca gagagctggg    120
aagatcagtg aaagacttgt gattacctca gaaatgattg aaaatatcca atctgttaag    180
gcatactgct gggaagaagc aatggaaaaa atgattgaaa acttaagaca gtaagttgtt    240
ccaataattt caatattgtt agtaattctg tccttaattt tttaaaaata tgtttatcat    300
```

<210> SEQ ID NO 135
<211> LENGTH: 300
<212> TYPE: DNA
<213> ORGANISM: Homo sapiens

<400> SEQUENCE: 135

```
attattaaaa ttcatatata agatgtagca caatgagagt ataaagtaga tgtaataatg     60
cattaatgct attctgattc tataatatgt ttttgctctc ttttataaat aggatttctt    120
acaaaagcaa gaatataaga cattggaata taacttaacg actacagaag tagtgatgga    180
gaatgtaaca gccttctggg aggaggtcag aattttaaa aaattgtttg ctctaaacac    240
ctaactgttt tcttctttgt gaatatggat ttcatcctaa tggcgaataa aattagaatg    300
```

<210> SEQ ID NO 136
<211> LENGTH: 360
<212> TYPE: DNA
<213> ORGANISM: Homo sapiens

<400> SEQUENCE: 136

```
gcatctattg aaaatatctg acaaactcat cttttatttt tgatgtgtgt gtgtgtgtgt     60
gtgtgttttt ttaacaggga tttggggaat tatttgagaa agcaaaacaa aacaataaca    120
atagaaaaac ttctaatggt gatgacagcc tcttcttcag taatttctca cttcttggta    180
ctcctgtcct gaaagatatt aatttcaaga tagaaagagg acagttgttg gcggttgctg    240
gatccactgg agcaggcaag gtagttcttt tgttcttcac tattaagaac ttaatttggt    300
gtccatgtct cttttttttt ctagtttgta gtgctggaag gtattttttgg agaaattctt    360
```

<210> SEQ ID NO 137

```
<211> LENGTH: 420
<212> TYPE: DNA
<213> ORGANISM: Homo sapiens

<400> SEQUENCE: 137
caaataagaa tatacacttc tgcttaggat gataattgga ggcaagtgaa tcctgagcgt      60
gatttgataa tgacctaata atgatgggtt ttatttccag acttcacttc taatggtgat     120
tatgggagaa ctggagcctt cagagggtaa aattaagcac agtggaagaa tttcattctg     180
ttctcagttt tcctggatta tgcctggcac cattaaagaa aatatcatct ttggtgtttc     240
ctatgatgaa tatagataca gaagcgtcat caaagcatgc caactagaag aggtaagaaa     300
ctatgtgaaa acttttttgat tatgcatatg aacccttcac actacccaaa ttatatattt    360
ggctccatat tcaatcggtt agtctacata tatttatgtt tcctctatgg gtaagctact     420

<210> SEQ ID NO 138
<211> LENGTH: 240
<212> TYPE: DNA
<213> ORGANISM: Homo sapiens

<400> SEQUENCE: 138
catgtagtga actgtttaag gcaaatcatc tacactagat gaccaggaaa tagagaggaa      60
atgtaattta atttccattt tcttttttaga gcagtataca aagatgctga tttgtattta    120
ttagactctc cttttggata cctagatgtt ttaacagaaa aagaaatatt tgaaaggtat     180
gttctttgaa taccttactt ataatgctca tgctaaaata aaagaaagac agactgtccc     240

<210> SEQ ID NO 139
<211> LENGTH: 300
<212> TYPE: DNA
<213> ORGANISM: Homo sapiens

<400> SEQUENCE: 139
gattcaagta atactattct tttattttca tatattaaaa ataaaaccac aatggtggca      60
tgaaactgta ctgtcttatt gtaatagcca taattctttt attcaggagt gcttttttga    120
tgatatggag agcataccag cagtgactac atggaacaca taccttcgat atattactgt    180
ccacaagagc ttaattttg tgctaatttg gtgcttagta atttttctgg cagaggtaag     240
aatgttctat tgtaaagtat tactggattt aaagttaaat taagatagtt tggggatgta    300

<210> SEQ ID NO 140
<211> LENGTH: 180
<212> TYPE: DNA
<213> ORGANISM: Homo sapiens

<400> SEQUENCE: 140
gtgatgtgaa tttagatgtg ggcatgggag gaataggtga agatgttaga aaaaaaatca      60
actgtgtctt gttccattcc aggtggctgc ttctttggtt gtgctgtggc tccttggaaa    120
gtgagtattc catgtcctat tgtgtagatt gtgttttatt tctgttgatt aaatattgta    180

<210> SEQ ID NO 141
<211> LENGTH: 420
<212> TYPE: DNA
<213> ORGANISM: Homo sapiens

<400> SEQUENCE: 141
tttcaggtac aagatattat gaaattacat tttgtgttta tgttatttgc aatgttttct      60
atggaaatat ttcacaggca ggagtccaat tttcactcat cttgttacaa gcttaaaagg     120
```

```
actatggaca cttcgtgcct tcggacggca gccttacttt gaaactctgt tccacaaagc    180
tctgaattta catactgcca actggttctt gtacctgtca acactgcgct ggttccaaat    240
gagaatagaa atgattttg tcatcttctt cattgctgtt accttcattt ccattttaac    300
aacaggtact atgaactcat taactttagc taagcattta agtaaaaaat ttcaatgaa     360 taaaatgctg cattctatag gttatcaatt tttgatatct ttagagttta gtaattaaca    420

<210> SEQ ID NO 142
<211> LENGTH: 600
<212> TYPE: DNA
<213> ORGANISM: Homo sapiens

<400> SEQUENCE: 142
taaccaagtg acaaatagca agtgttgcat tttacaagtt attttttagg aagcatcaaa     60
ctaattgtga aattgtctgc cattcttaaa acaaaaatg ttgttatttt tatttcagat    120
gcgatctgtg agccgagtct ttaagttcat tgacatgcca acagaaggta aacctaccaa    180
gtcaaccaaa ccatacaaga atggccaact ctcgaaagtt atgattattg agaattcaca    240
cgtgaagaaa gatgacatct ggccctcagg gggccaaatg actgtcaaag atctcacagc    300
aaaatacaca gaaggtggaa atgccatatt agagaacatt tccttctcaa taagtcctgg    360
ccagagggtg agatttgaac actgcttgct ttgttagact gtgttcagta agtgaatccc    420
agtagcctga agcaatgtgt tagcagaatc tatttgtaac attattattg tacagtagaa    480
tcaatattaa acacacatgt tttattatat ggagtcatta ttttaatat gaaatttaat    540 ttgcagagtc ctgaacctat ataatgggtt tattttaaat gtgattgtac ttgcagaata    600

<210> SEQ ID NO 143
<211> LENGTH: 360
<212> TYPE: DNA
<213> ORGANISM: Homo sapiens

<400> SEQUENCE: 143
ttccaatggt ttttattgaa gtacaatact gaattatgtt tatggcatgg tacctatatg     60
tcacagaagt gatcccatca cttttacctt ataggtgggc ctcttgggaa gaactggatc    120
agggaagagt actttgttat cagcttttt gagactactg aacactgaag gagaaatcca    180
gatcgatggt gtgtcttggg attcaataac tttgcaacag tggaggaaag cctttggagt    240
gataccacag gtgagcaaaa ggacttagcc agaaaaaagg caactaaatt atattttta    300 ctgctatttg atacttgtac tcaagaaatt catattactc tgcaaaatat atttgttatg    360

<210> SEQ ID NO 144
<211> LENGTH: 360
<212> TYPE: DNA
<213> ORGANISM: Homo sapiens

<400> SEQUENCE: 144
gggtgtttct tattttaaaa taattttct acttgaaata tttacaata caataaggga      60 aaaataaaaa gttatttaag ttattcatac tttcttcttc ttttcttttt tgctatagaa    120
agtatttatt ttttctggaa catttagaaa aaacttggat ccctatgaac agtggagtga    180
tcaagaaata tggaaagttg cagatgaggt aaggctgcta actgaaatga ttttgaaagg    240
ggtaactcat accaacacaa atggctgata tagctgacat cattctacac actttgtgtg    300
catgtatgtg tgtgcacaac tttaaaatgg agtaccctaa catacctgga gcaacaggta    360
```

-continued

<210> SEQ ID NO 145
<211> LENGTH: 6132
<212> TYPE: DNA
<213> ORGANISM: Homo sapiens

<400> SEQUENCE: 145

```
aattggaagc aaatgacatc acagcaggtc agagaaaaag ggttgagcgg caggcaccca      60
gagtagtagg tctttggcat taggagcttg agcccagacg gccctagcag ggaccccagc     120
gcccgagaga ccatgcagag gtcgcctctg gaaaaggcca gcgttgtctc caaactttt     180
ttcagctgga ccagaccaat tttgaggaaa ggatacagac agcgcctgga attgtcagac     240
atataccaaa tcccttctgt tgattctgct gacaatctat ctgaaaaatt ggaagagaa     300
tgggatagag agctggcttc aaagaaaaat cctaaactca ttaatgccct tcggcgatgt     360
tttttctgga gatttatgtt ctatggaatc tttttatatt taggggaagt caccaaagca     420
gtacagcctc tcttactggg aagaatcata gcttcctatg acccggataa caaggaggaa     480
cgctctatcg cgatttatct aggcataggc ttatgccttc tctttattgt gaggacactg     540
ctcctacacc cagccatttt tggccttcat cacattggaa tgcagatgag aatagctatg     600
tttagtttga tttataagaa gactttaaag ctgtcaagcc gtgttctaga taaataagt     660
attggacaac ttgttagtct cctttccaac aacctgaaca aatttgatga aggacttgca     720
ttggcacatt tcgtgtggat cgctcctttg caagtggcac tcctcatggg gctaatctgg     780
gagttgttac aggcgtctgc cttctgtgga cttggtttcc tgatagtcct tgccctttt     840
caggctgggc tagggagaat gatgatgaag tacagagatc agagagctgg gaagatcagt     900
gaaagacttg tgattaccct agaaatgatt gaaaatatcc aatctgttaa ggcatactgc     960
tgggaagaag caatggaaaa aatgattgaa aacttaagac aaacagaact gaaactgact    1020
cggaaggcag cctatgtgag atacttcaat agctcagcct tcttcttctc agggttcttt    1080
gtggtgtttt tatctgtgct tccctatgca ctaatcaaag gaatcatcct ccggaaaata    1140
ttcaccacca tctcattctg cattgttctg cgcatggcgg tcactcggca atttccctgg    1200
gctgtacaaa catggtatga ctctcttgga gcaataaaca aaatacagga tttcttacaa    1260
aagcaagaat ataagacatt ggaatataac ttaacgacta cagaagtagt gatggagaat    1320
gtaacagcct tctgggagga gggatttggg gaattatttg agaaagcaaa acaaaacaat    1380
aacaatagaa aaacttctaa tggtgatgac agcctcttct tcagtaattt ctcacttctt    1440
ggtactcctg tcctgaaaga tattaattc aagatagaaa gaggacagtt gttggcggtt    1500
gctggatcca ctggagcagg caagacttca cttctaatgg tgattatggg agaactggag    1560
ccttcagagg gtaaaattaa gcacagtgga agaatttcat tctgttctca gttttcctgg    1620
attatgcctg gcaccattaa agaaaatatc atctttggtg tttcctatga tgaatataga    1680
tacagaagcg tcatcaaagc atgccaacta gaagaggaca tctccaagtt tgcagagaaa    1740
gacaatatag ttcttggaga aggtggaatc acactgagtg gaggtcaacg agcaagaatt    1800
tcttttagcaa gagcagtata caaagatgct gatttgtatt tattagactc tccttttgga    1860
tacctagatg ttttaacaga aaaagaaata tttgaaagct gtgtctgtaa actgatggct    1920
aacaaaacta ggattttggt cacttctaaa atggaacatt taaagaaagc tgacaaaata    1980
ttaattttgc atgaaggtag cagctatttt tatgggacat tttcagaact ccaaaatcta    2040
cagccagact ttagctcaaa actcatggga tgtgattctt tcgaccaatt tagtgcagaa    2100
agaagaaatt caatcctaac tgagaccctta caccgtttct cattagaagg agatgctcct    2160
```

```
gtctcctgga cagaaacaaa aaaacaatct tttaaacaga ctggagagtt tggggaaaaa   2220
aggaagaatt ctattctcaa tccaatcaac tctatacgaa aattttccat tgtgcaaaag   2280
actcccttac aaatgaatgg catcgaagag gattctgatg agcctttaga gagaaggctg   2340
tccttagtac cagattctga gcagggagag gcgatactgc ctcgcatcag cgtgatcagc   2400
actggcccca cgcttcaggc acgaaggagg cagtctgtcc tgaacctgat gacacactca   2460
gttaaccaag gtcagaacat tcaccgaaag acaacagcat ccacacgaaa agtgtcactg   2520
gcccctcagg caaacttgac tgaactggat atatattcaa gaaggttatc tcaagaaact   2580
ggcttggaaa taagtgaaga aattaacgaa gaagacttaa aggagtgctt ttttgatgat   2640
atggagagca taccagcagt gactacatgg aacacatacc ttcgatatat tactgtccac   2700
aagagcttaa tttttgtgct aatttggtgc ttagtaattt ttctggcaga ggtggctgct   2760
tctttggttg tgctgtggct ccttggaaac actcctcttc aagacaaagg gaatagtact   2820
catagtagaa ataacagcta tgcagtgatt atcaccagca ccagttcgta ttatgtgttt   2880
tacatttacg tgggagtagc cgacactttg cttgctatgg gattcttcag aggtctacca   2940
ctggtgcata ctctaatcac agtgtcgaaa attttacacc acaaaatgtt acattctgtt   3000
cttcaagcac ctatgtcaac cctcaacacg ttgaaagcag gtgggattct taatagattc   3060
tccaaagata tagcaatttt ggatgaccct ctgcctctta ccatatttga cttcatccag   3120
ttgttattaa ttgtgattgg agctatagca gttgtcgcag ttttacaacc ctacatcttt   3180
gttgcaacag tgccagtgat agtggctttt attatgttga gagcatattt cctccaaacc   3240
tcacagcaac tcaaacaact ggaatctgaa ggcaggagtc aattttcac tcatcttgtt   3300 acaagcttaa aaggactatg gacacttcgt gccttcggac ggcagcctta ctttgaaact   3360
ctgttccaca aagctctgaa tttacatact gccaactggt tcttgtacct gtcaacactg   3420
cgctggttcc aaatgagaat agaaatgatt tttgtcatct tcttcattgc tgttaccttc   3480
atttccattt taacaacagg agaaggagaa ggaagagttg gtattatcct gacttttagcc   3540 atgaatatca tgagtacatt gcagtgggct gtaaactcca gcatagatgt ggatagcttg   3600
atgcgatctg tgagccgagt ctttaagttc attgacatgc caacagaagg taaacctacc   3660
aagtcaacca aaccatacaa gaatggccaa ctctcgaaag ttatgattat tgagaattca   3720
cacgtgaaga aagatgacat ctggccctca ggggccaaa tgactgtcaa agatctcaca   3780
gcaaaataca cagaaggtgg aaatgccata ttagagaaca tttccttctc aataagtcct   3840
ggccagaggg tgggcctctt gggaagaact ggatcaggga gagtactttt gttatcagct   3900
tttttgagac tactgaacac tgaaggagaa atccagatcg atggtgtgtc ttgggattca   3960
ataactttgc aacagtggag gaaagccttt ggagtgatac cacagaaagt atttattttt   4020
tctggaacat ttagaaaaaa cttggatccc tatgaacagt ggagtgatca agaaatatgg   4080
aaagttgcag atgaggttgg gctcagatct gtgataaac agtttcctgg gaagcttgac   4140
tttgtccttg tggatgggg ctgtgtccta agccatggcc acaagcagtt gatgtgcttg   4200
gctagatctg ttctcagtaa ggcgaagatc ttgctgcttg atgaacccag tgctcatttg   4260
gatccagtaa cataccaaat aattagaaga actctaaaac aagcatttgc tgattgcaca   4320
gtaattctct gtgaacacag gatagaagca atgctggaat gccaacaatt tttggtcata   4380
gaagagaaca aagtgcggca gtacgattcc atccagaaac tgctgaacga gaggagcctc   4440
ttccggcaag ccatcagccc ctcgacaggg gtgaagctct ttccccaccg gaactcaagc   4500
```

```
aagtgcaagt ctaagcccca gattgctgct ctgaaagagg agacagaaga agaggtgcaa    4560
gatacaaggc tttagagagc agcataaatg ttgacatggg acatttgctc atggaattgg    4620
agctcgtggg acagtcacct catggaattg gagctcgtgg aacagttacc tctgcctcag    4680
aaaacaagga tgaattaagt ttttttttaa aaaagaaaca tttggtaagg ggaattgagg    4740
acactgatat gggtcttgat aaatggcttc ctggcaatag tcaaattgtg tgaaaggtac    4800
ttcaaatcct tgaagattta ccacttgtgt tttgcaagcc agattttcct gaaaacccctt    4860 gccatgtgct agtaattgga aaggcagctc taaatgtcaa tcagcctagt tgatcagctt    4920
attgtctagt gaaactcgtt aatttgtagt gttggagaag aactgaaatc atacttctta    4980
gggttatgat taagtaatga taactggaaa cttcagcggt ttatataagc ttgtattcct    5040
ttttctctcc tctccccatg atgtttagaa acacaactat attgtttgct aagcattcca    5100
actatctcat ttccaagcaa gtattagaat accacaggaa ccacaagact gcacatcaaa    5160
atatgcccca ttcaacatct agtgagcagt caggaaagag aacttccaga tcctggaaat    5220
cagggttagt attgtccagg tctaccaaaa atctcaatat ttcagataat cacaatacat    5280
cccttacctg ggaaagggct gttataatct ttcacagggg acaggatggt tcccttgatg    5340
aagaagttga tatgcctttt cccaactcca gaaagtgaca agctcacaga cctttgaact    5400
agagtttagc tggaaaagta tgttagtgca aattgtcaca ggacagcccct tctttccaca   5460 gaagctccag gtagagggtg tgtaagtaga taggccatgg gcactgtggg tagacacaca    5520
tgaagtccaa gcatttagat gtataggttg atggtggtat gttttcaggc tagatgtatg    5580
tacttcatgc tgtctacact aagagagaat gagagacaca ctgaagaagc accaatcatg    5640
aattagtttt atatgcttct gtttttataat tttgtgaagc aaaattttttt ctctaggaaa    5700 tatttatttt aataatgttt caaacatata taacaatgct gtattttaaa agaatgatta    5760
tgaattacat ttgtataaaa taattttttat atttgaaata ttgacttttt atggcactag    5820
tatttctatg aaatattatg ttaaaactgg gacaggggag aacctagggt gatattaacc    5880
aggggccatg aatcaccttt tggtctggag ggaagccttg gggctgatgc agttgttgcc    5940
cacagctgta tgattcccag ccagcacagc ctcttagatg cagttctgaa gaagatggta    6000
ccaccagtct gactgtttcc atcaagggta cactgccttc tcaactccaa actgactctt    6060
aagaagactg cattatattt attactgtaa gaaaatatca cttgtcaata aaatccatac    6120
atttgtgtga aa                                                       6132
```

<210> SEQ ID NO 146
<211> LENGTH: 1480
<212> TYPE: PRT
<213> ORGANISM: Homo sapiens

<400> SEQUENCE: 146

```
Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80
```

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu His Pro Ala Ile Phe Gly
130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
            165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
            290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
            370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
            450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
            485                 490                 495

Ile Met Pro Gly Thr Ile Lys Glu Asn Ile Ile Phe Gly Val Ser Tyr

```
                500             505             510
Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Ile Val Leu Gly Glu Gly
            530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
            595                 600                 605

His Leu Lys Lys Ala Asp Lys Ile Leu Ile Leu His Glu Gly Ser Ser
            610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
            690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
            725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
            755                 760                 765

Val Leu Asn Leu Met Thr His Ser Val Asn Gln Gly Gln Asn Ile His
            770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
            805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
            850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
            915                 920                 925
```

```
Met Gly Phe Phe Arg Gly Leu Pro Leu Val His Thr Leu Ile Thr Val
    930             935                 940

Ser Lys Ile Leu His His Lys Met Leu His Ser Val Leu Gln Ala Pro
945             950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
                980                 985                 990

Asp Phe Ile Gln Leu Leu Leu Ile Val Ile Gly Ala Ile Ala Val Val
            995                 1000                1005

Ala Val Leu Gln Pro Tyr Ile Phe Val Ala Thr Val Pro Val Ile
    1010                1015                1020

Val Ala Phe Ile Met Leu Arg Ala Tyr Phe Leu Gln Thr Ser Gln
    1025                1030                1035

Gln Leu Lys Gln Leu Glu Ser Glu Gly Arg Ser Pro Ile Phe Thr
    1040                1045                1050

His Leu Val Thr Ser Leu Lys Gly Leu Trp Thr Leu Arg Ala Phe
    1055                1060                1065

Gly Arg Gln Pro Tyr Phe Glu Thr Leu Phe His Lys Ala Leu Asn
    1070                1075                1080

Leu His Thr Ala Asn Trp Phe Leu Tyr Leu Ser Thr Leu Arg Trp
    1085                1090                1095

Phe Gln Met Arg Ile Glu Met Ile Phe Val Ile Phe Phe Ile Ala
    1100                1105                1110

Val Thr Phe Ile Ser Ile Leu Thr Thr Gly Glu Gly Glu Gly Arg
    1115                1120                1125

Val Gly Ile Ile Leu Thr Leu Ala Met Asn Ile Met Ser Thr Leu
    1130                1135                1140

Gln Trp Ala Val Asn Ser Ser Ile Asp Val Asp Ser Leu Met Arg
    1145                1150                1155

Ser Val Ser Arg Val Phe Lys Phe Ile Asp Met Pro Thr Glu Gly
    1160                1165                1170

Lys Pro Thr Lys Ser Thr Lys Pro Tyr Lys Asn Gly Gln Leu Ser
    1175                1180                1185

Lys Val Met Ile Ile Glu Asn Ser His Val Lys Lys Asp Asp Ile
    1190                1195                1200

Trp Pro Ser Gly Gly Gln Met Thr Val Lys Asp Leu Thr Ala Lys
    1205                1210                1215

Tyr Thr Glu Gly Gly Asn Ala Ile Leu Glu Asn Ile Ser Phe Ser
    1220                1225                1230

Ile Ser Pro Gly Gln Arg Val Gly Leu Leu Gly Arg Thr Gly Ser
    1235                1240                1245

Gly Lys Ser Thr Leu Leu Ser Ala Phe Leu Arg Leu Leu Asn Thr
    1250                1255                1260

Glu Gly Glu Ile Gln Ile Asp Gly Val Ser Trp Asp Ser Ile Thr
    1265                1270                1275

Leu Gln Gln Trp Arg Lys Ala Phe Gly Val Ile Pro Gln Lys Val
    1280                1285                1290

Phe Ile Phe Ser Gly Thr Phe Arg Lys Asn Leu Asp Pro Tyr Glu
    1295                1300                1305

Gln Trp Ser Asp Gln Glu Ile Trp Lys Val Ala Asp Glu Val Gly
    1310                1315                1320
```

| | | | | | | | | | | |
|---|---|---|---|---|---|---|---|---|---|---|
| Leu | Arg | Ser | Val | Ile | Glu | Gln | Phe | Pro | Gly | Lys | Leu | Asp | Phe | Val |
| | 1325 | | | | 1330 | | | | 1335 | |

Leu Val Asp Gly Gly Cys Val Leu Ser His Gly His Lys Gln Leu
     1340             1345             1350

Met Cys Leu Ala Arg Ser Val Leu Ser Lys Ala Lys Ile Leu Leu
     1355             1360             1365

Leu Asp Glu Pro Ser Ala His Leu Asp Pro Val Thr Tyr Gln Ile
     1370             1375             1380

Ile Arg Arg Thr Leu Lys Gln Ala Phe Ala Asp Cys Thr Val Ile
     1385             1390             1395

Leu Cys Glu His Arg Ile Glu Ala Met Leu Glu Cys Gln Gln Phe
     1400             1405             1410

Leu Val Ile Glu Glu Asn Lys Val Arg Gln Tyr Asp Ser Ile Gln
     1415             1420             1425

Lys Leu Leu Asn Glu Arg Ser Leu Phe Arg Gln Ala Ile Ser Pro
     1430             1435             1440

Ser Asp Arg Val Lys Leu Phe Pro His Arg Asn Ser Ser Lys Cys
     1445             1450             1455

Lys Ser Lys Pro Gln Ile Ala Ala Leu Lys Glu Glu Thr Glu Glu
     1460             1465             1470

Glu Val Gln Asp Thr Arg Leu
     1475             1480

<210> SEQ ID NO 147
<211> LENGTH: 152082
<212> TYPE: DNA
<213> ORGANISM: Mus musculus

<400> SEQUENCE: 147

```
aattggaagc aaatgacatc acctcaggtc tgagtaaaag ggacgagcca aaagcattga       60
cctggtcctg gatatccaga tgtcgagtcc aacctgaatt tagccgaaca cagacctcat      120
tgcctcacgg agacatcatg cagaagtcgc ctttggagaa agccagcttt atctccaaac      180
tcttcttcag gtgagagggt actcagcgga tctttgcacg acacatgtg cctatgcagg       240
agaagggaat gaatatgggc agactttggg aaaacaggaa gagattttg ttgtgtttgt       300
tttgttttaa aaggtgtgtt gtcattcagt gctttaaagg aaataagcat ttttgtacaa      360
taaaatgaag ctgattgaat agagaacaaa atatacttgc aactgtgaat cagacttgca      420
acagccaaat atgctacgga gcaatagata tatttttt taatttcctg aaaaaagtta        480
tacttcataa gtgtacttaa tagaacattc ctaagattgg tctgttattt tctccaagaa      540
aagctgaccg caagtgcagt gcctgtgtaa taggtgctct gaaaacattt gttgactgaa      600
ttttttaaa agtccaggaa ttatattgta tttactttt gccgttgtaa tattgagtaa        660
gtctaacatg ctcatcacag ttacattatt cttttaaaa atgagcaagt cagttaaaat       720
atctaactt aaaagaaat aatataagca atgcattaaa aaagtgagtt accatgggga        780
tatgaaacta gagttttagc cactgaagct atattcaatt gacaattagg acattgttct      840
cttatcctac attgtcaaaa aaccaaaccc tcaatctaat aggattttta aattagaatt      900
taagttggaa gacctaggca agaattaagc gctttgtatt tgaagtgctc cgtggagctt      960
cgtctgctct gatcctgtag tgtgaatgaa tgaaagagc agcgctcatg ggtcctcagc      1020
tgactcaccc cccccccccc acacacacac caatgagtca gcacactgaa gtatcataag     1080
tgtcgaatat gttctcaacc tgccctatgc tgtgggtagg gggcaaggct cagccttagt     1140
```

```
cttcctgatg ttccttttc agccggtcta gagctcaagg ctgaggaaag acaagtgctt      1200
ctgcaggaga gctccccccg gtggttggga gagaaggaag ggcttcttc tttagaatga      1260 atatttgtgg tgccttttgt tacttcatct ataaatctag cttatcggtc tggatctatt    1320
ttcttattac ttacaaaatc agaatgtcac ttgacataca tgtgaggctt ttatgaaagc    1380
ctattgagga acctaaatgt caatgtgtct gtaaaggcaa gttttcagga gaatgaatat    1440
ctcttgtgtg gttttcccac taagtagtaa gaaacttcaa aattttcac ttatcaaagt    1500 gtttcaaaaa tttcccgttt ttataaccca cctaataaat tgtagtgtgc tttacaaatg   1560
ttcttaggct gatttggaaa ggaaatgtat tataatggct gtgaaatttg ttaagaacat  1620
actcatttct gccctccaaa tgatttcata atcagttgct ttaagaatag gtgtgtttt    1680 aagagtttag ttcctactat ttataggaac tgacatttag ctaagtacta gtcagtgatt   1740
ataaacttcc ttctggactt taattttcaa agagtaaaac ccttttctcc actggactag   1800
gcagtgccgc ctagtgacca gggcagtggg ccctggattc ccatggcctg gactcaggct   1860
gcagatctac tgcttagtag gcaagccctt tggtgtctct gcatgacttc agtgctacaa   1920
cttggagtct gtcagtgtga cacataatgt aatgggttag tctgttgagg aatatatgct   1980
gtgctttgag gacatgttag ctgcccttac tgttgtttac atgtttacat tcctcgaagt   2040
gctgggatcc tcactgtaaa ggacagtgag tttatttctg ctgggtgcac ttttgtgact   2100
atagcctgta tctatgccat ttgcttgaga agttagcata ggggatagat agcctcacgt   2160
agcatgggct tgttagatac ttagatgaaa gccatgctct tacatcagat ctccttcagt   2220
gccttagaat ttaacctatc ccatcaagct tagggttata aaagactcct aaaagctgac   2280
ttctatgtgt ctactattat ggtcttggtt ttggattata ttaattaaca ttttaattat   2340
ttagattatg ttactgagaa accaaaacaa gtttaataat aatttaagta cttttattt   2400 ttttaagttt tcagtaagta aaaaaatgga aagacattgg aattggtcta acacagaaga   2460
taattttacc atgaaaattt caagtaattt tttttacttt catggaaaat aaatgcatta   2520
acttgaaggt gtaatgataa catttatgaa ataagttgtt tcaaaacaag tggtgatata   2580
tttatacaga atttatgatt gacatattag tggaattaat tcctaaaaac ctttgatttg   2640
tagaaatgtt tgaactttac actttcatag agatttaaga aaaaagatta tgcctaacgt   2700
gtacctgtta gtgtgtgtgt gtgtgtgtat gtgcgcgtat gcatgttgt atgaccatag    2760 agtgcagtat aagctatcat ctcttgagtc atgtctctca ttggcctgaa tctcaccagt   2820
tatgttagac agacttgcca gtgaacccaa gggcttccc tgactctacc ttctcagcac    2880
tgggattaca atcttgtgtc actctgcccg ccttttcacc taggagcttg ggattgagct   2940
cggttcttca ttcatgtgaa gttcttctct gactgggtta tgaacagtcc caagaaattg   3000
ggtagcaaca tttccattct gtttgtgatc catattacag agattatact tgacaaaact   3060
taaggttatc caaatctgaa ggccactttt gatatactga ggatatggta tttagaaaac   3120
caagaattgc tgtcccttca gttgatggat gtcatacagt ggccacagct ccagatttca   3180
tttggctttt cttaatagaa atgggaaga agccacatct aggatggaga gaccctctgt    3240
ttggacagtg tacaagcact gcccgatact ggctctgtgc cagcaactta ggactccctt   3300 ctgtttatt tcttttcact gataatgttt ggttgttaca cagctcagaa atttcaactt    3360
gggatttatg ttaggttcat gtcagttttg tttagtttaa tcaacagttc taagagcacc   3420
tcttgtacag gacatgatga aatcatgatt ttgtgtatgt gcatatatat gtgtataata   3480
aatatctcta tacagtgaaa tttatttag ttgatatcac aattattaaa atttattta    3540
```

```
aggttttata gcacattact acacaatata ttttgatagt caattcctca gagcagagga   3600
agctattatc ttaaaaataa cttcttcaac attttgtttg atatacgatg aaatactact   3660
cagtgcacac tgatatacaa gggaaatcaa ggcttttgt tttctttatg gaagtttgac    3720
ttaactgtga taattcctaa gtgttaaaac atgtttaaga ggtccacaaa taatatcac    3780 cataaagtat gttattactg ttaatgccct tcataggaa cctgtaattt cactgcggta    3840
gcactataga taagtatagg attgccaaac cataagggaa gggcggtaac catttagcat   3900
gcagtgagat attatttgtt gagactttaa aaacacatct gagtcagcag agtttgggcc   3960
gttttgattt gctcttcacc atgcatcttg tgcatttcct cagagccaag tctgcaaagc   4020
agtgagtata agaggcgaaa actatgaaag aggtccactt atttggagat actaacagag   4080
ggatttcata aatacatttt tcatcatcag taagggaaac attttaatgg cttcccttca   4140
gctcttaaga atggaatgga tgcaccatgt agggttttct ttgtaaaatc agcattacaa   4200
agtggcctct tcatggactt gattgtcaga gaacttaggc ttttagcaag aatactctag   4260
tagttcagat gaggcttgtc aaaatgtcaa tttcagtata agccattaat tatcttttga   4320
cattaatgac tatttgaaat tgtaaactac ttttgtgttt agtattcaca tcatttcatg   4380
actccaggat tacatgatta taatacctgt ttcttgttga aattgtctca caatgctaaa   4440
catcatctat atgcagtata catacatact ctaccctcaa aataatggga caatcatttt   4500
gatacaatgg gtgaggggaa acaactgttg acacattttt taatagagta agtattcctt   4560 cacatttttcc ttgtgatgtt tatcatataa actcttcaga aggcagtcta ctttatgact   4620
ccttgttcta gggcagtagt tctcaacctg tgtgtttcaa gggttaaatg acccttacac   4680
atgtgttgca tataagctat cctacatatc agctcttcac catacaatga ataacaatag   4740
aagaattaga ctcatgaagt agcaacaaaa attatcttat aatttggatt caccataaca   4800
tgagaaactg tattaaagag ttccagcaat agaaaggttg aggaccactg cgctagggta   4860
agggaatggt ttggagattt ttgaagtctt tagcattgtt agacttctta gcttggaaga   4920
tattctcttg atatcataag attagctgtc ctccccaccc aagtcaaagg ggtatttccc   4980
cagtatttcc tgtaggtcat gatgactcag agcaatgttt ggagggcaat ttcattcact   5040 ccctttcac caccaccgta ctccatgctt ggcattaagg tggtagaggc gctgccctct    5100
gaatgaatga ataccttaaa actgatgatc tcaagccaca gagatcccta tcccatactc   5160
atggctgtct agcaaggttt gatagagaag tgttgtatag gaactgcaag aacaagtgag   5220
agaacagcag tggttcagag aaggtctgga gtctgtcctg aaagcatgtg acagaacttg   5280
ggaggtagat ctggaaacta gcaagggcta gacccctggg taccttatat atttcttagg   5340
gctttattgc actgctcatg aaatgaaagg tgggaaattt taagcaggca gagatgtgat   5400
tatttcaaga ttgttggcgt ttttttttt gttttttgt ttttttgttt tttttaaaga    5460
ctgacagaag ggatagagaa agatgcctga aagatgtttg ggaagcaaaa taatcatatt   5520
tttaaattag aggtggaagg tgagagtgag gaaaaaataa gagggcttgg atgggtcagt   5580
ttgggtggta gaatggtagg tgatacatac tatgaagtgg ggtccttcta ttagaggcag   5640
aggcctggtg tgaggttaga tgcctatgca agactgcagt ctctaaaaga aagtgcaact   5700
ggcttgaggt gggttataca gtttgaatga attctttgtc ttgtcaatac tgttttcaa    5760 caaataataa ttagtcagaa ctaatatttt atttggtagt gctaggcacc aaacccagac   5820
ccatgtctat attaaagcat tctcctacta aactgcaccc cagccccaag taattacttc   5880
```

```
ttagcagaga aattcctagc acttagttca gacagatttg ccaactaaca tttgcttttc    5940
tactccatta cacctgacat ttaatagtca ctgttttctt tacataaaaa tattggtctc    6000
tccctctctc tgtctctctg tctctctgtc tctgtctctg tctgtctgtc tgtctctctc    6060
tctctttctc tttctctctc tctctctctc tcacacacac acacacaatt aaaagccatc    6120
atggatcagt gtcagtgatc gagtaagaca ttaggtattc ccataattca gtgcatcaag    6180
tacataatta caatgagacc taaaaaatta ttcactcttt taagagttta tagacctgtt    6240
gaatttaaga gtccgagata gcaatcccaa tagcagggcc aaggattttt gcaacagaat    6300
ttgatgaacc agataggcac tataagatga gttcattatg gtgaggataa taaccttgaa    6360
atataaatgt gacttttag tgatgtgtta attatttatt tatgcaagcc tgtgtatgcg     6420
catttattta tcattactag tgagcctcta tacttaccag gtttctaaca gttaacagtc    6480
ttagactcta tataagaatt tattaaaaat tctgtttatt ctgcctaaag tttcattgta    6540
ttatttttaa taacgcaacc tttttttctt tgtaataaga tggctatcac attcatttat    6600
aggttctgta attatattac ttagtttaat tagactaggc attaatttg attcataaaa      6660
tcattgactg tttaaagtag ttgatatata ataaaatatt acagttaaaa atggactttc    6720
ttgaaaacaa aaattattga atatttaaaa aaattaatga aatctttcac ctgtgttgtt    6780
agcaaaatgt aacttcattt agaaatgtgt aatgtgttag tagtcctta ctcagccggc     6840
ccatggattc cctggagtat gaaactgctg acttgttggc acaggtgtca tcggagcctt    6900
gagagccagg tgctttgctg ccacagaagg ggagcagaag cagtctcttg tggttcactc    6960
tccttttgtc accattgtga ccactgcttc tgcagagtga catcagacac agtccagtgg    7020
atttacaact cattagtaaa gcagtatgtc agggctctgc acttaatgga aacttgttca    7080
gggttagtgg tgtggtaaga tggaacccag ctgtaagttg taatatttta ttatgtatca    7140
actactttac atagtcagtg attttataaa tcaaaattaa aacaggatga ggagattctt    7200
gaaattagaa ccttctactt cacaaacaac agccatttct atagcttttc tttactctga    7260
caaatactaa gtatctatat aggttctctg tggaatatag cacacacata aaatggaaaa    7320
tatattaaat atgccaagtc ctagatccca tgtgtacctg ttaattaaat ttatgggaaa    7380
gaacaacttc tatgatctcc tttaacaaat gctaaggtaa ttcttctttt tgctaacatc    7440
taaaatcatc aactcaacga taaaacaggt ttggataacc caacaggtct tcattgggct    7500
aacatcctcc tcctcctcct cctccccctc ttcctcctcc tcctcctctt cagtaaatta    7560
acaataaaga cacaaaaata ggtcaactcg gaattctgta gttttgcctc tatcttccag    7620
cccttattaa gtacactcaa gagattacat acattatctc agtgaagttt ttaatctgtc    7680
tttgataatt gcacatataa gaaatgtggt tttaggggac tgcagtttag cagccaccaa    7740
gctaagagat gtgatgtcag atgtatcttt agattggtgt aaatccagac ataaaatttt    7800
aatcaataca tcacacacct agaatagaat tgatcaatta tttcacatgg ctttatatat    7860
actttaatgt ttttttcttgg gtctgaaata atttttact gcatttgttt atagacaaca    7920
ttaaacaggc catcagttag tcttcttgga agggcttgtt gctttaacaa caacaaagaa    7980
ttactttatt ttatgtgtac agtagttttt ccagcttgtt tgtttgtgca cattctgcca    8040
gtggaagcca gaagagggtg ctgaatagac tggagttgca ggtagtggag agacatctga    8100
agatgctgaa aactgaggtg agggcctctg gaagagcagc tcttaagccc atctcttctc    8160
tgagccatct cttcagccca tttattcagt ctgtttctta gcataggtct ttatgacatc    8220
cacaggaggc aggatggaac tttcctaaaa ataacaatat ccttatagtt tactttcagt    8280
```

```
attatttgaa aacaaaacaa aacaaaacaa taaaaacaga caatatagca ggccagaaaa   8340
cgtggcagta gctaaacatt gtcacagtaa cagctcagtt acagtgagtg tgattccagc   8400
tgtgcttcct gtcctgaata aggtagctaa gtactaggca gtgccttttα ctcagcccca   8460 cttccctact ttccattttc tctctaggat accaagctgg gactttgagt tttcacctcc   8520
taaccctact tcccttcact ctctaagcac atcacagcca tctttggcat ctatgccagc   8580
attaccaccc agtacttgtt ctcatcattc atgtcatctg attttctat tggtcttcct    8640 tcttatccac ctgctaaggt tgcaggaagt ggtagagaca cctgatagat ggttcttcaa   8700
ttttatactt gtcactttat atatacaaat ttcagatttt cttcatatgg tagtatctat   8760
agttctttta gaaagtgctt ttatcagtaa gtcttcatgg aatttaaata cttcatgaaa   8820
tttctagtgt aaacatgtat gtatggcaat aaaagaattg cttttccaca aacaaaaaga   8880
tataaagtcc caaataaaag caaaacattt atataatatt ttaagcatta ttttcttgat   8940 tccctttct gtgttttaca caattatata cttctgaaat tgaattgtct tataattgat    9000
ttttttccca aacttctttc tggccatcag atccaggaat aaattattat caacacataa   9060
aagttgcata tttcctgtat cctgtgactt caagtgattt ttttttttta cttttggcat   9120
taatttcacc caacaatgtt gacttttaac tttgattgct tgatattcct tgagaaagag   9180
tactttatga tccagttttg gaagtatcag gtaatgtgta cttggatgct tgtctggcat   9240
gctaggcatt gtaattacag tagacattca ccaagtttag tactctacct taacttgaaa   9300
ttgtacacct gtcccagagg tgaaggggtt ctgaaggcag atttacacta taaacctatt   9360
catagattct aaagggcaag agtgattcag aaaactaatt tttacttgag tatgaaaatg   9420
gcttaggcta aaactttaat tatggttcca aaagtaataa gtactatat aaatgattat    9480 ataatttaa tttctaaaaa cagtatgtca tgtacatttt gacagtggaa gtgttggttt    9540
aatagtgaat ctcataatca gtgtcacctt agaatgaaca taaccacttt attttaaaaa   9600
catgataatg tcacctatgg tttgtcactt atcacttcct aggggttttg ttgccctggg   9660
ttatgctgtg atcttgtgtc aacaggtgta ctgcaggcat gctaggctgt taactgagtt   9720
tggctcatat gtcctatagg gacatgctca cttatgcact gtagagataa cagtaaatat   9780
cacagtaagt ttcaatattc accaaaaaag aaatgtccgg tgaagttttc ctatttgtag   9840 gactatatg ggactaaaat tatcatatat ttaagaatat gtaattttt attccttta     9900 ttcctaaaaa aaaaaaatga aaccaactca gtcactttaa aagatataca tttcagatca   9960
aaattttgtg gggtgtgtct ggagagtggc agatattagg attcaagatt tcaaagacat  10020
tgaaggtaga ttatgcttat cttgattgtg cctggcaatt tttgagtccc atgcttcatc  10080
tccccatgct tttagaaaag tctcacattt agcttctctg tcagttctta ggaaccagcg  10140
tgtagcggaa gaaatgtgca ctttggaatc aggcttagct ggagtcctca ttctgtgact  10200
tattaacgtg tgttcttagg cacttaatct ttctgatact caattattct cactgggata  10260
atgagttact ttcatttcaa cctggcctaa gaatataata atattcaata ttctctgagt  10320
acttactctg tatattagag ttctcctgag aataagaatc aatagtaaat ctatttaata  10380
tataagatta tttataaaga attagcttcc gtgactaaga aaactgtcaa gttcaatact  10440
tgcagggttg ttttcaaagt ggagactggg aaagctaata ttcaggtttg agttcaaaag  10500
cagtcgccag gagttcggtg tcatttgggg aggctggtct ttttttttgt cagactcatg  10560
ttttcagtgg attagggaag acagcttaca ttagagagca tgtagtggtg cacagacatc  10620
```

-continued

```
tggcttccct tgtgatttcc ggaacagaat taacacaaat aatagaacaa tccataacag   10680
gagctcaacc tgctctaacc taaatgctct catttaatgt tagtctgacc tccaagtatc   10740
ttatcaattg ccatagccat cacccctgtg aggactttct gtgtcttcag tgataagtag   10800
tgcaagatac agaatgcctc tttaataagt aaatggtaac agtcttatga acactaaggc   10860
acttaacacc tttccagtgt gtaacagact agctcgctct ttcctacatc taacattcct   10920
ctcctagaaa gtaggcacaa catgtcactg aattataatt ctctttccca aaatcccttg   10980
cccagtctac aagttttgtt taccatagac tttcatcctc aattgtgtgt gtgtgtgttc   11040
attgctgggt ttgaactcct gggtaaatgc agcatactaa gcaaatgctc tgaggcactg   11100
agttacactt ccaaccctca tcttaaattt taagtttatt ttaagcattc aggctactct   11160
ttttgctccg acatatttcc tttctgtttg gggcccatgt gtttgcagag gctgctatca   11220
catagtatat aaactgaatg gattagacac tcaaaattta tcgttatagt tctaaatgct   11280
acaaggctga catcaaggtg ttagttaatt gttttttccc aaggatgtga gtgagaatct   11340
attctgtgct ttctggccta gcgtttgtca gcatgctggt ggggatcctt agcatttttga   11400
gatctgtaga ggtatcacct ccagaggcac cctttttcaca gatttctcct tgtatcttca   11460
gataaatgtc caaaatcaat tcctttgtaa ggaaaacagt catgttgtct ggaacctact   11520
aaatgtgttt actccacatg ttttgagggt cataggttag aggggggtggg tgggtggatg   11580
agcaccttca tagaagcagg gggaggagga tgggataggg ggtttccagc agggaaacca   11640
ggaaaggggc taacatttaa aatgtaaata aataatatat ccaataaaaa agtaaataca   11700
tatatatcct taaaaatatg gagacactac agaggcacct gtaagacggg ataagggaac   11760
tatctaggga gtagttcatg aatctttagt atatctttag tatatctgta ctaaaacatt   11820
aatgaagatc aaatattgag aaggtttaga taatgaaaaa tatttcataa aatttttattc   11880
aacaaaatta aataaattct tggttgaata tttagtattg tgggccatta atgatatgta   11940
aaatgaacat gttatctctg accaagtaca aatcctcaat gtttatatta cattcttgta   12000
gagttggttt ttcttttctc ctttcggtgc cttgaccaga agtaatgaat aagcaaaacg   12060
tccttgcaat cagtgtcctt agggtgccat aaacatacta tgtttgtgga attaattact   12120
aacagatcaa ttcaccaagt ttctaatttg ctcagtgcaa tgaacaggac aatgaacata   12180
ggaagataaa ttatacacta tgttgtcctt atgaatttaa tcttgtgagg aaaaataagc   12240
agagtgaaat atcttaactt ttaaattcaa aaatttaaaa tattaagtga gaattatgtg   12300
ccatgttcag tggacagtgc agagtagaca gtgcagctta aacagagctc tttatgcaat   12360
gtggtataca gtttagtgta cttggggacc tgtggttgat aaagggagga atagagaaag   12420
gtggggtagg gtaggacagt gtacacagga gactgattaa ccagactgga gagagagagg   12480
ctcttcctga ccaatatcaa tgcactaaac cttcttagaa atagaagtca ggctttgttt   12540
caaggaagct gtcagttttt attcagtgta actcagcaaa atcagagatt agcttgctca   12600
gtgatggtga taggaaaatc ttttttaaata ttaagagcca ccctattatc agtgttttca   12660
tccagttgaa ctcctgcaga gttcaaaagc tggagagtct ggctcaatgt ttcctttaaa   12720
gttcattttc ttaaaaccta aatggaaaca aaagatcatg acatcttgag gaaaaaagga   12780
aaacaaaacc tttaaatagt tataaaaata attttttatta atctaccatg gtttgtgtta   12840
ggagctatcc ttttaagtac ctgattgcta agatggctaa cttgatctct taaattgctt   12900
attagaaaca atgaattaat cactattatt tatatatgtt atagtcttga aaaaatcagc   12960
aatttttaatt tttgacagat cttaaaaggt ttgtattaac atgcattgct atgcttaaat   13020
```

```
gaacataaaa atattaagta gagacttaaa gtaaggcctt ggagtagttt tctttcatgg   13080
caaatcctgg actaatctgg tcaacaactc cattccctgc tgaatctcaa ttttccaaag   13140
gaatacgtgg tgagaaaggg tgaggacgag cctctgtttt cctctcctgc agctctgggg   13200
agcttcagtg tttgttctta gtgatgccaa ggttttttgga caatgcaaat agaaatactt   13260
cgcctcccaa attcaggaac aggatatgaa ccttatagtc cgagtcatga actgtgccta   13320
cttacatcct cctcagcact aaaagggaaa aggcataaag atttgaaact tccatttcaa   13380
tttgttgcat aatagaaggt aaaaaggatt aaaatgacat taataaacaa atttcatatt   13440
taactgggag gtaggaaaat atccacagat gagaagccca aatcaaatgc cacaccactc   13500
ttctaatccc actggggatt cacagtgggt atcagtgcct taaaagtggc atcatactta   13560
aacaaacttg gggaagagga ggttaagaca atgaggaaaa tttcagactg acttatcaga   13620
ctagttgatt gcatggagaa ctatggaaac tatgtttacc acaaactgaa gtttaacctt   13680
gtcttcctgg taccaaatta cttcttctag aaaacattaa cattcttatt gtgtatacat   13740
ggaatgtgtt ttgattaaat cctcctccta tctctttccc tctcatatat cctcttcttc   13800
ctactacttt tgcctcccaa cttcatgtgc tcttatttat ttaaatttaa tacccactga   13860
agccattcag tactgcctta tatgactata tgtgcatgga gaccatctac taaacatacg   13920
tatccaccct ttcaggaatg ggcatccctg aatactgatt ctcccttccc cagcagctac   13980
ggattcccaa taacttctca gatagagcta agacttcatg agtcccttcc tagtccatgc   14040
tggggttttg actggcttaa tcctgttact attttcattt aaaaaatgat atagatgcct   14100
ctaatctctg ctgtatcatt ttatctgcca agcaaatcta tcaaatgaga aaatgatctc   14160
aaatgatgtg ggcagatgca ttttaaaatt acatttgtgt ctttgtgtgt gtgtgtgcac   14220
atatacacat gcacacacac actgctgtgt actaatgtat ggaggtcaga ggacaacttg   14280
taagtcagtc ctctctttct accatatagt ttctatgtgt tgagcttagg tcatcaaact   14340
tgacaccaac tacctcctaa gccatctgct ggtcctggaa tatatagaag tcattttgat   14400
gtaatgaatg acaaacatct atcaaaagac aaaaagaact tctttgtaca catagtgagg   14460
agctattaaa tgatttagat attgaagatc acgagaagtt gtactttgtg ttttatgtgc   14520
catggctcat gccagatgat atctgtagga atctaccacc tgtccagaac ctcatagaag   14580
ttctttgtct ctaagaaata attatgttct ttatacattt ggggaaaacc ttggagagtc   14640
aagtaggtat gcttccaaat atttagtcac tgtcagaatg acagtcatgg ctcagtaaag   14700
gacatgctta tttccgtgat aaatgaaaag tattgaattt gggtctttgt gatgccatct   14760
gataaagcaa aatgaacaaa gaaccacaat aaaggataca aagttctaga aagggggaga   14820
aaacactgaa ataaatcgaa taattatttt taaaaaagca gcaaggaaat gcgtatctcc   14880
catataggag atgtcatgaa tgccacttgt gcacagtcaa gtctttcagt tgcctagtca   14940
gaagccggga ggagcttatg cccatcttcc actttcacac ttccgtgagg atgcggtgag   15000
agtgcttctg acctctgtgt tccaggagat gattcaacac tgcacagagg gtcagttccc   15060
tgatagcaca gaggtttcca tctgaaagct tgcacacatg cctgtccata actcaggagc   15120
attgctacgg taaaactgca acaccaggct gtttcctgtc ttccttgttc ttttggtttc   15180
aaatatattt cttattgatg atgaaaatat cgctcagtaa tttgaaagcc attgtttcct   15240
cagaagtctc ctaaaaggaa actcgcatgt aggaaatagg cagcttcatg ggcaattag   15300 tactattttc ttggatttgg tgtaggtaca gtgatatctg tagcttcaca gaaaggcact   15360
```

```
taggctgctt tttcagagga cattggtact tgacagtaaa tgacatcctt tgtgtcttat   15420
gttacctcct aagatgagca ggattcctcc cctcccttcc cttcctctcc cttcccctcc   15480
tctcccctct gacctcccct ccaacctcct ctcccctcct ctcccctccc ctccccctccc  15540 ctccccctccc ctccttttcc ctccccccctt ccctcctctt cccttccctt tcctatttcc  15600
ttttctattt ttttcttgta gcgttgcttg ttgtctttag attttagaaa tgctcgtgtc   15660
ctctcactgc caacaaacac ttcttcattt ctatacaata tgatatcaca atgccatttt   15720
ttcccctcag aattcatagt agttccaaaa tctaagtttc tggctttgag agaccggaaa   15780
taaacaatgt ataacattca tgttgcttgt catcaaccgt taactggtcc catgagtttt   15840
ttacacactg tgatatcatt gtcaggagcc atcagaacaa ctgcgtatgt gaaaaggatt   15900
agagtttgaa aatcaccact ggaaagtttc accagttcta caagcatatc tatctcactt   15960
agaaaaccct tccagcacca acgttgattt ctcaacccctt cacactgctt ttctaactta  16020
tagctttatt gaggtagaat ttacacatca aacactttac ccatttacaa tatacaaaat   16080
aatgaatttt aagcatattt ataattttgt taaatatcac aaaataaatg taggaacctt   16140
tattcataca aagaaagaaa gaaagaaaga agaaagaaa gaaagaaaga agaaagaaa   16200 gaaaactatt cagctttctc atgcctatct gcagatctgt ttcaagggcc ttgtgtactt   16260
gaagcagata gagccacctg ggaagagcct acactgagaa actggcttca tcagactagc   16320
ccagaagcaa ggtcattggt tttatttatt tatttattta tttatttatt tagtggtttt   16380
tgtttgtttg tttgtttgat taatgattca tgtggaagaa gcaagcccac tgtagacaat   16440
gccattcatt agtaggtgac cttacaatat ataagaaagg aaatcctata agccatagag   16500
aacaaaccca taaacatact cctccttagg tcctctgctt cgattcctgt ctttaggttg   16560
ctgtttaagt tagttactgc cctgacttcc attcatgata aattgtgatg cacaagtgta   16620
agcttttctt cctcaagttg cttttggtca gtgtcttaac acagtagcag agaaacaagc   16680
tctatatttt gcctcccact tcttgttcta ggcaactgtt agtctacttc tgcctttatc   16740
ttgttgcttc ataaaaatga acaattcag tgttttgtga ctggtcttgt tcaatggttc    16800
aaaaagttga cactattatt acatggttca tcacttggtt tagggatata tatgttgtta   16860 agttttact tgacagttaa tgttttttaa ccatttgcct gttgtaaatg atactcatat     16920
gaatatcatt tgggtattag tttttatgta gatgtatgtt tttatccttt ggggtatata   16980
cctaagagtg gaatgggtaa gtcatgctgt aaatttatgc ttaatatttt aaatatctta   17040
ctgattattt tccaaaatat atacacaaat ttatattcct ctagcagaac acagggttac   17100 aatttccat acatttgcaa cgatttgtat gtttagtttg ttgttattac agcgattcta    17160
atgggtataa aatggaatct agctgtagtt ttgaattgca ttttcctact ttgtaatgac    17220
catttcatgt gcttactggt catttatgta atttctattt tagataaatt tttatccagc    17280
tcatgtaatt ttaaattttg gtttatgtct attactgagt tagaagtctt ttatatatct    17340
gatattaaaa ccacttagca gatatttgac ttgcagaaat tatatagact atacactatt    17400
ttctttattg tatattttaa aggataagaa gttttattca ttttatccat tttggttatt    17460
gttgtttatg cttctggtat tatatttaat tatgtgctac tttttcaaat taattatgaa    17520
atatggcaaa ttagacaaat aagctttgat attacatgcc tatttttaaa ttctaacttc    17580
acattaacaa attgcttaag catcactaga tccagtttca tatctataac atggatatgt    17640
aaggtctgtg cccagagctg gtccagtgcc acagtgctct gtacccaaat actgtccgga    17700
gagagctggt ctcccaggag tgccaacaca catgtgaaca caggtaagac caccactttt    17760
```

```
gattaaattc ctggcccaaa agggtctcgc ccagagccat caggacacag gaaccaagga    17820
acagctgggg acaggatcct tcagtttctg tctgtattct ggagcttacc ttgtgccaca    17880
gctctccata accaaattac tccaggaggg aactcccagg agtacagaca cacaggtttg    17940
aaggagggac aagccacagt cagagacagg aaggccagct aacagcagag atatcaagat    18000
ggcaagaggc aagggcaaga acataagcaa cagaaaccaa ggctacttgg catcatcaga    18060
aaccagttct cccaccacag ctatccctgg atactccaac aaaccagaaa agtaagactc    18120
tgaattaaaa tcatatctca tgatgatgat aagcgatgtt aagaaggata taaataactc    18180
tgtaaagaag tacaggggaa aacaggttaa cagctagaag ccttaaagag gaaacacaaa    18240
aattccttaa agaattacag aaaaacacaa acaggtcaag gaattgaaca aaaccttcca    18300
ggatctaaaa atggaaatag aaataataaa gaaatcacaa agggagacca gcctggagat    18360
agaaaaccta ggaaaaagat caggagttag atgcaagcat caccaacaga acacaagaga    18420
cagaaaagag aatctcaggt gcagaagata ccagagaaaa cattgacaca acagtcaaag    18480
aaaatgcaaa atataaaaat ctaacccaaa acatccagga aatccaggac acaatgagaa    18540
gaacaaacct aagaataata ggtgtagaag aaagtgaaga atcccaactt aagggccagt    18600
aaatatcttc aacaaaatta tagaaggaaa cttccctaac ctaaaggaag atacccat     18660 aagcatacaa gaagcctaca gaactccaaa tatattagat cagaaaagaa attcctccca    18720
tcacataata gtcaaaacac caaatgcaca aaacaaagaa agaatattaa aagcagtaag    18780
ggaaaaaggt caagtaacat ataccaggctg atctatcaga attacaccag acttctcacc    18840
agagactatg aaatctagaa gattctgggc agatgttata cagagcctaa gagaacgcaa    18900
atgccagccc aggttactat acccaacaaa actctcattt accatagatg gagaaaccaa    18960
gatattccat gacaaaaata aacttacaca atctctctcc acaaatccag tactataaag    19020
ggtaatagat ggaaaactcc aacacaagga gggaaactac accgtagaaa aagcatgaaa    19080
gtaatcttct ttcaacagat ccaaaagagg atccacacaa tcataaaaat aatataaaga    19140
ataacaggaa gcaacaatca ctattcttta gtatctctta acatcaatgg actcagtttc    19200
ccaataaaaa gacatagaat aacagactgg atacatacac agaacccagc attttgctgc    19260
atacaggaaa cccacatcag agacaaagac agaaattacc tcagagtaaa gggctgaaac    19320
caatttccca agcaaatggt cccaagaaac aagctggagt agccattcta atattaaata    19380
agatcaactt tcagcaaata gttatcaaaa agaataagga aggacacccc atatgcatca    19440
aaggaaaaat caaccaagaa gatctctcca ttctgaacat ctatgctcca aatgcaaggg    19500
cacccacatt cataaaagaa actttgtact acagctcaaa gtactcattg caccccacac    19560
attaatagtg ggagacttca acaacctgct ctcagcaatg gacagatcat gggaacagaa    19620
actaaacaga gacacagtga aactaacaga agttatgaac caaatggatc taacagatat    19680
ctatagaaca tttcacccta aaacaaaaga atatactttc ttctcagcac ctcgtggtac    19740
tgtctccaaa actgaccata taattggtca caaacaggc ctcaacatat acaagaagag    19800
tgaaataatc ctgtgcatcc tatcagattt tcaacagcaa caaaaataac agaaaaccca    19860
catccaaatg gaatctgaat gttctagtca atgataactt ggtcaaggaa gaagtaaaga    19920
aaaaaaaatt aaagactttt tagagtgtaa tgaaaatgaa ggcacaacat acccaaactt    19980
atgggacaca gtgaaagcag tgctaagaga aaaactcagc cccagtccc ttttaaaaga     20040 aactggagag agcatacact agcggcttga cagcacacct gaaagctcta gaacaaaaag    20100
```

```
aagcaaacac acccaagagg agtagacggc aggaaataat caaactcagg gctgaaatca    20160
accaagtaga aacaaaaaga actatacaaa gaacaaaatc aggagctggt tctttgaaaa    20220
aaaatcaaca atatagatga actcttagcc agactaacca gatgtcgcag agacagcatc    20280
caaattaaca aaatcagaaa tgaaaagtga tataaaaaac tgaaactgag gaaattaaaa    20340
aaaatcagat cctactacaa aagcctatat tcaactatac tggaaaatat ggatgaaatg    20400
gataattttc tagagagatg ctaaatacct aaattaaatc aggatcagat aaaccatcta    20460
aatagtccca taacccctaa agaaatagaa gcagccatta aaagtttctc aacagaaaga    20520
agcctaggac cagatggggtt tagtgcagaa ttctatcaga ccttcaaaga agacctaata    20580
acaatactct tcaaactgtt ccacaaaata gaaacagaag gaacactacc caattcattc    20640
tatgaagcca cagttatact cccttggaga tggaatggtt tctgtctaat caggaaccgg    20700
tcacaatttc ataagactat aaggacttca taagagattt ttttccatttt tatcatattt    20760 aatgttacaa atagattttt ttaagactgg ctgagtgcat attacttttta gcttcagatg    20820 atatcgtgta tatttaagag gcattttgca attatagatt attttgatga cttaaaaatg    20880
tcaataccga gttgtaaata ttaaaataaa ttcctacccc cacagtgaca cacctacttc    20940
aacaaggcca tacccctagt cactgctcat ctccttaatt ggcttatttg gacaggtggc    21000
tgagccttgt atttagcaat tgtggagcag ggacttccac cctcaatctc tggcaacaca    21060
tcatttcatt attagaaatg agatgtcatc ctataaaaaa ttagagttttt cacaaagaaa    21120 tggaatgaac taagctaaac agtcgggtta atatgtgctt gtttaaaaac taaaatacta    21180 gcattttttca taataaaatc tgaagctttt catggttaag tgaacagaac agtatatcga    21240
agatactagg tttttttttt ttttcctgtg aatgttagtg aactcttaaa aatacacacg    21300
agtctgctaa cttatagttg attagctagt ttctgttaga agtagccaaa attttggaga    21360
ccactatatt tttgaggaat accattttat aagtccattg agtatataca tggctgggca    21420
tgaatcaaga tgcataaagt cacttggata tgaggtgaag agctatcagg gataatggaa    21480
agacagaaaa ggagatcctc aatgcattgc ctcccgttgt tccaagcgaa ccaccgagac    21540
tcatgaaatg cctgactgac tataaattcc ttgcctgaac attactgaat ttacacaagt    21600
tcactgaata taatcagaat cactgaaaag aagaatggct tgaatttcat atcattattg    21660
caaagtgtct aaaacttgaa tgcctgtctt ttaattttttt aattttttttт tacttttgtt    21720 ttatatttct tagactgacc tgcagttgac agagagaact cactggtagg agacatttgg    21780
tttgatttat tggtttaatc tcaagatata aaatctttct cgaagatgac tctctggtga    21840
ttgcatagag ctaatagatt ttagttttta aaaattcttt ttagacttat aaagtatatg    21900
atgagtgttt tgcctgtatg taaatatgtg tactgcacat gcgcttggag ccctcagagg    21960
tcaaaacaag acatctgatc ccctggccct ggagtcccag atgtgagtca ccatgtcggt    22020
gctgagaatc aaaccctggt tctctgtaag agcagcaaat gctctaaacc actgatcatc    22080
cctcctgtcc ctatatttta gttttttataa tttacttttga accagtttca acttgggagc    22140
ataaatatag gttcatttta ttgtaacttc caaaagaaa tgctaactaa taataaaata    22200
caggtggtga gctgtgtgat gtgtgggtat attatatcac cgaattttat tttgccttca    22260
gtcgttgatc taaggttctc ttgttaaaac tagatgtcac tgtataacat aatatcttaa    22320
aaattctgag atagcaaaga aggttttatt aaaagcatct cacacattgt gttactttga    22380
aatgagctga aagctcattt atggggatgg ccactatatt ttatacatga gccaaaagaa    22440
tcatagttat atttttttcaa ggggataaga tgatttcaaa tttgcctcta aatgcttttt    22500
```

```
gaggcatggg tttggaggac agtaaaattc tacttactta aaaggtgatg tgtccaagaa  22560
aatcaagaag aaggaagacc aacgcatgca tacttcattc ctccttaggg aacaaaatac  22620
ccatggaagg agttaacaga dacaatgttt ggaactgaaa caaaaggatg gaccatccag  22680
agactgcctc accctgggat ccatcccata atcagccacc aaacgcagac actattgcat  22740
atgccagcaa gattttttgtg gaaaagaccc tgatatagct gtctcttgtg aggctatacc  22800
agtttctggc aaatacagaa gtggatgctc attgccatct attggatgga acacagggcc  22860
cccaatggag gaactagaga aattacccaa gagctgaagg ggtctgcaac cctataggtg  22920
aacaacaata tgaactaacc agtaccccca gagcttgtgt ctctatctgc atatgtatca  22980
gaagatggcc tagtcggcca tcaatgggaa aagaggctcc ttggtcttgc aaactttata  23040
tgcctcagta tgggggaatg ccagggccaa gaagtgggag tgggtgggta gaggagcagg  23100
gcaggggag ggtataggg actttcatga tagcatttga aatgtaaatg aagaatatat  23160
ctaataaaaa ttgaaaaata acataaaatg tgatgtgtca ttttaatatt ttcaaatcta  23220
ttgcgagcac aaggcttctg gtaggtggaa ttcatcttta aactgtgttc taaggaccac  23280
catccttcct gtcccatccc atcagccgtc tgagatttcc aatctcggcc agtcgtcaac  23340
acacgtgaat ctttctagct gaattgaact gtgaactagc tgctaagcac agccgttttt  23400
aaatttcaga ttgtagaacc taaattatga tatggtaaac aaaggttaaa gaggttgtca  23460
ctttgcattt attttgtacc ttgctgttat ggtattaagg gcatttgtgc ttgctgtctc  23520
tgaggaggta ggcatactac tattttatgc aggttagtcc tcttcccagt tctcatctgt  23580
agtagctaga agctgatcat ggaaagagtc cttataaagc agtgactgct gaaggtcatg  23640
agtcaggttt gcttttgttt tctggaaagg ggtttattat ttgtttacag atcacacccc  23700
caccctcagc ctagtagttt tcagttccct tactttaatc taagtttgtg tcttatttta  23760
atacaactca ctctacctac ttttgtaaag ctgaacatgg ttaaatgaat tcagaagaat  23820
gtgaagaaat ctttgatgtt agtaattcag aaaagttttg tgcctctgag taccatttcc  23880
taaccctggt aataaagcaa cagccctttt gtcctgtttg cctaacagga acttaagatg  23940
caaataaagt gctaatggtg tggaatttct ttggcaattg ctaaatagat actttaaaaa  24000
aattgtagta aactcttgct ttaagtttat ggagaataat agcccaaatc acaacatccc  24060
acaaggccat cttcctttta cctcctatac ttattgccag atacttttca gtgtcacttt  24120
ccttctgtga gatgctgggc aataagtacc tagctgtaga actaactttc tttctttctt  24180
tcttctttc tttctttctt tctttctttc tttctttctt tctttcttta tttcttcctt  24240
ccttccttcc ttccttcctt ccttccttcc ttcctttctc tctctctctc tctctctctc  24300
tctttctttc ttctttctaa atttattaga tattttcttt ttccttcctt ccttccttcc  24360
ttccttcctt ccttccttcc ttccttcctt cctttctttc tttctttctt tctttctttc  24420
tttctttctt tctttctttc ttaattttt attagatatt ttcttcattt acatttaaaa  24480
tgctatcccc aaagtcccct ataccctccc cctgccctgc tctccaaccc acccactctt  24540
gcttcctggc cctggaaatc ccctgtactg gggcatatgc tcttcccaag accaagggcc  24600
tctcctccca ttgatggctg actaggccat cctctgctac atatgcaact agagacatag  24660
ctctaggggg tactggttag ttcatattgt tgttccacct atagggttgc aaacccttt  24720
agctccttgg gtactttctc tagttccttc attaggggcc ctgtgttcca tccaatagct  24780
gactgtgagc atccacttct gtatttgcca ggcactggca tagcctcaca acggagagct  24840
```

-continued

```
atatcagggt cctgtcagca aaaattctta ggcaaatgga tcgatctggt ggatatcatc   24900
ctgagtgagg taacctaatc acaaaagaac atacatgata tgcactcact gataatctgg   24960
tattagccca gaaacctagg atattcaaga tacaatttgc aaaacacgtg tagtacccttt  25020
tcttagatga tgccactaga ggcactacac cattgtggca ccatttttcct catgcatcca  25080
gaccactttc ataaatattc actactttt ccctctcaca aaatgaccag tgaatcacag    25140
tgagctgtga agatatctag ttaacctttg tcaaagaagg cttttgttaa agtgtaagct   25200
ttcaagttaa agggagaaag tgacacacta aaccatagtc aatcactaat gtcttagcaa   25260
ggaatagata ataagtttac ttagtcttat ggattgacct aaatttagat tagccttaaa   25320
ggcaacttac agaacaatta aggacatagg gctggtgcta gtgatcaagc cagagatgga   25380
agtagtgtaa agaatatgga cccttataag ggagggagga gggtaatcat gaaggccacc   25440
tggaacattg tgtcctagag aggtatcaaa atgttgacat ttggcaagac atttctttgc   25500
tctctcaaat gactttgata gtgtcttagt tagggtttta ctgctgtgaa cagacaccat   25560
gaccaaggca agtcttataa aaacaacat ttaattgggg ctggcttaca ggttcagagg    25620
ttcagttcat tatcatcaag gtgggagcat ggcagtatcc aggcagactt ggcacagcag   25680
gagctgagag ttctatgtct tcatctaaag gcgactagtg gaagactgac ttccaggcaa   25740
ctagggtgag aatcttaaac ccacacccac agtgacacac ctactccaac caggtcacac   25800
ctattccaac taggtcacac ctccaaatgg tgccacttcc tggcccaaga atatacaaac   25860
catcatagat agagtatgtt tttctgttac atgtttatct tgcttctcag atactgactt   25920
ttggtggttt agtgtgcata tttcttcttc tttttttttt tttttacat cattaagaag    25980
tctcaataac gataaatctt agacatctct gagttacaaa aaggtgctga gggagaaacc   26040
agttttgtaa accactaaat ccagatgaat ttcttcctta agcaaataca caaaacgact   26100
tgcagtaatc acacatgtct ttaatctcag cactctagag gcagaaatag gtggatctct   26160
atgagttcaa ggtcagtatg gtttacagag tgagttccag gacagctagg gttacacaga   26220
aaatactgtc tcaaaataac aaaaaattta agctgagaaa tatctcattc ttttgaattt   26280
attttacaat tttctcttga tatatgattg attttttttta aatataattc tccttttctt   26340
ctcagcctgt cttcctctca tatttttcag gcttcctcta atacacacac acacatacat   26400
acatacatac atacatacat ttccaaaggc taatactttta atacttggtc accagttggt   26460
gaagctcttt ggggaggatt aagaggtgtg gccgtgtgtg tgtgtgtgtg tgtgtgtgtg   26520
tgttagaatt tctgattttt gtcattgtga aggttatcct gcctgttgcc ttaatagtta   26580
aagcagcatg tttgagcaaa tagggctaat ctgcttattt cttccatcat aaattatata   26640
ttaaattcct aataaatatc tacagtgtaa agagaacaga tggtgatgat tcatatttcc   26700
aagcaatgat atagtgataa ttatatcagc taactggtat aagctactca atgtttatac   26760
tcactttta atttttaaa actttaaaa aattttattc tttaatcctt tcttacagtc      26820
cagtctttct ctccctctca ctcttcccac tgaccactcc ctgtccccta ccttcccctt   26880
gtctccaaga gaatgtcacc atcttccacc ccaaacccaa cccccactcc accagacctc   26940
cctgggggcct caagtctcta gatactgctg gtcttcccat ggggccaccc tactcctcag  27000
gttcctctag ctttttcccca attcaaccac aggtttctcc agcttccata tattggttgg   27060
gtcctagtat ctgcatccaa ctctttcagg tgcttgttgg gccttctga gggcagtcgt    27120
gctaggttcc tgtctgcaag cacaccacag catcagtaac agtgttatag ctaacacatt   27180
gctgaattgc catgggctac ttttaggaaa gactacactg taatagattt cttgtctgtt   27240
```

```
agaactaagc aatggcatca gtttagagat gttagtgttt atgtgggtat atcaactaag   27300
atatgaatta ctgcatttat gtaagttgtc ttatttaact ttcatctttt tgtatgcata   27360
cagttggtat aagaatcatg tctacattag agacccaacc aagtgaataa atctgtctgc   27420
cctcttctct tttagctgga ccacaccaat tttgaggaaa gggtacagac accacttgga   27480
gttgtcagac atataccaag cccttctgc tgattcagct gaccacttgt ctgaaaaact   27540 agaaggtat gatcttatca ttgactttac tggcaaaaga aagatgtttt tcatgtcttt   27600
taaagaacag aaagctggaa tattagaggt tccatttaaa agtgatgcat ttaaataaaa   27660
tcgtactctt gatgaatctt gatctactca agaattaaac aatgaaacaa tgaattaaag   27720
ataataactt tcttaagaaa tggcctcttc tacaaaaata gataatgcat agtctgagaa   27780
tttctatcta gtgttggaat tgatgctttt tttactcttt gtcaagcatt cttaacaatg   27840
aggtgcattc ttagccttgg ccttttgata caaaatatca ttagtccagg ataactctaa   27900
actcactata taaccaggat ggcctcaaaa cctcttcctt tttgcattaa cctcctaaga   27960
actaaaggca tataccacca agtctggctt ttttgaaaat attttttaagt tgaagatttt   28020 tataatgatg gtggtctgag tgagaatggc ccccataagc ttatatattg aatacttggt   28080
actgagttgg agaggctgtt tgggaaggaa tgggaagtct tgcctttaag gtttcaaaag   28140
cccatgctgt tcccaattag ctctctctct ctctctctct ctctctctct ctctctctct   28200
ctctctctct ctctcagctg ccccaggatc atgcctgcct actgctaaac tccccaccat   28260
catgaactct ccctctcaaa gtataagctc ccaataaact aattcttctg taagttgtct   28320
gagtcacagt gtcctggcac aatagtataa aagtaactaa acaattata ttagtcaaaa   28380 tacataagcc agttgaatat tcttaaaata gtagtttctt ttatgattat tataagtagg   28440
agtagtttag ctttgtgata ttaaaacaaa atatatttgg aattttgag atgagaactt   28500 atgtattttt tctttctaat tttggtttat tatattgata atttcatgca agcatatatg   28560
tttttgtcaa gtccatcttt gattccagtc tactcaatgc ctatctgatc ctccccccc   28620 tcaccctccc agcttccatg tgcttttaa aaatcacagt tagagctacc atatgcggat   28680
aatataggac catctactgt gttgtgggtt gcctctccag ctgcatttct gaaaaccagc   28740
tctccattaa ttactagtag ctcctcaggt agtagtggga cttcataagc ccctctcatc   28800
catgctgaga ttctcttgac atgattgtat acaggtcttg tacatgcagt tgcagctgtt   28860
atgagttcat atgtgctgtc atgttcagca catactgtat ttctgcatgt atccaataac   28920
tttagctctt aaactcatcc tacatccact tctatgatga tccctgaaca tataggtatc   28980
ttatttatag ctgaggactc cacagtcatg tcttcatata ctgatcagtt gtagacctca   29040
aaattaattg ctatctactg caaaaagtag cttatctgat gaaggttgag gtatgcacaa   29100
atctgtaaat atagataact taggcagcag gttaatacta tgtctattta tcaggataat   29160
agtaataggt tctcccctgg gtaccaagca taactcctat cttgtgaagt gggccttcaa   29220
tccaatcaga aaaaggttaa ttacgtgagt tgacatcatt catgtctctg tgtcctactc   29280
atgggcatgt ctttctgaag ccagtcttca ttatagatgg cagtgtttat atgtaagcct   29340 gttactttt cctccagtca catgcataga attttcagca ctatgaccac cggccactat   29400
gggtgaagct tacttttgc tacctgattg atttttttt ttttttttt tacatttttt   29460 ggctcaagta tccaattact tgagcagtag ggtgttccca tcaaactctg gaagcttacc   29520
aaaaacattg gcaatatgta aagcctgtaa tatttggggg attatgggat cccagtaacc   29580
```

```
aaaaactcta gagagataat cactgcctgg cactgggaat ttttttatta atttacttta   29640
tatcctgatc atagcttccc cttcctcctc ttcttcctcc tccctctcaa cttacccct    29700
ctgttttcta caggatcctg tctgattaga tttcccaata agatttttta cttggattat   29760
tgatgttttt tcatttccag aatcatttta gtttgaaatt gtccaacaat tctcttaatt   29820
gaaggttatt atcctatctt ctaatgactt ctttacttca ttgatccctt tattctttt    29880
aatacattca tgcctttttc cagatgtttg aatatactca tactttatta ggtgctatta   29940
ttgtaggatt agtaatctgt tgaggaaaca tggtatcttg atttttcatg tttatttcct   30000
ttctatgctg agacttgtac atctcaaata gttgttgagt tccctccttc tccttttcat   30060
tcacatcact gcctttcact gaagtcatct acaatggcca tgagagtact aggtctcagt   30120
agggttgaga atgccatttc catctgtggt gcttttagag ggaatgtggg tctgagtaga   30180
tggcctaaga aagggtagcc agcttcctg ctacctgtac aaagatacat agttgaggca    30240
tctggagcaa aatttatgtg agctgaatgt gtgaatgcca ttatacttca tgggaaccat   30300
tatactttat gaatttgaat ctttcacatt tcaaccataa tttctcatct cggccactct   30360
ggaagaaaaa ccgtaattat cttcagctta cagataaaca catcatggct tagagataat   30420
gtaatttgcc aaccactgaa tgatgaataa ttcagtcctg gtgaatttat catagttccc   30480
ttttctgact attggttggg gccattgtga ttgtgagtga cagaagccta atcaactagg   30540
ttcatcaatt aagaagagga catttaatag ctcacaaagc ctaaagtatg tgagtgtcta   30600
gatagatgac tagcctgagg gctcagtggg tccaatatat ctgcactcaa atttctactt   30660
gtgatatttt ccctctgttg gcttatttc ttagattagt tttctcctca ggttgacctc    30720
tcagaactct atgcttatac ctgtctgctc cacagaagat aataagcctc ccttcccttc   30780
cttttcccctt ccccttcccc cttctctcct tccctccttc cctccttccc tccatccttc   30840
cttccttcct tcctctctgc ttttatttc atcaccaaat ttatagaatt atttagactt    30900
agttttatgt cccctattct gatagagttt ttaaaattta tctattgtgt tttaattcaa   30960
acactgtctc agactggata cataagttct agtaagaaat aaattctaac ctatattgtc   31020
tttgatacaa ttttgtatct ctttatctta tttcttatat atttatgaaa accactcctt   31080
tacccacttg gggagtgact gaagttctca gtctgtggct gagatccatt gattgactca   31140
tctgcttcaa ttttgtgacc atgagattga atctgcagtg tgaaaaccat gagcccactc   31200
tgtgttccta actaacttat gagctttgcc agtctggaac tcttttccct cattaagttt   31260
ctttactgtg ttgctggatt aataccatct acttttattg ataattgctc tagagctaca   31320
gatttttcaa gtcctatgat taaaaataac agcttctttt cccctcaagt ctatatgtct   31380
tccatttcat agctgacaat tctttgctgt tctcgtttcc acttgtttat cattcattta   31440
tatatcaatg cctgaaatat ggtttctcat cagactatgt tcctcaaact gcatagatga   31500
gggataacag tgacctgtta ctgtcaaatg tgacactttt ttttgtatt tactatccta    31560
ctgttattgg tatcttcatc ttgaaaccat ttctttgatt tatggacatt ctctcctctg   31620
catttcctag atcattaaat tataagtgaa gtattgatga aaattttta cgagacctat    31680
tgtgtggaga ttatactgct actatgtatt ttagtgcctt attttttta ttaaatttat    31740
ttacttattc cctttacaac tcaatatcag cccttcctct cctcccagta cccctgaca    31800
caagttctcc tccattactc ttctgaatgg gaagccccc tttgggtgtc cacccctcca    31860
ctctagcata tcaagtcact gtgggactag gtgactaggt atatcctctc ccacttagac   31920
tctctaaata ttacagatgg agaaactggc tctctgtttg tgaataaaga gtagaagaga   31980
```

```
accataggtt gactaggctt tatagatcag ctgccgttag catgtttctt agggaagtca    32040
tggtccatgt agtgcgactt ccaagctttt cattaatatc agttgtatgc tcttcctatc    32100
aagtgagata ggaccatatt tagttatgct aacttaatga taatgagaat agccattaaa    32160
gaaatccaag gcctttatct gatcattcag ttctggtctg tggtttatgg aattttttt     32220 catctcagga taatttgaaa attgagatga aagtgagact gagacatatt ttattccatt    32280
acaaaaattg taaatagttt ttttttaaa taaaaagcag tggtagtact gaaataaaac    32340
tttttcaata ctatttagta cctatcctta ctataaaaca tattttatt ttgctctatt    32400 ttcaaagagt tagatactat taaatgaatt cagtagttgg atatgaagtt taatgatggt    32460
tctctcattg ttttctttta aaactccaaa tgggtttttc ttgtgttaaa tcacaaaatg    32520 ttccccttc attagaatgt ctgttggtat tgtcattgtt caggtctctt ttaggcaacc    32580
aggttgtatt atggctgtca cttcactgtc atttctaaga gacatatctt aagtagactt    32640
tctggccttc tggctcttac agtgcttcag ccccttcttt caagagcccc acttctaaac    32700
aaagaactat agacaactga gagagaaatg ttttttttcta gaggtgagct ccctaattag    32760
ttatcaaatg ccaaggagtc atccctgaat catatttata caagcagcac taaaaggact    32820
caccaggttg tttgtatgta tgtatttatg tatgtaaata ttttaaaata ataatagata    32880
ttataatcaa agacatgagg ctatgaattt gagaaggaat gtggaagagg gacaggggag    32940
gggctgaagg gaagagacat aggaggggct agaacgtgaa caatgaaaga gaaaatgatg    33000
caaattatag tagttaaaat taaaatatat atatttaaaa caaaaaattc acctgatatt    33060
ttgttgtttg aaagttgcat attgtgaagt atgtgacagt taaaaacaca taaatatcat    33120
gaggtaacag gaaaaaagct taaaatatgt attttttgcat cttgttctga gcacaaaatgc   33180 attctcagtg ttatccatca tttgctcacc cttgtcattg cttttaagaa acctagtatg    33240
gttctttaac atacaaaact tagtatttt ataaatgaaa ctggacagag tgatttcatg    33300
gaagaccatc agattatgac agatatctat tgggcagttg gtactggagc aacttcacaa    33360
ggttttatca cttacatcac agttaatctc tttgacactc atgggacaga agtatgaag    33420 ggagatagag cagctcatat atttgcacct gcagttcact ggtttcattt tcttattcct    33480
tgcagagaat gggacagaga acaagcttca aaaagaatc cccagcttat ccacgccctt    33540
cggcgatgct ttttctggag attcctcttc tatgaatttt tgctatacct aggggtaaga    33600
atctcacgtg taaatatggt gtcatatatt attaagatat aatcatagtt ttgtgattac    33660
agaagggtga ggacaatctt gtaaccaaag ccttttgttt tctgtttagt atttgttttc    33720 attttttat atagaatttt attacaagtc caaacacaaa tgactgaaaa ttctatcaaa    33780
gataagtgaa aattcttaaa atgtagatct caattgatag ttcaaaatta gaatgggtcc    33840
aaaaatcaaa ttacttgttt caaaattatg ctcatttatg aatccagatt ataatgactt    33900
aatagtatat gaggttactg gcacctttac ttttctgtgc taaaaagag aatgttagaa    33960 ggcaatctca taccaagaat gagactccat tcagtcagtg ataccaagga atgtttatga    34020
tattttctgc tcagatagat agatagatag atagatagat agatagatag atagatagat    34080
agatagatag aggtaatgta atgttttatat tttgaaaaca tatatatgta tatatgtata    34140
aatagatata tagatagaat tatatagagt aatgtagatt aatgtttatg atattttgaa    34200
aacacacaca catatatgga gagagagaga gagagggaga gagagagaga ctgaattgtt    34260
tacaaaagat aataaaaatt taaatgagg tggtgaggtg cacatagaat gtattttgtc    34320
```

```
agcaccctat gtcttcatca ttgtaaagag aatagcagcc tgggaacctg ggctttgtgc    34380
tgtttaagaa ctttggatat atcccagatg tgttcagaag tggttattgt tttctgggtc    34440
atgcgagcat cactttgaag cttgatcata gcctgtaaaa agggtgacaa gtggaaagtg    34500
tgttgagtct gatgtatcaa ctcagcacaa tactgccttg gggtgttatg tttcatctgg    34560
gttgacttgc attgtatttc ttcaggtctt tatcctcaga ttgcatgggc tttggtttct    34620
cctcaaatga tgtatgaaca atatgtagcc gtgctactta ataattttta ttttatcctg    34680
tcccagaaaa agtcattaaa aatttatctt gataaaattg actataatta ctctagaatc    34740 tttctagtg ctattatttt ctagaagaaa ttcttctggt ctttcttaat ccatatatat    34800
gtatgaacat aaatgtatag atgtatagat ttgaatttct ttttaagcaa attcatgcat    34860
attatattat cacatatttc catgtagatt catatattat attcacatat aataaataat    34920
gtgttatata ttatagatct gttatttaat ggtagttcta tatatgaaag aaaagactat    34980 aaaaagata atataatttc ttctagtaga atatgtgtta taaatgcat atatagacac    35040 ataagatat agacagaaga atgagatatc gtttaaagat atctttgtgg tcatttttat    35100
cagtgagcac acccaagcat ttgaagatat tttcagtcaa gatctccttg tgagtagaca    35160
ttaagaagag ggagatgcag taaatatgaa aaaatatttta aaattttgaa gattaaaaat    35220
agcaaaaaaa aatcacaaag cattcacaat gtattaatta tctatggata gtgattagaa    35280
gtacttctga gacaaacgga gtgctggaat gtatctctgg acccatcaca gcctttggag    35340
ccgaagatca aatttctgca aatacccaat aaaatgggta aggaaaggtc ctgatgggag    35400
agagtagatg aatgtgcaga gtgagaaggc acgagaaaca aagtgagcag gacacagtgt    35460
aatgatgttg aagggtctct tttatccctc cccatccccc atacacagtt tcactgagat    35520
cacaaagttc agtgttgtaa aactgttgaa atctagatcc cacttattta ggtaagtata    35580
atttccaaga tctattattt atttcaattt aagttttatc ttaaaatatt tatttgacaa    35640
atataaattg tcattgtaga atatacagtg tatatttcaa tatatgtata caattttca    35700 tgatcaaata agggtaatta acatacagat cactcagtca tttaccattt ctttatggtg    35760
agaagagtaa aatactctcc tggttgtttt gagatactgt tgctaactat aatcactcta    35820
gcagaacgta ttccctcaat acttgaattt gttgctgata acagagcttt cccagcatcc    35880
tcgtccctcc tacccttact agtctttgtt atcttaactc ctcttccaac tcacagtgga    35940
aatgggacaa agttgagcca ttttaataag cttctactgt gtcaagtaac cgctgccgtt    36000
gctttactgt tgtgtgttct ttctgagcat tttcttcttc ctgttaaata aacaaacatt    36060
actgagacag atataacaat tgtacagata aagataacgg gacatacatt caaaatgtgt    36120
ttatattctt ggtcgctgta ggccatgata attgtggcat aacaattatt tagttgtttt    36180
cagtattgat agaaaaaaac actattaaaa atgccttcaa ctatgaaagg ttaagacaaa    36240
ggaaatacca ttacaaagga ccttatttct acaacagtga tgcaatttta aaatcatatt    36300
agctatagta catccccatt aactgtggac ttgttttttc tttatctgat tcagcagcca    36360
gacatagcat gctctttaat atttcagact tccagcagag aagagcaaca ggctgctgaa    36420
aacctaagta ggagaatcaa ctaaggataa tcatttttttt attttattttt attttttaaac    36480 tagatgtttt ctttatttac attgctaatt ttgtcccctt ttctcatttc ccctcaaaac    36540
cccccctgtc ccattcccct cccccttgctc actaacccac ccactcccac ttccctgacc    36600
tggcattccc ctacactggg gcatcaagcc ttcacaagac caagggcctc tcctcccatt    36660
gatgtcccac aaggtcatca tctgctatgt atgcagctgg agccatgggt ccctccatgt    36720
```

```
gttttctttg gttggtggtt tagtccctgg gagctctggg ggtactggtt agttcatatt   36780
gttgttcctc ctatagggct acaaacccct tccgctcctt gggtcttttc tctggctcct   36840
ctactgggga tgctgtgctt agtctaatgg ttggctgaga gcatccacct ctatatttgt   36900
caggtactgg cagagcctct caggagacag ctaaatcaga ctcctatcag caagcacttg   36960
ttggcatcca taatagtgtc tgggtttgat aactgtatat gggatggatc cccaggtggg   37020
acagtcactg gatgacattt ccttcagttt ctggctcaaa ctttgcctct gtatttccta   37080
caatgggtat tttgttcccc ctaagaagga ctgaagtatc ctcactgtgg tcttccttct   37140
tcttgagctt catgtggtct gtgaattgta tcttgggtat tgtgaacttc tgggctaata   37200
tccacttatc aatgaatgtg tgttcttttg tgattgagtt acctcactca ggatgagttc   37260
catccatttg cctaagaact tcatgaattc atcatttta atagctatgt agtactccat   37320
tgtgtaaatg tgccacattt tctgtattca ttcctctgtt gaaggatatc tgggttcttt   37380
ccagcttctg gctatcataa ataaggctgc tatgaacaca gtgatataag tgtccttatt   37440
acgtgttgga gcatcttcta ggtatatgcc caggagaggt attgctggat cctctggtag   37500
tcctatgtcc aattttctga gcaactgcca aattgatttc cagagtacca gcgtgcaatc   37560
ccactagcaa tggatgagtg ttcctctttc tccacatcct tgccagcatc tgctgtcacc   37620 tgagttttt atcttagcca ttctgattgg tgtgagatag actctcaggg ttgttttgat   37680
ttgcatttct ctgatgacta aggatattga atatttctct aggtgcttct cagccactcg   37740
atattcctta gttgagaatt ctttgtttag ctctgcaccc catttaaaaa tagcgttatt   37800
tgattctcta tagtcacttc ttgagttttt tgtatatatt ggatattagc ccactattgg   37860 atgtaggggtt ggtaaagatc ttttcccaat ctgttggttg ccattttgtc ctattgacag   37920
tgtcctttgc cttacagaag ctttgaaatt ttatgaggtc ccatttgtca attcttgatc   37980
ttagagcata aactatttgt gttttgttca gaaaaaaatt tcctctgtgc ttatgtgttg   38040
gagacgctgg tattggtacg gtgacaggca ggtagataaa tggaatagaa ttgaagacac   38100
agatatgaac ccacacatct atggtcacct gatctttgac aaaggagcta aaaccatcca   38160
gtggaaaaaa agacagcatt ttcaccaaat ggtgctggtt caactggcag ttatcatgta   38220
gaagaatgcc aatcgatcca ttcttatctc cttgtacaaa gctcaagtcc aaatggacca   38280
aggatcacca cataaaagca gataaactga aactaataga aagaaagtg aggaagagcc   38340 ttgagcacat gggcacagga gaaaattcag ggtaatctaa gggaagctaa ataagggaa   38400 tctgtaagca tgttcctgac agactgtgat caccagagag agcttgttac tgtagaagtc   38460
acaggtgtat actcacacgt atcttcgatt ccatgtttcc atcactacat gtaagtatca   38520
ttagttcagc ttaaatcgag acctttttt taagtccca gaaagctaac ggacatgaag   38580
aaagcctggt tctcacaatg ccacagttct tatattcccc agactgttat aaaagaggat   38640
ctgtctctca tatttagaca aagacaggct tttgaatcca agcctcctgc tcctgaagca   38700
agagtatttg cggtaattct gcttatgagt aggctctgcc tagggtactt tttcttcata   38760
catcccctca gtacgaatgc tctcagcaaa gcttctagag gcctgctatc taggattcac   38820
ttctcatctc tgtcccatcc ctgcgaacac ccacagctgg ttgcttctct ggattcagct   38880
tcactcacac ctgaactctt cctaagccat ttctctagcc cctctatatg tgttattatg   38940 tcatgttta cacttacata tctatgccac ttagaattta cttctccact gaattaagtt   39000
ccatgcatta aagttaaat tgttatatat atttgggtct tttactggaa tttctagata   39060
```

```
aatcagtata ctttctttga cctgtgaagt gtatacatgt atggtttaat atccagtagc    39120
ttaaatgttc atattatttt tattcttcaa atagtttcaa ttagaattta ttcctaaatt    39180
aaattcagaa taatttttatt tgttgtttta acaaatattt attggttaag catgctcact    39240
aagaatgtat tatatatgtc ataacacttg tgacaatata aacatatagc caataacctg    39300
gtgcaaattt attcatttt aaaatatact taaaatttt atgtgattac actaatctta    39360
caaaatggat taggtgaaac atcatctttg taatatgtag attttttag ttcagttagt    39420
ttttttaaaa tgtgcttagt agtttctgga atcaatcaca tatcatacta atacaggtgc    39480
ttttactttt ttatataatt catagctatc atttttctca ttaaattatc ttagctagac    39540
atttcagaat aatgttaggt ggtcatagta gtcaaggttc ttttgctttc ctgcctccca    39600
cacttgtgtt tatcaactat tcctgattct ggaagaaagt ctttcttagg ttaacaagca    39660
atgttgcgat tcagctttgt agaaatttta accagatact gatactttt atcaaattag    39720
ttatttcatt gttactgtga tattcacagc ttgttcagta gtatattagt attctgttag    39780
ttgatttctt ggtatcacta gcattaatat tctaaatgta acaatataca aaatgtgctt    39840
gcaacaagtg aaggtgatac tattacttag tagctgcaca agatatagca agaaactctt    39900
aaacctcaca tgctagcaaa gcaagcactc ctgaactaaa tccgcaggcc tgtaaaaatg    39960
cagtatttt ttttaagtat aaagataaag tccatataat ttagctgcaa gcctgagtct    40020
gcacttgttt ttgtatgaac ttttctctat ggtctgcata tgcactcaac acagacttac    40080
ctgtctgtct ctagaaacat ctgattattt gtcaggtaca atggaaatgg cttaagggta    40140
tgcatctaca gtgacttaga gctttgttct ggaagtgcat tcaggtgtcc cctggtcggc    40200
tgcagtgaga actgaattat tcctaccatg agtgcaagtc ttttagctag tttttacatg    40260
gtcacttacc cagatgacac atggtcttat agtgggaagg aagtatatat agactggcct    40320
ggaattcata ataatccttt tgcagccttc ctagataggg ttatactcat gtggcaggcc    40380
tctgcatagt actcctagac tcaggtcatg cttccagggg tgatgttata ggagcgaacc    40440
ttgtaggtaa ccagagtttg ccaataagga gaactgtcca acaacagaa gtgcctgagg    40500
tgacacagaa taaatataca ggaataagaa tagtaaggaa gaaggcatga actcgtgagg    40560
gagtcagatg ggacatggat ggagttggaa gtgagaaagt ggtaaagtgt ttctgtgtgt    40620
gtgaagtatt catgtatgaa attctcaaaa aataaatgga aaaatgggta tttgagtttt    40680
atgattctga atttagtgtt cttattgtca taaacattag tattaagctt attttctaag    40740
gaaaacaatt aagaaacttg cgttttgatt tatgcctgat aaaattgtta aaatacgtca    40800
ttgaatatta tcttatttaa aatagttttg catttttct attggataca attctatttg    40860
gagtagtatt tcaatgtggt gaaaattagg gaattttttt tcggaaaata gtctgagcag    40920
cagaggacat gcaactcgca tgcaccaatg ctgattttta aaagggct gtgctttata    40980
gattaactga ggtatcagtt acagttttc ttcacactta aaaatgtca tgtggatcta    41040
tgaatggttc cattgtaaat attagagaac atgatacata aaagagatta ggggaaatga    41100
tagaaggaga gagtctagaa gtgctggttt tgtccttgag aactgtgagg tagtaaggtt    41160
tatgctgtgc tctacaaacc atcttgttat tgaaattttc cagtaaagaa acaagctgta    41220
tcttactgtg tgaatatatg ctcctccaga gtaatactgt cagtgtcctt atgagatgac    41280
gtgtattgtt gaaagatga gtatgtcttg ctagttgagg caagatgaga tctaactcat    41340
tagtagcaat atgtaaaata ggcatgccat ttaaagtatt gaaagctata attactgtat    41400
taaattgtaa tcaaataatt aagcaaataa gtctagtatg ataaagtagg ttattgaaaa    41460
```

```
ctgtaatgga gttctaacat tagtaaacag aagaaaaaca tttaagctta taacttacaa    41520
cttgaaaaaa aatctgtgta tttataagag ccagaagctg gaaagaaccc agatgtccct    41580
caatagagga atggatacag aaaatgtggt acatttacac aatggagtac tactcagcta    41640
ttaaaaacaa tgagttcatg aaattcttag gcaaatggat ggaactagaa aacacacaca    41700
catggaggga cccatggctc cagccacata tgtagcagag gatgaccttg ttggcatcag    41760
tgggagaaga ggaccttggt cttgtgaagg cttgatgccc cagtgtcggg aaatgtgaag    41820
gtgggaaaga gggagtgggt gggtgggtgg gtggataggg gcacaccctc atagaagcag    41880
gagaatgggt gatgggatag ggaatctcca gagagggagt tcgttaaagg ggatagaatt    41940
tgaaatgtaa ataaataaaa tacccaataa aataaattat agataggcca tatcaccctg    42000
aatgtgcctg cttagtctct aatataattc aacatctaaa tatgttaaag atgtttagct    42060
atgtaataaa aatatgatgc atatgtaaga tgatgtacaa taagaaatat tttatatact    42120 tttttaaaata agttttattt attagatgtc tcaaacaatt ggcatattat atctgggtaa    42180
gaggttagaa attctttttg atacctccct ttttatttgg cataattcaa atccatttca    42240
accctgcatg taaaaggaaa gaattatatc tcattttgtg attatcttgg aaacttttcc    42300
aaaggcttga atcttctttt ctatgcagag ctttgaatta tactaatatg aagtgctgta    42360
tataaagtag agaatgagca tctacaataa aggcaatgat taatgacagt taggttgtag    42420
ttaattccct gtgaagatga aggtgagata caaaacatgg tcatattctg ggactggtgg    42480
gacaggtagt gttggcactt gggatttgga aaagccatca tagagaacaa tgaaaagcaa    42540
attaacagta aaaatttgat gtcacatcta tattaatctt ctttcaagat ttagccctaa    42600
gttctatttt actaagttat cataaaataa aaattgggag atgatgtctt tttgtaattc    42660
aaaggccatt tgtggttcaa atccatccat gtacatttag aagggttgat gaatcagttg    42720
aacggcttgg ttggtaatca gttttggatt attgaagttt atgggtttat tggaaactgg    42780
ctcaagatag agtgctctag tgcacacctt actgatgcac atacccagct ctacactggc    42840
aaagggaagg aacaggaccc aagcggctgg cttttaaataa taccagtggt gctggcatgc    42900
tcttccctcc tgaatccagc tccgctcaat ggttgtactc ttgagaagct gttccttctg    42960
atcataatac catggctcaa aatccttaaa gaagttcatt ttgaaatttc ttagtgtctt    43020
gcttttcttg gcctccattt cttcacctgc ctgcatagtg aaaacagttc gtacatgact    43080
gagagttgtg aaatcctctg ggacatattt taggaatggt ttgtgacatg tacatgttac    43140
tagttaatgt accacttcat caagtacccc tttacaatat agttgctatt catgcaggtt    43200
ttagtgaaca cctcacacaa acttgtctct aaatgacttt tgctgtaaac taataaccaa    43260
gtcttatttc agagtatgca caaagacact atcagcagtt tcataaattg tccaaccttc    43320
tctgtaaaat tattttaaat tattgtaaag atgaaatttt cataattaaa atgtgaacaa    43380
gaaatgaaat ttaatcactg ccttctcctg caggaagtca ccaaggctgt ccagcctgtc    43440
ttgctaggaa gaatcatagc atcctatgat ccagaaaaca aggtggaacg ttccattgcc    43500
atttaccttg gcataggctt atgccttctc ttcattgtca ggacactgct tcttcaccca    43560
gctattttgg gccttcatcg cattggaatg cagatgagaa cagctatgtt tagcttgatt    43620
tataagaagg taatactttt tggaagatgt tatttggtct tgttttacta tttcagtgct    43680
ggatattaaa ttcagggttt cttgtatgcc aggcaagttc tttgctgagt ttgctgccct    43740
gcacagtctc aggtattcta cctgacatgt cttcagtgcc ctaaatgtga gcttgtacaa    43800
```

```
gaataggtgt gaatacttat tcctgtttta ggtgcctatg aaatatatgg caggtgcaag    43860
tattgttctg agttatctat ccttgataat gcaaagtgat tcagtcgaca gttattaaat    43920
atcttctgta aattacctat atttcagatg tcatatttta ggggaagtat ttgaatagtt    43980
tagtggtttt ttttaattgt cacacaaaat agacaagtga gcagtaagct aaatcaatgt    44040
cagatttttt aatccacttt ttttcagtta aaatggcaaa tagtacaaga ctcattgaca    44100
aaatatcatc ctatgataaa attctatttt tactagcaat aatatatcac tgttaatgat    44160
aacctaagaa atacattccc accttagcca gctgccacag atggtgacag tgtcacagtg    44220
gtgacactca tccatctcca ctgtcttact ttgagtttga ttttttttgtc atccagtgaa    44280 ttctgaaact ttataacatt tttgaaatag catgtacgtt gagatcatgt gaacttaact    44340
ttgcttttct gcattcatta gctagataag aaggctttgt aggatctaaa tagattgaaa    44400
tgaacagtaa acctccctgc actccagcca cagccacctg ccaaaccaag caggcctctg    44460
accaagacaa agactctcct ctctgtggga cctagcctgg agccccgtcc tcctgccctt    44520
ttcccttctg cccggggtag agtctgcccg ccggttccca ctctgttctc agttcttctg    44580
tgacaggcat ctgaggtgtt caagactgag aacttgacgt tcctagcctc catgtggccc    44640
agggacccca gaactggctc ttctacaacc cccagtggaa ggcctgccca gtggtgccat    44700
gtgggtgtgt gcagttaaac gccctgcatc tgccttgcct agtggcccga gccctgatag    44760
gatgtgggat cccactttt ttttattag atatttctt tatttacatt tcaaatgtta    44820 tccccttttcc taatttcccc cctgaaaatc ccctatccta tcctctcctc cctcccctgc    44880
tccccatccc acccattccg gcttcctggc caggcattcc cctattctga agcatagaac    44940
cttcacagga ccaagggcct ctcctctcat tgatgactga ctaggccatc cacagctaca    45000
tatgcagcta gagccatgag tctctccatg tgttttcttt gattggtggt ttagtcccag    45060
ggagctctgg ggttactggt tagttcatat tgttgttcct cctagggagc tgcagacccc    45120
tttagctcct agggtccttt ctctagctcc ttcattgggg accctgtgtt ccatctaata    45180
gctaactgag catccccttc tgtattagtc aggtactggc agagcctctc aggagacagc    45240
tatatcagtt tcctgtcagc aagctcttgt tggcatctgc aatagtgtct ggggatccca    45300 cttttttaact cacatctaaa tgttgtctta aattttgaca aaactcaagt tatttcagtg    45360
gcaccaatgt gacttcattg ctctaccaag tgatcaaaga aagatatatt ggtggtattt    45420
agatattacc tttatctttg ctatttctt tctttagtaa cacattatat atatatttgg    45480
cttataaggg ctatgggtct gaaattgacc tctaacaagt aatccattat accactacag    45540
tacatactca aggtcagttg tgttataaaa tcttgatagc catactttat tgcttaaaaa    45600
acacttttat gccaggcgtg gtggcacacg cctttaatcc tagcacttgg gaggcagaga    45660
caggcagatt tctgagttca aggccagcct ggtctacaaa gtgagttcca ggacagccag    45720
gactacacag agaaaccgtg tctcaaaaaa aaaaaaaaa aaaaaaaaaa aaacaacaac    45780
aacaacaaaa aatcagtttt atgaaggcag agaagaacaa aaagaagtca gagtttaatt    45840
caatctctta tgctacaaaa tcatcaattc ataagttcca agaaacatg aataaacaaa    45900 aattttagag attatttgga atgtagaatc tataaacttg ctatcaaaga aaattgaatt    45960
tactttaata aatatttgtt aaaagtactt ctaataaaga taataactaa gcatatgtat    46020
attgcaccaa tgaattattt aaatgtgatc taatttttatc tacccacaag tttctactat    46080
agttgctatt atccttcttt taaggaaccc aaatcctata agaaagaac attgaaaaaa    46140 aaggtatttc aaaactttaa aatagataag taacagcctt agaaaatggt ttccaagtaa    46200
```

```
ttaggtaaaa cagaagtatg gaaacataat attgaggcaa aggacatgtg aagtaaaatg    46260
aaggggatgg ttaattggta atcaagtcct tagagatatt ggtgaagaat ttgaagctgc    46320
tgcatattta tttccctcac aacatcacct actgtgattg ctgatcaatt agtttatctt    46380
atagaccaca tttaacttcc cgatactggc ttatcaccaa agagtatgag gacatcttca    46440
tggttctcta gctggtccct acttgcactt tgtcttggct tgtcccgtag cttatatcca    46500
ttcccctatc cgtactgttt caggttcaag gcaaggacac ataggatcct tccaacaaca    46560
tctgcaattt atagtagaga aatccactcc cattaaattc tgaaaccaaa catgttatac    46620
tcaaaataat gaatactaac acaagctgaa ctttgcccat cattttgaag attaccaaga    46680
taactgaata ttaactatgt gctatggatg aagctccatg ctttagcctg tgcattgctt    46740
tatctgacac tgaaattcct tctaaacata tgtaatctac cacagtgggt tctccctctc    46800
ttcttatttc tctaataata ttttgtaatt acctatactc attccttctt catctttgct    46860
tctctaaata tatctatttt ataatttat ctctataaaa tctttcatat ttttaatcca    46920
aattttgagc ccactctaca ttctgccttc cttaactaat ttatcatatt atctatatga    46980
taaacacaca ctcacacaca tatgtgtgag tgtgtgtttg tgtatatata tatgaatttt    47040
ttctaggtta ctcccaggaa agaattgtat cttaataaat gctaattcct gatacataca    47100
gaacaatggt ttcatctat taaatactca acaaatatgt gatgagttga aacatataaa    47160
atgggtgctt tgctgcaaag ccatctaaca gaaaataagt tactaaattt caccaggcaa    47220
aggattactc tatttcatga tcataattta tctaataagt taaaacatta atttatagat    47280
aaataaatgt ttttaatcag tgatcttcca tgttttcct ttgtaatatt tgaagacttt    47340
gttttgttaa cataaaaata ctgattcagt tattagtaac atactttgt tggatttaag    47400 tacttttatc ccaaagaatt agtgaaggac tttatgaaaa aattaagaca aggattcact    47460
gccttaggtt ccatcttta tttctaaact ttcaattttt ttattgtttg acgtctttaa    47520
atggttacat aattaatttt agttatctgt atcctcagtt tctctctcat tccttgcctt    47580
ccctctctgg aactcattgt agcagtactc gtctatttta atgcctttt gcgtgtggct    47640 cattaagttt aatgagagca tgggtgcaat gatatttagt ggagcaaggg acgcttacat    47700
gtgttgcaga catgagaaca gaataggaca actcctctct aacaaccatg agcctgcctc    47760
acccatccta aaatgtttta ccatgtacag ataaccccag ctctaatggg ttcatgactg    47820
taagtggtat gtcctgtagc aaaggtgtgt gtctactctt tctataggtc agctcttaaa    47880
ttcttcatgc tcccacttct gccatgttct ctgaatcatg gtggaatgat acaaccttcc    47940
catttatgcc aaatattctg ttaccactta tttgccactg gttaggtttc tgcagtcacc    48000
gggaaccatt gtagtaagaa acttttacag taacagctgg gtgcaagctc taatctatgg    48060
tataaacatg agtagtgaga aggtagcttg ataacatgac catttagcag aataacagtt    48120
acttgcatac cttggtggtc aaagacctcc ccagtcagag acttaactag ggttacagaa    48180
ccaaatataa gttcccattt gtggaacagg ccatacatat aatcagcaag caggtagtca    48240
tcaccataag aattcactaa ctgctctact agaggacaca ttttacaaag gtatgtgatt    48300
actatagctt atagtcccag ctgggtaagg ctgatgatgc tttccccagt gacttgcata    48360
tgctgcctct ggcactacga accagtaagc aggaagctta cacttcatct ccatgacctg    48420
tgaccatagc atacaatact taacatcaag ttctggtagg tatccaagag cactgggaaa    48480
agcctgtgtt gtttggggca cctctgagat cccccttgtc agtcactcat agggaggtat    48540
```

-continued

| | | | | | |
|---|---|---|---|---|---|
| cccctacccca | gcactgggac | ttttgtttga | ttattcatgg | tatctgagag | gaatagcatc | 48600 |
| taaaagaaga | cctctattta | agcttttttaa | agattacata | tatttcttag | aactgtagaa | 48660 |
| tagtttacta | aaatggtaaa | tttgaactca | aatatgtata | gttttttaaac | aggttcaact | 48720 |
| attattaact | aatttctcaa | ggcatgatat | atgttattgg | caagacaaac | actaataata | 48780 |
| atgtttacaa | atctctatat | taaatcatct | tgataattgc | aatttgggac | acacttcatt | 48840 |
| actacatagg | atagcatatg | ttttcttgca | ttattggtga | cagagacaga | tgatgagtaa | 48900 |
| atgagtctct | gccagtgtat | ttctgtatgc | tgataagatt | gtattattgt | ggtgctggag | 48960 |
| agatggctca | gcagttaata | acactgacta | ttcttccgaa | ggtcctgagt | tcaaatccca | 49020 |
| gcagccacat | ggtggcttac | aaccatccgt | aatgagaact | gacaccctct | tctggtgcat | 49080 |
| gtgaagatat | aataattaat | aaatcttaaa | aaatagattg | tattattgca | aatcctatcc | 49140 |
| ccaccacata | gtcctctgtg | gaactccatt | ctgagaaagc | tagttaagtt | aaaactaggt | 49200 |
| agtgccattt | tgaagccact | caacagagaaa | tgcctcagcc | acccaaagta | gagggaagat | 49260 |
| gactgtctac | cctactcctt | attgaactct | ccactgtgaa | ctactacttg | ctactcttct | 49320 |
| tgctgtctac | tgtctcccca | ccatgttcct | ttcataagtc | tttaccttaa | gtagccctca | 49380 |
| accctggcct | ccattttcat | gtctaatgtg | taatactatc | ctcctctctt | tctctactgt | 49440 |
| ctctctctat | ttttcttact | tttgtcaaca | tattattaca | cttgatattc | taaaaatgaa | 49500 |
| aagctgagat | cctcacatga | ggaagatctg | gtagatttgt | cctttggggc | ctggcttacc | 49560 |
| tgactcagtg | taatatttat | ttctgttaaa | aaaataaaa | gaaaacaaa | tccccaaaac | 49620 |
| tcaaacaaaa | ccactcaaaa | caacaacaca | aaagattcaa | ccttatattt | tgcaagtgga | 49680 |
| aataaaatat | cattcttatt | gtcaaagaca | acaaagtttc | tatatgacag | aaaatatcta | 49740 |
| aatgtaagca | tttcaatata | tttgtttttc | agttgtatat | ttttaaagct | gaaaagtat | 49800 |
| aacagtaaca | aatatgaaac | aaggttgacc | tctcaggtta | agatacattc | agtcacatct | 49860 |
| tactaatgtg | ttattgatga | atacatttta | tatttgtttg | ttgacatcac | ctaacttgcc | 49920 |
| acttttctt | ttagactttta | aagttgtcaa | gccgcgttct | tgataaaata | agtattggac | 49980 |
| aacttgttag | tcttctttcc | aacaacctga | acaaatttga | tgaagtatgt | accattgact | 50040 |
| taatgtttta | tgcattttat | tagaaatcaa | acaattctaa | agaaagattt | atcctgcatc | 50100 |
| agctaacagt | gataagtagc | aaagtcccac | caatagctag | tttggctatt | tctggaaact | 50160 |
| gggaaagcta | gtcctgtagc | agagcaccat | tctgaggtca | ggtacgattg | cccaactcaa | 50220 |
| acatacctca | gcttgctctt | aataatgttt | ttcaaaactt | gatccttatc | agacttagct | 50280 |
| tgcttccttt | tagtataata | ctttaaattg | ttatgtactt | tgactaaata | tgatactctg | 50340 |
| agcagttctt | gttctgtgct | gtcttatgtc | acaagtaaat | tcaaggacct | tgaggacaga | 50400 |
| taccatgttt | tatttatctt | tgcattttca | atatttaata | gagcaagtgt | tacggctgaa | 50460 |
| ttgagtagca | gagagagaga | gagagagaga | gagagagaga | ggaaaacctt | tttgagagt | 50520 |
| cccttgttct | catgtgttct | gtgtgagaac | actagcttta | ttttaaaaag | gtattaataa | 50580 |
| aacctaggcg | caatttcaaa | gatacacaat | cttaattcca | ctgaataaaa | acataatgca | 50640 |
| taaattgtaa | tatgctaaga | accatgaatt | tattgattgg | ataactcttc | agtgttcatt | 50700 |
| ttcttccaca | tgtgtctctc | tgcttggttt | tgattgtgga | atgtaatata | ccacttgatt | 50760 |
| ttctctgtgc | ttttatttttt | cagggacttg | ccttggcaca | ttttatatgg | attgctcctt | 50820 |
| tacaagtgac | tcttctgatg | gggcttctct | gggacttgtt | acagttctca | gccttctgtg | 50880 |
| gccttggttt | actgataatc | ctggttattt | ttcaagctat | cctagggaag | atgatggtga | 50940 |

```
agtacaggta gtggtctttt tcaaagcttg aagaaatttg aattgggctt ctctaagccc    51000
taacaataaa actatgccat gtcacttaga agggattatt ttaattctgt aaataatttt    51060
ttctataaga aaaaggcaat tattttccct attggtctat agaatttctt tattcatgtt    51120
ctaagtaagg ttcagtacat tttatattca taaagtttag gtaaaatgga tattgtattt    51180
ctttgaactg gaaggaatgc ctaaattttg tatggaacaa actggcctct tcctctccat    51240
atagtagggc cattctacca aagcatttat tacttttatt ggtaatatga gttatatgat    51300
gtgcttattg cagagaattt gtagtttgcc tgtttgaatg tgatagaaag ttgaaaatct    51360
ggggctatac agacaggttt ctgttttagt ttgtatatgc tttcatttgc ttcacaaaat    51420
ggaggtgatc tcctcttaga gactttgtaa aggattggat tagagatatt gtccaaagtt    51480
catctaatgg cgggtatctg acactttta aaaatttttt ctcttcctgt ttttctgtga    51540
cagagcgtct ctctgtatcc ctggctgtcc tggatctcac tctgtagctg atctagaact    51600
cagaggtcta cctgcctctg cctcctgagt gctggattta aaagtgtgca ctggctatga    51660
ttttgtttgt tcccagctgt ttaataacaa aatgtttatc tatgtaataa aaatatggaa    51720
tttttcaaaa ttttgaatag ttattagtag ataatttgac ttgttttgt tattgattgt     51780
ttgatcaatt gattggttta cagagatcag agagctgcaa agatcaatga aagactcgtg    51840
atcacatcag aaattattga taatatctat tctgttaagg catattgttg ggaatcagcg    51900
atggagaaaa tgattgaaaa cttgagagag taagttgaca taattacaat actggtccaa    51960
ttttatattt aacatttaaa actgaccact caggtggatt ttcaactcaa ctcatctaaa    52020
actcaaatat atgtatgtcc tgagttttac atggtttata tgtcagtgcc tataatcatt    52080
ttggtgagca aatgttttct tttgtttttt gagactggtt ctcaatatac ccttggctag    52140
catagacctc tgtatgtaga tctagacctt aaaggcatgt gccaccacac ctgtccctgg    52200
cttatggttt tacagttgat tcagtttttt tgtagtgcat agatagttat ctcttactaa    52260
tgattctgct atactagttc acagttgttt catacccctta atttaattaa aacaatgatg    52320
aagatgctgg ggggctaatt gaaaccataa atggaaatac tgaaatatat aattgtaaga    52380
ggaaagggtg atcttgtatg acactgtact tcaagtatta tgacacaaag agcgggtgac    52440
agccacattt ggacaacttc tgttattctg agcctgagga ataatgacaa aggaaatttt    52500
ccttagggct actcatataa attgcttaca agaggctaag tcagtccttg taacaaaagc    52560
catctcctga gatggaatct ttacttagca cctgtgtgta tcttatcttc tttcacctca    52620
gataaccttt tgcagatcag taagattac ctctgaccaa aaaaaaaaa aaaaaaaaa       52680
gcacagcaag gctgatacat cattactaag ataattttgg gtaaaataac catgagcatt    52740
gctgtggcca tggaccgttt ttatttagtt gacttccgtg tcctaccaac tacagtcaag    52800
gaaatgtttt agacttctgg ggatgagcgg accacgaaag atactactaa tttaaagaca    52860
tgagatatat gagtatttca cagggaaaag gaaataaaga gtgctctttg caatggtgtg    52920
aatttgatta tttcatattc agggtgctgg agacctgtag acaatggtaa ctgagccaca    52980
gctgtgtgat tggaacaaca atggaaatgc ttaaatgtta agtcctttgc catgtaaata    53040
gaaatagcaa aaagagtgtt tattttccaa atactattgc tcacctgttt ttgttatgcc    53100
tttcaaggta aatctaggaa aggaattgca ttttctttct agaaacatcc ttaaagatct    53160
tggggaattg ttgagttgat aagagttgtt tctcacgtta acaggttgag tgctcccctg    53220
cactgcctgt aaacacagtc atggcagggc tggttatcac agaatccagt tttctcaggc    53280
```

| | |
|---|---|
| ttcataatca gcttgcagta ggccgttcct gtggctgacg ggttttttgtt tccttttttgg | 53340 |
| ggttggtttt cttttttttga cattggtatt ttacccctct tttcctcaca taataaaatc | 53400 |
| catctttcct attctgaatt tcaggctggt taattctaat agctagcatt tgtctggttg | 53460 |
| taacctgttt gatacatcat gaaattgtta cctgaaaaag ctggagagtt ctgacgtaaa | 53520 |
| aaggaaagca ggaattgctt taccccgcag agtaaataca atgttctagg ggagactgac | 53580 |
| tggatgttct taggattacc tcagcctaga aagctgttga actcggccaa aggctatgtt | 53640 |
| aatgttcttg aaaaaaaaat ctgccttttta ttgcttttta gccattaagg tactttcaat | 53700 |
| tttttatacg aaactgatag aattttttta tgactcataa aatgttaggg attttatgtt | 53760 |
| agtgtataga tgattctgtt gcgtgtttgg gatcaattat tcttttttcct atgtgacttc | 53820 |
| ttcctttttct gagctgttct aaaatattgg aacagttttg cactttact accatttgta | 53880 |
| aacattcttt cctttatata ataccaggct tatcaatgta ttttttttatc tctagaagaa | 53940 |
| agggatacac attgctcttt tacatctgct atgctgtcat ctaagcttaa ttacatctct | 54000 |
| acaagggaag tattacggtt tttttagtga tagaatcaca tttaattaga tggaagagtg | 54060 |
| tcttcctttta aacataagta agactagtcc atcttcagta caaatttatt gaaacactac | 54120 |
| aactcactag gctgatcaca atataggcta tacacatgac ctctatccgt gagctcaata | 54180 |
| gtatattgtt ttcttttgagg acttattttt tttttttttt agttctacca cttgacaata | 54240 |
| acacttgctt ctatggatta gaggaacagt ggaagcatag tgcctgtata tcatgtgcct | 54300 |
| tcctgcacca ggctgtagat cagatactgt tcctttccga cagagccttc attttgtgtt | 54360 |
| caccattggc ctttgcccac acaagaactg gttgtttta caaatgatca caattgggtt | 54420 |
| gaggtttatg gctcctggaa cagtggcgag gttgactgca gtattgttct ccatcttcct | 54480 |
| tttgtcacta aagcatttaa cctcttcctg tatatgttaa aaaagtaaat acctcccagt | 54540 |
| tgaagtacag actagaacag actagaggac tgcaactcta gtgaggtgcg actgcagata | 54600 |
| attacatgac aatgagaggg actaggaggg aggagctact ccctgctctt tgaaggaccc | 54660 |
| cctgcaactg agtgacttgg cctctgactc cagagtggct cctgggaagc tcaggcagca | 54720 |
| gctcagcaga tgtcagcaga tgtgactgag agacaatgcc cagtcacgtg tttctcactg | 54780 |
| ctctttgata tacacacctc gccagtgcta tttaaagcca agctagaatc tcaaaactac | 54840 |
| taagaatatg atggataact acagaactgt ccccttttgtt cataaagctt gtaacattgt | 54900 |
| tttcccttcc acacatcact tcaagcgtta ataagaagt tactaaagat ataaaaataa | 54960 |
| tataaaagta aatctatttta gataatacaa tttaaataaa ttttaattat aattataaat | 55020 |
| ttaattatga tagcaattga agttcttaat tgttttatgt taacaagcat tctgtgtaaa | 55080 |
| taaatggtat attcttttaag agtcatataa gctaattaag gtcaagagaa gttttgtaac | 55140 |
| ttgcccaaac tttggactgt atattcagat tttgtattct aagacacctg attattgaaa | 55200 |
| gaaaataacg tgtcacgtct tcttctgttt tgcacagggt ggagctgaaa atgacccgga | 55260 |
| aggcggccta tatgaggttc ttcactagct ctgccttctt cttttcaggg ttctttgtag | 55320 |
| tcttctatc tgtgcttccc tacacagtca tcaacggaat cgtcctacga aaaatattca | 55380 |
| caaccatttc attctgcatt gtcctacgta tgtcagtcac acggcagttc cccactgccg | 55440 |
| tacagatatg gtatgattct tttggaatga taagaaaaat acaggtaact tccatgatgg | 55500 |
| tatacttaca tgattttgga aacatttag aatttgtata gtggggaaaa tctctaaaat | 55560 |
| gaatttcttg attttggatt tattaatgga ttagatttcc actcttcatt ttcatacata | 55620 |
| atttcatgag cgcttacagt gaaaatctaa tgaaataaaa tcctaggaga ttttgtaggt | 55680 |

| | | | | | |
|---|---|---|---|---|---|
| caaatgaatt | taaaataatt | atttctataa | tctagaaaat | cccatccaag | aaatctgtga | 55740 |
| atagatcatt | tctaggcagc | ttgtaaatat | ccaaaaacat | tgaaaataaa | tttcagcagg | 55800 |
| aagttaaaaa | aatgttctag | ctagccctgg | aatgctcacc | ttgtaggcca | ctgtactttc | 55860 |
| ccatgaagca | ttgctatgtt | ccaagaactt | cagcttccag | cagaccagaa | agttacctga | 55920 |
| tccctggcca | ggtgggactt | acagggttat | tttgagcatt | aggtaagaag | tagtttattc | 55980 |
| agagcaagtt | gaataaactt | ctgagaaaaa | aaatgtctta | ttatcccttaa | aaatgtatat | 56040 |
| ttaaatattc | agtgcagaaa | gtaaatcatt | gtgaagaata | aatgtgggat | cgagggtaga | 56100 |
| ctgcttttta | agaggttctc | caattgttta | ccttggactg | atgtcacaaa | tgacagaaaa | 56160 |
| catgtaattt | tggcttttaa | atctgtttta | tttggtcttt | gaaacttttg | aattaattaa | 56220 |
| tagaaattag | aagtagagag | attatcatgt | gtacctctgt | ccacaggcat | ccatgtgtat | 56280 |
| tcacttacgt | gtattgagtg | tcttctggag | atttgcgatt | atgtagtaat | ttgggttccc | 56340 |
| acagttacag | caactgccct | caaatgtgta | tagcctgccc | agctcatcaa | atcttttaca | 56400 |
| gcctttccta | ttcagcgttt | cacccccaag | gttaaatcaa | cttgagttgt | gtgactagag | 56460 |
| cagtcactca | aacttagaat | catagtggct | ctatgacaaa | tcttatttcc | ctgctgacat | 56520 |
| caccctagtt | gggtggaggg | atgagagaag | aaagacagag | agaaggggag | agatgtaaga | 56580 |
| ggagaaatgg | gagtatctat | gaacagtaac | acagaaacat | ctaaaaaaaa | aaagagaag | 56640 |
| gaaatgagac | aaaccaatag | aggaagagag | gggggtacaa | ggaagaaaga | tcagagcaaa | 56700 |
| gattccaggt | gcacagattt | aagtcttatg | ctctccacct | ttcctaagaa | ccatgtggct | 56760 |
| ggaattctct | gatggaggcc | tttctcagag | aactgagaaa | tagttctatg | aagtccttct | 56820 |
| ccttcccttt | atataaggag | caatgattat | gatgttgctc | gtaaagagag | tgttaaaaaa | 56880 |
| aattgttgtt | cttttcactt | gtactagcct | tgaactggta | catgaataat | tgtcagggtt | 56940 |
| tcattagaaa | ttcatattct | atataacagt | ataagaaaga | aacaattgca | ctgatatcta | 57000 |
| atgtataaaa | ctaatttcat | acattaatat | atttaaagaa | tatattttga | ctatgatgag | 57060 |
| tcctactgct | tggtacttta | actttaagac | aattgtaacg | ttaatttatt | aagaaacaat | 57120 |
| ttctaattta | attgttaaaa | tccatacaag | acactgtaat | gttagagtgg | aagaagatat | 57180 |
| aacaatacat | ttttgctatt | gtgattctac | aattgaaaga | ttttttgtctt | cattgactag | 57240 |
| gatttcctgc | agaaacaaga | gtataaagta | ctggagtata | acttaatgac | cacaggcata | 57300 |
| atcatggaaa | atgtaacagc | attttgggag | gaggtgagat | ttctaaatat | ggtcgatttt | 57360 |
| taaaatatgt | aaacaattgt | gcttttttcct | tttcttgcac | ctaaatttct | actcaataac | 57420 |
| atataagatt | caaagatat | tatatctcat | agggatgtaa | ggagggctat | cctcttttat | 57480 |
| aaggtgaaaa | gtgggtaacc | aggaatatta | aatgcagcat | aaagtgcctt | tatttcttta | 57540 |
| aagtcatata | attgatttca | tataatgggc | caggaagatg | attaccttcg | atactagatc | 57600 |
| taaatcctgt | ctctgcaata | cactttccat | gtaatctaaa | tcatattatg | ttcaagttat | 57660 |
| taagcctcaa | gtgtcttcat | gtgtaaaata | gacattattt | ccctactgac | taagatgatt | 57720 |
| tacatggtct | gttcattagt | gcactttgca | aataatggtc | tttcagtgaa | gattaacttc | 57780 |
| tctaatcatg | actcctaagt | cttccctgcc | tatcactcag | aattgatgag | ccactgagtt | 57840 |
| cccatgagca | gcttccagca | gtttactcac | tctgtatgtg | gtgtaggtga | cctcatccag | 57900 |
| cctcaacatc | agtgagctga | tgacatgcaa | gtgcaaatct | ctaggcctaa | tttcaggctt | 57960 |
| gcatgctcct | catcaacttc | acagtcatca | ctcctcaagc | tttactgccc | tcgtgctcca | 58020 |

| | |
|---|---|
| gcatgttctc catctccttt cctggccaca ctgagaggca agctaggata ggatgcatta | 58080 |
| catgccaaac tttcactaga taaatatttc tttttaccgt gttcaacttc cattcttcct | 58140 |
| ccttactcct aattgaatcc tcaatgttga acttagaact actgtttatg aaaggtgaag | 58200 |
| atagacccat acatttgaaa tctagatgaa atacaacgtt acttcctttt ttcccttact | 58260 |
| attttaacct ttgcttttgt ggttctctct tgtttcaaga catcatcatt ccttttaata | 58320 |
| ctattgtttg ggtctgagtt ttcatattct ggagccttag tgatattggc ataatattaa | 58380 |
| aaaagggagt tgattctgta gaaagcaagg caagaacaat tgtgaggtgc aagtggatca | 58440 |
| taagaagtag cagacaatga attctcaggc aggttacctt taggaaagag gatcgttgga | 58500 |
| tggtgtggac ctaaaaatag attcacttaa aactaggcac acaagtttcc caggcttctt | 58560 |
| catgaccact atttgatgat atatattttg ctttggagac agtacctccg agcttccatt | 58620 |
| gggcaataga gaggcaagca attttttaaaa gaggatttct ctccacccca tacatactct | 58680 |
| tgtacagaaa aattattttg aatccactag caactttgtc acttgtattt gtagccaatg | 58740 |
| ataaatgttt ggagcaagtc ttagaggatt ggaagtgagg attgccttgt aaatctacct | 58800 |
| tgtgagctac ttgttttga cttttgctg agccaaagtc tacagtttta aagaggagg | 58860 |
| attgaaaaat tggtcttata tattatattg aagattaatt aatgtttatt tactaagtct | 58920 |
| gtaggaaaaa gggtatatgt gtatacttcc ttatagtctt ggtgtacaca cacacactca | 58980 |
| tacacacaca ctcacacata cacacacaca cacacacaca cacatacttt agccaataat | 59040 |
| atgagactga ggcaatgata agtaaaagtc tgataaagag aaattttgtt ctcattacac | 59100 |
| ataactattt ctcaaacaca ttcaaccata ctctccagaa accatgtgct ttatagttat | 59160 |
| atattataaa ttaattaata ctatgtatgt attttaatgg atcctgtacc atgtatttct | 59220 |
| taaactgatt gcatataaag ttttctatgg aaaatctgaa agcattatta tcttcaatgt | 59280 |
| gtatgaatag ggatttgggg aattactgga gaaagtacaa caaagcaatg gtgacagaaa | 59340 |
| acattccagt gatgagaaca atgtcagttt cagtcatctc tgccttgtgg gaaatcctgt | 59400 |
| gctgaaaaac atcaatttga atatagagaa aggagagatg ttggctatta ctggatctac | 59460 |
| tggatcagga aaggtactgt ctcttttaaat tgttaatttt ctgagaaatt tgtacacaaa | 59520 |
| tactgtaatt atgtaatttc tatccccctt tccagtatct tactccttcc atgtacccct | 59580 |
| cctcacttcc attaaaattc aagacctttt tgtttatgat tattatatat aatgttcttg | 59640 |
| atctattttg tgttttatat atacacgtgt ttagaactga tcactcaaga ttggataacc | 59700 |
| tatcagcgag ctaattttta aagaaaactg attctccctc ataacaattt tgcctgtaaa | 59760 |
| ttttcatcta ggggatggag ccttgtgaga taacctcata tgcattgtca tgtcaactgg | 59820 |
| taatgtcatc ctgtaggact tgtttagtta acagtgtttt gaatatttca taggtgtagc | 59880 |
| atctcattgt ctaggagata ctatctagca gtagacatgc ctgttttctg gctatgtttt | 59940 |
| agccacatct tccacaatta gccctgagcc ttaaatacag agtttgcatt gtagatgtat | 60000 |
| caacatggtc agttcttctt tgactagctc tagatctctg caatgctttg catccagtgc | 60060 |
| aaaaaaaaaa gatgtgtcta caaaaagtgg tgagaactat gcttacctgt ggctatgaag | 60120 |
| agaagtattt agaacccagt tagaaattat attagtttac aaaatggcag tagtaagagc | 60180 |
| tatgacctct ccagctatgg gtagtagtta ggtctacatt acaagattac taggtatgaa | 60240 |
| ttgaatactc ttaatgattt ggtcttaggt ctaatcaggc agctgttagg tatccctagg | 60300 |
| ataccactgt tgtaccattg atgttgtatt ttgccaagac atcaggtttt ttttttgttt | 60360 |
| gcttgttttt taatctattt atttcatatc attaagaatt taatttacta ttcatttctc | 60420 |

```
cttttttgtgt actttgaagt atatgtaata tttcagagaa aatcacatat gtatggaata    60480
tctggtgtaa tatatatata tatataaata aatatatata tatatatata tatatatgta    60540
atatgtagga atgtttgagt ataatgtata taagttgctt cagtaatgat ttccttcagg    60600
tttttcacat aattttatac ttttttgtat ataatttagc cttgtcatac atatagatgg    60660
ctttcaagaa aaccatcctt ttaaccgttc tttacttcag atctatttt aaaactggta     60720 caaaaaaaac cctgctttag atttcaccta tttctctata tatttgacat ctctctatat    60780
gtggattttt actgaataga cccaggcttg ctttttatat attattaaaa tatgtcaagt    60840
aagtgttaaa atgttaaaaa ttttaattta ttcagtggct atgttactcc ccacccagta    60900
ccaagaacaa tcaattatga tttggagaga tatctgacaa aatctaattg gctagaagtg    60960
aaaagcgctc agggattgtc acggtttcag atatgttctg tcatgtagat aatgatagat    61020
acttggtttt tggtagttac ctagataaat cattaaggac caaagaaatg aaatgtactt    61080
gagccaatgc tttgagcagc agagtacttg ctgtggggat ccataaaata gatccttgtt    61140
gcaatcagat tgttgtttta gagtaccttt cagtaataca aatatatatt tattaatctc    61200
taaaattcta tttcaaaata taaagcaatg ggagaggaag ggtgggaaga aaaagaggt     61260 gggagaaaaa taaggacaag gcagtgttgt tataaaataa aaatgaaaat taaggatcac    61320
aggagcctag catagatgtc tcctgagaag cttcatctag cagtggatgg aaccagatgc    61380
aaagacccac agccaaacat caggctgagc tcaggaagcc ttgtggaagg gttgggggta    61440
ggattgaaca agccagaggg ctcaaacaca ccacaaaaga cctacagagt caactaagct    61500
gggccgatgg gtgctcccag agatcaaagc aaacaaagag caggcaggag ttgttcctag    61560
gctcgctaca cgtttataga agatgtgcag cttggtcttc atgtgagtcc cctagtaact    61620
ggaccagggc tctctgattc tgttgcctgc agttggatcc cctaccccct agcaggaatg    61680
ctttgttggg gcctcactgg gagaggatgc aaaaatttaa tcctactgag acttgatgta    61740
ccagaccagg ctggtaccca aggtgggctt ctctttctct gaggagaagg ggaggtggta    61800 atggggtag ggatttgtga gaattcgact gggagagggg gctgaagcca ggatgtaaag     61860
tgaattaata aaccaattaa ttaatgaaaa caaaaagcat tctaaaaggt aatttgtttc    61920
tattttatac tagtatctta aacagggatt ttattttaaa gagttttata tgagattttg    61980
gaaatagcac aaattttcta atcactgtac attttgctta ttttctctc caattgtttt     62040 cttatctgtg acatagacat gttgttttgt tttattttat ttatttaaag actgaatgac    62100
ctttattgct catttttaat taattatttt atttatctac atctatgctc ccagaaatct    62160
tcaccctatt caccctcccc tttgcctctg agagggtatc taaggctggg catctctctt    62220
ctctgggaca tcaaatctct acaggattag gtgcatcttc tcacactggg gccagacaga    62280
tggcataggc atcttaaata aagtagctat aattttatat tctcttccta cagaaatgct    62340
tgctcctcag agtgttatt ctttcctcat tttctgatat ggaaatagag acagttttca     62400
cgattaaatg aaaatggtag cacaggaatc tgcataacta atgctataaa agacacagat    62460
gaccagaaac acactgtctg ctgaggaggg ggtattacta gcattacaca gaattttaaa    62520
aatgaattgt tcatgtactt aagatcaata catgaaagag gtataaaaat agctttggaa    62580
gcacagttgt tgaacttgtc agtagttaac catcaggcaa ttctatgaaa ccttaatgaa    62640
taagtaatta aaatctggga ctgttcttgc ctctcacaga aaattgctgt gaaggcgag     62700 aaagatctgg gttcccttct gacaacttac tcagagagac tgctgttttg taagaataag    62760
```

```
aaggaaaaac gattatttga ttgaaaaaat gtgaagctat aatataagat ttaaaatatt    62820
aatatttaaa gttaatttta tacctctcaa tttgatagtt tattatttaa gacttaaata    62880
taacctaata atcttatatg ttatacccett atatatttac agagattttt gtataggtat    62940
ctttggagta gtatggctat attttgaagt tctgtagtcc ttggttatag aaaaatttac    63000
aagatatgta gttaagtgag aaaagcaaaa caaaattttt gtatagtaat gctacaatgt    63060
actcaaggat actaaactat attattattt tccataaagt ctatattttg ttctactgga    63120
tacatttata atatctatat atgcttcata tttcacttat tcttaacagt ttcttcattc    63180
ataaggagct tggataaaaa aatcaatatt tttccttctc ctgctacctg tttttctttc    63240
taccaaatgg tacattagga gcccttctg tgtaagcacg gggacctaag cttgaattcc    63300
aagctcacat gttaggtgga tccataaccc cacaatgaga ggctcagaca gttggatcaa    63360
aggagctcac aggcagccag tgaagctgag actgtgagct tcagtttatt gagacacttg    63420
gtttgcctca agcaatggaa agagacatag aagatactag tatcctgctc tggcctctac    63480
atgtacacag aagggtacag gtgtccacat gttcacattg tagctctctc tctctctctc    63540
tctctctctc tctctctctc tctctctctc tctctctctc tcccccactc tgtgtgtata    63600
cacaaacttg acatccatca tttctttttt tattgtagtt ttttagaaa acatttatta    63660 ggttttttat tggatatttt ctttatttac atttcaactg ttatcctctt tccttgtttc    63720
ccctgtgaaa actcccctat cccatctccc ctctccctgc tcactcaccc acccactcct    63780
gcttctctgt cctggcattc ccatacatgg agcatcgatc ctttacagga ccaagggcct    63840
ctcctctcat tgatgtccca caaagccatc ctctgctata tatgtggcta gagccttgag    63900
taccgccttg tatactctgg ttggtggttt agaccctggg agatctgggg gtactggttg    63960
gttcattttg ttgttccct tcagtttctt gggtccttc tctagctcct ccattgagga     64020
ccctgtgctc agtcccatat gttttataa tttcttaaag atgaaagcaa attttcatac    64080
tagtaaaatg aaagtacttt ctaagactga atctgtgtta gtttattata atgaacacac    64140
tcatgtagtt agagcatagg ggcagcccat agcccaagag ctttcagcaa gtgctcactg    64200
tcaccagtct cttactacaa actgatcaca gcaatttaag taggggctcg ctcttctttg    64260
tgaaccttag tcctatgttg cccagatctc tttcatcccc tttgtatttt ttatgcctag    64320
aaaagtccct gtatcatgaa gtactaaaac atctttaatc aaatgagtta cactctttaa    64380
acattgggag acttgtgatt ggaataattg gacgcaagaa agggataagt aatttgatca    64440
aacaatttag ctgttgtttt tatttgtaga catcactcct gatgttgatt tgggagaac     64500 tggaagcttc agagggaatt attaagcaca gtggaagagt ttcattctgc tctcaatttt    64560
cttggattat gccgggtact atcaaagaaa atatcatctt tggtgtttcc tatgatgagt    64620
acagatataa gagtgttgtc aaagcttgcc aactacagca ggtaagcata tttatgaaaa    64680
atgctgattg tgttagctac ttgtgtcagt gttgtgataa aattgcttga ctactcacct    64740
tgaaaagggt tttattttaa attcttttca gggatgatac cgtccatctt ggcaaaggag    64800
gggcaggaat gggaagatgg cgagacatgt tatatccata gtcaggaagc agacagccag    64860
caggaagtgg ggcttcaagg cctaattcta gtagcttact ttctccagta aagctccaag    64920
ttgtaaacac tgtcctaccc cagtgtaccc ccaactggaa ataatgtttt caaacacatg    64980
agcccattgt aggtatttca cgttcacacc actacatgga ttatgctcat tcagtcttca    65040
gactaaccaa attacacagt tagttctcta ttgagttaat gtaaacatgt caaggacccc    65100
ctaggattaa gctggagtgg gtgggtcagt gaataaaacc atgctcctac tttaagttta    65160
```

```
caaaattata aatagatgca gtttattttt aaagtgtgtt tgggtgttgt aaaaataaaa   65220
attccttatg catgggtgt ggtacttcat gagtgcaatc ctaatactca agagactgaa   65280
gcaaaaaggt catgaagttg aagccagtct tagctgtcta atgagttcta ggccagtctg   65340
gatcacatgg taggatcatg ctaaaaacta acaaaccaaa agtctgtatg aattcaaatg   65400
gagtattttg tgtacacttt gagaccacag tgaaagaga agctatccta gaaacttgtg    65460
ctaaccttga agaagatagc catactttcc caaaagtcct tcttctacaa catgggggtt   65520
gatgtgttct gggcttgtta ccagatctgt ttttagaaga gttttctgg gcaagaattg    65580
gagggagtaa taagtcttac ttggcttatt ttggggggtgg tggggggtgag ataggggtggt 65640
actttcttgc tagatttaga ttttgctttg cttgagtatg tattttccca tataaatgat   65700
ttcacagatg atattttgag taatcaaagt cgatctacaa aatgtacata atccaaatat   65760
agcatttata cattactatt aataaattta gagctgtgga tcatccatgc aacaagtatt   65820
tacaacattc tggacacagg tagatcattg gaatgcttag atgaagaaaa ttgtatttat   65880
tgttaaagct tcatagtagg atggtatata ttaataatag aggattatat ggtttgtata   65940
gtatatatca ataaaatagt gagagaagga gaagcaaaat atattgttct ttcatttgga   66000
tgcaaggaca tattacaatt attttatagt gtatgattta ttgtgttta gaatagttac     66060
agtggtacag tgatgaccac ccttttagaa cccctgaaaa gaaactccat attcattaat   66120
agtcaaatcc tattttttta aaatattttt tattattaca tattttcatc aattacattt   66180
agaatgctat cccaaaagtc ccccatacc tccccccca cttccctacc cacccattcc      66240
cactttttgg ccctggcatt cccctgtact ggggcatata aagtttgtgt gtccaatggg   66300
cctctctttc cagtgatggc cgattaggcc atcttttgat acatatgcag ctagagtcaa   66360
gagctccgga gtactggtta gttcataatg ttgttgcacc tacagggttg cagatctctt    66420
tagctccttg gttactttct ctagctcctg cattgggggc cctgtgatcc atccaatagc   66480
tgactgtgag catccacttc tgtgtttgcc aggcccggc ctagtctcac aagagacagc    66540
tatatcaggg tccttttcagc aaaatcttgc tagtgtatgc aatgatgtca tcgtttggag  66600
gctaattatg ggatggatct ctgggtatgg cagtctctag atggtccatc cttttgtctc   66660
agctccaaac tttgactctg taactctatg caaccactga tctatctcca taaattctcc   66720
tggtccttt ctttttcaca ttttacataa aggaaattta ttgagaattt catacatata   66780
tctagtgtat gttttatcta atccatctct ctctatcttt cctttaactt ctctcatact   66840
cccttcaacc acttcaccca cccacatctg tgctctgcct taaccttcag agttcagtct   66900
gtgatcctag tatatggcct tgtacccatg ctatgctggc agctctaagg aaattttaat   66960
gtaaagcaat taatgtaaag caattagttt tcatcgactt agacttgctg tgctttatac   67020
agtgtcctga agagtgatag aaacagacca ataatgaatt tagttaaaaa tgggggaaaa    67080
aagagaatat tttaggagta aaagaagaa acagagagac tccatcaggg tctacccaaa    67140
aatagcagcc tccacatgca gaaaagggta ataatattcc tgatggtgtg attctttgta   67200
gaattctgag gttcacaggg aaagcgagcg gcccaagagt tctttattag gaacattgga   67260
actatgaaaa aagagagcca gactggactt aagaagtagg gaaatggggt ctggttgttt   67320
agagtaactg atagttgccc agtgaaacat tcggtataag atccttccag taaacactaa   67380
gttattttg cttcttttga aatatagaat aaatatcacta cagagaaaag caggaaaata   67440
ctttgagagc cagttgttct tagaaagtga attctgtaga gacaaagttg ttaaggacaa   67500
```

```
gaagagcctc caaaccaaag aataatgaaa agacattgat atgatatcaa tattgacaaa    67560
actggtcata gcgaagatga taacaatggc attttaaatt tttggctacg tgacatagtt    67620
aacaaaattt gggtatctat ggaagaaatg aaaatgacag cagagcctgg aggtttggaa    67680
tgtggatgca ctggctttct gcttagtgtc ggtgagagct ggaagtcact ccactttagt    67740
gtatcttcag accccaaaa ctatatgtgt cattcctta tgtccgactg ttttggtttg    67800
atttccagtg ctataatttt gaccaaaaac atcttcaggg agaaaaggga taatgtggct    67860
tacacttcct ggtcacagtt gatcattggt gaactcagag taaggaacta aaggtgggaa    67920
cttgaagcag aaaccaaaaa gaatgctata ttctcatctg ttctttgtct tgctagcagg    67980
cttacactta cctagctttc tcttacaaag tagaatacct gccaggaagt ggcaccaccc    68040
aaaggttgtc tgggccctcc cacatcaatt agccatcaag acaacttccc acagatatga    68100
atagtccagt tgcactggaa aaatttctat ttccaggtga ctctgtccaa tttcaataaa    68160
aactgtctac tttaggagag tcaaggtgaa tagcaaatga aagcttaacc atctctcata    68220
taaaggattt atatgataaa tttgggggaa acaaacttaa ggttctaatt tctatatgct    68280
atgacagttg ttgggttaaa gtcagtggtg aaatttgagc ctacttggat aattcaggaa    68340
gcccctctct aagagaagac ttcttgaaga gcaggtcaaa aagaaaggta acattatgta    68400
taaaagaaaa tgaataggtg tgaaaccacc tattgcaggg attataagca tcttgataga    68460
gccacggtgc aattaaagag aatgaatgag caggaatgga tttagggaac cagacctggg    68520
aggtttatcc tagagaactg ttagcaagag tgctgtgaga gctttgaagt ctgtccctgt    68580
cattctggga tgatggagag cacaattaag gtgggtacca catgaagctt agcacagcat    68640
aaatagcata gactttgaaa tcgtacaaag ctgagtcata aggttattta acttgtgcca    68700
atactcggct tttctgctct gcaataggaa gctaatatcg cctattctat gcttttgta    68760 aagtgctcta gtacatagaa agttcaccat aagtaaagca ccagttatta ttattactgt    68820
catcatcatt ggcaatagtg ctctgttcac ggttgtgact agaagaaggg agactaatag    68880
gaaactattt cagttacaca gattatggtc atgatgtaca agagacaaca gttatataaa    68940
agaattgtgg gaatatagga agttatttat gtaattttta ttcaatggaa aggacatcag    69000
tgaaaaaaat ggttattcat ggagaataag gtatttctgc aaataatgtc tttaaaagtg    69060
tataaatggg ttcaagatta agaaatctga gatctttaaa acaacagtca gaaaaatgga    69120
catgtatagg tcatggcctc aagaaggaca cagagagtga acaaagtaga gggtcgcaga    69180
tgtggctgac aaggaacaat ggaggggact aggaagggct taataaatag ttatgaaata    69240
gttatacact ctagattttc gttttaacg tattgcatac atagatcttc aattacttct    69300
agaccatttc ctgttgttat gctttcaaag attatttcac ttttactgct ctccaaagct    69360
tcccattaac tgtgtgacag tgtctgccta gcctcctcta gtggagaatg aactcagggt    69420
cttgccgaac ctctgtcatc atatgcctag ttagtctcca aaccctcagg gtttctgttt    69480
tcatgcattc cattgtgtgt tatctaggct ctgtcttta gttttagttt tgagactgtt    69540
ctgtcactct cactcacacc ctctatcttg ctctcgttga aattaaaggt ctccttttcc    69600
tcagctgttg ctacttggac taccctcagc tttccttagc tgcctgtggt tctttgccca    69660
gggctgagac tcctgaactt ttccccttct gcattaaaaa gcccattggt gtcattgttg    69720
ttgattgtcc ctttaatttg caatacccct cttttcctta gttaaataaa atgtgaagta    69780
aaactatttt tttaatttta aagaatccct aagtctttgt tcctttgtg ccactgcttt    69840 ttgccaccaa gttagaacct tttagttaac atttgaaagg cttttttctt aaatcccttt    69900
```

```
gctctttaaa atggcaaatg tagtattaca atgagctatg tatatgctgt ggtattatct    69960
tttgaactac agagtaaagt tctgaacaca acaactctaa aaatgttaat ttaatttagt    70020
ctatttagtg tactgataga atagtccatt tttactggat gactgttttg aatggtttg     70080 aggtaacatg atggttggga aattttgct cagcaaaggt tctgtgagtg ttgtggtctc     70140
agaatctgag cagattggtt cttgaatgag cacactttt ggaagcttgg gatgattgtg     70200
cttgtctgac tacaaagaaa agcatcagga gtctccctg tgtccagtga ctgaaacttc     70260
catgtttgtt tctgttatat aaacacacat ttggtcaggt acataaggaa cttcaacaca    70320
ctaaaatacc ttgttttctt agataaataa aatgttaagt aaaacgtctt tttttaaatt    70380
ttaaagaatc cctaagtctt tttcctttt tatgccactt tttaccatat atacatatac     70440
atacgcatac acacgtgcat atgcacatac atacatacat acatcacac gtatgtatgt     70500 ataatgacaa tttaagaatg caggaatttt gatcacagga acacagtata cctacagagc    70560
tcagtggctc aagagctggc accaacacaa gaaccccctca gcatgatctg tggacggtcc   70620
catttgcgaa acccagacat tcatgactct gtttgcattc tgactgctga agttgatctg   70680
tttctcagtg tgctgcatca aggcttggaa tcagagatgg ggatgggata tcctcttcct   70740
catgcttgtg attttgttca actccgagat cttcaaagtc ccctgtgtgt cgtgatgctc   70800
agtgtcacag gagtatgtga gtgtggaagg gcaaagcatg cacaacatat ttcacatagt    70860
tttctgattt cagtctgttg ttggaaatta ttcactagat gaggcagctc aaggggaag    70920 ggcatggtgg ttctgttgat agaatgattt ttagcatgaa gtctcaaata aatatgttat    70980
gggttttttt ttgtttgttt ttttttttac ttttaagctc tcctttggga aaaatctcca    71040
tgctttgctt tttaaaaatg aattttagag tctagatttt aagacaacag gcttttaggt    71100
gaattgagag tcacttgcaa acactgttct gcgtccttgt gtccattggc tctcttcatt   71160
ttcctctgcg ggccattagg gtttccttga cacatttctt ttcagggccc agcactagag    71220
actgttctag cttttgagaga agaactagtg tgatgtagct ctagtagaat aacatgtctt    71280
atgaaattag agtcctattt cagtgttgag agagagcaag ggcttacact gttctctcat    71340
ctaccttctc tgcctcacac agccccagtg acaagagaat tctggacagg ccagtgtttg    71400
agcaataaat gatttgatgg tctttattct gtgactcatt ttcttataaa agtacctggg    71460
tttggagaag taattaaagt ttataatact ttatggtggg gcgtaaggat gggcaatgtg    71520
caaaggaggt caggggctta ggatatgtaa tcagtttcca caaaattatt gtgatgcttt    71580 tgaaccaca aaatgatcct catcaagtaa gtatctgtca tgacagccat tacacacgca      71640
ctgcagcaaa aattactatg tgagctgaag aaggaggaat cgtgcatgtc tttctctttc    71700
atagctgctt agtggttttt gtatttaact tgctagagaa aatactgaga agaaaattgt    71760
caagaattca gtaaaagatt aaaaaaaaga agaagaacca tcttgggaga gaaattggca    71820
agaagttatt aaaaagttgg gagggaaata agctgagaaa tgagggtgtt ccaaaaaata    71880
aattccacca tagagattcc acatgactaa ctgaatttga atttgacctc tggctctcca    71940
tgttctgcat gactaaccta tgagaaggtg agacttaacc tttgaatagt caacttacca    72000
agttggataa ttcacagctt tacagttaga agtaatgaga agataagtgc cataggactc    72060
agcattgtac tagctcagac ataatgtata tctaaagaag atatttgaaa cacattgaac    72120
tatgtccctt tcaaccagaa taaatcacat tgactatacc gtaccatgga ctacctataa    72180
tttactgatt atatgtgatt aggaaacact agatattatt tactataaca tgaagccaag    72240
```

```
aatacttata gaattactga accagaacta aatgggaatg ccatgatatt ttatagtctg   72300
aactggtatt tcactgcatt tgagccttgg aacttaaaaa atatgtacta gctaatattt   72360
agggaaagag tatctatggc agcattgtgc taagcacgcg catgaactgg cccatggagt   72420
tgtctcttct gatttattta gtgatagctt caccaagagt ttgcagtaga gtgaaaatat   72480
gctgacttca aaatgcaggc taggctttag gccctaagcg catgaagttc ccgtgctaat   72540
tatcaggtta acacatcaga gttcttaagt cacaaaaacc aaaatagcac caggatagcc   72600
actcctagtg agatttgaag tcaacagagc agtagcttat gaacataatt ataactgtct   72660
gaacagacta cctcatgagt agactgtgaa actatgacat gtaagcctga ccttcatatt   72720
taaaacaaaa acaataggga aacttacaaa gataaaaata attttataca aatccttatt   72780
atgtgtttcc agtttctacc ttttttaagg tataggaaac ccagattcag agttctccat   72840
atttagatgg tgaataatat tatttaaacc aagaaaaaat ataattttag atgcaggatg   72900
gtgctccgaa gacccctagct aaacttcaca ttcgtggaaa atttgacatt ttaccagact   72960
tgtaactcta tagatgttca caaaagctta cccagagaag gaatcctggt gtttgctaaa   73020
ttgaatgtga agtcttctct agataggtga aatgttctag cattgacagc tattagaagt   73080
aactccatga tgataggata agtgctttta tttatattgc ttattcttgg tttagattga   73140
tgaattaaaa agaaattgat atcagctggg tatgatggca catgccttaa tcccagcatg   73200
tgggagatag aggcagacgt gtctctgagt ttgaggtcag cctggtttac agagcgagtt   73260
ccaggacagc cagggctaca acacagatgg agcctgtaga agaaagaaa gaaagaaaga   73320 aagaaagaaa agaaagaaag aaagaaagaa aggaaggaag gaaggaagga aagaaaggaa   73380
ggaaggaaag aaaggaagaa aggaaggaaa gaaaggaaga aggaaggaaa ggaaggaaga   73440
aaagaaaaga aaaggaagga aagaaaggaa ggaaagaaag gaaggaaaga aaggaaggaa   73500
agaaaggaag gaaagaaagg aaagaaagag agaaagagag aaagagagag agagagagag   73560
aaaggaagga agaaaaaaag gaaggaagga aggaaggaag agggaaaagg aaaggaaggg   73620
aaaggaaaga gaaagtgtgc gtgtgtgtga gggagagaga gagggagaga gagagagaaa   73680
gaaagaaagg aaggaagaag gaaggaaaag gaaaggaaag gaaggaaag gaaagagaaa   73740 gtgtgcttgt gtgtgaggga gagagagaga gggagagaga gagagaaaga aaggaagaaa   73800
gaaagaaaga aagaaagaaa caaaggaagg aagaaggaag gaaaaggaag ggaaaggaaa   73860
gagaaagtgt gcgcgtgtgt gagggagaga gagagggaga gaaagaagag agagggagag   73920
agaagaaaaa ggagagaaga agaagaggag gaggaggagg aggaggagga gaaggagaag   73980
gagaagaaga agaagaagaa gaagaagaag aagaagaaga gaagaagaa gaagaagaag   74040 aagaagaaag ttgttaatct cagcaacttt tcactgagct cccactataa gcacaatggt   74100
gcaataagca cagtagatgt tgcctgcagg tataactagt aacttgtcta tagtgagatt   74160
tttgttacaa aaatttatag caggatggca tatattcatt cagtaaatat ttttgaatat   74220
atgcatcaag ctaatgatta taccaaactc tgggaattac actggtaaga aaggcacaat   74280
gcttgctcta aaagaggttt ttttttttt cctcatagaa aagaacaatt aaagattagc   74340
ataggttaat gtatcgtatg tttccttaggg ctcttttata cattaggaag ttaacaatgt   74400
tctcctaaaa gatgatggaa gtttccccgc aaggaagtga catctaagtg agagctgaat   74460
gaagaagcag aagaacattt taggaaggga acagaatgta caagggtgca gaaccaaaag   74520
aagatactgt acccggcaac gtggggagcc ttgtgcatat agtagagtaa gcatgggcat   74580
ctgtaaagga aaggctgtgt gaagaggggc gaactgggga acggaaaggt agtcacattc   74640
```

```
tcagaaccca ttctgctata ctcaggaact cagactttaa agcttaggag attcaccaaa    74700
ggctttaaag taggaggtaa tgccacacaa ttaccttttt caaagatgtt ttcagttata    74760
atgtatagtt atcatgctct caattaaatg actagcaaag ctgctggcag atagataatt    74820
tcggttatct atctgagaga cagagacaga aggattctcc aagtcagggc ccaccttgtc    74880
tgtgtagtga gttccaggca agctggagct acacagtgag actgttaaaa caaacaaaca    74940
aacaaacaaa caaacacaaa tttaaaaact attcactgag cataaaatat aagatgtaat    75000
agtgactata gtcaccatgc tacagggtag atctctagaa cctattcatc ttgtctgaga    75060
cattctgtct tatgaatact tctctatgat ggtgctattt gctgagcaag ttgacacaat    75120
aaaagcattg tgcttcatta tggaaatctg aagggatgt agaattgtga tgtatacatt    75180
ctatcaaaat gtatagaaac taagaagggc aaaaagtagg taaggtatat aagtagaata    75240
tttgtttaaa atatctaaaa caactaaaca tgtaatactc gagctaattg ataattaaga    75300
gaataagcac aactgagtgg caataggagg ctccgcggag gggatctccc aaaggctcag    75360
tgcagaagag cagagatgac ttacagcaca acaaggccaa tccatagagc aggctgttag    75420
tctgagctca gtacatgaag ggcaccttca tttggagaat taagaaatg aaaataagat    75480 attacatatg aaaatataag gtcagtgtag tgggaaatta aagaattcca tattcgttgg    75540
aaagttttta ctacgtttcc ttgtggcatc attgctttag aacaaaggac acacttagac    75600
aaggatcttt gttctcagct tacattttac tcaaaggaga tagacttttc acaggaaggc    75660
agctcttgag agacaagaga ttagttggga acttcaaagg tagtgggggtt tgaagctctt    75720 ctaagaatct gagttataag agacttcata ataggaacca gaaaataatt tggggaacat    75780
agtctagata acacaagatg ttctattgaa gtatggtatt cttccccca ggcattagag    75840 ttgtcctagc attagggata ggtatagtta gaggagaaaa taaggaattg taccacttaa    75900
atatccatac tgccaatgcc ataggagtta tttagagagt ttccttgcat ctgagctcgt    75960
gctatccaga agtctatgac taaatgagtc tgaatgaggc ataataggat tacagacact    76020
gaatagcatt tgaaaggatt tttggctggc tggctggctg gttggttggt tggtttcatt    76080
tagtaaaagc cagagaaatc cagttcccat atcattctct agctgtaggg gagttcagga    76140
atcccagcac ttttctattt ctggacactc tttccctgca cacataaaat cactgcactc    76200
tacagttcct ctcttaagaa tgcttgagct atccattctg aatataaacc cagatctata    76260
acacaaggaa gtacacaata gcaatagcta tatttatatt catacataca cacatgaaaa    76320
ctgattataa aacagtttag tttgtgttat gattttatac acacacacac acacacacac    76380
acacacacac acacacacat atatatatat atatatatat atatatatat atatatatat    76440
gctctcttct gtatgaggat gtgtgcatat catggtaaat gtgtagaggt cagatggcaa    76500
cattgggtac tgagctttac tgtctaccat gtttgaggca gagttgttcc ttttgttgct    76560
atatacacta ggctagttgg cttgtgagct actggatctc aggcagttct cctgctctac    76620
ttttcatctt ccagtacagg cataatggga ttacagacac tcagggcgtc tagttttaat    76680
gtggatcctg gggatcccaaa ctcaaattgt tgggcctgtg aggcaggtgc tttatcccac    76740
tgcaccatct ttccaggcca gagcctttag tgttgatgga aactactata acatcaatat    76800 ttatatttt ctttgttata ataaagatga tgttaagtgt tttttttttc tgctataaac    76860
ttggttacta ttcactggtg aaggtaaatc ttttatcttt taaatcgatg aaaaatctta    76920
caccaccatc cttttttagca gagcttagtc ttttgaaaat gtttcttcat gcagctattt    76980
```

| | | | | | |
|---|---|---|---|---|---|
| gtaataaagt | ttgacttatg | tcaacaacct | atcttattta | ttagacataa | gccaatttaa | 77040
| atgagctcct | tagtgtctgc | attctgttat | gaggcttaca | tctgtggatc | tctgtcagag | 77100
| tctactaggt | atctgcttac | cacactcaaa | tgtacaataa | gctatgtaga | aatgatcact | 77160
| agatttttct | cttttttccag | tgctttcttg | gctgcccatt | ttcccatcct | gacttcttcc | 77220
| tacctgtttt | tcctaccttt | ctcttccatt | ggctatcttc | tgtatgcaca | aaacaaagca | 77280
| gtgttttgtg | cttttttaagc | cttattaaca | atggcattaa | ctatccagtg | attcaccgtt | 77340
| agagatatgc | tttattgagc | agcattcccc | tgaagttaat | gttcccttaa | ccctggcttc | 77400
| tcactgtgcc | caccctcttc | ttcccacaag | cgtctgtatt | gtcaaggttg | ttctaaaaat | 77460
| gataagccag | ccatataaaa | gtttatggta | ttttcctatc | ttcaaagcta | caggaagctc | 77520
| aaataaactc | agcaaatatt | gctcaattac | acaagactat | taaatgtaac | accccacccct | 77580
| tctaaaaagc | acctcctctt | ctatatcttt | ccctttttctt | tcttagtata | acagcctaga | 77640
| tcattatggc | tctattgtgt | gatcaggtca | gagcaaatga | ggttcatatt | aacaagtttc | 77700
| cttaataact | tctggcttgt | ttgatatagt | tgaaggatac | caagatgata | aattctaaat | 77760
| ttctaagaga | agtcagtggt | aaatgtgaat | aaatggaaca | taccacaata | agtatgttct | 77820
| ctagtcctta | atgataaagt | aagttaatct | ttattgcaca | cttattatag | tattactttg | 77880
| accctctcca | gtgtgcttat | ctcagcgttt | tcaagtgttt | tacaacctca | aacacacaca | 77940
| ttgtgttgtg | tgcacagtct | gctttgaagt | tgacatttgc | ctttctgacg | aggctgtaat | 78000
| aaaggaagtc | aaccacctga | gagaacaagt | gtcagatgag | gatttcaggc | cctggcgagc | 78060
| accgctgttc | agggtaagt | gcagaaaccc | aggttccttc | cagatgcctt | tgagtcacca | 78120
| caggtgcagc | aattttaaac | aaataaagtt | tctgtgaatt | agctcaagag | cctcaccttta | 78180
| gtttggcaga | tatttgatgt | tatttgtaga | taaactacac | cgaaaaaata | aataaaatat | 78240
| caaaaaatta | aaataaatta | aaattgggaa | tagagaataa | tttgaaagaa | aagttaataa | 78300
| tgttctcctt | ctataagagt | agtctttgat | tacataagtt | tatatttcag | gataagacag | 78360
| ttttctttta | ttaaacaaaa | ttcttctgga | cacttaataa | gcatgtgcaa | gggcctctat | 78420
| ttcatccata | gcaccaattt | aaaaaaaaaa | aaaacctaaa | cgaaaatcca | acagctaatt | 78480
| ttatagaata | ttttatagct | aatttttatcg | tcaaatatta | tctaataccc | ttgtctagga | 78540
| cccttattcc | aatagatgca | tttcttcaag | gagttttatg | gataaatgcc | cctcaccccc | 78600
| caaaaaaaat | ttccagagaa | ttttcagtat | taacaaagaa | aagtagcccc | tgtagctgtg | 78660
| tgccaggctt | cctctaaaag | ccacgtgtgc | tcgtgcagca | ttctaaagag | ctcacaacac | 78720
| accctaatgg | atggtcatgt | acccatgctc | atactgggca | acactagttg | aactaagggg | 78780
| attattgata | aaaataaaaa | gacaaggttt | gagtaagaat | ggggtaaggt | gtagaagggg | 78840
| gcgttagagg | gaggaaactg | tgggatttat | atgatcaaag | tgcattgtat | aaatgtgtgg | 78900
| ggttttcaaa | aagaatatat | gtatatacat | atatttcaaa | aagaatatct | atgcattatc | 78960
| tatgccatta | acaaaaacca | ggaaaaaatg | gaagggatgg | atgaggaggg | tttgcaggga | 79020
| gggagggaat | ggataaatgt | aattatgtta | tagtctcaga | cataaaaata | aagattaaaa | 79080
| acaaatcctc | atgataggca | cgagtgatat | aacagttttt | aaattgtgat | ttttacaggt | 79140
| ggggaaaatc | tatgaagtct | gaaaccaaca | cccttaagat | aaatatatta | ccagatttga | 79200
| gtatccttag | tagtcagcaa | aggtcaatgt | ttaacgatgc | atgcaaaaca | gagtgctttg | 79260
| ttttaaatca | aacagaatgt | taagtactca | taaatttgca | gacggatgag | gcataaactg | 79320
| agtaatcaaa | ccaagtgctc | agattaaagg | aggatattgg | cgtgctgatg | tattaggctg | 79380

```
taatgagtgc aatctcagta gatccccgct gcctgtccct catttcactc tcagcagcat    79440
gaaatcttca ctcacggagt gaaagttacc catatttctc ttcacgagtg gattcagtcc    79500
ataaacaaca gttcaaacct tggctcagta ggcagatcta ctttcatacc attgaaagtc    79560
aattcctaga aataatatgt tatagaagag aacatgtatg tctcagtgtt cttattttgt    79620
tcaatgttaa aagcctggat agcatcacca aaactgtgcc acaaaactct aagattcagc    79680
aaatagaata atgaaatatg tattttttcca atccatttaa tacaagttac acccatatat    79740
gcagttcagc tttaaaattc acatacagta taatttgcac acattattct ctaacttatt    79800
cagttcccgt tatcttttta agatataaca ataccctatat acatgtttat acactaattt    79860
agggatgagt gagtgtgtac atgtggcaga cggctcagat ggaggtctgc agtgtcagtc    79920
cttcatcctt gacggccatt aatgagtgtt tgctgggagg agaggtcctt ggtcctgtga    79980
aggctccata gatgcctcag tgtaggggaa ttcaaggtgg ggggaggtgg gagtgggtgg    80040 gtgggggag ggatactatc atagaagggg gggtggtata gggggtgtac gtgggggggg    80100
aacgggaaag gggataacat ttggaatgta aataaagaaa aatatccaat aaaaaaacct    80160
tcctatcagt gactttaatc ttttttggtca ttctgactcc taaatcaaaa tttctattat    80220
tttgtctcta ttctatttag atgaatatgt aagagattat aaatatactt tcatgtttat    80280
taactatctt gatttcctaa catttaaact tgaacacttt ttgtaagata taatgatgga    80340
taaaatatgt attatataga tcactgctat aggaaacaat tgaatgaaga gtccagtttt    80400
gttttgaagt ccttaactga gtttgtcttg agactacctc tacattcatg aatgtttccg    80460
gcaggattac taaaatagat ttctattttg aaaacataag aactattagc taattttttga   80520 cataaaaatc accaagctgc tttgccaaat tctcccttgg actaaattgg tataatattc    80580
tcccatacca accatcaatc ctactttagg atcagagttg cagtgggctc ttcagactgc    80640
ccatctatcc tatgtgtttc cttttccaca gtatctcccc caattaaact cttggacatt    80700
tgatatcatg ttggaatctg gttggagaat tttgactgat agctgcatat attacattat    80760
catcttctgt agtgatagtt tttcttataa ttttatatag tcaattttat ctaaatgcca    80820
ttttatgttt tgacatttct gacttctctt aaagatgttc gttagagcaa aaaataaaga    80880
cattctgtcc taatagtttt acatttttcat ttatcaagaa tatgggttat tagaattata    80940
tggtgtgcag ttttatgttg acattttaca ctcttaatta aaatataatg gctgcttttc    81000
ccgctcccct tccttccctc cattccttct catgtcccct ctctccaaac ccttccattt    81060
cacctctctt tcaaattggt gtcctctttta ttgttgttac atgcatatgc ataaatatgt    81120
aaatactcat atcttagaat tagccaaggg tggtttaact agatggaggg catgctcaat    81180
agtgagattt ttctatttag gaaagtaatg tgatatatct taatcataga aactttttaat   81240 atcactcttc ttcatcctga tcaaagtggt cagaatacag atttctagat ttctttgaac    81300
aaatctactc tactttgaag aaatttagtc cactgctgtt tctgttgaaa aagaaattga    81360
ctttgcatgt tagctctatg atcaaattgt agacaaacat ttaagataac tagctcttcc    81420
ttacagaaaa gtcatctaaa gatataaatg ggaaacaact attcagttca caataatggc    81480
aaaccttaaa gtatttagtg attgttatag ctctcatggg acatttacag aatatgaaga    81540
aaatgataaa tcttattgaa gtattgaatt caacatctga atcaggatta aaaacatttt    81600
tgatttagtg ttgcaaacta gaattctatg taagtgcaag gtatttaaaa gttgcaaata    81660
aattctaata aggttatctt aaactaaact taatatataaa tcttagaagt aatttattga    81720
```

```
caaattattt tggtggaatt tttgcttcat catatgtaga cttgatatca tggtatttgt  81780
acttcttata tttgaaatgt tagtgaggaa gaattactgc attaaaattg ttcaagtcag  81840
cacttgagac tatgttagct catcttttaa tgatatatta tttcaatagt tgacatggct  81900
actatgtcaa aaactaagaa agccaactct ttcatgaggt aggattatat tttatcagat  81960
attaaatgat ataaatttt atttaaaatc aaggacccaa aagtccagaa aatattaata  82020
tagaaataaa aaaatggatc agaaaaataa gagaacccag aactaggaac catgacagat  82080
gatagaggca tcagtaaacc attcatttga tgattattgt tgccttgtaa caaatgaaag  82140 ataggtaga caaatagaaa actgtgccat aagggttttg aacatttat tttgaaaata  82200 gtattcaaga taacacatat agctagctgg tggggagtag atacatttat ttcacaaaat  82260 cttttttgcac atgataagtg atatgcacag tgaaaaaaag agaaacgaat ggagtttttt  82320
atatgcagcc tataaagttg caaaaactac atacaaatat tagacacttc aaagaagaaa  82380
atgcaacaca gcaaatattt aaaatctttg tgattaagaa aaatgtaaat gaaaagagaa  82440
aattagcaaa aattatcata atcatactag tacaacttag taaattgtaa tttaactctt  82500
tagttgcttt gtaaagcaat ctggtggtaa cttttgaaag tagaacatat gcatttgata  82560
tagtcatcct actcatgaga atatatcttc cagctacaga tcacaaaagc atatatgtat  82620
tcagtgatat taatagtagg ctttgtaggg aggaagtggg gagcaattgc tagggaagaa  82680
ttgcatgcct caccatttta atgtagtctg gactacaaag agaaaccaat gacttcaaat  82740
gaaccacctg gaagcagctt gcatggatca gctctcttgt agtattctgt tctcacagtg  82800
ttgtaagtac tgaaacattt atttttctga gtgcctcacc ttatagtgtg tcactcagcc  82860
aagagtatgg ggattacaaa cactgtttgt tctagtggaa atctcacatc tgtcattacg  82920
tcatcatctt caaaacagga gggagtgttt tagagacgtg atggtagtga acctgaatcc  82980
ccttcctttt tcctttcttt ttaaaaaagc aataaggtaa cagaggaaat aaatataaaa  83040
ttgtatttac tcttgtgaaa taaaatcacc aacaatctgt gctagctagt ttttatgcca  83100
caggtagagt tttatgacat gagctagaat aatttgggaa cagagaagtt caattgagaa  83160
aatgcctcac cagattggcc tgtggacaag cctatgggaa attttcttgg ttgaggattg  83220
tgggaggtcc cagttcatga tggttggtgc cacctctagg ccagtggtcc tgggtgctat  83280
aagaaagcag gctaaggagc cacatggagc aaatcagtaa gtagcactcc tccatggcct  83340
gtgtttcact ccctgcttcc agattcctgc ctgagttcct gcactggctt ccctcagtga  83400
tggacataaa agttgcaaaa tgaaataaac cctttcttcc ccaagttgct tttggtcctc  83460
tgttatcaca gtaacaaaca aacaactaac aaagacccca tgtctgcaat ggtgtatgtg  83520
ggaagtcact gatttatccc aagtctttgg tcacgctgtc aggaatgctt gttagacggg  83580
gttccttgtt aaaagtgaat agcatggcaa tctaaggagg tgatagaaaa catgagaggg  83640
ggctgggagg agagaatatt aaaggaaatt ggtacctaac ttgatcacat tttaactact  83700
caagtgaagc tcttcatgga aggcctcgaa cattctctct gtggtgtgtg ctttattcct  83760
atcgtctaaa taattaacat gccatgtata ctgttgtata atacgttgta aaattgtttt  83820
ttaagaagtt agattgttac ttaattctcg ctccaggatt agagcttatc ttctaaatta  83880
ggtttacact gtctggagtc ctggactatt tcttacaaac ccaggtcgtc ttttactgtg  83940
ccttcatagt tgttactaca gaaaagatca ttattgggca aggaatggca tatgtgacag  84000
gagaggagta gtaagtggac aaggacagaa aaataatgga agtggtgagg atgtttgtgt  84060
tgttgtttgg gaagatgaat gaaagaatgc ggaaataaac tgacatgtcc cgttgttagc  84120
```

```
cactgaagaa tgcagaaata aactgacatg tcccgttgtt agccactgaa gaatgcggaa    84180
ataaactgac atgtcccatt gttagccact gaagaatgag gaaataaact gacatgtcct    84240
gttgttagcc actgaagaat gcagaaataa actgacatgt cctgttgtta gccactgaag    84300
aatgcagaaa taaactgaca tgtcctgttg ttagccactg aagaatgcag aaataaactg    84360
acatgtcctg ttgttagcca ctgaagaatg tggaaataaa ctgacatgtc ctgttgttag    84420
ccactgaagt tgcctgcatg tttctgtggg tgtggagagt tttgttttag cttttcttat    84480
taacaggctt attcagtctt ttgacatttt ttaaaagtga ttttaagttg aaagtatatt    84540
tgaatggcac ttgagtttat atgatgggct tatgggtagt ctttgaatat aaacattccc    84600
caaataaata gttgcatctg aagaaaaatg ttcttttcaa ttttggattg tgcatgctaa    84660
attttatttc tggtgttatg ctttggataa taggacatca ccaagtttgc agaacaagac    84720
aacacagttc ttggagaagg tggagtcaca ctgagtggag gtcagcgtgc aaggatttct    84780
ttagcaaggt aaatatttaa ctgttggtct tgtgagcact tgctgtaaat actatggggt    84840
tttaattata catacacatt tctcttctgc ttcctgttct gtctctggaa ttgatgctttt   84900 ttctttaaga actatagaca ttataatatt caaatttggt aaagatggtg gtttttttttt  84960 ttcaaaatgt atacttttca aaatgtatac tcttatttat atttgtccaa acttgttgtt    85020
atggtgcatg gattgttatg aagagaaaag tatagaattc taaagaaaaa agaaaaggaa    85080
aattacaagt ttctattaat cccccctttt tccctgtccc cagatgcctc tgatttgaat    85140
ttctgtttat tcttctaagt ttagatatac acattttcaa ttttttaattt ttagaacata   85200 atctatgata gtataacaaa aataggaagg taaatgatgt cactaaggtt tctcatttgt    85260
ttacagacaa aggacaaggt ctccctattt agaaattagg atctttctgt gtttgtttct    85320
gtatactagg atgaaagtgt gtgccaccac acccggtaag ctttatactg aatacatgct    85380
ttcatttgtg atgctgattg tcctcatggt catgtttaat tattgtcaga acgaaagtat    85440
tttatttaaa ttgtagcttc cgtttaaaga caattggtgg tatgggatttt caaatgctct   85500 ctaattttat tgaaacaaaa ttcttactac attaccaaag ctgttaatga gaaattacat    85560
tggctcagtg gtatcttggt atcttggcca tttatcttcc atctcctgga aaagtaaaca    85620
ctaagtatca caactgatcc ttgataccat tccttctccc cctcccttttg tctgtgtgcc   85680 tgcctgtctg tctgtctctg aatgtatgtt tatgatctca atccccatac aagactagaa    85740
gcagaaattg ttttctttat tttatggaag aaatcacaag ataattgagg tagtcagaca    85800
ttaacttgcc aaaggccaca aggaaatgat acagtcacta tttaatcaag gtcatcttga    85860
ctccttacat taaactatgc ttcggtctgg aaaatacact gcgaaatcag atcaatagat    85920
agaatttcca gacaatggct tcaaaatgat tggaagctaa ttcccttatc tgtgtggcaa    85980
aagtcatatc ttaagcattc catttgagtt ttaagtaaaa tatggtatgt gacttcagta    86040
tagtattaac atttactagt ttaagattta gtcatatttg ctatgtacaa tatatggcac    86100
tactcaaaac agttgtctac tatttttata gttgcacatg ttattctcat ttacatatgc    86160
aataaatatg tcatccactt ttatatgaag aatatacaca ttttaatctt gagaaactgg    86220
ccacacatgt gaatgagagt ttttaccttg gttttgcact aataatttac caatatattc    86280
agagtaaatt ttacagaaaa tcactttta ttcccactta ctgtttaagg taaaggagtc    86340
atatccagtg atggcttctt gttggcagag tcttgagaca gcacacacaa aaaaatcata    86400
tgtcaagaaa aaaaggaat gtgtgtgtgt tctctgttat tcctttcctc atgaagccac    86460
```

```
cattatccaa tcatgaaacc ccaccttgat aatcttactt aatcctcatc attttgcaaa   86520
atgaccacca acagctttgc tgttggacta agtttccatc ttcttcctgc ctctgatgga   86580
tatgaaatct atattagttt cagaatggac aaatatattt gattatatta cagagaaata   86640
aataaaatct aaatgttgat aaagacagga gagttcattt ttatggagtc cattagctct   86700
tctgtttcct tccagacaat ttatagcata aagggcttgt ttgtttgttt gtttatttt    86760 attcttaat  ccttttttac agttcagaat tcatccccct cccagtctgc ccccgactgc   86820
tccccatccc atacctcctc cctacccta  acctccatcg ccaagaggat gtccccaccc   86880
tgagcataaa agagcattat gacttaatct ggaattttt  ttgctatttc tattttattc   86940 attgttttc  ttatttgtga tgattaagta catttaaaa  acaaaagtat caataaatag   87000
tttctacagc atgtcctctg taactgggat agaggtagca ttattagtaa tcacacttga   87060
aaaaagtaag atgtataaag aaattatttc cttttgtta  gtttggaaaa tataccttta   87120 tattttcct  attgtaagtc aactcaaatt gttttagtt  tcaatttcaa gtgaaataag   87180
agctggggag agatagctca ttggtgagga gcgctggctg tcttccaaa  ggctccaggc   87240 ttgagtcaca gtactaatct gcttcacaat catctgtaat tggtaaccca gcacacctga   87300
catttccttt tggtctccat aggcactgaa cacacatggt acacatacat gtaggtaaaa   87360
accgtcaaac acacagtaca gaagttacta acagtactcc ctgtgctctg tgctgtgaca   87420
cgtgtgcttt cagtacatgg ttttgatgac cattgtataa cacaagttct gtgtttaaaa   87480
tatctattct caatgacgta aaagatcttg agggatccta acttctttc  cattttgttt   87540 atagagcagt atataaagat gctgatttgt acctattaga ttccccttt  ggatatctag   87600 atgtttttac tgaagaacaa gtatttgaaa ggtatgttct atgactgagt tacttataat   87660
gctcatgtta aaagataata aatgtctgtt tcaccaaagg ctgcatatta gcatattagc   87720
tccagagtaa tatccactat ttctattgct caaaacatca ggatctagca cagtgcttat   87780
tcagtcctgg catcccctta atggtcaagg gtgaagttgc ttctgccaca cccttttctg   87840
atgatcacat ctgaagccaa tttcttgatt gctatcctgt tctaacagtt gatatttaag   87900
aatcgtttat attttgctat cttgaaaagt cttccagtat tttaagtagt ttacttttaa   87960
aattccacct accattctgt attagtattt ttattttatg ttgttttaga aagaaaataa   88020
tgtttattgg taaatgccca tactgtacct ctgtcttagt cctctttaga tgccctctt   88080 tggtcacaga gaacatagat atttccttaa agttttatt  agagcccaaa tgggtgtaaa   88140
atctctaaga ggtaacatta gttataccat ttgatttcaa atgttaaaat aattttatgg   88200
gcaacaaagt agcttattag aatagacatt atagcactct agaaacaaat gagttttgt    88260 tttaaggata gaatgtagtg tgtgtgttaa gatggtttga ttatttattg atttatttca   88320 aactttact  ttaggacatt gtgctaaagg gttgaaatat tctagagccc tgcttattgt   88380
gtcttaaaat atgtggaata acatgtttca ctaatggact ttactgtact tacacatgaa   88440
gccagcaggt ctcagtcctg aagctacttt tattcagagg tggaatacta tggcatgttt   88500
gttttgacat tttccgttta cgtttctgtt gcatggtgtt tattagcatg gtttatccgg   88560
ccacaatccc aagaacatcg tgatctctga atgaagggcc aagtcccaac aatgccatct   88620
ctagcccaca gatcccagtc ctcattgttg ctcataagct tccgatcaaa tctatagtga   88680
agaagtcctt tatgacaat  gtattttcat agttcccttc atcttctctt gcttattcta   88740
atctaatgca aacggctgta gaaggtccta gtacatttct gcctcccgca aagctttttg   88800
catctccttc actacagctg tgcattaaca ttgtcttctg agtctctaaa gttgtttttgt  88860
```

```
aattcccatt gcatcaagtt ctctgtgtcc attacagtct gaatgctgac cactttaagc    88920
atataacact ctgtaagaca aacattttct tcttttattc tttctttttt ctctttcttt    88980
ttttttcttt tttctttttt tttagatgca agctggctct cttttccctg atgattctca    89040
atattattta ttcttcaact tgaggttaat aatcagagag agcctaaaca ttgtatttta    89100
tttactaaag ctacatcatt aaggctttga taattgttaa ttcatttatt tattcacttt    89160
acaaaactcc tctcctccca gtatcaccct cacaaatttg cccccccccc cccatgagtc    89220
ttctcagaga agaggatgtc cccttggccg ttggatacct gccagccatg ggacatcaag    89280
tcacagcaca agcctatcct ttcccaatga ggcctgacta agcagctcag ctggaggaag    89340
gtaattccag tggcaggcaa tagattcaga gacagccccg ctgcagttgt taggggaccc    89400
acatgaaggc caaacagcac aactgctaca tatggtttag tctctgcagg ctctctggtt    89460
ggtgcttcag tctttctgag ctcccatggg cccaggttag tatactctgt aggtcttttgt    89520 ggtgtcctta acccctctac ctccctcagt cctatcccct actcttacaa aagactcccc    89580
caaatctgct taatgcttgg ctgtggatct ctgcatctgt ttccatcacc tgctggatga    89640
agcctctaaa gagacacatt tgctagggtt ctatgtgcaa acataatatc attaatagtg    89700
ttgggagttg gctctctccc atgggatagg tatcaaattg gaccagacac tggtgaactt    89760
ccttcaatct ctatattttt tagtattttt tttatatttt tattatctgt aatcattttt    89820
ttaaagtgca gtcgttatcc ccctcctgtt ctgccctctg acagttcttc atctcattcc    89880 tcctcccccta tatccaagat gatgtctcta caccccacac atgcccaca ccgcaccaga    89940 cctccccatt ccctgggggcc tctcaagggt taggtgcatg catcttctct cattgatgcc    90000
agaataggcc atcctcagat gtaaaatatgt ttcccaacta gtgtatgctg cctggtgggt    90060
ggctcagtgt ctgagagatt tggggaagtt caggtttgtt gagacagcta gtctttctat    90120
tggatcaccc tcttcgtcag attcttccag ccttttcccta gttcaaccac aggggtcccc    90180
aacttctgat cattggatct gcttctgtct cagtcatctc tttgttgggc ctctcagagg    90240
gcagccatgc taggctcctg tttataagta catcatagca tcagtaatag catcagacct    90300
tggagactca cgctgagatg gctcccagtt tggaccagtc agtggacctc cttttccctca    90360 ttctttctc cattttttgtc cctgcagttc ttttagacag gaataattct aggtctgagt    90420
tttggattgt acaatggcaa ccccatccct ccatgccctg tctttctact ggaggtggac    90480
tctataagtg ctctctcaac actgttgggt attttaccta aggtccctttt gagtcctgaa    90540 agtctctcac ttctcaggtc tctggtatat tctagaaggt ccccccacat cccacctcct    90600
gagttgcctg ttttcattca ttctgcttgc cctcagtgct tcactcctgt ttcctaccct    90660
gctaatacct gaacatgtta tgaaattctt aggcaaatgg atgtcctcat tcttaatagc    90720
tgcctagtat tcattgtgta aatgtaccac attttctgta tctattcttc tgttgtggga    90780
catctgggtt gtttacagct tctggatatc aaaaataagg ctactataaa cacagtggac    90840
ttgtagcatg gtgggacatc ttttttggtat atgcctagga acagtatagc tggctcttca    90900
tttacaatta tttctaatttt tctgaggaac ctccagattt atttccaaag ttgttgtacc    90960
agctagcaat cccaccagca atagaggagt gttcctctta ttccacattt ttgccaaaat    91020
gtgctgtgac ctgaggtttt gatcttaacc attctgattg gtgtaaaggt ggaatctcga    91080
ggtcatttta tttgcatttc cctgatcaaa aaggactttg aacatttctt taattgccat    91140
tcaaaatttc tctgccgtga attctctgtt tagttctata ccccattttt tttattggaa    91200
```

-continued

```
gtttttttgt ggaagttagc ttctttagtt ctttatatat tttggatatt agtcaactat   91260
gagatgtggg attagtggag atttttcccc caatctgtag gttgccaatt tgtcctattg   91320
acaatgtcca ttgccttaca gaagctttac agtttcatga agtcccattt atcaattctt   91380
gatcttagag cctgagtcat tggagttttg tataggaaat ccccacccac accccctaat   91440
ccccaaattt ctccccaacc tccatggcca tgagttcaag gctctttccc attttttcttt  91500
tctgttagat ttatcttatc tggctttttt tgttaaggtt cttgatccac ttggacttga   91560
gctttgtgca aggtgacaaa tataaatcta ttttaattca tttacaaact gactcccagt   91620
tagatcagca ccatttattg acggttcttt tttacctttg tatattttt gcttctttgt    91680
caaagatcaa gtatccataa gtatgtgctt ttactgttgg gtcttcaatt caattccatt   91740
aatcaactga tctgtctctg taccaaaacc attcaggttt gttttttgtt ttttgttttg   91800
ttttgttttg tttttatcac tattgctgta tagtatagct tgaggtcagg gtgatgattt   91860
cctcagaagt tcttttattg ttatgaattg ttttgctttt cctgtttttt tggtttcttt   91920
ccagatgaaa ttgagaattg ttcttttccat gtctttgaag aattgtgttg gaattttaat  91980
gggtattgca ttgaatctgt agactccttt tgtaggatgg ccattttac tatgttaatc    92040
ctaccaatcc atgagcatgg aagatctttc cattttctga tgatttcttt cttgagagac   92100
ttgaagttct tgtcatgcag atctttcact tgtttggtta gttccccaa gatattctct    92160
ctctctcttt cttccttcct tccttccttc cttccttcct tccttccttc ctttcttct    92220
tccttctttt ccttctctat ttcttttcttt gtttctttct ctcattctct cttttttttct  92280
ttttctttt tttctttctt tttcttttt ttttctttt ttttttttt tttggtgttt        92340
ccctattttc attctcagcc ctgtttatcc ttagtataaa ggaaggctac tgatttgttt    92400
gagtaaattt tacattcagt cactttgctg aagatgtttg tcagctgtag aagttctctg   92460
gtaggatttt ggggtcactt atgtatacta tcatatcatc tccaaatagt gataccttga    92520
cttttttctt gccagtttgt atccccttca tctccttttg ttgtcttatt gctctggcta    92580
gaaccttgaa aactatattg aataggtatg gggagagtga gcatccttgt cttgttcctt   92640
atttagtgg gattgcttca agtgtctctc catttaattt gatattttct gttggtttgc    92700
tgtatattgc ttttattatg tttagatatg ggccctgaat tcatgatctc tccaatactt   92760
ttaacatgaa ggcatgttat attttgtcaa atacttttc agcatctaat gggatgatca    92820
tgtgattttt ttctttgagt ttgttgatat agttgattat attaatgtat tttcttatat   92880
tgaaccaacc ttgcagccct ggaatgaagc ctacttcatt gtggtgaatg accgttttaa   92940
tgtgtgctta gattcagttt gctttatgag tactttctga agttcttttg ttgttgttgt   93000
tgggtctgtg tatagtttag ataacagagt aattatgtca tcatagagtg aattaggtag   93060
cattccttct gtttctattt tatggaatag tttgaggagt gttggctctt ctttgaaagt   93120
ctgtgtgatg ccttccttagc agaaaggttg ccacaaaatt ttacatgagt ctttctatgt  93180
ggtccagagc acaaagtacc tttgtctgaa ttacttgttc aaatcttcca ggagccactg   93240
tactgttttt gtttgttcag ttgttgtttt cctttatata taataatttt agcttcactt   93300
gtttgggggg agctcctttg tatctgtaga acctgcatag tgccagaaat atgaactagc   93360
actgtagcca tatgcatttc agaagtctgt ttccagcagg actctagttt aagacaaaga   93420
gaaaattcca ttaaatgaaa ttccccccctt ccccaatgct attttatga tgctctgact    93480
atagttgcca atgtttactg tcataaactt acctaaaatt atattattta acttaagag    93540
aatttaatgg ttcttatttt tttatatttt aatggataaa aggaacagat tttccctgta   93600
```

```
gtatccactg caatacttaa cttttttttt cctttccat tttttattag gtatttagct    93660
catttacatt tccaatgcta taccaaaagt cccccatacc cacccacccc cactccccta    93720
cccacccact cccccttttt ggccctggtg ttccctgta  ctggggcata taaagtttgc    93780
gtgtccaatg ggcctctctt tccagtgatg gccgactagg ccatcttttg atacatatgc    93840
agctagagtc aagagctccg gggtactggt tagttcataa tgttgttcca cctatagggt    93900
tgcagatccc tttagctcct tgggtacttt ctctagctcc tccattggga gccctgtgat    93960
ccatccatta gctgactgtg agcatccact tctgtgtttg ctaggccccg gcatagtctc    94020
acaagagaca gctacatctg ggtccttcg  ataaaatctt gctagtgtat gcaatggtgt    94080
cagcgtttgg atgctgatta tggggtggat ccctggatat ggcagtctct acatggtcca    94140
tcctttcatc tcagctccaa actttgtctc tgtaactcct tccaagggtg ttttgttccc    94200
acttctaagg aggagcatag tgtccacact tcagtcttca ttttttcttga gtttcatgtg    94260
tttaggaaat tgtatcttat atcttgggta tcctaggttt tgggctaata tccacttatc    94320
ggtgagtaca tattgtgtga gttcctttgt gaatgtgtta cctcactcag gatgatgccc    94380
tccaggtcca tccatttgcc taggaatttc ataaattcat tttttttttca attttttatt    94440
aggtatttag ctcatttaca tttccaatgc tataccaaaa gtcccccata tccacccacc    94500
cccactcccc tgcccaccca ctccccctt  ttggccctgg tgttcccctg tactggggca    94560
tataaagttt gcaagtccaa tgggcctctc tttccactga tggccgccta ggccatcttt    94620
tgatatatat gcagctagag tcaagagctc cggggtactg gttagttcat aatgttgttc    94680
cacctatagg gttgcagatc cctttagctc cttggctact ttctctagct cctccattgg    94740
gagccctatg atccatccat tagctgacag tgagcatcca cttctgtgtt tgctaggccc    94800
cggcatagtc tcacaagaga cagctacatc tgggtccttt cgataaaatc ttgctagtgt    94860
atgcaatggt gtcagcgttt ggatgctgat tatggggtgg atccctggat atggcagtct    94920
ctacatggtc catcctttca tctcagctcc aaagtttgtc tctgtaactc cttccatgga    94980
tgttttgttc ccaaatctaa ggaggggcat agtgtccaca cttcagtctt cattcttcat    95040
gagtttcatg tgtttagcaa attatatctt atatcttggg tatcctaggt ttggggctaa    95100
tatccactta tcagtgagta catattgtgt gagttccttt gtgaatgtgt tacctcactc    95160
aggatgatgc cctccaggtc catccatttg gctaggaatt tcataaattc attctttta     95220
atagctgagt agtactccat tgtgtagatg taccacattt tctgtatcca ttcctctgtt    95280
gagggggcatc taggttcttt ccagcttctg gctattataa ataaggctgc tatgaacata    95340
gtggagcatg tgtccttctt accagttggg gcatcttctg gatatatgcc caggagcgga    95400
attgctggat cctccggtag tactatgtcc aatttttctga ggaaccgcca gactgatttc    95460
cagagtggtt gtacaagcct gcaatcccac caacaatgga ggagtgttcc tctttctcca    95520
catccacgcc agcatctgct gtcacctgaa ttttttgatct tagccattct gactagtgtg    95580
aggtggaatc tcagggttgt tttgatttgc atttccctga tgattaagga tgttgaacat    95640
ttttttcaggt gcttctctgc cattcggtat ttttcaggtg agaattcttt gttcagttct    95700
gagcccatt  ttttaatggg gttatttgat tttctgaagt ccaccttctt gagttcttta    95760
tatatgttgg atattagtcc cctatctgat ttaggatagg taaagatcct ttcccaatct    95820
gttggtggtc ttttttgtctt attgacggtg tcttttgcct tgcagaaact ttggagtttc    95880
attaggtccc atttgtcaat tctcgatctt acagcacaag ccattgctgt tctgttcagg    95940
```

```
aattttteee  ctgtgcccat  atcttcaagg  ctttteecca  ctttctectc  tataagtttc   96000
agtgtctctg  gttttatgtg  aagttccttg  atccacttag  atttgacctt  agtacaagga   96060
gataggaatg  gatcaattcg  cattcttcta  catgataaca  accagttgtg  ccagcaccaa   96120
ttgttgaaaa  tgctgtcttt  cttccactgg  atggttttag  ctcccttgtc  gaagatcaag   96180
tgaccatagg  tgtgtgggtt  catttctggg  tcttcaattc  tattccattg  gtctacttgt   96240
ctgtctctat  accagtacca  tgcagttttt  atcacaattg  ctctgtagta  aagctttagg   96300
tcaggcatgg  tgattccacc  agaggttctt  ttatccttga  caagactttt  tgctatccta   96360
ggttttttgt  tattccagat  gaatttgcaa  attgctcctt  ctaattcgtt  gaagaattga   96420
gttggaattt  tgatggggat  tgcattgaat  ctgtagattg  cttttggcaa  gatagccatt   96480
tttgcaatgt  tgatcctgcc  aatccatgag  catgggagat  ctttccatct  tctgagatct   96540
gtaggaaaat  gttattggag  gacagtcaac  tttattaggt  atttctcagt  tgtaatgttt   96600
tatcttaaag  aaaacagatt  agtcaacata  aaatataaga  gaaaattcat  taaaaactaa   96660
aaatagaaaa  tctctaacat  cttagaagtt  atatggacat  ataaacttta  ggaacatata   96720
ataattcttt  tattttctag  aaaaataaat  caagaccaaa  gagaaaatga  tttggttaaa   96780
atcagatact  tgattattta  aaattgtatt  tgattttatg  tctgctagta  tttactttac   96840
agtaagatat  gctatttcat  actgcaattc  atgaggcacc  taagagttat  gatggagtgg   96900
ttatttgtat  aagtgtatta  aataaagcaa  taaaatgcta  tgatagattt  tatgcaatga   96960
aactttatgc  tgaagttaaa  tatacatcac  tatttatgaa  gtaatatctt  atatcttttt   97020
tatatttcca  aagctgtgtt  tgtaaattga  tggccaacaa  aactaggatt  ttggttacat   97080
ctaaaatgga  acacttaagg  aaagctgaca  aaatactaat  tttgcatcag  ggcagtagct   97140
attttatgg   gacattttct  gagctacaaa  gtctacgtcc  agacttcagt  tcgaaactca   97200
tggggtatga  acttttgac   cagtttactg  aggaaagaag  aagttcaatt  ctaactgaga   97260
ccttacgcag  gttctcagta  gacgattcct  ctgccccgtg  gagcaaaccc  aaacagtcgt   97320
ttagacagac  tggagaggtg  ggagaaaaaa  ggaagaactc  tattctaaat  tcattcagct   97380
ctgtaaggaa  aatttccatt  gtgcaaaaga  ctccattatg  tatcgatgga  gagtctgatg   97440
atctccaaga  aaagagactg  tccctagttc  cggattctga  acagggggag  gctgctctgc   97500
cgcgcagcaa  catgatcgcc  accggcccca  catttccagg  cagaagaaga  cagtctgttt   97560
tggatctgat  gacgttcaca  cccaactcag  gctccagcaa  tcttcagagg  accagaactt   97620
ctattcgaaa  aatctcctta  gtccctcaga  taagcttaaa  tgaagtggat  gtatattcaa   97680
ggagattatc  gcaagatagc  acactgaaca  tcactgaaga  aattaacgaa  gaagatttaa   97740
aggtatatac  ccgtcaagtc  ttaagataca  tctcatccta  accccataat  tggagtaaat   97800
tttgtcacat  actatgtatt  tcatggcatc  ccattgtggt  ctatgggcta  aggatacaaa   97860
gtccattacc  tgtgtaagca  acttgaaaca  taaaactatt  tctggttatc  attgaaatat   97920
catccccacc  ccacaaatgt  gtggtaagcc  aaaacagggc  ctcagtgttg  agttttteta   97980
ctagactcat  gaaatgatat  tcactttat   aacttaataa  ttgtctcctt  agtgttttt   98040
ctaggaaaag  gcggaataga  gtattatata  aacaaatact  tgcatttatg  tagacaccaa   98100
aaagtgtttt  taaggcatgg  ccttgataag  gattacacac  acctggcttc  ttgacaagat   98160
aaattcacat  tcctgcctgc  atttagttag  catatatttt  ctaacctttc  agatttgtgt   98220
tgtgtttttt  aaagggtttc  tctaaggaag  atatgtgcag  ctcggcatat  attagtgaca   98280
gtagtcagat  taaagttctt  aactctatgt  gttaaggagc  aaaacgacct  ctcttaaaat   98340
```

```
agaaagcagt ggaaaacaag agggcgattg tttaccagtg gatgtacctt agatgaagtt    98400
aaagcagagt cctagtggat gatatattta atggtgactg tctttaatat aaagttaact    98460
tttgggcagt tgcaattcat ttagtatctc tgggcctgag ttcactctgt tgtgaaataa    98520
aggaataagt aattctcaaa aatatatgct cgatatttct ataatctaaa actgatttgc    98580
taaaagataa ttcatctata tgatttaata tccatctaaa taaaattacc aaattgaagt    98640
atatacattt tggtttgtgt gcattttaaa gaatgctttc tttacctgat tttgttacta    98700
agttatcaat tatttcacct tccaggcaac acactttttg tctccttcac tgtgacatca    98760
ttgtccctat taacaaagaa ataaaataaa gttctgagaa attcagtatc ttcatacatt    98820
caaacatcct acgatgttac catttggtct tgattttaaa taaagggcag tttagttcaa    98880
caatctaatt tttaatcagt aaaccttatt ccaggttaat aggcttcctt ctttgtgagt    98940
ctaatggcac ttaatgaact tcatggattt tatgagggca tcgtttccct ttagaatata    99000
tagactctct ttttctcaca ttttataat gtagcttcca aaagacaaag gcttttagag     99060
gctgtatttg gaattggatt ttgtaactta agttgtagct agaaaagcaa ccatgtaatg    99120
cctaaggact atacaaatat aagccagctt ctaaaataga agactcaagt agctagcaaa    99180
ttctacattg cccttgtctc tggctcactg aatcaagctc aatcatgaag agtttgggag    99240
cttcactcat ttgacaaaag gtgtgggctg taaagcattt acatgctaag gtttgggaag    99300
tctcactgtg tttggtactt tataaactat attgcttgag cagacatcct attctctgtg    99360
gccatcatca cccgtggcat ttttagtggc tttattttt taaagatcct tggctgtaaa     99420
tggtactgtt cccttatttc cctgaattca taataaaagc tcagtggcag catggagtag    99480
gattgtctca gaatcacact tcttttctca ggagtgtttt cttgatgatg tgatcaagat    99540
accccggtg acaacatgga acacatacct acgatatttt actctccata aaggcttact     99600
gctagtgctg atttggtgcg tactggtttt tctggttgag gtaagtatgt ttgtttggaa    99660
attgtcactg tgagtttaaa tttaggataa aaaagctgta tgtattcata tgagcatgta    99720
cacatgtgta tgtgcatgtg tacaacggta gtttcctgta aagttcatcg cttctgaaaa    99780
ccaagaggag ctgacgaggc agctatgtgg ttaagggcac tggttgcttt cccagacaac    99840
ctagccaaat tcccagaccc cacatggtgg tttacagcat ctgtaactga agtctcagga    99900
acctggtact ctttcctggc ctctgtgtgt acaacatgtg tgtagtacac agatgtgtgc    99960
aggcaaaaca ttcatacaca gaaaataag ttaaaacttt ttaaaatcca cagttagaat    100020
tactattgat atttagtac ttcagacata aggaaatatg cataaataca aatgctatat    100080
atgatgaatt gtcataaaat aaaatttatt gggaatattt tttataatca gcatattttg    100140
attcataagt attgtaaaga gattactata acaaaatcaa taacataact atgtcatctc    100200
aagtaacatt ttttgttgtt tttgtgacaa ggggtcctaa aatccacaca tctaacaagt    100260
aaaataatag tttgttattt ataatcctca catcattat tacacctcca tacatttagt     100320
ttttaacaga ttcagaagcc caacctacaa agagtgaata tgagttgaag ttaagtactg    100380
aaaagaattc tagatgtcca tctagatgat ctaatgaggc aggcagtgac tcatgtggta    100440
atgatcctta cttgcctgct gtaccttgt ctcaggcagt gttcatcgag ggaagctttc     100500
acaatgatgt aattacttca ttgtgtgctg acctgctgca caagaatgca gtattagtca    100560
ctctattatt tttcctgttg ccatgataaa gcacctaaaa gttaaggaaa ggagatatat    100620
atgtgctttc tgtttgaggg aacatattcc acagaggctg ggaaggcatg atagcagaag   100680
```

-continued

```
tagcaggttg gtaggtcata ttgcaagcac actttggaag caaatagtga aaaagtgggg   100740
ccaggctgta aacctgaagg cctgctcaag aaccgaagga ttccatagcc ttcctaaaca   100800
gcacagtagc ttgagaccaa gtattcaaac acaggagtct ttagcacatt ttacatccaa   100860
atcatcaaca gtcacctgag gggaaaaaaa agacattttg ggaaaggaag tcagggggaca  100920
ggggcagggt tcatagtgga caaaattcaa tgatgcactt gtcagaaaac aatctaatgg   100980
tgtgcttttc tttcttttcg tcttccttcc ttccttcctt ccttccctcc ttccttcctt   101040
ccttccttcc ttccttcttt tcattttttgt cagtatctta taggcattgt ccagttaaat  101100
agctctcaaa tgctagatta aagaaaagca atgatatgca caattttaca actaaacaac   101160
atatttgcta atgtttatgt tgttttcctt caatcaaaat ttacatagac tttgtttaag   101220
tctaaacttt ttttctttgt gtcagtgcca atgtgtagat ttcttttggc tactggaatg   101280
tttcttggta cattccatca tggaacaggt gccaatccac agtggcagtt tagttttttaa 101340
agcactgttt aagtcctaag tgacaagaaa ttcccaaatg catatcctcc tccattaaag   101400
tgatttagat aattttaagt cttaataagg actgtatttc catttagatt tatgacttta   101460
tagcatctct tctgtgtgtg atcccttttg taataggaaa taaactttgt ggcccacgct   101520
gtcttttctt attccttcac agctacttaa attagtggtg ggggaaataa tatttctcag   101580
tcatgtgtta ttttgaaaaa gtgtatattt tgtattttcc ctcaaaagca atgttgtctc   101640
taagttctta acactgaaca aatagactaa tatttctatt gtgctgctct ttctagtgcc   101700
ccttcttggc agtgtattat ggacaagaga gggaaaatgt aaacactgga ttaatggatg   101760
tttacaataa cctgatggtg tgtagagtgc agcatctcaa gatcctgttt gctccttggt   101820
cttgtggtct ttaagactgt gtcaaaggcc tgctgtgtct gtttgttaat aaggagttgt   101880
tttacatcag taataaaatg gagattatag tgaacttcta taaaactacc tttgctagtc   101940
agtgttagag tccctttagc acatcatctt tattgtgaat gtggatttta gggttatatt   102000
tgtcccacaa aatatgtgaa aatctgcaaa ttatggtgta ttacattcca tgtgatatgg  102060
caccgtgtgt tacctcccca ccttaggaat aaaaatgatt attacttatt ttgttgctgc   102120
ttcagcgtaa tcctccaaga gtaccctttct ttgaaaaatt acatgaactt tatatagtct  102180
tgaatcattt tgaagtgaaa taatagtgtg tattccatta tctctttaat tcccaaatat   102240
ttttcctaaa ggcttcctac caagtatttg aaaaaatttt tatctactgt agtcagtaaa   102300
tatagcttgg attggtcaat ctatgtgata gacaagaaac tactttgtta ggatctaggc   102360
ctccattggt aactacgtat ttctcttatt gcttctattc agagtgtgtt ggcagtgctg   102420
gtgctgctga ttttttctctt cttggatcaa aggagatgta atggagaagt ggctcagaac   102480
atgtgcccca tctagggtct agagtcattt gattagtctg aagattgagg aagacttttc   102540
tataagaata aagacatttt aaaagcttag attattacca ggtttctagt tttgcattaa   102600
cttgagtctt aagacatcag aagttttttct ttcttactga gacagtacac agagactatg   102660
tgtacattga gaaaacatga caattaaaat aataccatta gatcttcatc atagaagtta   102720
ataagataaa ctaaaataaa atatattatt taaacagaca acccttacct ttcctgtatg   102780
attcaataaa tagtgtttgt ggaaaaatga atgtgcaaaa tgagagagtg gaattccata   102840
agcttaatgt gctcttaacc aatagcaatt gctgaagtga cttcagaggt gtaaagccaa   102900
gacactaaga gtgtgtgcac ttcgatgttg gtcatattga atttagaaat gggtgtggaa   102960
ggcttagata aagacgctag aaaaaaaatca actgtggatt gttccattgc aggtggctgc   103020
ttctttatttt gtgttatggt tgcttaaaaa gtgagtatgc cacactttat gtggattgtg   103080
```

```
ttttgtttat atttagaggt tataaactat tttaatatat actatgttca ttacaccctt    103140
ccatattcct gctgattatg aggggagaaa ccatgtttca ataattcttc aatttctgag    103200
gagactgggt cccagaacaa agataccaaa ttctgcactc gtgctccatg tgtaaaactg    103260
ttttttacac atacaataca atagtatttt gcatatagcc taggcatatc accacatata    103320
ctttaaaaca tttctagatt tatatgatgc ccagtataat gtaattttca tgtaagtagt    103380
tatatccttt agagaaatga tgataagaaa aataagtatg tgcgtgttca ctaaagatgc    103440
aattttaaga ataattttct cagtaaactg atggctgaat ccatagatac acaggagata    103500
cataaggttt gctatatttg ttcaagttga aagctgttca gtgcctttat ctcttcattt    103560
ctaaaatata tgttgttttc agttttcatg aaatgcaata aaatatatga agcaacagtt    103620
catatttaat agtttctact aattattttg ttcaaataag aatcaattac atctatttca    103680
attatgagaa accttaacac cttttggcaa tacaaaattt ataaaactaa gggtatagtc    103740
tcttttaaag tcagcatttc atgtttcctt atacttattt ttattagtga ttcacttggc    103800
aagtttggtt gtcaaataat cctttttcttt tgttttacag caaccctgtt aacagtggaa    103860
acaatggtac taaaatttcc aatagctcct atgttgtgat catcaccagt accagtttct    103920
attatatttt ttacatttac gtgggagtgg ctgacacttt gcttgccctg agcctcttca    103980
gaggtttgcc gctggtgcat acgttaatca cagcatcaaa aatttgcac aggaaaatgt    104040
tacactccat tcttcacgcc cctatgtcga ccatcagcaa gctgaaagca ggtacttgtg    104100
actaggtata aagtggagct gcccgcttgc catctgtgtg gctcatcggc ctgcctgcct    104160
tcagtagcag catgagcggg aacacaggca tctgcccctc atccaactac cttgtttggc    104220
atttctaaga tactgcaggc aagcataccc atgctcccca gcatttctgt atcagcctag    104280
tagagtaaat tatcttgtta caatgtgatt tgcgttcagt ggactcactt gaagcaacct    104340
cttttggata acttgacctt ctcacatact tatcttgatg ggaaaaaaaa taactgtttc    104400
ttgtgcctct tcaagagtgg tcatatgaat gcattagatg actttgggg gaggggata    104460
gtttttaatt attatgagac aattatagta catgatcctt gtataatgca tttgacaccg    104520
atttaattac agtcacagaa agtaagataa tttgaaaaat agaaccaaac atttcaaaac    104580
ctatggtaag aagggtcttt gaaaatgtgg tgcattgatt cgcctctgag ttagcttact    104640
ttaaagacca tgaagataat aagcctccta agttctcctt cactggagag cctgctgtgt    104700
gacactaagc cagggaagtc ctggcgcata caaataatta agtatcatt catgtcaggc    104760
atagaaattc aactaaatgt agagaaagct acagtattga gacctttta ctgtaatctg    104820
tctaaaaatc tcaaatgtgc atcagatttt tttaggtgac aaaattaagt gttgatgtat    104880
gaaaaagatt atatttatcc tggagcccctt atgcctcggc aaagggttgc ctcatttgca    104940
tatgatcctg gtcatcctct tttagtctaa gaatcttaaa actaaggaaa tgggcaattc    105000
actctttaag agaggcgttc tctcacattt ctggcagaat tgaacatgga cacgtggaaa    105060
ggacacagac atttgaggct taggcttagt ttggccacac accattggta gtaatggctg    105120
tcagcagcct acgtgaaatg aatattagca tatttctgcc attctttttct gtgaggttgt    105180
tgctctcaaa ggaagtgaac catcctcttt ctcccaaaat ccactcacag cgccctctcc    105240
gccctctctg ttttccctct cagtgatcac catacattct tcttttctca tttgtcttcc    105300
caaaatgtca tctgtgtctc aggttagttc ctaaccactt tatgctgtgt tcctccttat    105360
tcaacctcct ggacctaagc agcaagatga cctcaagaga tttccaatca gcctgcactc    105420
```

```
attatttggt agctgtggta catatagttt gcttttaatt aaaaaaagtt attagattca 105480
tggtttatga ttctcatctg atactgaatt attctgctat actttgcaac aacttggaat 105540
ttcccttgga tgagctcttc agaattgtgc attgaccatg cttttccttg acagtaattt 105600
tctcaggctt ttttttttcct gttactttct cccactttgt catactcaaa ttgcgatcat 105660
acagacacat aataaaggtc ctcagcaaaa tgcggttata atacacagat gctcctggtt 105720
gaaataaaat ttgaaatata aatatcacta tgagtatact attttgccca agcatacttt 105780
cagttttaaa tagttattac aaatgtcatg gaatatacat tatttctctg acttatttat 105840
ggaaggatat ccataatggg tatccatata atatattcat aaaatatcct aaattaatat 105900
gttttctaat gtatcacatg tctgcataag acttttact tttgtctgtg ggtcatataa 105960
aatagacatg gaattatcta tcctattgac ttcaaaaatc tcctatctgg gaaaagagat 106020
aagttatatg tacacacaca agcagctgtg atatacagca cgtatgtagt ctctgcaact 106080
caggcataca gacaaggaca ggaagagatt tttttccaga tgcagtaaat accctactct 106140
cttgcagaca ggctatttga attgaaccag gaaagaggta cagatttgac aagaggagac 106200
agggctttta gatagaaagg aacaacacat aggcaaagta ggaaaaggta gactaaagaa 106260
gacatactta ccagaagcag tgggtttgaa tagcaggatc taggttagtt aaggacaaat 106320
tatgggaaac tattaaatat taaagaattt tggactttaa tccagtaggt aatagtgaac 106380
gagtgataag gttcactatt acattgttgc catagtgttg tgttacactt tatctgttgg 106440
cttagctcct tttttagaag atgaattcct gcactacaag gagaatgact taatcacctc 106500
cctgtagcca gcattaccaa agcatgtagt agacatggaa ttttagttc attgacacaa 106560
caatcaagac tcaaatgggg tgaatctgga atttagaata caggttgaag cttatattcc 106620
cagtgaagaa gatagacaaa ataaaaaagg aagtctggtg tgtactgaga gagacagctg 106680
tgggttttgg atcagcatat ctaaatggca gaaaactcca cagggagggt gtatgtgccc 106740
tgtttggtgg agttgaacat aaaaaattga tgaaagcacc gccattaaga cacccttgaaa 106800
ccgagagcag cagaagtgag gcccaagggg tacgatgacc agacattcct accccttaatt 106860
atagtaagaa cttgattaaa gacactgctt ggagctgagt cgtaggggac tatgtgtttt 106920
ataaaagttc aaaagtagga ggcaataact taaataaata catagaattc tcaacaaagc 106980
taatatttgt aagttcttga atttctgact agatgataat tcttatttta aatgattttg 107040
ctgtgctgtg aatttaggat aaaatatatt ggtgtccttc taaaagtgat taatatttga 107100
gaatatttat ttgtatcaca ggtgggattc ttaacagatt ctccaaagat atagcaattt 107160
tggatgactt tctgcctctt accattttg acttcattca ggtttgtaaa gaataactat 107220
tatcaagttt ttctatttgc cataaagttt tgtgaataat ttcaaaagga agcaagtgaa 107280
tttgttgcta attttccaca tactagttga agtcctggct agtgaataag ttttatgaag 107340
aacagcaatg tttaatagtc ataaatttag tgaattcagt aactagctat gtctatctat 107400
ttcaggcatg ccctggatat gatactatcc tcttgaattg gtttgaaagg tacaaaagac 107460
agttttccgc ccaatcattg accataaaat ttgactcata gaacatttct taagtccaac 107520
actgaaatga aaatgaagtt cctggagagg ctacactcta atccagccat acccatgaac 107580
acttaaacac aaatttagct aagcagtttc cccacaaaag tataacttaa tggaaggatg 107640
aaaaatggat tgttgaaaaa atgtgaagga aagaaaatat ttagagcctc tgaggctctc 107700
ccttagtgac tgctgtgaca gacctccagg gtagccatgc tatggagatg actgaaagtc 107760
acttaataac aaaagaaggc cattgagtgg agaccaaagt gaccatgaaa gcatcacatt 107820
```

```
aggactccaa tgtcaaagga cttacaggag ttgtaagctg atactcttgc ctgttgaatc 107880
aggcagtttt ctgagctccc tgttggcttc ctgaagcttc agagagcaaa tgcacttgga 107940
gaagtagttg taacacaaca tggtccttgt tggaatgaca cagtctcata gcttgtccct 108000
tcccttctct ttaaaatagt actgcatctc tgaaaacttg gaaaaaatgt ggaactattg 108060
cccctgtatg tatacacaca agccacatca gcagatgcag agaaagcagc tgttggttca 108120
cctcctctga aatgattgac ataattaaat acacttactg tactaagtga actgtgtttt 108180
ggatttcctt cattgctgtg tttaaagata taactttacg gtagcagcac ctactggaat 108240
tttttttaacc caagttttga tttatgtact caaaagtgtt agtttatgtg tgtttcttta 108300
gcatgagaca tttgtttccc agtctcagaa aataaaccaa aggtccgtaa taaaagtata 108360
ctaaatacta tatactaata taatataatg caatataata tagtatggtc aaaaactgga 108420
atgtggatat ctatctgaat ctgcctacaa aagtcttaaa aatggtgctt gagtgatata 108480
tatatttatg gtctcctaag tatctcttgt tatttagttt atctcagaaa tctgggagag 108540
ctaattttca aatatttatc ttacaaatta aaggttattt gacatttgtg atggctttca 108600
agtccttttta tgtatcttaa acacttttat ttcaggttct agagctgcta aagcttcatg 108660
aggtagcaaa tctctcagag cttttctttg agctgagatc taccctgccc atttcccttc 108720
aggacaccag ccagaaagcc catggaaact agtggagaat tagcgtatga aagttacact 108780
aagttggttt taaagttagc acatgtttga tgtcatgtgg accatttatt tggtaaactg 108840
tagtgaggtt gcaaacagta ttctaatttt ctggggtgta atacagtaag atgtctgcat 108900
tgcatggcag aattcatttt gatagtgtgg ctagaaaaat acttaatttc aaattaaatc 108960
catctactat aaacctttg agttactgga gtatctccag ttattacagt aggcataggt 109020
gaggtgagat ataaataaca cttattaaat aatactcctt tcaatattac atatgaaaaa 109080
ttagagtcag aaaagtgaac ttgtcaacat gactaaacct aggtttaaaa cagatatttg 109140
taatttaaaa tgttctgtta agaatgtttc attttaaacg actccaacaa aatcacaaaa 109200
gataatattt atactaaaat tattttgaaa ttttaatttt tcaatggaca ggatgaagaa 109260
aatcataatc atttcacatt tacttcttat aaaatttaga gtgtgtgata aataaaaata 109320
tcccaagaac agaaagcacc gtgtaaagct tcagcagctg aactatcaca tcagcaaact 109380
aaacaatttg aacattgttt ctctgcagcc ggcagactgc cttcgagctg caccttatt 109440
catggatgca tgtttcctca ctgagaatag tgcagtctaa aacgtgtgt agacacagct 109500
cagcaatgcc cctgtccact taacaaagtg aaaatgtctc tcactaccat gttctctttg 109560
accccgcagt tggtgttcat tgtgattgga gctataatag tcgtctcggc attacaaccc 109620
tacatcttcc tagcaacggt gccagggcta gtagtcttta ttttactgag ggcctacttc 109680
cttcatacag cacagcagct caaacaactg gaatctgaag gtacagcatg gaatgcattg 109740
caggggttcc tggaagtggg tgaggggac cacatttact aaccactata ctgctttaaa 109800
tctctaatta tataacagtg gtgtgtgtgt gtctgtgtgt gtgtctgtgt gtgtgtctgt 109860
gtctgtgtct gagtagtagt agtagtagta tgtgtgtggg catacttgct cgtgcaggca 109920
tgtgtgggaa ccaaaggcta cctttgtcaa ttgcttctct tctttttttcc cttatcatct 109980
tctttctact tcctccttct ctgttccctc cctccctccc ttccctctcc ctctctcccc 110040
cctccccca ccatccctct tttcttcctt cctcccttc ttccttccct tctctctctc 110100
tcatgagttt ctcacagaac ctggcatttg ctggttcagc tggactggct ggccagggag 110160
```

```
gccccgggac ccatgtgtct tcatctctag cattacagac attcagtaca ggcccaaagt   110220
ttttcatgtg tgcttggaat ctgacctcag gttcttatgt ttgtgtagca gacatattac   110280
cgactgaact ctcccggccc aacaatgaaa cttataaagt acgtgaggat tgactttgtt   110340
aactactatg gctttgtttt ggctttcaaa caagtgtata cccttaccat tgtgtatgca   110400
tagacatgca tacgttctta tactgctcaa agtcaaaacc agcaatgcta ttttcctca    110460
gagtttctcc cagatttcaa gtgagactgg atggaattct tccatttggc ttatcgtctt   110520
caggcctttc cttattggcc tggcttggtt aatctttgct ccatctcctt aggaagcatc   110580
tctttcagaa ggaaccttgg tgtgaggcaa ttattttttt aatattttt attaggtatt    110640
ttcctcattt acacttccaa tgctatccca aaaccccca tacccccca ctcccctacc     110700
cacccactcc cacttcttgg ccctggcgtt ccctgtact gggcatata agtttgcaa      110760
gtccaatggg cctctctttg cagtgatggc agactaggcc atcttttgat acatatgcat   110820
ctagagtcaa gagctccggg gtactggtta gttcataatg ttgtttcacc tatagggttg   110880
cagatcccttt agctccttg ggtacttct ctagctcctc cattgggggc cctgtggtcc    110940
atccaatagc tgactgtgag catccacttc tgtgtttgtt aggccccggc atagtctcac   111000
tagagacagc tatatcaggg tcctatcagc acaatcttgc tagtgtgtgc aatggtgtca   111060
gcatttggaa gctgattatg ggatggatac ctggatatgg cagtctctag atggtcgatc   111120
cttttcatcac agctccaaac tttgtctctg taactccttc catgggtgtt ttgttctcaa  111180
ttctaagaag gggcaaagtg tccacacttt ggtcttcgtt cttcttgagt ttcatgcgtt   111240
tagcaaattg tatcttatat cttggatatc ctaagtttct aagccaatat ccacttatca   111300
gtgagtacat attgtgtgag ttccttttta ttttaagag agtaaactta atgtgtgttt    111360
ctgctttgaa acttaggagc taaatcaatt cacagaaatt ctacactgag agacttagag   111420
attgagtctc aaagacaaa acccattttc tcagcagtta ctaatttagg attagccaag    111480
aatattgact actcttagac aaggaaatgt gagttaacaa ggaaagtggt tctgtccact   111540
acctacctat ctaccatggt cagcaggtaa aagggcaggg ccatgcactt taaaagtaaa   111600
ttccggtttc agtgagaagc ccacaccata gatgcttatc gtgaagttac tctggagttc   111660
atctttgtca gaaacatggt agtatgaaat tctgttctgt attgcaagct gtacattatc   111720
tcctatggga tgatttacag gcaggagtcc aattttcacc caccttgtga caagcttaaa   111780
aggactctgg acacttcgag ccttccgacg ccagacttac tttgaaactc tgttccacaa   111840
agctctgaat ttgcacactg ccaactggtt tatgtatctg gcaaccttgc gctggttcca   111900
aatgagaata gacatgatat ttgtcctctt cttcattgtt gttaccttca tctccatttt   111960
aacaacaggt aatctgaact tattttttg tcagtgatta aaatgccata tgtttatatt    112020
aaaatattta gatgattta agtagacttg tagagcttac aagtaatttc tttgcatttc    112080
tgttgttttg tttctaaata atttatttaa aggtttatat ggtattgtta ctagtttcac   112140
tatttaagaa taatgagaca ctgagtcaga tagcaaatat gtgactaaca agaaaaatgt   112200
ctttttcatg ccaatgttgg aaatctatat ggggaaagaa aaacatattt gtatacacat   112260
gcacacatgt acacacactt atcatttcac acttcctgta aaatttcttc acttaacaac   112320
tacttattgg taaaattctt gtctaatatg aatttgaata ataaaaatt agcatagaag    112380
taaaataact gacataaaag tgcattattt ttcaaatata aatgttctga aatttaggat   112440
cttcaaggaa aaataagtc acaataagaa aaattaaaat ctatacagat aaatgagtat    112500
tttaaggtgc tggatttctg agtcaaaatg ctatgttact tatatataca ccattttatt   112560
```

```
atatataaaa tattgtatat tatttatagc aaaatttcag agcgaatgac acatcaatgc   112620
cagatttgca acattatttg attataagaa cagaattgct caactccaat gaagcagcct   112680
ttgacaagtt atcaaattgt gtcatgcagc ctcagggtgg gtatcacact tgattacctg   112740
aaggaaccag cacaggcact ggagagtcag gcataagtat gactcatgta gatactggtt   112800
tctgttctct tcattctgtg gatgatgcat ttctttctca ctctgtctct ctgtatctct   112860
ctgtctttct ctgtctctct atgtcatatc tatatctata tacacacata tataatatta   112920
tataatatat ttgtatataa taaatgtata ttatgtatat atttcatgta taatacatat   112980
ataatatata cacatataac atatatatat atatatatat atatatatat atatatatat   113040
atatatatat gagagagaga gatctgtgta tgtgtctccc tctctcttcc tccctgccct   113100
ctctcagaat aatagttatc ttcatttaac aggaccataa cacatgagct tcatgtgcca   113160
tcttcattct tcttcttgaa ttaatggtat ggatcctgtg tccaattatt aaatcctaga   113220
gaaggcaaaa aacatattcc ttctggcttt gggcccactg cagattgaca actgctatga   113280
ggatggttaa cttacccata tattgctttc ttcatgcatg gctatgaaat gaatctatat   113340
gtaggtatat ttgtggatac acatatagtc atttttgacac cttaaaataa tttttggaag   113400
gtataatatt gattatttgt atataaggta attcagaggg gatcaaagat gactaaatta   113460
catggattaa gacttcacaa ttaactcaag ccaatgtatc acatgctgta tcagactgta   113520
tattatgact aagtcctggg ttactaaggc cagtactcaa aatcttcact agtcaacaca   113580
gtagaacctc caactgtgat gagcagcaca gcccaggaac ccagccataa ccaaccaact   113640
ctattggtct taatttttatt gatgatatta acttacatta atttacagcc attaattaac   113700
ttccctaatt ccctaatcgt gtgggcagat gcacactaat aacactttca taatattgtg   113760
tgatattttg tgtaatacag tgtagtcttg tttgtaataa atggccagtg attattaaat   113820
aatactactt ggtattaaaa tattacccta cttttttta accctcagaa taagaaatgt   113880
ataagggacc tatataaaat gaactattaa caattttcaa tatattattt gatattaaca   113940
cagcataaca tgtgttatct atggtgtacc taagaaggag aaaatgtcaa catgaaattt   114000
ttcagctatt aataggatga cttgttcatc ttgatgttta actttatagt aatttaatgg   114060
tagattaagc attatcattt gggatatgat atcctaactt taaaataatt tatgaacact   114120
tatcttaaaa atatttgtag tcataatcct catttttaa aattttaatt agttgccctt   114180
tctaatccta aatgaaattt actctaaaat aacatattaa cactgttctt ttcaagcaga   114240
ttgggcattt ttcttcttgc ttttaatgta atgtgcaaac ttctccctta aatggctggc   114300
attagttttc tgactgcctg gtgacaagtg aagactcctt tcttagaaac agcttttgat   114360
gagcagagac catgacccttt acagaggtgc tcagcacatg tgctagtgct actcggatgg   114420
atgtggccct cctttgagtt ctgtacagga tctcatttcc tatttatttt tatctatcta   114480
tctacctatc tatctatcta tctatctatc tatctatcta tctatctatc tattcactca   114540
tttatggtgt ggtattcaat cagtatttgt ttatattgtt acatacagag taagagtaga   114600
caattactca ctaccaacat taccttcaag acctaagcat catttaaaag tgcagcagtt   114660
cccaatattc agtcactatt tgattttaaa ttctggatga aagcttactc aatgaaggca   114720
ttattgttca aaggagtcac taaaactgca ttaaattgaa acataaattt attggcaagc   114780
gatgagagag agatgaatac aataattcac agaagagaga aataacatat actttgttca   114840 aaacccttttt ccatgtctag gtgaaggaga aggaacagct ggtattattc taactttagc   114900
```

```
tatgaatatc atgagtactt tgcagtgggc tgtgaactca agcattgata cagatagctt   114960
ggtaagttac tattttaat  tttatgaaaa gttgagagaa caaaacaaaa agagtaggca   115020
ctaacatatg aaatatatat atatatatta ctcagtttaa gaaataaaat attcaggtta   115080
ctttaaggac attctgtatt ccacattaag ctgtggcatg atttatcttt cgtcctcatg   115140
gattatcatt attatgtgtc tttgccctgg agttttccaa agcaaatctt agaagtggaa   115200
gacattgctg aggttagaat ctccccaaac ttggcttcac taacgccaaa ttactccagt   115260
ctgttgtgcc actatatact tccagcaaga gagcatgtga atgtttccag cagtatttct   115320
tattcaggct tttacaattt tgccagcttg atgaatgtga agtaactact aaaatttctg   115380
gataacttag taagtctcta ttgttgacca cttggatttt tattgttgtt tatttctgtt   115440
aaatgcttgt ttctgttatt tgcaacctga tgaggtttga tgtgcttgtt tgttttttcct  115500 tatgttatag gtgttcttaa gtcctggatc agtcatcagt tctatacatt tcaatggccc   115560
ttgagccagt ggcttactc  acagtatacc ttaatgaatg gaaacattga atttgataga   115620
gagtagttta ttttccttta cctttatggc ttgtgcattt ggtgtcttgt ttatgaaatc   115680
cttctgtata ttaggtttcc acattcaaca gcctgacatt tttcataatc ctcttgtctt   115740
attttgaaaa tgtctggtca tagtgtttgt cattgctctg ttcctttgtg cttaacggat   115800
gctgtcttgc atttgaggac tttgtgtgtt caaagaccat atttggtgta ttcttccata   115860
gagtgagagc ctgaagtgat atttgtgtgc taaaatgata caaggacta  ctaattcaca   115920 agggccaggg caagaaatga aaagaggttc cataaacttc cctatttata ttttaataaa   115980
agccatatta tcagttagac tttagaattg gcctgagaat gtcataactg atttcttttt   116040
acatatttga ttacagttat ttgtgtcagt aaggaatgtc cataccacag catgagtgtg   116100
gagggttcaa agggaaactg gtggggctca cctccctctt ttcaccatgt gggtcctagg   116160
ggctgaactc aagtcatcgg gcttagcagc agttgccatc acatgctgat ctgtcattgc   116220
ggacctgtca ctgaagctta aggctttgga catacattca tccattcctt atgtcatttc   116280
taagaggtct agaatccata caactccctt tacttccatt tcagacacc  cattcatgtg   116340 attgcaaaat ttctatagtt ataatatata aatacataca gtatattttt ttcataaata   116400
tgtcacaagg gaaaaaccta aaatctttta aagcctcttc ttgtttgttc attttcatca   116460
ttccatgagg cagcttagta attccttgaa atacagtttt cttaggtttt atttagttag   116520
accagtccct agtctcttct ccacacttct tggttttgtg ttggaattag ctgaagaaga   116580
ttatataaat gctgtttcta tttacttaaa tttttaaaac tatgacttca taattcaaaa   116640
cccttgtgca cattatatat ttctttacat aaaaattctc ttcttgtaca tgtacaattc   116700
cctttgcaac cttaattttc tggcttaatc acatagccaa acttttgaca ttgcaacaca   116760
atgttgtcac ctacagagtt cacactcaag atatgtacag ttaagctcct aaacttagtc   116820
acacacattc aacctaagat tttcagtaag tagtaagttt tgatttgtg  ttgggcttct   116880 ttcatagctc tgtttgtgca gctggatgtg gcctgtgaac tgtggattgg acagtcctgt   116940
tagaatagcc tttgcacagg ctgacaaaac cgttgctaaa tacatttcta cttcatgtat   117000
ctagtgtcca tgaaagacac ttaaagtatt tctccaggtt ttcccatggc tatgctagac   117060
tttgttgtct gacattgtat ctttcatggt gtgtgaaagg accctttaca gacctattgt   117120
gtttgtgaca tggtctatga aatgtatcaa tatttgcagt tgattacgtt tcaaaagta    117180 atgctctttt gtttaatatc aaagagcgta tgttagtttg catctctttg ccaagcaatg   117240
ctggcgggcc ttcctgggtg ttggtggtcc cttcctgcta ttacctccca tcgtgctggt   117300
```

-continued

```
ctcacctgca ctgctgcgaa aactacccgg tagtgctctt cttcccacct cttgcttggg 117360
aatctgaagg gagaatgtct gatcagtggc cagtagtgct cttctttcca cctcttcctt 117420
gggaatctga agggagaatg tctggtcagt gctttcagat ttcacaccca cctgatgtaa 117480
ccccaaggtt ttacaacact aagcaaaaac tcagtgtgat gtaattttat cttactgtgc 117540
tttaaactgc atcaagagtg atctgagttt aaaatggaac aaatacaatg ttttctttac 117600
tatattataa agctaagtac aaggctattc aggaaaaact tcagagttgg aataattact 117660
tcatttccca tctgtcccaa tttaaaaatt aatacagtca atttgactat gaagttatga 117720
atatagcagt ataactttgt ttttattttc tacctgttac atacccacat atctctagct 117780
ttctttatct ctcagctatt aaatccaata tcacaacaac acaagttatg ttgtgtttat 117840
tatcacatat ctggaatgct gatactcaga actatccagc aacctttca ttatgttttc 117900
ataataaaat ttactcccaa gctctttcct ttatttctac atcctttag acattataat 117960
aattctattc tttaaactct tagccaaaga ccttttctata tatctcacag aaatacatac 118020
atataaccag aaataattcc cttacatctc tctactatct ctttctcttt tgtcttttta 118080
aaatttttt aattaattt ttacactcca tattccattc cccaccccc catccactct 118140
cccactgctc cacatcacac acttcctccc cactccccca tccccactc ctccaccccc 118200
acctgatctc taaactccct ggggcctcca gtctcttaag ggttaggtgc atcatctctg 118260
aatgaacaca gatctggaag tcctctgctg tatgtgtgtt gggtgcctca tatcagctgg 118320
tgtatgctgc ctgtttggtg gtccagtgtt tgagagatct caaggttaat tgagactgct 118380
gctcctccta caggatcacc cttctcagct tctttcagcc ttccctaatt caacaacagg 118440
ggtcagctgc ttccattggt tgaatgcaaa tatctgcatc tctttcagct gcttgttggg 118500
tctttcagag ggcagtcatg atagatccct ttttgtgagc actccatggc ctcagtaata 118560
gtgtcaggaa tgccttttga gctggatccc actttgggcc tgttgctgga ccttcttttc 118620
ctcaggtttc ctctccattc caatccctgc aattctttca gacaggaaca attatgggtc 118680
agagatgtga ctgtgggatg acaaccccat ccctcacttg atgtcctgtc ttactgctgg 118740
agctgagggc cagcaggaag agtggaaaca gggcaacctc aggaaatagg aggttggggg 118800
gggggggacg acgaccctcc agaatgcacc agaggcctgg gaggtaagag actctcagga 118860
atcaaaggga gggaccttag atgaaatgcc caacagtagg gagagggaac ttatagagct 118920
ctttcttaat gtagcatact actagaaaat cttgcagtag acatgacatc ttagagtatg 118980
agtacaggtt tattgaatct ctagtcatat gtactctctt tacccatgtc cttgcttcta 119040
tctagaggca agtcctgtgt agttgcctgc cctttatgag acttttcacc agtgaatact 119100
ttcatttggt ctccagtttc tgccctaatt atttgacctg tttacagcaa aacttctaaa 119160
gagattgcct ttctctgtta tatcttctgt tctttacaca gtttcttcca tattcatcac 119220
ccatgtgagt cacaataaac atcatgtaca aagcaatgtc cttgtcttct gaagttgttg 119280
agcactattt cacatggatg aatccttata ctatttcatt tttctgctac ctcctgggcc 119340
ttcatctcat gtatccttta aatcatcatt tgtattactt cttctttcca catgcattct 119400
ctatagctat tggtatctaa ccccatggtt caaaagttgt tctcttgatga attatagatt 119460
catatattta gtgtacatct ctctattcct ctctatacat gtccagctac catcttgata 119520
cctccatgaa tctataaaat attctgctag attgttttct agtagatttg acatgcaagc 119580
atatgagttc ctgtacatca cctcagagtg cacatatgat cttaagtggc catcgaaatg 119640
```

-continued

```
atacaaagtt tatactccct gaaaggccaa ataaataaat gagagccaac aaaggtataa 119700
aaggtgatat tttaaacttg gcagtattaa accatctggt gtctaagagg ttgctcacac 119760
ataatttctt catttgataa ctcatatcct tccagaactt tctaccacag aaggaacaga 119820
aagtgagcag tcttaatatg tgaatgccat tgccttcgtt tttcaagaag accagcaaat 119880
aagcatccct gtttccacta gattattgaa ctgaactgta tgtccctagt aaaagaagg  119940
aagttgcaaa gttaagaaca atgagcttat aagacttcca tttagatcac tattagtgaa 120000
gttccagaaa gttcttgcat ggttggtgca atctgagaag agttttctgt cagcacaaag 120060
tcactctgtg tctcctttgt gctctcatca cctgtgttta ttttgggttc cactgaggat 120120
caggtgacta attgtagaat gagcaacatg aaatgtggga ggacaaaaaa gaatttctcc 120180
ttccttcatg actgccgtca ccaaatgtcc ttgtattgaa agcagttcct gttgtaccaa 120240
tctgacggat gagttaattc atcctctttg tcttttgcct cctttaatg gtagcttgat  120300
tgtggtttgt tgttgttctt acaagtcttt gtggtgtatt tttcaagaca ttatgcattc 120360
aaccgcaaag agccttgcat ttcttctgg ctcagacact aaaaagttga gtgcctttag   120420
acaagtcatt tttcctcatt tccaaggcct tatttcctc ctctgtaaaa ttaaatggtt   120480
tggttaggaa tttttcagat tgctggcatg tttgacattc tctctctgct gaacccttcc 120540
atataaaaat ataaactctt aacctacatg tagatattat ttcagttctt aggaaatcca 120600
cacaccaacc ctatcctgaa tgctgacatt cattgaatac tagcctgtag ttactacagc 120660
tgactcagta tgttactaca gccaacaaag aaaaagtaac taatagaatg atattttga  120720
accttgaatt aagacaagaa atttaacagc cccctcagga attgctggag tgtacaaaat 120780
tgtgtgataa acttggaaaa ttgactaggg ctttggtcct gccactttat cttcctggtt 120840
taggttttgt cctatgtaca atgaaaggat ggattagatc atgggctctc tcagtctggc 120900
tacagatgaa taaagctgct ttttcaggtt cacagaggcc agggaaatta gttcttctgc 120960
tggggcaagt atcagggcct gttttctgta ttttgaaatg tgcccaggtg attctaatgt 121020
gtatggaggc ctttaaatca ctggattaag tggtcctgca gattcctttt tgctttgaat 121080
gtctgtgagt cacgttacaa ggattagcaa attttttcta ttaaggttga atgaaaata  121140
gtttcagctt tgtaagctta tgggctcatg acagcaactc aactcaacct tgtatgaca  121200
aagcagccat agacgttcat gagtggtgtg tgtgtttcat ttcactttgg caattattat 121260
tttcagttta tttgaatttt gagtggtttg ggtttgagag atagggagaa aatatgaaat 121320
tgagaggata gagagatagt aagtagaatc tggaagaaac tgggggaaga ggaaagaata 121380
tagtcaaaat acgtaaaaaa aatataaatg aacctaaaat aacaaatcaa aatatcctat 121440
caagaattca gtattttcct ctaagcatct atattttgaa atattctaac ttctccaaag 121500
cattctgtca gtcagcttca ttttctgtat gtaacatgaa tacttaggta agcatcattg 121560
acagcacaaa acatggtttg ctagtggtcc ttccatttac tagtaactat accctgtagg 121620
ctaagcatga gtagaaatat ggccactatg tcatattcct ccactccatc tgcttatata 121680
ttgtattcac caactaatgc tatgcaagag gcctggtttg gtctgtggta catacaccag 121740
tgacactcca ttgaaaggat tgattttct ctttcccagc aaatatcaat tgcaaatagt  121800
ttattagtta agggtgagac atgtccaatt ccccttccc  ttctcagccc tgagagtttt 121860
gtctgctttg aacatgtggc aaccttgtga atgctatcac tgtctctgtg agttcacttg 121920
tgtacaatcc tgttgtatct ggatgacact atttccttga aatcatctac caccacttgc 121980
tatctccct tcctataaat ctctcagttt tgagaggagt ggttctctca ttctctgcac   122040
```

```
attgtccagt catggattgt tttgttcatt agtttctgct gtaaggaaag gcttctctga 122100
tggtggctga gtgaggcact aatctatggg tacaacatta ggtcattaag agacatgttc 122160
ctgttatatt ctttaggctg aataatagaa gtaggctttc ccctacagcc catgacctac 122220
ctaataaggt ttttgcccac tttagatgtg tcaagtatcc tatctcatgg aataggtctt 122280
aactccaatt atctaattgt tggttagtct ataatacttg tgcctctatt gcacttctat 122340
tatagtttct ggatttgtag ctagatgata ttaatgattt gtaattactt tatgtgtgtg 122400
gggggtttgc ctgcatctga tcaccatatg tatatctgat gtccatggag acaggagac 122460 agtgttagat cctctggaac tggagttata gacagttgtt agctacttta tgaatgttga 122520
gaaccaaaac caagtcccct agaagaatag cctgtgctct taaccactga actatctctc 122580
aatcctcccc cataatgaca tttttgtctg ggattgatga acattttggg catgggaaac 122640
aatgtcacta ttgccatgac tttggagtgc ttggtcattc attgaagcat aattttgtta 122700
ttctgccttc taaagaacta agtaaaatta gcaaatattt ttatgagaca tttctggatt 122760
cctgaaaatg ctgtaatgac ttctgtgatt agctagaaaa gatgaacagg aaaatttaga 122820
gtcgttttca tgataaccga gttgcctcct ttataaatta acattgaaag gaagctattg 122880
aactacattt tgttcttgcc atcatcattg tcatcttggt gcttagatta gtacatttag 122940
gcattactgt aaggataata acagttttaa ggattacctc ttcctcaata tatttagggg 123000
aaggctttgg ctcttaatac aattaatgta ccagaaatta caagcacacg aatcgcaagc 123060
aaacatttca ctttatcttg gctacattcc aatttgaaag aataagaacc tatgctatgt 123120
taagttttct tgtccataaa taaaaaacag attcagtgtt ttagcacctg gctcacctgg 123180 ctctccttt gtcctttgcc tttaaagtat gagaacatgg tgttaattcc ttacctgact 123240
tcattgtaat ttaactctag ccacacagag attttttccta tccatggggc tgactaacct 123300
tcctgggtag ggctgcccat actccttcct tcctaaatct tctaagcaca gcagacagca 123360
gcttgagact ggggagtatg tcagtctaca gctataatga taattaccaa tgctgagtga 123420
ctgtctagcg ctaagacacc aaggttttta catacccatgt ggaaatatat agtagacaat 123480
cctttaagaa aggattaagt gagttttgca agttttatga aaacagatag gggtaatctc 123540
tgcaggggta atctctgctg tagtatgtgg aagaataacc tgtcatatgt gctttcctga 123600
tggagagatg cttccaaggt gccgcccacc ctttgagggt ctccaggtt gtgatgggca 123660 gctcctatga tgaacacact atgctcaagg ctgacccggt ggtgtttctt aacactctca 123720
cctgctttaa ggatcaatta aagtggcaga gaaagttcat tgaggaaatt tgagaactct 123780
gtgccatttg cagcaagaaa aacaatttga agcaagaagt ttaaggtcca cagctcagag 123840
caacccaact ccaggtctct gagccccacc cccacccca gcgctagcag gaagtggaat 123900
ttgatgtgca gccagcctat gatgtcctta tgaaatgaga aactacaaga actttgactc 123960
caatagctac aacaaaatct atacccaact catccatgag tgcatcacgc taaagaagaa 124020
ggatgaattc ttgatctgct tcacagacat ccatcaaaac ttcctgaggt atcgtgcacc 124080
caggctatgg actctcctct gtctggtcaa gcactggtat caactgtgta aggagaagct 124140
gagggagcca ctgtccccac agtatcccct ggagctgctc acagtctatg cctgggaatg 124200
caggctccaa gacagctctg gactacatac agcccagtgc ttctgaactg tcttagaact 124260
gatcactaac tatccatgtc tttgaatcta ctggacatgg tgttatgatt ttaaacatga 124320
gatctctgac tacttgcgca gagagatcca aaacgacagg cctctgatcc tggatccagc 124380
```

```
agactcaaca aggaatgtgg ctgggtcaga cttacaggcc tggcaccttc tggcaagaaa   124440
ggctctgatc tggatgcgtt cgagactttc tttatgaact gtgatgtgtc ctttgtgaat   124500
ggctgggaag tgccaccaga gagaaagaaa tgtgtcttcc agtgagtact gcagtacttg   124560
cccaggaggc tccagagtca gggcatgcac tcactcctct gctgcaagac cttgatctag   124620
agaggacagg aaggtgctca aggcttcagt gaggggcatc cagcctgtga tcagactcca   124680
ggcttctgat tcctgcctgc ccatggacag ccttcctcac agcctgattc atctgccttg   124740
tcctccaaca gtgttctctg ggagtaagac tctgaaggaa agagaagaac tcaagcttga   124800
cttccatcta tctacccatt gggaggttct acctcccca aaatttctga tcatcagcaa   124860
taaaccacag gaagccatga gtgggtgtgt gtactctgag ggatgtatcc tcatcccaca   124920
aagaaactgt tcagcattgc acgtagccct ggagccctgg agccctgag ccctggagcc   124980 ctggagccct ggagccctgg agccctggag ccctggagcc ctggagccct ggagccctgg   125040
agccctggag ccctggagcc ctggaaattt gacaagtgtt catcaagctg cactatttct   125100
tcaacatgca ggctggggtt acagcagtgc aggaaaataa aattgcaagc actttaaaat   125160
gtatgacttt aaaacttagg tgggtgtgtt aggatgagac ctgaagcact gatttaaagc   125220
aaaatgcatt gaaaaaaaag aataaatggg ataataagtt cagagttact tggggaacca   125280
gccctgccta tggcctaggc atttattaat aatattaagc ctctccgttt ttattcaggt   125340
actggcacat gggtgaaaaa gcccatggct atataaaact agtgttctat gttataacct   125400
ctgactaatc cagttagcaa tatacagttt tagactaaga aaatgagata taaattccca   125460
gtcttgaaga catacccttat catcctcaca gcattgccat tatcactgca tagtagagaa   125520
aacaatggct ttattagtta gtgaaaaagg tttacatgtc tttgtatggt taagcactag   125580
atgttctgaa gattccgttc ttcgagtaca agaaatactg tggacattta caatagtgag   125640
taggatcatc accaggggac ataatcttca ggtcttgact tggatcgacc tttccacagg   125700
cccttgagtc agtctggttt ctgtcactgc aacaaaatac ctggtgtaaa ccccatgaag   125760
aaatgaaatg tttctttggg cttacacagt ccccgaagtg tcagtccatg gttacctgcc   125820
ttgacttcag tccttttgctg aggcagaaca tcatggcaac aggaatatgt gttagagaag   125880
gcagcttacc tcatggcagc caggaagtgg ggttagggat ttaggattgg ggacaaactc   125940
tcaggggcca actttcagta gttatccata cctcccaatg tttctactat actctaaaag   126000
ccccatcatc ttggaaccaa gcctttatct tggagtgaca tttacaatcc aacttataac   126060
tactaggttt tagggacaag ggtaggttca agagagatat atgttggatc atcattcagg   126120
cactgagggg gtcattagca tgactagcat ggcagggggt gtctctatcc ttctccattt   126180
aggaatctgc tacctgcaag tcctgttccc gggaaggatg ggctccttat tttctgactt   126240
gatattacct ctatagttaa tttggtatgt acaatttgaa ttctattttt gtaagaagga   126300
cctaccaaat tgcttgagct ttccacaaag ctgagatccg tttttataga ggatatgaaa   126360
ttttgacagg gaaatcaagc gtacaatgaa taggacttca actttcctgt agttagtttt   126420
ttattattgt tgcttttgct gtacggaggg aagaactctg gctaattgag accctcttag   126480
ttttgtagtg gagctgagct ctttcgcagg ctcctttgtg agttctcttt ccatgactca   126540
ccgaagttcc tgtcttgtct acaagaatca tctgggagac ttggtcttgt tctgtcttct   126600 cttttttgcag aaccttcttg gtttcttcca tgcttcttag gatacaggac aggacaccttt   126660 cttgcacctt gcccatattc atgcttcata tcgtgagtcg aggagggtga ctgttctcgg   126720
acatcctaag ttaatcaatg acaaaatttt tttctaaaac tcctaagtct tcagtgttcc   126780
```

```
agacagtgga ttttcatttt tataagcaac agtcttgctt tcttgcccaa gctgacatct  126840
gagcctgaac tcaaatgacc acttcttaga agacatgaat acctacagtt gtatgtctct  126900
ttgggacttg gcctttgaag cataaaagtc attgttcata tgactacaaa atgctgaact  126960
gttactatgt cttgactttt aaaagactgt ttgtgagact tgaaagaatg ctgtggttcg  127020
ggggtgactc ctccttctag aggcaatcaa catgctgaca gcccctggt tcaagaaatt  127080 ggttagtgac tagtctattc cataatggca tttcagtagt tgctacttta tctgactgtc  127140
agaaaacgtc ctcagatatt gaattgaact acactttgct catattgtta taacgagtgt  127200
tggttaggga tattttcacc agggtgagaa tagttagact tgaggttcat tttaagcatt  127260
gatattgtaa gaaacaactt ataaactttt atttttaaca ctcaataagt atgtgctgtc  127320
tagcacatag aatgttaaat gttctggatt tgtctttaat ggtgactatc actgatcaag  127380
ttaggctaca gtgcttcagt caaagaaatg tgtattactt ttcaaatgac caaatccccc  127440
catctctctc tctctctctc tacatataca tatatatgta tatatatata tatatata  127500 tatactccat catatattca tttactaatt gttcaaatag ataatatctg ttgtcatcat  127560
attttaaaat tatcacaaca aagttaatca gattattaaa atcagagtat aaaataaaa  127620 ttaaagcagc attcttttgt tgttgaaaat ttgccaagtt cctgtatttc tgtgtgcact  127680
aaatatgtac tttattaaat gtcatattgg aatatttata aaccagattg ttgcattaac  127740
tttttccaag gaaaggtgaa caaatgtatt ttcactccca accagacact gaagaagggc  127800
aaaagtaaga atttcatcca agtctaactt ggtgaacaat gagtttattg agagtacaat  127860
aagcatggat gacggatcac ttacagactg tgagcgaaca taaaacactt tcacactaca  127920
atgttcaact ctagcatgga tgatgacctt gtggaagctg ctccaacgtg ccctacttcc  127980
tctcttaggg tctcccaaga tcacttcagc tgaaagggaa gagaaacaga aggggactga  128040
tggttggagt cccagaggag ggtcccgaac tctactctcc tcccttctag tatggagcat  128100
cactatagac ctagctgtca gtgaatatta tcctgtctat tttgccacat ggctaccagg  128160
cccaagcata tctccactct aagatgagga agaacaagc cactcttcca caattccatg  128220
gaattgagaa tataaccttt atataaagtc acctttgct aatgatgcaa attgatttca  128280
aagtaatatt tattagaagt gtaaactttt tcactttcta tctgtgcaat aacttaaaca  128340
ttgtggattc actaaaaatt gatatatgcc ttcagttcca gtactcagaa ggtagagaca  128400
gacagatctc tatacattca agggcagcct ggtctacaga atgagttcca gaaaagctag  128460
agctacacac acacaaaaga aaaaccctgt tttgaaaaaa cacccccccc cccaacgaaa  128520
aagaaggaga aaaaagaaa ttgactaagc atcaggtgtc tacaaataac ttagttgaca  128580
tacaggatta tagatgttaa agaaagtgga gaggcagtac tgtctgcagt gctacaatct  128640
tacaacataa tatgtagtac tgtcatagtg gggaaaagag ttctctttga catcatctat  128700
gcccttgaga atactttggt tatttgtgtg tggactgcgt aactgagatt taagcaatca  128760
caaaaataaa caggtctcta cagaacccaa ttatatgtgt cttagttgtt tcgctggcta  128820
aacatttaat tatatctaat tatttcctgt tacttcactg aaaaccctgt caaataacct  128880
agtgacagtt ttcttgcatc ataatttaaa ggttatcttt ttaggcaacg tcaaactaat  128940
tatggccact gtctagagtt ttcaaacaaa caaacatact gttattttca tttcagatgc  129000
gatctgtgag cagagtgttt aagtttattg atatacaaac agaagaaagt atgtacacac  129060
agataattaa agaactacct agagaaggat catctgacgt tttagtcatt aagaatgagc  129120
```

```
atgtgaagaa aagtgatatc tggccctctg gaggcgaaat ggttgtcaaa gaccttactg   129180
tgaaatacat ggatgatgga aatgccgtat tagagaacat ttcttttcca ataagtcctg   129240
gacagagggt gagatttcag cattacttgc tttgttagtg ggtcccaact accagagcaa   129300
tatgttcgta aaaccatttt gtaacataat tatataatca gtatcccctta tacatagttg   129360
aaggtgtgac tgtgcaaagt ttttatgttt catatgaaat ttgaattaca gactctacac   129420
aacaggttat tgtaaatgtg attgtatttg aatgtgacta tacttgcaaa tatgtaagat   129480
tttccaactg cagatgcctt taaatacaca cagacaccaa aaatacaacc atcactatga   129540
acagtagcac caaattggtt gattggcaca gtataaatta atccatccct taattaactt   129600
agatgaaact ttaaacttga gtgattttct tgcaggcaat gggtagttat atcttagttc   129660
tttgggccac tctgtcagtc catgtttctc aagtggtgca tttagaccat gagcatctag   129720
agtggtaggc acacattcag gcattataac ttgttctgct ttttgttcct tgcttttgct   129780
ctttatccct attttttacct tgaatccttt tctttctgtt gctgttcctt agtatttatg   129840
attccaagac tttctcattt cctaacatag cgattctact tttgtggttt ttatgagttt   129900
ctctagaggt cacaatatat attcacaatg aatccaggtc cattttaaaa gaataatgtt   129960
atcacataag aggcatcagc accctgtagt cccaattgct ctctcatgtg tgtcatattc   130020
ttcctatggg tcattttgtg tattcacaga taatatgtgc aaatagatgt tattaaaatg   130080
actttaagta agcttccctg ttagatccag taagagtaag aaaagcattt tagtttctaa   130140
aatgcttcct ttattcattt agcttcaagt ttgcaactcc ttgtagatct gagttgtgtc   130200
ttttctctga gtaagttctc ttaacatatc tttcaagata agcccattga cagcacatag   130260
cttctgtgtt ggtttgataa tttcttactt tgccataagt tttaaaagat aactgcacaa   130320
ggttcacgat cctagtttgg cagagttttg ctttcctct tcttttctac tcgtttcctg    130380
actttgtggt gtccataaag ttataagtca ttcttatctc aaattgtttt gttttgtttt   130440
tttgagacag ggtttctctg tgtagccctg gctatcctgg aactcactct gtagatcggg   130500
ctggcctcaa actcagaaat ccgcctgcct gtgcctccca aatgctggga ttaaaggtgt   130560
gtgccacttt aggggaaatt ttcctgaaca taatgccata acttatgctc tgagatcagg   130620
aatcaacaaa ttggacctta taaaattgca agattctgt aaagcaaggg acactgtcaa    130680
taggacaaaa tggcaaccaa catatttgga aaagatcttt atcaatccta catgatgaaa   130740
ggctaatagt caatatatat aaagaactca ggaaattaga ctttagataa tcaaatagct   130800
gatttaaaat ggtgtaaaga gcttaaaaaa aaagaaaga aagaaggtg tgtgccacga    130860
ctgcctggcc ctcaatattt aataaataat atattttta ctgggctttc ttcaagagga    130920
tttctttaaa aaattttttg tacttttaag atgatatgct gtggtatggg ttttagcttt   130980
taagcaacat tctggttatt tttctctgtg tatggattga gtatatgaca ctaattttg    131040
agggaaccct cttagtaact attatttgaa atatcccct ctatctttct cagcatcctt    131100
ttcttctctt tttctttctt cttcatttct gtcttcttc tctttctggt atctacatta    131160
tatacaagtt acacctttcc taattgtgcc atgattcttg gatatgctgg gggaggggt    131220
tgttgttgt gcagaggcat gttggtgttg gctgctttta gtaacatatc ctcaagctca    131280
gggttctttc ctcacacatg tctaaactat tgttgaactc ctcaaggcat cctccatctt   131340
tgttgtacat ggttttgtt tgtttgctta cctgcttgat tttttttttt ttgctatact    131400
tgtagaagtc ttttgatttt gctttagaat gacgcctttc tgtttactaa ggatccatct   131460
gttactatat gccaattttt tcatgatgaa atccttatca cattagtcat agttgttttg   131520
```

```
cattcccaac gtatgaatta gagtgtcatt gtcacatctg gctttgttct atcctagtat  131580
tgcttattat ttcctctttt ccctttcaac atgtctcatt gttttttctt gagagggaac  131640
atagatgacg tgcttgggaa agggaccgtg ataataggct gttagtaata gactggctat  131700
gctgtgttgg actgtagagt tctgtagctg catagttatg ttagagaaat tacattttcg  131760
gctgtgagct tttaaatggc accagcttag ttactttagg tagtacagac tggttagagt  131820
gagttagcac taaatattac tgtttcctaa agtcagttag tctgggcttt tggaaaaaaa  131880
atctctaagt tacaaatgat aaaatagtct cactcaagat gggccttaaa tgggagaccg  131940
tgctctggcc taacagaatg atcactgtct tgtggggtcc ttgaaagcta gggaaacttc  132000
ctctagtctt cctgtgaggt cactggaggc tgacaggaat tgtttccctc tccatggtcc  132060
acaatgagcc caggtcatct tctcagtgta gtgcttgtac ttgctccctc cagctgtctg  132120
cttgctggtt tctgctggtc tctgtgactg tatctgcttg cctttctctc tggctctagg  132180
ggcagagtca ttcgttctat ggttttacct ttctgacaga aaatgtgttg cttacctttt  132240
tacttaagat ggagtgactt ttcagttagt ggtagcacat acctttaatc ccagcacttg  132300
agattcctgt gaattcaagg ccagcctggt tcacagagta agttccagaa caaccaaggc  132360
tacacaaaag accctgtctt taaaaaacaa aaacaaacaa caacacaacc caaaaagaat  132420
agcaatgttc tctacaaatg aagacatcta aataggtgct ggatttgtta aaagtgcacc  132480
ccattctgcc tttatagaat ctggcgtgag gctgctgact catttaacaa tctgagtggc  132540
ccatgtgtct tattaacaat aaacagatgt gtcgacatat gagaggctca gttataatca  132600
cccatgaatc tgatgtttca tttgattgtc tgtcttggtt tctggggacc acaaggaaac  132660
aagataatta tagtgcactt ccctctgcca ttaaagtgca gagaaggtgc tttaagggga  132720
ctgtgcccca actgcgctac tcttgacaca atggaattcc tgctcctacc tagtttggca  132780
ctgaatagct ctccagattg tagtctgatt tatgttgatc taaattttgc agagctgagg  132840
tgcattgagg ttaataaaaa cgttgactca tacttaggac acatctttaa agcttgtttg  132900
caggaagtac tcttagaaat aagaagataa ttagtatgtg acaattactc aaccagacaa  132960
ccttgttagg gtacaaatca attaagttcc ttgctgttga aaaactggtc agacttaata  133020
catgccagca ctttgatgtg aggaaactag agcaatagac aaagggtttc aagctaaaga  133080
aagtatttat tcattgcctc tcaggccagt attatgccag cataagaact gagttttctg  133140
aaaatgtatt tccttctgga ggaaatgcag tgaactcatt taccccctact aggtccattc  133200 aaggtccttt ctgccaacta tcctgtaatg aacttagcac tcttccatcg gtccactgtc  133260
actttctttt ttcctcctgt acatcacctg cactgaccga ttctgatttc ttatttaact  133320
tatttaacat tgcagtattg gaaaaatcct aacatggtga atgtgtattt gtatggcatg  133380
gtctagcaca gagatgggag catgcagtgt gaaattcctc cagatttta aattaatgct  133440 ttatctagtc attgaacaaa attattgtat tatttattta taaggtacaa taatatgtat  133500
gctcattcat ttgctctcct atctgactgt ctttcagtcc acctcaatat ttcttgagta  133560
cctttttaaa gccaagtaca catgggtcct tttattcctc cattcttcca gccatctcac  133620
tttcccatcc tttcaccctc caatctgact atcagctaat ccaagtattt attatttaag  133680
tacaccatta ttccagatgg agaaactgaa aaaacaatca aaacggataa actatgcaac  133740 cttttgttgaa tttatattct ttatgtaaat acaaagctac aagaaggaga aaataaatca  133800
ttacaaaatt cttcttcata acatttgttt attttcccaa caacaatgat ttatataaat  133860
```

```
taccttgtag agctcttttg agggttagga aggcaattat tcttgtcact gtcctttacc   133920
agcttatcac aaaggcctac attattgcca agtaatttac tcagtaaatt attattattt   133980
ccattggttg tggcccatgc caccattgga gtttataagt tattactagt ctacaatgaa   134040
ataagtatag agtctgtaaa tatttagaaa ttcatttttt aatttattta aagtactgat   134100
ttgcagttca ttaaaaacag atggttttc accaaccaca tatatgtaaa gaacactttt    134160
caaaaagacc attttctcct taagagggtc aaacaatagg aaataaaggg gcagtgtgaa   134220
cagcatgaaa caaatttaag tgttgcatat atactgcagc ttattctgtg atcagttagt   134280
cattgcaagg aactgagctt atatcataac aaagaatgtg agctttgagg ctacctgga    134340
caactgatct ctgtaatggg aagtagcctt aatctgatgc tgtgctcttg cagctgtggt   134400
ctttgcataa tgagaacagt ttaatatcct ttttgcttct tagagtttcc ttcttgccag   134460
aagagtcata tgttagttag catttgattc aaacattgct gagaagctga gtgatcttgg   134520
ctctcgactc aacctgaatt ctgtgagaat gtatacttta ctgaacatgc ctgtatctta   134580
tcatcaggcc tgaacttgac actgctcatt ccttaagggc agaatccatc tgcctcttca   134640
atgccggggc ccaatccctg daccttgtac atgctagaca actgtacatg ctccaccaat   134700
gaggaaataa gtttagtcca gggacagtaa gtagtgttag gcctatttg agtaaacttc    134760
aagtttgtat ccatattcaa aagtacatcg ggcagcaggt ccctgcttct ggtttgagct   134820
gacgtgcatc aagatagact gtttttactc ttccttgact ttaaatggac actttctccc   134880
tttttctcat tagtaaaagt cagtggtcaa tgaagcccac atcaggaata cagttctgta   134940
tggccagttt ctgatttcag ttgcagatta tgatgagttc cagatcagtt ccagatagtg   135000
atgagaattc ggagtgtgta aacaggctta cgtggctcca tgagaagaga acccattcca   135060
ctgctttctg tccaaggagc agtgctgatt ggataatagg tgctatcctt ggtgcaagag   135120
taatgccatc actttctcct tctaggtggg gctcttagga agaactggat caggaaaaag   135180
tactttgctt tcagcatttt tacgaatgtt gaacattaaa ggtgatatag agattgatgg   135240
tgtctcatgg aattcagtga ccttacaaga atggaggaaa gctttcggag tgataacaca   135300
ggtgagcaca aaaatgtaaa aagcaatacg aattaacatt tttatcatta tttgacatac   135360
ttaagaaatt catatcactc tgcaaaatat atttggtggg tcctaccatc tcgtctactg   135420
tgcaagagaa ctgtagcata tggaatgaga gtacctccca atgtctggaa ttctgcgtgg   135480
tgtatatttc ttaaagtgtt ttgatagtgt tctcccaaag cacaatctgt aacagcagcc   135540
tgggtagttc cttgtgcagg cttcctagtc ttgcttaagt acttgatctc cgagggagtg   135600
atagcagcct gtagataaat gctttgcaag atgtggaaga tgcttctgag atcataagct   135660
ctcggaagca ggacatagtg gaattgaaag ttgaagtgca gtgatgtttt cccttttggag  135720
tctgagtagg aagaagtatg tcaggtcaat ctagattctt ataaagggca gtgtttgatt   135780
caggcagtac agcatctcga acatcgccat ttagtgctat tctgtctgtg ttactgcaca   135840
tgctgatttc ttgtgtagag gagaaacggc aatggttgcg ggcaacatga cccaaatgtg   135900
aaccaagaga tgctgaagcc agaagaattg cagtatttct gctgctgttg gcccttttct   135960
ctgagacttt tcctcctttt gtgctactag acactaaatc caacccacta agatggctct   136020
ttgaagcact tctgtatttt taacacaaaa ttaacattcc gggactatca ccaggtagac   136080
caactacaaa gctagaccaa gaaaatgctt gtacttcttg ataaatgatc ttcacagaac   136140
atttgctcct ttcaagtggt gagacaatag atactgtaac caccaaactg atgctttcaa   136200
tttgttttcta tggtgtgcca tttttttcaa atgcttcatc ttggctgaag ttgtggaaac   136260
```

```
actgtgtgtt caaaaacaca aaagggattg tcagatggcc taaagaaaaa gaaacgctag 136320
gagtacaagg ttcctgaggt gagagcacta gtcgagtaaa aatgctaagg ccagtggaag 136380
ggtgtggttg tctgagaagc actgctgttg gacttgccca ggtcctgtgc tgccagttga 136440
actaaagcag ggtaggcttt gccttggttg ctcttgttcg aacacattgg cctacaagaa 136500
gcgtcaacct ctaaaacttc tatcctcttg ctcatcatcg tagctgctac acaatagaag 136560
ggctccgtct tcctcactag ctctgcttag gagcttactt atgccaggca cagagtacac 136620
tgcagtgggc cagagctgga aaatctcccc tgcctttctg cctaaatgac tcttcagact 136680
tgactcaatt catgtctgct cttttatgga ttcaaggctt acatttaaaa aaaaaaaaa 136740 gaaaaagga aaaaaaaag tgtgttcagg gcatccttca gaaatactga agggtctctg 136800
gaacatcagc cagcatggtt aacatgtctc agtgacaatt tttgaatgtc atgtgaaacc 136860
taaggaagga aggagagaga gagagagaga gagagagaga gagagagaga gagagagaga 136920
gagagagaga gcaaaccaag tccttatatg cttgatgtct aaactacggg ttactttgct 136980
tttcctatct tttcttggaa cgtgaggatt gcagcatgct tctccttttcc ttagaaagat 137040 aaaagaagga gaaagtgaa tatccacaga aaactaacta gtttggtctg ctttttcatc 137100
ttttcttttc tcctctgtct cctttaacaa ggatgtactt cagaaggtcc cacactgagc 137160
tagtgtaatg ttaaaggttc actggccact ggttctcaga tacatgaaac aggtattttg 137220
aaaagtaccc tcttatacag agatccaaaa gcatttgctg ggcagtcaca aaggtcctg 137280 ttggtttgga cggttcttaa caattttttc cctccttta tagtttagta actacatagc 137340
aatctcagaa tacgtgcagc ccagaattca gactatcatg tgcattccaa aacagagcct 137400
ctttcatttg ttctgagtca agcagagcag gcagtgaagc cgatagatgg catctgattt 137460
actttggcaa ttagagcacc aagaagaaag cacccactaa tgctgcgcct ggctaggcag 137520
ataattaata aaaagcaact attttaaagc ttcagttaca attttggaag gctgtaagtt 137580
cttctgagta aaggactaga agttttttcct tttgttgatt actattgtat gtggtatgtg 137640
tctgagagga ggggagaatg ggtggggtat tcatcacgtc atggctcact tggagaggtc 137700
agcacacaac tttcaggaac aagttctccc cttccagcat ggcatttaga cactggattc 137760
aggtcatcag ggctgtgtgg caagcgtgag ttatccactg agccatctca ctggctcctt 137820
ttcttaatga attgaaaata ctcaccatcc acccatcatt ctcaccacag acagaggtga 137880
ggcatctttt gttttgaaag agatcagaca gcatgtatag atataaacag tgaaattggt 137940
ggtgacagct taaaattcac tatataaaat aattacatct tgtgcttaca attataatat 138000
cacagtcatt ttatttatat caaatgtaga gatactactt gccattaata tgccagagaa 138060
gttccagtcc aacctgtaaa cttctaatga gaaactcaaa acgatgttca tagtcgtgtg 138120
acagaaatta aaaacagaaa cagtaaagcc aaagtgagtg gctgagagtt agtaatgaaa 138180
ccatagctgc ctgtaagctg tgggctaaca agggagtata taggcagaga gaactgtcca 138240
gattaagcta gctgtcactc ctgccagtac atctgtgtct ttcctgtcct gctgttttgt 138300
ctcccttctt ttcttgtttt ctctctgatt gcagaaaaca tgtaactgtt tactggttag 138360
acattatgaa ttgaggggtt ttcttttcttt gtttgttttg ggggtatttt tttaacacaa 138420
atactttgct tgactgccca aacccagatg ggatctcaaa ccttgcttat gtatttctgc 138480
gtgtagttct aatatgtctc attttcaaat tatccacata tctcccttaa ttatgcaaga 138540
tttaaacaga gtgaccagaa aatggaagca gagttataaa aagaaggata gaaatacata 138600
```

```
gtaaaatact tttcttctga gttttctccg ttgtaagaca tctaacataa caccttggat    138660
gagaagaatt caaaagacag tgttctatgc tgaatcatta aatgttgctg tctctcacat    138720
gtgtggttct ttcagcattt ggaccctaat ctgtataatc ttaggacagc tatataattt    138780
ctctgtcata gtttccttgt ttgtaaaatg agtatagtaa taataacaat tatttgtact    138840
ttgggggaaa ttgaacgaga aatacttaaa cttttacttc ccacatggct tgataattat    138900
cctctgttat ggtagttatt attttaatt cagtgggggt ggggagtcat gtctcctctg     138960
tctttctact ggactggggg tatgttcat gaataagtat gaataagtat gaataaatga     139020
gcttgcacaa tttcacaaag aaagttgtaa tgaatacatg ccatagagtg tcataaagtt    139080
tataggttta gaatgattgg gtacatggag ttctaggcag gaagactgtg aacaatcaaa    139140
aggataggtc agtgtgaagg gaaagggaga agggtcagag ggaaccacag cttagagggt    139200
attagacgtc atggcatggt ccagtaggaa ggggctaatt ctcctgggct gaggaaggga    139260
atggagaacg tttggtggca cattgctata tacatgatga actagcaaat gattatactg    139320
tgatgtggtt aattagaact tactgaggta gacagttgga cagagtgtag aattcaaggg    139380
agggcagaaa aataactgtc atgtccaatt ttcaaattag tataacacaa tttagctatt    139440
tcagagacta aactttgaaa cctttgatta tatgcttttgg ttagaaaaca tttttatgta    139500 tcttggaaa tgtttatact aaaactttgt agtataaaaa ctgttaggaa gctgggcagt      139560
ggcagcgcat gcctcggcag aggcagtcag atctctgaat tcgaggccag cctggtttac    139620
agagtgagtt ctaggacagc cagggctgca catagaaacc ttgtctcaaa aaaaaaaaa     139680 aacaacaaag aaaaaacaac ctgtaatgaa gcactctgga tttctagaaa actaaacttt    139740
aactatcctg tatgcagtct tttatattta aatcaatagc atatacactg gtagtatagc    139800
aatctatatt tgttacaaac tgttaatagt tcttagtaga aatatgtcat tcataatttt    139860
atagttgggc cacatttcaa gggaactatt catgatgtac acatacatac ataagcaggg    139920
gtagtcattt ctcctattaa tctattttat attaagtgca atcaccacat aagctggatt    139980 acttttttt catttgacat ctagtactat aaagcatatt agctgttgca acgatatatg     140040
gtcagctgtg ggaagtccat gtaggcttag ccacttccac agagttgagg agtggaggca    140100
gcagctgcag ggaggagatg ggacatgtgg ggaacaatga tgatctcttt gttctgctta    140160
gagtctcaag aactgctcat tatagcatac atgacattaa ataaatatca aatatttgct    140220
tgccctaact gacttattag tgagtagttt ctttttaaggg cgacagggga tccctgggat    140280
gtgacagctt caggtgcatt ttttaattgg tgcacagcag atctgagagt gccatgctgg    140340
ccaaatcatt ccacttctca gggccttcat tttgaatatg taaaccagag agagagggtt    140400
taggttgacc tccaaagacc tttaggttag acagaggagt ttgaggatga ttaaacagct    140460
taggaaacaa gtaagacctc tgctggcacc gtgaaggcaa gggactgcca gattctcttt    140520
gaattaaagg aatggaatgt ctgattgatg gtatacaatt gaattctagc tgaaccggtt    140580
tctttagttg atttttcttt aaaattggat atgttgtcca ttaccttta ccagacatga     140640 aattatgaag gaaagcctgc aagatttctg agttgtgata aatctaccac acctacagct    140700
tctagattcc tgcagcttc tttccttcat aattttgaat gtgtatctgc ttaaaataaa     140760
ttagttaaaa catcataaat ttagtaaact agtatacatt atagatttta tgactaaaag    140820
ttaaataatt tctgaagcac ccgtaggaat cttcacaggt gtattgggtt gttagtgtta    140880
cacttaaaga actgtgatag ctgtgagcat ttgggtcaca tttagagatc tctctctgtc    140940
tctgtctctc tctgtctctc tgtctctcac acacacacac acacacacac acggagaggg    141000
```

```
ggagggagga gagaaaaaga ggaggagggg agggaaggat gagagagaga actttattag  141060
ccagaaaaat agccttatag aagttaactt tcaaatctga ggaaaaacag catttactct  141120
gattgttatt attttctact tttacttctt cacgtctgct cactcatttg ggacttttgc  141180
tgagcttatt caaaatttgc atctaaaaaa gaaagtaaag acatggcctt cgacactcat  141240
agatatccac ggacttagta attttctttg atacacacta ccgagattgg gctccatctt  141300
catatgtaac aaagaataac tctgaaactc taatcctctt ttttctattt cctgtgtgtt  141360
ggaattaagg gcacatacta cagtgccaag tttatatgct tctgggataa gacccaaggc  141420
ctcttgcaaa ttaagtaagc attttttgcc aactgagcca catccccacc aactaaactt  141480
ggtgttattt aaggaatgaa agtataagaa ataattgggg agcttgtttg gtctgaggat  141540
aaggaacagt gcccctagga aatgaagctt gatttgaaac ctgaaggata tagattgttg  141600
tgtgaagatc agggaggata agatttccag ctgagaagaa aacttaggtg actaagctaa  141660
gaaagtgtgt gcttagaata gaatggagtg gaaaggagcc ctgagatctt gggaccatcg  141720
taaggatatt gtacccttag tgaaggggaa agtcattgac attttcatg aattacttgg  141780 gtatattgta agagaagcaa aagtataaag aagaagatca atttaggaag ctcctgcagt  141840
gacacaaaaa ggactagtga tagtttggca tgttcagtgg gaacagaaat tgagaaagaa  141900
attgatttga catatagttt gaggataata taaatgacca atgactcatt tttaagataa  141960
gctgaggaat aagatgaatt atgagtgact ctcagttcct gatgtgcact gagatggaga  142020
tgcagaaagg acaaaagtag ggtggcattt ctctgcttta caaagcatgg ggatgaaaga  142080
gactgggttc ctatgagcaa ctgtctgttt taaagataaa acatcttgtc cattcctttc  142140
attcttccgg gataatgaaa ttattctgtt tgtcccaagt aaatatttct attgtatatt  142200
tcaactaaat atataactct ttcaaagtta cagagatgca accaaaacaa taagaggaaa  142260
gaaaattatt ttagacattg acatcaaaaa ttttttgcca gtcttgtata tataaagagt  142320
actaaatatt attttaaaa tattattacc tgagatctct taagacagtg gttttctctt  142380
aagcacatgg tccacctaag tggaagtgtt actgcaagtg gagcatcttg acaatggtca  142440
tacagtgcta tttgcacacc agagcatctg cctcttccct agcacacatg cccctgaaca  142500
aacggttgat ctatgatcac atgggtttct gagttgtcct ttcagcttct ctttgttcat  142560
agaagtaaga agatgtgtaa agggatgtta gtagaagaag agtctcaatt cttcccagag  142620
cacagtggcc tcaatttcct tatctcaagg gcattgaaat aaaaaaaatc caaaagagt  142680 tttaaatgtt gccctatttt tctttaaaat gatgtaaagc aaatgtagaa aagtatgact  142740
agctaatggg taccatagat gataggcagt tttacacatc taccagtgtg tgtatgtgtg  142800
aatacagaaa tgcatgtata ctcaccttgt agcacagtgc tctagtggat gctcatttgt  142860
tccttttctt acttgaaatt ggtttgaata agagaaaaa cattaaaaga tgtataggtt  142920
atttatactt tctaattatc tttaccattg cagaaagtat ttatcttttc tggaacattc  142980
agacaaaacc tggatcccaa tggaaaatgg aaagatgaag aaatatggaa agttgcagat  143040
gaggtaagga tgacaaataa agtagtttta aagaagtaga tcatacacac aagtgtggtt  143100
gccatagatg ataggcagtt ttacacatct actggtgtgt gcatgtgtga acacagaaat  143160
gcatgtatac tcaccttgta gcacagtgct ctcatttact ggcacatcct tgtcagaacc  143220
tttgactcat ccccctttca ggagtgtcgc tcctttccat atactctatt cgtggtgctt  143280
tactaaagtt ctatagaccc ttgctcctag acgacgtatg tttctctcac tattttgaag  143340
```

```
actgagaagt ccaaggttaa ggagccagca gacagtattt actatctgct aaggccctac 143400
ttgctgtcac tcccgaggtg ttttctgca cctcactcag tataagtggt cagtgagcgc 143460
tgtggagcct cttttcatta tagtgttaat tccatctatg gggtactcag agcccatgac 143520
ctaatcactt cctaaacatt ttatttatg tctcagtagc actgccttgg acagtcaggt 143580
gttaacatga gtttctgaag acatgcggac ctagaactcc ctcctttcct ccctccaag 143640
ttatgtcttg ttcttatgaa aatagattac tccacttaaa caaatgccaa agtcttaaca 143700
cattttggtg tcagtgtaca actggaaatc acaaagtctc aattcagcca ccatgagact 143760
tgggacttta ggttttcat gttggcattc caccattccc tgcactttgc ccattgttgt 143820
tcccttgatg ttcgctcttc ggcctccccc agaacagatc ttgccaggag ctttgaagcc 143880
tctgagtgct aaatgctaac cccttgagta accaaccttta accttctcct aataaaatga 143940
actgagatta accgttttc attatcaggg tttccttatt acccagcaaa cacaaggttt 144000
ttaaagaaaa cattaactaa attgctagtg atatactgta agatccttga tgtacttta 144060
cagagtgacc tgtcagaata cagtgtgctg ggagagagct tgggaaagaa ggaattagcc 144120
tttgtaaagc ttaccaggta ttgccaagtc tccataaaat ttgcaggaaa ctgagatcat 144180
aaaatcatct aaaatgttag gagataggtt tagaagactt tagattccag aataatacag 144240
gtagttatgt gattagattt tgtctaccag tccatctta gatgtacgtt ttcattggat 144300
tctcttttta aatttatgtt cataaagatg ctgctcctga gctaaccgta atgtcccatg 144360
gtttgagtaa gagtgacaaa ttttttgctg aagagtccac aaagaaacat aaacaccaac 144420
ccctagctta cagcagcagg caggagattt aggttaaagg caggaatcct aggctttaat 144480
cctgtatggt tgatgatcca atatagtcaa ataggaacac gttgaggtgt gtcagcctac 144540
taaggcacta ggacaaaagt ctaaccttcc tgccctggtt catggcagct tgctgcccta 144600
ttcagctctg gggatctttc ttttttttt taattttttt attttaaaaca attttttaaa 144660
tatttttat tacatatttt cctcaattac atttccaaag ctatcccaaa agtcccccat 144720
accctccccc cccacttccc tacccaccca ttcccatttt tttggccctg gcgttcccct 144780
gtactgggc atatacagtt tgcgtgtcca atgggcctct cttttccagtg atggccaact 144840
aggccatctt ttgataccta tgcagctaga gtcaagagct tcggggtact ggttagttca 144900
taatgttgtt ccacctatag ggttgcagat ccctttagct ccttgggtac tttctctagc 144960
tcctccattg ggagccctgt ggtccatcca atagctgact gtgagcatcc acttctgtgt 145020
ttgctaggcc ccggcatagt ctcacaagag acagctacat ctgggtcctt tcgataaaat 145080
cttgctagtg tatgcaatgg ctttctaaag gctgcatctt tagcctactt ctcacccctc 145140
cctgtgctgc tgctggacag ggttcctgtt gtacactgac tgcttaaagg acctttatga 145200
tttggtcttt gctgctctac tttcagcccc agccccatg tgtcctgtga gtccactact 145260
gtgaattta atttctttta gagcacagtg tgctgctctc tgttctatgg tacgggttgg 145320
ggcagttgtt tctgcttttt accttctggt ttctggacct gggaaaccct tgcagagcac 145380
tactcctgct ccttctcacc attcaagcct tccttcacac atcactttgt tctgaactcc 145440
atcctgaccc tcctgctttg ggaaaagaga ctttcctagg tatagctatg cctcggctcc 145500
tcaaaatttc ctacactgaa tcaaaattca cctcttggct actccatatc tcctatgatt 145560
atggaatcat gccctgctct ctgttgttcc tgcagtagtt ggatccctgg gtggttttg 145620
ataagtactg actgaatgat ctgagcaagt aaagaattct tttaactcat gtaaaatatg 145680
ttgtgaaaat atcctcatgc ttaatgccca atagacatta ctaccttcat ctcagtaaag 145740
```

```
gtcttgcaag atggctggcg gattctgaaa agaactgcag ccctgacttg gggccctctg 145800
ctgttttagc cctactaagc tatgtgatct tggccccttg actctggctc ttagatgtgg 145860
ggactttgtt tgtttgtttg tgtttcctta ttagaataat ttttaaattt atcatcttta 145920
catcctaata gtcaagggaa ctgttgtaga gacaatttaa atagcagaaa cagggaccct 145980
gtaagtggga catttccctg agaagtttgc agaatggaaa cacaaggagc tgagggtatc 146040 cattttaca ttgcccacta gtgcttacag gcaaagcata atccaccttt tttactgaaa 146100
aaaaaaaact gtcatagaaa acaaaaatcc tacaaatact tctgagtagt ttggtataga 146160
gtactgattt atctaaacat atttgaatac ttttaacttt gttatttgat ggatggtcat 146220
agagttaaag atttacagag tacagtatat aatttctgag ctaaaactag cactaattca 146280
ttcattctta agttctaatg cttaaagact catagtacat attaaatgaa tgactgaaag 146340
gaagatgaat gaatgaatga atggattaat aaatatatga atgaatgaat gaatgaatga 146400
atgatgaatt gttgaggctg agagtgttcc taactgaaaa acacatattt gctttcaaga 146460
aatgtatggt ctaacaggga aaaaatacac aattctaata caggatgcct ggctgtcctg 146520
tgggtaggca aggatattta agagagtaat cagactgagc agaaggacaa accctgagaa 146580
tgttaagctg tataaagaat taaaagttga tgctgctgga cacagtagta ggtgtgtgtg 146640 tggggggcgga ggaggtcagg atgtcctgtg ggccacatga gaacaattat attttatttt 146700
tccagtaaaa gaacttctgt aggatttaaa acagagaaat gatccaagtt caaacctgca 146760
ttttagggag agctcttaaa tatttctgtg acatgttgac aatttgactc attgatactt 146820
gcagtatgat gtttaagaaa tgacagaagg ccagacgagg atcagtgtgc cagaactgac 146880
aaaaagaacg gtttcagaaa ccctggggga acttctaggc tggagagagg cattgaaagc 146940
cattagctta aacatacaca ttgatgccat gtacataacc aaaatctgga cacaggaggg 147000
gaggggacat tggtgttgaa acctgatatg gatgggacaa agctgtatag tatagtatcc 147060
cctgtgatac accaggcagt cttccttgtc ttctgtgcct acattcccta ctatctcagg 147120
aaccttttaa acattaacga gtttacacaa agggtagttt taacaagcca catgtttgaa 147180
cttccataat gagcacataa gagtctggca ttaacaatga tatgagccac ttctgaactc 147240
atctccaaaa tcatgaatct ttcttaaggc cttatctaac tctgcacatg ttagagtgat 147300
atgggtatat atcttacctg tacatacaaa attccagatt catgaagcac aagaaacaat 147360
cctgtctgta tttatttaac tcttatacac ctagtggttc ttagcaaaga agacacaatg 147420
tacatgtatt gaataaggaa aaaccaccaa gacatctata attatgcctt aattttgaca 147480
gactactttt tgatctttt attaaacccc ctttaaaatt gcagtttaaa aatataagcc 147540
attaattcta aaataatctt catattctac cctaacaata agagccttta aatttagtc 147600 gtgttccatt tttaactaag taacttctta ctttatgaga aagttatcag tttctcagat 147660
tttataagtg aaggagataa gtattatgat ggcatgattt ttttaaagcc tcctcagcta 147720
attttcatga tatttctcat cctgtattac agatagaaga tgaacatgtc atgctatgtt 147780 ttctacccctt tctgctcttg aatcctttgc catcagttat aatggagtga ataactgtgt 147840
tctctatctg ttatctttaa agcccatatt gaattgtatt gcaattgcat ctatccatct 147900
atctatatct gtatctgtac ctatccatct atataatgtg acaggaatag gtataattgt 147960
ttatcactgc tagggaacat gacacttaca aggtgaacac tgaatgattt tgtaatcaag 148020
tgtggggctg aaagaaaatcc tccagtctgt ttagagctac cgatattatt gccagatttt 148080
```

```
ggttactcaa actaagtagg agttgggagt tgagggtgat gtgaaattta ttctgtgcaa   148140
actcatgtct gcttttagaa tgcaagcctc ttaagtgatt ttagttatgc cccttctaag   148200
cacagtgttt ttctttattt tctacaggtt ggactcaagt ctgtaataga gcagtttcct   148260
ggacagctca actttaccct tgtggatggg ggttatgtgc taagccatgg ccataagcaa   148320
ttaatgtgct tggcccgatc agttctcagt aaggccaaga tcatactgct tgatgagccc   148380
agtgcccatc tagaccccat gtaagttcca aaaatcttta gataatcatg caatagaagt   148440
agagtccttg aagttacctc atattggtac aaattcccat tcagctacca cacctacaag   148500 taggggggtac aaaataattt tccagggggaa aaatcactat ttaacatgag cacaagtact   148560
tttttttttt tcaacaagag ctttgttttt cctcctgact ggagtctgga atttataaac   148620
ccttcaacct cattaacaca taataaatac ttagttaggt atgcacacac ttatggcttc   148680
cctctgtatc ctatttatat cataaataca ttaacagcac aaaataaata actgatgctg   148740 aatctcacata aaatgtagtc tcatttttat gaaattttct tctaagcatt tgctttatta   148800
gtgtatgaaa ttatattaaa tacttagaat ggcttaaaag ctgattgtag ctcattctgt   148860
atcatcatta tcctaaaagt atttttaagt aaagaattaa gtccatagaa tactatacgt   148920
attgtcaaag ataaaggcag aaaattcaca ctctataatg tcttatgtgg tattttcttg   148980
ctttgctaga ataccaag tcattcgacg agttctaaaa caagccttcg ctggttgcac   149040
agtcatcctc tgtgaacaca ggatagaagc gatgttggat tgccagcgat ttttggtaag   149100
tcatttacac ttgattgata tctcattctc catttattta aataatcctg cacagctgga   149160
tttgcacacc ctttcttcac acttatgtca cacatttacc acctaccctc agtctctttc   149220
cctggacttg agctatgaag tggtgaggaa atttagcaca cttctctggt atcatatcac   149280
taaacgacac tgtagataag gtaactatgc tttcagatct tttgtggcga acaagtcaca   149340
aaatgtacaa ttgaaaaaaa aaatgtctgt ttcttacagt aactcagctt cccatgggga   149400
agataagggt gggccttacc attagtggtt caatgtagta ggagagaagc ctgttccatc   149460
atccccatta ctactggaac tcagggtagt gtccctgtca gacaccttct cattctcccc   149520
ccgcccccaa aaaaagtca ctgttcctgt ttagacatgg gaagttccaa ggatcatgta   149580
aaatttttac tttcccaagg cttttgaata ttctggaggt aaatgctttt ttactgaagc   149640
acttttgatc ctattgttat tgcccagtta caagtgccta gagagtagat gcatctcttg   149700
ttctgtggtg gtcaagtaca gggactaggt aaggggctct actctctgac ctcaagcttg   149760
caaacagttt aacatgcact gaaggcgtta ttctctgtca ttcctggcca atttgaaacc   149820
tttcggcctc aaccccaggt atgaggaagc tcaaagttaa tggttatata tagctcggtt   149880
taagagtgcg tgggtcattg attattttgc tttgcaaagc tccttcagtt cctcaactgt   149940
tctctgaagg atggcaacag ctagtattac attaattttt caaatcccta tcgctacttt   150000
cccggatgtg aaagctaaga gaaaagtaca agctctgaat cctgtgcttt ctttggactt   150060
ttgttcttct ttgggcctgg ctcagtttat gtgtcagcac tggcctgctc ttcactcaga   150120
ggtctcacta atgccctctc ccttaggtca tagaagagag caatgtctgg cagtacgact   150180
cccttcaggc acttctgagt gagaagagta tcttccagca ggccattagc tcctcggaaa   150240
agatgaggtt cttccagggc cgccactcca gcaagcacaa gcctcggacg caaattactg   150300
ctctgaaaga gggagacagaa gaagaagttc aagaaacccg tctctagtgc tgggatgctg   150360
aggaagcaac tcagtgcact gagtccattc ccagaaccca tgcagaatga aaaagccag   150420 gcatttccca tgcttctaac cccagtgctg gggacacaga gacaggtgga tccctgggggc   150480
```

```
tctgtggcaa gtgatcctag cccacaaaga gagttccagg ctgggcacct gagggacaat    150540
acctgtggat atactcttgc ttccacatgc aagtacatat acacatgcat gcacattagt    150600
ggacatacac acagaaaagc aaagaagaag gaaagaggga agaaaatagt gcaaataatt    150660
gcaaaacgat catgtatgga gtctgctcat ggacttagag gaggtgaact ctactacctg    150720
tgcctttgaa agaagggtga agcctgcgac ttgctcttta agagactgtt ttggaagaga    150780
gttcaaaaac gttcatatgg gtatgggtaa ctgactttcc agcagtagtc aaattgtttg    150840
aacttcagat agttgataat gaccacttgt gtattgcaag gcagattttt ctgaaaacat    150900
ttgcccccta atagtagctg aaaaagcagc tataaatgcc aaccaggtta gtcattcggc    150960
ttattgttca gtacagctgg ttaatttgca ttattgaaga actgaaatta tagtgcttag    151020
atataggaca aagtaaagag aactaaaaac agtgtcttat ataactcaaa gcccaactta    151080 cttctcctcta agatatgtat tgccttctat acattgtctg ccccattcca agcaaatgtt    151140
agaatattat acaaaatact gggtggtatt gattgaaaga tgcccgacat ctggtgatct    151200
agtaacccat caggattaag gatatccagg tcttggaaat taaggttaag accatctagc    151260
cttactaccg tacagctaaa cattcttatt accagaataa gacctaggaa aagaactgtt    151320
tcagtcccat aaagtggcct ggataatttc cttgatatgg aaatcgacac acttatgttc    151380
ccagaaagca acagatcttt aagacttctg aagtgaagga aggttgtgtt agtgcaaact    151440
agtgcagccc agtgccaggt ccaggagtta acatgtagac aggccatgga ctgtgtgggt    151500
agatgctcat ggaaatgtgc agtagtatgt tcatgtgctc tcagctagct gtgtgtactt    151560
caaactgtct ccacagagtt gttggggaga cactctgaaa aagaattaat tgtgaattag    151620
ttttatatac tttgttttat aatttgtgat gcaaatgaaa atttctctgg gaaatattta    151680
ttttagtaat aatgtttcaa actcatatat aacaatgctg tattttaaga atgattacat    151740
aatgacttat atttgtataa ataattttt atatttgaaa tgttaacttt ttatagcact    151800
agctatttta aaacagggga gtgaggagga cagggatgat aaggatcatt caacttcatg    151860
ttgtgaagac gagctgatgt aaatcttgta cccatctgtg tggttctcag acaacacatg    151920
ctctctttta atgcagcttt gaagaagatg gtaccaaagg ttaagacggc ccctgatgg    151980 gcacatcaac ttctgaactg caaactaagc tttagaggaa tgtattatat ttattactgt    152040
aatagaatat catgtgtcaa taaatccctt ttatttgtgt ga                       152082
```

<210> SEQ ID NO 148
<211> LENGTH: 6305
<212> TYPE: DNA
<213> ORGANISM: Mus musculus

<400> SEQUENCE: 148

```
aattggaagc aaatgacatc acctcaggtc tgagtaaaag ggacgagcca aaagcattga      60
cctggtcctg gatatccaga tgtcgagtcc aacctgaatt tagccgaaca cagacctcat     120
tgcctcacgg agacatcatg cagaagtcgc ctttggagaa agccagcttt atctccaaac     180
tcttcttcag ctggaccaca ccaatttttga ggaaagggta cagacaccac ttggagttgt     240
cagacatata ccaagccccct tctgctgatt cagctgacca cttgtctgaa aaactagaaa     300
gagaatggga cagagaacaa gcttcaaaaa agaatcccca gcttatccac gcccttcggc     360
gatgcttttt ctggagattc ctcttctatg gaattttgct atacctaggg gaagtcacca     420
aggctgtcca gcctgtcttg ctaggaagaa tcatagcatc ctatgatcca gaaaacaagg     480
```

```
tggaacgttc cattgccatt taccttggca taggcttatg ccttctcttc attgtcagga    540
cactgcttct tcacccagct attttttggcc ttcatcgcat tggaatgcag atgagaacag   600
ctatgtttag cttgatttat aagaagactt taaagttgtc aagccgcgtt cttgataaaa    660
taagtattgg acaacttgtt agtcttcttt ccaacaacct gaacaaattt gatgaaggac    720
ttgccttggc acattttata tggattgctc ctttacaagt gactcttctg atggggcttc    780
tctgggactt gttacagttc tcagccttct gtggccttgg tttactgata atcctggtta    840
tttttcaagc tatcctaggg aagatgatgg tgaagtacag agatcagaga gctgcaaaga    900
tcaatgaaag actcgtgatc acatcagaaa ttattgataa tatctattct gttaaggcat    960
attgttggga atcagcgatg gagaaaatga ttgaaaactt gagagaggtg gagctgaaaa   1020
tgacccggaa ggcggcctat atgaggttct tcactagctc tgccttcttc ttttcagggt   1080
tctttgtagt cttctctatct gtgcttccct acacagtcat caacggaatc gtcctacgaa   1140
aaatattcac aaccatttca ttctgcattg tcctacgtat gtcagtcaca cggcagttcc   1200
ccactgccgt acagatatgg tatgattctt ttggaatgat aagaaaaata caggatttcc   1260
tgcagaaaca agagtataaa gtactggagt ataacttaat gaccacaggc ataatcatgg   1320
aaaatgtaac agcattttgg gaggagggat ttggggaatt actggagaaa gtacaacaaa   1380
gcaatggtga cagaaaacat tccagtgatg agaacaatgt cagtttcagt catctctgcc   1440
ttgtgggaaa tcctgtgctg aaaaacatca atttgaatat agaaaagga gagatgttgg    1500 ctattactgg atctactgga tcaggaaaga catcactcct gatgttgatt tgggagaac    1560 tggaagcttc agagggaatt attaagcaca gtggaagagt tcattctgc tctcaatttt    1620 cttggattat gccgggtact atcaaagaaa atatcatctt tggtgttttcc tatgatgagt   1680 acagatataa gagtgttgtc aaagcttgcc aactacagca ggacatcacc aagttttgcag  1740 aacaagacaa cacagttctt ggagaaggtg gagtcacact gagtggaggt cagcgtgcaa   1800
ggatttcttt agcaagagca gtatataaag atgctgattt gtacctatta gattcccctt    1860
ttggatatct agatgttttt actgaagaac aagtatttga agctgtgtt tgtaaattga    1920 tggccaacaa aactaggatt ttggttacat ctaaaatgga acacttaagg aaagctgaca   1980
aaatactaat tttgcatcag gcagtagct attttttatgg gacatttct gagctacaaa    2040 gtctacgtcc agacttcagt tcgaaactca tggggtatga tacttttgac cagtttactg   2100
aggaaagaag aagttcaatt ctaactgaga ccttacgcag gttctcagta gacgattcct   2160
ctgccccgtg gagcaaaccc aaacagtcgt ttagacagac tggagaggtg ggagaaaaaa   2220
ggaagaactc tattctaaat tcattcagct ctgtaaggaa aatttccatt gtgcaaaaga   2280
ctccattatg tatcgatgga gagtctgatg atctccaaga aaagagactg tccctagttc    2340
cggattctga acaggggag gctgctctgc cgcgcagcaa catgatcgcc accggcccca    2400
catttccagg cagaagaaga cagtctgttt tggatctgat gacgttcaca cccaactcag   2460
gctccagcaa tcttcagagg accagaactt ctattcgaaa atctccttta gtccctcaga   2520
taagcttaaa tgaagtggat gtatattcaa ggagattatc gcaagatagc acactgaaca   2580
tcactgaaga aattaacgaa gaagatttaa aggagtgttt tcttgatgat gtgatcaaga   2640 taccccggt gacaacatgg aacacatacc tacgatattt tactctccat aaaggcttac    2700
tgctagtgct gatttggtgc gtactggttt ttctggttga ggtggctgct tctttatttg    2760
tgttatggtt gctaaaaaac aaccctgtta acagtgaaa caatggtact aaaatttcca    2820
atagctccta tgttgtgatc atcaccagta ccagtttcta ttatattttt tacatttacg   2880
```

```
tgggagtggc tgacactttg cttgccctga gcctcttcag aggtttgccg ctggtgcata    2940
cgttaatcac agcatcaaaa attttgcaca ggaaaatgtt acactccatt cttcacgccc    3000
ctatgtcgac catcagcaag ctgaaagcag gtgggattct taacagattc tccaaagata    3060
tagcaatttt ggatgacttt ctgcctctta ccatttttga cttcattcag ttggtgttca    3120
ttgtgattgg agctataata gtcgtctcgg cattacaacc ctacatcttc ctagcaacgg    3180
tgccagggct agtagtcttt attttactga gggcctactt ccttcataca gcacagcagc    3240
tcaaacaact ggaatctgaa ggcaggagtc caattttcac ccaccttgtg acaagcttaa    3300
aaggactctg gacacttcga gccttccgac gccagactta ctttgaaact ctgttccaca    3360
aagctctgaa tttgcacact gccaactggt ttatgtatct ggcaaccttg cgctggttcc    3420
aaatgagaat agacatgata tttgtcctct tcttcattgt tgttaccttc atctccattt    3480
taacaacagg tgaaggagaa ggaacagctg gtattattct aactttagct atgaatatca    3540
tgagtacttt gcagtgggct gtgaactcaa gcattgatac agatagcttg atgcgatctg    3600
tgagcagagt gtttaagttt attgatatac aaacagaaga agtatgtac acacagataa     3660 ttaaagaact acctagagaa ggatcatctg acgttttagt cattaagaat gagcatgtga    3720
agaaaagtga tatctggccc tctggaggcg aaatggttgt caaagacctt actgtgaaat    3780
acatggatga tggaaatgcc gtattagaga acatttcttt ttcaataagt cctggacaga    3840
gggtggggct cttaggaaga actggatcag gaaaaagtac tttgctttca gcattttac    3900 gaatgttgaa cattaaaggt gatatagaga ttgatggtgt ctcatggaat tcagtgacct    3960
tacaagaatg gaggaaagct ttcggagtga taacacagaa agtatttatc ttttctggaa    4020
cattcagaca aaacctggat cccaatggaa aatggaaaga tgaagaaata tggaaagttg    4080
cagatgaggt tggactcaag tctgtaatag agcagtttcc tggacagctc aactttaccc    4140
ttgtggatgg gggttatgtg ctaagccatg gccataagca attaatgtgc ttggcccgat    4200
cagttctcag taaggccaag atcatactgc ttgatgagcc cagtgcccat ctagacccca    4260
taacatacca agtcattcga cgagttctaa acaagccttt cgctggttgc acagtcatcc    4320
tctgtgaaca caggatagaa gcgatgttgg attgccagcg attttggtc atagaagaga    4380 gcaatgtctg gcagtacgac tcccttcagg cacttctgag tgagaagagt atcttccagc    4440
aggccattag ctcctcggaa aagatgaggt tcttccaggg ccgccactcc agcaagcaca    4500
agcctcggac gcaaattact gctctgaaag aggagacaga agaagaagtt caagaaaccc    4560
gtctctagtg ctgggatgct gaggaagcaa ctcagtgcac tgagtccatt cccagaaccc    4620
atgcagaatg aaaaaagcca ggcatttccc atgcttctaa ccccagtgct ggggacacag    4680
agacaggtgg atccctgggg ctctgtggca agtgatccta gcccacaaag agagttccag    4740
gctgggcacc tgagggacaa tacctgtgga tatactcttg cttccacatg caagtacata    4800
tacacatgca tgcacattag tggacataca cacagaaaag caaagaagaa ggaaagaggg    4860
aagaaaatag tgcaaataat tgcaaaacga tcatgtatgg agtctgctca tggacttaga    4920
ggaggtgaac tctactacct gtgcctttga aagaagggtg aagcctgcga cttgctcttt    4980
aagagactgt tttggaagag agttcaaaaa cgttcatatg ggtatgggta actgactttc    5040
cagcagtagt caaattgttt gaacttcaga tagttgataa tgaccacttg tgtattgcaa    5100
ggcagatttt tctgaaaaca tttgcccccct aatagtagct gaaaaagcag ctataaatgc    5160
caaccaggtt agtcattcgg cttattgttc agtacagctg gttaatttgc attattgaag    5220
```

```
aactgaaatt atagtgctta gatataggac aaagtaaaga gaactaaaaa cagtgtctta    5280
tataactcaa agcccaactt actttcctct aagatatgta ttgccttcta tacattgtct    5340
gccccattcc aagcaaatgt tagaatatta tacaaaatac tgggtggtat tgattgaaag    5400
atgcccgaca tctggtgatc tagtaaccca tcaggattaa ggatatccag gtcttggaaa    5460
ttaaggttaa gaccatctag ccttactacc gtacagctaa acattcttat taccagaata    5520
agacctagga aaagaactgt ttcagtccca taaagtggcc tggataattt ccttgatatg    5580
gaaatcgaca cacttatgtt cccagaaagc aacagatctt taagacttct gaagtgaagg    5640
aaggttgtgt tagtgcaaac tagtgcagcc cagtgccagg tccaggagtt aacatgtaga    5700
caggccatgg actgtgtggg tagatgctca tggaaatgtg cagtagtatg ttcatgtgct    5760
ctcagctagc tgtgtgtact tcaaactgtc tccacagagt tgttggggag acactctgaa    5820
aaagaattaa ttgtgaatta gttttatata ctttgtttta aatttgtga tgcaaatgaa     5880
aatttctctg ggaaatattt attttagtaa taatgtttca aactcatata taacaatgct    5940
gtattttaag aatgattaca taatgactta tatttgtata aaataatttt tatatttgaa    6000
atgttaactt tttatagcac tagctatttt aaaacagggg agtgaggagg acagggatga    6060
taaggatcat tcaacttcat gttgtgaaga cgagctgatg taaatcttgt acccatctgt    6120
gtggttctca gacaacacat gctctctttt aatgcagctt tgaagaagat ggtaccaaag    6180
gttaagacgg cccctgatg ggcacatcaa cttctgaact gcaaactaag ctttagagga     6240
atgtattata tttattactg taatagaata tcatgtgtca ataaaatcct tttatttgtg    6300
tgaaa                                                                6305
```

<210> SEQ ID NO 149
<211> LENGTH: 1476
<212> TYPE: PRT
<213> ORGANISM: Mus musculus

<400> SEQUENCE: 149

```
Met Gln Lys Ser Pro Leu Glu Lys Ala Ser Phe Ile Ser Lys Leu Phe
1               5                   10                  15

Phe Ser Trp Thr Thr Pro Ile Leu Arg Lys Gly Tyr Arg His His Leu
            20                  25                  30

Glu Leu Ser Asp Ile Tyr Gln Ala Pro Ser Ala Asp Ser Ala Asp His
        35                  40                  45

Leu Ser Glu Lys Leu Glu Arg Glu Trp Asp Arg Glu Gln Ala Ser Lys
    50                  55                  60

Lys Asn Pro Gln Leu Ile His Ala Leu Arg Arg Cys Phe Phe Trp Arg
65                  70                  75                  80

Phe Leu Phe Tyr Gly Ile Leu Leu Tyr Leu Gly Glu Val Thr Lys Ala
                85                  90                  95

Val Gln Pro Val Leu Leu Gly Arg Ile Ile Ala Ser Tyr Asp Pro Glu
            100                 105                 110

Asn Lys Val Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His Arg Ile Gly Met Gln Met Arg Thr Ala Met Phe Ser Leu Ile
145                 150                 155                 160

Tyr Lys Lys Thr Leu Lys Leu Ser Ser Arg Val Leu Asp Lys Ile Ser
                165                 170                 175
```

```
Ile Gly Gln Leu Val Ser Leu Leu Ser Asn Asn Leu Asn Lys Phe Asp
            180                 185                 190

Glu Gly Leu Ala Leu Ala His Phe Ile Trp Ile Ala Pro Leu Gln Val
            195                 200                 205

Thr Leu Leu Met Gly Leu Leu Trp Asp Leu Leu Gln Phe Ser Ala Phe
            210                 215                 220

Cys Gly Leu Gly Leu Leu Ile Ile Leu Val Ile Phe Gln Ala Ile Leu
225                 230                 235                 240

Gly Lys Met Met Val Lys Tyr Arg Asp Gln Arg Ala Ala Lys Ile Asn
            245                 250                 255

Glu Arg Leu Val Ile Thr Ser Glu Ile Ile Asp Asn Ile Tyr Ser Val
            260                 265                 270

Lys Ala Tyr Cys Trp Glu Ser Ala Met Glu Lys Met Ile Glu Asn Leu
            275                 280                 285

Arg Glu Val Glu Leu Lys Met Thr Arg Lys Ala Ala Tyr Met Arg Phe
            290                 295                 300

Phe Thr Ser Ser Ala Phe Phe Phe Ser Gly Phe Phe Val Val Phe Leu
305                 310                 315                 320

Ser Val Leu Pro Tyr Thr Val Ile Asn Gly Ile Val Leu Arg Lys Ile
            325                 330                 335

Phe Thr Thr Ile Ser Phe Cys Ile Val Leu Arg Met Ser Val Thr Arg
            340                 345                 350

Gln Phe Pro Thr Ala Val Gln Ile Trp Tyr Asp Ser Phe Gly Met Ile
            355                 360                 365

Arg Lys Ile Gln Asp Phe Leu Gln Lys Gln Glu Tyr Lys Val Leu Glu
            370                 375                 380

Tyr Asn Leu Met Thr Thr Gly Ile Ile Met Glu Asn Val Thr Ala Phe
385                 390                 395                 400

Trp Glu Glu Gly Phe Gly Glu Leu Leu Glu Lys Val Gln Gln Ser Asn
            405                 410                 415

Gly Asp Arg Lys His Ser Ser Asp Glu Asn Asn Val Ser Phe Ser His
            420                 425                 430

Leu Cys Leu Val Gly Asn Pro Val Leu Lys Asn Ile Asn Leu Asn Ile
            435                 440                 445

Glu Lys Gly Glu Met Leu Ala Ile Thr Gly Ser Thr Gly Ser Gly Lys
            450                 455                 460

Thr Ser Leu Leu Met Leu Ile Leu Gly Glu Leu Glu Ala Ser Glu Gly
465                 470                 475                 480

Ile Ile Lys His Ser Gly Arg Val Ser Phe Cys Ser Gln Phe Ser Trp
            485                 490                 495

Ile Met Pro Gly Thr Ile Lys Glu Asn Ile Ile Phe Gly Val Ser Tyr
            500                 505                 510

Asp Glu Tyr Arg Tyr Lys Ser Val Val Lys Ala Cys Gln Leu Gln Gln
            515                 520                 525

Asp Ile Thr Lys Phe Ala Glu Gln Asp Asn Thr Val Leu Gly Glu Gly
            530                 535                 540

Gly Val Thr Leu Ser Gly Gly Gln Arg Ala Arg Ile Ser Leu Ala Arg
545                 550                 555                 560

Ala Val Tyr Lys Asp Ala Asp Leu Tyr Leu Asp Ser Pro Phe Gly
            565                 570                 575

Tyr Leu Asp Val Phe Thr Glu Glu Gln Val Phe Glu Ser Cys Val Cys
            580                 585                 590

Lys Leu Met Ala Asn Lys Thr Arg Ile Leu Val Thr Ser Lys Met Glu
```

-continued

```
            595                 600                 605
His Leu Arg Lys Ala Asp Lys Ile Leu Ile Leu His Gln Gly Ser Ser
610                 615                 620

Tyr Phe Tyr Gly Thr Phe Ser Glu Leu Gln Ser Leu Arg Pro Asp Phe
625                 630                 635                 640

Ser Ser Lys Leu Met Gly Tyr Asp Thr Phe Asp Gln Phe Thr Glu Glu
                645                 650                 655

Arg Arg Ser Ser Ile Leu Thr Glu Thr Leu Arg Arg Phe Ser Val Asp
                660                 665                 670

Asp Ser Ser Ala Pro Trp Ser Lys Pro Lys Gln Ser Phe Arg Gln Thr
                675                 680                 685

Gly Glu Val Gly Glu Lys Arg Lys Asn Ser Ile Leu Asn Ser Phe Ser
690                 695                 700

Ser Val Arg Lys Ile Ser Ile Val Gln Lys Thr Pro Leu Cys Ile Asp
705                 710                 715                 720

Gly Glu Ser Asp Asp Leu Gln Glu Lys Arg Leu Ser Leu Val Pro Asp
                725                 730                 735

Ser Glu Gln Gly Glu Ala Ala Leu Pro Arg Ser Asn Met Ile Ala Thr
                740                 745                 750

Gly Pro Thr Phe Pro Gly Arg Arg Gln Ser Val Leu Asp Leu Met
                755                 760                 765

Thr Phe Thr Pro Asn Ser Gly Ser Ser Asn Leu Gln Arg Thr Arg Thr
770                 775                 780

Ser Ile Arg Lys Ile Ser Leu Val Pro Gln Ile Ser Leu Asn Glu Val
785                 790                 795                 800

Asp Val Tyr Ser Arg Arg Leu Ser Gln Asp Ser Thr Leu Asn Ile Thr
                805                 810                 815

Glu Glu Ile Asn Glu Glu Asp Leu Lys Glu Cys Phe Leu Asp Asp Val
                820                 825                 830

Ile Lys Ile Pro Pro Val Thr Thr Trp Asn Thr Tyr Leu Arg Tyr Phe
                835                 840                 845

Thr Leu His Lys Gly Leu Leu Leu Val Leu Ile Trp Cys Val Leu Val
850                 855                 860

Phe Leu Val Glu Val Ala Ala Ser Leu Phe Val Leu Trp Leu Leu Lys
865                 870                 875                 880

Asn Asn Pro Val Asn Ser Gly Asn Asn Gly Thr Lys Ile Ser Asn Ser
                885                 890                 895

Ser Tyr Val Val Ile Ile Thr Ser Thr Ser Phe Tyr Tyr Ile Phe Tyr
                900                 905                 910

Ile Tyr Val Gly Val Ala Asp Thr Leu Leu Ala Leu Ser Leu Phe Arg
                915                 920                 925

Gly Leu Pro Leu Val His Thr Leu Ile Thr Ala Ser Lys Ile Leu His
930                 935                 940

Arg Lys Met Leu His Ser Ile Leu His Ala Pro Met Ser Thr Ile Ser
945                 950                 955                 960

Lys Leu Lys Ala Gly Gly Ile Leu Asn Arg Phe Ser Lys Asp Ile Ala
                965                 970                 975

Ile Leu Asp Asp Phe Leu Pro Leu Thr Ile Phe Asp Phe Ile Gln Leu
                980                 985                 990

Val Phe Ile Val Ile Gly Ala Ile  Ile Val Val Ser Ala  Leu Gln Pro
                995                 1000                1005

Tyr Ile  Phe Leu Ala Thr Val  Pro Gly Leu Val Val  Phe Ile Leu
    1010                1015                1020
```

-continued

```
Leu Arg Ala Tyr Phe Leu His Thr Ala Gln Gln Leu Lys Gln Leu
1025                 1030                1035

Glu Ser Glu Gly Arg Ser Pro Ile Phe Thr His Leu Val Thr Ser
1040                 1045                1050

Leu Lys Gly Leu Trp Thr Leu Arg Ala Phe Arg Arg Gln Thr Tyr
1055                 1060                1065

Phe Glu Thr Leu Phe His Lys Ala Leu Asn Leu His Thr Ala Asn
1070                 1075                1080

Trp Phe Met Tyr Leu Ala Thr Leu Arg Trp Phe Gln Met Arg Ile
1085                 1090                1095

Asp Met Ile Phe Val Leu Phe Phe Ile Val Val Thr Phe Ile Ser
1100                 1105                1110

Ile Leu Thr Thr Gly Glu Gly Glu Gly Thr Ala Gly Ile Ile Leu
1115                 1120                1125

Thr Leu Ala Met Asn Ile Met Ser Thr Leu Gln Trp Ala Val Asn
1130                 1135                1140

Ser Ser Ile Asp Thr Asp Ser Leu Met Arg Ser Val Ser Arg Val
1145                 1150                1155

Phe Lys Phe Ile Asp Ile Gln Thr Glu Glu Ser Met Tyr Thr Gln
1160                 1165                1170

Ile Ile Lys Glu Leu Pro Arg Glu Gly Ser Ser Asp Val Leu Val
1175                 1180                1185

Ile Lys Asn Glu His Val Lys Lys Ser Asp Ile Trp Pro Ser Gly
1190                 1195                1200

Gly Glu Met Val Val Lys Asp Leu Thr Val Lys Tyr Met Asp Asp
1205                 1210                1215

Gly Asn Ala Val Leu Glu Asn Ile Ser Phe Ser Ile Ser Pro Gly
1220                 1225                1230

Gln Arg Val Gly Leu Leu Gly Arg Thr Gly Ser Gly Lys Ser Thr
1235                 1240                1245

Leu Leu Ser Ala Phe Leu Arg Met Leu Asn Ile Lys Gly Asp Ile
1250                 1255                1260

Glu Ile Asp Gly Val Ser Trp Asn Ser Val Thr Leu Gln Glu Trp
1265                 1270                1275

Arg Lys Ala Phe Gly Val Ile Thr Gln Lys Val Phe Ile Phe Ser
1280                 1285                1290

Gly Thr Phe Arg Gln Asn Leu Asp Pro Asn Gly Lys Trp Lys Asp
1295                 1300                1305

Glu Glu Ile Trp Lys Val Ala Asp Glu Val Gly Leu Lys Ser Val
1310                 1315                1320

Ile Glu Gln Phe Pro Gly Gln Leu Asn Phe Thr Leu Val Asp Gly
1325                 1330                1335

Gly Tyr Val Leu Ser His Gly His Lys Gln Leu Met Cys Leu Ala
1340                 1345                1350

Arg Ser Val Leu Ser Lys Ala Lys Ile Ile Leu Leu Asp Glu Pro
1355                 1360                1365

Ser Ala His Leu Asp Pro Ile Thr Tyr Gln Val Ile Arg Arg Val
1370                 1375                1380

Leu Lys Gln Ala Phe Ala Gly Cys Thr Val Ile Leu Cys Glu His
1385                 1390                1395

Arg Ile Glu Ala Met Leu Asp Cys Gln Arg Phe Leu Val Ile Glu
1400                 1405                1410
```

-continued

| | | | | | | | | | | | | |
|---|---|---|---|---|---|---|---|---|---|---|---|---|
| Glu | Ser<br>1415 | Asn | Val | Trp | Gln | Tyr<br>1420 | Asp | Ser | Leu | Gln | Ala<br>1425 | Leu Leu Ser |
| Glu | Lys<br>1430 | Ser | Ile | Phe | Gln | Gln<br>1435 | Ala | Ile | Ser | Ser | Ser<br>1440 | Glu Lys Met |
| Arg | Phe<br>1445 | Phe | Gln | Gly | Arg | His<br>1450 | Ser | Ser | Lys | His | Lys<br>1455 | Pro Arg Thr |
| Gln | Ile<br>1460 | Thr | Ala | Leu | Lys | Glu<br>1465 | Glu | Thr | Glu | Glu | Glu<br>1470 | Val Gln Glu |
| Thr | Arg<br>1475 | Leu | | | | | | | | | | |

<210> SEQ ID NO 150
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 150
cctttcaggg tgtcttactc accat                                        25

<210> SEQ ID NO 151
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 151
cctcttacct cagttacaat ttata                                        25